United States Patent
Wu et al.

(10) Patent No.: US 11,433,053 B2
(45) Date of Patent: Sep. 6, 2022

(54) LSD1 INHIBITOR AND PREPARATION METHOD AND APPLICATION THEREOF

(71) Applicant: CSPC ZHONGQI PHARMACEUTICAL TECHNOLOGY (SHIJIAZHUANG) CO., LTD., Shijiazhuang (CN)

(72) Inventors: Lingyun Wu, Shanghai (CN); Li Zhang, Shanghai (CN); Lele Zhao, Shanghai (CN); Jianjun Sun, Shanghai (CN); Zhaoguo Chen, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 137 days.

(21) Appl. No.: 16/479,602

(22) PCT Filed: Jan. 24, 2018

(86) PCT No.: PCT/CN2018/073961
§ 371 (c)(1),
(2) Date: Sep. 17, 2019

(87) PCT Pub. No.: WO2018/137644
PCT Pub. Date: Aug. 2, 2018

(65) Prior Publication Data
US 2020/0345700 A1    Nov. 5, 2020

(30) Foreign Application Priority Data

Jan. 24, 2017    (CN) .......................... 201710060400.5
Aug. 24, 2017    (CN) .......................... 201710736745.8
Dec. 28, 2017    (CN) .......................... 201711460525.3

(51) Int. Cl.
*C07D 207/09*    (2006.01)
*C07D 207/335*    (2006.01)
(Continued)

(52) U.S. Cl.
CPC ........ *A61K 31/4245* (2013.01); *A61K 31/135* (2013.01); *A61K 31/165* (2013.01); *A61K 31/277* (2013.01); *A61K 31/40* (2013.01); *A61K 31/4035* (2013.01); *A61K 31/41* (2013.01); *A61K 31/415* (2013.01); *A61K 31/417* (2013.01); *A61K 31/4188* (2013.01); *A61K 31/4192* (2013.01); *A61K 31/4196* (2013.01); *A61K 31/422* (2013.01); *A61K 31/423* (2013.01); *A61K 31/426* (2013.01); *A61K 31/428* (2013.01); *A61K 31/437* (2013.01); *A61K 31/4375* (2013.01); *A61K 31/44* (2013.01); *A61K 31/4439* (2013.01); *A61K 31/451* (2013.01); *A61K 31/4545* (2013.01); *A61K 31/472* (2013.01); *A61K 31/519* (2013.01); *A61K 31/55* (2013.01); *A61K 33/243* (2019.01); *A61P 35/00* (2018.01);
(Continued)

(58) Field of Classification Search
CPC ................ C07D 271/06; C07D 207/09; C07D 207/335; C07D 209/44; C07D 211/18; C07D 211/34; C07D 213/38; C07D 217/26; C07D 223/16; C07D 231/12; C07D 233/64; C07D 249/06
See application file for complete search history.

(56) References Cited

U.S. PATENT DOCUMENTS 6,770,368 B2      8/2004  Luhn
8,722,743 B2 *    5/2014  Ortega Munoz ....... A61P 31/22
                                                            514/619
(Continued)

FOREIGN PATENT DOCUMENTS

CN    102947265 A    2/2013
CN    103124724 A    5/2013
(Continued)

OTHER PUBLICATIONS

PubChem Compound Summary for CID 65458891, Schembl22629417. Retrieved Feb. 13, 2021 from https://pubchem.ncbi.nlm.nih.gov/compound/Schembl22629417, created Oct. 24, 2012 (Year: 2012).*

(Continued)

*Primary Examiner* — Matthew P Coughlin
(74) *Attorney, Agent, or Firm* — Houston Beshining Law Office PLLC; Liangang Ye

(57) ABSTRACT

A cyclopropylamine compound as a lysine-specific demethylase 1 (LSD1) inhibitor. Particularly, the present invention relates to a compound represented by formula (I) and a pharmaceutically acceptable salt thereof. The present invention also provides an application of the same in preparing a drug for treating an LSD1-related disease.

30 Claims, No Drawings

(51) Int. Cl.
*C07D 209/44* (2006.01)
*C07D 211/18* (2006.01)
*C07D 211/34* (2006.01)
*C07D 213/38* (2006.01)
*C07D 217/26* (2006.01)
*C07D 223/16* (2006.01)
*C07D 231/12* (2006.01)
*C07D 233/64* (2006.01)
*C07D 249/06* (2006.01)
*A61K 31/4245* (2006.01)
*A61P 35/00* (2006.01)
*A61K 33/243* (2019.01)
*A61K 31/135* (2006.01)
*A61K 31/165* (2006.01)
*A61K 31/277* (2006.01)
*A61K 31/40* (2006.01)
*A61K 31/4035* (2006.01)
*A61K 31/41* (2006.01)
*A61K 31/415* (2006.01)
*A61K 31/417* (2006.01)
*A61K 31/4188* (2006.01)
*A61K 31/4192* (2006.01)
*A61K 31/4196* (2006.01)
*A61K 31/422* (2006.01)
*A61K 31/423* (2006.01)
*A61K 31/426* (2006.01)
*A61K 31/428* (2006.01)
*A61K 31/437* (2006.01)
*A61K 31/4375* (2006.01)
*A61K 31/44* (2006.01)
*A61K 31/4439* (2006.01)
*A61K 31/451* (2006.01)
*A61K 31/4545* (2006.01)
*A61K 31/472* (2006.01)
*A61K 31/519* (2006.01)
*A61K 31/55* (2006.01)
*C07C 211/40* (2006.01)
*C07C 233/58* (2006.01)
*C07C 255/46* (2006.01)
*C07D 249/08* (2006.01)
*C07D 257/04* (2006.01)
*C07D 261/20* (2006.01)
*C07D 263/56* (2006.01)
*C07D 271/06* (2006.01)
*C07D 277/28* (2006.01)
*C07D 413/04* (2006.01)
*C07D 413/06* (2006.01)
*C07D 413/10* (2006.01)
*C07D 413/14* (2006.01)
*C07D 417/04* (2006.01)
*C07D 471/04* (2006.01)
*C07D 487/04* (2006.01)

(52) U.S. Cl.
CPC .......... *C07C 211/40* (2013.01); *C07C 233/58* (2013.01); *C07C 255/46* (2013.01); *C07D 207/09* (2013.01); *C07D 207/335* (2013.01); *C07D 209/44* (2013.01); *C07D 211/18* (2013.01); *C07D 211/34* (2013.01); *C07D 213/38* (2013.01); *C07D 217/26* (2013.01); *C07D 223/16* (2013.01); *C07D 231/12* (2013.01); *C07D 233/64* (2013.01); *C07D 249/06* (2013.01); *C07D 249/08* (2013.01); *C07D 257/04* (2013.01); *C07D 261/20* (2013.01); *C07D 263/56* (2013.01); *C07D 271/06* (2013.01); *C07D 277/28* (2013.01); *C07D 413/04* (2013.01); *C07D 413/06* (2013.01); *C07D 413/10* (2013.01); *C07D 413/14* (2013.01); *C07D 417/04* (2013.01); *C07D 471/04* (2013.01); *C07D 487/04* (2013.01)

(56) References Cited

U.S. PATENT DOCUMENTS

| | | | |
|---|---|---|---|
| 9,751,885 | B2 | 9/2017 | Tomita et al. |
| 2013/0090386 | A1 | 4/2013 | Ortega Munoz et al. |
| 2013/0231342 | A1 | 9/2013 | Munoz et al. |
| 2014/0018393 | A1 | 1/2014 | Johnson et al. |
| 2014/0371176 | A1 | 12/2014 | Johnson et al. |
| 2015/0266881 | A1 | 9/2015 | Tomita et al. |
| 2019/0100507 | A1* | 4/2019 | Liu ............... C07D 417/12 |

FOREIGN PATENT DOCUMENTS

| | | | |
|---|---|---|---|
| CN | 103857393 | A | 6/2014 |
| CN | 105051005 | A | 11/2015 |
| CN | 107200706 | A | 9/2017 |
| JP | 2013525331 | A | 6/2013 |
| JP | 2014515013 | A | 6/2014 |
| RU | 2286142 | C2 | 10/2006 |
| WO | 9967203 | A1 | 12/1991 |
| WO | 9967203 | A1 | 12/1999 |
| WO | 2011131697 | A1 | 10/2011 |
| WO | 2012135113 | A2 | 10/2012 |
| WO | 2014058071 | A1 | 4/2014 |
| WO | 2015123408 | A1 | 8/2015 |
| WO | 2015123465 | A1 | 8/2015 |
| WO | 2017157322 | A1 | 9/2017 |
| WO | WO-2017157322 | A1 * | 9/2017 ........... C07C 211/37 |

OTHER PUBLICATIONS

PubChem Substance Record for SID 150935613, AKOS014796194, Source: AKos Consulting & Solutions. Retrieved Feb. 13, 2021 from https://pubchem.ncbi.nlm.nih.gov/substance/150935613, created Oct. 24, 2012 (Year: 2012).*

National Center for Biotechnology Information (2021); PubChem Compound Summary for CID 64553428; Retrieved Aug. 12, 2021 from https://pubchem.ncbi.nlm.nih.gov/compound/64553428, which was created Oct. 23, 2012 (Year: 2012).*

National Center for Biotechnology Information (2021); PubChem Substance Record for SID 150017877, AKOS013878522, Source: AKos Consulting & Solutions. Retrieved Aug. 12, 2021 from https://pubchem.ncbi.nlm.nih.gov/substance/150017877, which was available Oct. 23, 2012 (Year: 2012).*

Chen et al. Molecular Medicine Reports 2016, 14, 2511-2517 (Year: 2016).*

Extended European Search Report of EP18743959.1 dated Jul. 9, 2020.

X. Wang et al., "Medicinal chemistry insights in the discovery of novel LSD1 inhibitors", Epigenomics, 2015, vol. 7, No. 8, p. 1379-1396.

A. Bird, "Perceptions of epigenetics", Nature, 2007, vol. 447, p. 396-398.

J.T. Lynch et al., "LSD1 inhibition: a therapeutic strategy in cancer", Expert Opin. Ther. Targets, 2012, vol. 16, No. 12, p. 1239-1249.

Y. Shi et al., "Histone demethylation mediated by the nuclear amine oxidase homolog LSD1", Cell, vol. 119, p. 941-953, 2004.

D. P. Mould et al., "Reversible inhibitors of LSD1 as therapeutic agents in acute myeloid leukemia: Clinical significance and progress to date", Medicinal Research Reviews, 2015, p. 586-618.

R. Anand et al., "Structure and mechanism of lysine-specific demethylase enzymes", Journal of Biological Chemistry, 2007, vol. 282, No. 49, p. 35425-35429.

P. Stavropoulos et al., "Crystal structure and mechanism of human lysine-specific demethylase-1", Nature Structural & Molecular Biology, 2006, vol. 13, No. 7, p. 626-632.

(56) References Cited

OTHER PUBLICATIONS

Y. Chen et al. "Crystal structure of human histone lysine-specific demethylase 1 (LSD1)", Proc Natl Acad Sci USA. 2006, vol. 103, No. 38, p. 13956-13961.
T. Maes et al., "KDM1 histone lysine demethylases as targets for treatments of oncological ans neurodegenerative disease", Epigenomics, 2015, vol. 7, No. 4, p. 609-626.
E. Metzger et al., "LSD1 demethylates repressive histone marks to promote androgen-receptor-dependent transcription", Nature, 2005, vol. 437, p. 436-439.
Y. Zheng et al., "A systematic review of histone lysine-specific demethylase 1 and its inhibitors", Medicinal Research Review, 2015, vol. 35, No. 5, p. 1032-1071.
International Search Report and Written Opinion of PCT/CN2018/073961 dated Apr. 18, 2018.
Jan. 26, 2021 Russian Office Action issued in Russian Patent Application No. 2019126468.
Feb. 3, 2021 Australian Office Action issued in Australian Patent Application No. 2018213637.
Aug. 17, 2021 Australian Second Office Action issued in Australian application No. 2018213637.
Oct. 5, 2021 First Office Action issued in Japanese application No. 2019560449.
RN-2029527-51-1, 2016.
RN-1552738-41-6, 2014.
RN-1548685-16-0, 2014.
RN-1523193-21-6, 2014.
RN-1480517-57-4, 2013.
Mar. 17, 2022 Chinese Office Action issued in Chinese Patent Application No. 201880008005.5.

\* cited by examiner

LSD1 INHIBITOR AND PREPARATION METHOD AND APPLICATION THEREOF

CROSS REFERENCE TO RELATED APPLICATION

The present application is a National Stage of International Application No. PCT/CN2018/073961, filed on Jan. 24, 2018, which claims priorities of the Chinese Patent Application No. CN201710060400.5 filed on Jan. 24, 2017, Chinese Patent Application No. CN201710736745.8 filed on Aug. 24, 2017 and Chinese Patent Application No. CN201711460525.3 filed on Dec. 28, 2017, the contents of which are incorporated herein by reference in their entireties.

FIELD OF INVENTION

The present invention relates to a class of cyclopropylamine compounds which are inhibitors of lysine-specific demethylase 1 (LSD1) and the use thereof in preparation of a medicament for the treatment of LSD1 related diseases. Specifically, it relates to a compound of formula (I) and a pharmaceutically acceptable salt thereof.

PRIOR ARTS

Epigenetics regulates the expression of genes through different mechanisms, including covalent modifications to histones, such as methylation or demethylation; covalent modifications to DNA, such as methylation or methylolation; and recombination of nuclear chromatin [Xueshun Wang, Boshi Huang. Takayoshi Suzuki et al., Epigenomics, 2015, 1379-1396;]. Although these modifications do not alter the underlying sequence of DNA. This epigenetic change may persist through cell division throughout the cell life cycle or cell iteration process [Adrian Bird, Nature, 2007, 396-398]. Therefore, epigenetic dysfunction can trigger and participate in various pathological processes of diseases [James T Lynch, William J Harris & Tim C P Somervaille, Expert Opin. Ther. Targets, 2012, 1239-1249], such as various solid tumors, hematoma, viral infections, neurological abnormalities and other diseases. Therefore, epigenetics is now a research hotspot in the field of drug research and development. Lysine-specific demethylase (LSD1, also known as KDM1A) is the first demethylase found in 2004 and belongs to the family of flavin adenine dinucleotide (FAD)-dependent amino oxidases. [Yujiang Shi, Fei Lan, Caitlin Matson et al., Cell, 2004, 941-953] [Daniel P. Mould, Alison E. McGonagle, Daniel H. Wiseman et al., Medicinal Research Reviews, 2015, 586-618]. The LSD1 structure consists of three major components: the N-terminal SWIRM domain. The C-terminal amino oxidase domain (AOL), and the centrally protruding Tower domain. [Ruchi Anand, Ronen Marmorstein. The Journal of Biological Chemistry, 2007, 35425-35429]. The C-terminal amino oxidase domain includes two active pockets, one for the FDA-binding site and the other for the site to recognize and bind to the substrate [Pete Stavropoulos, Günter Blobel, André Hoelz, Nature Structural & Molecular Biology, 2006, 626-632]. The function of the SWIRM domain has not yet been clearly concluded, it is not directly involved in FAD or substrate binding, but mutation or removal in this region will reduce the activity of LSD1. Therefore, it is speculated that this region may affect the active region by adjusting the conformation effect [Yong Chen, Yuting Yang, Feng Wang et al., Biochemistry, 2006, 13956-13961]. The Tower domain is the binding domain of LSD1 to other protein factors. LSD1 binds to different protein factors and acts on different substrates, which plays a different role in regulating histones and gene expression. For example, when LSD1 is combined with CoREST, it will preferentially act on histone H3K4, demethylation will remove the activation-related histone marks and inhibit gene transcription; upon binding to the androgen receptor protein, recombinant LSD1 preferentially acts on H3K9, which activates androgen receptor-associated gene transcription by demethylation [Ruchi Anand, Ronen Marmorstein. The Journal of Biological Chemistry, 2007, 35425-35429: Tamara Maes, Cristina Mascaról, Alberto Ortega et al., Epigenomics, 2015, 609-626: Eric Mctzger, Melanie Wissmann, Na Yin et al., Nature, 2005, 436-439]. In addition, LSD1 has some non-histone receptors, such as p53, E2F1, DNMT1 and MYPT1, etc [Yi Chao Zheng, Jinlian Ma, Zhiru Wang, Medicinal Research Reviews, 2015, 1032-1071].

LSD1 is a FAD-dependent amino oxidase in which proton transfer is considered to be its most likely oxidative mechanism [Daniel P. Mould, Alison E. McGonagle, Daniel H. Wiseman et al., Medicinal Research Reviews, 2015, 586-618]. First. The N—CH$_3$ bond of the substrate is converted into an imine bond by proton transfer. This imine ion intermediate undergoes a hydrolysis reaction to form a demethylated amine and a formaldehyde on the other side. During this catalytic cycle. The FAD is reduced to FADH2, which is then oxidized back to the FAD by a molecule of oxygen, while generating a molecule of H$_2$O$_2$ [Yujiang Shi, Fei Lan, Caitlin Matson, Cell, 2004, 941-953].

LSD1 is an indispensable regulator in epigenetics that alters histones by demethylation and is therefore referred to as the "eraser" enzyme in vivo. LSD1 regulates gene expression and regulates cell proliferation and differentiation.

In recent years, a large number of structurally diverse compounds have been developed as LSD1 selective inhibitors, as well as LSD1 and MAO-B dual inhibitors. Two of them have entered the human clinical trial stage. However, in the face of a huge unmet market. There is still a need for candidate compounds with better activity and better pharmacokinetic parameters to advance clinical trials to meet treatment needs.

The structure of HCI-2509 is as follows:

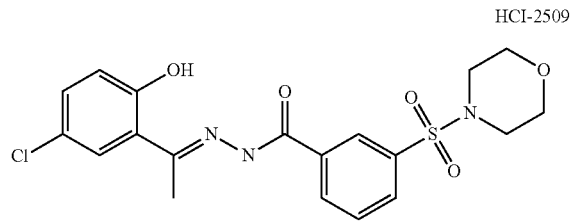 [SMILES: C/C(=N\NC(=O)c1cccc(S(=O)(=O)N2CCOCC2)c1)c1cc(Cl)ccc1O]

HCI-2509

CONTENT OF THE PRESENT INVENTION

The present invention provides a compound of formula (I), a pharmaceutically acceptable salt or a tautomer thereof,

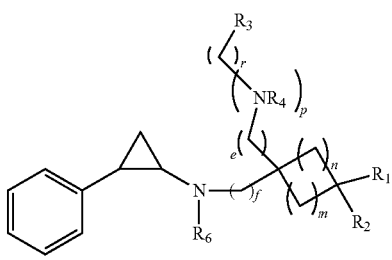

(I)

wherein,
f is 1 or 2;
r is 0, 1 or 2;
e is 0, 1, or 2;
p is 0 or 1;
m is 0, 1 or 2;
n is 1 or 2;
each of $R_1$ and $R_2$ is independently selected from the group consisting of H, F, Cl, Br, I, OH, CN, $NH_2$, —COOH and a $C_{1-3}$ alkyl optionally substituted by 1, 2 or 3 of R;

or, $R_1$ and $R_2$ are connected together to form a 3-6-membered ring;

$R_3$ is selected from the group consisting of H, F, Cl, Br, I, OH, CN, $NH_2$, —COOH, —$CONH_2$ and -L-R, or selected from the group consisting of $C_{1-6}$ alkyl, phenyl, 5-12 membered heteroaryl, $C_{3-7}$ cycloalkyl and 4-8 membered heterocycloalkyl, each of which is optionally substituted by 1, 2 or 3 of R;

$R_4$ is H, or selected from the group consisting of $C_{1-6}$ alkyl and $C_{1-6}$ heteroalkyl, each of which is optionally substituted by 1, 2 or 3 of R;

$R_5$ is selected from the group consisting of phenyl, 5-10 membered heteroaryl, $C_{3-10}$ cycloalkyl, 4-10 membered heterocycloalkyl, 5-6 membered heterocycloalkyl-C(=O)— and 5-6 membered heterocycloalkyl-$C_{1-3}$ alkyl-, each of which is optionally substituted by 1, 2 or 3 R;

$R_6$ is H, or selected from the group consisting of $C_{1-6}$ alkyl and $C_{1-6}$ heteroalkyl, each of which is optionally substituted by 1, 2 or 3 R;

L is —C(=O)—, or selected from the group consisting of —$C_{1-6}$ alkyl- and -5-9 membered heteroaryl-, -4-8 membered heterocycloalkyl-, -phenyl-, —$C_{3-6}$ cycloalkyl, each of which is optionally substituted by 1, 2 or 3 of R;

R is selected from the group consisting of H, F, Cl, Br, I, OH, $NH_2$, CN, COOH and $NH_2$—C(=O)—, or selected from the group consisting of $C_{1-6}$ alkyl, $C_{1-6}$ heteroalkyl, phenyl-$C_{1-6}$ alkyl-, phenyl, 5-6 membered heteroaryl, phenyl-C(=O)—, $C_{3-6}$ cycloalkyl-C(=O)—, $C_{3-6}$ cycloalkyl-C(=O)—NH, $C_{3-6}$ cycloalkyl-NH—C(=O)— and $C_{3-6}$ cycloalkyl-$C_{1-3}$, each of which is optionally substituted by 1, 2 or 3 of R';

R' is selected from the group consisting of F, Cl, Br, I, OH, $NH_2$, COOH, $C_{1-3}$ alkyl, $C_{1-3}$ alkyl substituted by 1-3 halogen(s), $C_{1-3}$ alkyl-NH—, N,N-di($C_{1-3}$ alkyl)-amino, $C_{1-3}$ alkyl-O—C(=O)—, $C_{3-6}$ cycloalkyl and $C_{1-3}$ alkoxyl;

each of the "hetero" in the 5-12 membered heteroaryl, 4-8 membered heterocycloalkyl, $C_{1-6}$ heteroalkyl, 5-10 membered heteroaryl, 5-6 membered heteroaryl, 5-6 membered heterocycloalkyl, 4-10 membered heterocycloalkyl is independently selected from the group consisting of —NH—, —S—, N, —O—, =O, —C(=O)—, —NH—C(=O)—, —O—C(=O)—, —S(=O)$_2$—, —S(=O)—, —C(=O)—NH—;

in any above cases, the number of the heteroatom or the heteroatomic group is independently 1, 2, 3 or 4.

In some embodiments of the present invention, R' is selected from the group consisting of F, Cl, Br, I, OH, $NH_2$, Me, Et, $CF_3$, $CHF_2$, $CH_2F$, $NHCH_3$, $N(CH_3)_2$, COOH, —C(=O)—O—$CH_3$, —O—$CH_3$ and

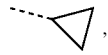

and other variables are as defined in the present invention.

In some embodiments of the present invention, R is selected from the group consisting of H, F, Cl, Br, I, OH, $NH_2$, CN, COOH and $NH_2$—C(=O)—, or selected from the group consisting of methyl, ethyl, propyl, isobutyl, tert-butyl, $C_{1-4}$alkoxyl, phenyl-$C_{1-3}$ alkyl-, phenyl, pyridyl, 1,2,4-triazolyl, phenyl-C(=O)—, $C_{1-3}$ alkyl-C(=O)—, $C_{1-3}$ alkyl-NH—, cyclopropyl-C(=O)—, $C_{1-3}$ alkyl-O—C(=O)—$C_{1-3}$ alkyl-, $C_{1-3}$ alkyl-O—C(=O)—, $C_{1-3}$ alkyl-S(=O)$_2$—, cyclopropyl-C(=O)—NH—, cyclopropyl-NH—C(=O)—, $C_{1-3}$ alkyl-NH—C(=O)—, cyclobutyl-$CH_2$— and $C_{1-3}$ alkyl-C(=O)—NH—, each of which is optionally substituted by 1, 2 or 3 of R', and other variables are as defined in the present invention.

In some embodiments of the present invention, R is selected from the group consisting of H, F, Cl, Br, I, OH, $NH_2$, CN, COOH and $NH_2$—C(=O)—, or selected from the group consisting of Me, Et,

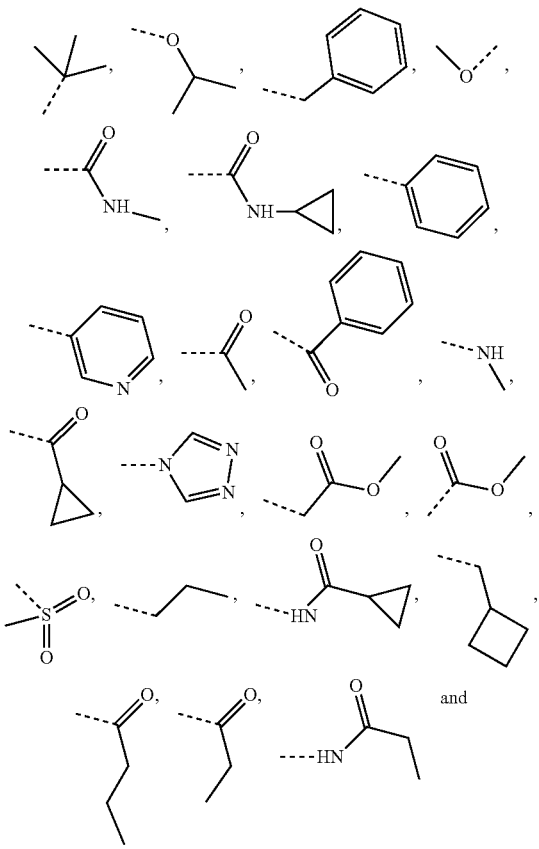

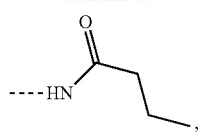

each of which is optionally substituted by 1, 2 or 3 of R', and other variables are as defined in the present invention.

In some embodiments of the present invention, R is selected from the group consisting of H, F, Cl, Br, I, OH, NH$_2$, Me, Et, —CF$_3$, CN, COOH,

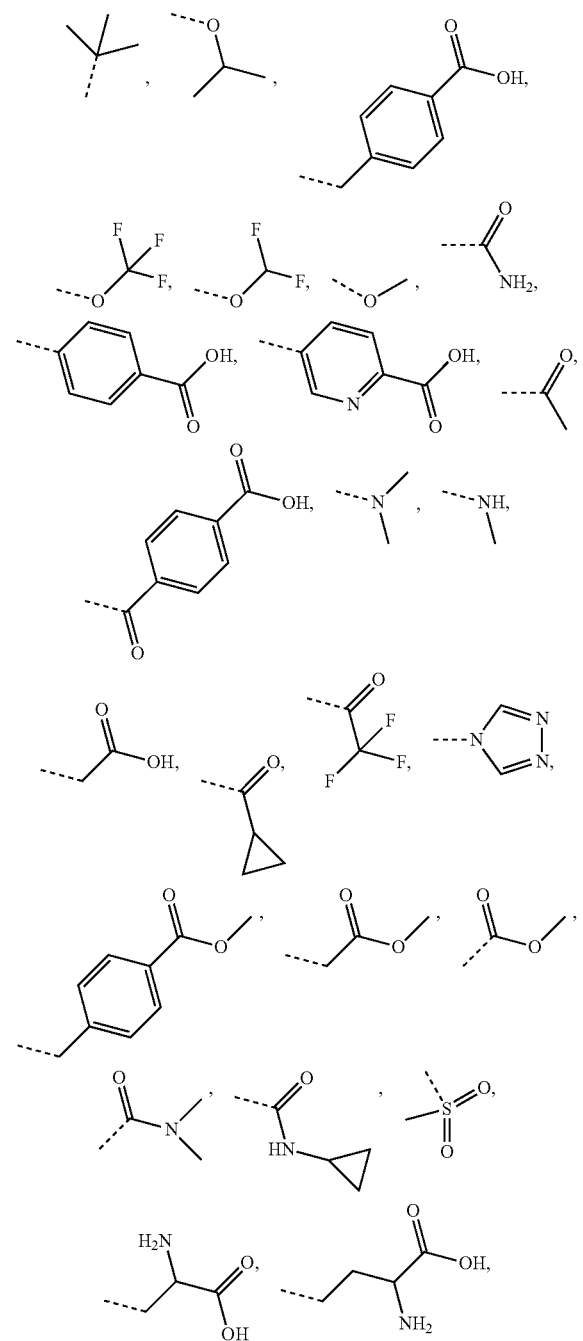

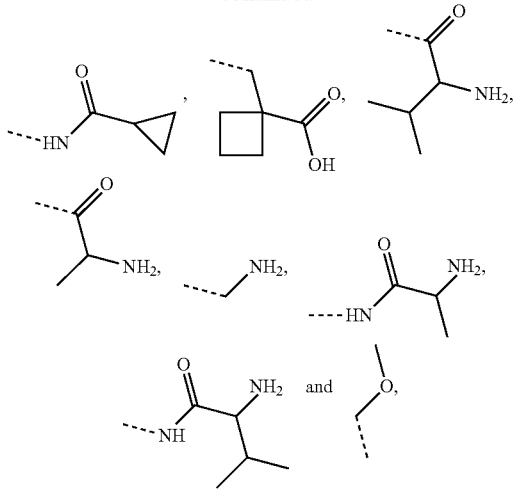

and other variables are as defined in the present invention.

In some embodiments of the present invention, each of R$_1$ and R$_2$ is independently selected from the group consisting of H, F, Cl, Br, I, OH, CN, NH$_2$, —COOH, Me and Et, and other variables are as defined in the present invention.

In some embodiments of the present invention, L is —C(=O)—, or selected from the group consisting of —C$_{1-3}$ alkyl-, -phenyl-, -5-6-membered heteroaryl-, -5-6-membered heterocycloalkyl-, —C$_{3-6}$ cycloalkyl-, each of which is optionally substituted by 1, 2 or 3 of R, and other variables are as defined in the present invention.

In some embodiments of the present invention, L is —C(=O)—, or selected from the group consisting of -1,2,4-oxadiazolyl-, -methyl-, -ethyl-, -1,3,4-oxadiazolyl-, -isoxazolyl-, -oxazolyl-, -piperidyl-, -1,2,3-triazolyl-, -cyclopropanyl- and -phenyl-, each of which is optionally substituted by 1, 2 or 3 of R, and other variables are as defined in the present invention.

In some embodiments of the resent invention, L is —C(=O)—, or selected from the group consisting of

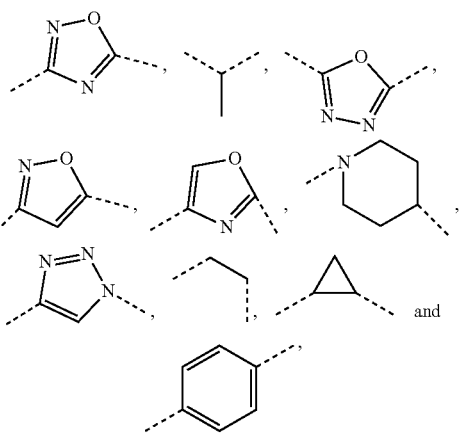

each of which is optionally substituted by 1, 2 or 3 of R, and other variables are as defined in the present invention.

In some embodiments of the present invention, L is selected from the group consisting of

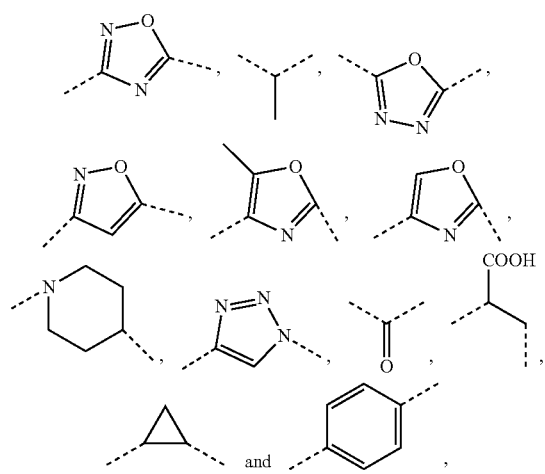

and other variables are as defined in the present invention.

In some embodiments of the present invention, R₅ is selected from the group consisting of phenyl, pyridyl, piperidinyl, pyrrolidinyl, azetidinyl, cyclohexyl, cyclobutyl, benzo[d][1,3]m-dioxacyclopentenyl, piperidyl-2-keto, 7-azaspiro[3.5]nonyl, cyclohexyl-CH₂—, 3a,7a-dihydro-1H-indolyl, pyrazolyl, pyridyl, 3a,7a-dihydrobenzo[d]thiazolyl, pyrimidinyl, cyclopentyl, spiro[3.3]heptanyl, bicyclo[2.2.2]octyl, octahydrocyclopenta[c]pyrrolyl, 2-azaspiro[3.5]nonyl, piperidinyl-C(=O)—, 4,5,6,7-tetrahydro-1H-benzo[d]imidazolyl, 5,6,7,8-tetrahydroimidazo[1,2-a]pyridyl, piperidinyl-CH₂—, bicyclo[1.1.1]pentyl and piperazinyl, each of which is optionally substituted by 1, 2 or 3 of R, and other variables are as defined in the present invention.

In some embodiments of the present invention, R₅ is selected from the group consisting

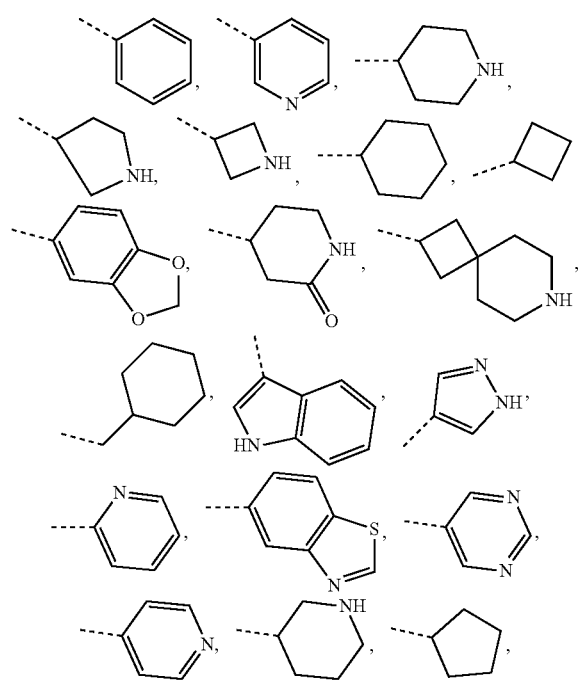

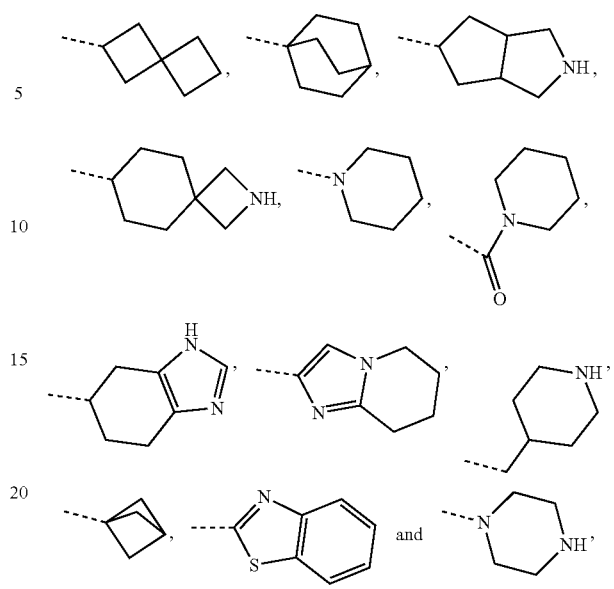

each of which is optionally substituted by 1, 2 or 3 of R, and other variables are as defined in the present invention.

In some embodiments of the resent invention, R₅ is selected from the group consisting of

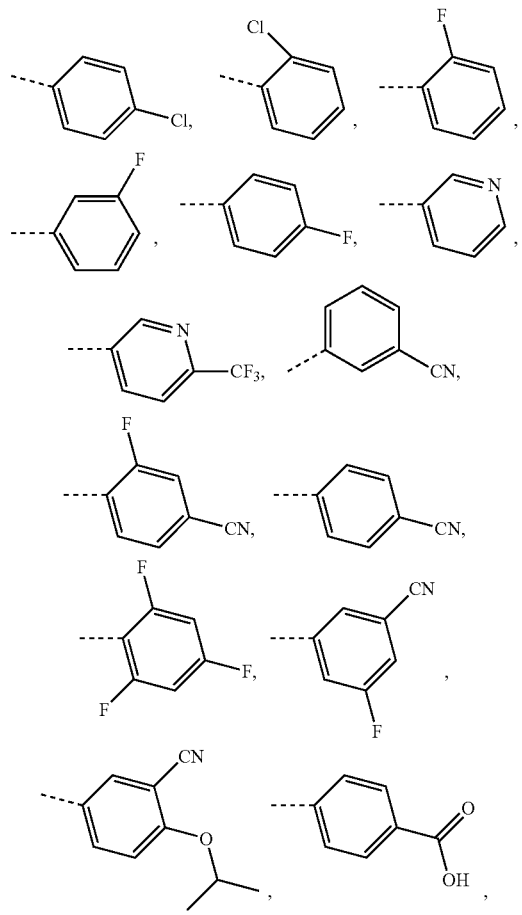

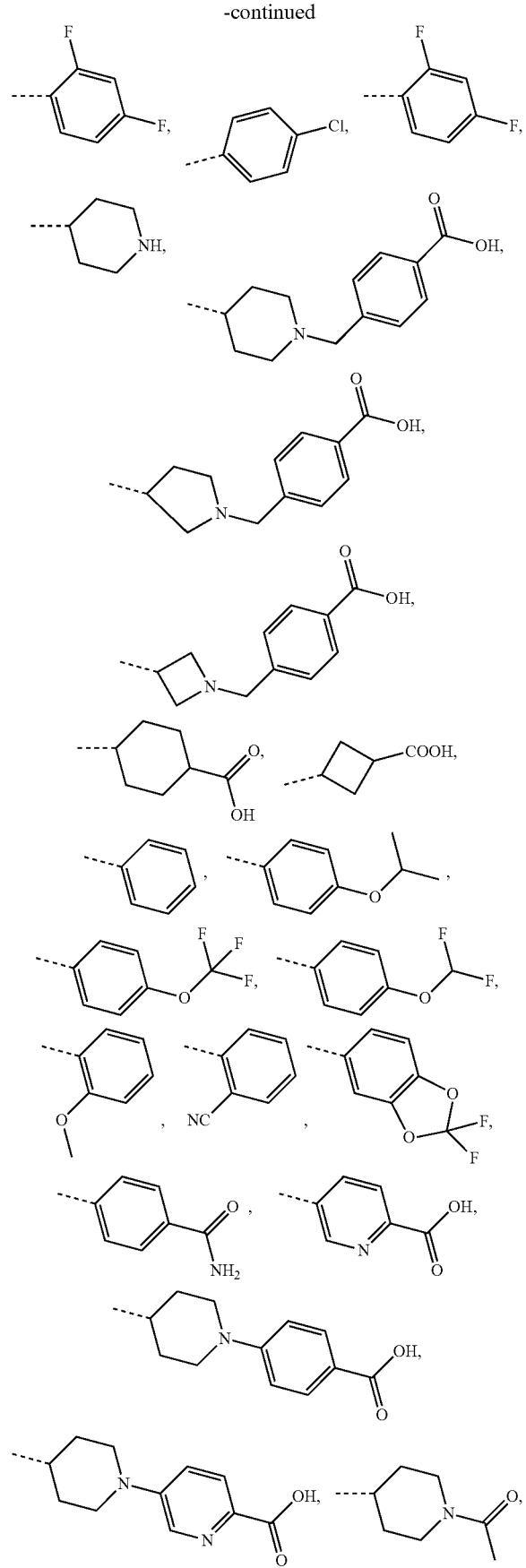
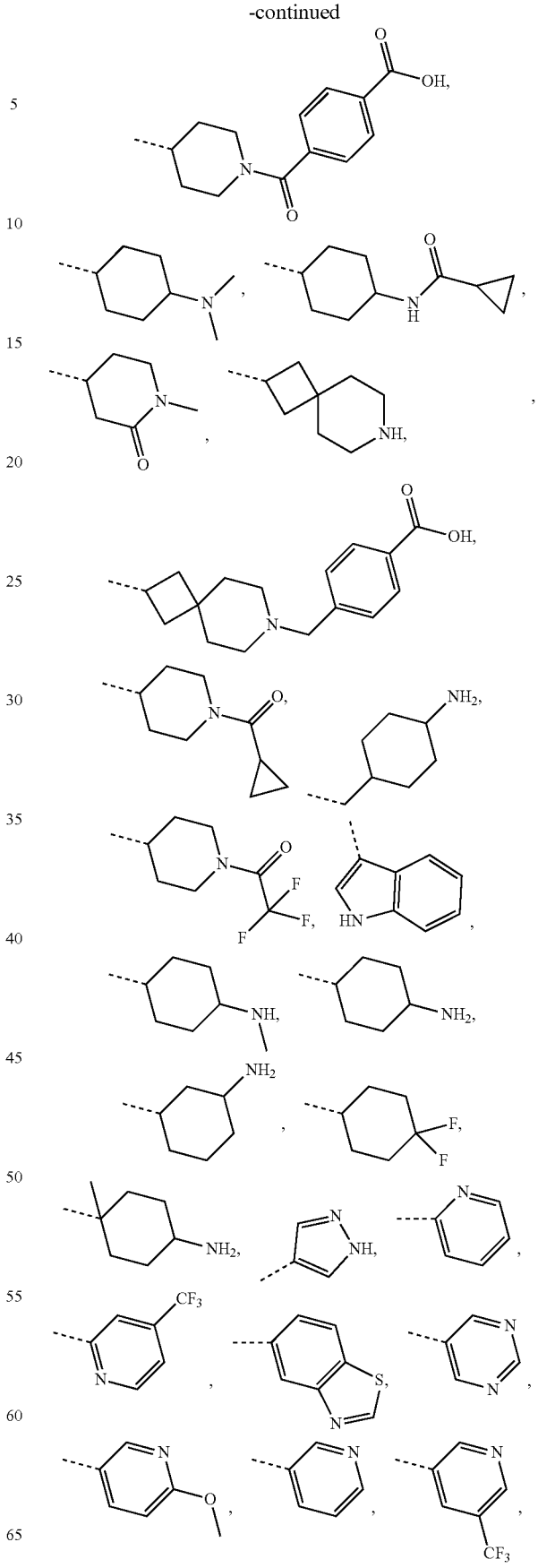

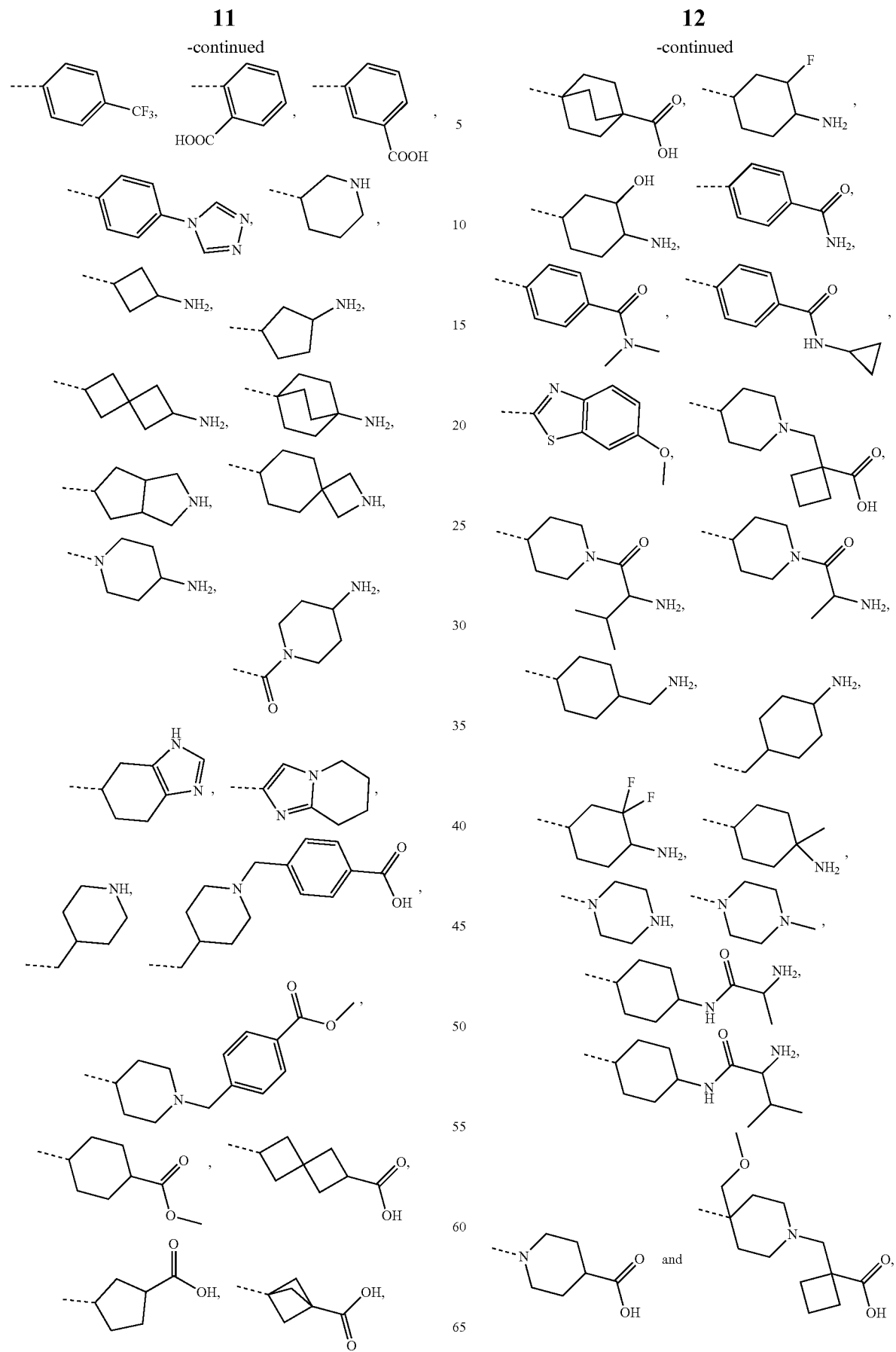
and other variables are as defined in the present invention.

In some embodiments of the present invention, L-R$_5$ is selected from the group consisting of:
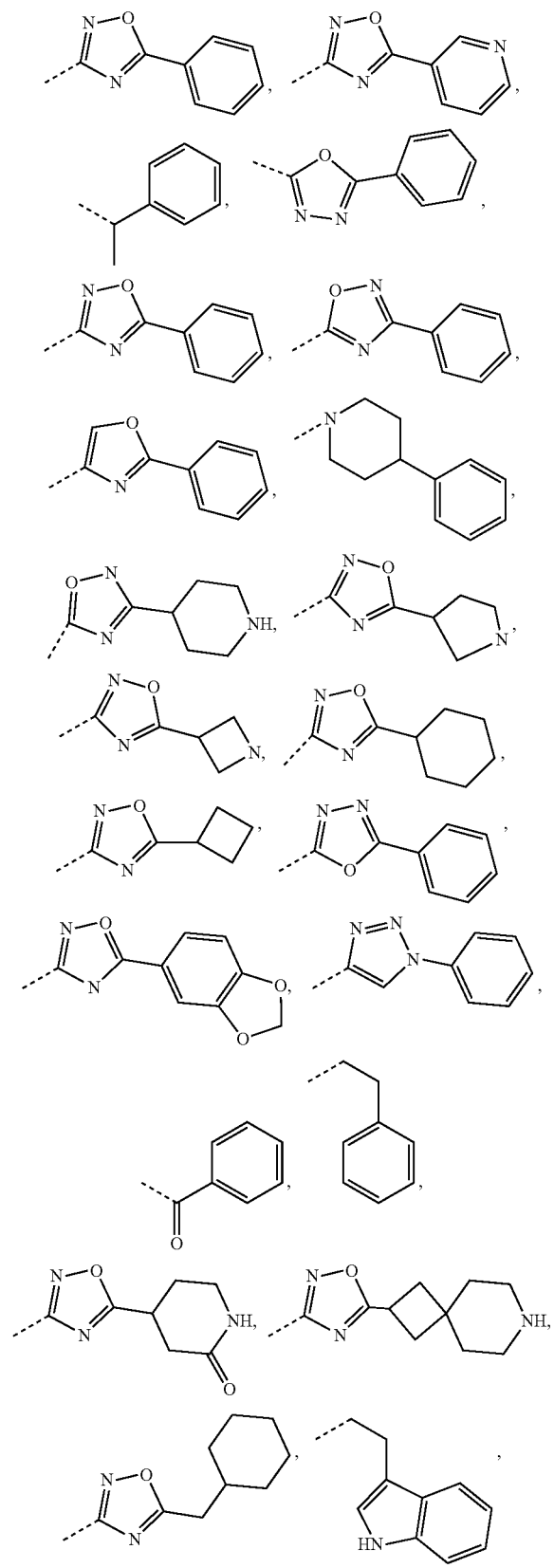
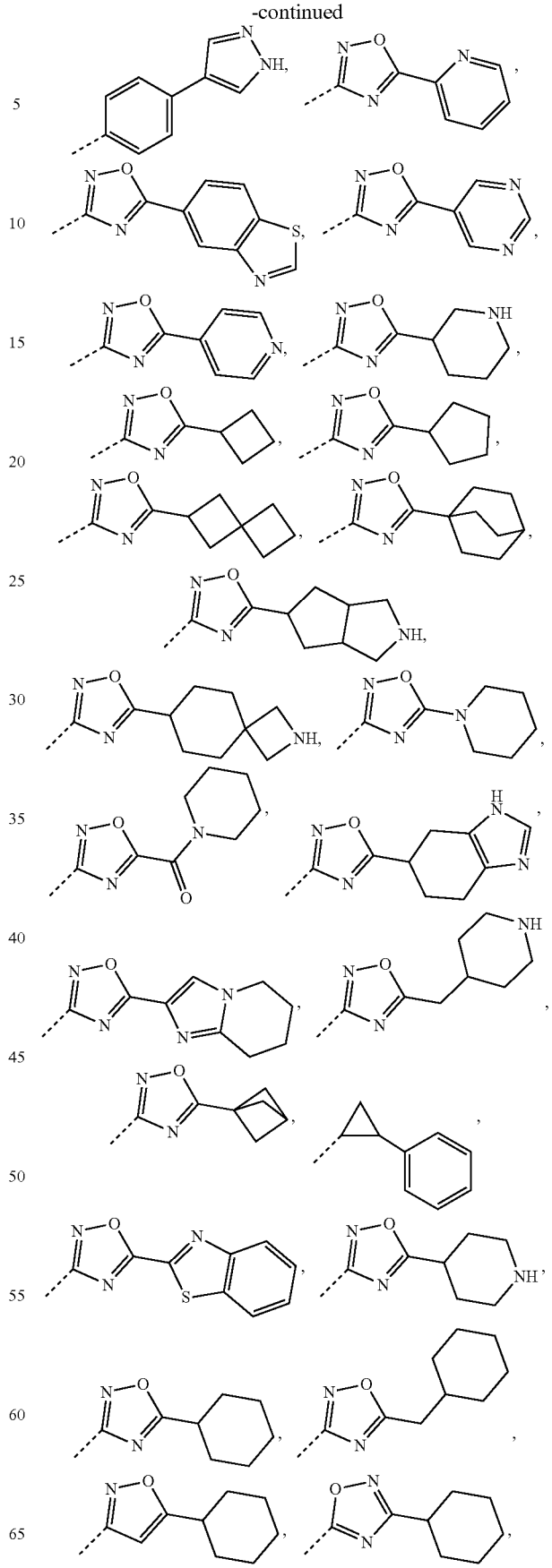

-continued
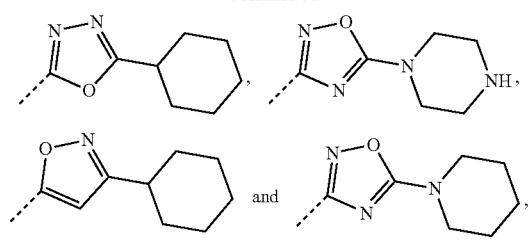
each of which is optionally substituted by 1, 2 or 3 of R, and other variables are as defined in the present invention.
In some embodiments of the resent invention. -L-R₅ is selected from the group consisting of
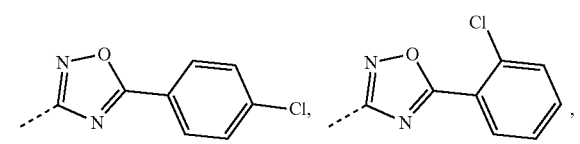
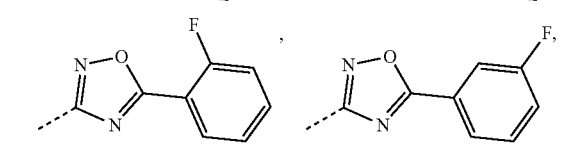
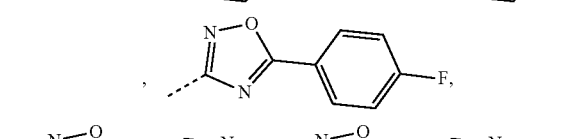
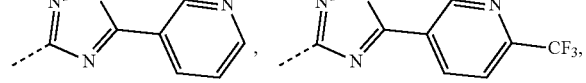
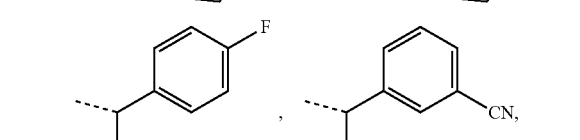
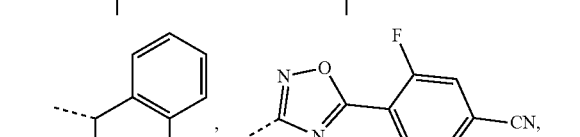
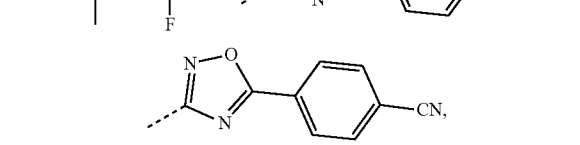
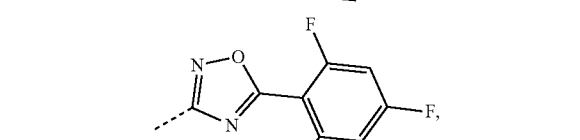
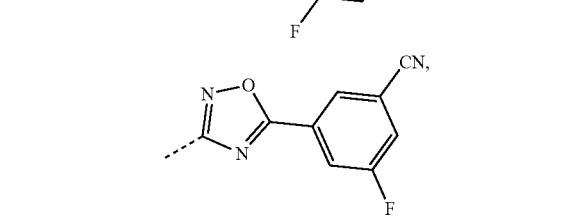
-continued
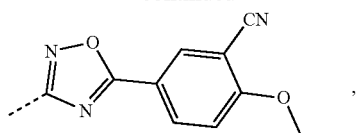
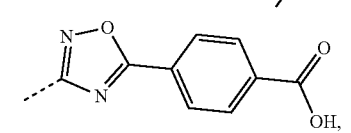
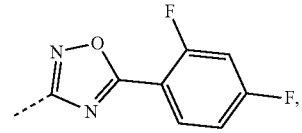
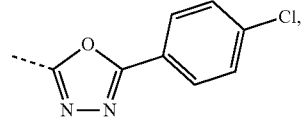
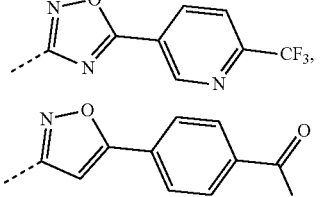
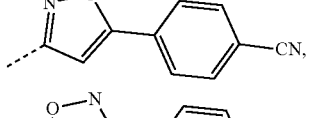
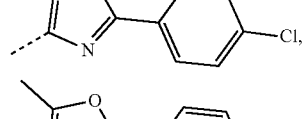
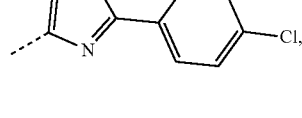
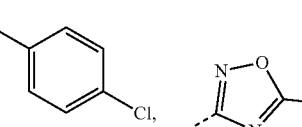
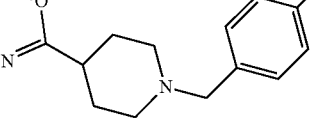
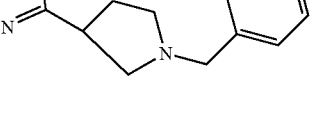

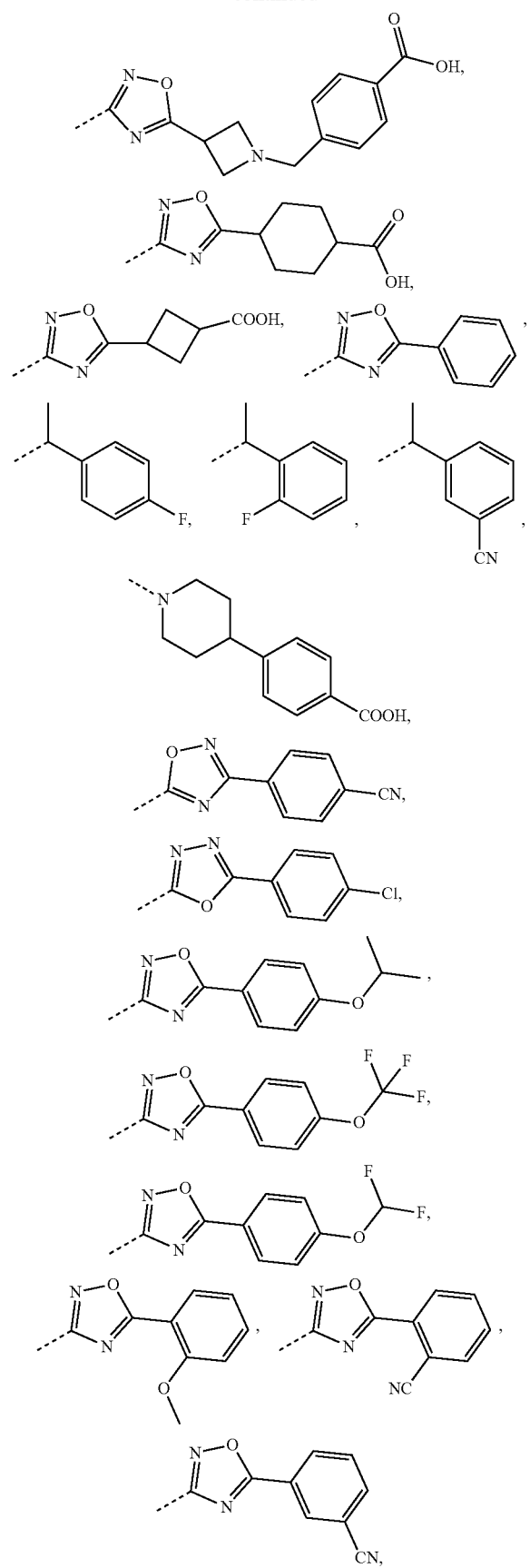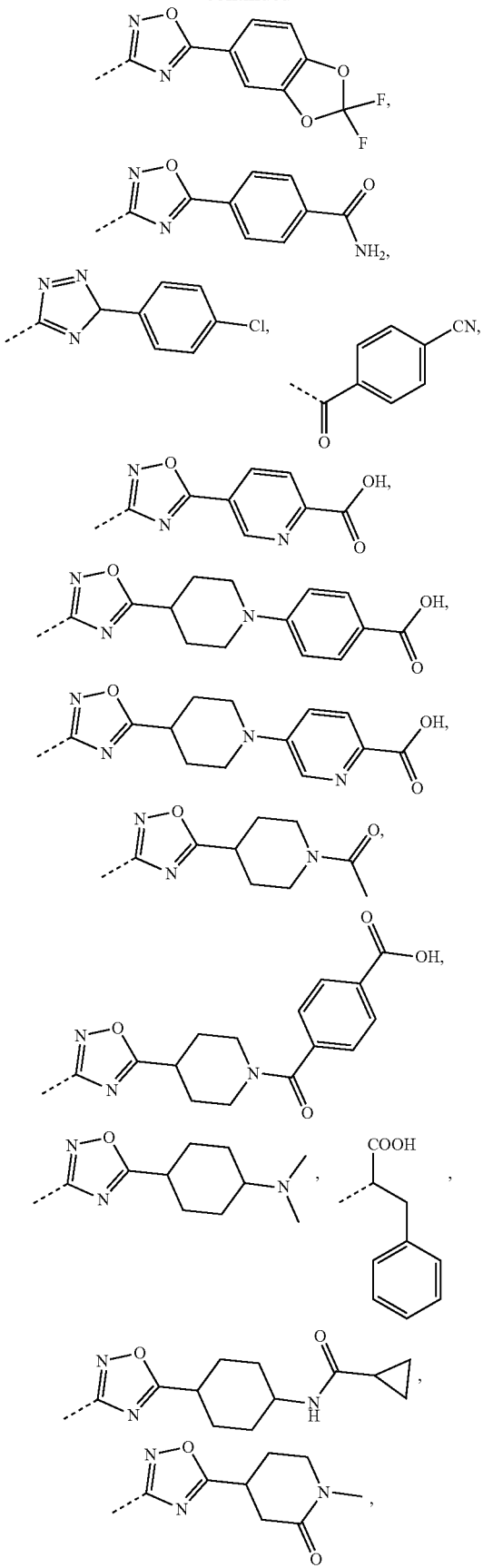

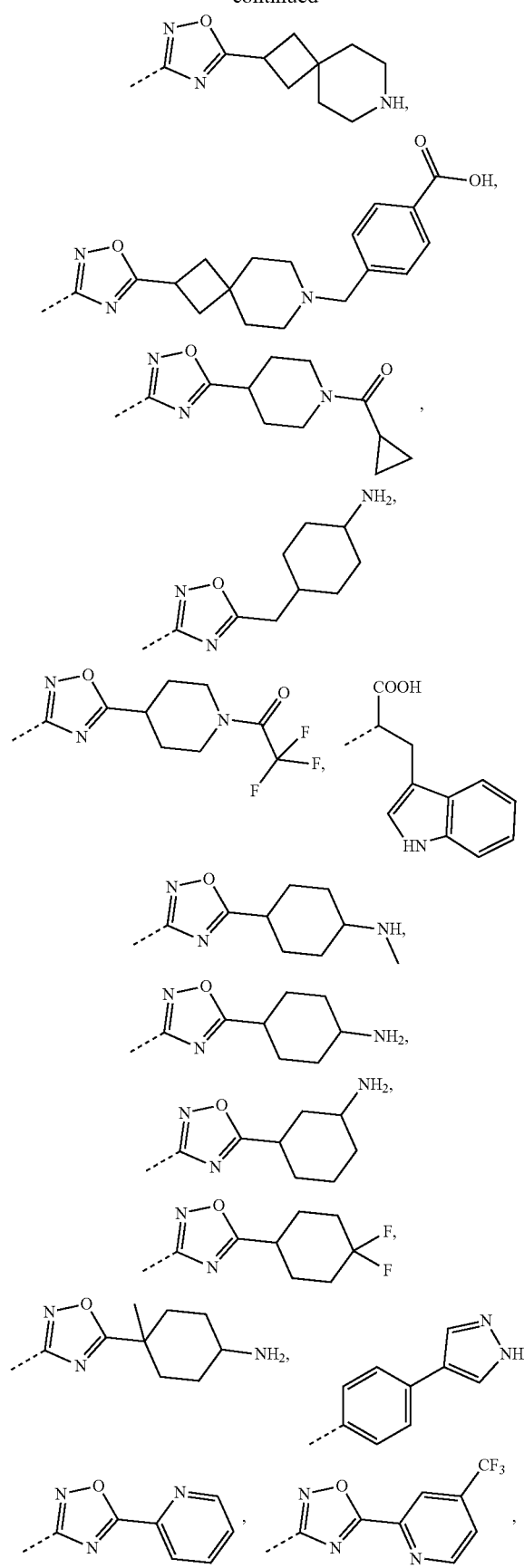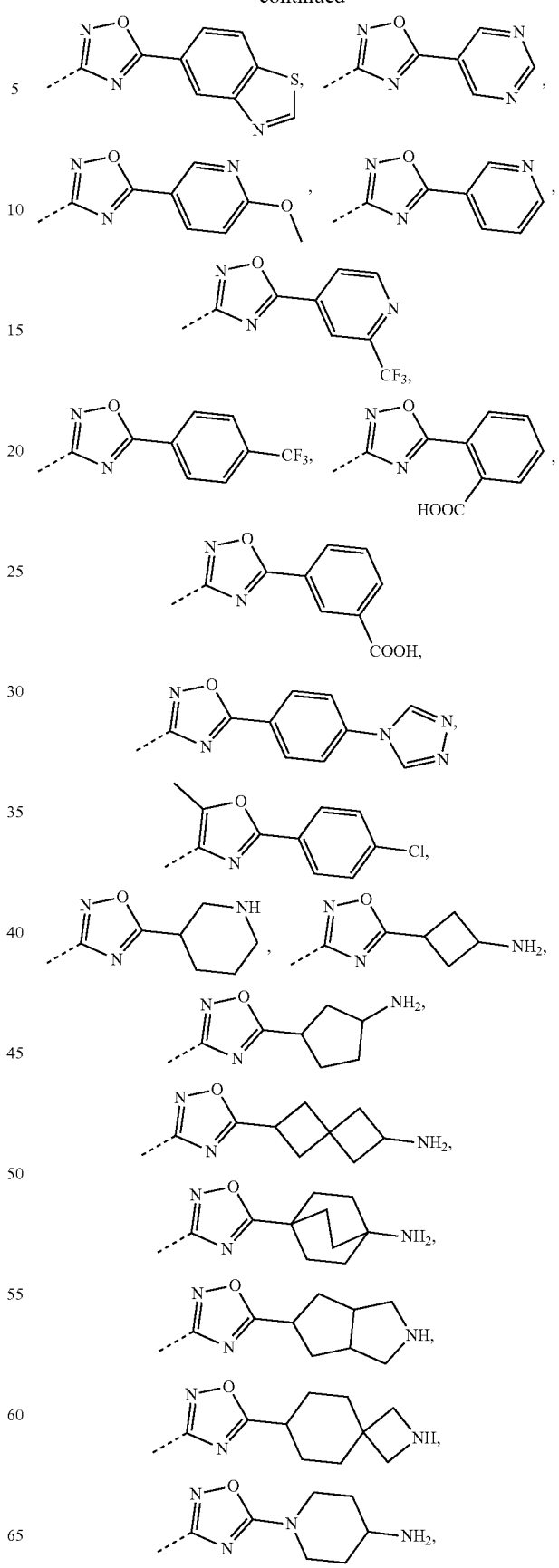

-continued
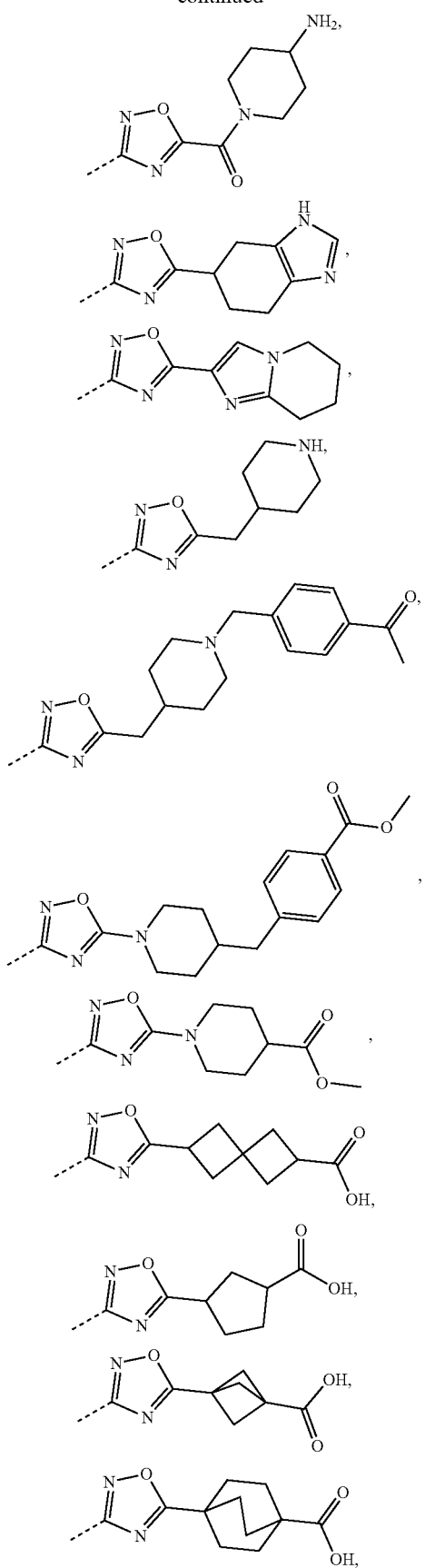
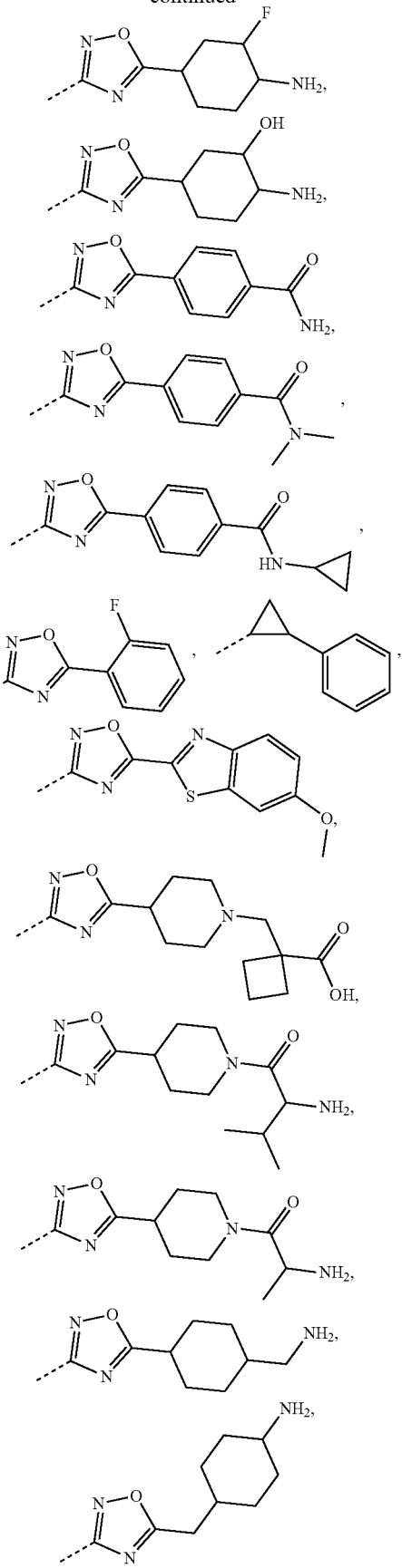

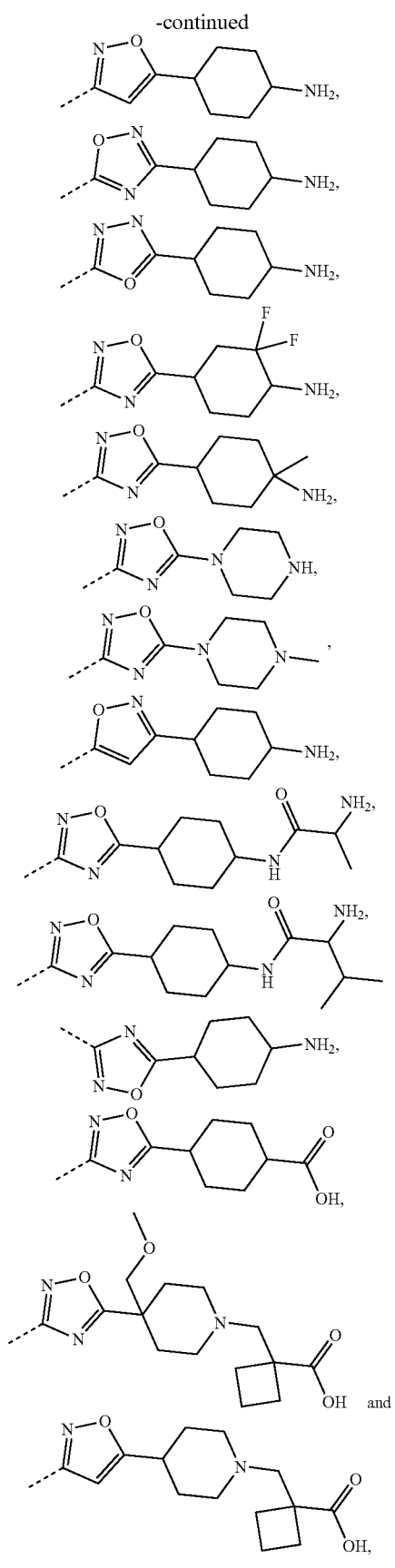

and other variables are as defined in the present invention.

In some embodiments of the present invention, $R_3$ is selected from the group consisting of H, F, Cl, Br, I, OH, CN, $NH_2$, —COOH, —$CONH_2$ and -L-$R_5$, or selected from the group consisting of $C_{1-3}$ alkyl, phenyl, pyrrolidinyl, 1H-imidazolyl, 1H-1,2,4-triazolyl, pyridyl, thiazolyl, thienyl, pyrrolyl, 2H-tetrazolyl, 6,7-dihydro-5H-pyrrolo[1,2-a]imidazolyl, imidazo[1,5-a]pyridyl, oxazolyl, benzo[d]isoxazolyl, benzo[d]oxazolyl, 1,2,3,4-4H-2,7-naphthyridinyl, 1,2,3,4-tetrahydroisoquinolinyl, 2,3,4,5-tetrahydro-1H-benzo[d]azepinyl, azetidinyl, isoindolyl, piperidinyl, 2,3,4,5-tetrahydro-1H-benzo[b]azepinyl, 2,3-dihydro-1H-pyrrolo[3,4-c]pyridyl, benzoisoxazolyl, 5,6,7,8-tetrahydropyridopyrimidinyl, 3a,7a-dihydrobenzo[d]thiazolyl, 2,4,5,6-tetrahydropyrrolo[3,4-c]pyrazolyl, 1,4,5,6-tetrahydropyrrolo[3,4-c]pyrazolyl, piperazinyl, morpholinyl, octahydropyrrolo[3,4-c]pyrrolyl, 1,4-azaheptyl, cyclohexyl and 1,2,4-oxadiazolyl, each of which is optionally substituted by 1, 2 or 3 of R, and other variables are as defined in the present invention.

In some embodiments of the present invention, $R_3$ is selected from the group consisting of H, F, Cl, Br, I, OH, CN, $NH_2$, —COOH, —$CONH_2$ and -L-$R_5$, or selected from the group consisting of Me, Et,

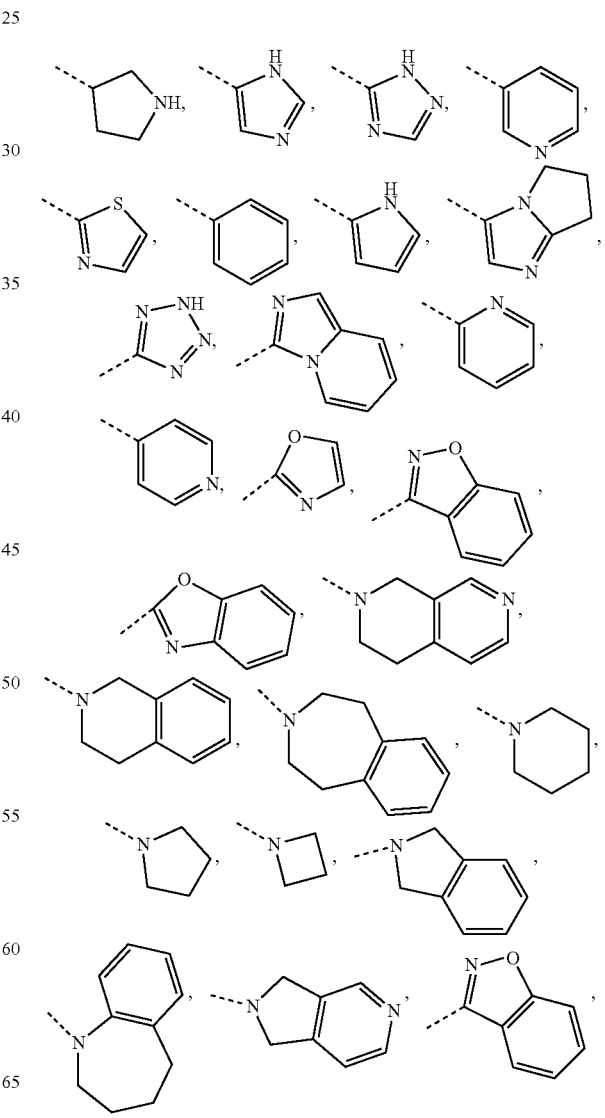

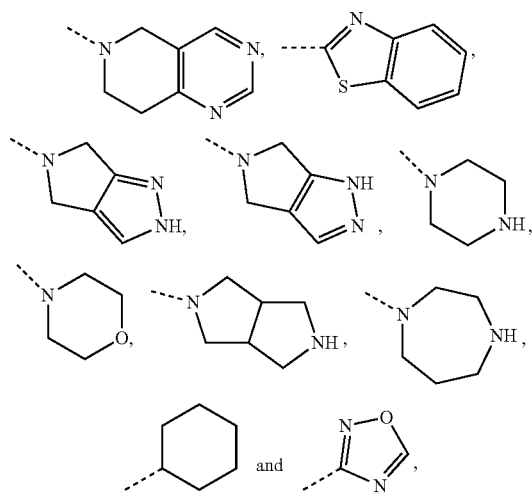
each of which is optionally substituted by 1, 2 or 3 of R, and other variables areas defined in the present invention.
In some embodiments of the present invention, $R_3$ is selected from the group consisting of H, F, Cl, Br, I, OH, CN, $NH_2$, —COOH, Me Et,
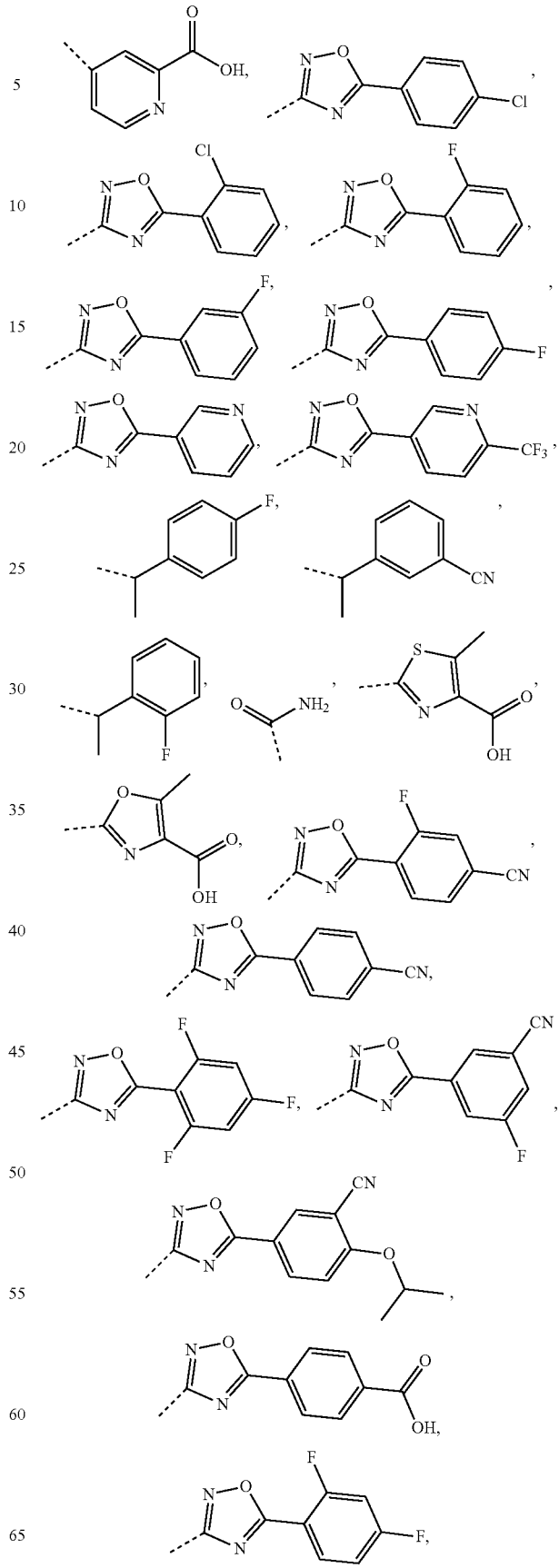

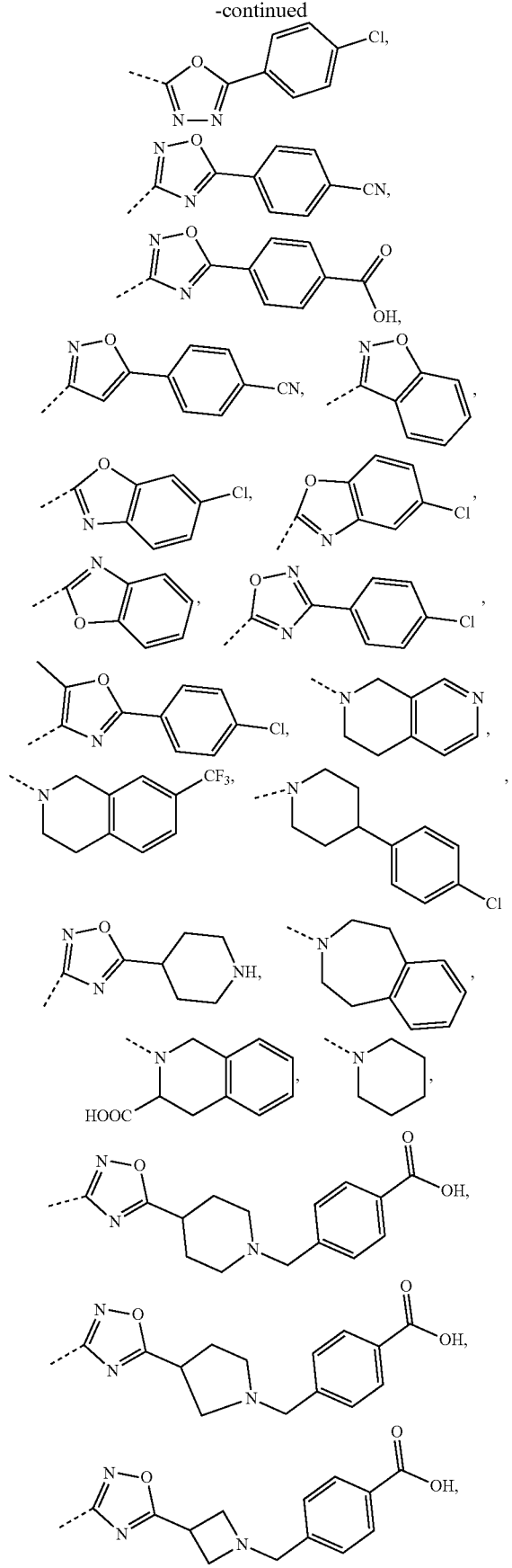
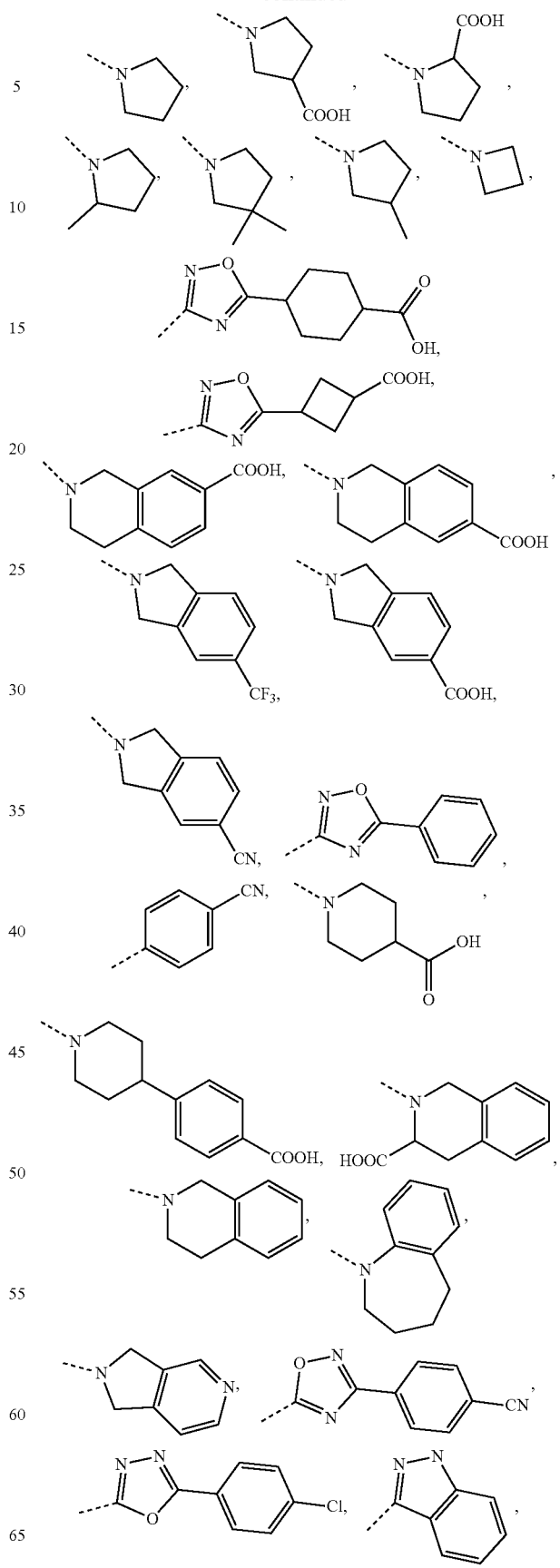

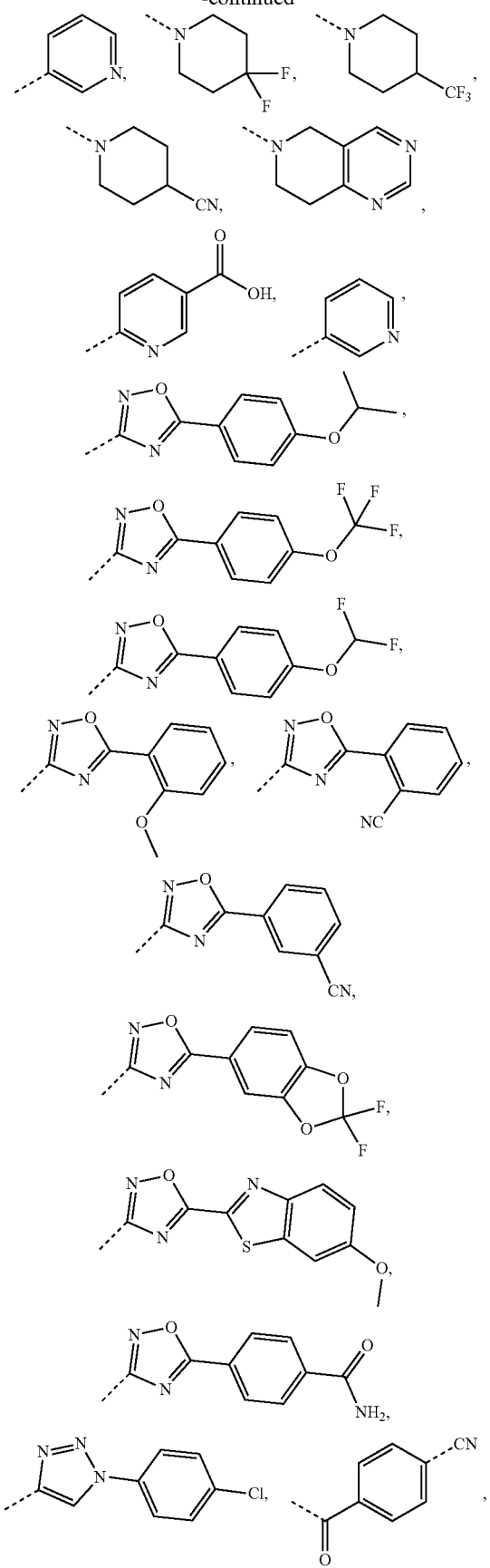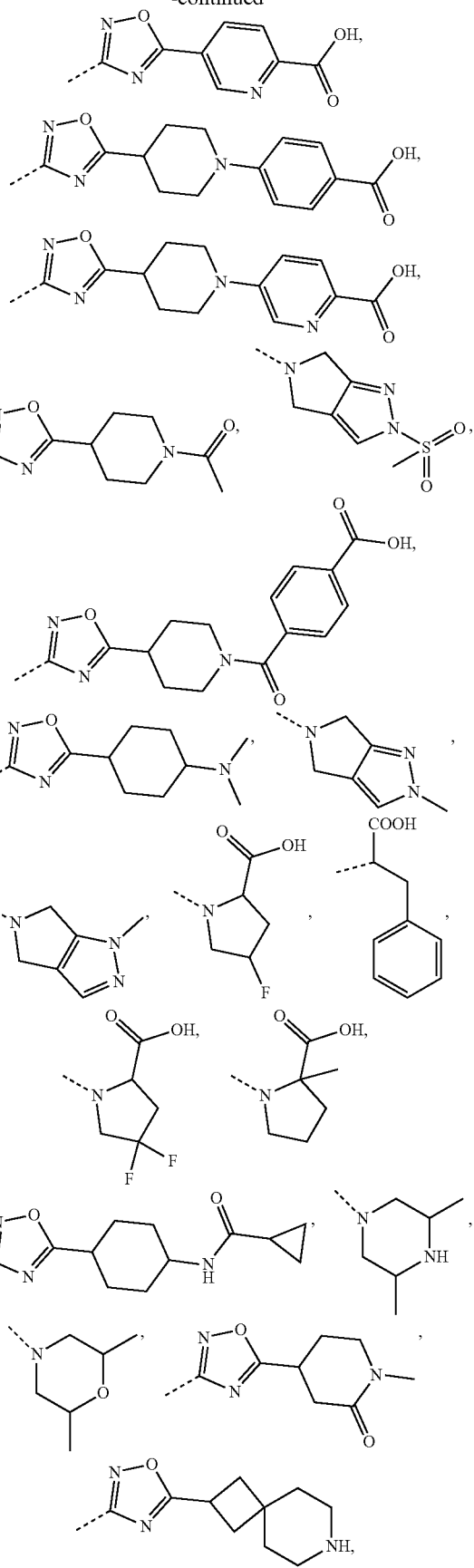

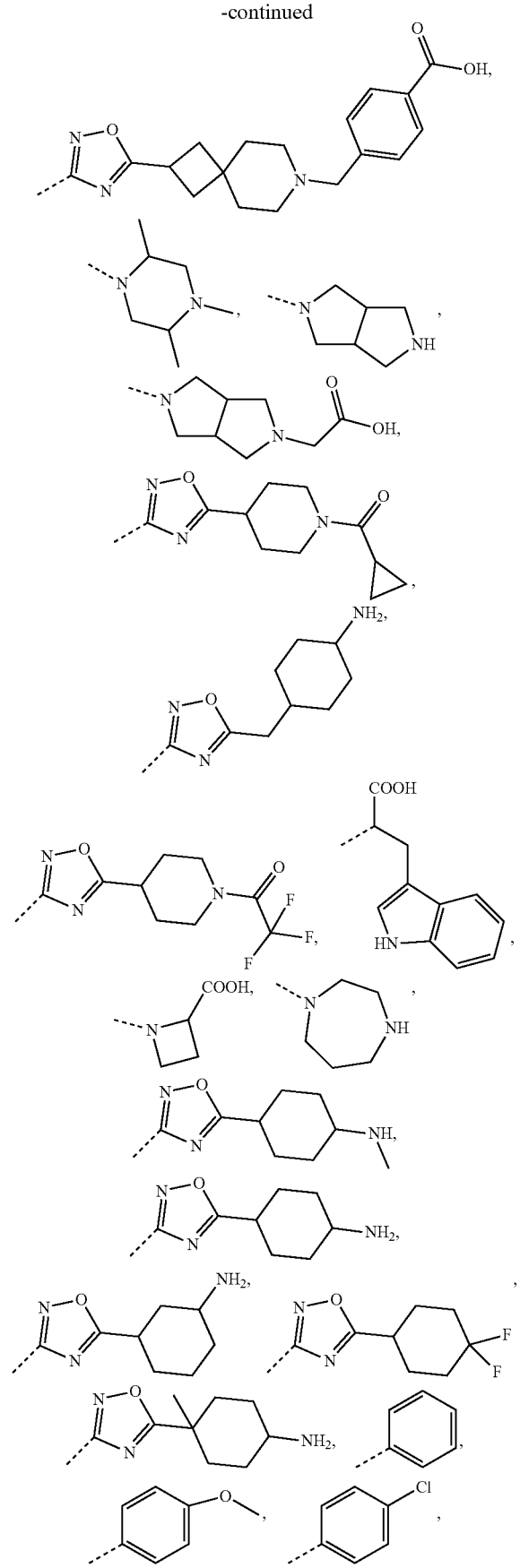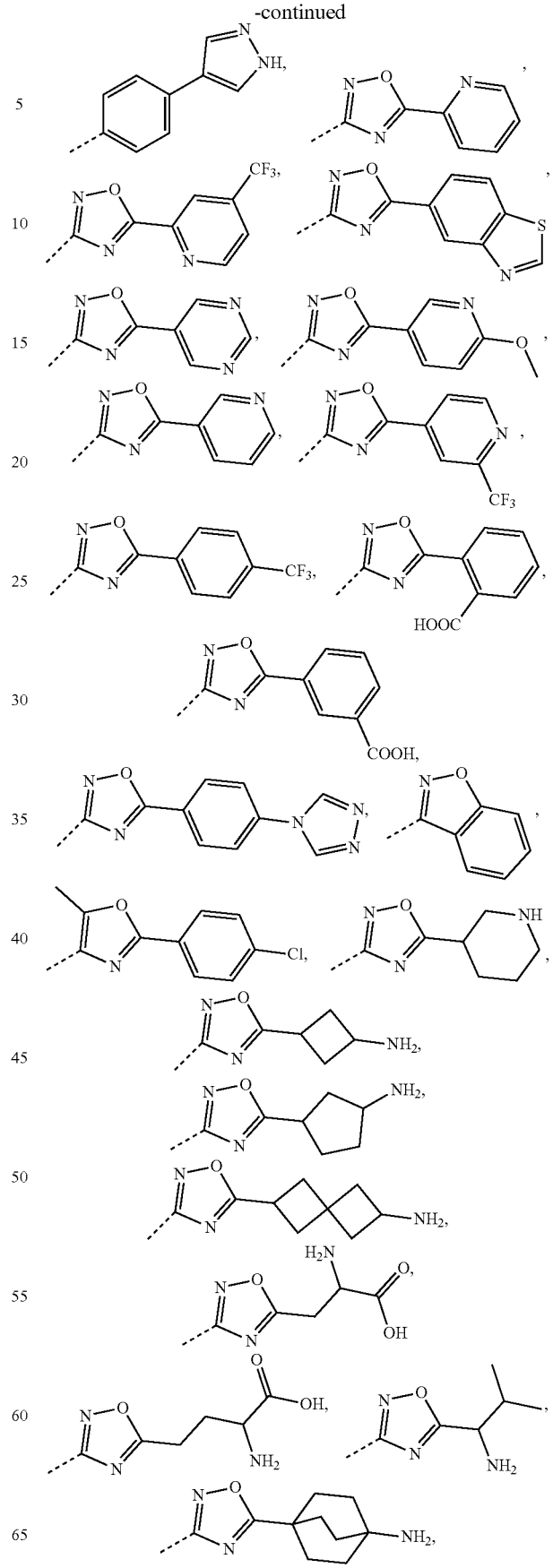

33
-continued
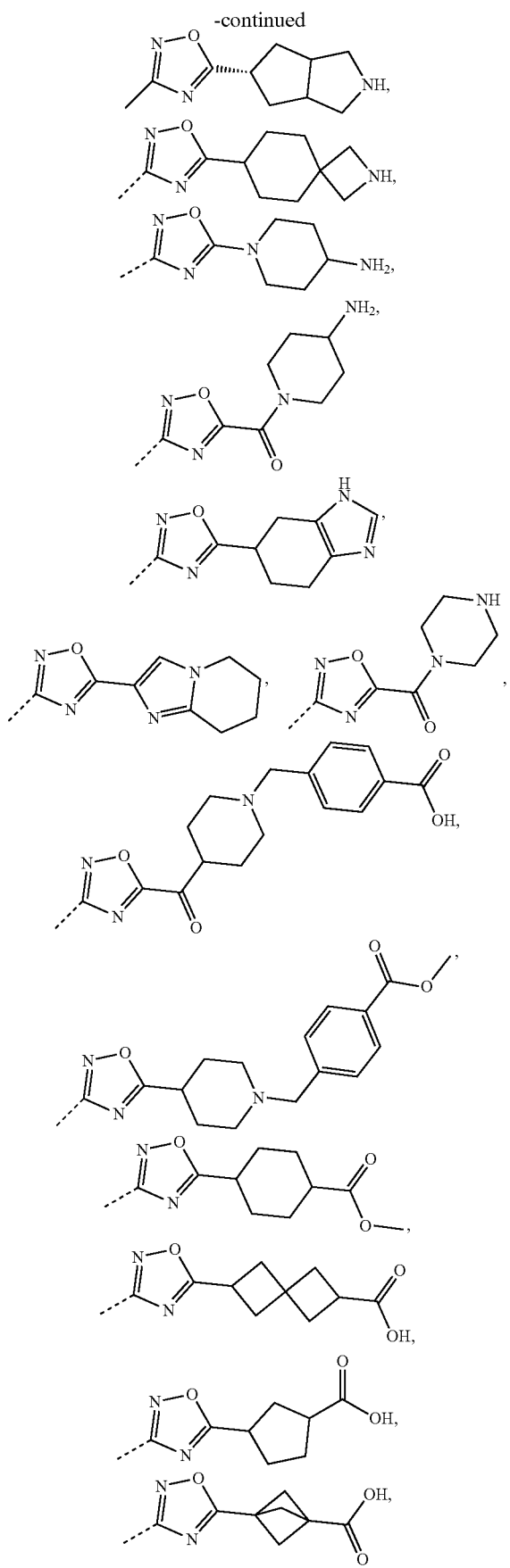
34
-continued
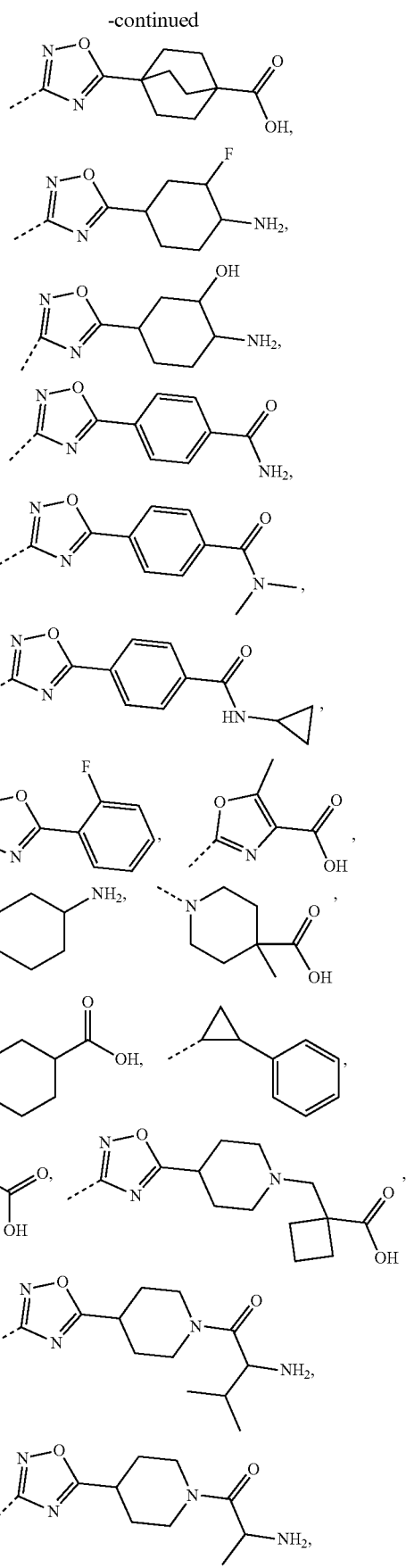

-continued

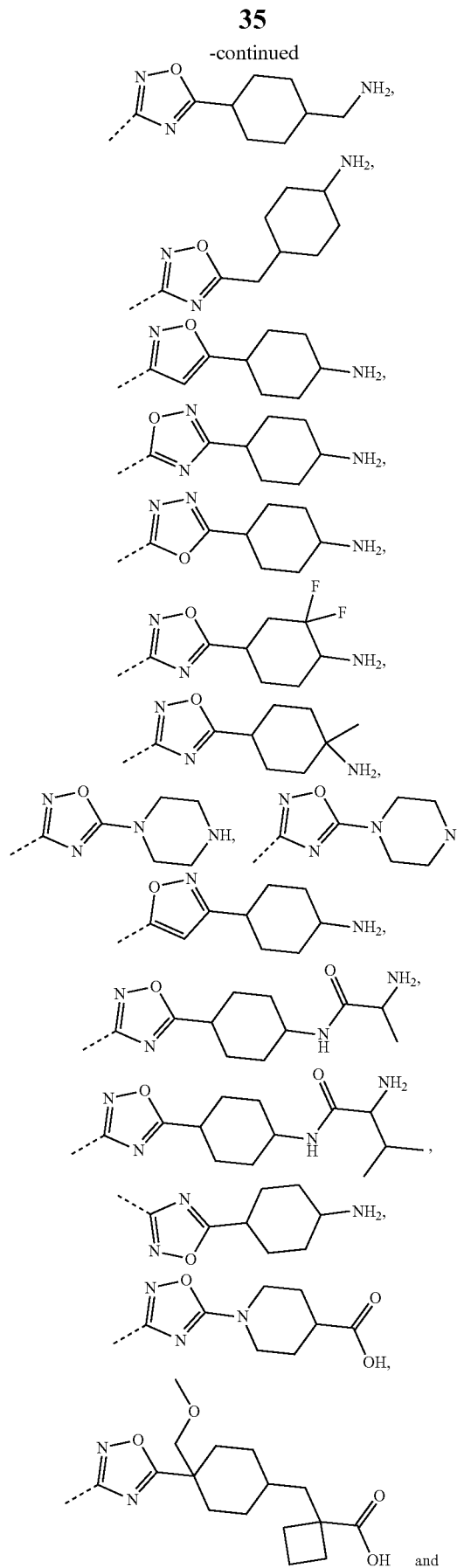

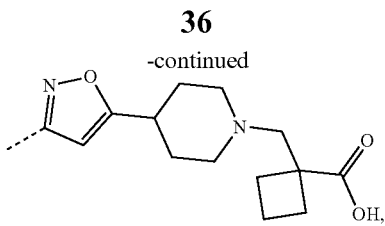

and other variables are as defined in the present invention.

In some embodiments of the present invention, R₄ is H, or selected from the group consisting of $C_{1-3}$ alkyl and $C_{1-4}$ alkyl-O—C(=O)—, each of which is optionally substituted by 1, 2 or 3 of R, and other variables are as defined in the present invention.

In some embodiments of the present invention, R₄ is selected from the group consisting of H, Me, Et and

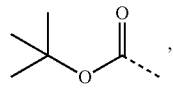

and other variables are as defined in the present invention.

In some embodiments of the present invention, R₆ is H, or selected from the group consisting of $C_{1-3}$ alkyl and $C_{1-4}$ alkyl-O—C(=O)—, each of which is optionally substituted by 1, 2 or 3 of R, and other variables are as defined in the present invention.

In some embodiments of the present invention, R₆ is selected from the group consisting of H, Me, Et and

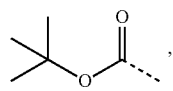

and other variables are as defined in the present invention.

In some embodiments of the present invention the structural unit

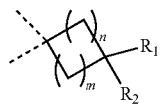

is selected from the group consisting of

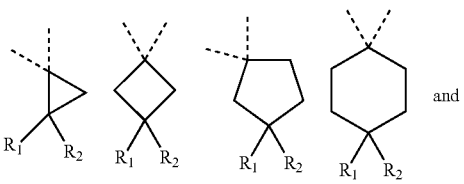

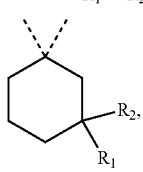

and other variables are as defined in the present invention.

In some embodiments of the present invention, the structural unit

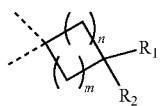

is selected from the group consisting of

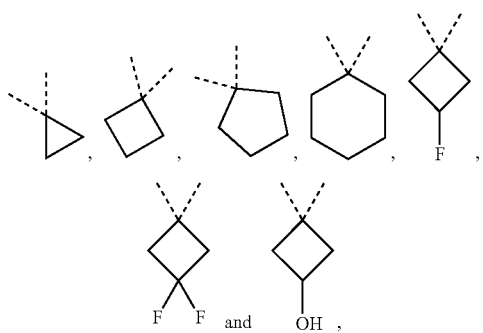

and other variables are as defined in the present invention.

Other embodiments of the present invention can be obtained by the arbitrary combination of the above variables.

In some embodiments of the present invention, the compound, pharmaceutically acceptable salt or the tautomer thereof is selected from the group consisting of

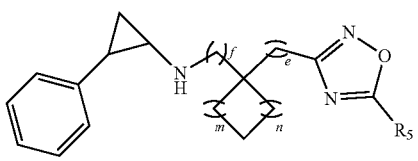

(I-1)

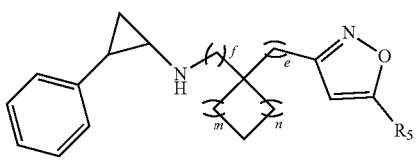

(I-2)

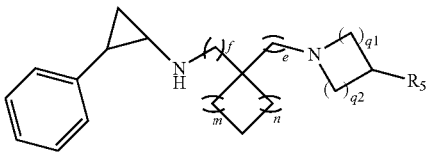

(I-3)

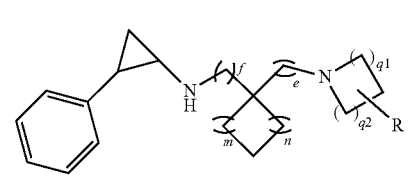

(I-4)

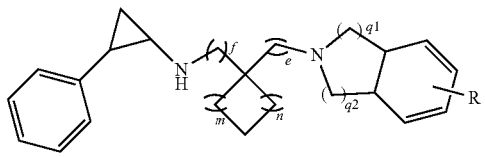

(I-5)

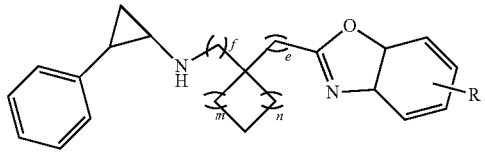

(I-6)

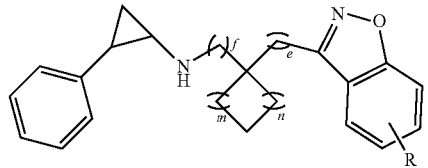

(I-7)

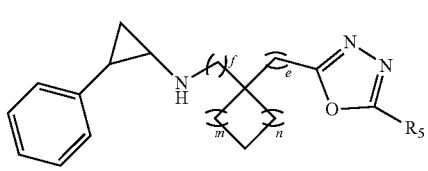

(I-8)

wherein,
e, f, m, n, $R_5$, R are as defined in the present invention;
each of $q_1$ and $q_2$ is independently 1 or 2.

The present invention provides a compound of formula (I), a pharmaceutically acceptable salt or a tautomer thereof,

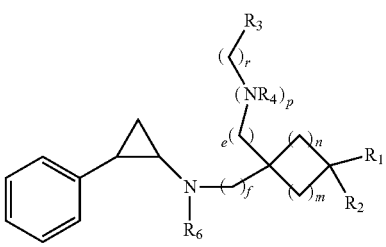

(I)

wherein,
f is 1 or 2;
r is 0, 1 or 2;
e is 0, 1, or 2;
p is 0 or 1;
m is 0, 1 or 2;
n is 1 or 2;
each of $R_1$ and $R_2$ is independently selected from the group consisting of H, F, Cl, Br, I. OH, CN, $NH_2$ and —COOH, or is a $C_{1-3}$ alkyl optionally substituted by 1, 2 or 3 of R;
or, $R_1$ and $R_2$ are connected together to form a 3-6 membered ring;
$R_3$ is selected from the group consisting of H, F, Cl, Br, I, OH, CN, $NH_2$, —COOH, —$CONH_2$ and -L-$R_5$, or selected from the group consisting of $C_{1-6}$ alkyl, phenyl, 5-12 membered heteroaryl, $C_{3-7}$ cycloalkyl and 4-8 membered heterocycloalkyl, each of which is optionally substituted by 1, 2 or 3 of R;

R₄ is H, or selected from the group consisting of $C_{1-6}$ alkyl and $C_{1-6}$ heteroalkyl, each of which is optionally substituted by 1, 2 or 3 of R:

R₅ is selected from the group consisting of phenyl, 5-10 membered heteroaryl, $C_{3-10}$ cycloalkyl, 4-10 membered heterocycloalkyl, phenyl, 5-6 membered heterocycloalkyl-C(=O)— and 5-6 membered heterocycloalkyl-$C_{1-3}$ alkyl-, each of which is optionally substituted by 1, 2 or 3 of R;

R₆ is H, or selected from the group consisting of $C_{1-6}$ alkyl and $C_{1-6}$ heteroalkyl, each of which is optionally substituted by 1, 2 or 3 of R;

L is —C(=O)—, or selected from the group consisting of —$C_{1-6}$ alkyl- and -5-9 membered heteroaryl-, -4-8 membered heterocycloalkyl-, -phenyl-, -3-6 membered cycloalkyl-, each of which is optionally substituted by 1, 2 or 3 of R;

R is selected from the group consisting of H, F, Cl, Br, I, OH, NH₂, CN and COOH, or selected from the group consisting of $C_{1-6}$ alkyl, $C_{1-6}$ heteroalkyl, phenyl-$C_{1-6}$ alkyl-, phenyl, 5-6 membered heteroaryl, phenyl-C(=O)—, $C_{3-6}$ cycloalkyl-C(=O)— and $C_{3-6}$ cycloalkyl-C(=O)—NH, each of which is optionally substituted by 1, 2 or 3 of R';

R' is selected from the group consisting of F, Cl, Br, I, OH, NH₂, COOH, $C_{1-3}$ alkyl, $C_{1-3}$ alkyl substituted by 1-3 halogen(s), $C_{1-3}$ alkyl-NH—, N,N-di($C_{1-3}$ alkyl)-amino, $C_{1-3}$ alkyl-O—C(=O)— and $C_{3-6}$ cycloalkyl;

each of the "hetero" in the 5-12 membered heteroaryl, 4-8 membered heterocycloalkyl, $C_{1-6}$ heteroalkyl, 5-10 membered heteroaryl, 5-6 membered heterocycloalkyl, 4-10 membered heterocycloalkyl is independently selected from the group consisting of —NH—, —S—, N, —O—, =O, —C(=O)—, —NH—C(=O)—, —C(=O)—, —S(=O)₂— and —S(=O)—;

In any above cases, the number of the heteroatom or the heteroatomic group is independently 1, 2, 3 or 4.

In some embodiments of the present invention, R' is selected from the group consisting of F, Cl, Br, I, OH, Me, Et, CF₃, CHF₂, CH₂F, NHCH₃, N(CH₃)₂, COOH, —C(=O)—O—CH₃ and

and other variables are as defined in the present invention.

In some embodiments of the present invention, R is selected from the group consisting of H, F, Cl, Br, I, OH, NH₂, CN and COOH, or selected from the group consisting of methyl, ethyl, propyl, isobutyl, tert-butyl, $C_{1-6}$ alkoxyl, phenyl-$C_{1-3}$ alkyl-, phenyl, pyridyl, 1,2,4-triazolyl, phenyl-C(=O)—, $C_{1-3}$ alkyl-C(=O)—, $C_{1-3}$alkyl-NH—, cyclopropyl-C(=O)—, $C_{1-3}$alkyl-O—C(=O)—$C_{1-3}$ alkyl-, $C_{1-3}$ alkyl-O—C(=O)—, $C_{1-3}$ alkyl-S(=O)₂—, cyclopropyl-C(=O)—NH—, each of which is optionally substituted by 1, 2 or 3 of R', and other variables are as defined in the present invention.

In some embodiments of the present invention, R is selected from the group consisting of H, F, Cl, Br, I, OH, NH₂, CN and COOH, or selected from the group consisting of Me, Et,

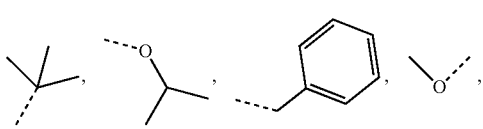

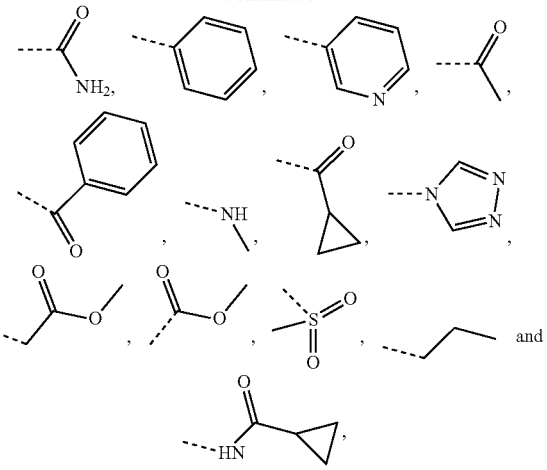

and each of which is optionally substituted by 1, 2 or 3 of R', other variables are as defined in the present invention.

In some embodiments of the present invention, R is selected from the group consisting of H, F, Cl, Br, I, OH, NH₂, Me, Et, —CF₁, CN, COOH,

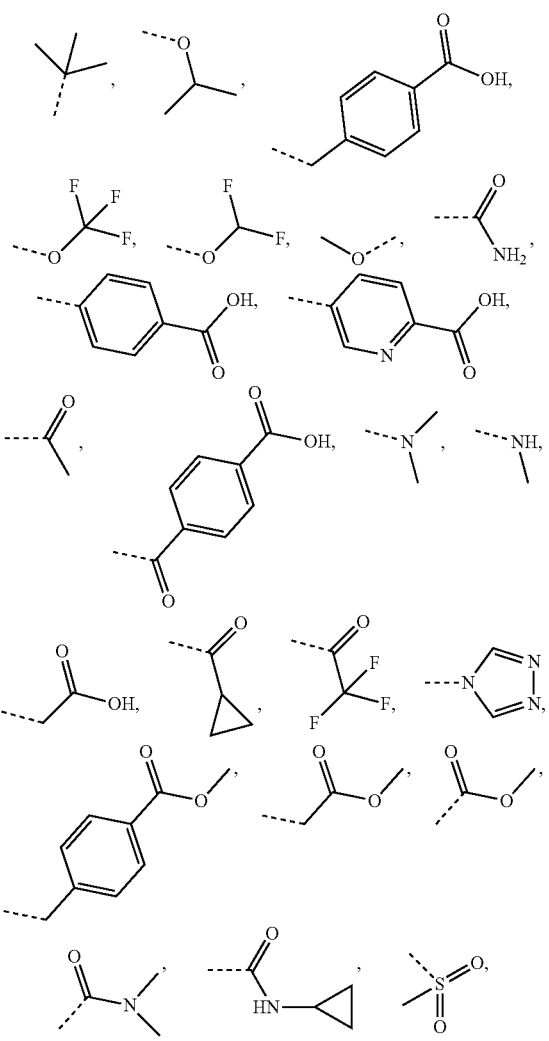

-continued

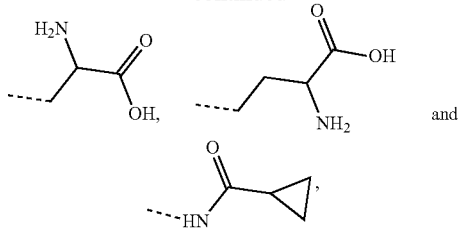

and other variables are as defined in the present invention.

In some embodiments of the present invention, each of $R_1$ and $R_2$ is independently selected from the group consisting of H, F, Cl, Br, I, OH CN, $NH_2$, —COOH, Me and Et, and other variables are as defined in the present invention.

In some embodiments of the present invention, L is —C(═O)—, or selected from the group consisting of $C_{1-3}$ alkyl, phenyl, 5-6 membered heteroaryl, 5-6 membered heterocycloalkyl, 3-6 membered cycloalkyl, each of which is optionally substituted by 1, 2 or 3 of R, and other variables are as defined in the present invention.

In some embodiments of the present invention, L is —C(═O)—, or selected from the group consisting of 1,2,4-oxadiazolyl, methyl, ethyl, 1,3,4-oxadiazolyl, isoxazolyl, oxazolyl, piperidyl, 1,2,3-triazolyl, cyclopropanyl and phenyl, each of which is optionally substituted by 1, 2 or 3 of R. and other variables are as defined in the present invention.

In some embodiments of the resent invention L is —C(═O)—, or selected from the group consisting of

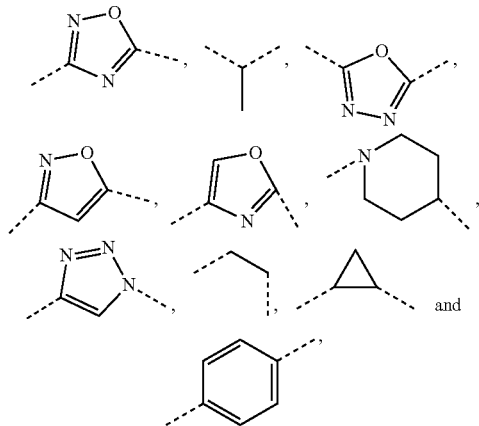

each of which is optionally substituted by 1, 2 or 3 of R, and other variables are as defined in the present invention.

In some embodiments of the present invention, L is selected from the group consisting of

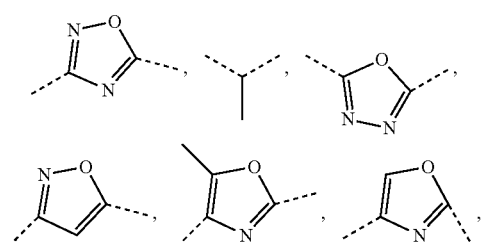

-continued

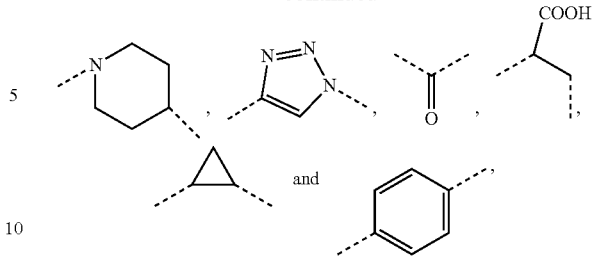

and other variables are as defined in the present invention.

In some embodiments of the present invention, $R_5$ is selected from the group consisting of phenyl, pyridyl, piperidinyl, pyrrolidinyl, azetidinyl, cyclohexyl, cyclobutyl, benzo[d][1,3]m-dioxacyclopentenyl, piperidyl-2-keto, 7-azaspiro[3.5]nonyl, cyclohexyl-$CH_2$—, 3a,7a-dihydro-1H-indolyl, pyrazolyl, pyridyl, 3a,7a-dihydrobenzo[d]thiazolyl, pyrimidinyl, cyclopentyl, spiro[3.3]heptanyl, bicyclo[2.2.2]octyl, octahydrocyclopenta[c]pyrrolyl, 2-azaspiro[3.5]nonyl, piperidinyl-C(═O)—, 4,5,6,7-tetrahydro-1H-benzo[d]imidazolyl, 5,6,7,8-tetrahydroimidazo[1,2-a]pyridyl, piperidinyl-$CH_2$— and bicyclo[1.1.1]pentyl, each of which is optionally substituted by 1, 2 or 3 of R, and other variables are as defined in the present invention.

In some embodiments of the present invention, $R_5$ is selected from the group consisting of

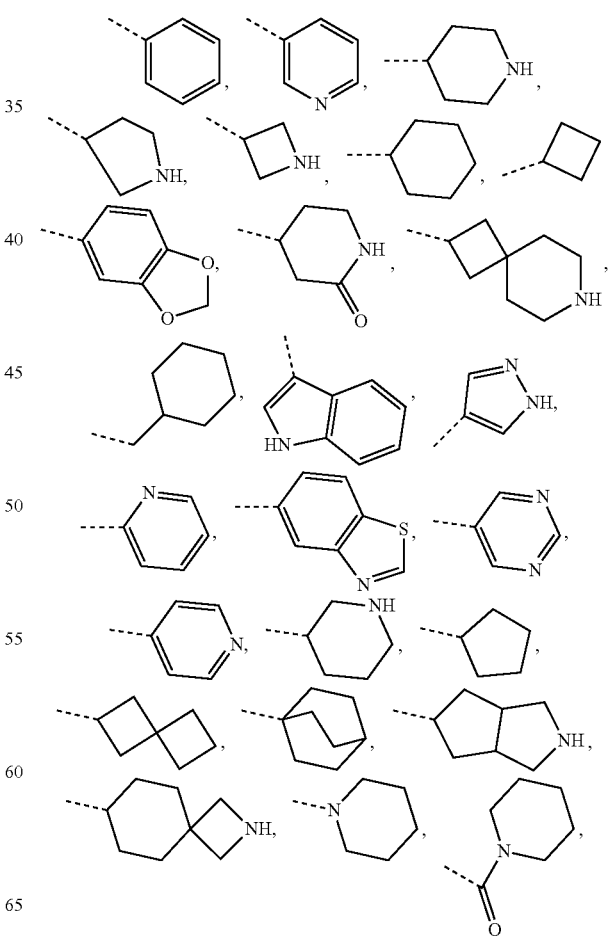

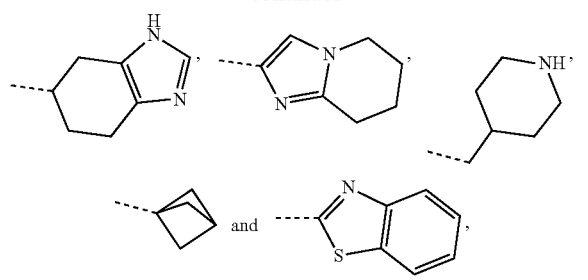
each of which is optionally substituted by 1, 2 or 3 of R, and other variables are as defined in the present invention.
In some embodiments of the present invention, $R_5$ is selected from the group consisting of
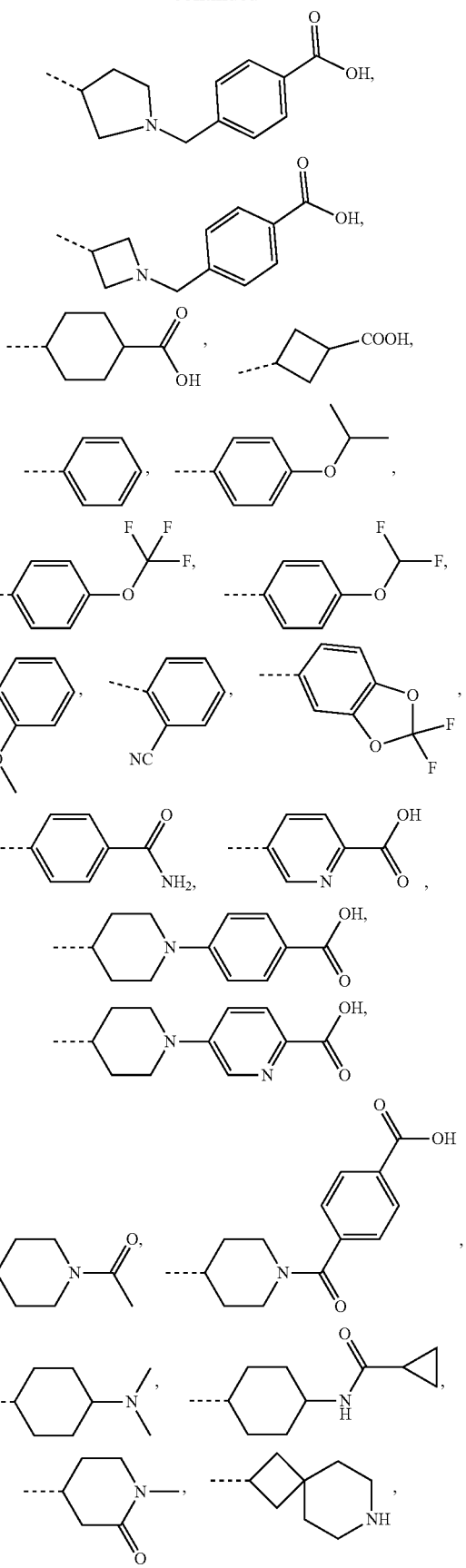

-continued
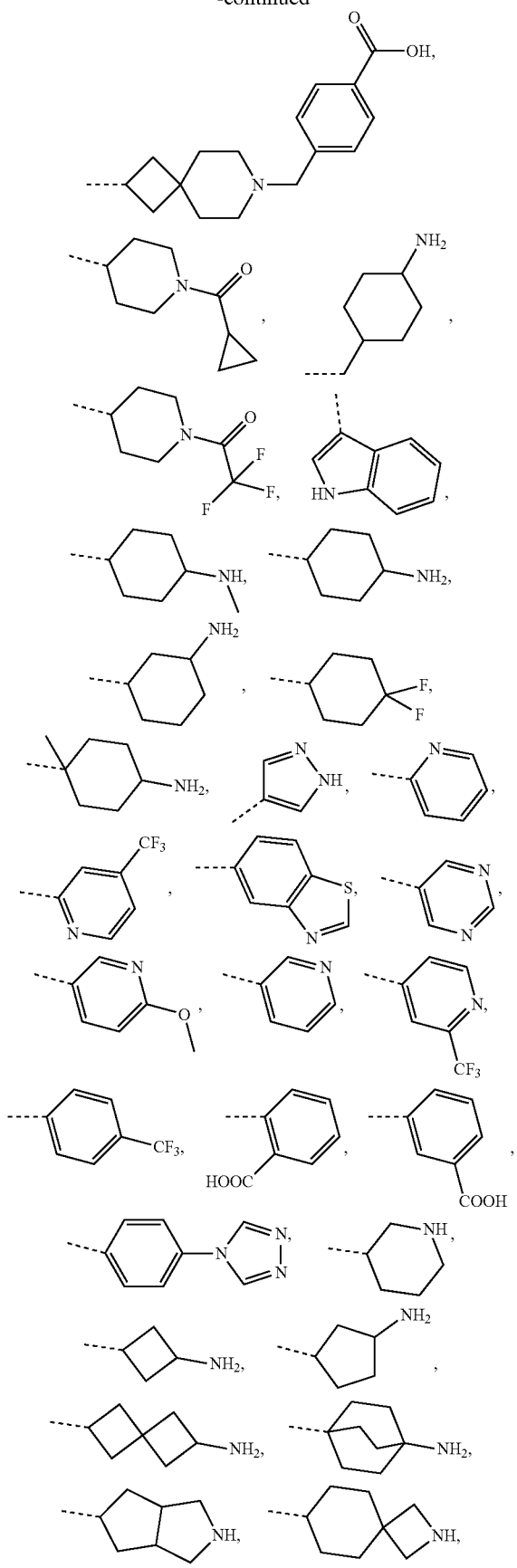
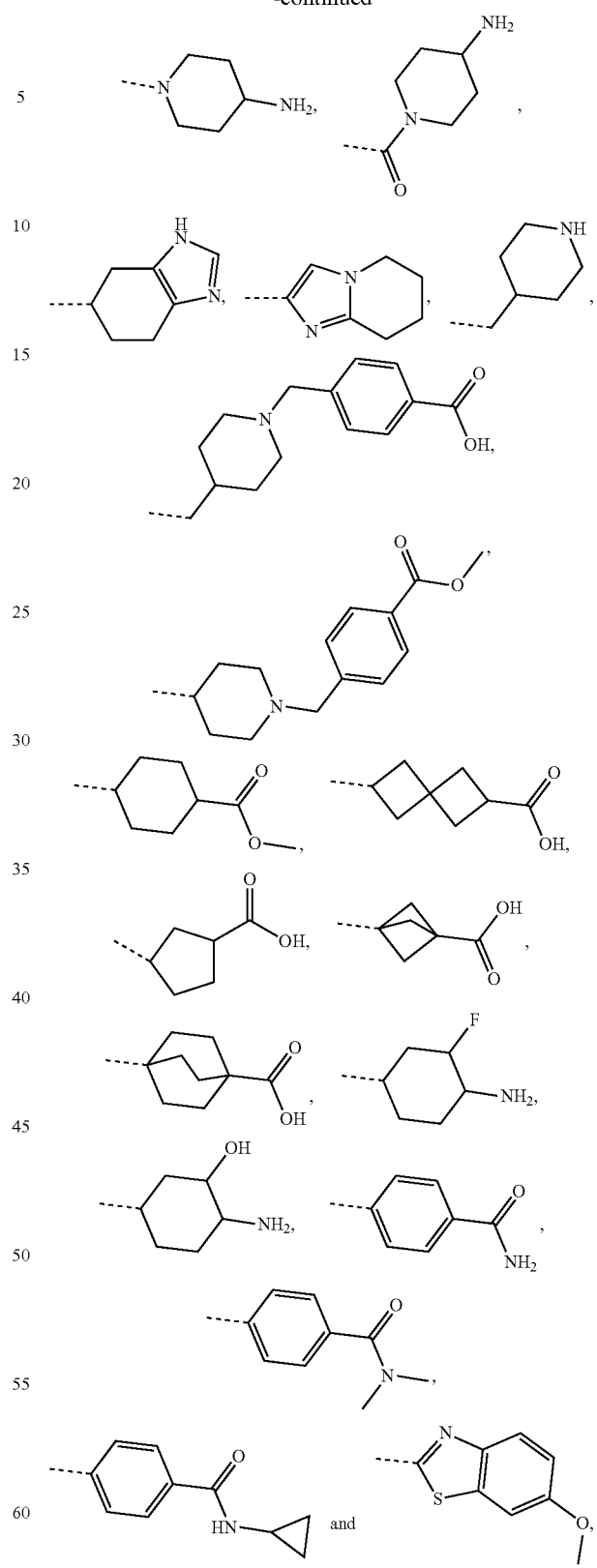
and other variables are as defined in the present invention.
In some embodiments of the resent invention. -L-R₅ is selected from the group consisting of:

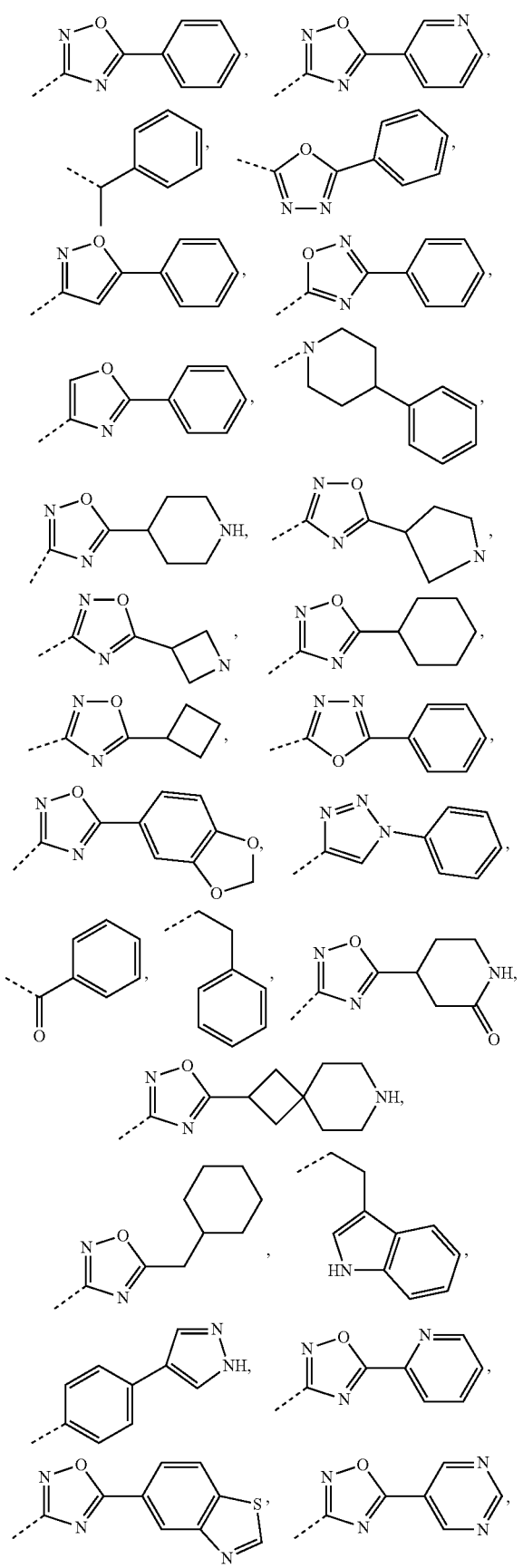
-continued
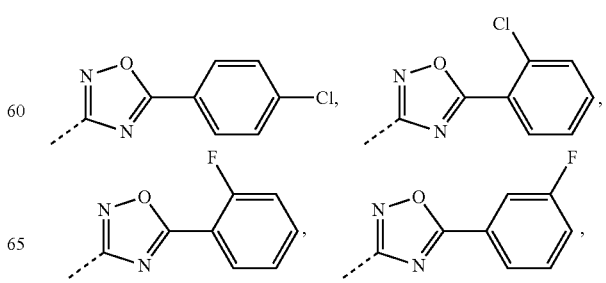
each of which is optionally substituted by 1, 2 or 3 of R, and other variables are as defined in the present invention.
In some embodiments of the resent invention -L-R$_5$ is selected from the group consisting of

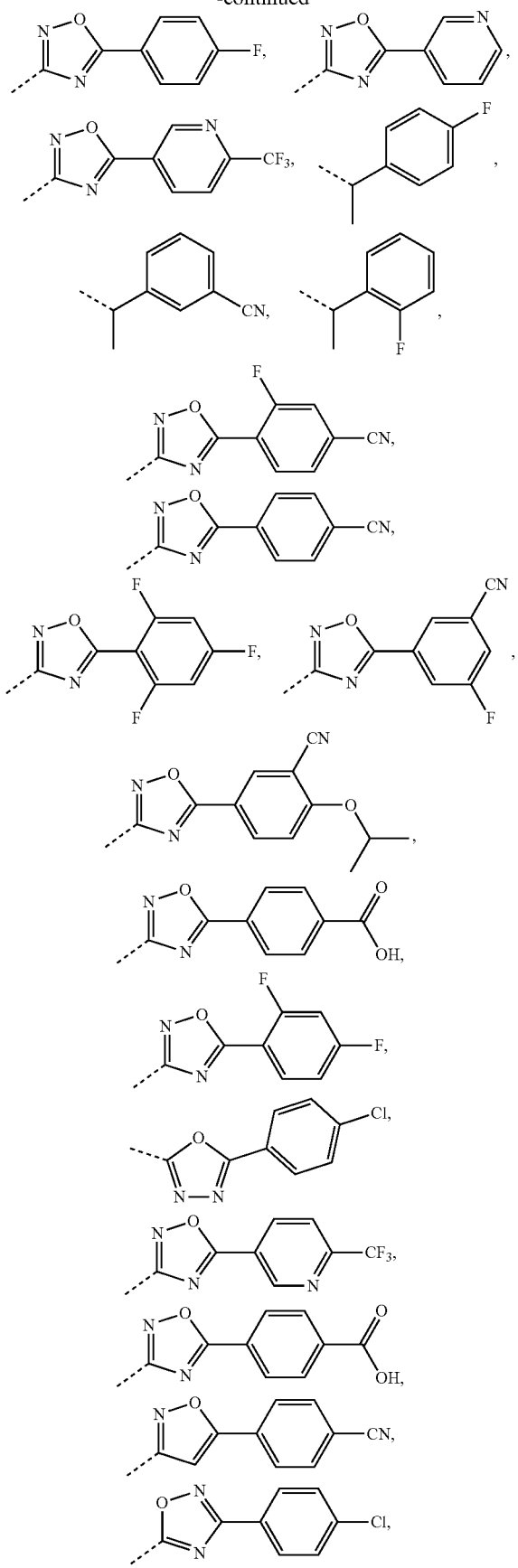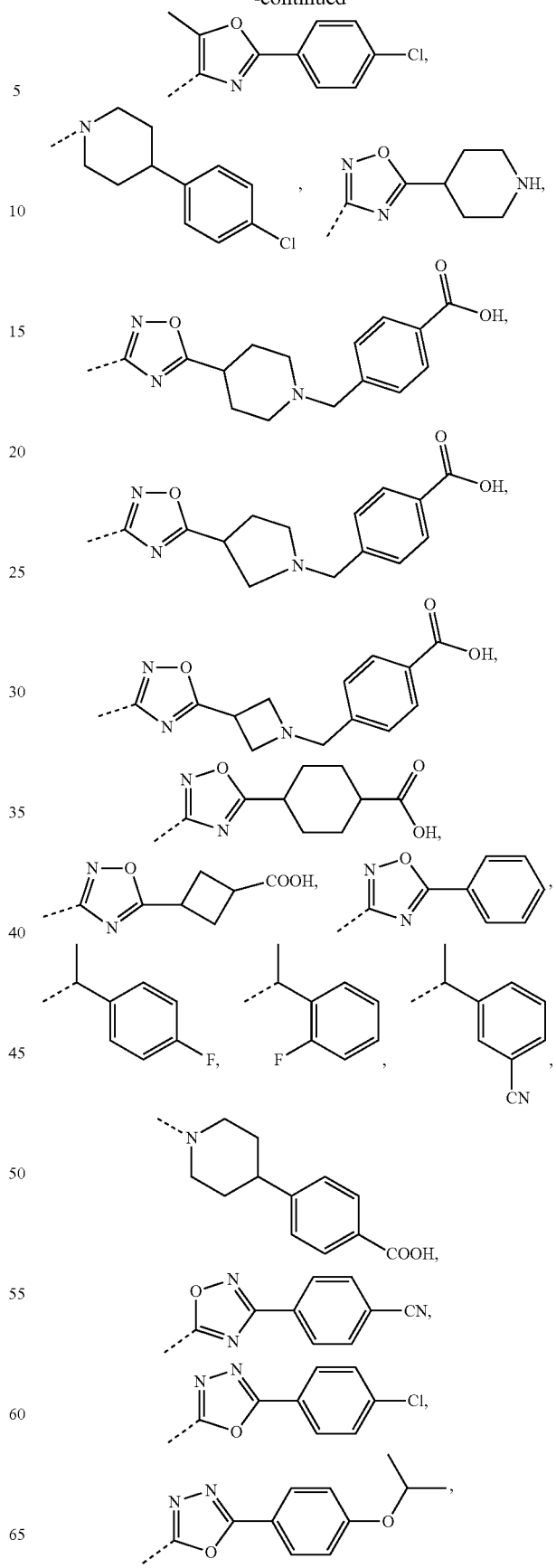

-continued
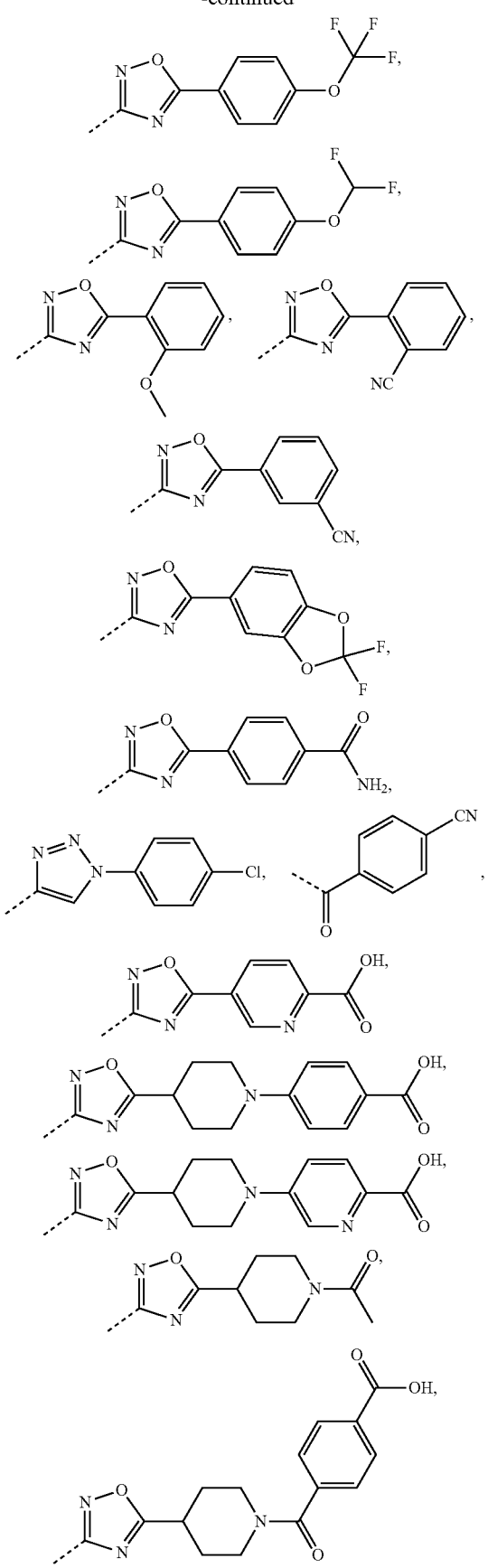
-continued
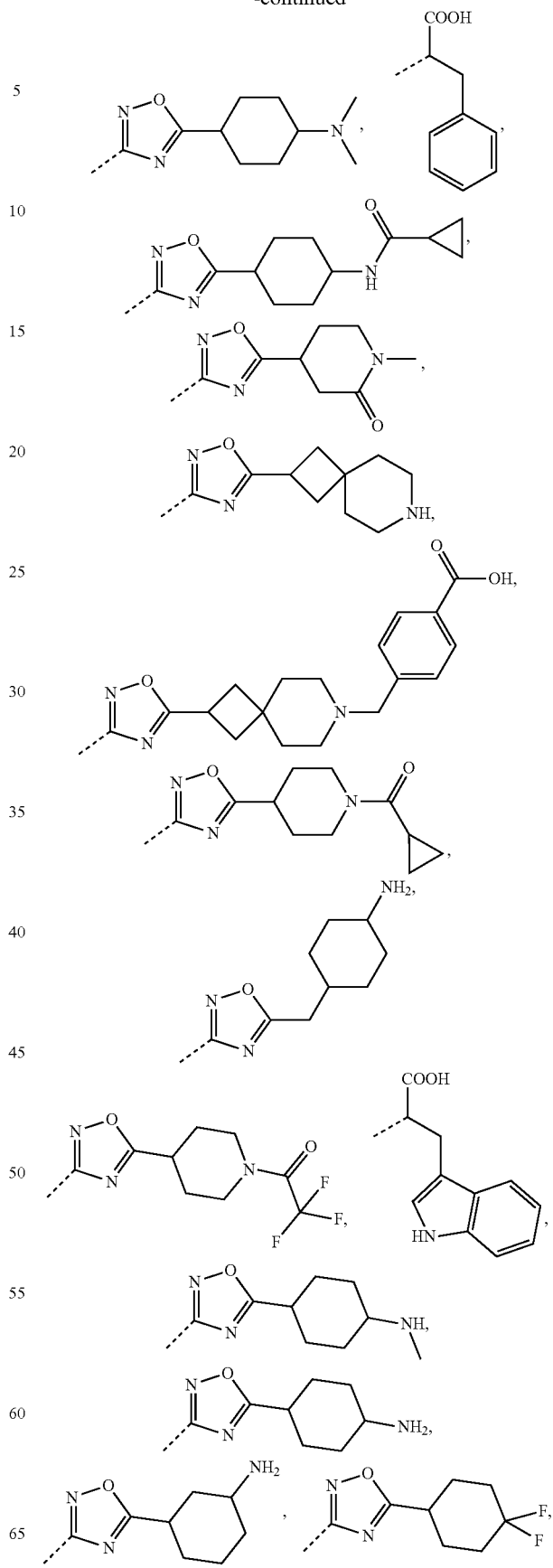

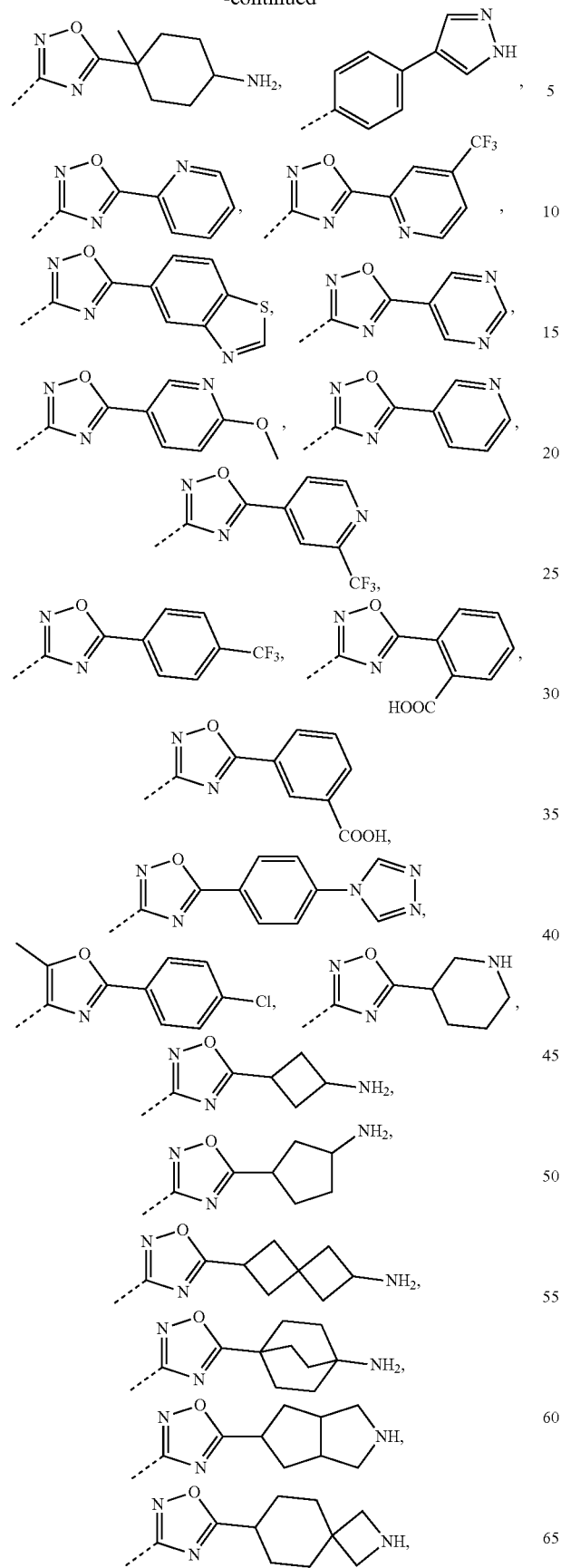
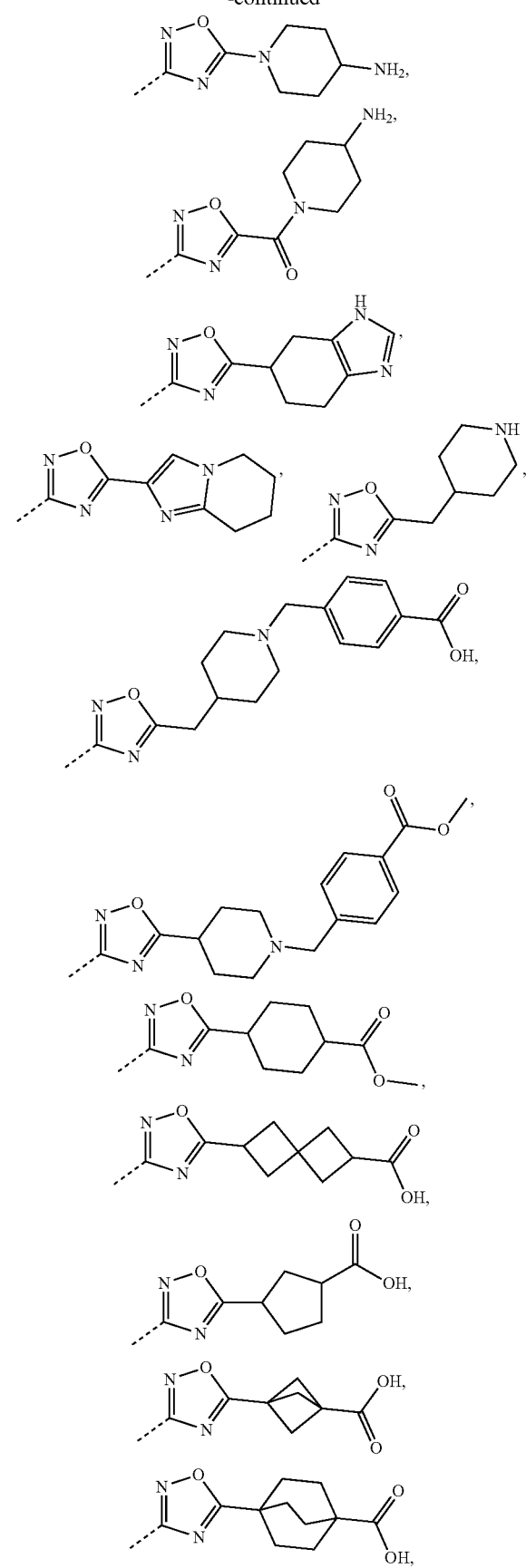

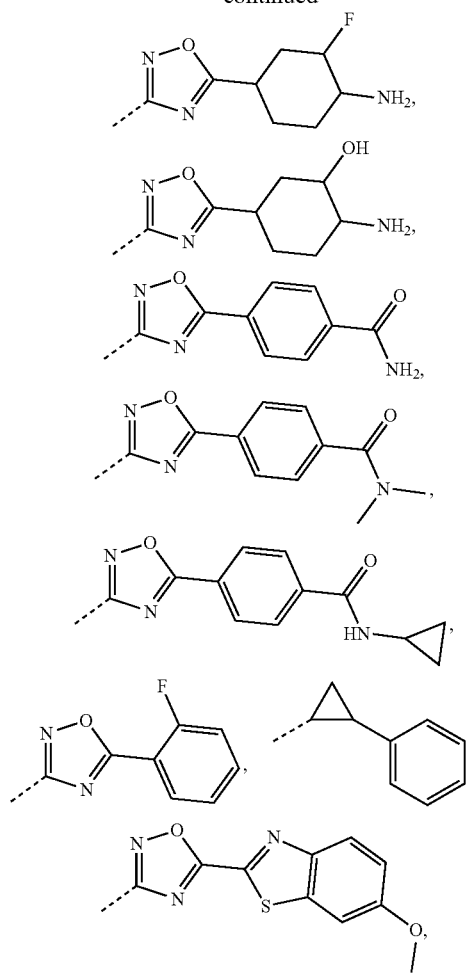

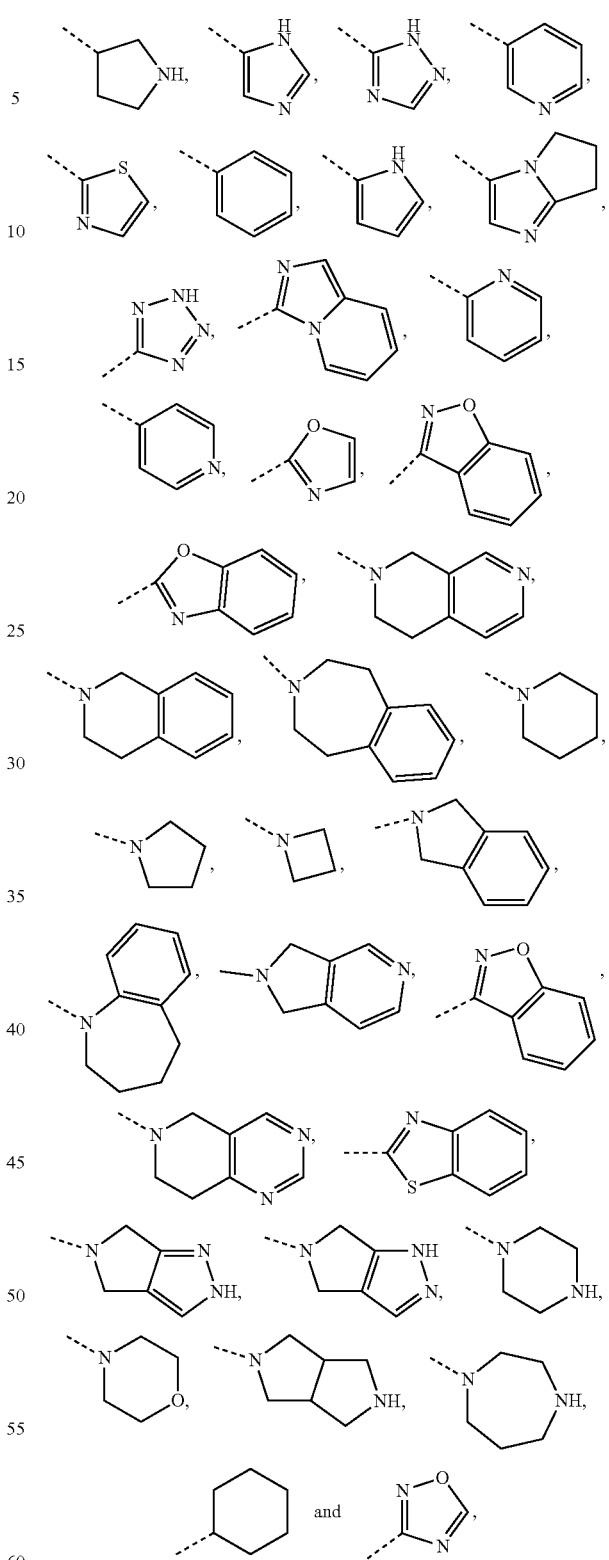

and other variables are as defined in the present invention.

In some embodiments of the present invention, R₃ is selected from the group consisting of H, F, Cl, Br, I, OH, CN, NH₂, —COOH, —CONH₂ and -L-R₅, or selected from the group consisting of C₁₋₃alkyl, phenyl, pyrrolidinyl, 1H-imidazolyl, 1H-1,2,4-triazolyl, pyridyl, thiazolyl, thienyl, pyrrolyl, 2H-tetrazolyl, 6,7-dihydro-5H-pyrrolo[1,2-a]imidazolyl, imidazo[1,5-a]pyridyl, oxazolyl, benzo[d]isoxazolyl, benzo[d]oxazolyl, 1,2,3,4-4H-2,7-naphthyridinyl, 1,2,3,4-tetrahydroisoquinolinyl, 2,3,4,5-tetrahydro-1H-benzo[d]azepinyl, azetidinyl, isoindolyl piperidinyl, 2,3,4,5-tetrahydro-1H-benzo[b]azepinyl, 2,3-dihydro-1H-pyrrolo[3,4-c]pyridyl, benzoisoxazolyl, 5,6,7,8-tetrahydropyridopyrimidinyl, 3a,7a-dihydrobenzo[d]thiazolyl, 2,4,5,6-tetrahydropyrrolo[3,4-c]pyrazolyl, 1,4,5,6-tetrahydropyrrolo[3,4-c]pyrazolyl, piperazinyl, morpholinyl, octahydropyrrolo[3,4-c]pyrrolyl, 1,4-diazaheptyl, cyclohexyl and 1,2,4-oxadiazolyl, each of which is optionally substituted by 1, 2 or 3 of R, and other variables are as defined in the present invention.

In some embodiments of the present invention, R₃ is selected from the group consisting of H, F, Cl, Br, I, OH, CN, NH₂, —COOH, —CONH₂ and -L-R₅, or selected from the group consisting of Me, Et, each of which is optionally substituted by 1, 2 or 3 of R, and other variables are as defined in the present invention.

In some embodiments of the present invention, R₃ is selected from the group consisting of H, F, Cl, Br, I, OH, CN, NH₂, —COOH, Me, Et,

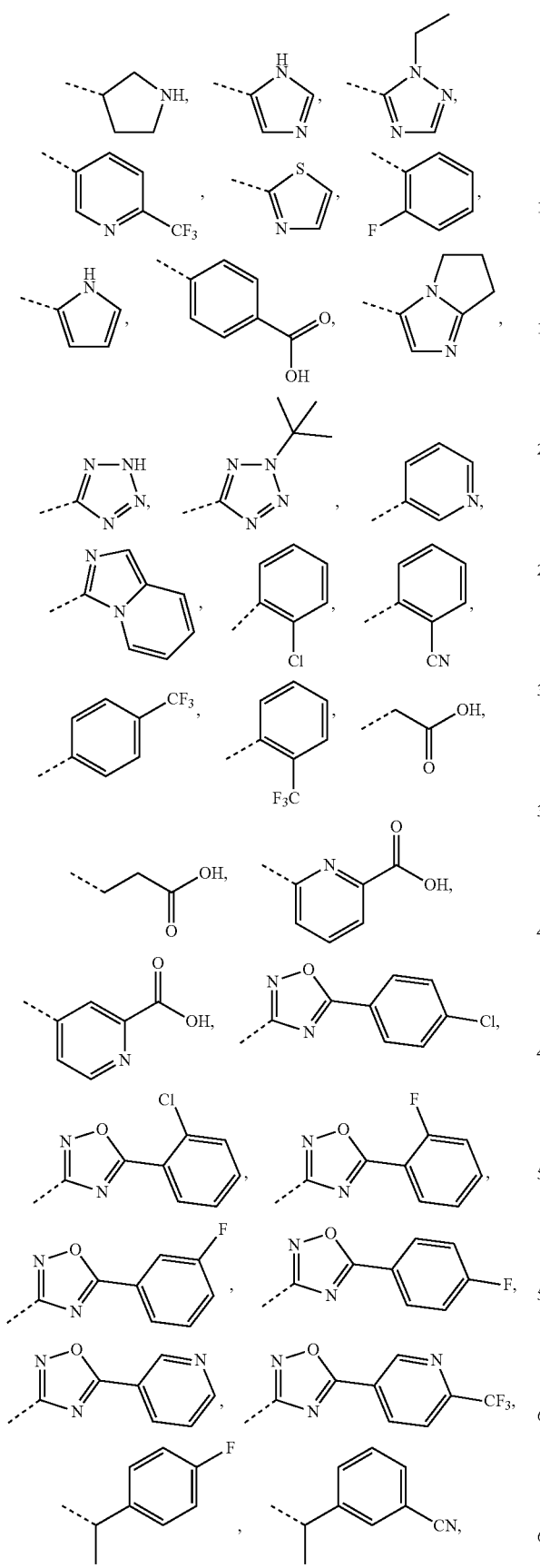
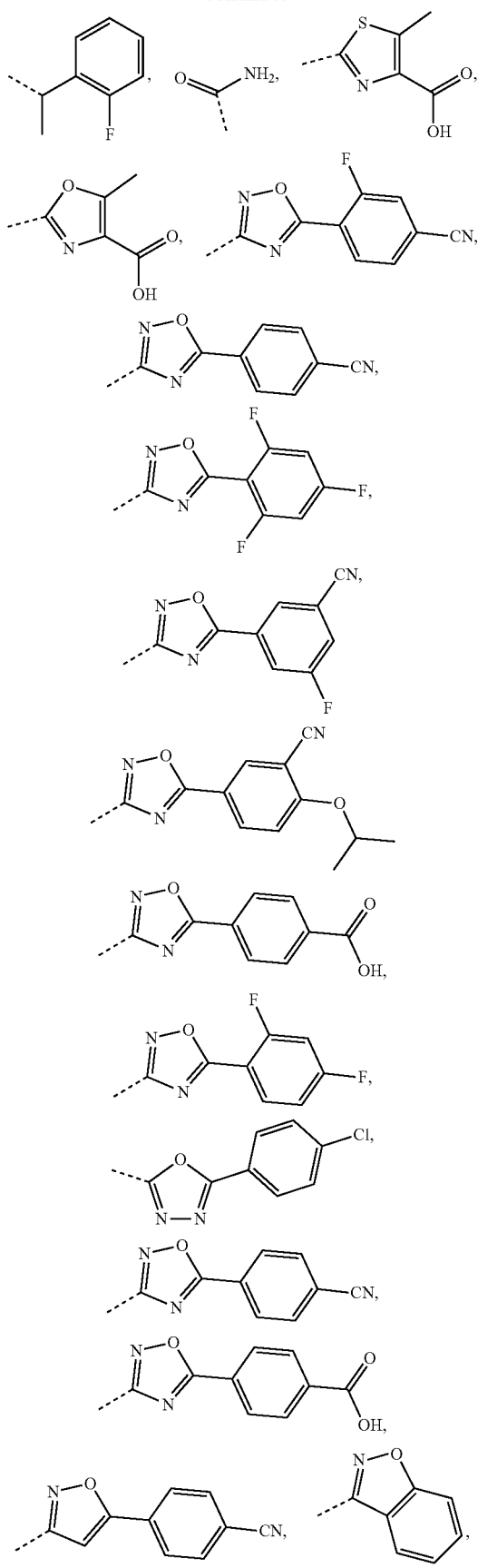

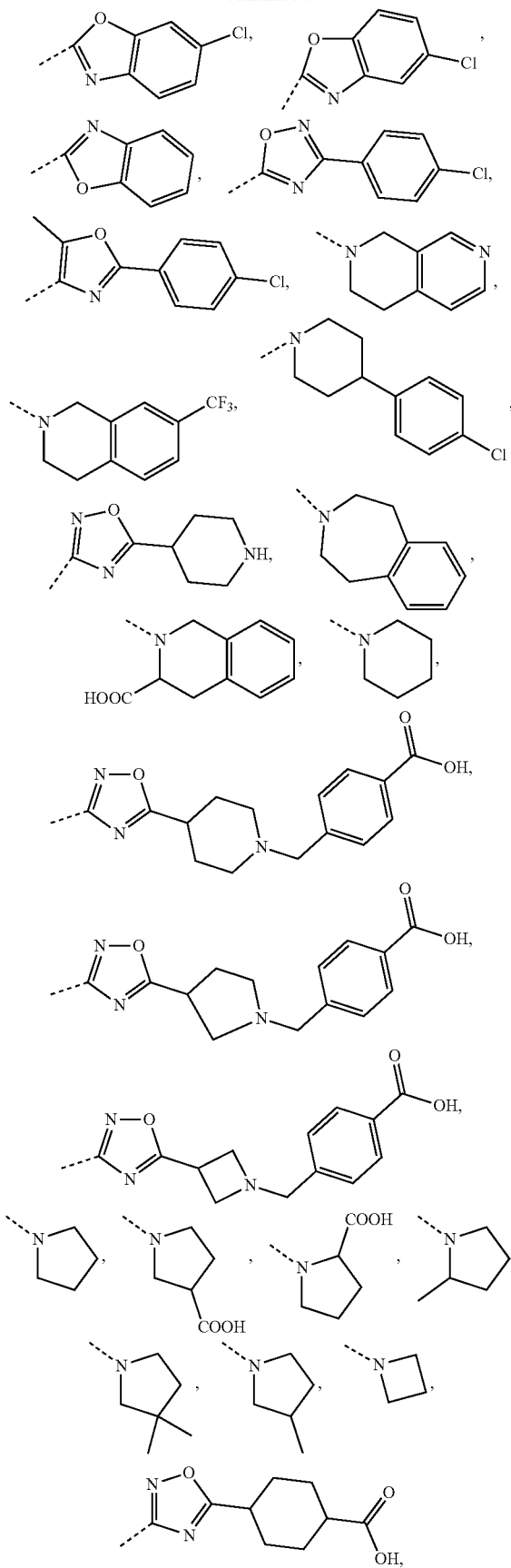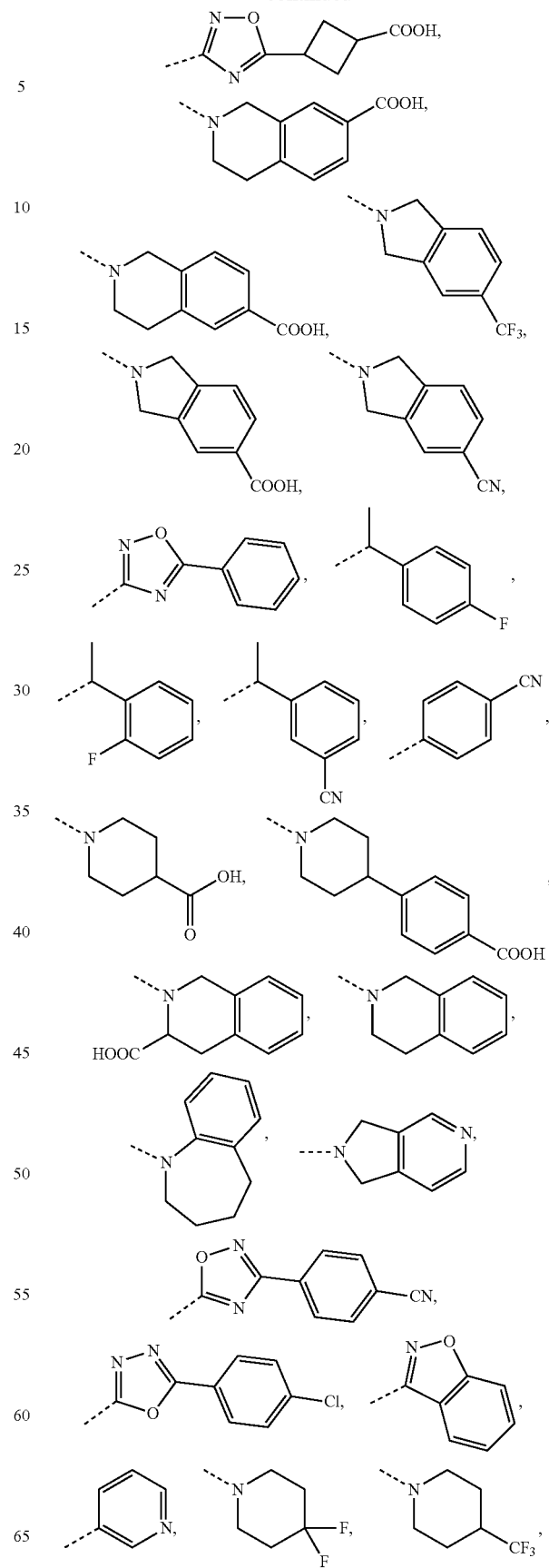

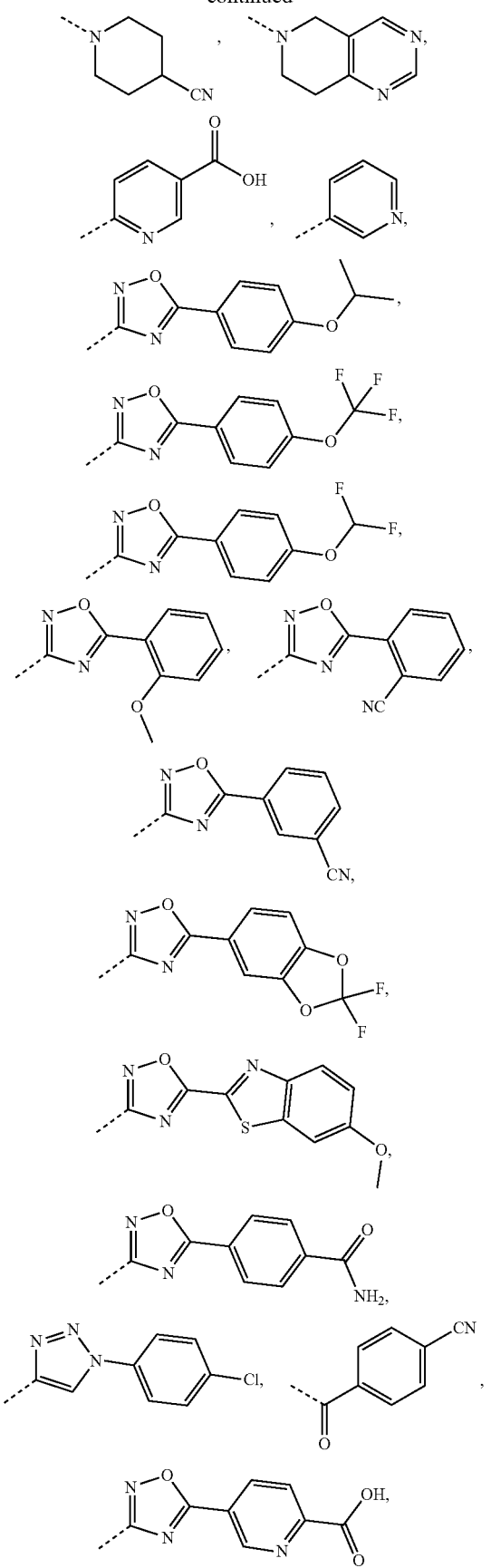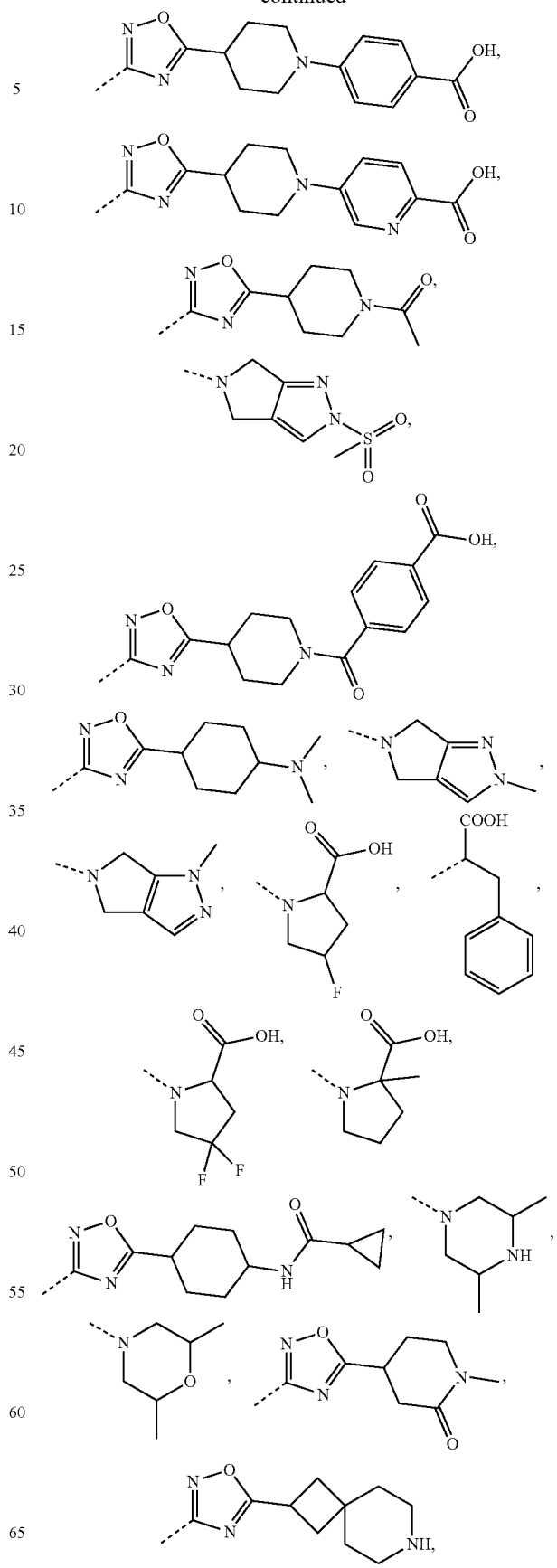

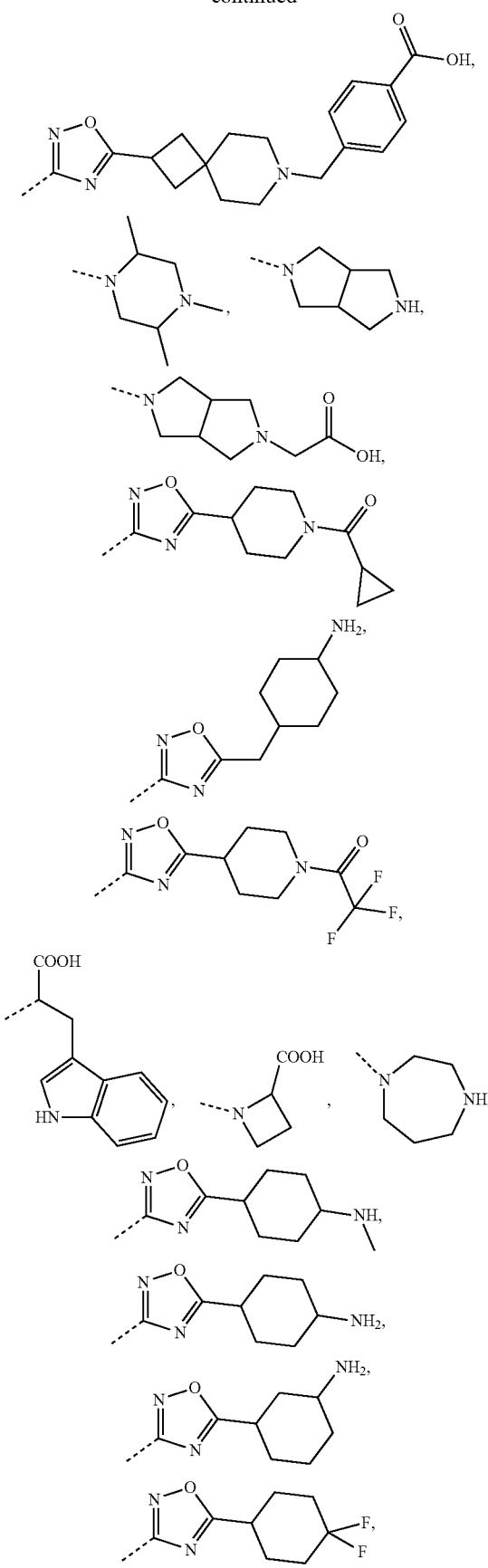
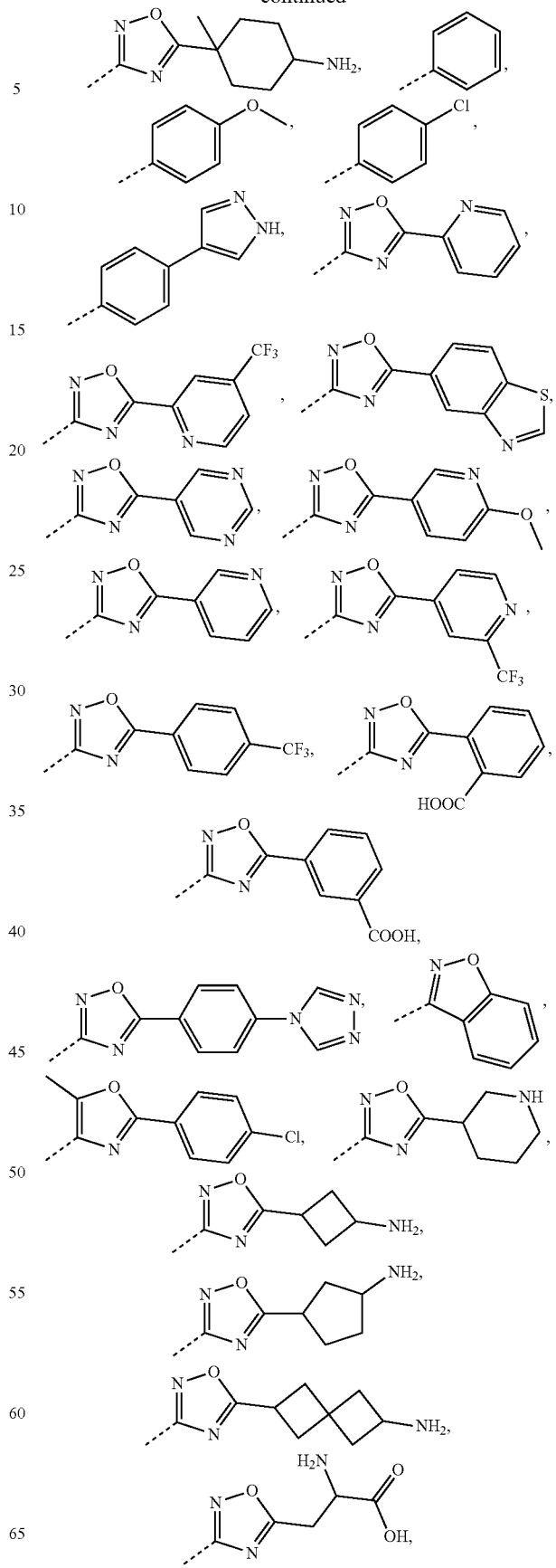

-continued
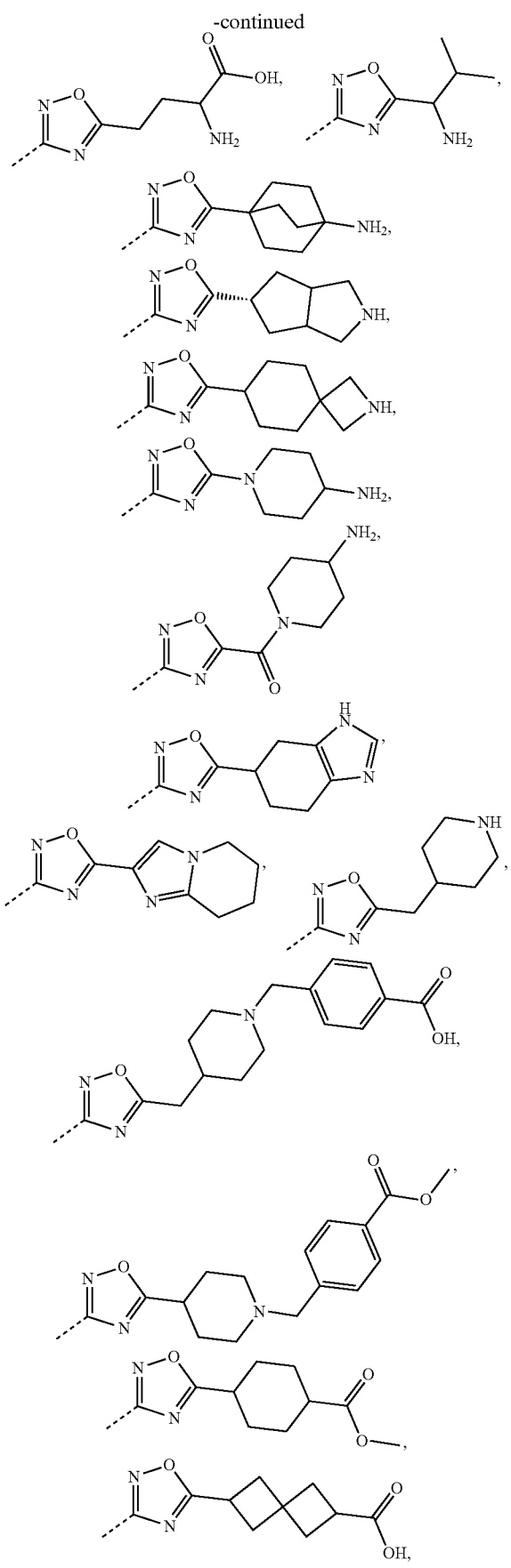
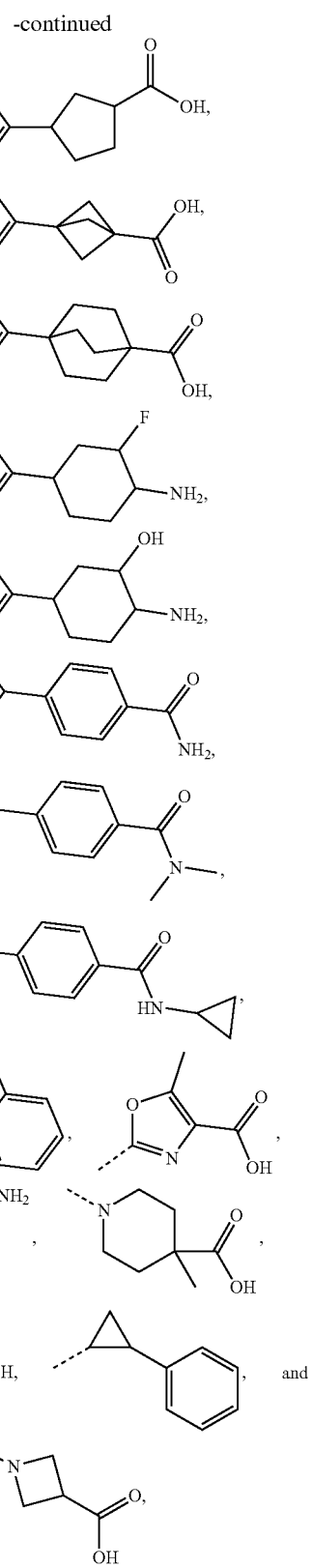
and OH and other variables are as defined in the present invention.
In some embodiments of the present invention, $R_4$ is H, or selected from the group consisting of $C_{1-3}$ alkyl and $C_{1-4}$ alkyl-O—C(=O)—, each of which is optionally substituted by 1, 2 or 3 of R, and other variables are as defined in the present invention.

In some embodiments of the present invention, R$_4$ is selected from the group consisting of H, Me, Et and

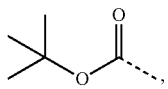

and other variables are as defined in the present invention.

In some embodiments of the present invention, R$_6$ is H, or selected from the group consisting of C$_{1-3}$ alkyl and C$_{1-4}$ alkyl-O—C(=O)—, each of which is optionally substituted by 1, 2 or 3 of R, and other variables are as defined in the present invention.

In some its of the present invention, R$_6$ is selected from the group consisting of H, Me, Et and

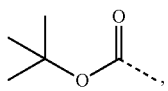

and other variables are as defined in the present invention.

In some embodiments of the invention, the structural unit

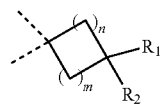

is selected from the group consisting of

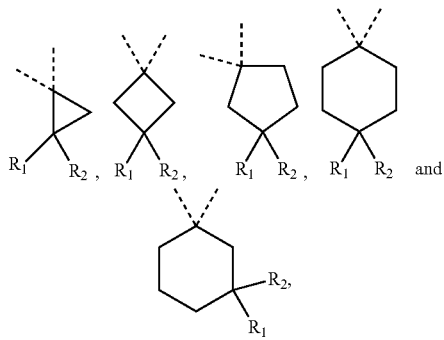

and other variables are as defined in the present invention.

In some embodiments of the resent invention, the structural unit

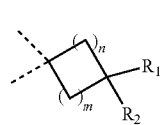

is selected from the group consisting of

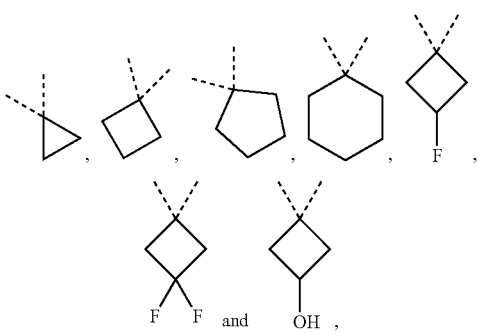

and other variables are as defined in the present invention.

In some embodiments of the present invention, the compound, the pharmaceutically acceptable salt or the tautomer thereof is selected from the group consisting of

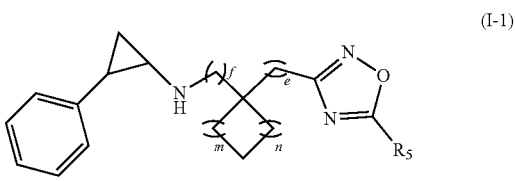 (I-1)

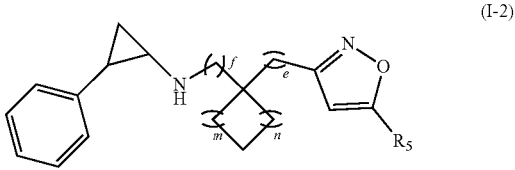 (I-2)

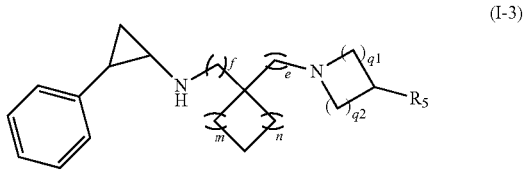 (I-3)

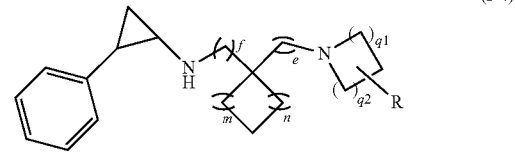 (I-4)

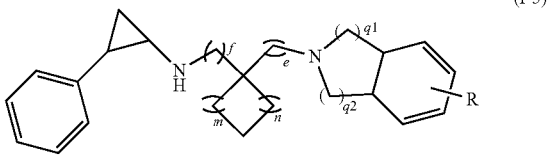 (I-5)

 (I-6)

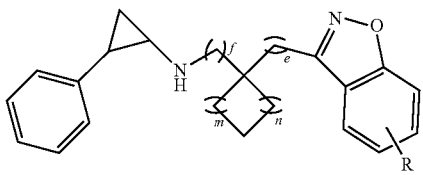

(1-7)

wherein, e, f, m, n, R₅, R are as defined in the present invention:

each of $q_1$ and $q_2$ is independently 1 or 2.

The present invention provides a compound of formula (I), a pharmaceutically acceptable salt or a tautomer thereof.

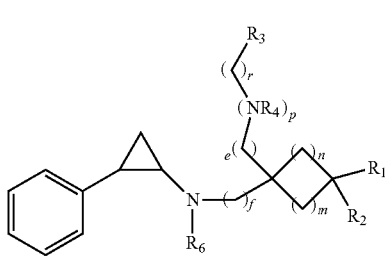

(I)

wherein, f is or 2;

r is 0, 1 or 2;

e is 0, 1, or 2;

p is 0 or 1;

m is 0, 1 or 2;

n is 1 or 2;

each of $R_1$, $R_2$ is independently selected from the group consisting of H, F, Cl, Br, I, OH, CN, NH₂ and —COOH, or is a $C_{1-3}$ alkyl optionally substituted by 1, 2 or 3 R;

or, $R_1$ and $R_2$ are connected together to form a 3-6 membered ring;

$R_3$ is selected from the group consisting of H, F, Cl, Br, I, OH, CN, NH₂, —COOH, —CONH₂ and -L-R, or selected from the group consisting of $C_{1-6}$ alkyl, phenyl, 5-12 membered heteroaryl, $C_{3-7}$ cycloalkyl and 4-8 membered heterocycloalkyl, each of which is optionally substituted by 1, 2 or 3 of R;

$R_4$ is H, or selected from the group consisting of $C_{1-6}$ alkyl and $C_{1-6}$ heteroalkyl, each of which is optionally substituted by 1, 2 or 3 of R;

$R_5$ is selected from the group consisting of phenyl, 5-9 membered heteroaryl, $C_{3-7}$ cycloalkyl, 4-8 membered heterocycloalkyl, each of which is optionally substituted by 1, 2 or 3 of R;

$R_6$ is H, or selected from the group consisting of $C_{1-6}$ alkyl and $C_{1-4}$ heteroalkyl, each of which is optionally substituted by 1, 2 or 3 of R;

L is selected from the group consisting of $C_{1-6}$ alkyl, 5-9 membered heteroaryl and 4-8 membered heterocycloalkyl, each of which is optionally substituted by 1, 2 or 3 of R;

R is selected from the group consisting of H, F, Cl, Br, I, OH, NH₂, CN and COOH or selected from the group consisting of $C_{1-6}$ alkyl, $C_{1-6}$ heteroalkyl and phenyl-$C_{1-6}$ alkyl-, each of which is optionally substituted by 1, 2 or 3 of R';

R' is selected from the group consisting of F, Cl, Br, I, OH, NH₂, Me, Et, CF₃, CHF₂, CH₂F, NHCH₃, N(CH₃)₂ and COOH;

each of the "hetero" in the 5-12 membered heteroaryl, 4-8 membered heterocycloalkyl, $C_{1-6}$ heteroalkyl and 5-9 membered heteroaryl is independently selected from the group consisting of —NH—, —S—, N, —O— and =O;

in any above cases, the number of the heteroatom or the heteroatomic group is independently 1, 2, 3 or 4.

In some embodiments of the present invention, R is selected from the group consisting of H, F, Cl, Br, I, OH, NH₂, CN and COOH or selected from the group consisting of methyl, ethyl, propyl, isobutyl, $C_{1-6}$ alkoxy and phenyl-$C_{1-3}$ alkyl-, each of which is optionally substituted by 1, 2 or 3 of R', and other variables are as defined in the present invention.

In some embodiments of the present invention, R is selected from the group consisting of H, F, Cl, Br, I, OH, NH₂, Me, Et, —CF, CN, COOH,

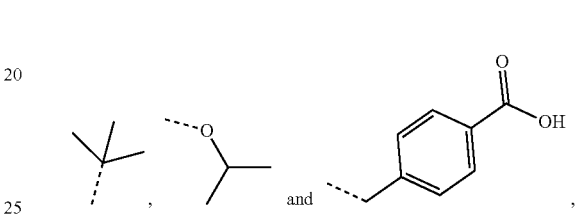

and other variables are as defined in the present invention.

In some embodiments of the present invention, each of $R_1$ and $R_2$ is independently selected from the group consisting of H, F, Cl, Br, I, OH, CN, NH₂, —COOH, Me and Et, and other variables are as defined in the present invention.

In some embodiments of the present invention. L is selected from the group consisting of $C_{1-3}$ alkyl, 5-6 membered heteroaryl and 5-6 membered heterocycloalkyl, each of which is optionally substituted by 1, 2 or 3 of R, and other variables are as defined in the present invention.

In some embodiments of the present invention, L is selected from the group consisting of 1,2,4-oxadiazolyl, methyl, ethyl, 1,3,4-oxadiazolyl, isoxazolyl, oxazolyl and piperidyl, each of which is optionally substituted by 1, 2 or 3 of R, and other variables are as defined in the present invention.

In some embodiments of the resent invention, L is selected from the group consisting of

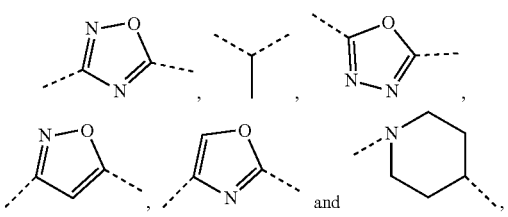

and other variables are as defined in the present invention.

In some embodiments of the present invention the group consisting of

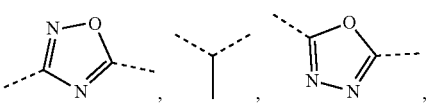

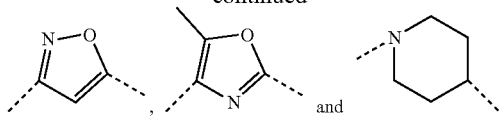

and other variables are as defined in the present invention.

In some embodiments of the present invention, $R_5$ is selected from the group consisting of phenyl, pyridyl, piperidinyl, pyrrolidinyl, azetidinyl, cyclohexyl and cyclobutyl, each of which is optionally substituted by 1, 2 or 3 of R, and other variables are as defined in the present invention.

In some embodiments of the present invention, $R_5$ is selected from the group consisting of

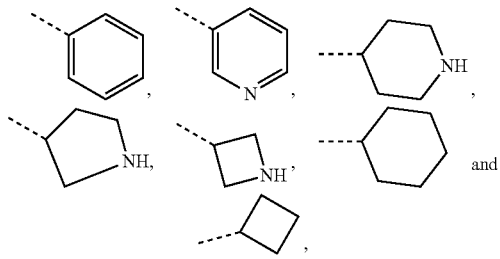

each of which is optionally substituted by 1, 2 or 3 of R, and other variables are as defined in the present invention.

In some embodiments of the resent invention $R_5$ is selected from the group consisting of

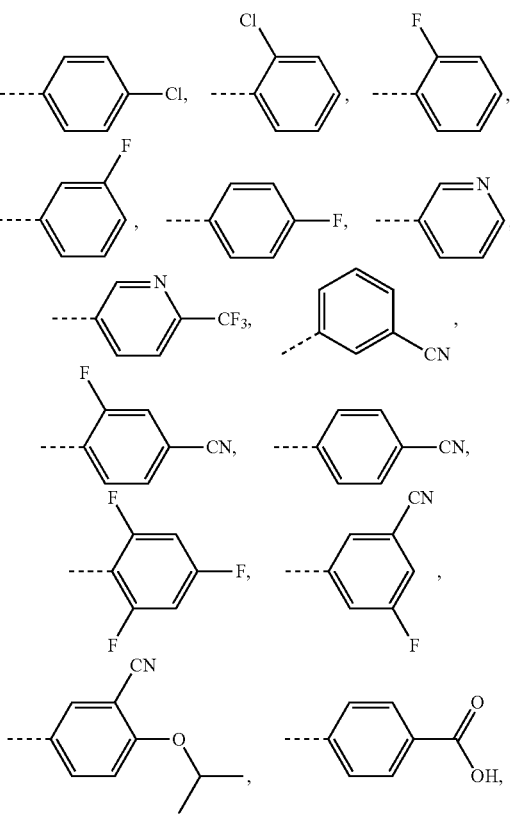

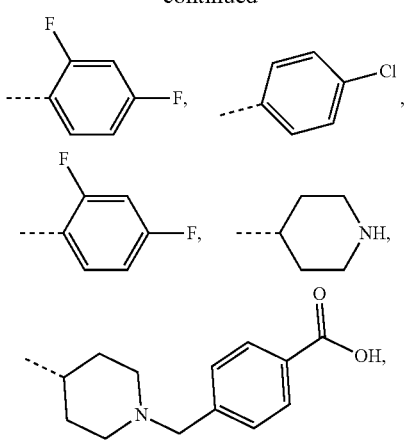

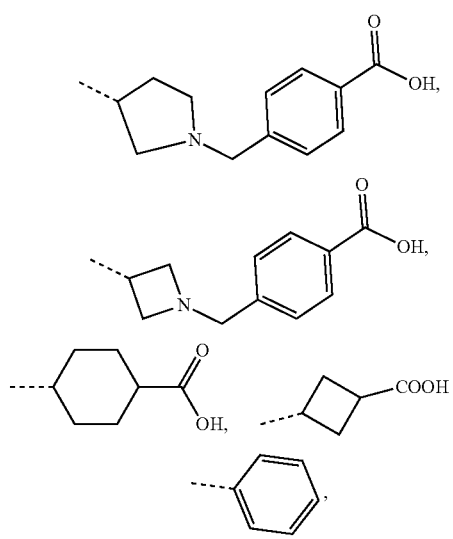

and other variables are as defined in the present invention.

In some embodiments of the resent invention, -L-$R_5$ is selected from the group consisting of

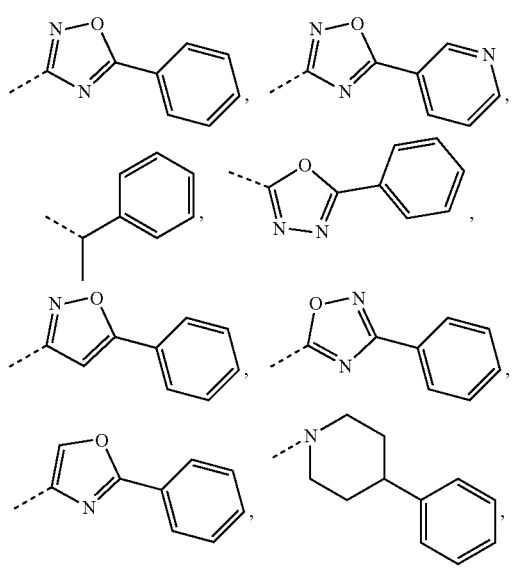

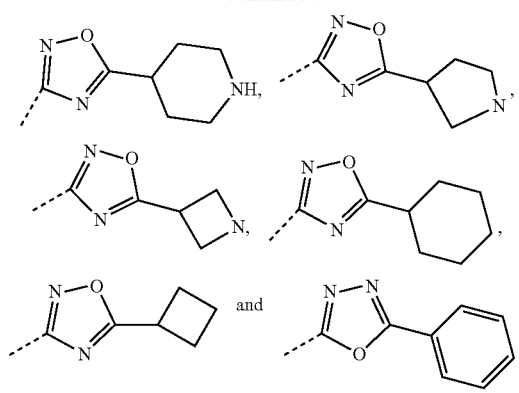
each of which is optionally substituted by 1, 2 or 3 of R, and other variables are as defined in the present invention.
In some embodiments of the resent invention -L-R$_5$ is selected from the group consisting of
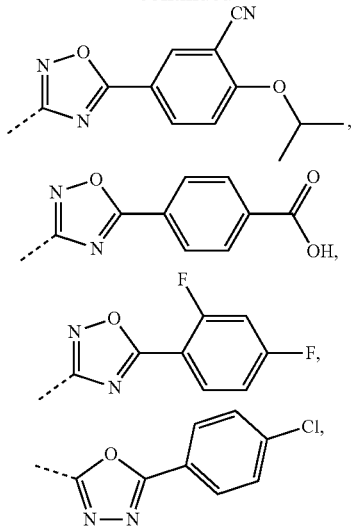

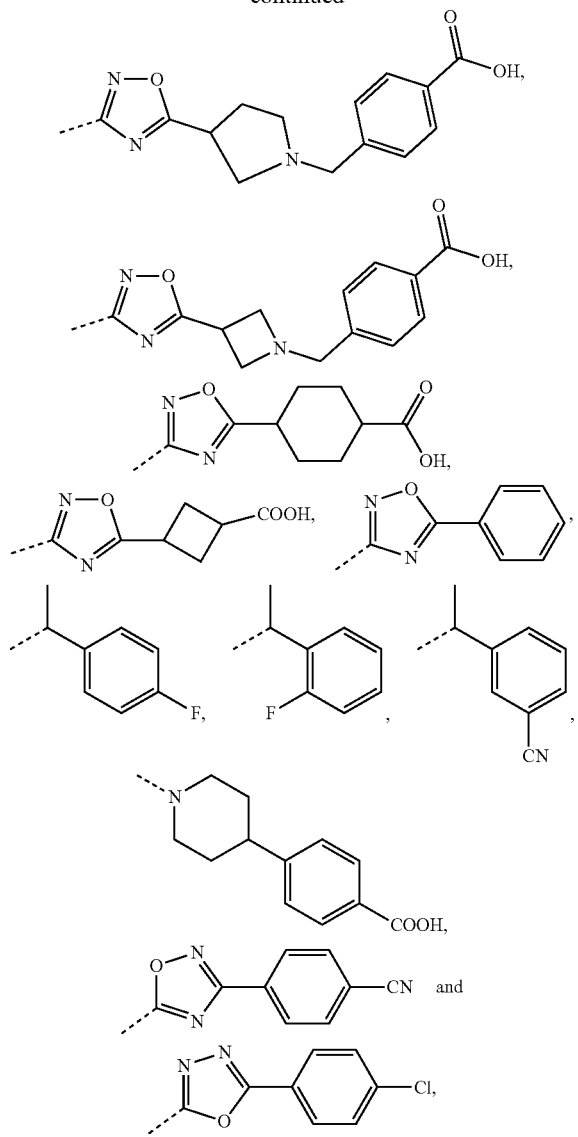

and other variables are as defined in the present invention.

In some embodiments of the present invention, $R_3$ is selected from the group consisting of H, F, Cl, Br, I, OH CN, $NH_2$, —COOH, —$CONH_2$ and -L-$R_5$, or selected from the group consisting of $C_{1-3}$ alkyl, phenyl, pyrrolidinyl, 1H-imidazolyl, 1H-1,2,4-triazolyl, pyridyl, thiazolyl, thienyl, pyrrolyl, 2H-tetrazolyl, 6,7-dihydro-5H-pyrrolo[1,2-a]imidazolyl, imidazo[1,5-a]pyridyl, oxazolyl, benzo[d]isoxazolyl, benzo[d]oxazolyl, 1,2,3,4-4H-2,7-naphthyridinyl, 1,2,3,4-tetrahydroisoquinolinyl, 2,3,4,5-tetrahydro-1H-benzo[d]azepinyl, azetidinyl, isoindolyl, piperidinyl, 2,3,4,5-tetrahydro-1H-benzo[b]azepinyl, 2,3-dihydro-1H-pyrrolo[3,4-c]pyridyl, benzoisoxazolyl, and 5,6,7,8-tetrahydropyridopyrimidinyl, each of which is optionally substituted by 1, 2 or 3 of R, and other variables are as defined in the present invention.

In some embodiments of the present invention, $R_3$ is selected from the group consisting of H, F, Cl, Br, I, OH, CN, $NH_2$, —COOH, —$CONH_2$ and -L-$R_5$, or selected from the group consisting of Me, Et,

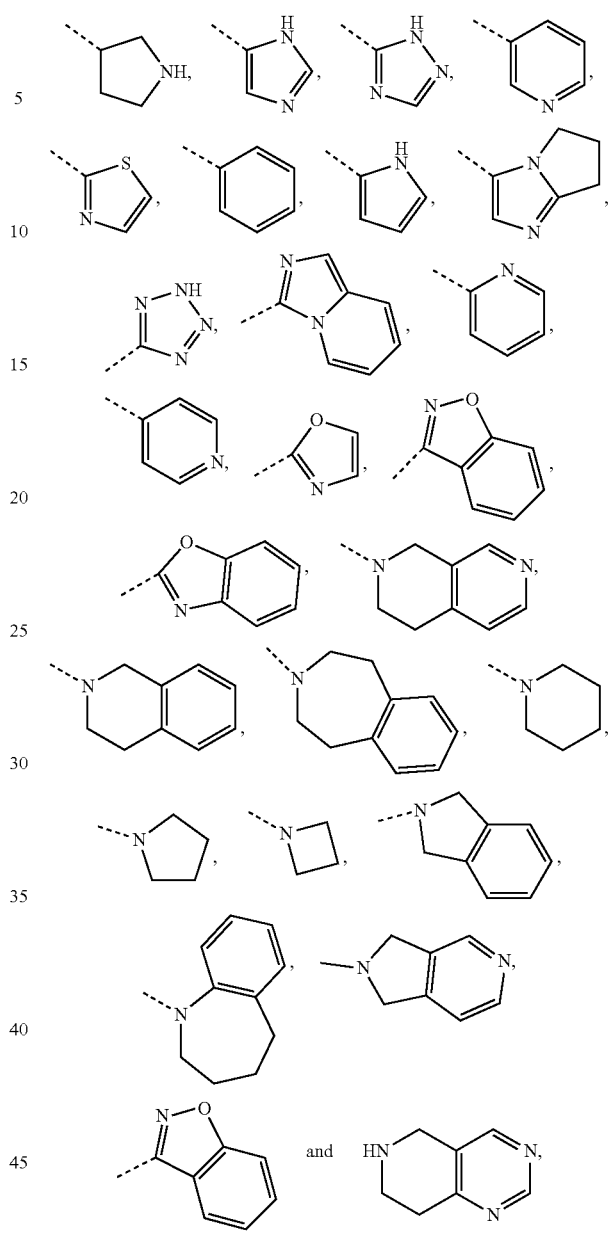

each of which is optionally substituted by 1, 2 or 3 of R, and other variables are as defined in the present invention.

In some embodiments of the present invention, $R_3$ is selected from the group consisting of H, F, Cl, Br, I, OH, CN, $NH_2$, —COOH, Me, Et,

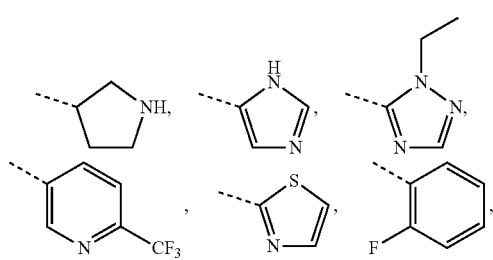

-continued
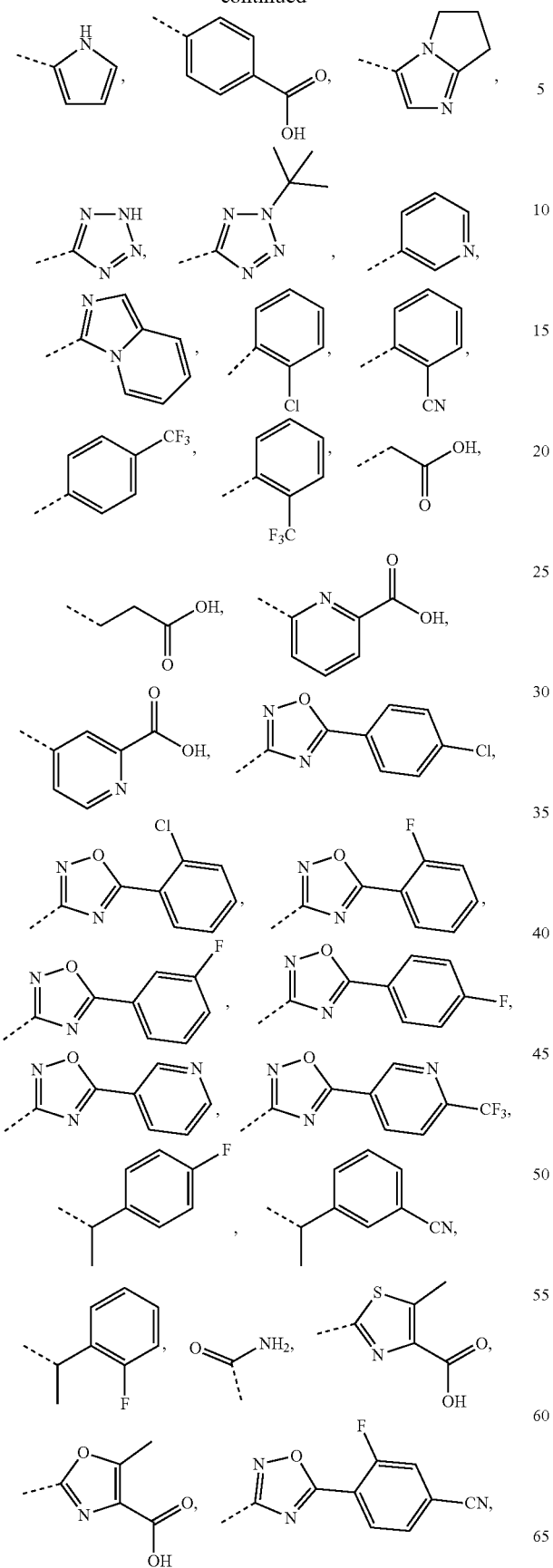
-continued
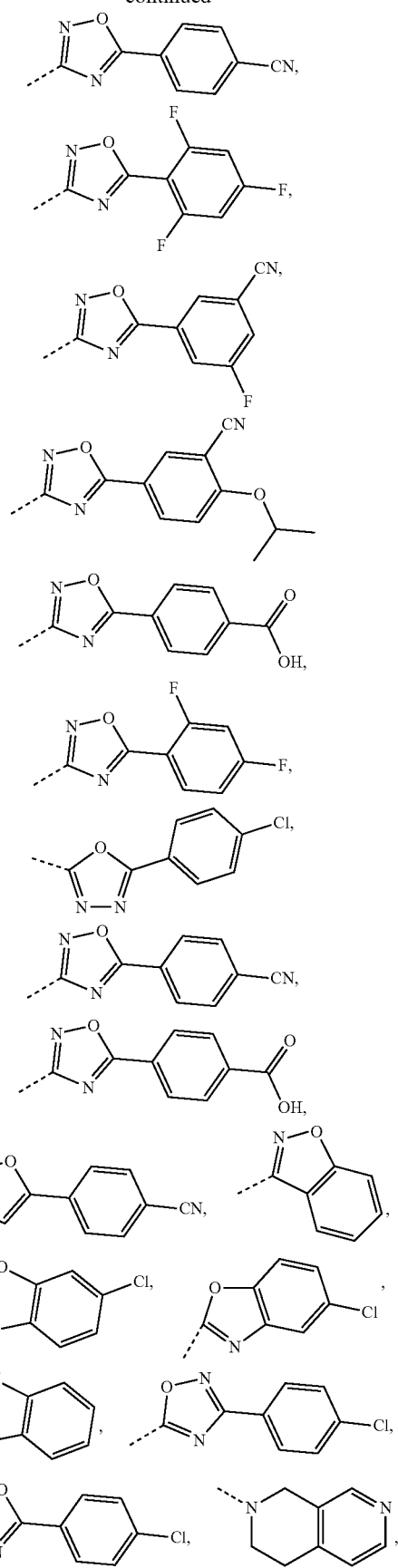

-continued

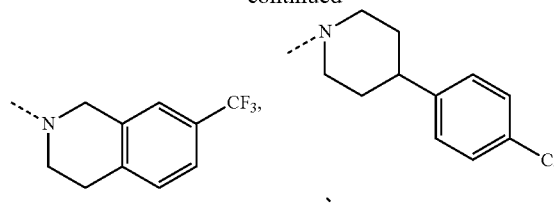
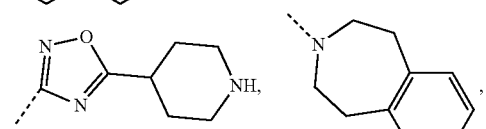
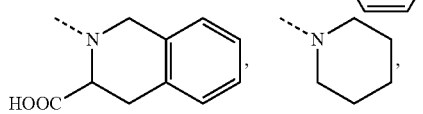

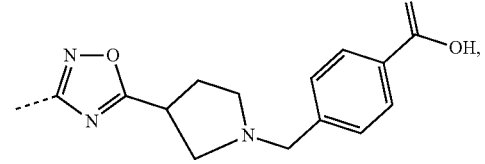
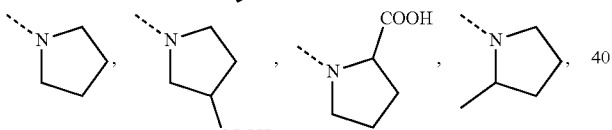
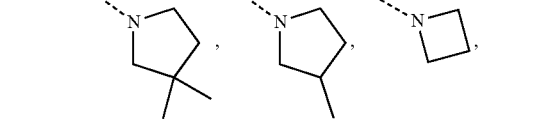
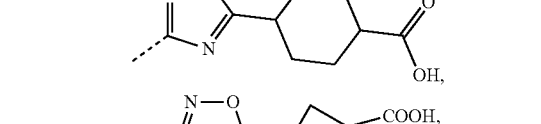
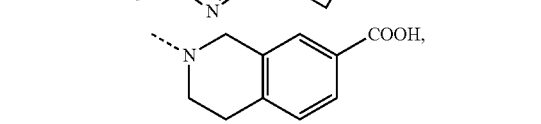
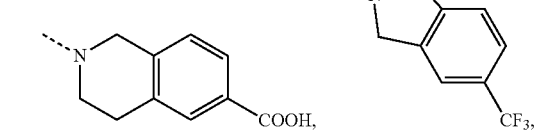

-continued

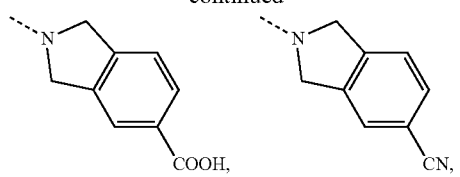
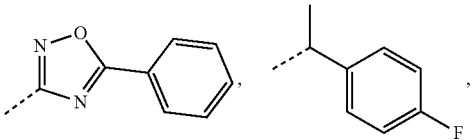
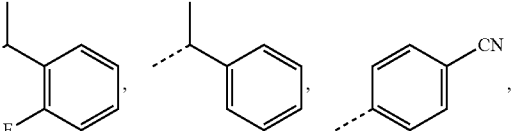
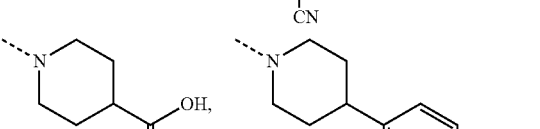

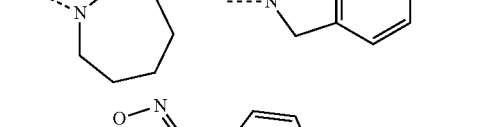
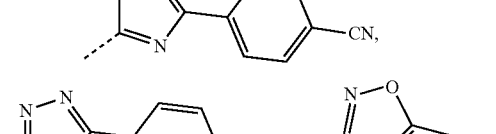
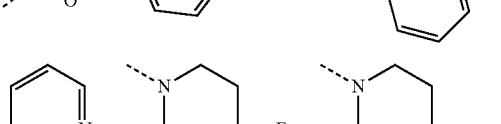
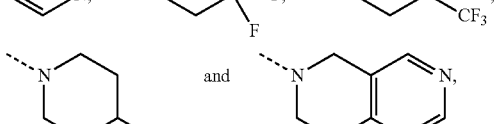
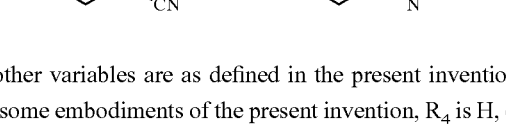

and other variables are as defined in the present invention.

In some embodiments of the present invention, $R_4$ is H, or selected from the group consisting of $C_{1-3}$ alkyl and $C_{1-4}$ alkyl-O—C(=O)—, each of which is optionally substituted by 1, 2 or 3 of R, and other variables are as defined in the present invention.

In some embodiments of the present invention. $R_4$ is selected from the group consisting of H, Me, Et,

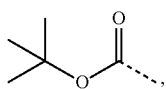

and other variables are as defined in the present invention.

In some embodiments of the present invention, $R_6$ is H, or selected from the group consisting of $C_{1-3}$ alkyl and $C_1$ alkyl-O—C(=O)—, each of which is optionally substituted by 1, 2 or 3 of R, and other variables are as defined in the present invention.

In some embodiments of the present invention, $R_6$ is selected from the group consisting of H, Me, Et and

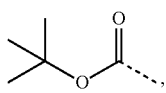

and other variables are as defined in the present invention.

In some embodiments of the resent invention the structural unit

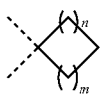

is selected from the group consisting of

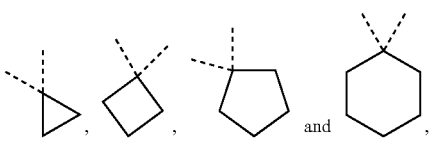

and other variables are as defined in the present invention.

In some embodiments of the present invention, the compound, the pharmaceutically acceptable salt or tautomer thereof is selected from the group consisting of (I-1)

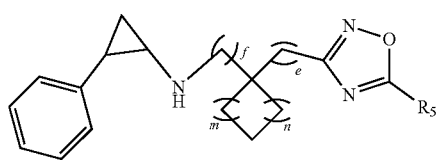

(I-2)

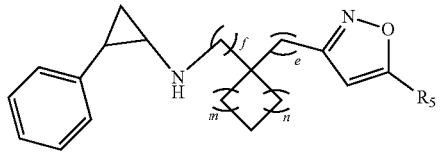

(I-3)

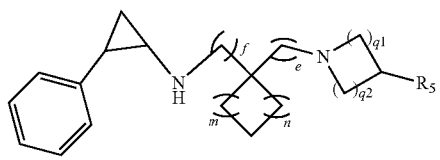

(I-4)

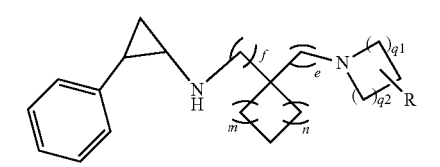

(I-5)

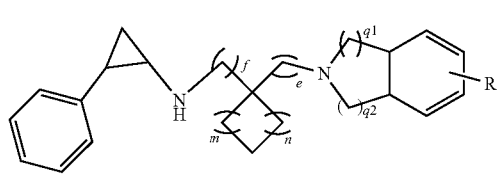

(I-6)

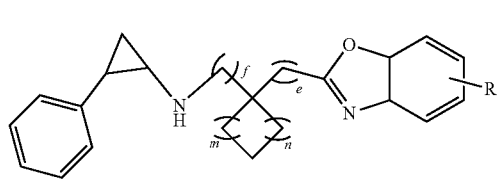

(I-7)

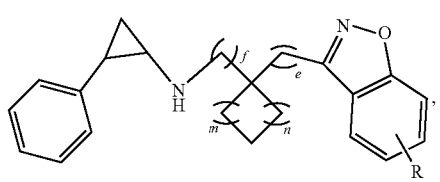

wherein e, f, m, n, $R_5$, R are as defined in the present invention; each of $q_1$ and $q_2$ is independently 1 or 2.

The invention also provides a compound, a pharmaceutically acceptable salt or a tautomer thereof which is selected from the group consisting of

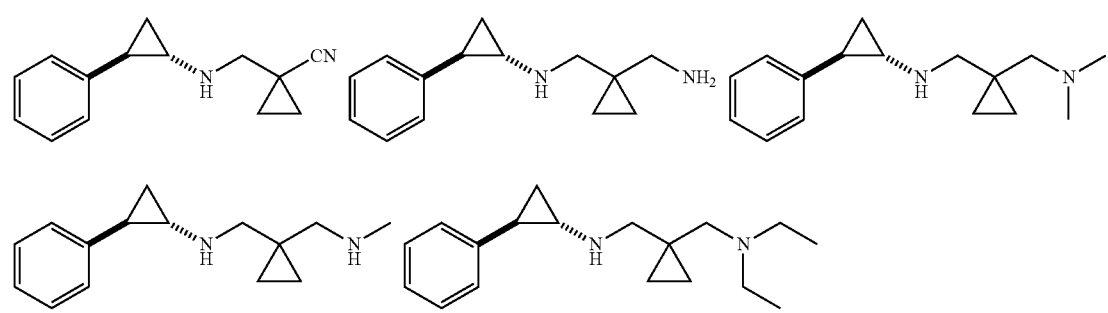

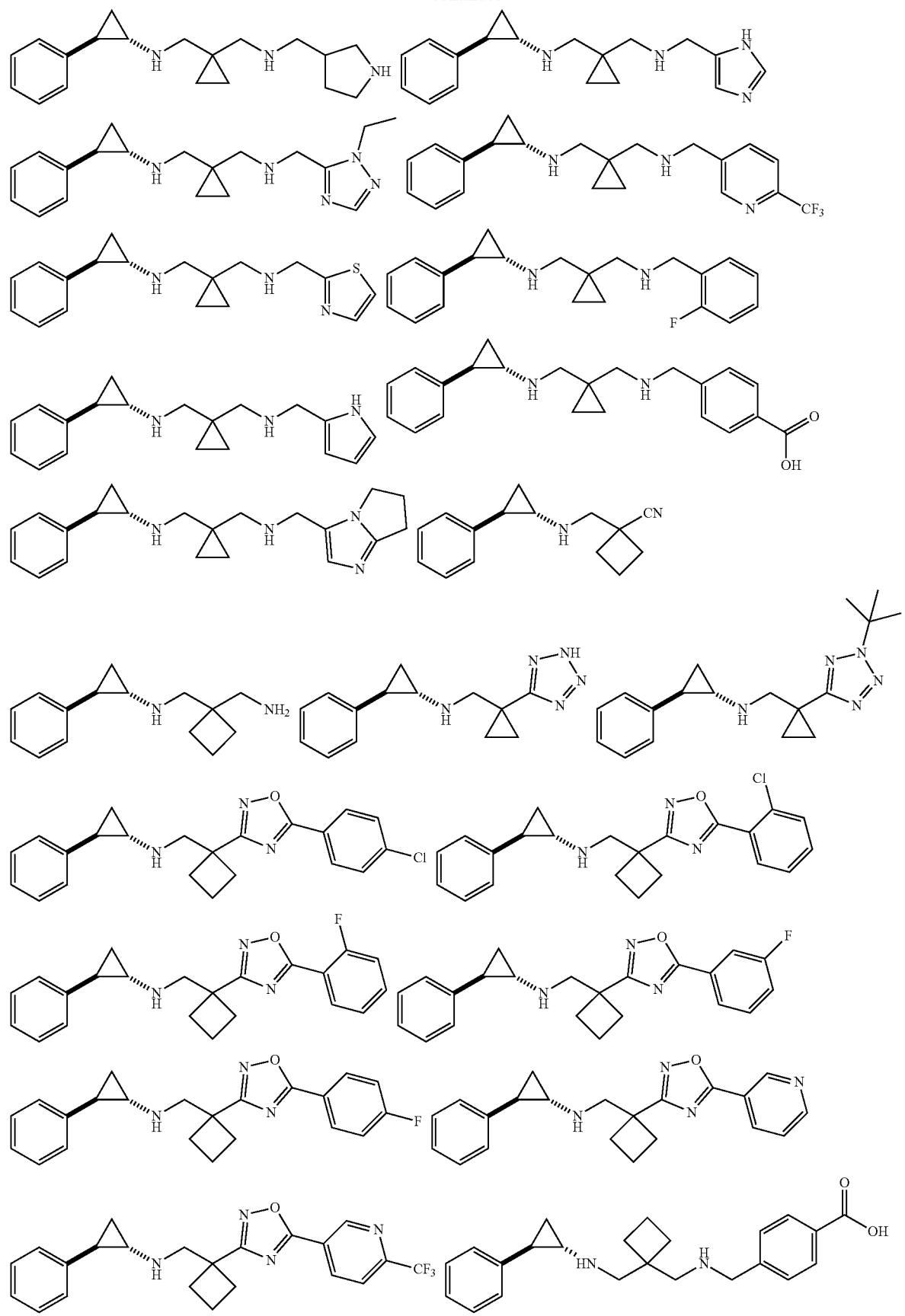

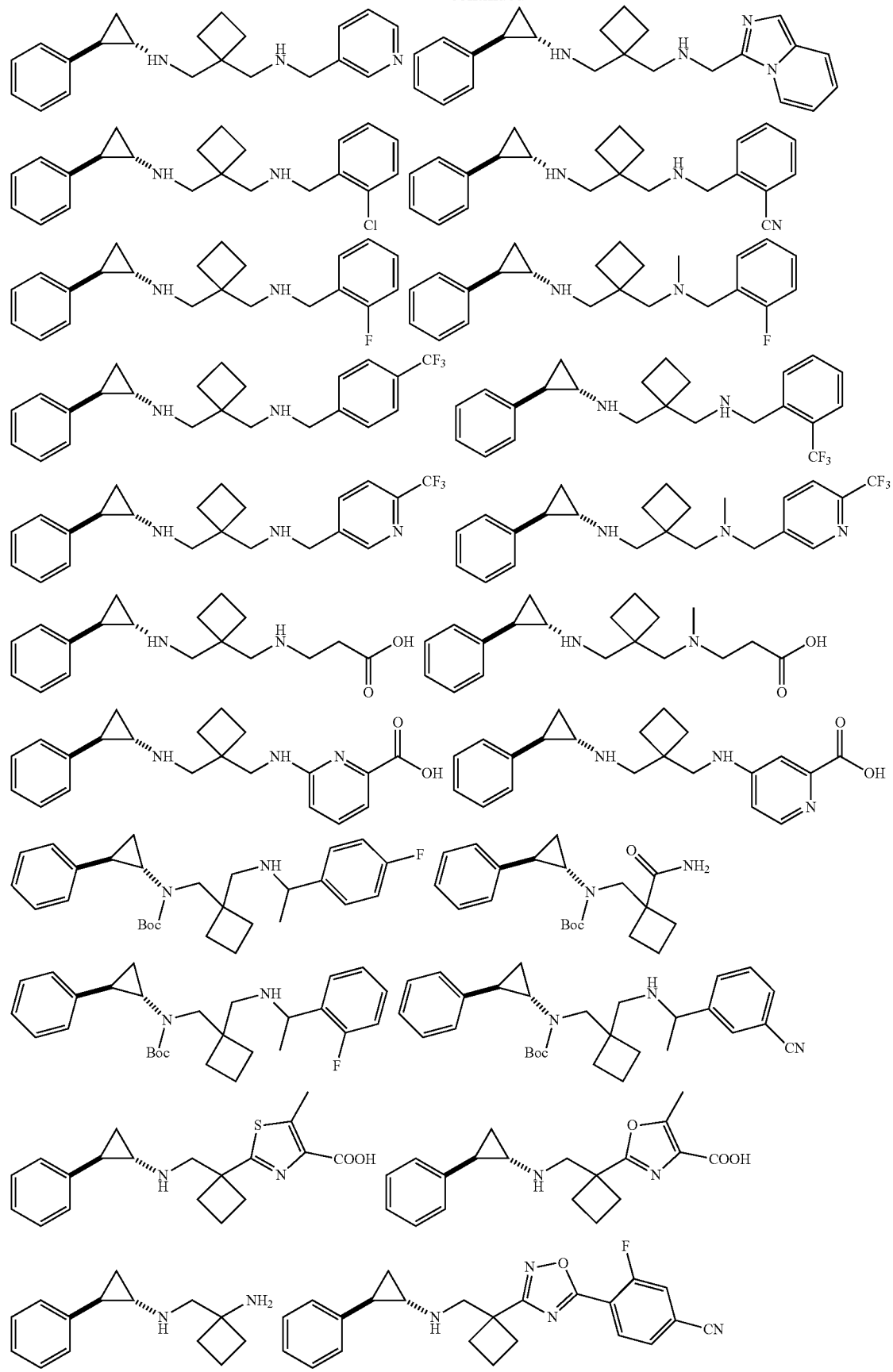

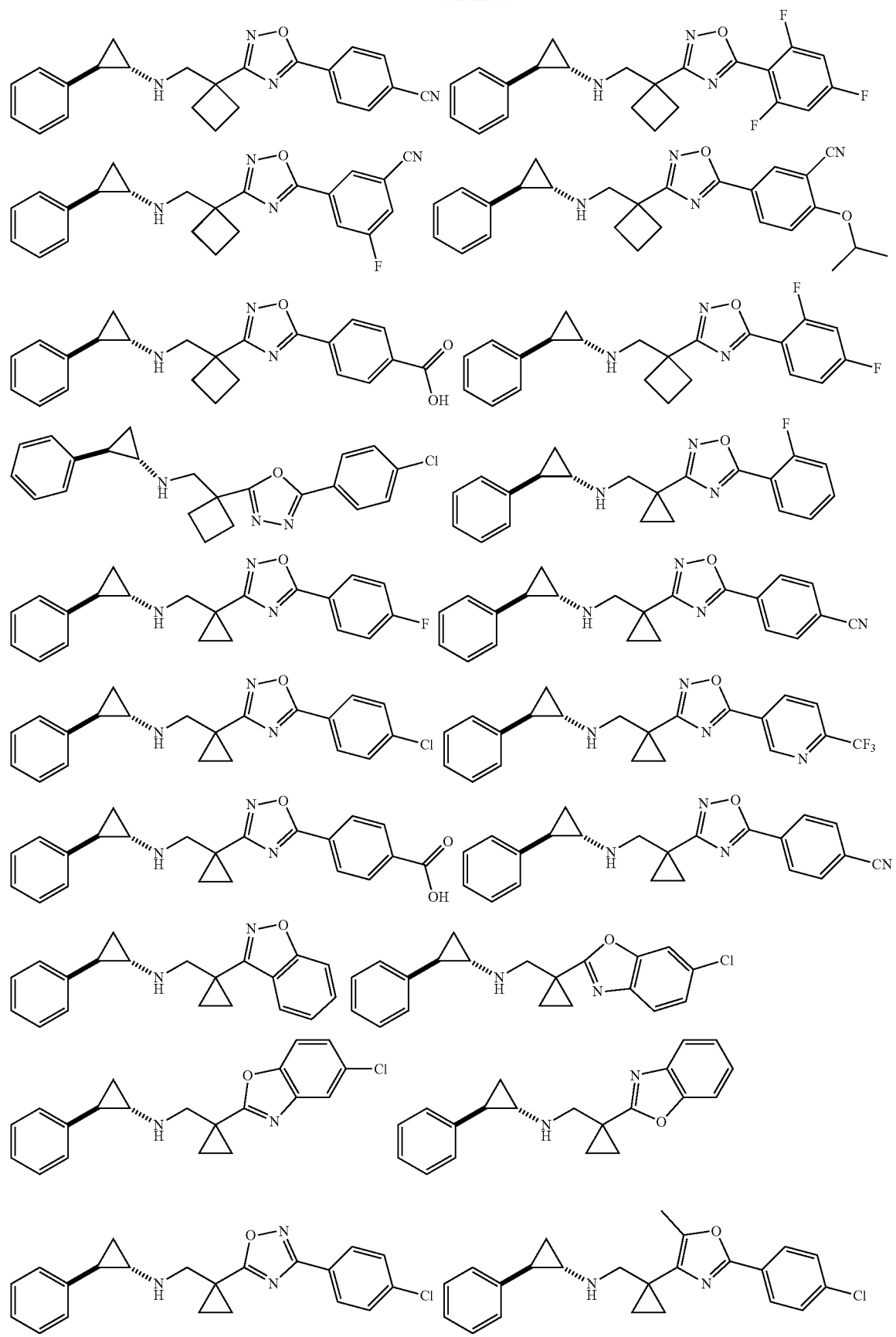

-continued
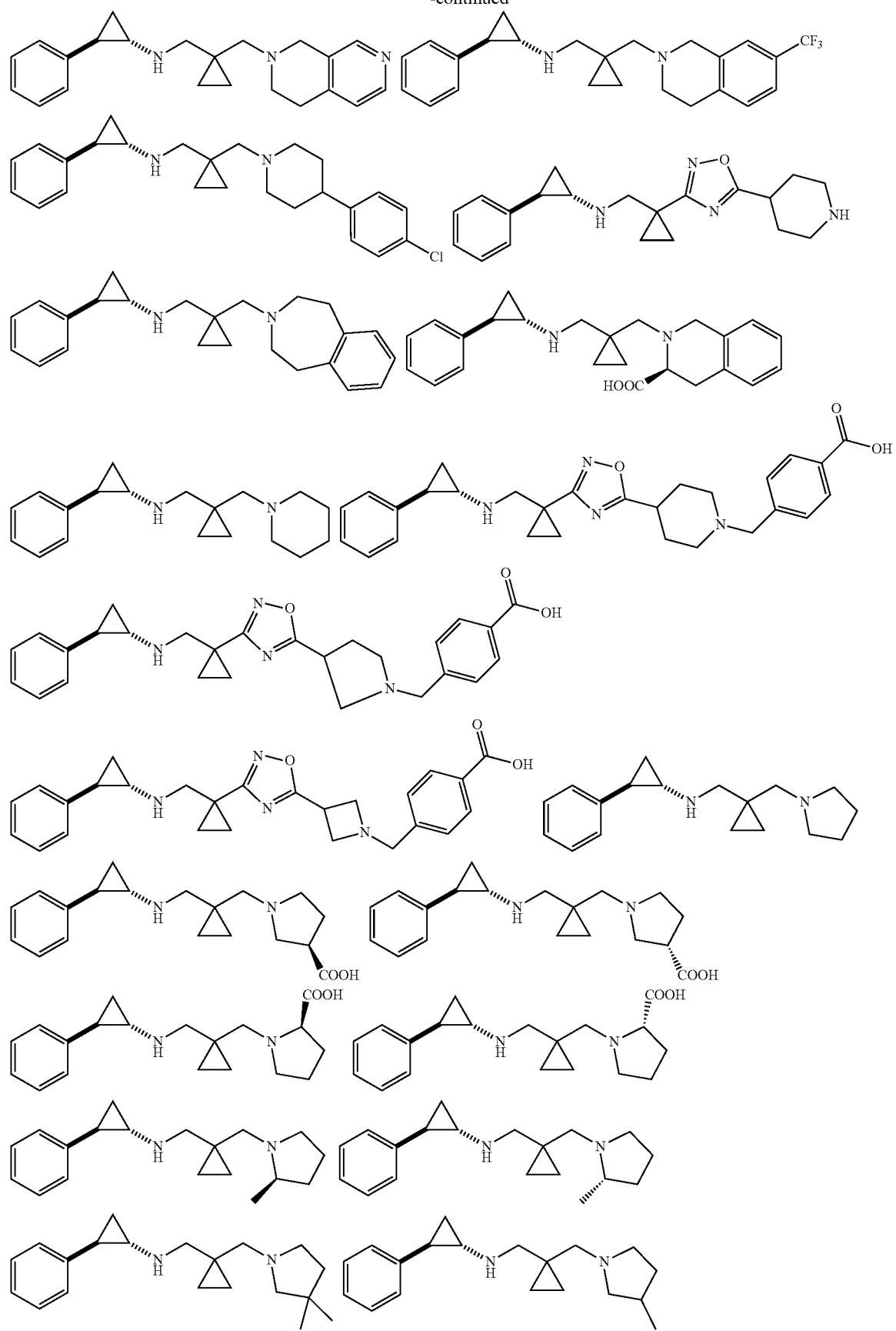

-continued
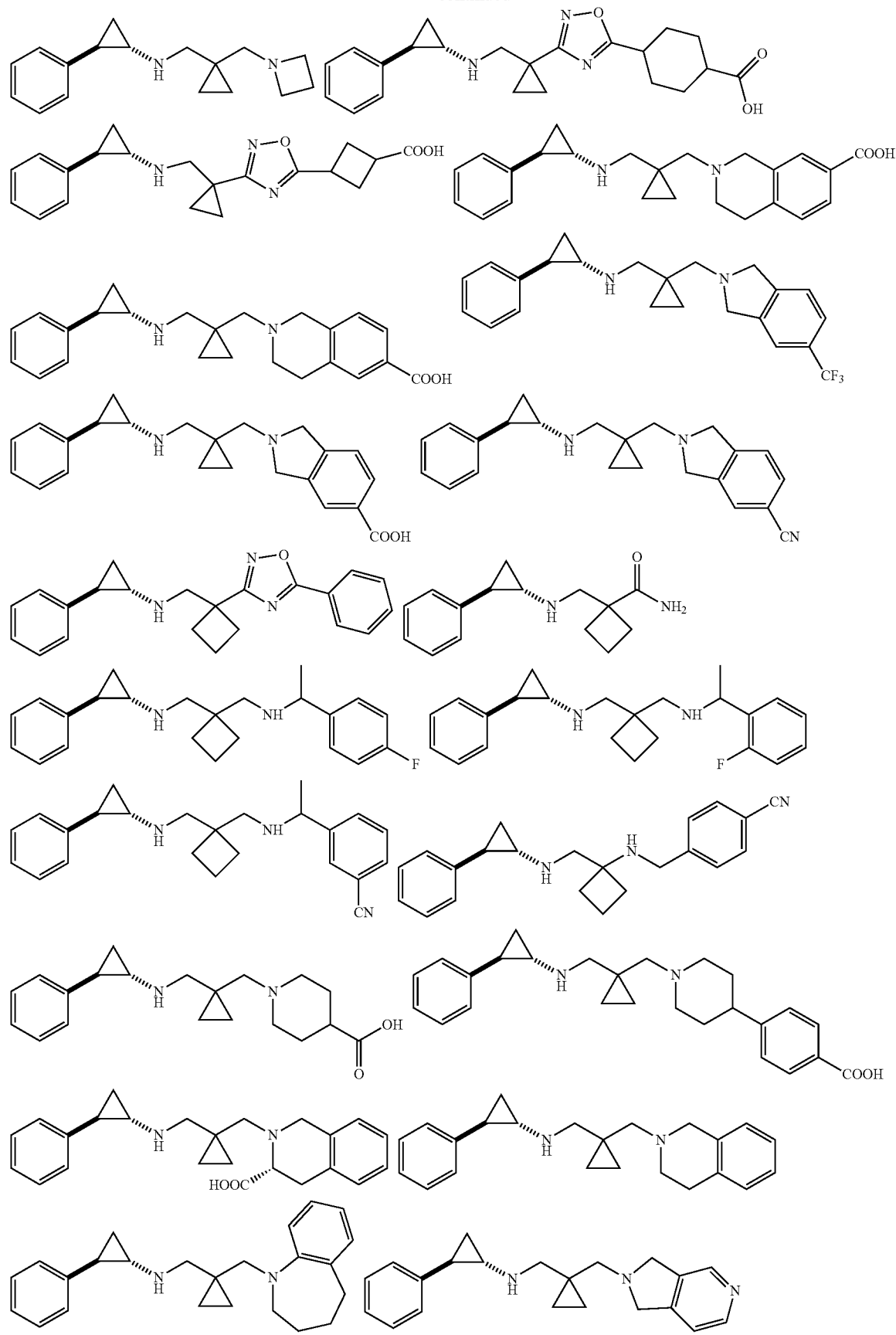

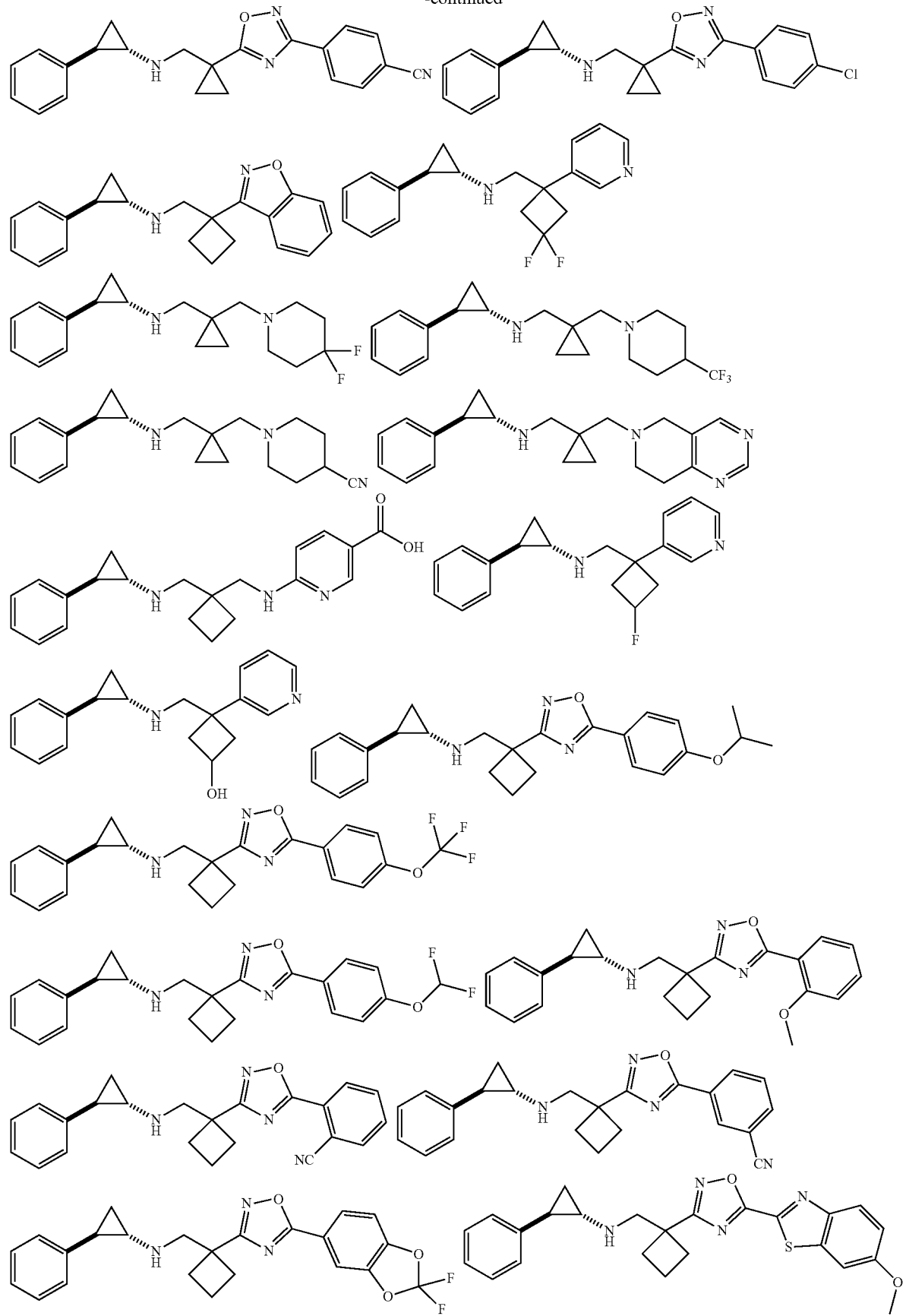

95 96
-continued
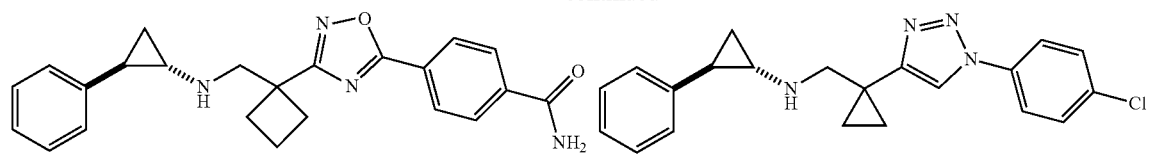
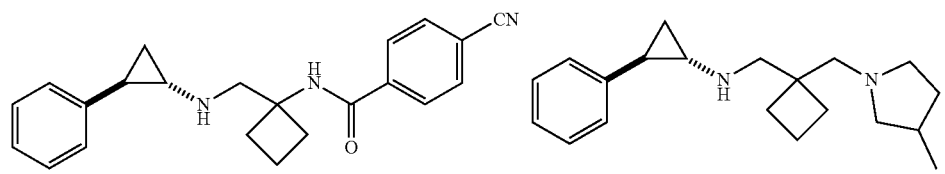
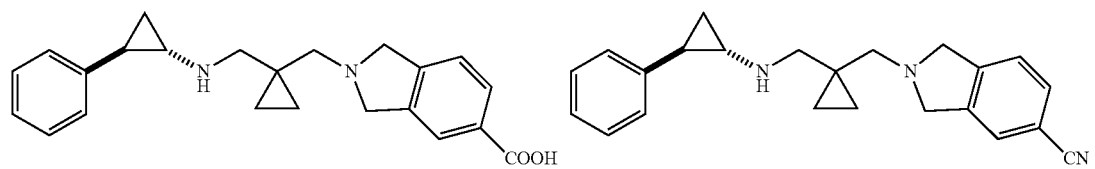
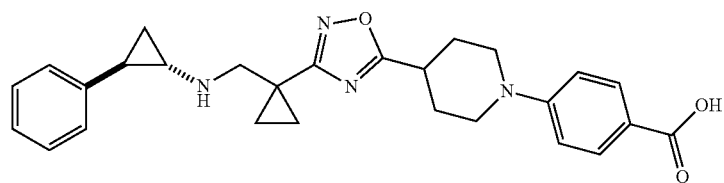
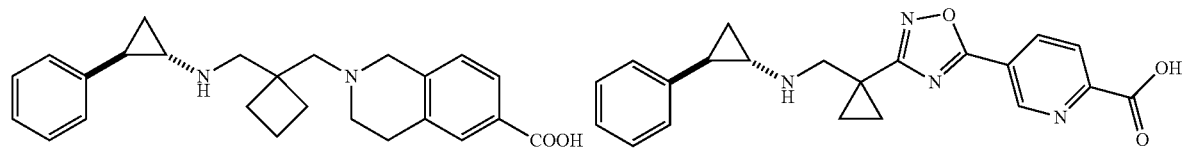
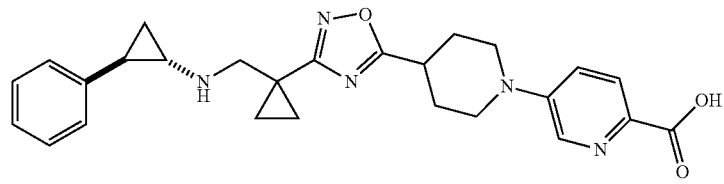
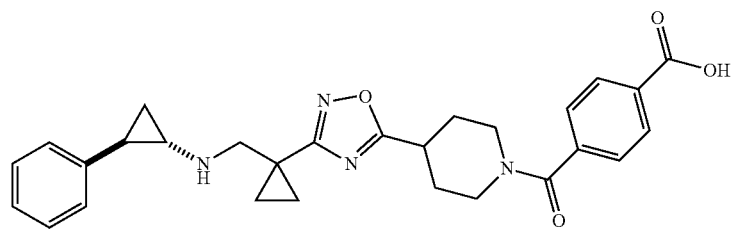
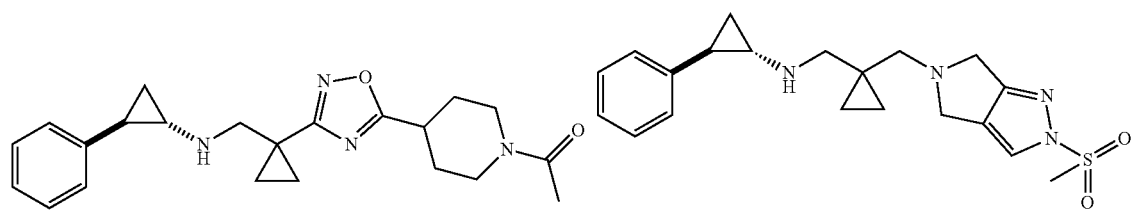
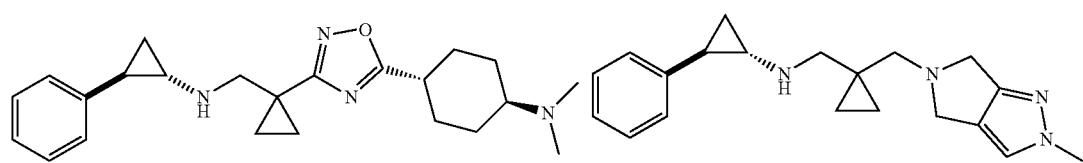

-continued
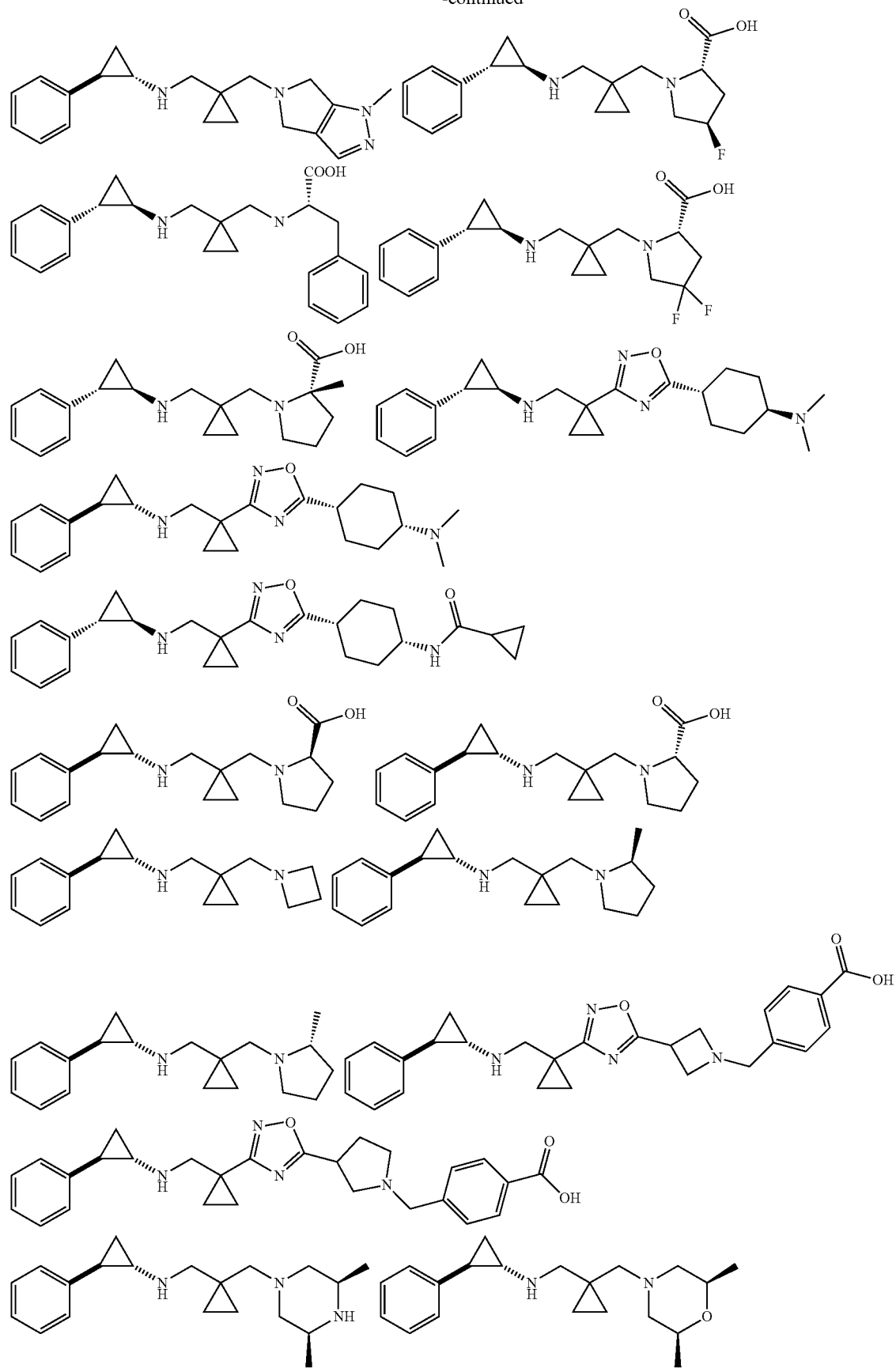

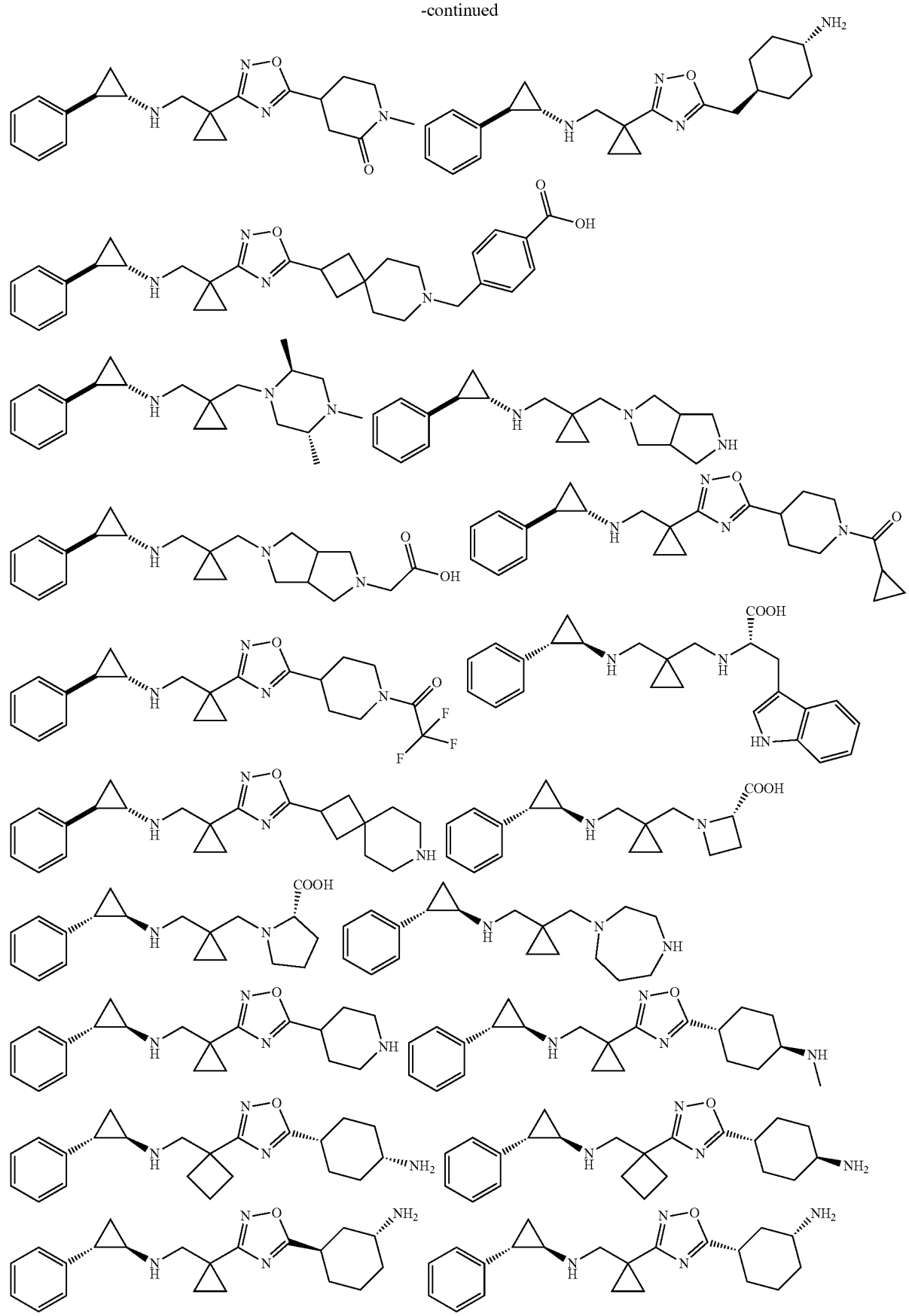

-continued
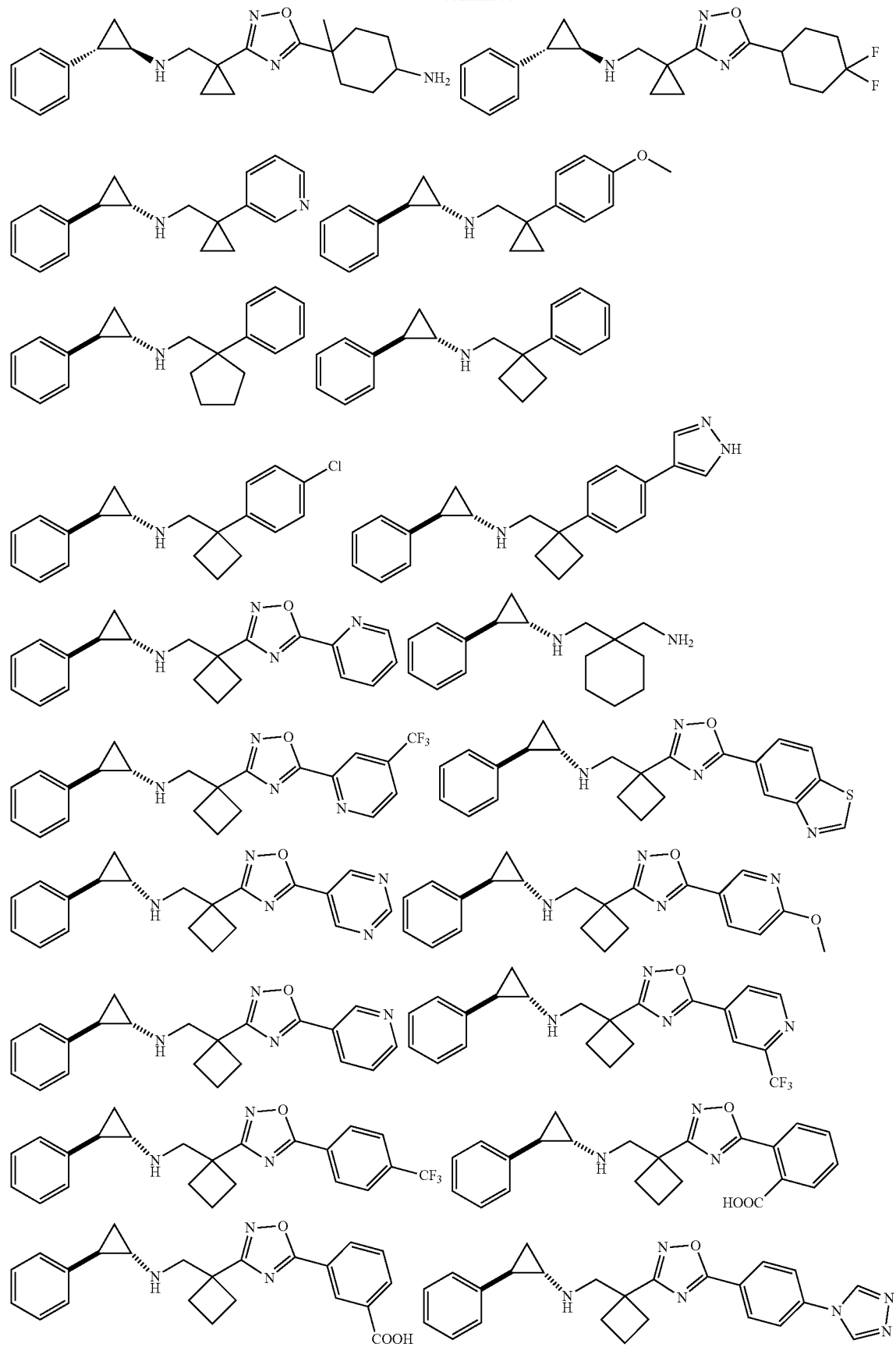

-continued
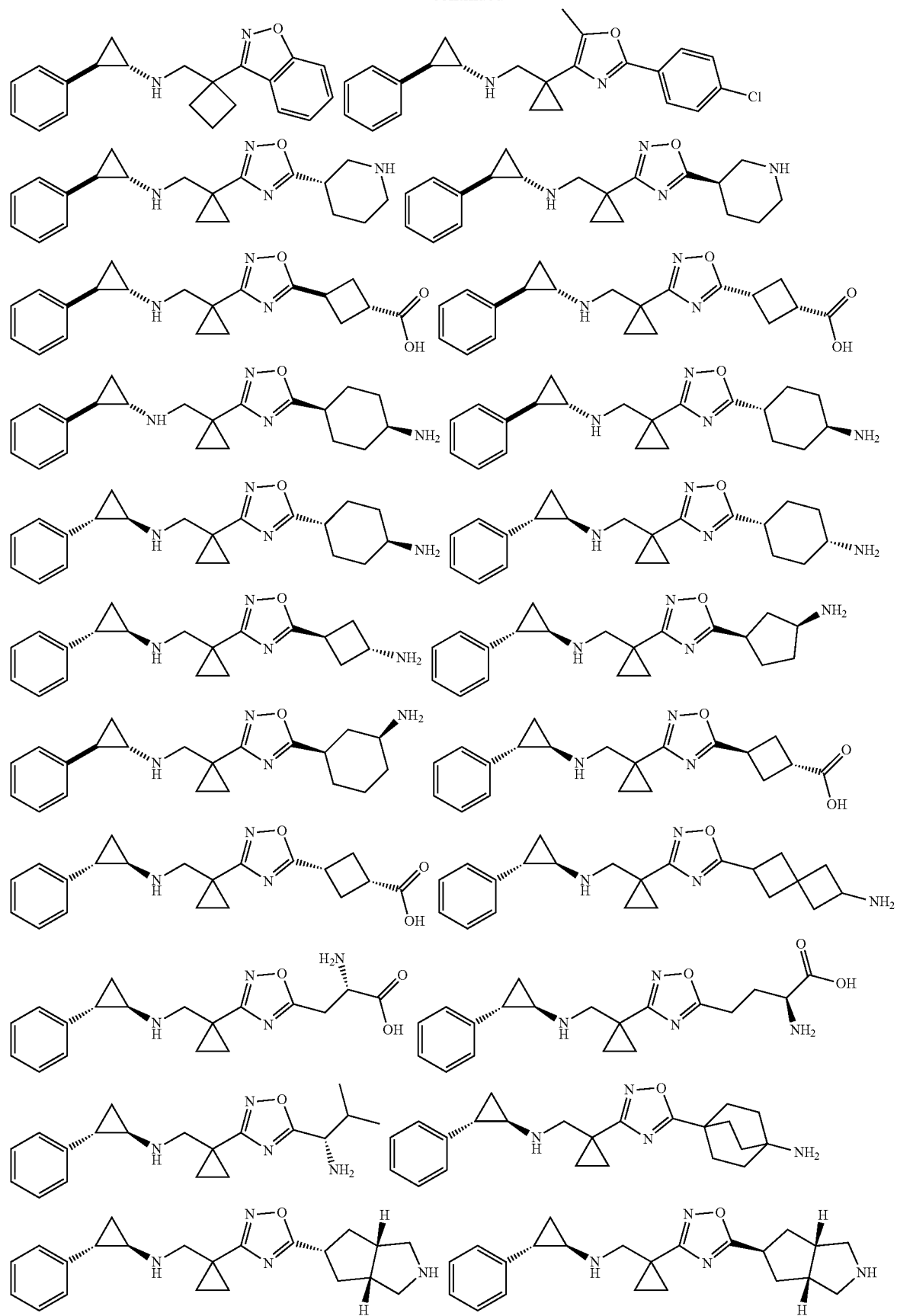

-continued
| 105 | 106 |
|---|---|
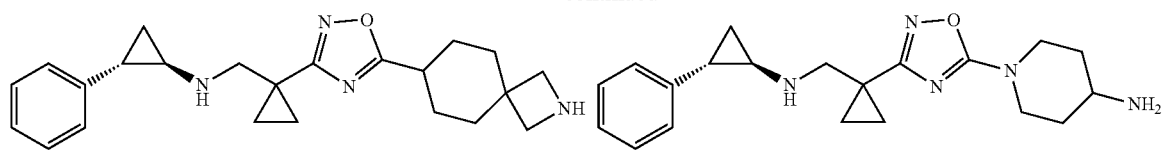
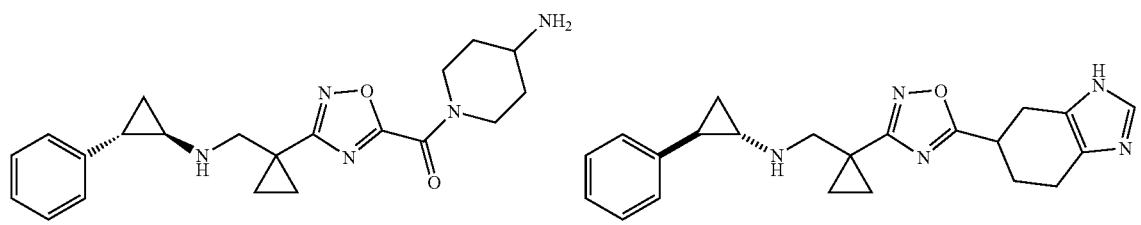
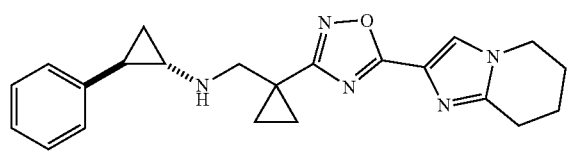
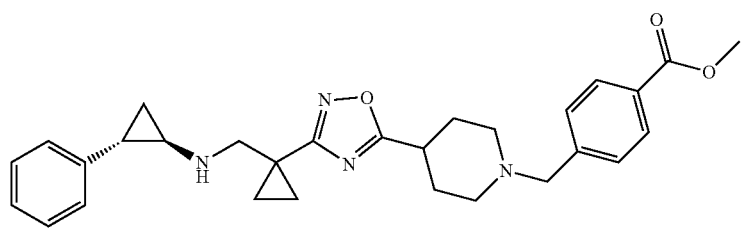
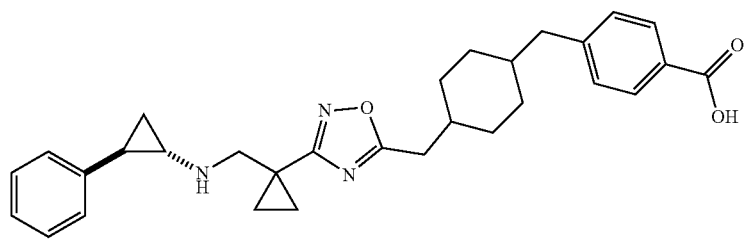
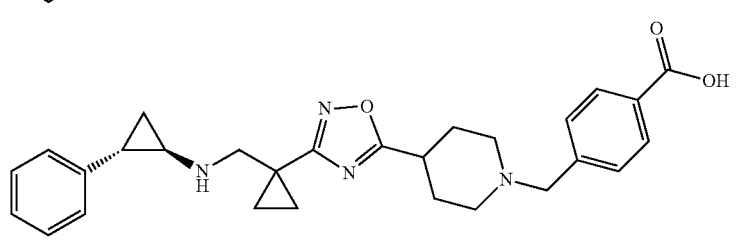
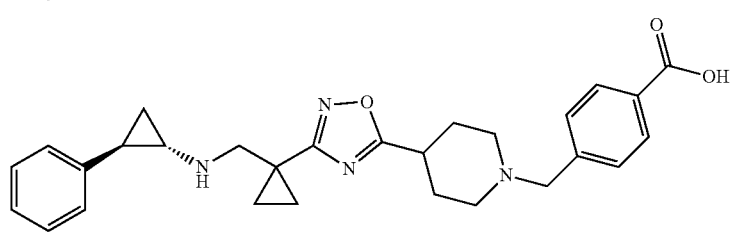
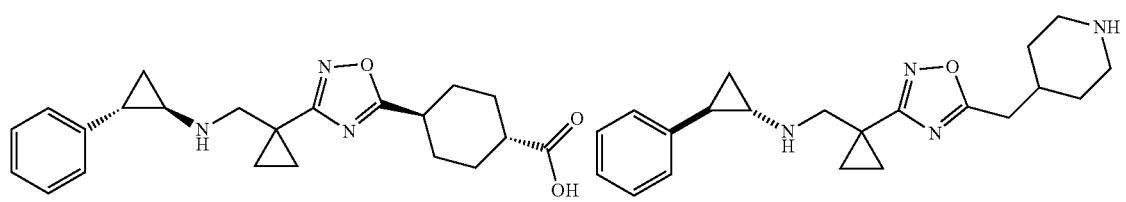

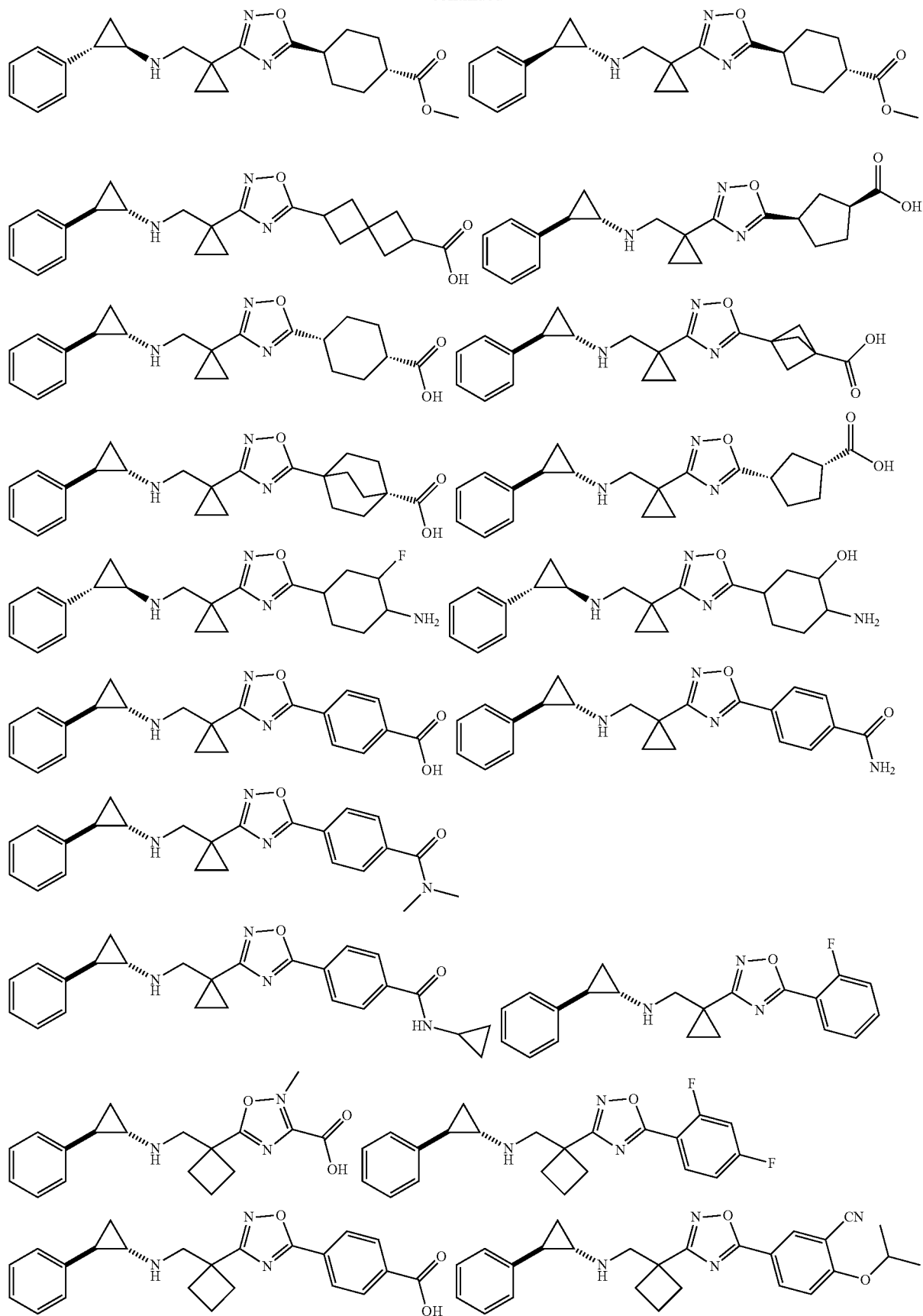

109 110
-continued
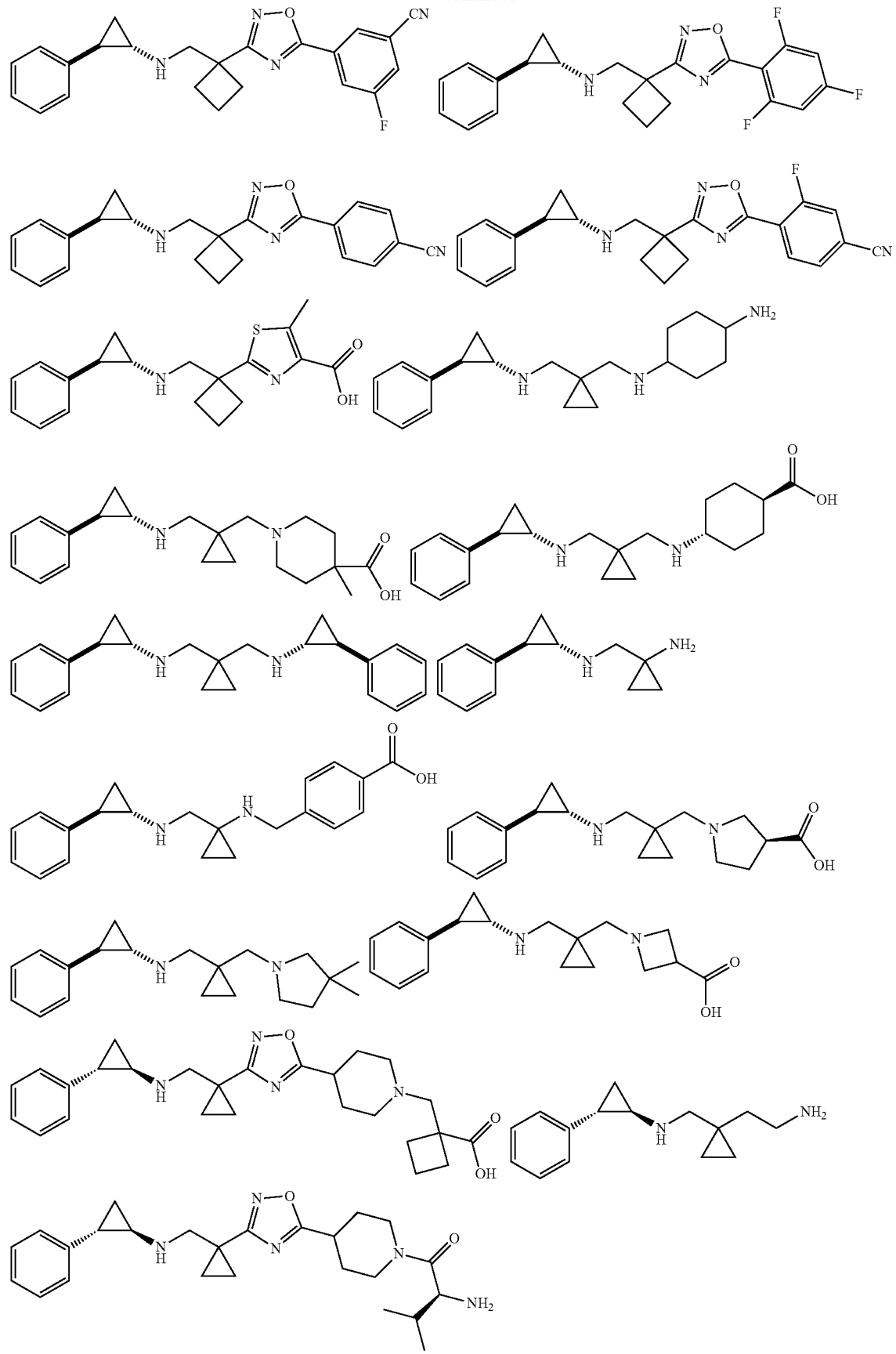

-continued
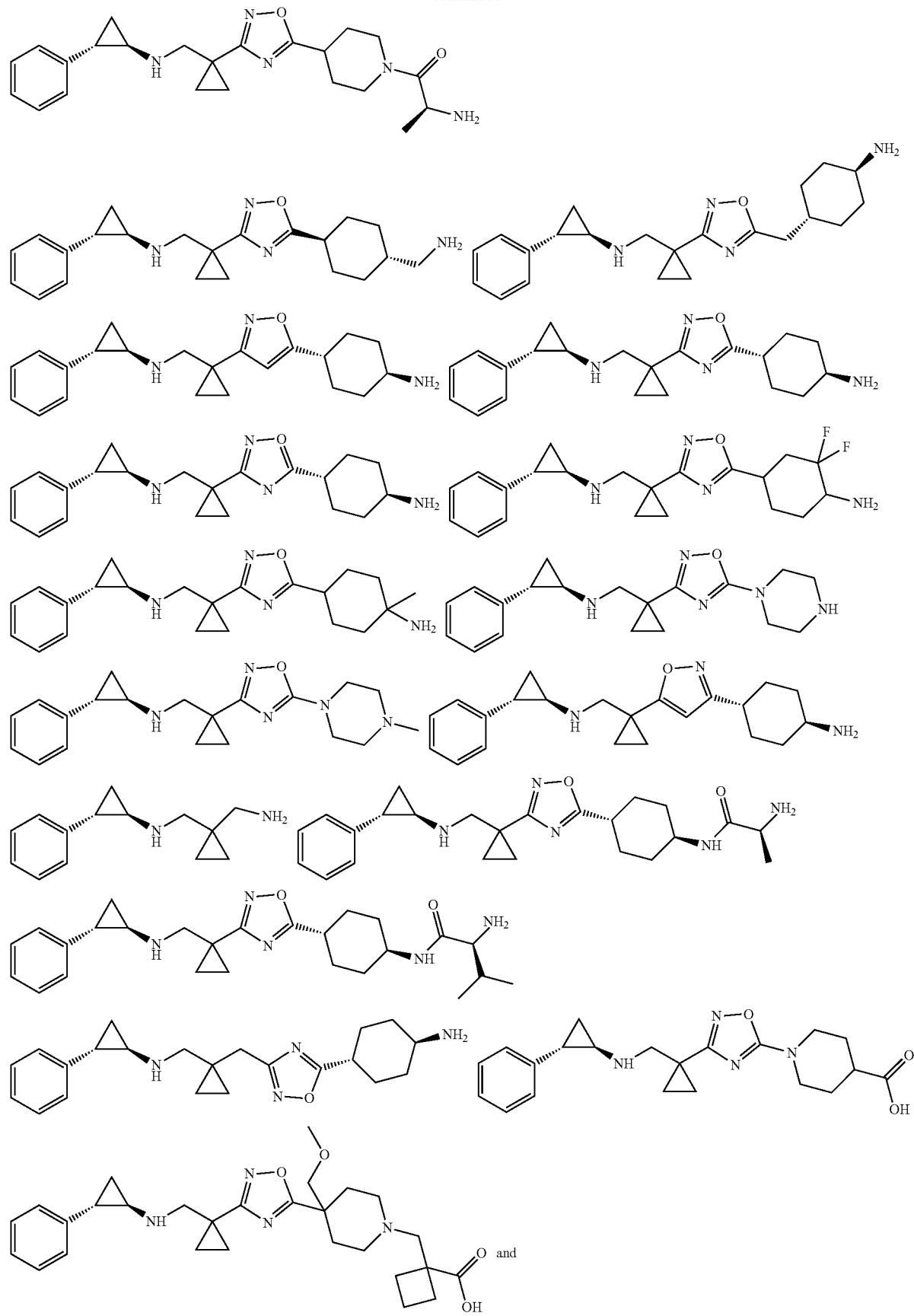

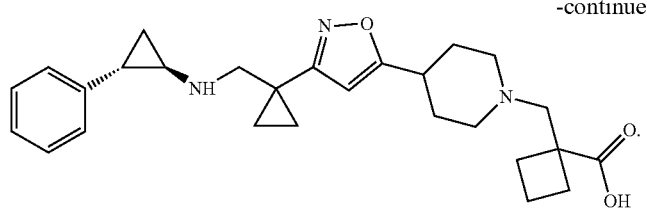

The invention also provides a composition, including a therapeutically effective amount of the above compound as an active ingredient, or the pharmaceutically acceptable salt as an active ingredient, and a pharmaceutically acceptable carrier.

The present invention also provides a use of the above compound or the pharmaceutically acceptable salt or the composition comprising the same in manufacturing a medicament for treating LSD1-related diseases.

Definition and Description

Unless otherwise indicated, the following terms when used in the descriptions and the claims of the present invention have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present invention that is prepared by reacting the compound having a specific substituent of the present invention with a relatively non-toxic acid or base. When the compound of the present invention contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present invention contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid. Tartaric acid, and methanesulfonic acid, and the like; and an salt of amino acid (such as arginine and the like), and a salt of an organic acid such as glucuronic acid and the like. Certain specific compounds of the present invention that contain both basic and acidic functional groups can be converted to any base or acid addition salt.

The pharmaceutically acceptable salt of the present invention can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof. Generally, non-aqueous media such as ether, ethyl acetate, ethanol, isopropanol or acetonitrile are preferred.

In addition to the salt form, the compound provided by the present invention also exists in prodrug form. The prodrug of the compound described herein is the compound that readily undergoes chemical change under physiological condition to be converted into the compound of the present invention. Additionally, the prodrug can be converted to the compound of the present invention by a chemical or biochemical method in vivo environment.

Certain compounds of the present invention can exist in a nonsolvated form or a solvated form, including hydrated form. Generally, the solvated form is equivalent to the nonsolvated form, and both are encompassed within the scope of the present invention.

The compound of the present invention may have a specific geometric or stereoisomeric form. The present invention contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present invention. The substituent such as alkyl may have an additional asymmetric carbon atom. All these isomers and mixtures thereof are encompassed within the scope of the present invention.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(D)" or "(+)" stands for dextrorotation, "(L)" or "(−)" stands for levorotation, "(DL)" or "(±)" stands for racemization.

Unless otherwise specified, the absolute configuration of a stereogenic center is represented by a wedged solid bond (  ) and a wedged dashed bond (  ), and the relative configuration of a stereogenic center is represented by a straight solid bond (  ) and a straight dashed bond (  ).

A wave line ( ~ ) represents a wedged solid bond ( ~ ) or a wedged dashed bond ( ~ ), or represents a straight solid bond ( ~ ) or a straight dashed bond ( ~ ).

The compounds of the invention may be present in particular. Unless otherwise indicated, the terms "tautomer" or "tautomeric form" refer to the fact that the different functional isomers are in dynamic equilibrium at room temperature and can be rapidly converted into each other. If tautomers are possible (as in solution), the chemical equilibrium of the tautomers can be achieved. For example, proton tautomers (also known as prototropic tautomers) include interconversions by proton transfer, such as keto-enol isomerization and imine-enamine isomerization. The valence tautomer includes the mutual transformation of some bonding electrons. A specific example of keto-enol tautomerization is the interconversion between two tautomers of pentane-2,4-dione and 4-hydroxypent-3-en-2-one.

Unless otherwise specified, the terms "enriched in one isomer", "isomer enriched", "enriched in one enantiomer" or "enantiomer enriched" refer to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the terms "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomer of certain compound of the present invention is to be obtained. The pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl). The compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present invention may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, hydrogen can be replaced by heavy hydrogen to form a deuterated drug, and the bond composed of barium and carbon is stronger than the bond composed of common hydrogen and carbon. Compared with undeuterated drugs, deuterated drugs have reduced side effects and increased drug stability, enhanced the efficacy and prolonged the biological half-life of the drug. All isotopic variations of the compound of the present invention, whether radioactive or not, are encompassed within the scope of the present invention.

The term "pharmaceutically acceptable carrier" refers to any agent or carrier medium which is capable of delivering an effective amount of the active substance of the present invention, does not interfere with the biological activity of the active substance and has no toxic side effect on the host or patient. The representative carrier includes water, oil, vegetable and mineral, cream base, lotion base, ointment base and the like. The base includes a suspending agent, a thickener, a penetration enhancer and the like. Their formulations are well known to the skilled in the cosmetic field or the topical pharmaceutical field.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e. =O), it means two hydrogen atoms are substituted. Positions on an aromatic ring cannot be substituted with a ketone. The term "optionally substituted" means an atom can be substituted with a substituent or not, unless otherwise specified. The type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When a bond of a substituent can be cross-linked to more than one atom on a ring, such substituent can be bonded by any of its atoms.

For example, the structural unit

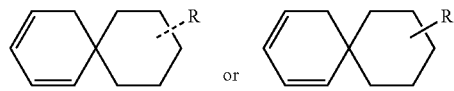

means that the substituent R can be located at any position on cyclohexyl or cyclohexadiene. When the listed substituents are not indicated by which atom is attached to the substituted group, such a substituent may be bonded through any of its atoms, for example, the pyridyl group as a substituent may be bonded to the substituted group through any one of the carbon atoms on the pyridine ring. When the enumerative linking group does not indicate the direction for linking, the direction for linking is arbitrary, for example, the linking group L contained in

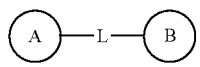

is -MW—, then -MW— can link ring A and ring B to form

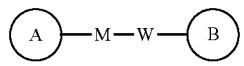

in the direction same as left-to-right reading order, and form

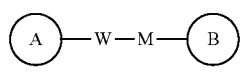

in the direction contrary to left-to-right reading order. Combinations of the linking groups, substituents and/or variants thereof are permissible only if such combinations result in stable compounds.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand. The term "5-7 membered herocycloalkyl ring" includes pyridyl and piperidinyl, but excluding phenyl. The term "ring" also includes a ring system containing at least one ring, wherein each ring independently meets the above definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and 1, 2, 3 or 4 ring heteroatoms independently selected from N, O and S, wherein any of the above heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment. The total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and 1, 2, 3 or 4 ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e, C, O, N or S) link two non-adjacent carbon or nitrogen atoms. A preferred bridged ring includes, but not limited to one carbon atom. Two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1,2,3-triazolyl, 1,2,4-triazolyl, 1,2,5-triazolyl, 1,3,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof, they can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl, the aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl. Tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —CH—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CHO—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "alkyl" refers to a linear chain or branched saturated hydrocarbon group, can be mono-substituted (e.g., —CH$_2$F) or poly-substituted (e.g., —CF$_3$), can be monovalent (e.g., methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, the term "alkenyl" refers to an alkyl group having one or more than one carbon-carbon double bonds at any position on the chain, can be mono-substituted or poly-substituted, and can be monovalent, divalent or multivalent. Examples of alkenyl include ethenyl, propenyl, butenyl, pentenyl, hexenyl, butadienyl, pentadienyl, hexadienyl, and the like.

Unless otherwise specified, the term "alkynyl" refers to an alkyl group having one or more than one carbon-carbon triple bonds at any position on the chain, can be mono-substituted or poly-substituted, and can be monovalent, divalent or multivalent. Examples of alkynyl include ethynyl, propynyl, butynyl, pentynyl, and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, cycloalkenyl includes any stable cyclic or polycyclic hydrocarbyl having one or more than one unsaturated carbon-carbon single bonds at any position on the ring, can be mono-substituted or poly-substituted, and can be monovalent, divalent or multivalent. Examples of the cycloalkenyl include, but are not limited to, cyclopentenyl, cyclohexenyl and the like.

Unless otherwise specified, cycloalkynyl includes any stable cyclic or polycyclic hydrocarbyl having one or more carbon-carbon triple bonds at any position on the ring, can be mono-substituted or poly-substituted, and can be monovalent, divalent or multivalent.

Unless otherwise specified, "cycloalkenylalkyl" or "cycloalkenylalkyl" refers to a cycloalkenyl substituted alkyl.

Unless otherwise specified, "cycloalkynyl" or "cycloalkynylalkyl" refers to a cycloalkynyl substituted alkyl.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo(C$_1$-C$_4$) alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g., one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of the above aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g, methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g, acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl acyl such as alkanoyl (e.g, actyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present invention can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present invention.

The solvent used in the present invention is commercially available. The present invention employs the following abbreviations: aq stands for water; HATU stands for 0-(7-azabenzotriazol-1-yl)-N,N,N',N'-tetramethyluronium hexafluoro-phosphate; EDC stands for N-(3-dimethylaminopropyl)-N'-ethylcarbodiimide hydrochloride; m-CPBA stands for 3-chloroperoxybenzoic acid; eq stands for equivalent, equivalent, CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for acetic acid esters; EtOH stands for ethanol; MeOH for methanol; CBz stands for benzyloxycarbonyl, an amine protecting group; BOC stands for t-butylcarbonyl is an amine protecting group; HOAc stands for acetic acid; NaCNBH$_3$ stands for sodium cyanoborohydride; Rt stands for room temperature; O/N stands for overnight; TH stands for tetrahydrofuran; Boc$_2$O stands for di-tert-butyldicarbonate; TFA stands for trifluoroacetic acid; DIPEA stands for diisopropylethylamine; SOCl$_2$ stands for thionyl chloride; Carbon disulfide; TsOH stands for p-toluenesulfonic acid; NFSI stands for N-fluoro-N-(phenylsulfonyl) benzenesulfonamide; NCS stands for 1-chloropyrrolidine-2,5-dione; n-Bu$_4$NF stands for tetrabutylammonium; iPrOH stands for 2-propanol; mp stands for melting point; LDA stands for diisopropylamino lithium; FAD stands for flavin adenine dinucleotide; TMSOTf stands for trimethylsilyl trifluoromethanesulfonate Ester; Alloc represents allyl formate; DIBAL-H represents diisobutylaluminum hydride.

Compounds are named manually or by ChemDraw® software, the commercially available compounds use their vendor directory names.

As a novel LSD1 inhibitor, the compound of the present invention has remarkable activity in vitro and has further research value, and can be used as an exploration and verification of in vivo activity of various disease models.

DETAILED DESCRIPTION OF THE PREFERRED EMBODIMENT

The following examples further illustrate the present invention, but the present invention is not limited thereto. The present invention has been described in detail in the text, and its specific embodiments have also been disclosed, for one skilled in the art, it is obvious to modify and improve the embodiments of the present invention within the spirit and scope of the present invention. The reference materials used in reference example 1 and reference example 2 were trans-racemate.

Reference Example 1

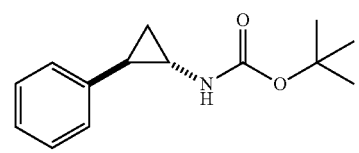

A-1

Synthetic Route:

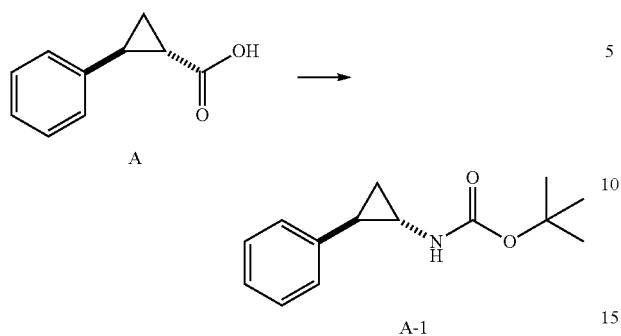

Compound A (26.0 g, 160 mmol), diphenylphosphoryl azide (44.1 g, 154 mmol) and triethylamine (24.3 g, 231 mmol) were dissolved in tert-butanol (250 mL) under nitrogen. The solution was stirred at 90° C. for 12 hours. Water (500 mL) was added to the reaction mixture and the mixture was extracted with ethyl acetate (300 mL×2). The organic phases were combined, washed with saturated brine (300 mL×1) and dried over anhydrous sodium sulfate, followed by filtration and concentration under reduced pressure. And the obtained crude material was purified by silica gel column chromatography (8:1 petroleum ether/ethyl acetate, Rf=0.45) to give compound A-1 (27.0 g). $^1$H NMR (400 MHz, CDCl$_3$) δ 7.30-7.26 (m, 1H), 7.20-7.19 (m, 1H), 7.16-7.14 (m, 1H), 7.15-7.10 (m, 2H), 2.80-2.70 (m, 1H), 2.08-2.04 (m, 1H), 1.48 (s, 9H), 1.22-1.16 (m, 2H).

Reference Example 2

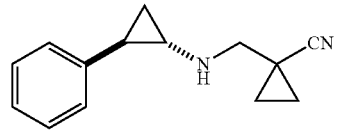

Synthetic Route:

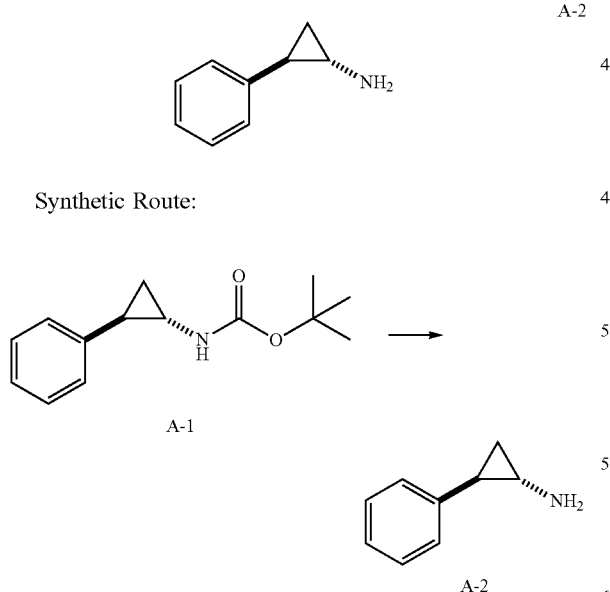

Compound A-1 (27.0 g, 115 mmol) was dissolved in ethyl acetate (100 mL), hydrochloric acid/ethyl acetate (4 M, 260 mL, 1.04 mol) was added at 0° C. The reaction solution was stirred at 25° C. for 2 h. The reaction solution was concentrated under reduced pressure to remove solvent. The residue was adjusted to pH=8 by saturated sodium bicarbonate solution and extracted with ethyl acetate (100 mL×2). The organic phase was washed with saturated brine (100 mL) and dried over anhydrous sodium sulfate, followed by filtration and concentration under reduced pressure to give compound A-2 (11.1 g). $^1$H NMR (400 MHz, CDCl$_3$) δ 7.19-7.16 (m, 2H), 7.09-7.07 (m, 1H), 6.96-6.94 (m, 2H), 2.50-2.46 (m, 1H), 1.81-1.77 (m, 1H), 0.99-0.95 (m, 1H), 0.93-0.90 (m, 1H).

Example 1

Synthetic Route:

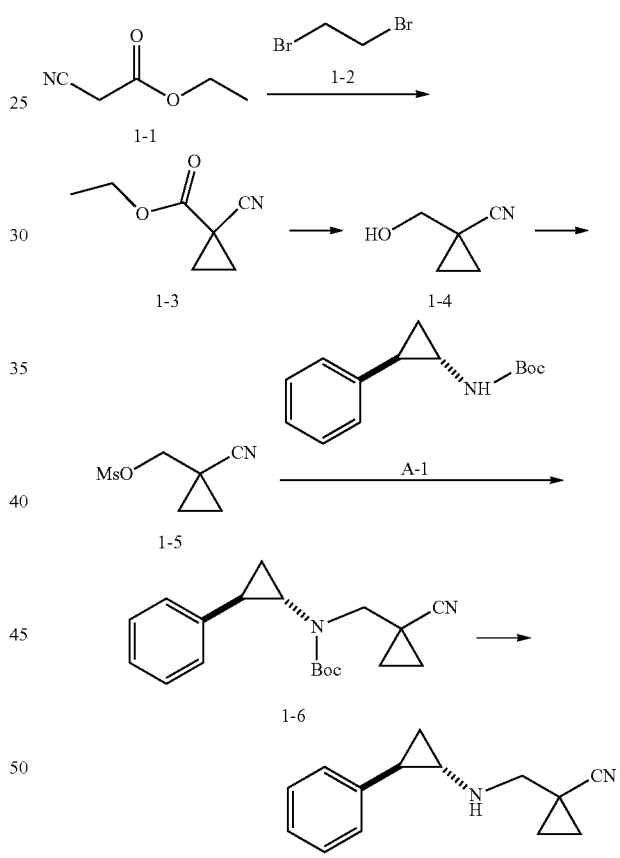

Step 1

Compound 1-1 (10.60 g, 93.7 mmol) was dissolved in anhydrous N,N-dimethylformamide (10 mL), cesium carbonate (61.1 g, 187 mmol) and compound 1-2 (21.1 g, 112 mmol) were added portionwise at 0° C. The reaction solution was stirred at 0° C. for 30 min and then warmed to room temperature and then stirred for 2 h. Water (50 mL) was added to the mixture and the mixture was extracted with ethyl acetate (50 mL×2). The organic phases were combined, washed with saturated brine (50 mL×1), dried over anhydrous sodium sulfate, filtrated and concentrated under reduced pressure. The obtained crude product was purified by silica gel column chromatography (3:1 petroleum ether/ ethyl acetate, Rf=0.34) to give compound 1-3 (2.10 g). $^1$H NMR (400 MHz, CDCl$_3$) δ 4.26 (q, J=6.8 Hz, 2H), 1.68 (t, J=3.2 Hz, 2H), 1.62 (t, J=3.2 Hz, 2H), 1.33 (t, J=6.8 Hz, 3H).

Step 2

Compound 1-3 (2.10 g, 15.9 mmol) was dissolved in methanol (20 mL), and lithium borohydride (0.492 g, 22.6 mmol) was added portionwise at 0° C., and the mixture was stirred at room temperature for 1 h. Water (10 mL) was added to the mixture. The mixture was adjusted to pH=7 by adding hydrochloric acid (1 mol/L), extracted with ethyl acetate (50 mL×5). The organic phases were combined, washed with saturated brine (50 mL×1) and dried over anhydrous sodium sulfate, followed by filtration and concentration under reduced pressure to give compound 1-4 (2.20 g). $^1$H NMR (400 MHz, CDCl$_3$) δ 3.63 (s, 2H), 2.20 (s, 1H), 1.29 (dd, J$_1$=5.2 Hz, J$_2$=2.0 Hz, 2H), 0.99 (dd, J$_1$=5.2 Hz, J$_2$=2.0 Hz, 2H).

Step 3

Compound 1-4 (1.90 g, 19.5 mmol) was dissolved in dichloromethane (20 mL), methanesulfonyl chloride (4.70 g, 41.0 mmol) and triethylamine (4.16 g, 41.1 mmol) were added portionwise at 0° C., and the mixture was stirred at room temperature for 1 hour. The reaction was quenched with water (10 mL) and sodium hydroxide solution (5 mL, 1 mol/L). The reaction mixture was adjusted to pH=6 by adding 1N hydrochloric acid, extracted with ethyl acetate (30 mL×2). The organic phases were combined, washed with saturated brine (50 mL×1) and dried over anhydrous sodium sulfate, followed by filtration and concentration under reduced pressure. The obtained crude material was purified by silica gel column chromatography (1:1 petroleum ether/ethyl acetate, Rf=0.30) to give compound 1-5 (330 mg). $^1$H NMR (400 MHz, CDCl$_3$) δ 4.14 (s, 2H), 3.09 (s, 3H), 1.43-1.40 (m, 2H), 1.16-1.13 (m, 2H).

Step 4

Compound A-1 (221 mg, 0.954 mmol) was dissolved in anhydrous N,N-dimethylformamide (5 mL), sodium hydride (76.1 mg, 1.90 mmol, 60%) was added at 0° C. and stirred for 0.5 h, and then compound 1-5 (200 mg, 1.14 mmol) was added. The reaction mixture was stirred at room temperature for 24 h. Water (10 mL) was added to the mixture. The mixture was extracted with ethyl acetate (50 mL×3). The organic phases were combined, washed with saturated brine (50 mL×2) and dried over anhydrous sodium sulfate, followed by filtration and concentration under reduced pressure, and the obtained crude material was isolated and purified by a thin layer chromatography (4:1 petroleum ether/ethyl acetate. Rf=0.46) to give compound 1-6 (145 mg). $^1$H NMR (400 MHz, CDCl$_3$) δ 7.30-7.26 (m, 2H), 7.21-7.17 (m, 1H), 7.14-7.12 (m, 2H), 3.45-3.38 (m, 2H), 2.99-2.95 (m, 1H), 2.17-2.12 (m, 1H), 1.44 (s, 9H), 1.35-1.25 (m, 4H), 1.05-0.99 (m, 2H). MS-ESI calculated [M+H]$^+$ 313, found 313.

Step 5

The compound 1-6 (70.0 mg, 0.224 mmol) was dissolved in ethyl acetate (2 mL), hydrochloric acid/ethyl acetate (4 mol/L, 4 mL) was added dropwise at 0° C. The reaction mixture was stirred at room temperature for 1 h, followed by concentration under reduced pressure, and the obtained crude material was purified by preparative high-performance liquid chromatography to give compound 1 (38.0 mg). $^1$H NMR (400 MHz, Methonal-d$_4$) δ 7.37-7.30 (m, 2H), 7.25-7.23 (m, 1H), 7.20-7.17 (m, 2H), 3.47-3.39 (m, 2H), 3.08-3.04 (m, 1H), 2.58-2.53 (m, 1H), 1.61-1.55 (m, 1H), 1.49-1.42 (m, 3H), 1.31-1.28 (m, 2H). MS-ESI calculated [M+H]$^+$ 213, found 213.

Example 2

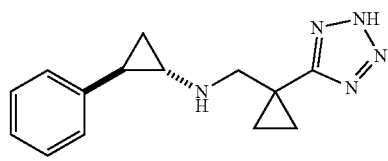

Synthetic Route:

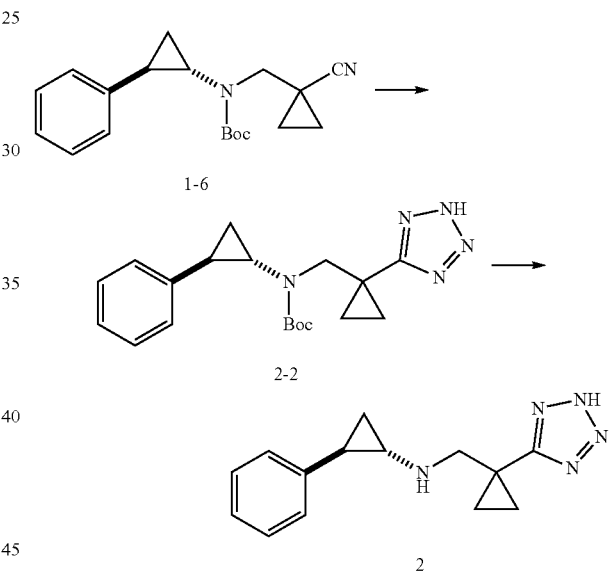

Step 1

Compound 1-6 (100 mg, 0.321 mmol), trimethylsilyl azide (147 mg, 1.28 mmol) and di-n-butyltin oxide (26.3 mg, 0.105 mmol) were dissolved in anhydrous dioxane (2 mL). The reaction solution was heated to 140° C. by microwave for 2.5 h. The reaction mixture was concentrated to give compound 2-2 (120 mg). MS-ESI calculated [M+H]$^+$ 356, found 356.

Step 2

Compound 2-2 (80 mg, 0.225 mmol) was dissolved in anhydrous dichloromethane (2 mL), trifluoroacetic acid (2 mL) was added dropwise at 0° C. The reaction solution was stirred at 0° C. for 1 hour, followed by concentration under reduced pressure, and the obtained crude material was purified by preparative high-performance liquid chromatography to give compound 2 (46.0 mg). $^1$H NMR (400 MHz, Methonal-$d_4$) δ 7.32-7.28 (m, 2H), 7.24-7.20 (m, 1H), 7.17-7.15 (m, 2H), 3.78-3.70 (m, 2H), 3.11-3.06 (m, 1H), 2.57-2.54 (m, 1H), 1.59-1.54 (m, 1H), 1.43-1.38 (m, 5H). MS-ESI calculated [M+H]⁺ 256, found 256.

Example 3

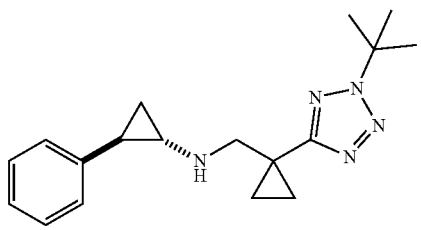

Synthetic Route:

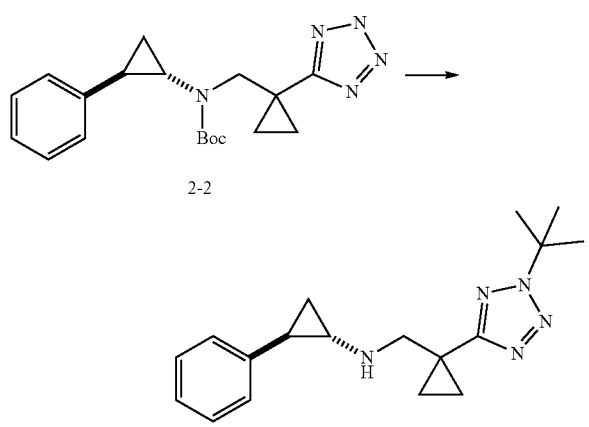

The synthesis of compound 3 (12.0 mg) was referred to the second step of example 2. ¹H NMR (400 MHz, Methonal-$d_4$) δ 7.33-7.29 (m, 2H), 7.25-7.23 (m, 1H), 7.18-7.16 (m, 2H), 3.78-3.70 (m, 2H), 3.12-3.08 (m, 1H), 2.58-2.55 (m, 1H), 1.72 (s, 9H), 1.58-1.55 (m, 1H), 1.43-1.36 (m, 5H). MS-ESI calculated [M+H]⁺ 312, found 312.

Example 4

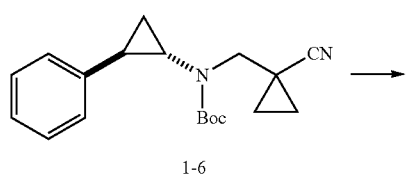

Synthetic Route:

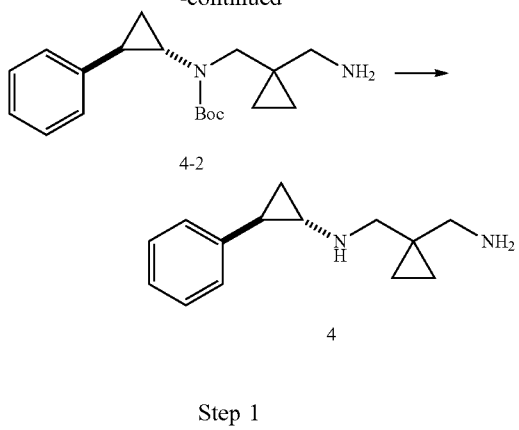

Step 1

Compound 1-6 (70.0 mg, 0.224 mmol) was dissolved in methanol (5 mL), sodium borohydride (67.8 mg, 1.79 mmol) and cobalt dichloride (116 mg, 0.896 mmol) were added portionwise at 0° C., and the mixture was stirred at room temperature for 3 h. Ethyl acetate (20 mL) and 1N NaOH solution (1 mL) were sequentially added to the mixture, and then the mixture was filtered through celite. The filtrate was diluted with water (10 mL), extracted with ethyl acetate (20 mL×3). The organic phases were combined, washed with saturated brine (30 mL×2) and dried over anhydrous sodium sulfate, followed by filtration and concentration under reduced pressure, and the obtained crude material was isolated and purified by thin layer chromatography (10:1 dichloromethane/methanol, Rf=0.32) to give compound 4-2 (45.0 mg). ¹H NMR (400 MHz, CDCl₃) δ 7.28-7.25 (m, 2H), 7.19-7.16 (m, 1H), 7.08-7.06 (m, 2H), 3.54-3.50 (m, 1H), 3.03 (brs, 2H), 2.76-2.74 (m, 1H), 2.60 (d, J=13.6 Hz, 1H), 2.41 (d, J=13.6 Hz, 1H), 2.11-2.06 (m, 1H), 1.04 (s, 9H), 1.28-1.17 (m, 3H), 0.50-0.46 (m, 2H), 0.39-0.30 (m, 2H).

Step 2

The synthesis of compound 4 (24.0 mg) was referred to the fifth step of example 1. ¹H NMR (400 MHz, Methonal-$d_4$) δ 7.31-7.28 (m, 2H), 7.23-7.18 (m, 3H), 3.39-3.28 (m, 2H), 3.17-3.12 (m, 2H), 3.06-3.02 (m, 1H), 2.75-2.70 (m, 1H), 1.73-1.68 (m, 1H), 1.38-1.33 (m, 1H), 0.95-0.92 (m, 2H), 0.89-0.86 (m, 2H). MS-ESI calculated [M+H]⁺ 217, found 217.

Example 5

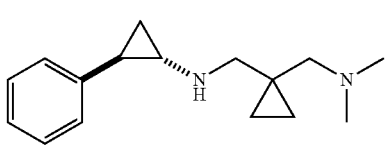

Synthetic Route:

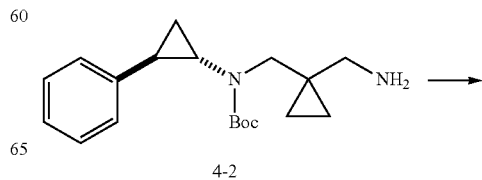

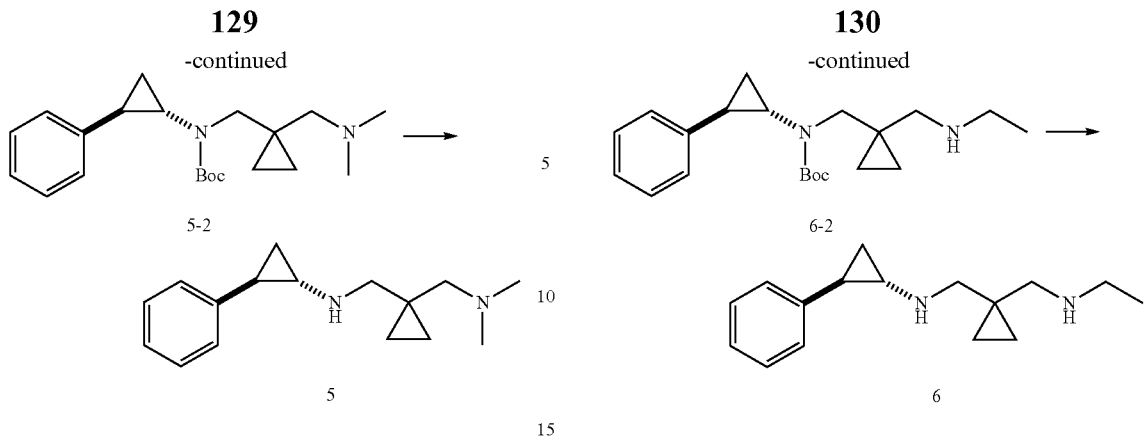

Step 1

Compound 4-2 (100 mg, 0.316 mmol) was dissolved in dichloromethane (5 mL), paraformaldehyde (42.7 mg, 0.474 mmol) was added. The mixture was stirred at room temperature for 1 h. And then acetic acid (18.9 mg, 0.316 mmol) and sodium triacetoxyborohydride (200 mg, 0.316 mmol) were added and the mixture was stirred at room temperature for 23 h. Water (10 mL) was added to the mixture. The mixture was extracted with dichloromethane (50 mL×3). The organic phases were combined, washed with saturated brine (50 mL×2) and dried over anhydrous sodium sulfate, followed by filtration and concentration under reduced pressure, and the obtained crude material was isolated and purified by preparative high-performance liquid chromatography to give compound 5-2 (30.0 mg). $^1$H NMR (400 MHz, CDCl$_3$) δ 7.30-7.24 (m, 2H), 7.18-7.15 (m, 1H), 7.11-7.09 (m, 2H), 3.52-3.44 (m, 1H), 3.30-3.26 (m, 1H), 2.79-2.75 (m, 1H), 2.14 (s, 6H), 2.09-2.05 (m, 1H), 1.34 (s, 9H), 1.32-1.17 (m, 4H), 0.59-0.51 (m, 2H), 0.40-0.35 (m, 2H). MS-ESI calculated [M+H]$^+$ 345, found 345.

Step 2

The synthesis of compound 5 (13.0 mg) was referred to the fifth step of example 1. $^1$H NMR (400 MHz, Methonal-d$_4$) δ 7.32-7.28 (m, 2H), 7.23-7.19 (m, 3H), 3.45-3.30 (m, 4H), 3.10-3.06 (m, 1H), 2.95 (s, 6H), 2.80-2.75 (m, 1H), 1.77-1.72 (m, 1H), 1.37-1.32 (m, 1H), 1.03-1.01 (m, 2H), 0.95-0.90 (m, 2H). MS-ESI calculated [M+H]$^+$ 245, found 245.

Example 6

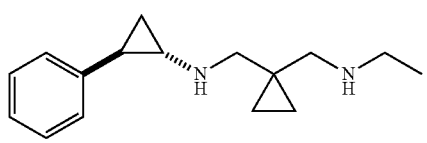

Synthetic Route:

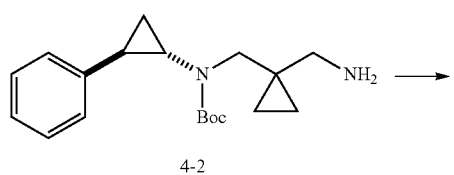

Step 1

The synthesis of compound 6-2 (38.0 mg) was referred to the first step of example 5. $^1$H NMR (400 MHz, CDCl$_3$) δ 7.30-7.25 (m, 2H), 7.21-7.17 (m, 1H), 7.06-7.03 (m, 2H), 3.49-3.45 (m, 1H), 3.08-3.01 (m, 2H), 2.99-2.92 (m, 1H), 2.80-2.74 (m, 2H), 2.68-2.65 (m, 1H), 2.16-2.11 (m, 1H), 1.50-1.40 (m, 12H), 1.29-1.24 (m, 3H), 0.96-0.90 (m, 2H), 0.73-0.68 (m, 1H), 0.59-0.54 (m, 1H). MS-ESI calculated [M+H]$^+$ 345, found 345.

Step 2

The synthesis of compound 6 (18.0 mg) was referred to the fifth step of example 1. $^1$H NMR (400 MHz, Methonal-d$_4$) δ 7.32-7.28 (m, 2H), 7.23-7.18 (m, 3H), 3.44-3.31 (m, 2H), 3.19-3.06 (m, 5H), 2.77-2.72 (m, 1H), 1.75-1.70 (m, 1H), 1.38-1.33 (m, 4H), 0.95-0.90 (m, 4H). MS-ESI calculated [M+H]$^+$ 245, found 245.

Example 7

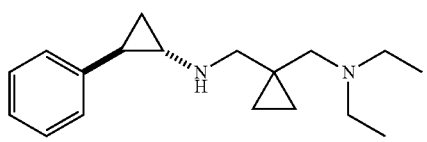

Synthetic Route:

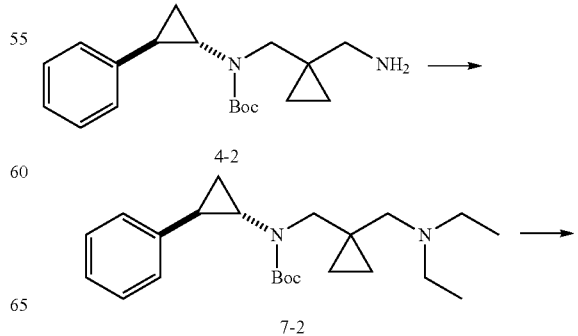

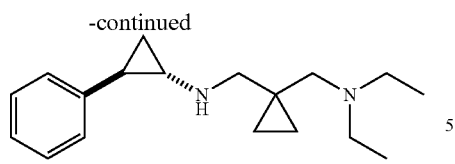

7

Step 1

Compound 4-2 (84.0 mg, 0.265 mmol) was dissolved in anhydrous N,N-dimethylformamide (1 mL), and sodium hydride (31.8 mg, 0.796 mmol, 60%) was added at 0° C., the mixture was stirred for 1 h. And then ethyl iodide (91.1 mg, 0.584 mmol) and tetrabutylammonium iodide (9.81 mg, 0.0265 mmol) were added, and the mixture was stirred at room temperature for 2 h. Water (10 mL) was added to the mixture. The mixture was extracted with dichloromethane (50 mL×3). The organic phases were combined, washed with saturated brine (50 mL×2) and dried over anhydrous sodium sulfate, followed by filtration and concentration under reduced pressure, and the obtained crude material was isolated and purified by thin layer chromatography (10:1 dichloromethane/methanol, Rf=0.36) to give compound 7-2 (40.0 mg). MS-ESI calculated [M+H]$^+$ 373, found 373.

Step 2

The synthesis of compound 7 (8.0 mg) was referred to the fifth step of example 1. $^1$H NMR (400 MHz, Methonal-d$_4$) δ 7.32-7.28 (m, 2H), 7.24-7.18 (m, 3H), 3.47-3.37 (m, 4H), 3.31-3.25 (m, 4H), 3.13-3.09 (m, 1H), 2.76-2.71 (m, 1H), 1.74-1.69 (m, 1H), 1.38-1.29 (m, 7H), 1.04-0.97 (m, 2H), 0.96-0.93 (m, 2H). MS-ESI calculated [M+H]$^+$ 273, found 273.

Example 8

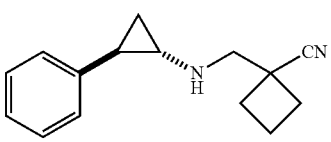

Synthetic Route:

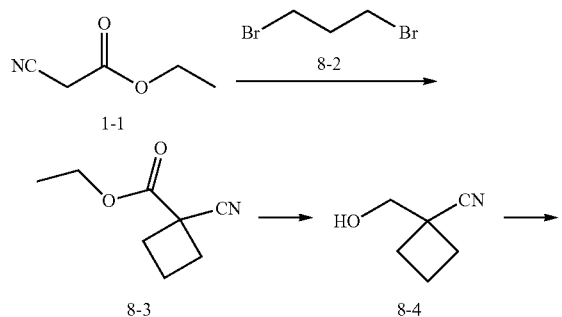

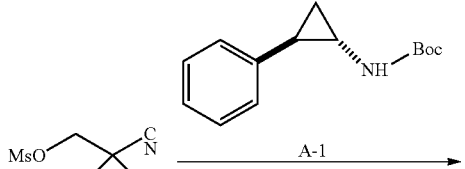

8-5

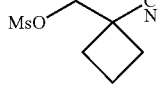

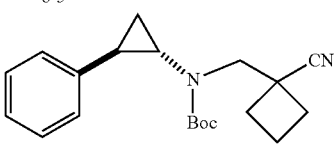

8-6

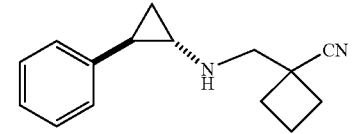

8

Step 1

Compound 1-1 (5.30 g, 46.8 mmol) was dissolved in anhydrous N,N-dimethylformamide (20 mL), 1,8-diazabicyclo[5.4.0] undec-7-ene (15.7 g, 103 mmol) was added, and the mixture was stirred for 0.5 h. Then compound 8-2 (10.4 g, 51.5 mmol) was added, and the mixture was stirred at 80° C. for 12 h. The mixture was cooled to room temperature, diluted with water (150 mL), extracted with ethyl acetate (250 mL×2). The organic phases were combined, washed with saturated brine (250 mL×1) and dried over anhydrous sodium sulfate, followed by filtration and concentration under reduced pressure, and the obtained crude material was isolated and purified by silica gel column chromatography (3:1 petroleum ether/ethyl acetate, Rf=0.68) to give compound 8-3 (3.20 g). $^1$H NMR (400 MHz, CDCl$_3$) δ 4.26 (q, J=6.8 Hz 2H), 2.74-2.67 (m, 2H), 2.64-2.57 (m, 2H), 2.29-2.11 (m, 2H), 1.31 (t, J=6.8 Hz, 3H).

Step 2

The synthesis of compound 8-4 (1.54 g) was referred to the second step of example 1. $^1$H NMR (400 MHz, CDCl$_3$) δ 3.80 (s, 2H), 2.54-2.47 (m, 2H), 2.35-2.15 (m, 4H).

Step 3

The synthesis of compound 8-5 (1.81 g) was referred to the third step of example 1. $^1$H NMR (400 MHz, CDCl$_3$) δ 4.35 (s, 2H), 3.13 (s, 3H), 2.62-2.57 (m, 2H), 2.28-2.10 (m, 4H).

Step 4

The synthesis of compound 8-6 (450 mg) was referred to the fourth step of example 1. $^1$H NMR (400 MHz, CDCl$_3$) δ 7.30-7.21 (m, 2H), 7.19-7.16 (m, 1H), 7.14-7.06 (m, 2H), 3.45-3.41 (m, 1H), 2.89-2.81 (m, 1H), 2.51-2.25 (m, 2H), 2.23-2.05 (m, 6H), 1.41 (s, 9H), 1.34-1.31 (m, 2H).

Step 5

The synthesis of compound 8 (38.0 mg) was referred to the fifth step of example. $^1$H NMR (400 MHz, Methonal-d$_4$) δ 7.34-7.30 (m, 2H), 7.26-7.19 (m, 3H), 3.68 (s, 2H), 3.13-3.09 (m, 1H), 2.61-2.56 (m, 3H), 2.43-2.36 (m, 2H), 2.29-2.12 (m, 2H), 1.63-1.57 (m, 1H), 1.45-1.40 (m, 1H). MS-ESI calculated [M+H]$^+$ 227, found 227.

Example 9

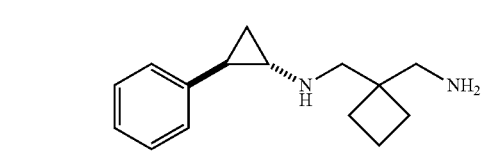

Synthetic Route:

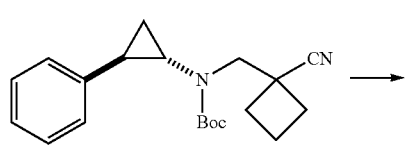

8-6

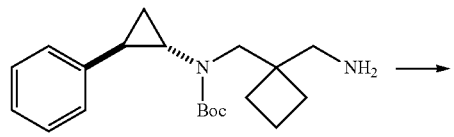

9-2

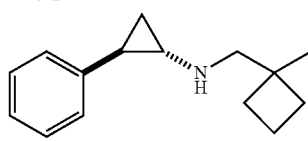

9

Step 1

The synthesis of compound 9-2 (150 mg) was referred to the first step of example 4. $^1$H NMR (400 MHz, CDCl$_3$) δ 7.28-7.24 (m, 2H), 7.19-7.15 (m, 1H), 7.08-7.06 (m, 2H), 3.53 (d, J=14.4 Hz, 1H), 3.23 (d, J=14.4 Hz, 1H), 2.78 (d, J=13.6 Hz, 1H), 2.65 (d, J=13.6 Hz, 1H), 2.60-2.58 (m, 4H), 2.14-2.09 (m, 1H), 2.05-2.00 (m, 1H), 191-1.82 (m, 2H), 1.76-1.70 (m, 2H), 1.39 (s, 9H), 1.34-1.29 (m, 1H), 1.23-1.18 (m, 1H).

Step 2

The synthesis of compound 9 (18.0 mg) was referred to the fifth step of example 1. $^1$H NMR (400 MHz, Methonal-d$_4$) δ 7.37-7.30 (m, 2H), 7.25-7.20 (m, 3H), 3.49 (s, 2H), 3.28 (s, 2H), 3.12-3.09 (m, 1H), 2.77-2.72 (m, 1H), 2.13-2.05 (m, 6H), 1.76-1.70 (m, 1H), 1.42-1.36 (m, 1H). MS-ESI calculated [M+H]$^+$ 231, found 231.

Example 10

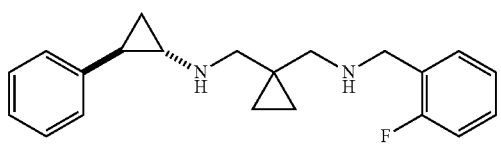

Synthetic Route:

 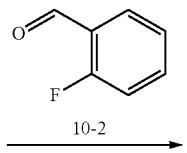

4-2

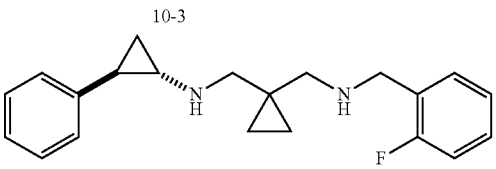

10-3

10

Step 1

Compound 4-2 (80.0 mg, 0.253 mmol) and 10-2 (31.4 mg, 0.253 mmol) were dissolved in anhydrous dichloromethane (2 mL), and acetic acid (45.5 mg, 0.758 mmol) was added to the reaction mixture. After reacting at 30° C. for 1 hour, sodium triacetoxyborohydride (161 mg, 0.758 mmol) was added. Then the mixture was stirred at 30° C. for 1 hour. The mixture was diluted with dichloromethane (10 mL) and washed with saturated sodium carbonate aqueous solution (5 mL×3), water (5 mL×2) and sodium brine (10 mL×2). The organic phase was dried over anhydrous sodium sulfate, followed by filtration and concentration under reduced pressure, and the obtained crude material was isolated and purified by thin layer chromatography (dichloromethane/methanol=10:1) to give compound 10-3 (56.0 mg). $^1$H NMR (400 MHz, CDCl$_3$) δ 7.46-7.40 (m, 1H), 7.30-7.28 (m, 1H), 7.24-7.04 (m, 6H), 7.03-6.97 (m, 1H), 3.89-3.76 (m, 2H), 3.60-3.45 (m, 1H), 3.13-3.00 (m, 1H), 2.81-2.72 (m, 1H), 2.54 (d, J=12.8 Hz, 1H), 2.37 (d, J=12.8 Hz, 1H), 2.12-2.05 (m, 1H), 1.40 (s, 9H), 1.25-1.12 (m, 2H), 0.60-0.52 (m, 1H), 0.46-0.33 (m, 3H). MS-ESI calculated [M+H]$^+$ 425, found 425.

Step 2

Compound 10-3 (56.0 mg, 132 μmol) was dissolved in ethyl acetate (1 mL), hydrochloric acid/ethyl acetate (4 mol/L, 3 mL) was added at 0° C., and the reaction mixture was stirred at room temperature 1 hour. The reaction solution was directly concentrated under reduced pressure, and the obtained crude product was purified by preparative high-performance liquid chromatography to give compound 10 (28.0 mg). $^1$H NMR (400 MHz, D$_2$O) δ 7.50-7.39 (m, 2H), 7.36-7.29 (m, 2H), 7.29-7.09 (m, 5H), 4.26 (s, 2H), 3.33-3.19 (m, 2H), 3.19-3.07 (m, 2H), 2.95-2.85 (m, 1H), 2.53-2.44 (m, 1H), 1.51-1.42 (m, 1H), 1.37-1.30 (m, 1H), 0.84 (s, 4H). MS-ESI calculated [M+H]$^+$ 325, found 325.

Example 11

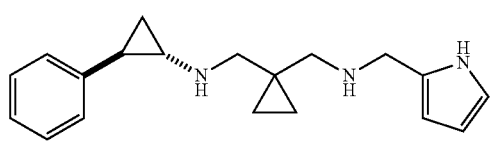

Synthetic Route:

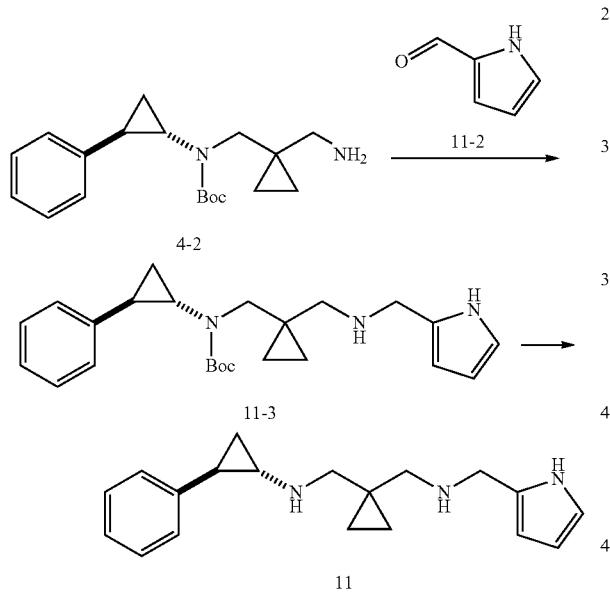

Step 1

The synthesis of compound 11-3 (26.0 mg) was referred to the first step of example 10. $^1$H NMR (400 MHz, CDCl$_3$) δ 7.30-7.26 (m, 2H), 7.26-7.23 (m, 1H), 7.06-7.02 (m 2H), 6.88-6.81 (m, 1H), 6.12-6.06 (m, 2H), 4.1-400 (m, 2H), 3.46 (d, J=15.2 Hz, 1H), 3.01 (d, J=15.2 Hz, 1H), 2.82-2.72 (m, 1H), 2.66-2.59 (m, 1H), 2.53-2.42 (m, 1H), 2.16-2.09 (m, 1H), 1.45 (s, 9H), 1.23-1.14 (m, 2H), 0.72-0.61 (m, 3H), 0.53-0.42 (m, 1H). MS-ESI calculated [M+H]$^+$ 396, found 396.

Step 2

The synthesis of compound 11 (8.0 mg) was referred to the second step of example 10. $^1$H NMR (400 MHz, D$_2$O) δ 7.39-7.34 (m, 2H), 7.32-7.27 (m, 1H), 7.21-7.17 (m, 2H), 6.94-6.90 (m, 1H), 6.38-6.30 (m, 1H), 6.25-6.18 (m, 1H), 4.27-4.19 (m, 2H), 3.31-3.20 (m, 2H), 3.13-3.03 (m, 2H), 2.95-2.89 (m, 1H), 2.56-2.47 (m, 1H), 1.56-1.48 (m, 1H), 1.42-1.34 (m, 1H), 0.88-0.81 (m, 4H). MS-ESI calculated [M+H]$^+$ 296, found 296.

Example 12

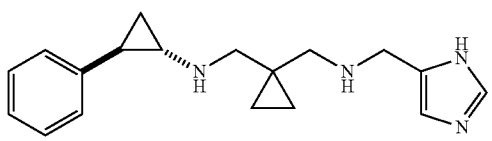

Synthetic Route:

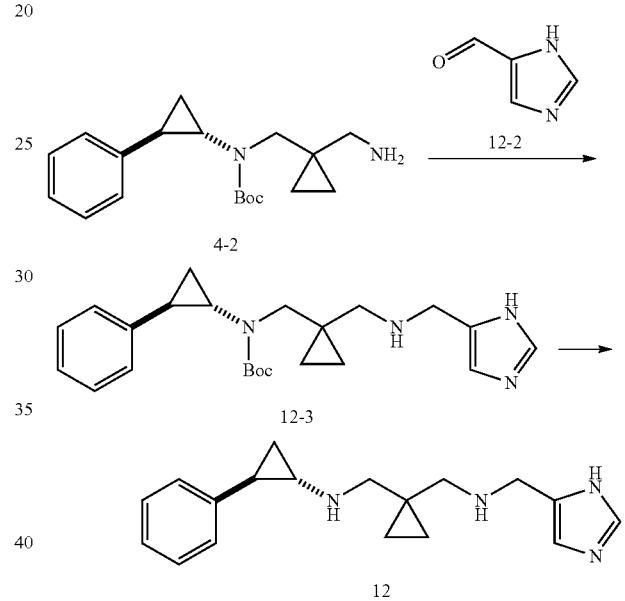

Step 1

The synthesis of compound 12-3 (30.0 mg) was referred to the first step of example 10. $^1$H NMR (400 MHz, CDCl$_3$) δ 7.31-7.27 (m, 1H), 7.26-7.15 (m, 3H), 7.13-6.98 (m, 3H), 4.19-3.97 (m, 1H), 3.78-3.40 (m, 2H), 3.32-2.82 (m, 2H), 2.80-2.65 (m, 2H), 2.18-2.10 (m, 1H), 1.43-1.38 (m, 9H), 1.24-1.12 (m, 2H), 0.96-0.77 (m, 2H), 0.72-0.67 (m, 1H), 0.62-0.49 (n, 1H). MS-ESI calculated[M+H]$^+$ 397, found 397.

Step 2

The synthesis of compound 12 (6.0 mg) was referred to the second step of example 10. $^1$H NMR (4001 MHz, D$_2$O) δ 8.77-8.73 (m, 1H), 7.69 (s, 1H), 7.40-7.33 (m, 2H), 7.33-7.26 (m, 1H), 7.22-7.17 (m, 2H), 4.42 (s, 2H), 3.40-3.28 (m, 2H), 3.28-3.17 (m, 2H), 3.03-2.96 (m, 1H), 2.60-2.57 (m, 1H), 1.60-1.50 (m, 1H), 1.45-1.37 (m, 1H), 0.92 (s, 4H). MS-ESI calculated [M+H]$^+$ 297, found 297.

Example 13

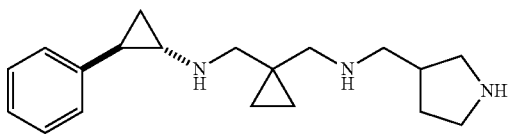

Synthetic Route:

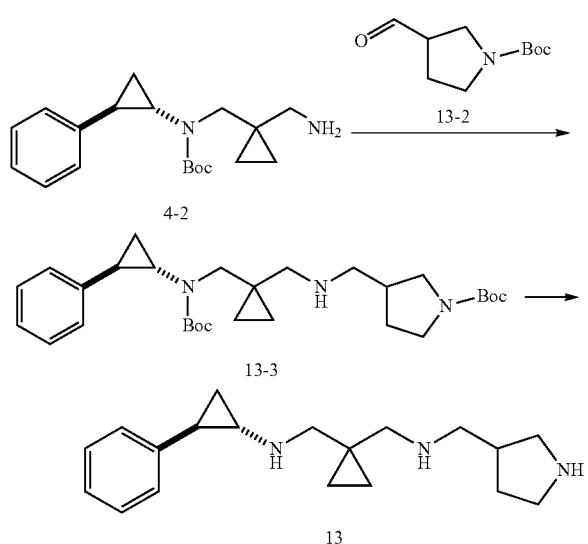

The synthesis of compound 13-3 (50.0 mg) was referred to the first step of example 10. $^1$H NMR (400 MHz, CDCl$_3$) δ 7.31-7.27 (m, 1H), 7.26-7.22 (m, 1H), 7.21-7.15 (m, 1H), 7.10-7.00 (m, 2H), 3.64-3.37 (m, 4H), 3.40-3.20 (m, 1H), 3.10-2.91 (m, 2H), 2.82-2.72 (m, 1H), 2.65-2.46 (m, 3H), 2.40-2.30 (m, 1H), 2.13-1.97 (m, 2H), 1.65-1.55 (m, 1H), 1.45 (s, 9H), 1.42 (s, 9H), 1.29-1.10 (m, 2H), 0.64-0.30 (m, 4H). MS-ESI calculated [M+H]$^+$ 500, found 500.

Step 2

The synthesis of compound 13 (9.00 mg) was referred to the second step of example 10. $^1$H NMR (400 MHz, D$_2$O) δ 7.41-7.35 (m, 2H), 7.33-7.27 (m, 1H), 7.24-7.17 (m, 2H), 3.68-3.57 (m, 1H), 3.51-3.43 (m, 1H), 3.42-3.29 (m, 3H), 3.25-3.11 (m, 4H), 3.09-2.99 (m, 2H), 2.84-2.72 (m, 1H), 2.63-2.57 (m, 1H), 2.41-2.29 (m, 1H), 1.89-1.73 (m, 1H), 1.65-1.52 (m, 1H), 1.48-1.39 (m, 1H), 0.97-0.86 (m, 4H). MS-ESI calculated [M+H]$^+$ 300, found 300.

Example 14

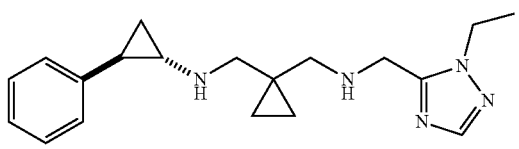

Synthetic Route:

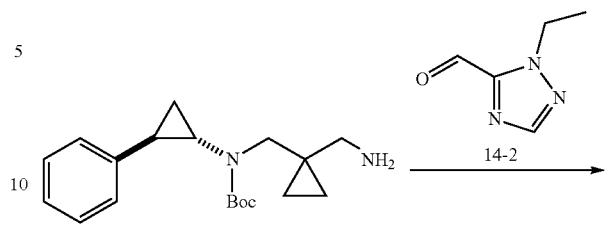

Step 1

The synthesis of compound 14-3 (30.0 mg) was referred to the first step of example 10. MS-ESI calculated [M+H]$^+$ 426, found 426.

Step 2

The synthesis of compound 14 (1.30 mg) was referred to the second step of example 10. $^1$H NMR (400 MHz, D$_2$O) δ 8.02 (s, 1H), 7.39-7.34 (m, 2H), 7.32-7.27 (m, 1H), 7.21-7.17 (m, 2H), 4.56-4.50 (m, 2H), 4.19 (q, J=7.2 Hz, 2H), 3.50-3.36 (m, 2H), 3.34-3.23 (m, 2H), 3.07-3.00 (m, 1H), 2.61-2.53 (m, 1H), 1.61-1.53 (m, 1H), 1.47-1.42 (m, 1H), 1.39 (t, J=7.2 Hz, 3H), 0.95 (s, 4H). ESI calculated [M+H]$^+$ 326, found 326.

Example 15

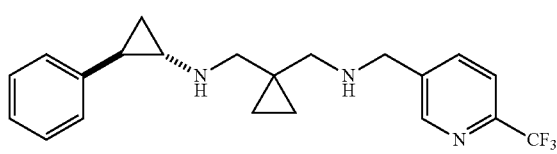

Synthetic Route:

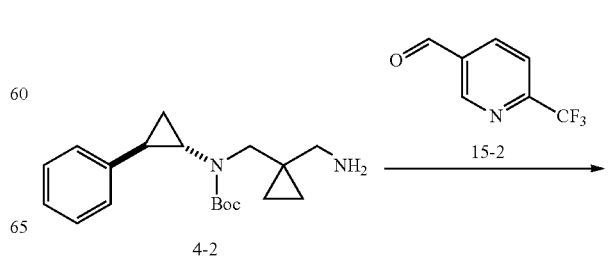

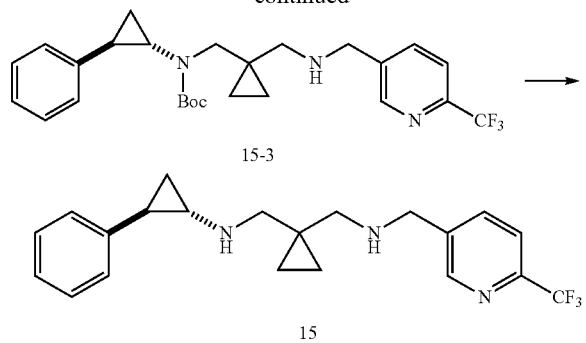

15-3

15

Step 1

The synthesis of compound 15-3 (40.0 mg) was referred to the first step of example 10. ¹H NMR (400 MHz, CDCl₃) δ 8.66 (s, 1H), 7.91 (d, J=8.0 Hz, 1H), 7.63 (d, J=8.0 Hz, 1H), 7.29-7.25 (m, 2H), 7.21-7.15 (m, 1H), 7.11-7.03 (m, 2H), 3.87-3.78 (m, 2H), 3.64-3.52 (m, 1H), 3.12-2.96 (m, 1H), 2.84-2.74 (m, 1H), 2.54 (d, J=12.4 Hz, 1H), 2.27 (d, J=12.4 Hz, 1H), 2.13-2.05 (m, 1H), 1.42 (s, 9H), 1.27-1.18 (m, 2H), 0.60-0.51 (m, 1H), 0.42-0.29 (m, 3H). MS-ESI calculated [M+H]⁺ 476, found 476.

Step 2

The synthesis of compound 15 (23.0 mg) was referred to the second step of example 10. ¹H NMR (400 MHz, D₂O) δ 8.74 (d, 0.1.6 Hz, 1H), 8.20 (dd, J₁=1.6 Hz, J₂=8.4 Hz, 1H), 7.93 (d, J=8.4 Hz, 1H), 7.37-7.30 (m, 2H), 7.29-7.22 (m, 1H), 7.19-7.12 (m, 2H), 4.42-4.32 (m, 2H), 3.40-3.27 (m, 2H), 3.27-3.16 (m, 2H), 3.02-2.93 (m, 1H), 2.59-2.50 (m, 1H), 1.55-1.48 (m, 1H), 1.42-1.33 (m, 1H), 0.95-0.85 (m, 4H). MS-ESI calculated [M+H]⁺ 376, found 376.

Example 16

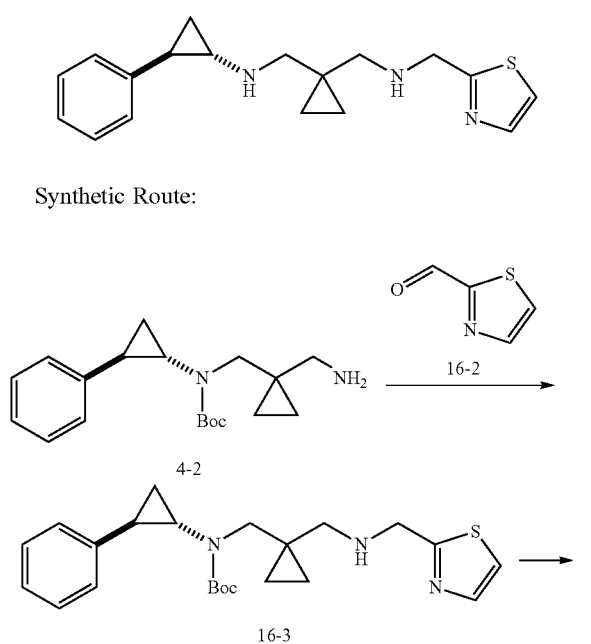

Synthetic Route:

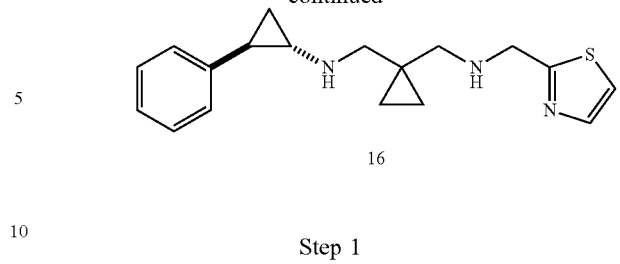

16

Step 1

The synthesis of compound 16-3 (50.0 mg) was referred to the first step of example 10. ¹H NMR (400 MHz, CDCl₃) δ 7.76-7.69 (m, 1H), 7.35-7.27 (m, 2H), 7.27-7.23 (m, 1H), 7.23-7.15 (m, 1H), 7.15-7.03 (m, 2H), 4.18-3.99 (m, 2H), 3.77-3.42 (m, 1H), 3.10-2.98 (m, 1H), 2.86-2.48 (n, 3H), 2.19-2.03 (m, 1H), 1.54-1.32 (m, 9H), 1.31-1.04 (m, 3H), 0.60-0.52 (n, 1H), 0.46-0.34 (in, 2H). MS-ESI calculated [M+H]⁺ 414, found 414.

Step 2

The synthesis of compound 16 (14.0 mg) was referred to the second step of example 10. ¹H NMR (400 MHz, D₂O) δ 7.82 (d, J=3.6 Hz, 1H), 7.66 (d, 3.6 Hz, 1H), 7.34-7.29 (m, 2H), 7.27-7.22 (m, 1H), 7.16-7.12 (m, 2H), 4.59 (s 2H), 3.37-3.27 (m, 2H), 3.25-3.16 (m, 2H), 2.97-2.92 (n, 1H), 2.55-2.47 (m, 1H), 1.54-1.46 (m, 1H), 1.40-1.33 (m, 1H), 0.87 (s, 4H). MS-ESI calculated [M+H]⁺ 314, found 314.

Example 17

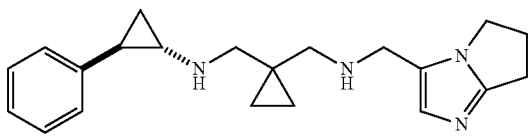

Synthetic Route:

Step 1

The synthesis of compound 17-3 (40.0 mg) was referred to the first step of example 10. $^1$H NMR (400 MHz, CDCl$_3$) δ 7.29-7.24 (m, 2H), 7.21-7.13 (m, 1H), 7.10-7.03 (m, 2H), 6.95 (s, 1H), 4.15-4.05 (m, 2H), 3.66-3.58 (m, 2H), 3.55-3.45 (m, 1H), 3.30-3.17 (m, 2H), 3.02-2.90 (m, 1H), 2.80-2.71 (m, 1H), 2.70-2.59 (m, 2H), 2.53-2.42 (m, 1H), 2.26-2.12 (m, 2H), 1.41 (s, 9H), 1.28-1.13 (m, 2H), 0.60-0.48 (m, 1H), 0.40-0.23 (m, 3H). MS-ESI calculated [M+H]$^+$ 437, found 437.

Step 2

The synthesis of compound 17 (14.0 mg) was referred to the second step of example 10. $^1$H NMR (400 MHz, D$_2$O) δ 7.55 (s, 1H), 7.37-7.31 (m, 2H), 7.30-7.23 (m, 1H), 7.20-7.13 (m, 2H), 4.33 (s, 2H), 4.28-4.23 (m, 2H), 3.39-3.25 (m, 2H), 3.22-3.09 (m, 4H), 3.00-2.94 (m, 1H), 2.81-2.71 (m, 2H), 2.57-2.50 (m, 1H), 1.57-1.46 (m, 1H), 1.42-1.37 (m, 1H), 0.89 (s, 4H). MS-ESI calculated [M+H]$^+$ 337, found 337.

Example 18

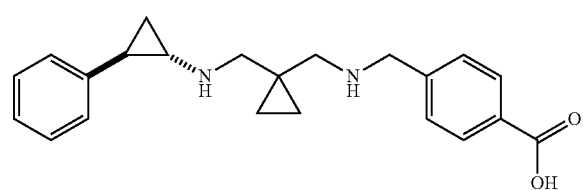

Synthetic Route:

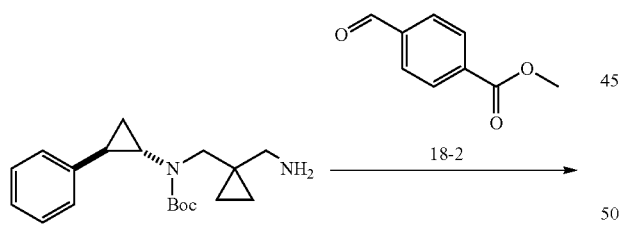

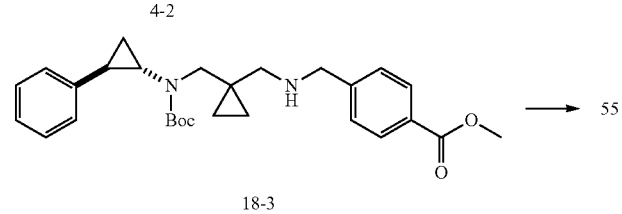

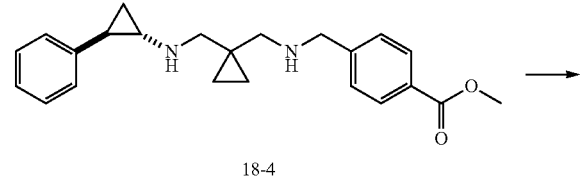

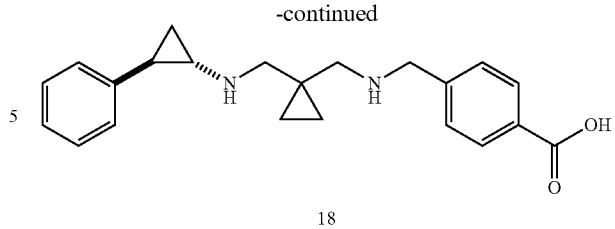

18

Step 1

The synthesis of compound 18-3 (80.0 mg) was referred to the first step of example 10. $^1$H NMR (400 MHz, CDCl$_3$) δ 8.03-8.00 (m, 1H), 7.99-7.96 (m, 1H), 7.48 (d, J=8.4 Hz, 2H), 7.42 (d, J=8.4 Hz, 1H), 7.25-7.23 (m, 1H), 7.21-7.14 (m, 1H), 7.07-7.03 (m, 2H), 3.90 (s, 3H), 3.57-3.48 (m, 1H), 3.08-2.97 (m, 1H), 2.79-2.73 (m, 1H), 2.61 (d, J=12.4 Hz, 1H), 2.42 (d, J=12.4 Hz, 1H), 2.12-2.05 (m, 1H), 2.01-1.93 (m, 1H), 1.40 (s, 9H), 1.25-1.13 (m, 3H), 0.61-0.47 (m, 3H), 0.43-0.36 (m, 1H). MS-ESI calculated [M+H]$^+$ 465, found 465.

Step 2

The synthesis of compound 18-4 (60.0 mg) was referred to the second step of example 10. MS-ESI calculated [M+H]$^+$ 365, found 365.

Step 3

Compound 18-4 (60.0 mg, 0.165 mmol) was dissolved in tetrahydrofuran (3 mL) and water (1 mL). Lithium hydroxide (139 mg, 3.29 mmol) was added to the reaction mixture. The mixture was stirred at room temperature for 16 hours, and then stirred at 50° C. for 16 hours. The reaction solution was cooled to room temperature, adjusted to pH=5 with diluted hydrochloric acid (1 mol/L), and concentrated under reduced pressure. The obtained crude product was isolated and purified by preparative high-performance liquid chromatography to obtain 18 (7.00 mg). $^1$H NMR (400 MHz, Methonal-d$_4$) δ 8.02 (d, J=8.0 Hz, 2H), 7.47 (d, J=8.0 Hz, 2H), 7.27-7.22 (m, 2H), 7.16-7.11 (m, 1H), 7.07-7.02 (m, 2H), 4.20 (s, 2H), 3.13 (s, 2H), 2.87 (s, 2H), 2.42-2.36 (m, 1H), 1.94-1.88 (m, 1H), 1.10-1.02 (m, 2H), 0.68-0.61 (m, 4H). MS-ESI calculated [M+H]$^+$ 351, found 351.

Example 19

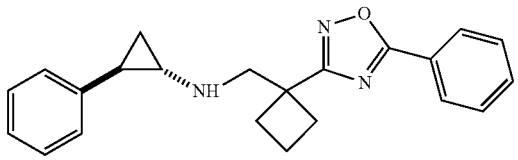

Synthetic Route:

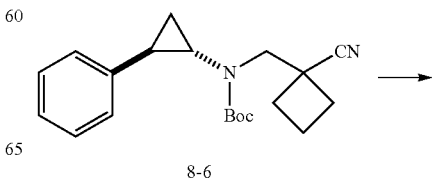

8-6

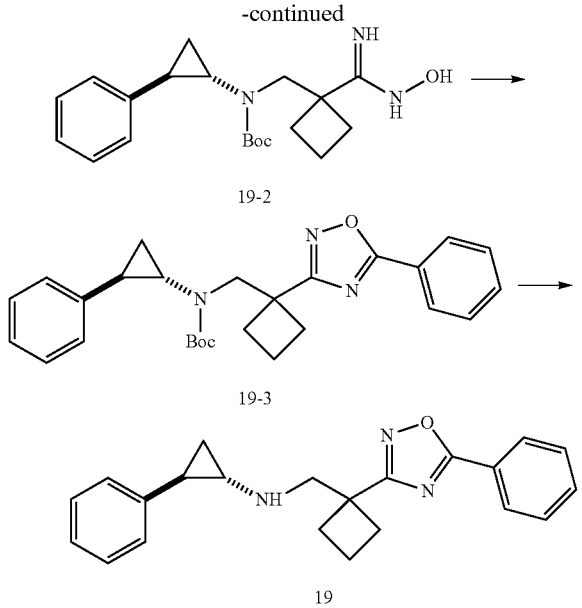

Step 1

Compound 8-6 (1.8 g, 5.51 mmol) was dissolved in anhydrous ethanol (20 mL), hydroxylamine hydrochloride (767 mg, 11.1 mmol) and diisopropylethylamine (2.85 g, 22.2 mmol) were added to the reaction mixture. The mixture was stirred at 80° C. for 12 h. The solvent was concentrated under reduced pressure. The mixture was diluted with water (100 mL), extracted with ethyl acetate (80 mL×3). The organic phase was washed with saturated brine (50 mL×2) and dried over anhydrous sodium sulfate, followed by filtration and concentration under reduced pressure, and the obtained crude material was isolated and purified by silica gel column chromatography (1:1 petroleum ether/ethyl acetate, Rf1=0.5, Rf2=0.3) to give compound 19-2 (760 mg). $^1$H NMR (400 MHz, CDCl$_3$) δ 7.25-7.23 (m, 2H), 7.17-7.14 (m, 1H), 7.08-7.07 (m, 2H), 4.51 (brs, 2H), 3.79-3.75 (m, 1H), 3.50-3.47 (m, 1H), 2.83-2.79 (m, 1H), 2.39-2.26 (m, 2H), 2.11-1.87 (m, 5H), 1.39 (s, 9H), 1.30-1.16 (m, 2H). MS-ESI calculated [M+H]$^+$ 360, found 360.

Step 2

Benzoic acid (24.5 mg, 0.201 mmol) and carbonyldiimidazole (35.2 mg, 0.217 mmol) were dissolved in anhydrous N,N-dimethylformamide (2 mL). Compound 19-2 (60.0 mg, 0.167 mmol) was added to the reaction mixture, and the mixture was heated to 110° C. and stirred for 10 hours. The reaction solution was cooled to room temperature, water (30 mL) was added to the mixture. The mixture was extracted with ethyl acetate (20 mL×3). The organic phases were combined, washed with saturated brine (20 mL×2) and dried over anhydrous sodium sulfate, followed by filtration and concentration under reduced pressure to give compound 19-3 (80.0 mg). MS-ESI calculated [M+H]$^+$ 446, found 446.

Step 3

Compound 19-3 (80 mg, 0.179 mmol) was dissolved in anhydrous dichloromethane (2 mL). Trifluoroacetic acid (2 mL) was added dropwise at 0° C. The reaction solution was stirred at 0° C. for 1 hour, concentrated under reduced pressure to remove the solvent, and the crude product was purified by preparative high-performance liquid chromatography to give compound 19 (30.0 mg). $^1$H NMR (400 MHz, Methonal-d$_4$) δ 8.17 (d, J=7.2 Hz, 2H), 7.68-7.58 (m, 3H), 7.28-7.15 (m, 5H), 3.88 (s, 2H), 3.09-3.08 (m, 1H), 2.69-2.69 (m, 2H), 2.59-2.57 (m, 1H), 2.43-2.41 (m, 2H), 2.24-2.21 (m, 2H), 1.60-1.57 (m, 1H), 1.39-1.32 (m, 1H). MS-ESI calculated [M+H]$^+$ 346, found 346.

Example 20

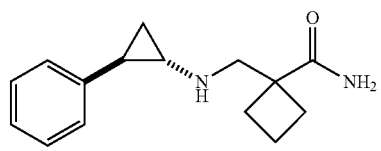

Synthetic Route:

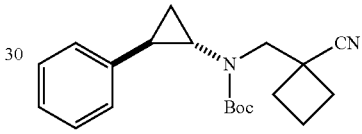

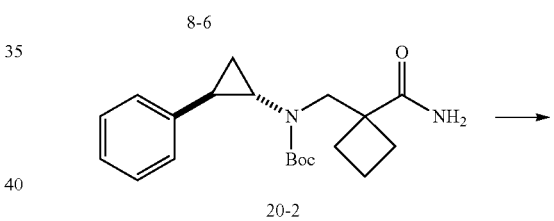

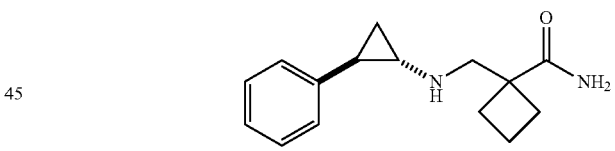

Step 1

The synthesis of compound 20-2 (300 mg) was referred to the first step of example 19. MS-ESI calculated [M+H]$^+$ 345, found 345.

Step 2

The synthesis of compound 20 (60.0 mg) was referred to the third step of example 19. $^1$H NMR (400 MHz, Methonal-d$_4$) δ 7.31-7.27 (m, 2H), 7.22-7.17 (m, 3H), 3.58 (s, 2H), 3.04-3.01 (m, 1H), 2.65-2.61 (m, 1H), 2.52-2.47 (m, 2H), 2.21-2.01 (m, 4H), 1.65-1.55 (m, 1H), 1.36-1.31 (m, 1H). MS-ESI calculated [M+H]$^+$ 245, found 245.

Example 21

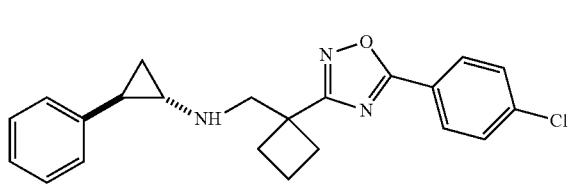

Synthetic Route:

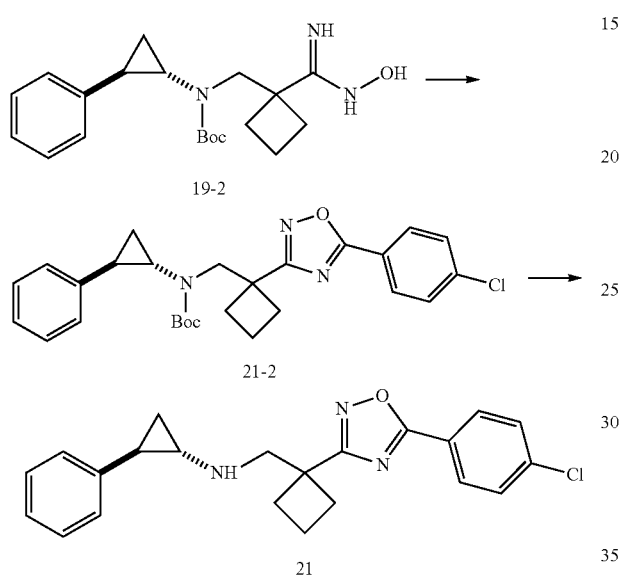

Step 1

The synthesis of compound 21-2 (75.0 mg) was referred to the second step of example 19. MS-EST calculated [M+H]⁺ 480, found 480.

Step 2

The synthesis of compound 21 (38.0 mg) was referred to the third step of example 19. ¹H NMR (400 MHz. Methonal-d₄) δ 8.14 (d, J=8.8 Hz, 2H), 7.63 (d, J=8.8 Hz, 2H), 7.29-7.25 (m, 2H), 7.20-7.14 (m, 3H), 3.87 (s, 2H), 3.07-3.05 (m, 1H), 2.67-2.65 (m, 2H), 2.58-2.56 (m, 1H), 2.44-2.41 (m, 2H), 2.23-2.19 (m, 2H), 1.59-1.57 (m, 1H), 1.38-1.36 (m, 1H). MS-ESI calculated [M+H]⁺ 380, found 380.

Example 22

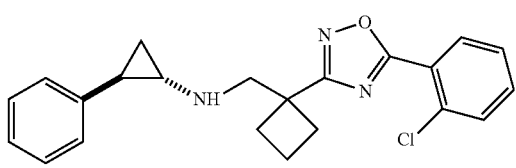

Synthetic Route:

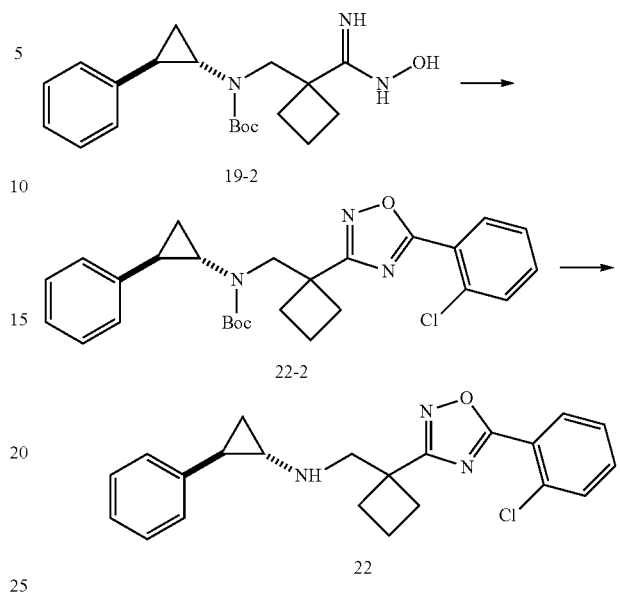

Step 1

The synthesis of compound 22-2 (80.0 mg) was referred to the second step of example 19. MS-EST calculated [M+H]⁺ 480, found 480.

Step 2

The synthesis of compound 22 (35.0 mg) was referred to the third step of example 19. ¹H NMR (400 MHz, Methonal-d₄) δ 8.15 (d, J=8.4 Hz, 1H), 7.67-7.63 (m, 2H), 7.55-7.53 (m, 1H), 7.28-7.26 (m, 2H), 7.21-7.15 (m, 3H), 3.89 (s, 2H), 3.09-3.08 (m, 1H), 2.70-2.67 (m, 3H), 2.47-2.42 (m, 2H), 2.25-2.21 (m, 2H), 1.62-1.59 (m, 1H), 1.39-1.37 (m, 1H). MS-ESI calculated [M+H]⁺380, found 380.

Example 23

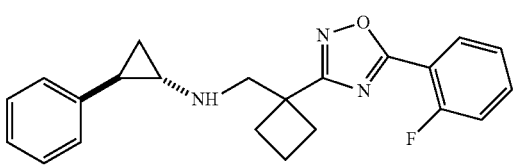

Synthetic Route:

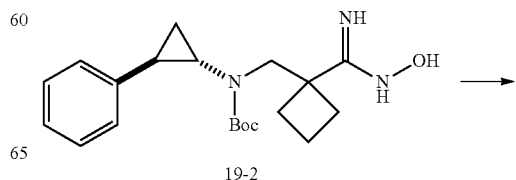

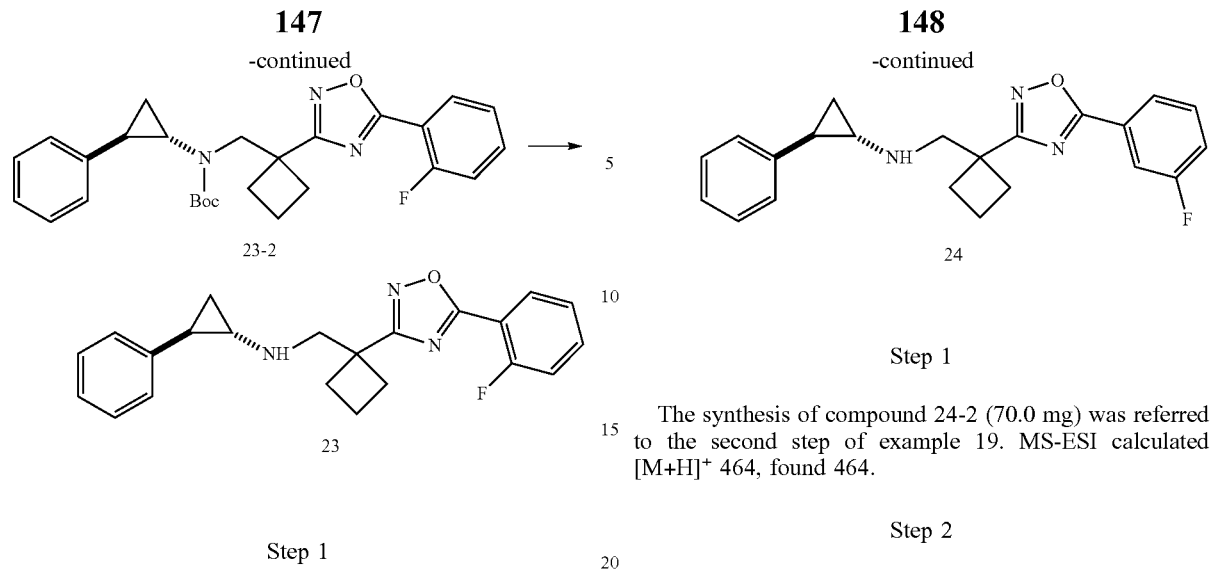

Step 1

The synthesis of compound 23-2 (70.0 mg) was referred to the second step of example 19. MS-ESI calculated [M+H]⁺ 464, found 464.

Step 2

The synthesis of compound 23 (31.0 mg) was referred to the third step of example 19. ¹H NMR (400 MHz, Methonal-d₄) δ 8.19 (t, J=1.6 Hz, 1H), 7.73-7.71 (m, 1H), 7.42-7.38 (m, 2H), 7.27-7.25 (m, 2H), 7.20-7.15 (m, 3H), 3.89 (s, 2H), 3.09-3.08 (m, 1H), 2.69-2.67 (m, 2H), 2.59-2.58 (m, 1H), 2.46-2.43 (m, 2H), 2.24-2.21 (m, 2H), 1.62-1.59 (m, 1H), 1.38-1.36 (m, 1H). MS-ESI calculated [M+H]⁺ 364, found 364.

Example 24

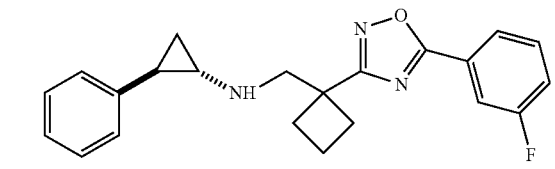

Synthetic Route:

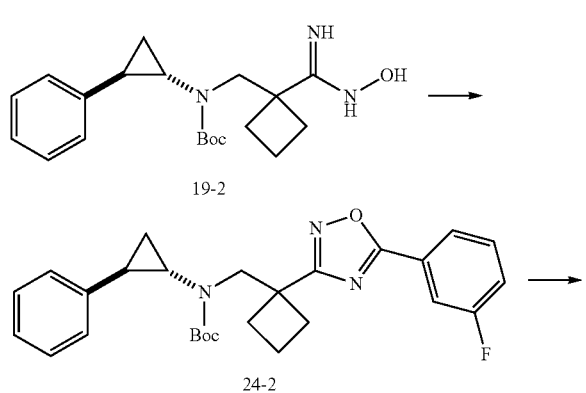

Step 1

The synthesis of compound 24-2 (70.0 mg) was referred to the second step of example 19. MS-ESI calculated [M+H]⁺ 464, found 464.

Step 2

The synthesis of compound 24 (36.0 mg) was referred to the third step of example 19. ¹H NMR (400 MHz, Methonal-d₄) δ 8.00 (d, J=8.0 Hz, 1H), 7.89-7.88 (m, 1H), 7.65-7.64 (m, 1H), 7.45-7.44 (m, 1H), 7.27-7.25 (m, 2H), 7.21-7.15 (m, 3H), 3.88 (s, 2H), 3.09-3.07 (m, 1H), 2.69-2.66 (m, 2H), 2.59-2.58 (m, 1H), 2.45-2.43 (m, 2H), 2.25-2.21 (m, 2H), 1.62-1.60 (m, 1H), 1.39-1.37 (m, 1H). MS-ESI calculated [M+H]⁺ 364, found 364.

Example 25

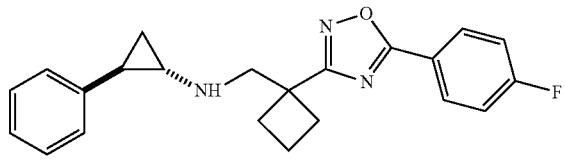

Synthetic Route:

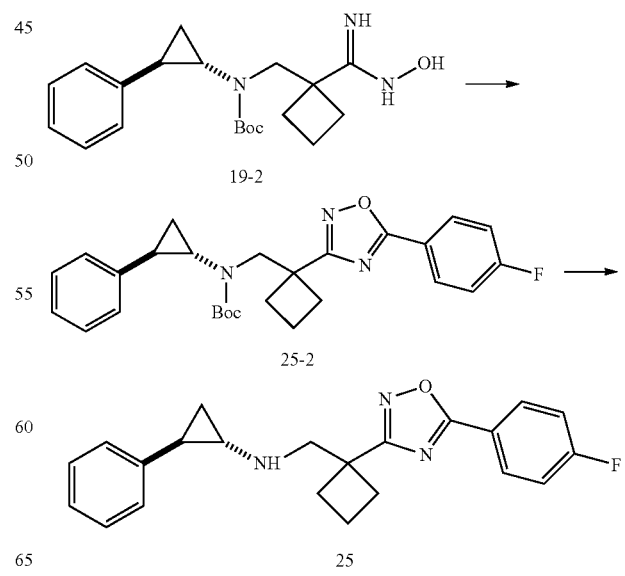

Step 1

The synthesis of compound 25-2 (70.0 mg) was referred to the second step of example 19. MS-ESI calculated [M+H]+ 464, found 464.

The synthesis of compound 25 (31.0 mg) was referred to the third step of example 19. ¹H NMR (400 MHz, Methonal-d₄) δ 8.25-8.19 (m, 2H), 7.38-7.33 (m, 2H), 7.28-7.26 (m, 2H), 7.21-7.15 (m, 3H), 3.87 (s, 2H), 3.09-3.07 (m, 1H), 2.67-2.65 (m, 2H), 2.59-2.56 (m, 1H), 2.42-2.41 (m, 2H), 2.24-2.20 (m, 2H), 1.60-1.58 (m, 1H), 1.39-1.35 (m, 1H). MS-ESI calculated [M+H]+ 364, found 364.

Example 26

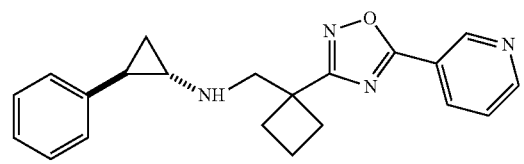

Synthetic Route:

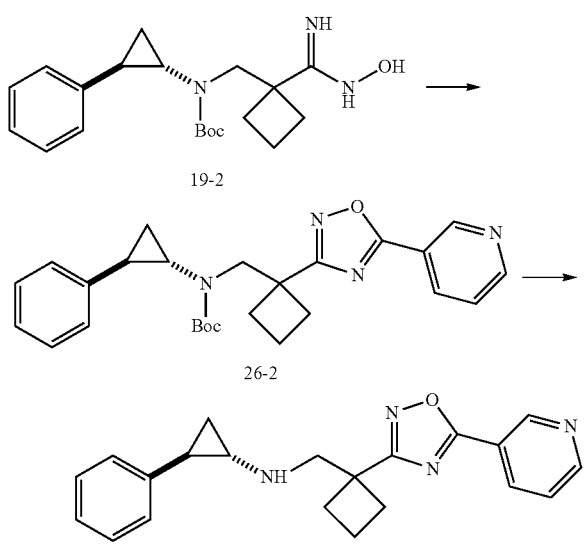

Step 1

The synthesis of compound 26-2 (70.0 mg) was referred to the second step of example 19. MS-ESI calculated [M+H]+ 447, found 447.

Step 2

The synthesis of compound 26 (42.0 mg) was referred to the third step of example 19. ¹H NMR (400 MHz, Methonal-d₄) δ 9.62 (s, 1H), 9.26 (d, J=8.0 Hz, 1H), 9.16 (d, J=5.6 Hz, 1H), 8.36-8.32 (m, 1H), 7.26-7.23 (m, 2H), 7.16-7.13 (m, 3H), 3.91 (s, 2H), 3.08-3.06 (m, 1H), 2.70-2.63 (m, 3H), 2.50-2.49 (m, 2H), 2.23-2.22 (m, 2H), 1.67-1.65 (m, 1H), 1.35-1.34 (m, 1H). MS-ESI calculated [M+H]+ 347, found 347.

Example 27

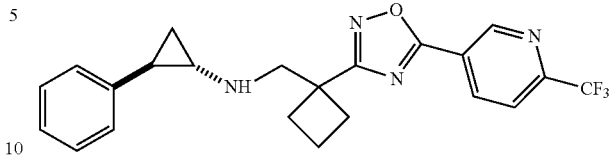

Synthetic Route:

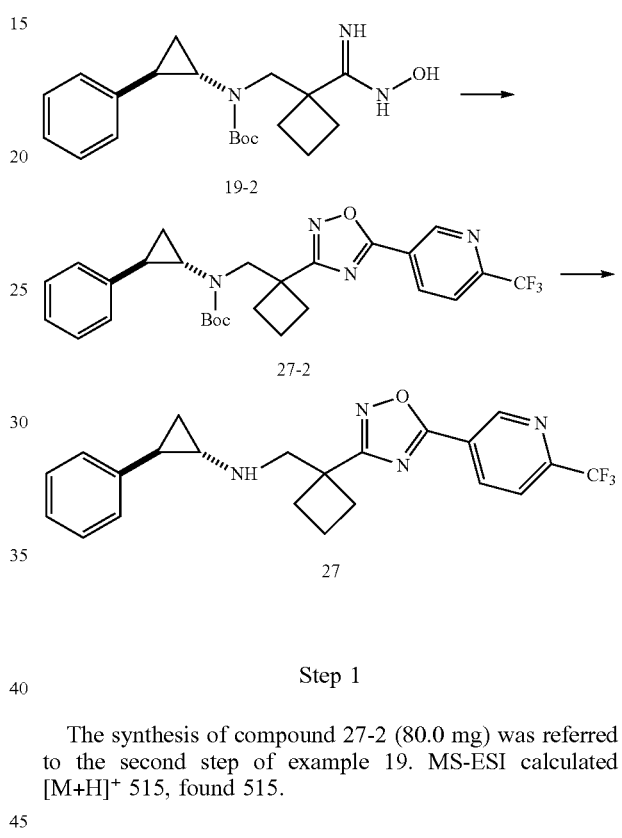

Step 1

The synthesis of compound 27-2 (80.0 mg) was referred to the second step of example 19. MS-ESI calculated [M+H]+ 515, found 515.

Step 2

The synthesis of compound 27 (42.0 mg) was referred to the third step of example 19. ¹H NMR (400 MHz, Methonal-d₄) δ 9.42 (s, 1H), 8.75-8.73 (m, 1H), 8.08 (d, J=8.4 Hz, 1H), 7.27-7.23 (m, 2H), 7.17-7.13 (m, 3H), 3.91 (s, 2H), 3.07-3.06 (m, 1H), 2.72-2.67 (m, 2H), 2.56-2.55 (m, 1H), 2.48-2.46 (m, 2H), 2.26-2.22 (m, 2H), 1.61-1.60 (m, 1H), 1.38-1.36 (m, 1H). MS-ESI calculated [M+H]+ 415, found 415.

Example 28

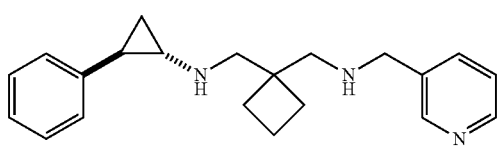

Example 29

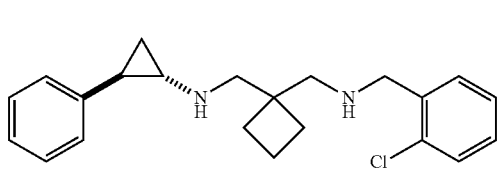

Synthetic Route:

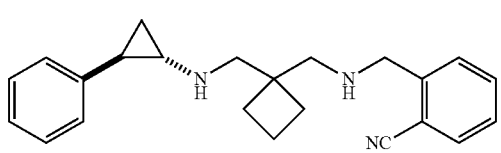

Step 1

The synthesis of compound 29-3 (40.0 mg) was referred to the first step of example 28. ¹H NMR (400 MHz, CDCl₃) δ 7.49 (d, J=6.8 Hz, 1H), 7.33 (d, J=8.0 Hz, 1H), 7.26-7.19 (m, 3H), 7.17-7.14 (m, 2H), 7.08-7.06 (m, 2H), 3.87 (s, 2H), 3.60-3.56 (m, 1H), 3.30-3.26 (m, 1H), 2.68-2.63 (m, 3H), 2.12-2.09 (m, 1H), 2.04-1.99 (m, 1H), 1.87-1.74 (m, 5H), 1.38 (s, 9H), 1.33-1.29 (m, 1H), 1.22-1.16 (m, 1H). MS-ESI calculated [M+H]⁺ 455, found 455.

Step 2

The synthesis of compound 29 (31.0 mg) was referred to the second step of example 28. ¹H NMR (400 MHz, D₂O) δ 7.49-7.47 (m, 2H), 7.41-7.29 (m, 4H), 7.25-7.22 (m, 1H), 7.14-7.13 (m, 2H), 4.42 (s, 2H), 3.40 (s, 2H), 3.35 (s, 2H), 2.93-2.89 (m, 1H), 2.51-2.50 (m, 1H), 2.00-1.95 (m, 6H), 1.49-1.46 (m, 1H), 1.37-1.33 (m, 1H). MS-ESI calculated [M+H]⁺ 355, found 355.

Example 30

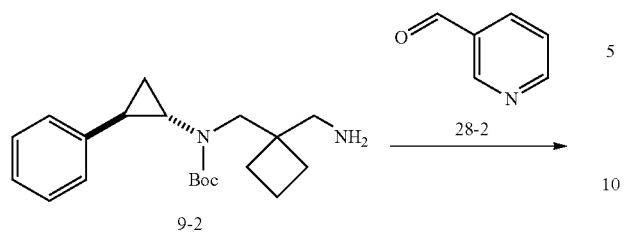

Synthetic Route:

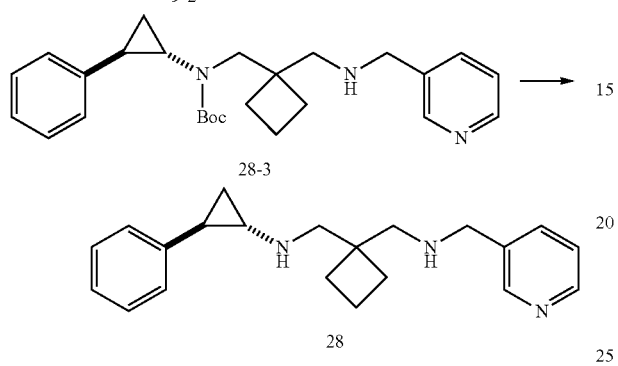

Step 1

Compound 9-2 (50.0 mg, 0.151 mmol) and 28-2 (16.2 mg, 0.151 mmol) were dissolved in anhydrous dichloromethane (2.00 mL), and acetic acid (27.3 mg, 0.454 mmol) was added to the reaction mixture. After stirring at 30° C. for 1 hour, sodium triacetoxyborohydride (96.2 mg, 0.454 mmol) was added, and stirring was continued at 30° C. for 16 hours. The mixture was diluted with dichloromethane (10 mL), washed successively with saturated sodium carbonate aqueous solution (5 mL×3), water (5 mL×2) and saturated brine (10 mL×2). The organic phase was dried over anhydrous sodium sulfate, followed by filtration and concentration under reduced pressure, and the obtained crude material was isolated and purified by thin layer chromatography (dichloromethane/methanol=10:1, Rf=0.34) to give compound 28-3 (35.0 mg). ¹H NMR (400 MHz, CDCl₃) δ 8.54 (s, 1H), 8.47 (d, J=4.8 Hz, 1H), 7.71 (d, J=6.8 Hz, 1H), 7.26-7.23 (m, 3H), 7.18-7.15 (m, 1H), 7.06-7.04 (m, 2H), 3.78-3.69 (m, 2H), 3.69-3.51 (m, 1H), 3.26-3.23 (m, 1H), 2.64-2.57 (m, 1H), 2.56 (s, 2H), 2.09-2.02 (m, 2H), 1.82-1.75 (m, 5H), 1.38 (s, 9H), 1.32-1.31 (m, 1H), 1.30-1.19 (m, 1H). MS-ESI calculated [M+H]⁺ 422, found 422.

Step 2

Compound 28-3 (35.0 mg, 83.0 μmol) was dissolved in anhydrous dichloromethane (2 mL) and trimethylsilyl trifluoromethanesulfonate (36.9 mg, 0.166 mmol) was added at 0° C. The mixture was stirred at 0° C. for 30 minutes. The reaction mixture was quenched by the addition of a drop of water, and concentrated under reduced pressure. The obtained crude product was isolated and purified by preparative high-performance liquid chromatography to give compound 28 (32.0 mg). ¹H NMR (400 MHz, D₂O) δ 8.93 (s, 1H), 8.80 (d, J=6.0 Hz, 1H), 8.69 (d, J=8.4 Hz, 1H), 8.07-8.04 (m, 1H), 7.32-7.28 (m, 2H), 7.24-7.22 (m, 1H), 7.21-7.13 (m, 2H), 4.52 (s, 2H), 3.46 (s, 2H), 3.40 (s, 2H), 3.00-2.95 (m, 1H), 2.58-2.51 (m, 1H), 2.03-1.94 (m, 6H), 1.53-1.50 (m, 1H), 1.39-1.35 (m, 1H). MS-ESI calculated [M+H]⁺ 322, found 322.

153

Synthetic Route:

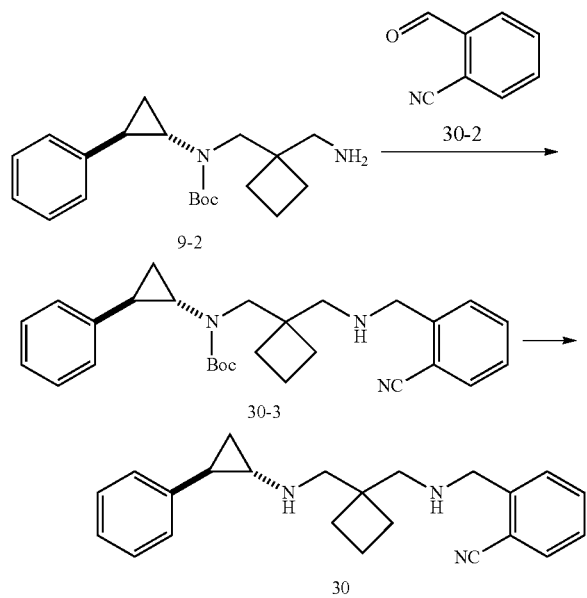

Step 1

The synthesis of compound 30-3 (33.0 mg) was referred to the first step of example 28. $^1$H NMR (400 MHz, CDCl$_3$) δ 8.88 (d, J=6.8 Hz, 1H), 7.62-7.60 (m, 1H), 7.55-7.53 (m, 1H), 7.49 (d, J=6.8 Hz, 1H), 7.25-7.22 (m, 2H), 7.14-7.10 (m, 3H), 4.78-4.77 (m, 2H), 4.42-4.48 (m, 1H), 4.10-4.07 (m, 1H), 3.67-3.63 (m, 1H), 3.44-3.38 (m, 1H), 2.93-2.90 (m, 1H), 2.20-1.89 (m, 7H), 1.45-1.41 (m, 1H), 1.33 (s, 9H), 1.28-1.27 (m, 1H). MS-ESI calculated [M+H]$^+$ 446, found 446.

Step 2

The synthesis of compound 30 (21.0 mg) was referred to the second step of example 28. $^1$H NMR (400 MHz, D$_2$O) δ 7.89 (d, J=8.0 Hz, 1H), 7.72-7.70 (m, 1H), 7.61-7.56 (m, 2H), 7.26-7.20 (m, 3H), 7.11-7.08 (m, 2H), 4.92 (s, 2H), 3.84 (s, 2H), 3.43 (s, 2H), 2.97-2.94 (m, 1H), 2.54-2.48 (m, 1H), 2.18-1.85 (m, 6H), 1.55-1.50 (m, 1H), 1.40-1.35 (m, 1H). MS-ESI calculated [M+H]$^+$ 346, found 346.

Example 31

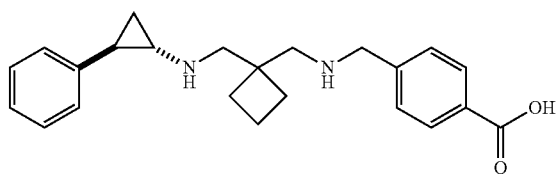

154

Synthetic Route:

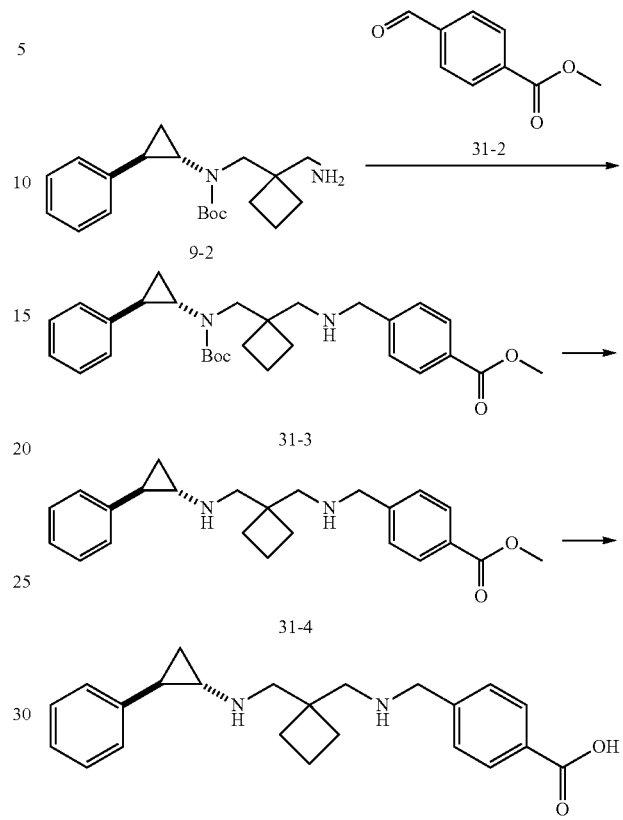

Step 1

The synthesis of compound 31-3 (70.0 mg) was referred to the first step of example 28. $^1$H NMR (400 MHz, CDCl$_3$) δ 7.98 (d, J=8.0 Hz, 2H), 7.43 (d, J=8.0 Hz, 2H), 7.26-7.23 (m, 2H), 7.16-7.15 (m, 1H), 7.06-7.05 (m, 2H), 3.90 (s, 3H), 3.81-3.76 (m, 2H), 3.57-3.53 (m, 1H), 3.28-3.24 (m, 1H), 2.64-2.62 (m, 1H), 2.57-2.56 (m, 2H), 2.12-2.07 (m, 1H), 2.06-1.99 (m, 1H), 1.83-1.76 (m, 5H), 1.38 (s, 9H), 1.33-1.30 (m, 1H), 1.19-1.17 (m, 1H). MS-ESI calculated [M+H]$^+$ 479, found 479.

Step 2

The synthesis of compound 314 (50.0 mg) was referred to the second step of example 28. MS-ESI calculated [M+H]$^+$ 379, found 379.

Step 3

Compound 31-4 (50.0 mg, 0.132 mmol) was dissolved in tetrahydrofuran (3 mL) and water (1 mL), and then lithium hydroxide (111 mg, 2.64 mmol) was added. The mixture was stirred at room temperature overnight. The reaction mixture was adjusted to pH=6 with 1N aqueous hydrochloric acid, and concentrated under reduced pressure. The crude product was purified by preparative high-performance liquid chromatography to give compound 31 (31.0 mg). $^1$H NMR (400 MHz, D$_2$O) δ 7.90 (d, J=8.8 Hz, 2H), 7.49 (d, J=8.8 Hz, 2H), 7.24-7.20 (m, 2H), 7.17-7.15 (m, 1H), 7.05-7.03 (m, 2H), 4.25 (s, 2H), 3.31 (s, 2H), 3.21 (s, 2H), 2.81-2.78 (m, 1H), 2.42-2.38 (m, 1H), 1.90-1.84 (m, 6H), 1.41-1.30 (m, 1H), 1.26-1.22 (m, 1H). MS-ESI MS-ESI calculated [M+H]+ 365, found 365.

Example 32

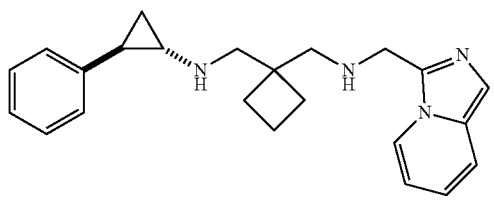

Synthetic Route:

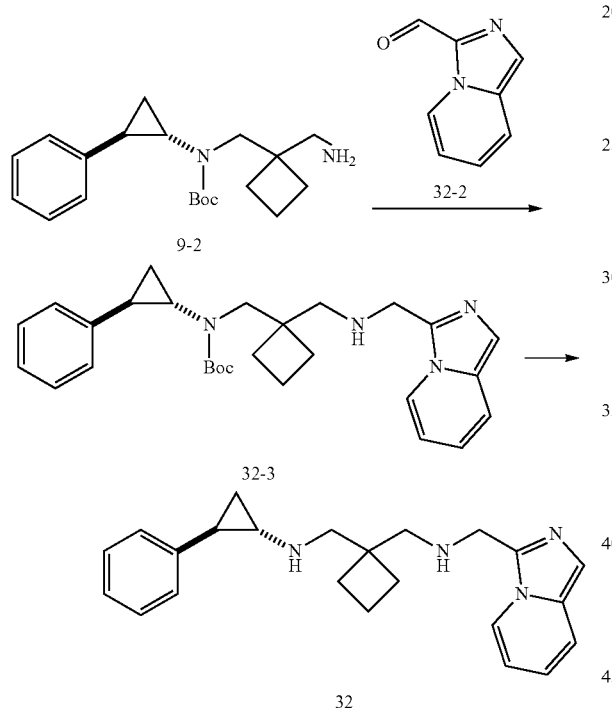

Step 1

The synthesis of compound 32-3 (27.0 mg) was referred to the first step of example 28. $^1$H NMR (400 MHz, CDCl$_3$) δ 8.31 (d, J=4.8 Hz, 1H), 7.39 (d, J=8.8 Hz, 1H), 7.32 (s, 1H), 7.26-7.23 (m, 2H), 7.17-7.13 (m, 1H), 7.06-7.04 (m, 2H), 6.67-6.65 (m, 1H), 6.51-6.50 (m, 1H), 4.22-4.13 (m, 2H), 3.53-3.50 (m, 1H), 3.22-3.14 (m, 1H), 2.63-2.61 (m, 1H), 2.58 (s, 2H), 2.08-2.05 (m, 1H), 1.98-1.93 (m, 1H), 1.76-1.59 (m, 5H), 1.37 (s, 9H), 1.31-1.28 (m, 1H), 1.17-1.13 (m, 1H). MS-ESI calculated [M+H]+ 461, found 461.

Step 2

The synthesis of compound 32 (3.0 mg) was referred to the second step of example 28. $^1$H NMR (400 MHz, Methonal-d$_4$) δ 8.30 (d, h=7.2 Hz, 1H), 7.50 (d, J=9.2 Hz, 1H), 7.34 (s, 1H), 7.25-7.21 (m, 2H), 7.17-7.13 (m, 1H), 7.03-6.98 (m, 2H), 6.78-6.75 (m, 1H), 6.64-6.62 (m, 1H), 4.21 (s, 2H), 2.76 (s, 2H), 2.69 (s, 2H), 2.19-2.15 (m, 1H), 1.90-1.85 (m, 2H), 1.79-1.74 (m, 5H), 0.94-0.89 (m, 2H). MS-ESI calculated [M+H]+ 361, found 361.

Example 33

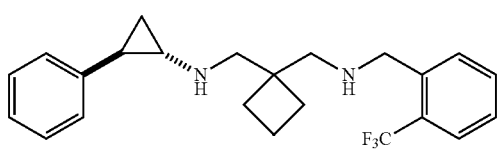

Synthetic Route:

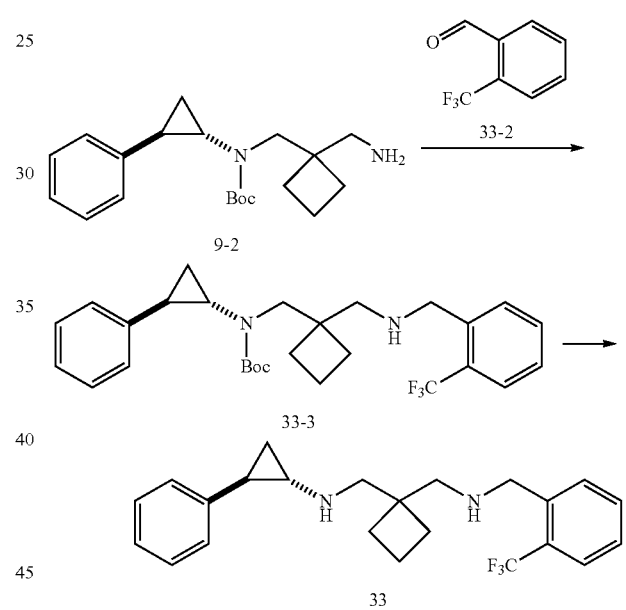

Step 1

The synthesis of compound 33-3 (25.0 mg) was referred to the first step of example 28. MS-ESI calculated [M+H]+ 489, found 489.

Step 2

The synthesis of compound 33 (20.0 mg) was referred to the second step of example 28. $^1$H NMR (400 MHz, D$_2$O) δ 7.76 (d, J=8.0 Hz, 1H), 7.64-7.63 (m, 2H), 7.58-7.52 (m, 1H), 7.31-7.27 (m, 2H), 7.23-7.21 (m, 1H), 7.14-7.12 (m, 2H), 4.44 (s, 2H), 3.41 (s, 2H), 3.39 (s, 2H), 2.95-2.92 (m, 1H), 2.54-2.49 (m, 1H), 2.00-1.94 (m, 6H), 1.50-1.49 (m, 1H), 1.36-1.33 (m, 1H). MS-ESI calculated [M+H]+ 389, found 389.

Example 34

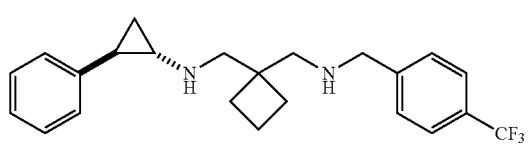

Synthetic Route:

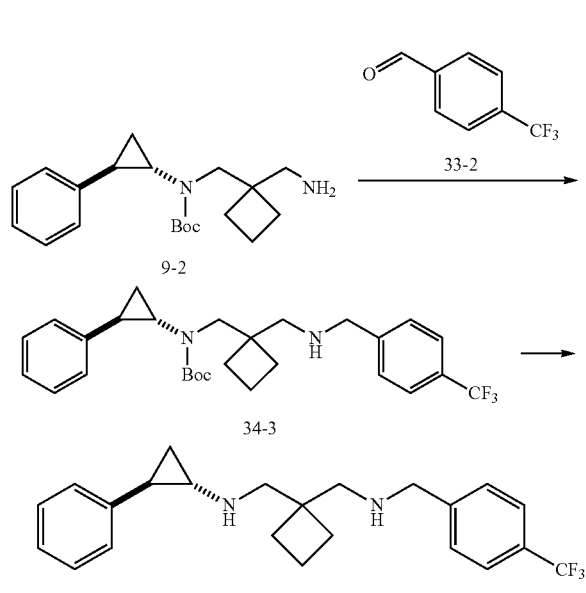

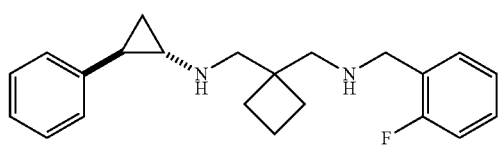

Step 1

The synthesis of compound 34-3 (20.0 mg) was referred to the first step of example 28. MS-ESI calculated [M+H]$^+$ 489, found 489.

Step 2

The synthesis of compound 34 (12.0 mg) was referred to the second step of example 28. $^1$H NMR (400 MHz, D$_2$O) δ 7.68 (d, J=8.4 Hz, 2H), 7.58 (d, J=8.4 Hz, 2H), 7.27-7.24 (m, 2H), 7.20-7.18 (m, 1H), 7.10-7.08 (m, 2H), 4.29 (s, 2H), 3.36 (d, J=2.0 Hz, 2H), 3.23 (s, 2H), 2.90-2.87 (m, 1H), 2.49-2.47 (m, 1H), 1.93-1.85 (m, 6H), 1.45-1.42 (m, 1H), 1.31-1.27 (m, 1H). MS-ESI calculated [M+H]$^+$ 389, found 389.

Example 35

Synthetic Route:

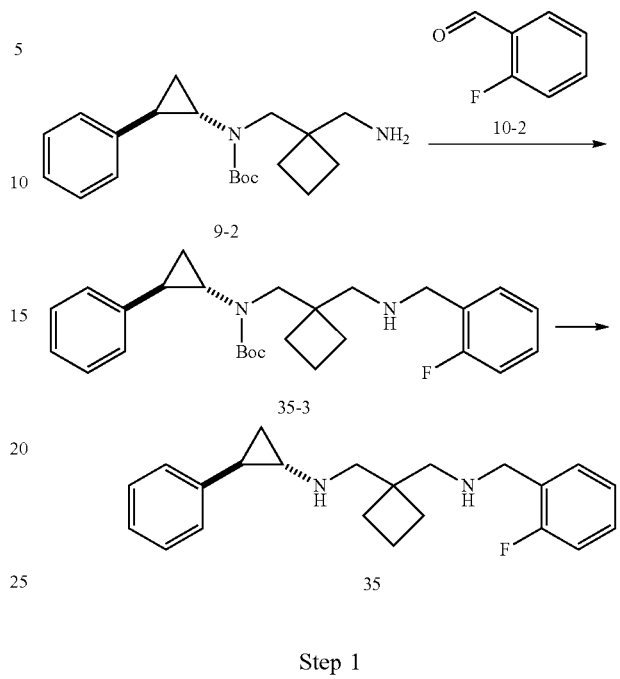

Step 1

The synthesis of compound 35-3 (77.0 mg) was referred to the first step of example 28. MS-ESI calculated [M+H]$^+$ 439, found 439.

Step 2

The synthesis of compound 35 (12.2 mg) was referred to the second step of example 28. $^1$H NMR (400 MHz, D$_2$O) δ 7.47-7.43 (m, 2H), 7.43-7.29 (m, 2H), 7.24-7.12 (m, 5H), 4.33 (s, 2H), 3.39 (s, 2H), 3.29 (s, 2H), 2.91-2.88 (m, 1H), 2.50-2.47 (m, 1H), 1.96-1.94 (m, 6H), 1.48-1.45 (m, 1H), 1.36-1.33 (m, 1H). MS-ESI calculated [M+H]$^+$ 339, found 339.

Example 36

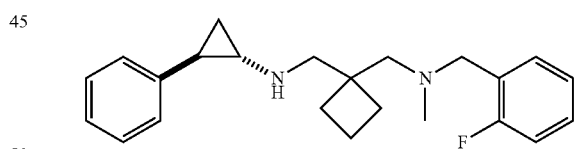

Synthetic Route:

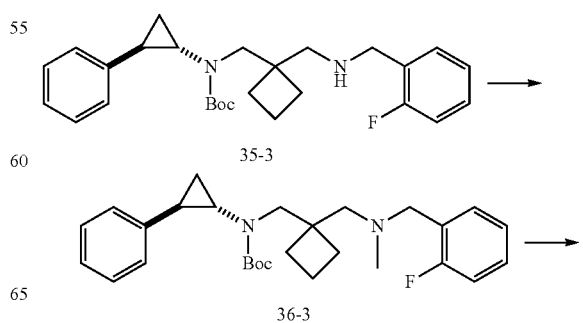

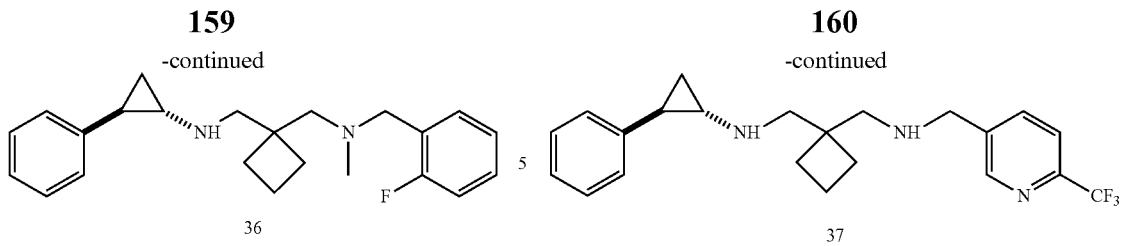

36

37

Step 1

Compound 35-3 (30.0 mg, 0.680 mmol) was dissolved in methanol under nitrogen. 37% aqueous formaldehyde (27.7 mg, 0.342 mmol) and acetic acid (20.5 mg, 0.342 mmol) were added and the reaction mixture was stirred at 25° C. for 10 min. Sodium cyanoborohydride (12.9 mg, 0.205 mmol) was added, and the mixture was stirred at 25° C. for 50 min. Water (50 mL) was added to the mixture. The mixture was extracted with ethyl acetate (50 mL×2) and washed with saturated brine (80 mL×1). The organic phase was dried over anhydrous sodium sulfate, followed by filtration and concentration under reduced pressure, and the obtained crude material was isolated and purified by thin layer chromatography (4:1 petroleum ether/ethyl acetate, Rf=0.34) to give compound 36-3 (30.0 mg). MS-ESI calculated [M+H]$^+$ 453, found 453.

Step 2

The synthesis of compound 36 (14.5 mg) was referred to the second step of example 28. $^1$H NMR (400 MHz, D$_2$O) δ 7.43-7.42 (m, 2H), 7.29-7.21 (m, 2H), 7.16-7.10 (m, 5H), 4.34 (s, 2H), 3.44 (s, 2H), 3.34 (s, 2H), 2.92-2.89 (m, 1H), 2.79 (s, 3H), 2.53-2.47 (m, 1H), 1.91-1.90 (m, 4H), 1.89-1.88 (m, 2H), 1.50-1.48 (m, 1H), 1.35-1.32 (m, 1H). MS-ESI calculated [M+H]$^+$ 353, found 353.

Example 37

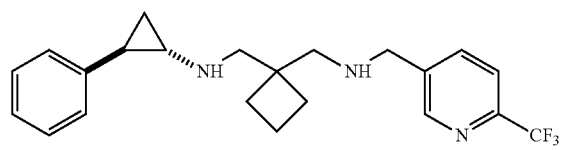

Synthetic Route:

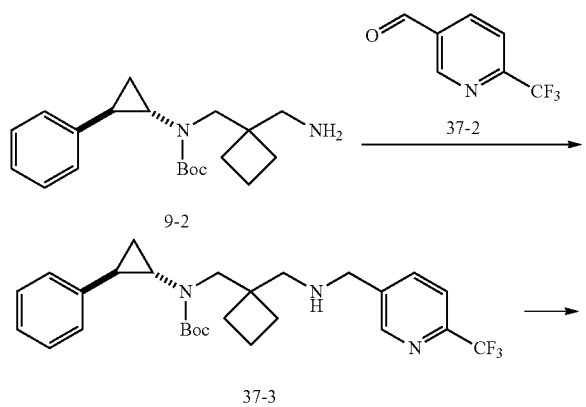

Step 1

The synthesis of compound 37-3 (127.0 mg) was referred to the first step of example 28. MS-ESI calculated [M+H]$^+$ 490, found 490.

Step 2

The synthesis of compound 37 (12.5 mg) was referred to the second step of example 28. $^1$H NMR (400 MHz, CH$_3$OD) δ 9.03 (d, J=1.6 Hz, 1H), 8.46 (dd. J$_1$=1.6, J$_2$=8.0 Hz, 1H), 7.94 (d, J=8.0 Hz, 1H), 7.34-7.31 (m, 2H), 7.24-7.21 (m, 3H), 4.56 (s, 2H), 3.59 (d, J=4.0 Hz, 2H), 3.54 (s, 2H), 3.18-3.16 (m, 1H), 2.82-2.80 (m, 1H), 2.15-2.13 (m, 6H), 1.82-1.76 (m, 1H), 1.41-1.38 (m, 1H). MS-ESI calculated [M+H]$^+$ 390, found 390.

Example 38

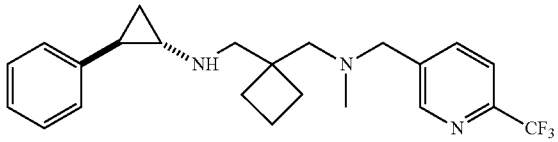

Synthetic Route:

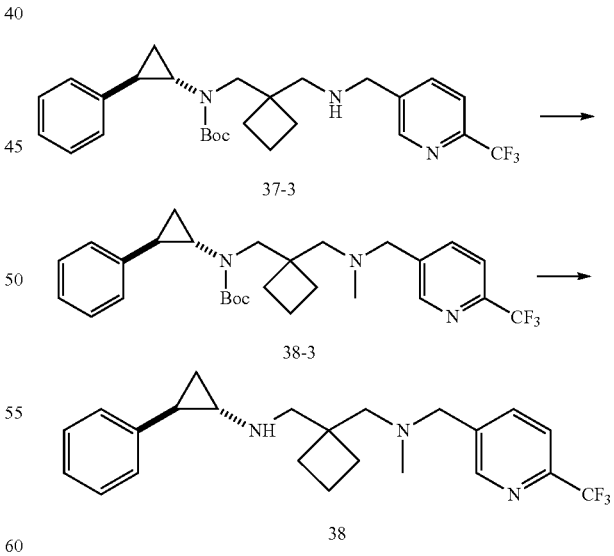

Step 1

The synthesis of compound 38-3 (53.0 mg) was referred to the first step of example 36. MS-ESI calculated [M+H]$^+$ 504, found 504.

Step 2

The synthesis of compound 38 (20.4 mg) was referred to the second step of example 28. ¹H NMR (400 MHz, D₂O) δ 8.72 (d, J=2.0 Hz, 1H), 8.17 (dd, J₁=2.0, J₂=8.0 Hz, 1H), 7.87 (d, J=8.0 Hz, 1H), 7.29-7.25 (m, 2H), 7.21-7.18 (m, 1H), 7.12-7.10 (m, 2H), 4.45 (s, 2H), 3.47-3.43 (m, 4H), 2.97-2.95 (m, 1H), 2.73 (s, 3H), 2.53-2.52 (m, 1H), 2.04-1.92 (m, 6H), 1.52-1.49 (m, 1H), 1.36-1.32 (m, 1H). MS-ESI calculated [M+H]⁺ 404, found 404.

Example 39

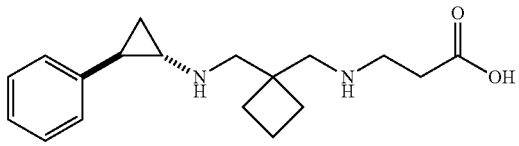

Synthetic Route:

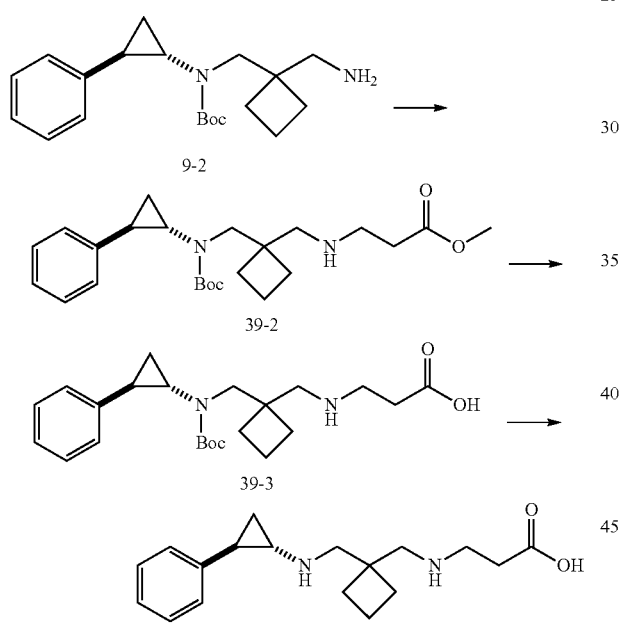

Step 1

Compound 9-2 (100 mg, 0.302 mmol) was dissolved in isopropanol (5 mL) under nitrogen. Then triethylamine (153 mg, 1.51 mmol) and methyl acrylate (78.2 mg, 0.907 mmol) were added to the mixture. The reaction mixture was heated to 80° C. in a sealed tube and stirred for 12 hours. Water (20 mL) was added to the mixture. The mixture was extracted with ethyl acetate (20 mL×1). The organic phases were combined, washed with saturated brine (20 mL×1) and dried over anhydrous sodium sulfate, followed by filtration and concentration under reduced pressure, and the obtained crude material was isolated and purified by silica gel column chromatography (1:1 petroleum ether/ethyl acetate, Rf=0.21) to give Compound 39-2 (30.0 mg). ¹H NMR (400 MHz, CDCl₃) δ 7.26-7.23 (m, 2H), 7.17-7.15 (m, 1H), 7.07-7.05 (m, 2H), 3.66 (s, 3H), 3.51-3.47 (m, 1H), 3.24-3.20 (m, 1H), 2.83 (t, J=7.2 Hz, 2H), 2.66-2.62 (m, 1H), 2.57-2.56 (m, 2H), 2.46 (t, J=7.2 Hz, 2H), 2.10-2.05 (m, 1H), 1.84-1.74 (m, 8H), 1.38 (s, 9H).

Step 2

Compound 39-2 (30.0 mg, 72 μmol) was dissolved in water (1 mL) and tetrahydrofuran (4 mL). Then lithium hydroxide monohydrate (8.6 mg, 0.360 mmol) were added and the mixture was stirred at 25° C. for 12 hours. The aqueous phase was adjusted to pH=5 with 1M aqueous hydrochloric acid and extracted with dichloromethane/methanol (10:1) (20 mL×2). The organic phases were combined, washed with saturated brine (20 mL×1) and dried over anhydrous sodium sulfate, followed by filtration and concentration under reduced pressure to give compound 39-3 (20.0 mg). MS-ESI calculated [M+H]⁺ 403, found 403.

Step 3

The synthesis of compound 39 (11.1 mg) was referred to the second step of example 28. ¹H NMR (400 MHz, D₂O) δ 7.32-7.29 (m, 2H), 7.25-7.23 (m, 1H), 7.16-7.14 (m, 2H), 3.44 (s, 2H), 3.32 (t, J=6.8 Hz, 2H), 3.28 (s, 2H), 2.98-2.97 (m, 1H), 2.78 (t, J=6.8 Hz, 2H), 2.56-2.51 (m, 1H), 2.00-1.95 (m, 6H), 1.53-1.52 (m, 1H), 1.38-1.36 (m, 1H). MS-ESI calculated [M+H]⁺ 303, found 303.

Example 40

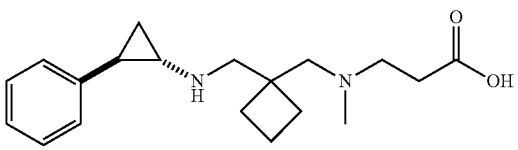

Synthetic Route:

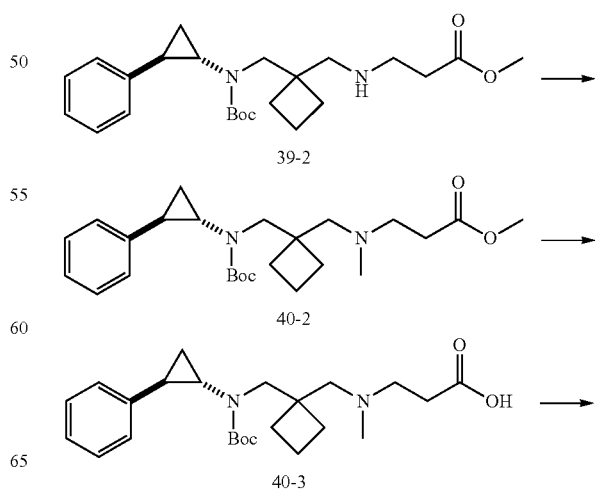

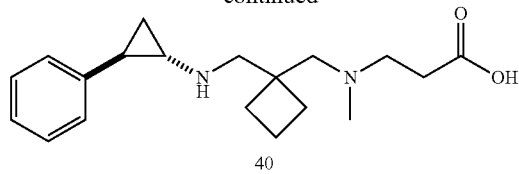

40

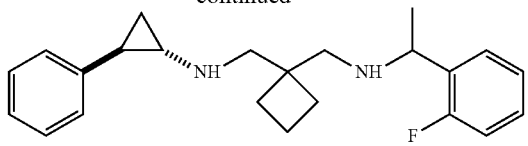

41

Step 1

The synthesis of compound 40-2 (70.0 mg) was referred to the first step of example 36. MS-ESI calculated [M+H]+ 431, found 431.

Step 2

The synthesis of compound 40-3 (70.0 mg) was referred to the second step of example 39. MS-ESI calculated [M+H]+ 417, found 417.

Step 3

The synthesis of compound 40 (22.5 mg) was referred to the second step of example 28. $^1$H NMR (400 MHz, D$_2$O) δ 7.35-7.31 (m, 2H), 7.27-7.23 (m, 1H), 7.19-7.17 (m, 2H), 3.58 (s, 2H), 3.44-3.34 (m, 4H), 3.06-3.03 (m, 1H), 2.90-2.80 (m, 5H), 2.63-2.58 (m, 1H), 2.14-1.98 (m, 6H), 1.59-1.58 (m, 1H), 1.41-1.39 (m, 1H). MS-ESI calculated [M+H]+ 317, found 317.

Example 41

Step 1

Compound 9-2 (35 mg, 0.106 mmol) was dissolved in tetrahydrofuran (5 mL) under nitrogen. Then p-fluoroacetophenone (14.6 mg, 0.106 mmol) and tetraethyloxytitanium (48.3 mg, 0.212 mmol)) were added to the mixture. The reaction mixture was stirred at 60° C. for 11 hours. Then sodium borohydride (12.0 mg, 0.317 mmol) and methanol (1 mL) were added, and the mixture was stirred at 25° C. for 1 h and water (20 mL) was added. The mixture was extracted with ethyl acetate (20 mL×1). The organic phase was washed with saturated brine (20 mL×1) and dried over anhydrous sodium sulfate, followed by filtration and concentration under reduced pressure, and the obtained crude material was isolated and purified by thin layer chromatography (20:1 dichloromethane/methanol, Rf=0.54) to give Compound 41-3 (20.0 mg). MS-ESI calculated [M+H]+ 453, found 453.

The synthesis of compound 41 (3.2 mg) was referred to the second step of example 28. $^1$H NMR (400 MHz, D$_2$O) δ 7.42-7.40 (m, 2H), 7.24-7.22 (m, 2H), 7.18-7.14 (m, 1H), 7.07-7.05 (m, 4H), 4.38-4.33 (m, 1H), 3.29-3.11 (m, 3H), 2.88-2.85 (m, 1H), 2.79-2.76 (m, 1H), 2.46-2.37 (m, 1H), 1.89-1.70 (m, 6H), 1.57 (d, J=6.8 Hz, 3H), 1.44-1.35 (m 1H), 1.27-1.21 (m, 1H). MS-ESI calculated [M+H]+ 353, found 353.

Example 42

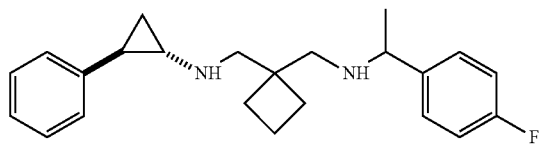

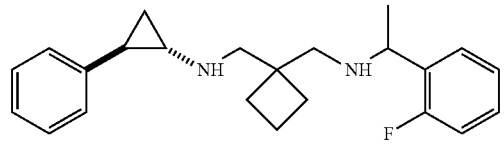

Synthetic Route:

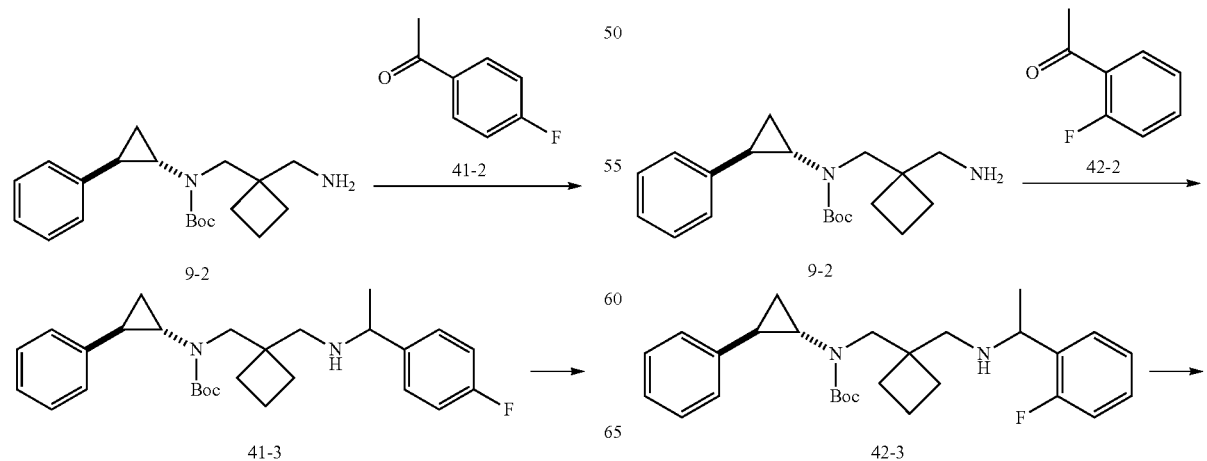

Synthetic Route:

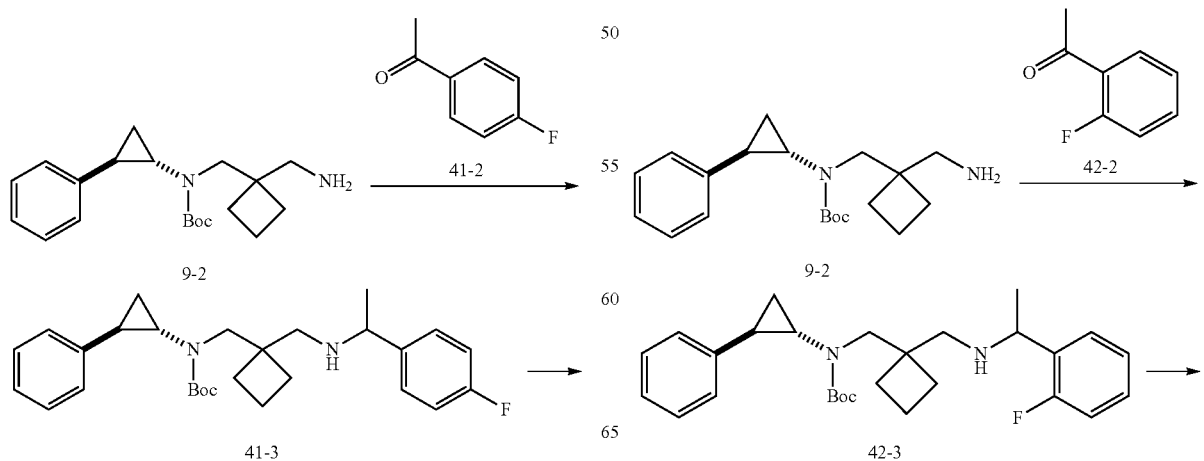

-continued

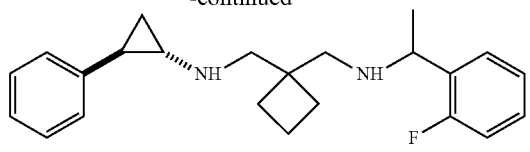

42

Step 1

The synthesis of compound 42-3 (25.0 mg) was referred to the first step of example 41. MS-ESI calculated [M+H]+ 453, found 453.

Step 2

The synthesis of compound 42 (4.0 mg) was referred to the second step of example 28. ¹H NMR (400 MHz, D₂O) δ 7.44-7.43 (m, 1H), 7.28-7.25 (m, 1H), 7.21-7.19 (m, 2H), 7.10-7.08 (m, 5H), 4.64-4.59 (m, 1H), 3.32-3.27 (m, 3H), 2.97-2.93 (m, 1H), 2.84-2.80 (m, 1H), 2.48-2.39 (m, 1H), 1.91-1.80 (m, 6H), 1.62 (d, J=−6.8 Hz, 3H), 1.47-1.37 (m, 1H), 1.29-1.25 (m, 1H). MS-ESI calculated [M+H]+ 353, found 353.

Example 43

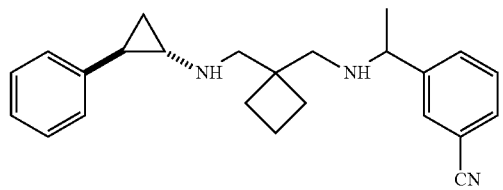

Synthetic Route:

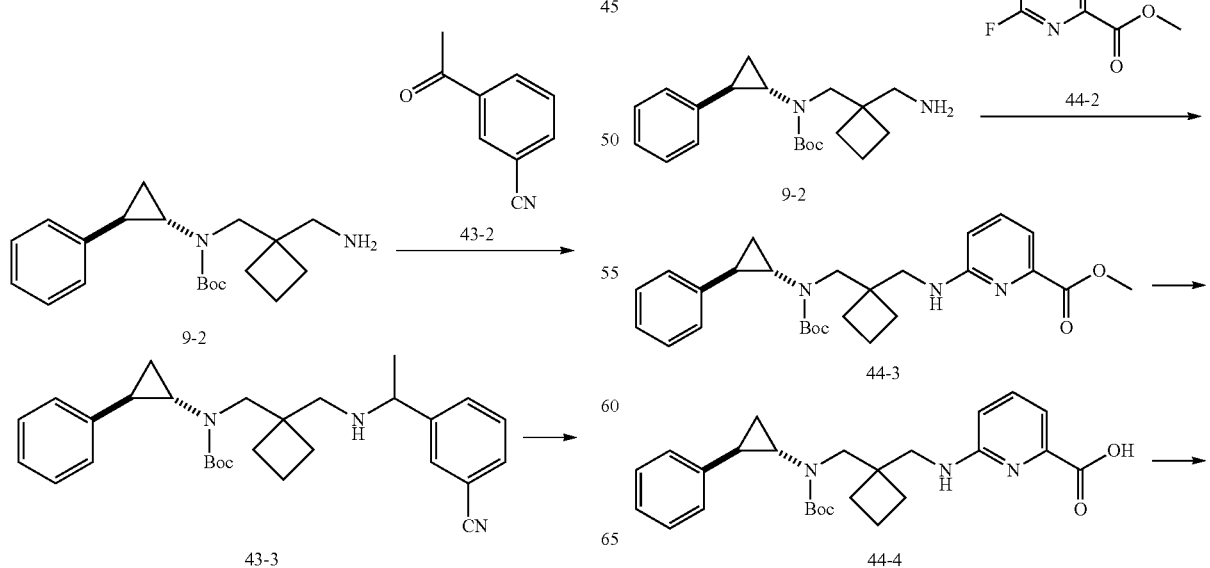

-continued

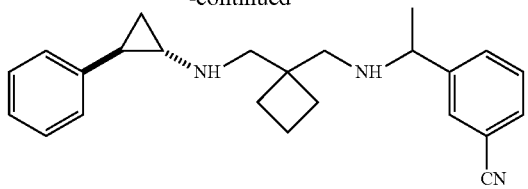

43

Step 1

The synthesis of compound 43-3 (30.0 mg) was referred to the first step of example 41. MS-ESI calculated [M+H]+ 460, found 460.

Step 2

The synthesis of compound 43 (3.4 mg) was referred to the second step of example 28. ¹H NMR (400 MHz, D₂O) δ 7.82 (d, J=1.6 Hz, 1H), 7.76-7.70 (m, 2H), 7.57-7.53 (m, 1H), 7.30-7.28 (m, 2H), 7.24-7.20 (m, 1H), 7.12-7.10 (m, 2H), 4.51-4.45 (m, 1H), 3.31-3.17 (m, 3H), 2.94-2.91 (m, 1H), 2.85-2.84 (m, 1H), 2.50-2.40 (m, 1H), 1.94-1.80 (m, 6H), 1.65 (d, J=6.8 Hz, 3H), 1.48-1.40 (m, 1H), 1.32-1.28 (m, 1H). MS-ESI calculated [M+H]+ 360, found 360.

Example 44

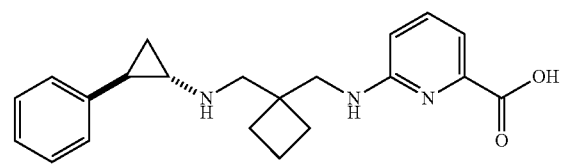

Synthetic Route:

-continued

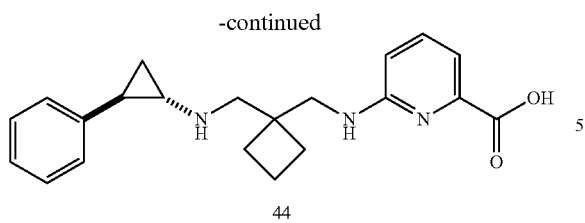

44

Step 1

Compound 9-2 (70.0 mg, 0.212 mmol) was dissolved in dimethyl sulfoxide (5 mL) under nitrogen, diisopropylethylamine (82.1 mg, 0.635 mmol) and compound 44-2 (49.3 mg, 0.318 mmol) were added at 25° C., and the reaction mixture was stirred at 100° C. for 12 hours. Water (20 mL) was added to the mixture. The mixture was extracted with ethyl acetate (20 mL×1). The organic phase was washed with saturated brine (20 mL×3) and dried over anhydrous sodium sulfate, followed by filtration and concentration under reduced pressure, and the obtained crude material was isolated and purified by thin layer chromatography (1:1 petroleum ether/ethyl acetate, Rf=0.5) to give Compound 44-3. MS-ESI calculated $[M+H]^+$ 466, found 466.

Step 2

The synthesis of compound 44-4 was referred to the second step of example 39. MS-ESI calculated $[M+H]^+$ 452, found 452.

Step 3

The synthesis of compound 44 was referred to the second step of example 28. $^1$H NMR (400 MHz, D$_2$O) δ 7.90-7.86 (m, 1H), 7.30 (d, J=6.8 Hz, 1H), 7.16-7.07 (m, 4H), 7.00-6.98 (m, 2H), 3.52 (s, 2H), 3.39 (s, 2H), 2.89-2.85 (m, 1H), 2.44-2.39 (m, 1H), 1.99-1.93 (m, 6H), 1.49-1.44 (m, 1H), 1.30-1.25 (m, 1H). MS-ESI calculated $[M+H]^+$ 352, found 352.

Example 45

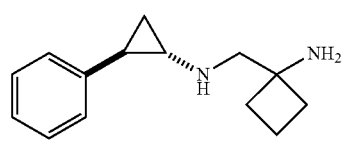

Synthetic Route:

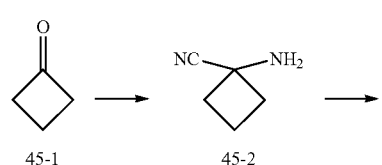

-continued

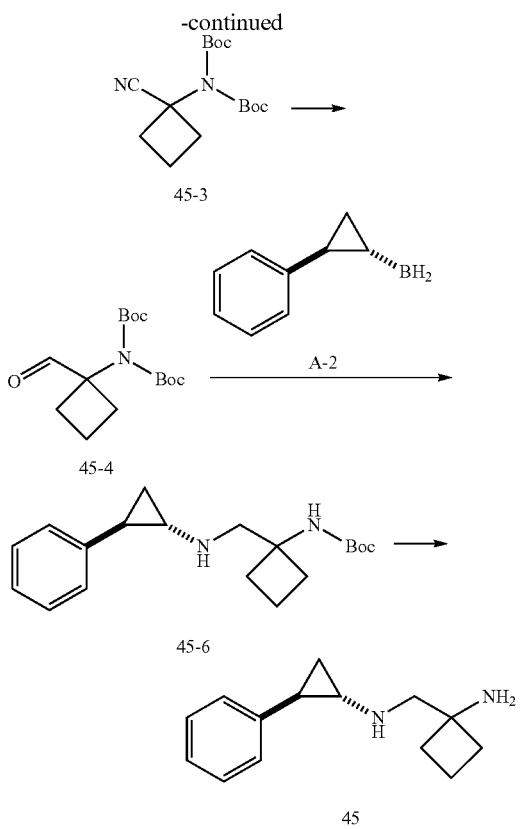

Step 1

Compound 45-1 (2.00 g, 28.5 mmol) was dissolved in methanol (20 mL) under nitrogen, aqueous ammonia (17.0 g, 485 mmol), sodium cyanide (1.75 g, 35.7 mmol) and ammonium chloride (3.05 g, 57.1 mmol) were added at 25° C., and the mixture was stirred at 25° C. for 12 h. Water (30 mL) was added to the mixture. The mixture was extracted with ethyl acetate (80 mL×1). The organic phase was washed with saturated brine (80 mL×1) and dried over anhydrous sodium sulfate, followed by filtration and concentration under reduced pressure to give compound 45-2. $^1$H NMR (400 MHz, CDCl$_3$) δ 2.66-2.58 (m, 2H), 2.17-2.02 (m, 4H), 1.84 (br s, 2H).

Step 2

Compound 45-2 (1.65 g, 17.2 mmol) was dissolved in di-tert-butyl dicarbonate (5 mL), and the mixture was stirred at 90° C. for 12 h. The reaction mixture was separated and purified by silica gel column chromatography (5:1 petroleum ether/ethyl acetate, Rf=0.6) to give compound 45-3. $^1$H NMR (400 MHz, CDCl$_3$) δ 2.78-2.73 (m, 2H), 2.42-2.33 (m, 2H), 2.20-2.08 (m, 1H), 1.91-1.83 (m, 1H), 1.53 (s, 18H).

Step 3

Compound 45-3 (500 mg, 1.69 mmol) was dissolved in dichloromethane (20 mL) under nitrogen, di-isobutylaluminum hydride (1 M in toluene, 6.76 mL, 6.76 mmol) was added at −78° C., and the reaction mixture was stirred at −78° C. for 3 hours. Water (20 mL) was added to the mixture. The mixture was extracted with dichloromethane (20 mL×1). The organic phase was washed with saturated brine (30 mL×1) and dried over anhydrous sodium sulfate, followed by filtration and concentration under reduced pressure to give compound 45-4. ¹H NMR (400 MHz, CDCl₃) δ 9.53 (s, 1H), 2.39-2.35 (m, 2H), 2.28-2.26 (m, 2H), 1.86-1.81 (m, 2H), 1.36 (s, 18H).

Step 4

The synthesis of compound 45-6 was referred to the first step of example 28. MS-ESI calculated [M+H]⁺ 317, found 317.

Step 5

The synthesis of compound 45 was referred to the second step of example 28. ¹H NMR (400 MHz, Methonal-d₄) δ 7.36-7.30 (m, 2H), 7.27-7.22 (m, 3H), 3.73 (s, 2H), 3.19-3.15 (m, 1H), 2.78-2.73 (m, 1H), 2.49-2.37 (m, 4H), 2.20-2.07 (m, 2H), 1.78-1.72 (m, 1H), 1.48-1.42 (m, 1H). MS-ESI calculated [M+H]⁺ 217, found 217.

Example 46

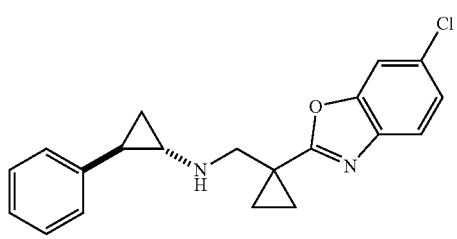

Synthetic Route:

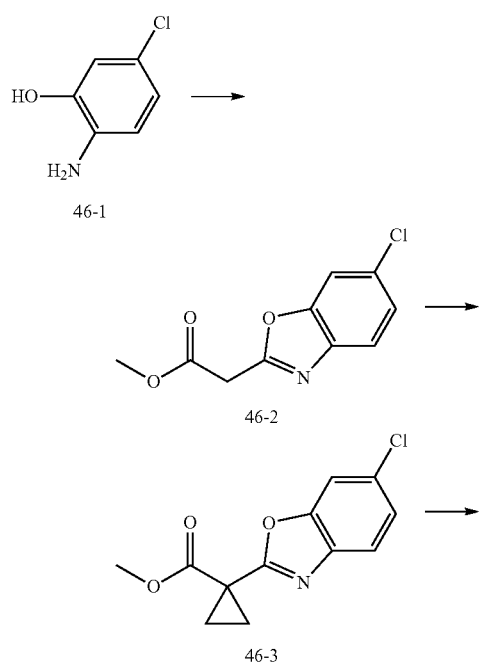

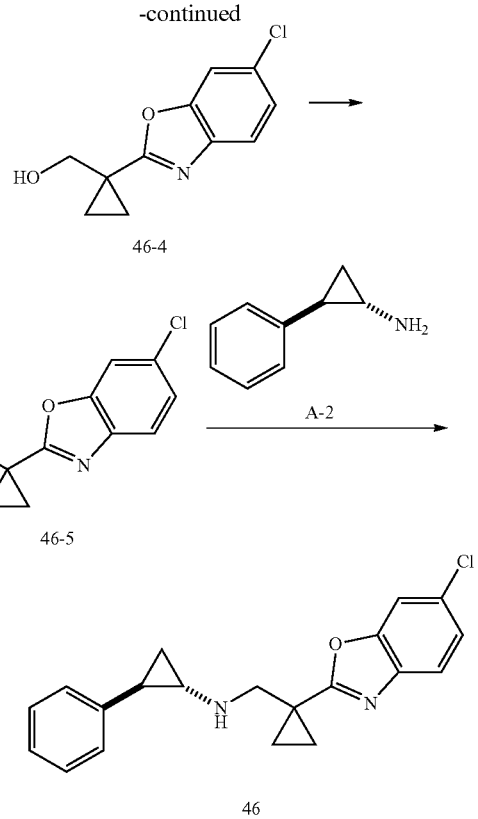

Step 1

Compound 46-1 (200 mg, 1.39 mmol) was dissolved in dimethyl malonate (3 mL) under nitrogen, and p-toluenesulfonic acid (12.0 mg, 69.5 μmol) was added at 25° C. The mixture was stirred at 140° C. for 12 h and then isolated and purified by silica gel column chromatography (5:1 petroleum ether/ethyl acetate, Rf=0.7) to give compound 46-2. ¹H NMR (400 MHz, CDCl₃) δ 7.63 (d, J=2.0 Hz, 1H), 7.38 (d, J=8.4 Hz, 1H), 7.26 (dd, J=2.0, 8.4 Hz, 1H), 3.96 (s, 2H), 3.72 (s, 3H).

Step 2

The synthesis of compound 46-3 was referred to the first step of example 1. ¹H NMR (400 MHz, CDCl₃) 7.69 (d, J=2.0 Hz, 1H), 7.46 (d, J=8.4 Hz, 1H), 7.34 (dd, J=2.0, 8.4 Hz, 1H), 3.78 (s, 3H), 1.84-1.81 (m, 2H), 1.71-1.68 (m, 2H).

Step 3

The synthesis of compound 46-4 was referred to the second step of example 1. MS-ESI calculated [M+H]⁺ 224, found 224.

Step 4

Compound 46-4 (24.0 mg, 0.11 mmol) was dissolved in dichloromethane (2 mL) under nitrogen, Dess Martin reagent (91.0 mg, 0.215 mmol) was added at 25° C., and the mixture was stirred at 25° C. for 1 hour. Saturated sodium carbonate (20 mL) was added and the mixture was extracted with dichloromethane (20 mL×1). The organic phase was washed with saturated brine (20 mL×1) and dried over anhydrous sodium sulfate, followed by filtration and concentration under reduced pressure to give compound 46-5. MS-ESI calculated [M+H]+ 222, found 222.

Step 5

Compound 46-5 (24.0 mg, 0.180 mmol) and A-2 (40.0 mg, 0.180 mmol) were dissolved in anhydrous dichloromethane (10 mL), and acetic acid (32.5 mg, 0.541 mmol) was added to the mixture. After stirring at 25° C. for 1 hour, sodium triacetoxyborohydride (115 mg, 0.541 mmol) was added. The mixture was stirred at 25° C. for 11 h. The mixture was diluted with dichloromethane (20 mL) and washed successively with saturated sodium carbonate aqueous solution (20 mL×1), saturated brine (20 mL×1). Then the mixture was dried over anhydrous sodium sulfate, followed by filtration and concentration under reduced pressure. The residue was isolated and purified by high-performance liquid chromatography to give compound 46. $^1$H NMR (400 MHz, Methonal-$d_4$) δ 7.58 (d, J=2.0 Hz, 1H), 7.46 (d, J=8.4 Hz, 1H), 7.31 (d, J=2.0 Hz, 1H), 7.20-7.19 (m, 2H), 7.10-7.09 (m, 1H), 7.01-6.99 (m, 2H), 3.25-3.13 (m, 2H), 2.49-2.45 (m, 1H), 1.95-1.90 (m, 1H), 1.46-1.43 (m, 2H), 1.22-1.16 (m, 2H), 1.11-1.09 (m, 1H), 1.02-0.97 (m, 1H). MS-ESI calculated [M+H]+ 339, found 339.

Example 47

Synthetic Route:

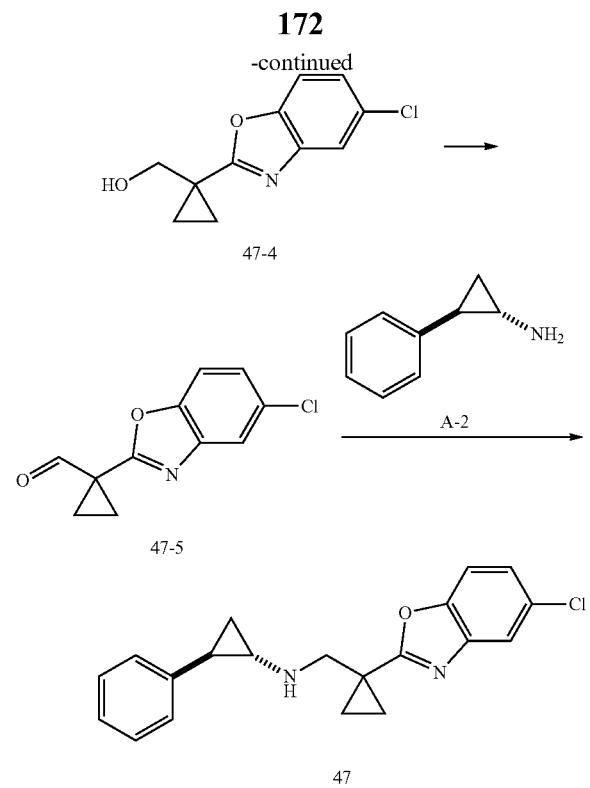

Step 1

The synthesis of compound 47-2 was referred to the first step of example 46. $^1$H NMR (400 MHz, CDCl$_3$) δ 7.65 (d, J=8.4 Hz, 1H), 7.57 (d, J=2.0 Hz, 1H), 7.35 (dd, J=2.0, 8.4 Hz, 1H), 4.04 (s, 2H), 3.81 (s, 3H).

Step 2

The synthesis of compound 47-3 was referred to the first step of example 1. $^1$H NMR (400 MHz, CDCl$_3$) δ 7.61 (d, J=8.4 Hz, 1H), 7.56 (d, J=2.0 Hz, 1H), 7.33 (dd, J=2.0, 8.4 Hz, 1H), 3.78 (s, 3H), 1.83-1.80 (m, 2H), 1.70-1.67 (m, 2H).

Step 3

The synthesis of compound 474 was referred to the second step of example 1. MS-ESI calculated [M+H]+ 224, found 224.

Step 4

The synthesis of compound 47-5 was referred to the fourth step of example 46. MS-ESI calculated [M+H]+ 222, found 222.

Step 5

The synthesis of compound 47 was referred to the fifth step of example 46. $^1$H NMR (400 MHz, Methonal-$d_4$) δ 7.55-7.52 (m, 2H), 7.32 (dd, J=2.0, 8.4 Hz, 1H), 7.20-7.16 (m, 2H), 7.10-7.06 (m, 1H), 7.00-6.98 (m, 2H), 3.23-3.14 (m, 2H), 2.48-2.44 (m, 1H), 1.94-1.90 (m, 1H), 1.47-1.41

(m, 2H), 1.19-1.10 (m, 3H), 1.09-0.96 (m, 1H). MS-ESI calculated [M+H]⁺ 339, found 339.

Example 48

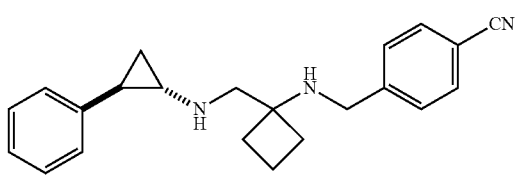

Synthetic Route:

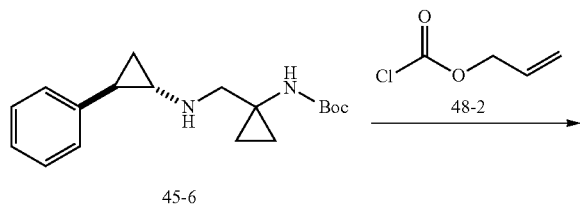

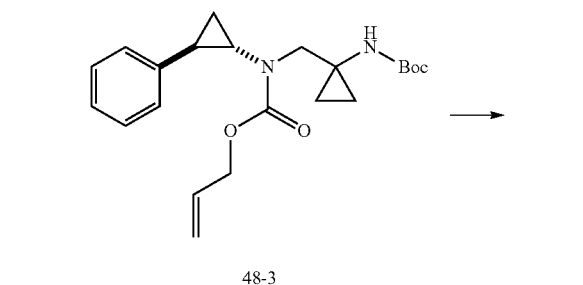

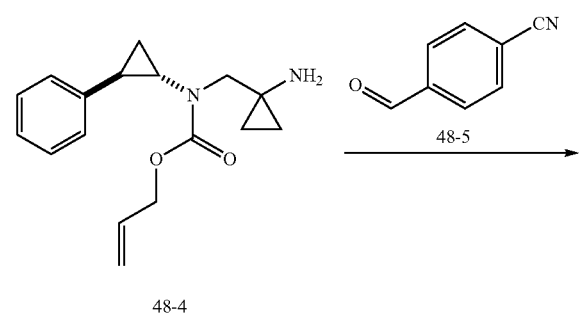

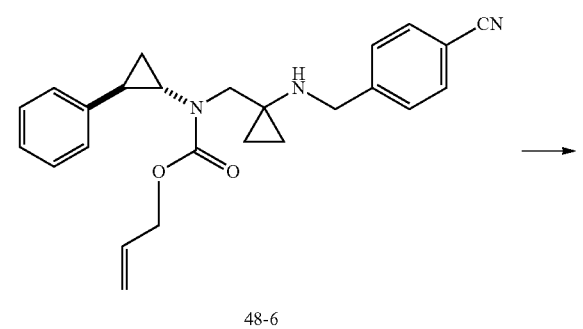

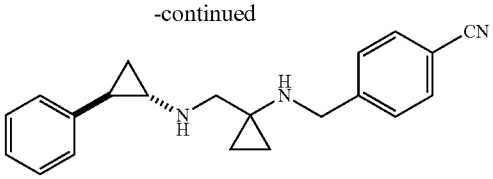

48

Step 1

Compound 45-6 (4.00 g, 12.6 mmol) was dissolved in anhydrous dichloromethane (40 mL). Triethylamine (3.84 g, 37.9 mmol) and allyl chloroformate (1.83 g, 15.2 mmol) were added at 0° C. The reaction mixture was stirred at 25° C. for 2 hours. Water (50 mL) was added to the mixture and the mixture was extracted with dichloromethane (20 mL×1). The organic phase was washed with saturated brine (50 mL×1) and dried over anhydrous sodium sulfate, followed by filtration and concentration under reduced. The residue was isolated and purified by silica gel column chromatography (5:1 petroleum ether/ethyl acetate, Rf=0.8) to give compound 48-3. MS-ESI calculated [M+H]⁺ 401, found 401.

Step 2

Compound 48-3 (4.00 g, 9.99 mmol) was dissolved in anhydrous dichloromethane (50 mL), and trimethylsilyl trifluoromethanesulfonate (4.44 g, 20.0 mmol) was added at 0° C. The reaction mixture was stirred at 0° C. for 0.5 h. And water (1 mL) was added to the mixture, and the mixture was concentrated under reduced pressure. The residue was isolated and purified by silica gel column chromatography (1:1 petroleum ether/ethyl acetate, Rf=0.1) to give compound 48-4. MS-EST calculated [M+H]⁺ 301, found 301.

Step 3

The synthesis of compound 48-6 was referred to the first step of example 28. MS-ESI calculated [M+H]⁺ 416, found 416.

Step 4

Compound 48-6 (32 mg, 77.0 μmol) was dissolved in tetrahydrofuran (5 mL) under nitrogen, and diethylamine (56.3 mg, 0.077 mmol) and tetratriphenylphosphine palladium (8.90 mg, 7.70 μmol) were added. The reaction mixture was stirred at 70° C. for 12 h. Water (20 mL) was added to the mixture and the mixture was extracted with ethyl acetate (20 mL×3). The organic phases were combined, washed with saturated brine (20 mL×1) and dried over anhydrous sodium sulfate, followed by filtration and concentration under reduced pressure, and the residue was isolated and purified by high-performance liquid chromatography to give compound 48. ¹H NMR (400 MHz, Methonal-d₄) δ 7.81-7.79 (m, 2H), 7.75-7.73 (m, 2H), 7.24-7.20 (m, 2H), 7.16-7.12 (m, 3H), 4.35-4.27 (m, 2H), 3.84 (s, 2H), 3.14-3.04 (m, 1H), 2.78-2.66 (m, 1H), 2.55-2.47 (m, 2H), 2.41-2.28 (m, 2H), 2.13-1.96 (m, 2H), 1.76-1.66 (m, 1H), 1.35-1.30 (m, 1H). MS-ESI calculated [M+H]⁺ 332, found 332.

Example 49

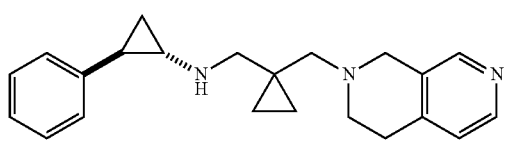

Synthetic Route:

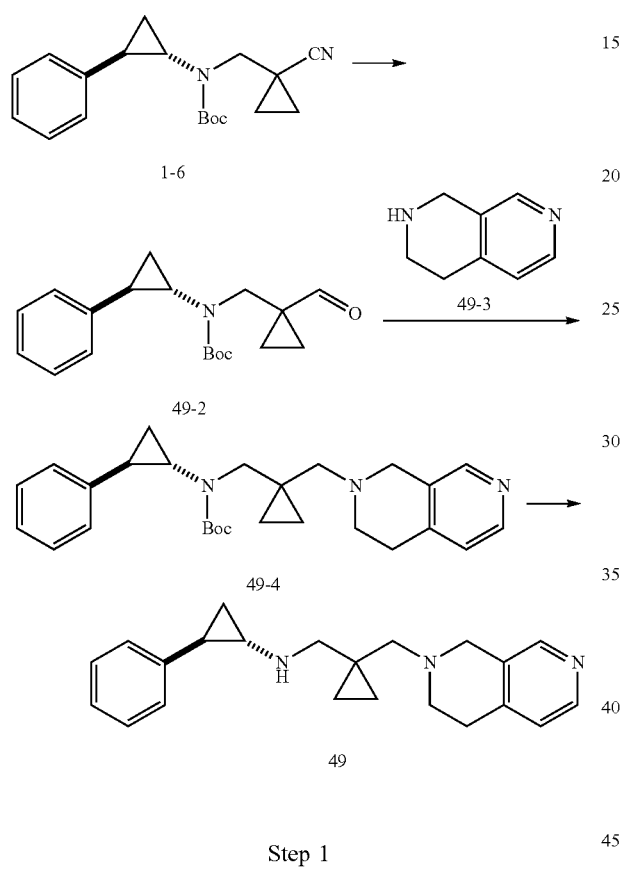

Step 1

Compound 1-6 (4.00 g, 12.8 mmol) was dissolved in dichloromethane (50 mL) under nitrogen, and diisobutyl-aluminum hydride (1 M in toluene, 25.6 mL, 25.6 mmol) was added at −78 V. The reaction solution was stirred at −78° C. for 3 hours. Saturated sodium potassium tartrate aqueous solution (100 mL) was added to the reaction mixture, and the mixture was stirred at 25° C. for 12 hours. The mixture was extracted with dichloromethane (100 mL×1). The organic phases were combined, washed with saturated brine (100 mL×1) and dried over anhydrous sodium sulfate, followed by filtration and concentration under reduced pressure, and the residue was isolated and purified by silica gel column chromatography (4:1 petroleum ether/ethyl acetate, Rf=0.7) to give compound 49-2. $^1$H NMR (400 MHz, CDCl$_3$) δ 9.00 (s, 1H), 7.26-7.24 (m, 2H), 7.12-7.08 (m, 1H), 7.03-7.01 (m, 2H), 3.71-3.63 (m, 2H), 2.63-2.59 (m, 1H), 2.07-2.02 (m, 1H), 1.34 (s, 9H), 1.25-1.19 (m, 2H), 1.14-1.08 (m, 4H).

The synthesis of compound 49-4 was referred to the first step of example 28. MS-ESI calculated [M+H]$^+$ 434, found 434.

Step 3

The synthesis of compound 49 was referred to the second step of example 28. $^1$H NMR (400 MHz, Methonal-d$_4$) δ 8.94 (s, 1H), 8.77 (d, J=6.0 Hz, 111), 8.05 (d, J=6.0 Hz, 1H), 7.32-7.28 (m, 2H), 7.24-7.20 (m, 3H), 4.91-4.66 (m, 2H), 4.3-3.3 (m, 8H), 3.18-3.14 (m, 1H), 2.85-2.75 (m, 1H), 1.80-1.75 (m, 1H), 1.39-1.34 (m, 1H), 1.15-1.08 (m, 4H). MS-ESI calculated [M+H]$^+$ 334, found 334.

Example 50

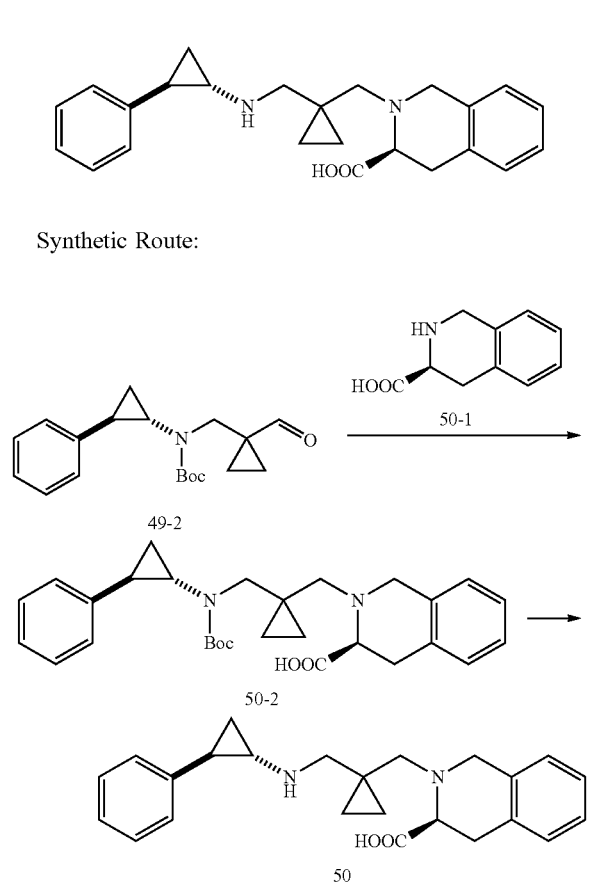

Synthetic Route:

Step 1

The synthesis of compound 50-2 was referred to the first step of example 28. MS-ESI calculated [M+H]$^+$ 477, found 477.

Step 2

The synthesis of compound 50 was referred to the second step of example 28. $^1$H NMR (400 MHz, Methonal-d$_4$) δ 7.33-7.30 (m, 6H), 7.26-7.18 (m, 3H), 4.69-4.49 (m, 4H), 3.70-3.47 (m, 2H), 3.41-3.35 (m, 1H), 3.26-3.05 (m, 3H), 2.73-2.68 (m, 1H), 1.73-1.64 (m, 1H), 1.42-1.35 (m, 1H), 1.00-0.84 (m, 4H). MS-ESI calculated [M+H]$^+$ 377, found 377.

Example 51

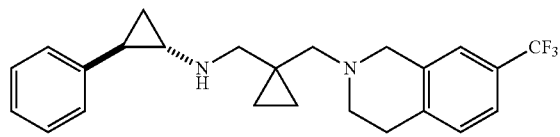

Synthetic Route:

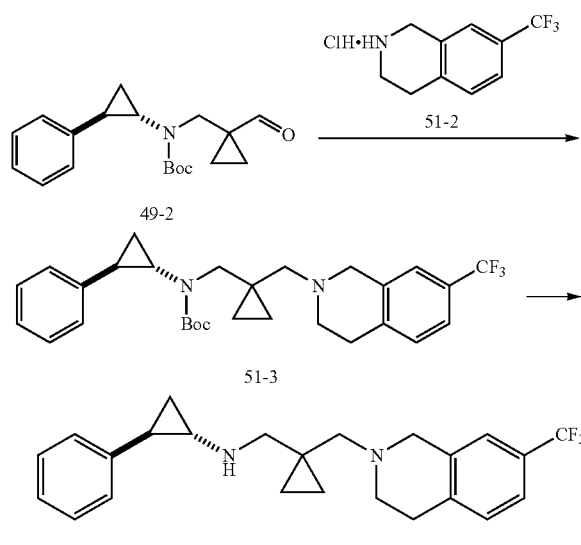

Step 1

Compound 51-2 (45.2 mg, 0.190 mmol) was dissolved in anhydrous dichloromethane (10 mL). Triethylamine (19.3 mg, 0.190 mmol) was added, and the mixture was stirred for 0.5 h. Compound 49-2 (50.0 mg, 0.159 mmol) and acetic acid (28.6 mg, 0.476 mmol) were added to the reaction mixture, and mixture was stirred at 25° C. for 0.5 hour. Sodium triacetoxyborohydride (101 mg, 0.176 mmol) was added and stirring was continued at 25° C. for 11 h. The mixture was diluted with dichloromethane (20 mL) and washed successively with saturated sodium carbonate aqueous solution (20 mL×1), saturated brine (20 mL×1), then dried over anhydrous sodium sulfate, followed by filtration and concentration under reduced. The residue was isolated and purified by thin layer chromatography (2:1 petroleum ether/ethyl acetate, Rf=0.3) to give compound 51-3. MS-ESI calculated [M+H]$^+$ 501, found 501.

Step 2

The synthesis of compound 51 was referred to the second step of example 28. $^1$H NMR (400 MHz, Methonal-d$_4$) δ 7.66-7.62 (m, 2H), 7.51-7.49 (m, 1H), 7.33-7.29 (m, 2H), 7.25-7.19 (m, 3H), 4.88-4.86 (m, 1H), 4.53-4.49 (m, 1H), 4.10-3.90 (m, 1H), 3.85-3.47 (m, 5H), 3.27-3.22 (m, 2H), 3.13-3.12 (m, 1H), 2.79-2.72 (m, 1H), 1.82-1.68 (m, 1H), 1.36-1.31 (m, 1H), 1.11-0.96 (m, 4H). MS-ESI calculated [M+H]$^+$ 401, found 401.

Example 52

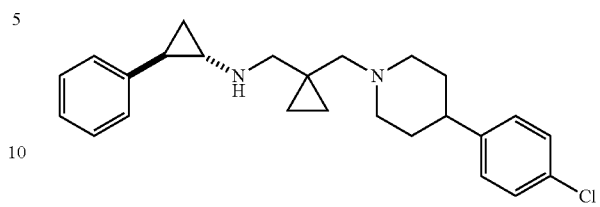

Synthetic Route:

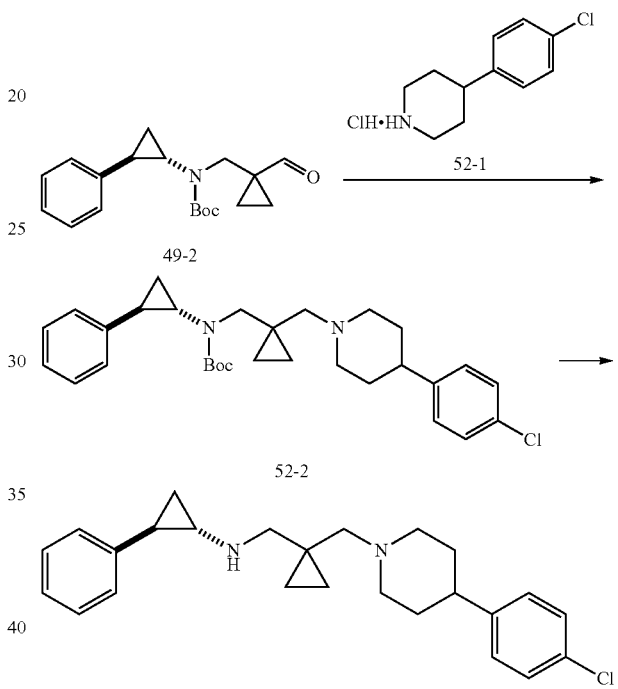

Step 1

The synthesis of compound 52-2 was referred to the first step of example 51. MS-ESI calculated [M+H]$^+$ 495, found 495.

Step 2

The synthesis of compound 52 was referred to the second step of example 28. $^1$H NMR (400 MHz, Methonal-d$_4$) δ 7.37-7.31 (m, 6H), 7.26-7.22 (m, 3H), 3.87-3.82 (m, 2H), 3.55-3.52 (m, 1H), 3.45-3.40 (m, 1H), 3.37-3.34 (m, 1H), 3.30-3.27 (m, 1H), 3.20-3.12 (m, 3H), 2.96-2.90 (m, 1H), 2.83-2.77 (m, 1H), 2.36-2.27 (m, 2H), 2.12-2.09 (m, 2H), 1.79-1.74 (m, 1H), 1.41-1.35 (m, 1H), 1.06-1.03 (m, 2H), 1.00-0.95 (m, 2H). MS-ESI calculated [M+H]$^+$ 395, found 395.

Example 53

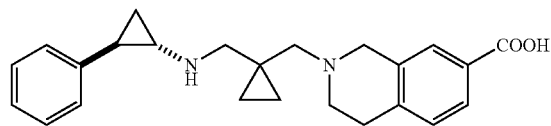

Synthetic Route:

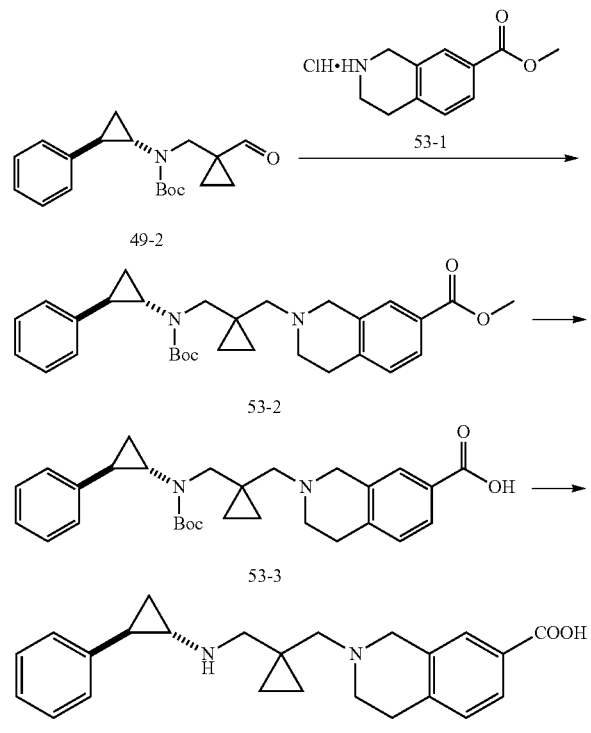

Step 1

The synthesis of compound 53-2 was referred to the first step of example 51. MS-ESI calculated [M+H]$^+$ 491, found 491.

Step 2

The synthesis of compound 53-3 was referred to the second step of example 39. MS-ESI calculated [M+H]$^+$ 477, found 477.

Step 3

The synthesis of compound 53 was referred to the second step of example 28. $^1$H NMR (400 MHz, Methonal-d$_4$) δ 7.97-7.96 (m, 2H), 7.42-7.39 (m, 1H), 7.33-7.29 (m, 2H), 7.25-7.19 (m, 3H), 4.87-4.80 (m, 1H), 4.51-7.48 (m, 1H), 4.12-3.88 (m 1H), 3.86-3.46 (m, 4H), 3.33-3.21 (m, 3H), 3.15-3.05 (m, 1H), 2.88-2.79 (m, 1H), 1.82-1.67 (m, 1H), 1.38-1.31 (m, 1H), 1.11-0.97 (m, 4H). MS-ESI calculated [M+H]$^+$ 377, found 377.

Example 54

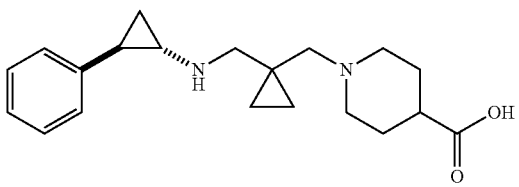

Synthetic Route:

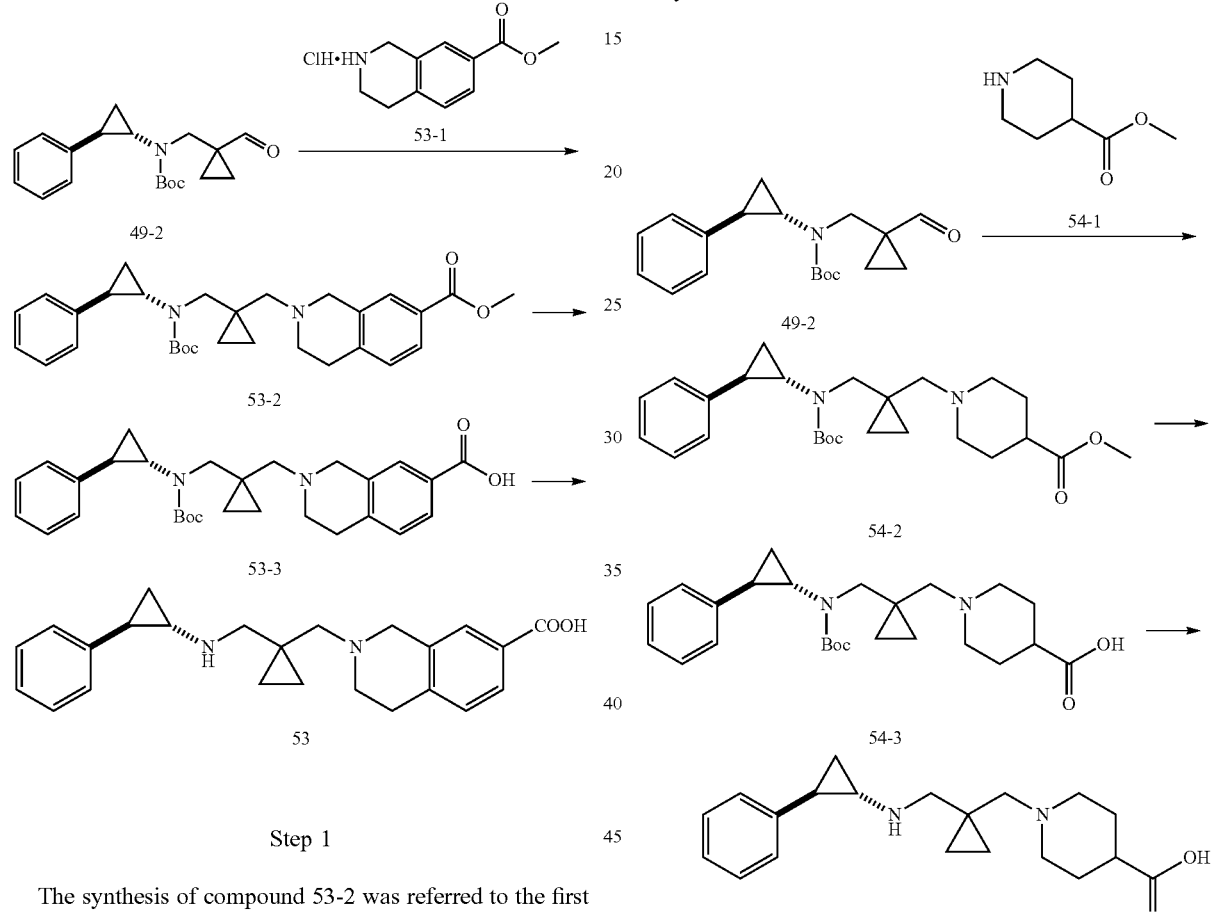

Step 1

The synthesis of compound 54-2 was referred to the first step of example 28. MS-ESI calculated [M+H]$^+$ 443, found 443.

Step 2

The synthesis of compound 54-3 was referred to the second step of example 39. MS-ESI calculated [M+H]$^+$ 429, found 429.

Step 3

The synthesis of compound 54 was referred to the second step of example 28. $^1$H NMR (400 MHz, Methonal-d$_4$) δ

7.34-7.30 (m, 2H), 7.26-7.21 (m, 3H), 3.80-3.64 (m, 2H), 3.50-3.46 (m, 1H), 3.39-3.36 (m, 1H), 3.29-3.22 (m, 2H), 3.15-3.11 (m, 1H), 3.06-2.91 (m, 2H), 2.79-2.74 (m, 1H), 2.70-2.58 (m, 1H), 2.28-2.13 (m, 4H), 1.77-1.72 (m, 1H), 1.40-1.35 (m, 1H), 1.03-0.93 (m, 4H). MS-ESI calculated [M+H]$^+$ 329, found 329.

Example 55

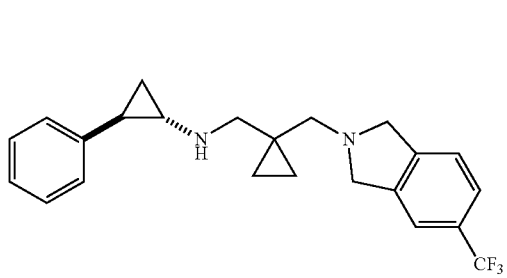

Synthetic Route:

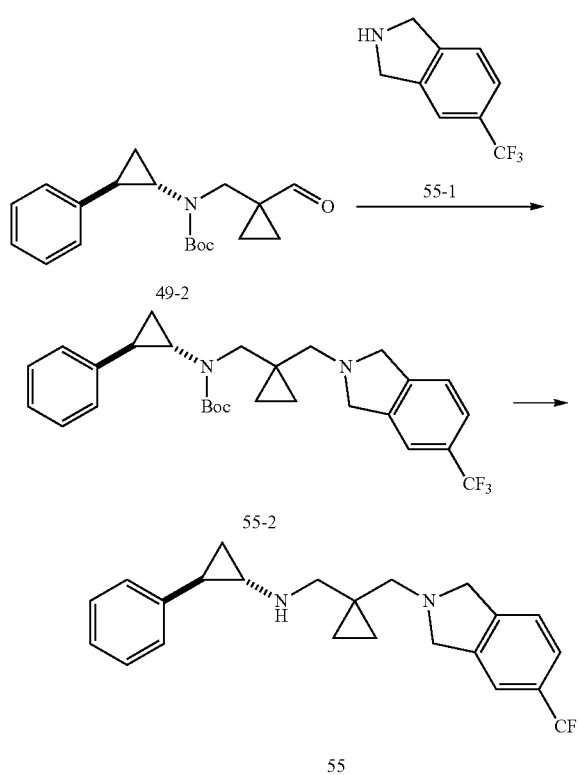

Step 1

The synthesis of compound 55-2 was referred to the first step of example 28. MS-ESI calculated [M+H]$^+$ 487, found 487.

Step 2

The synthesis of compound 55 was referred to the second step of example 28. $^1$H NMR (400 MHz, Methonal-d$_4$) δ 7.38-7.35 (m, 2H), 7.29-7.20 (m, 3H), 7.11-7.09 (m, 2H), 6.81 (d, J=8.0 Hz, 1H), 3.59-3.53 (m, 2H), 3.39-3.36 (m, 2H), 3.30-3.20 (m, 2H), 3.08-3.04 (m, 2H), 3.02-2.98 (m, 1H), 2.60-2.50 (m, 1H), 1.64-1.58 (m, 1H), 1.39-1.34 (m, 1H), 0.95-0.86 (m, 2H), 0.81-0.73 (m, 2H). MS-ESI calculated [M+H]$^+$ 387, found 387.

Example 56

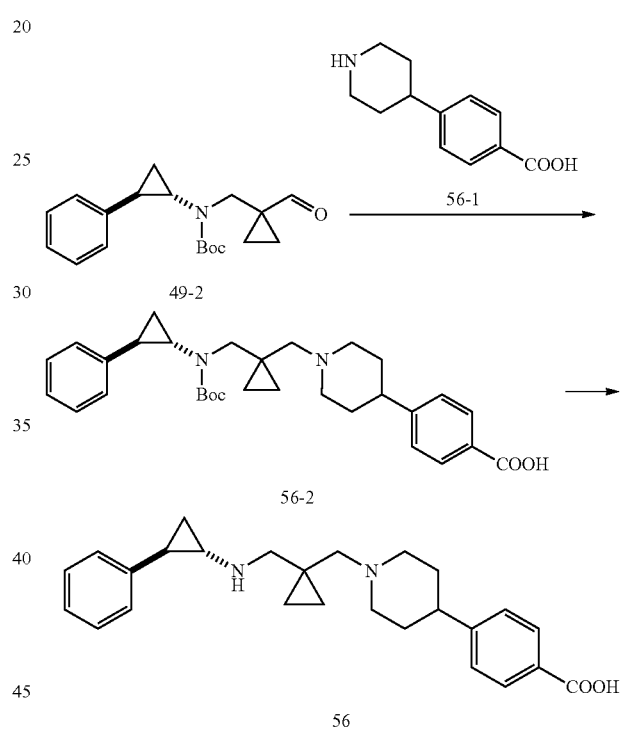

Synthetic Route:

Step 1

The synthesis of compound 56-2 was referred to the rust step of example 28. MS-ESI calculated [M+H]$^+$ 505, found 505.

Step 2

The synthesis of compound 56 was referred to the second step of example 28. $^1$H NMR (400 MHz, Methonal-d$_4$) δ 8.03 (d, J=8.0 Hz, 2H), 7.45 (d, J=8.0 Hz, 2H), 7.35-7.31 (m, 2H), 7.27-7.22 (m, 3H), 3.93-3.81 (m, 2H), 3.55-3.52 (m, 1H), 3.45-3.41 (m, 2H), 3.30-3.26 (m, 1H), 3.18-3.15 (m, 2H), 3.08-2.94 (m, 1H), 2.81-2.76 (m, 1H), 2.37-2.34 (m, 2H), 2.18-2.13 (m, 2H), 1.78-1.73 (m, 1H), 1.42-1.31 (m, 2H), 1.05-1.03 (m, 2H), 0.99-0.97 (m, 2H). MS-ESI calculated [M+H]$^+$ 405, found 405.

Example 57

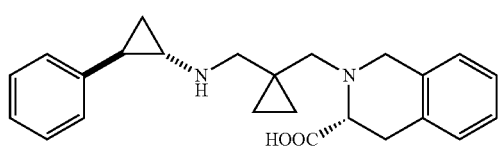

Synthetic Route:

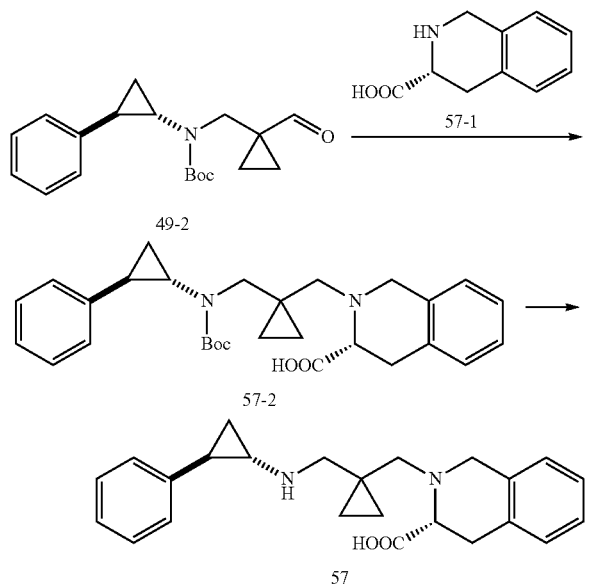

Step 1

The synthesis of compound 57-2 was referred to the first step of example 28. MS-ESI calculated [M+H]$^+$ 477, found 477.

Step 2

The synthesis of compound 57 was referred to the second step of example 28. $^1$H NMR (400 MHz, Methonal-d$_4$) δ 7.39-7.30 (m, 6H), 7.28-7.20 (m, 3H), 4.81-4.77 (m, 2H), 4.70-4.51 (m, 1H), 3.88-3.62 (m, 3H), 3.47-3.43 (m, 1H), 3.24-3.21 (m, 2H), 3.09-3.08 (m, 1H), 2.78-2.70 (m, 1H), 1.80-1.68 (m, 1H), 1.43-1.34 (m, 1H), 1.04-0.97 (m, 3H), 0.95-0.80 (m, 1H). MS-ESI calculated [M+H]$^+$ 377, found 377.

Example 58

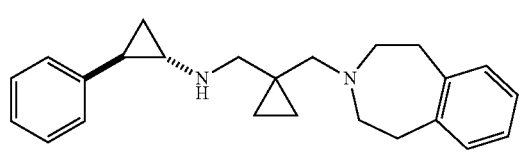

Synthetic Route:

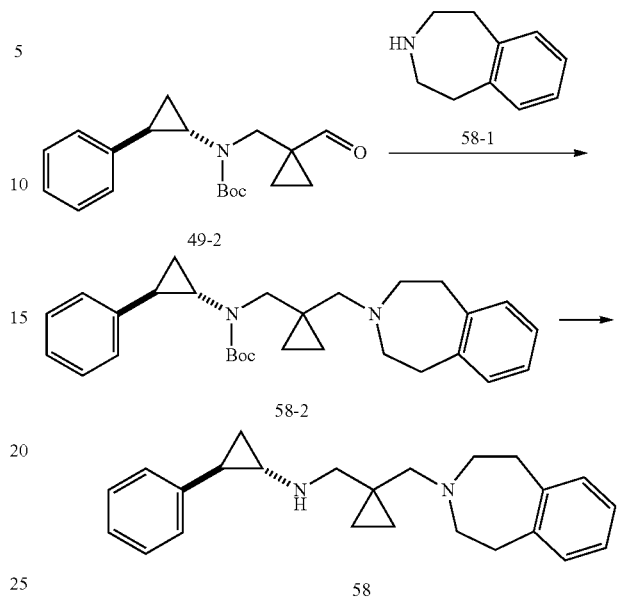

Step 1

The synthesis of compound 58-2 was referred to the first step of example 28. MS-ESI calculated [M+H]$^+$ 447, found 447.

Step 2

The synthesis of compound 58 was referred to the second step of example 28. $^1$H NMR (400 MHz, Methonal-d$_4$) δ 7.34-7.30 (m, 2H), 7.26-7.22 (m, 7H), 3.97-3.95 (m, 2H), 3.63-3.57 (m, 2H), 3.54-3.47 (m, 2H), 3.36-3.33 (m, 2H), 3.22-3.18 (m, 1H), 3.10-3.00 (m, 4H), 2.82-2.78 (m, 1H), 1.80-1.76 (m, 1H), 1.41-1.37 (m, 1H), 1.10-1.06 (m, 2H), 0.95-0.91 (m, 2H). MS-ESI calculated [M+H]$^+$ 347, found 347.

Example 59

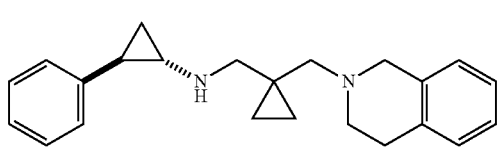

Synthetic Route:

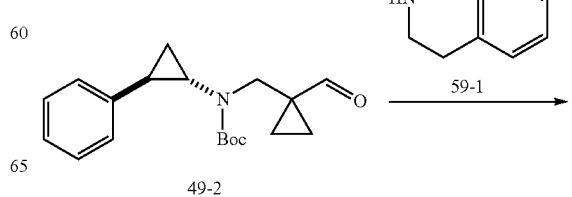

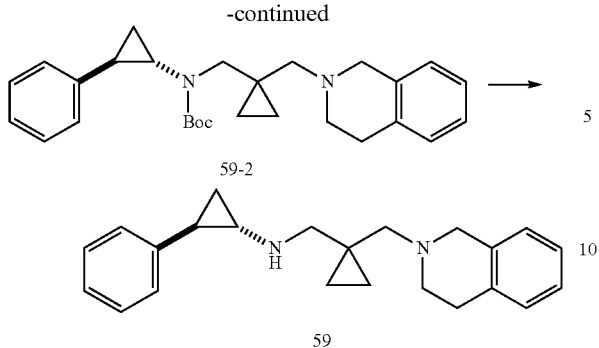

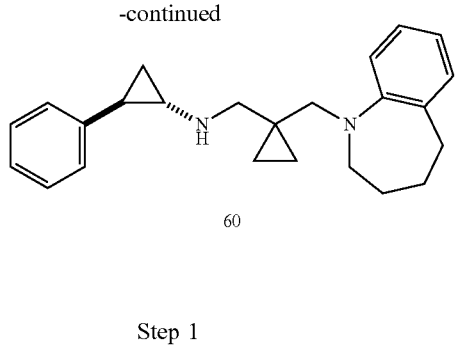

Step 1

The synthesis of compound 59-2 was referred to the first step of example 28. MS-ESI calculated [M+H]⁺ 433, found 433.

Step 2

The synthesis of compound 59 was referred to the second step of example 28. ¹H NMR (400 MHz, Methonal-d₄) δ 7.35-7.26 (m, 6H), 7.25-7.20 (m, 3H), 4.76-4.46 (m, 2H), 3.97-3.45 (m, 5H), 3.20-3.16 (m, 2H), 3.10-3.09 (m, 2H), 2.84-2.70 (m, 1H), 1.81-1.67 (m, 1H), 1.38-1.31 (m, 1H), 1.11-0.97 (m, 4H). MS-ESI calculated [M+H]⁺ 333, found 333.

Step 1

The synthesis of compound 60-2 was referred to the first step of example 28. MS-ESI calculated [M+H]⁺ 447, found 447.

Step 2

The synthesis of compound 60 was referred to the second step of example 28. ¹H NMR (400 MHz, Methonal-d₄) δ 7.39-7.28 (m, 6H), 7.24-7.14 (m, 3H), 4.33-3.77 (m, 2H), 3.75-3.34 (m, 2H), 3.20-2.87 (m, 5H), 2.75-2.37 (m, 2H), 2.09-1.96 (m, 2H), 1.86-1.48 (m, 2H), 1.31-1.29 (m, 1H), 0.86-0.10 (m, 4H). MS-ESI calculated [M+H]⁺ 347, found 347.

Example 60

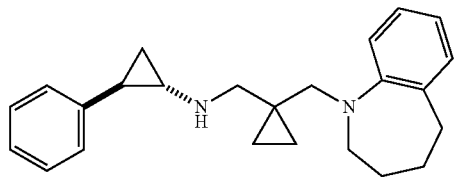

Synthetic Route:

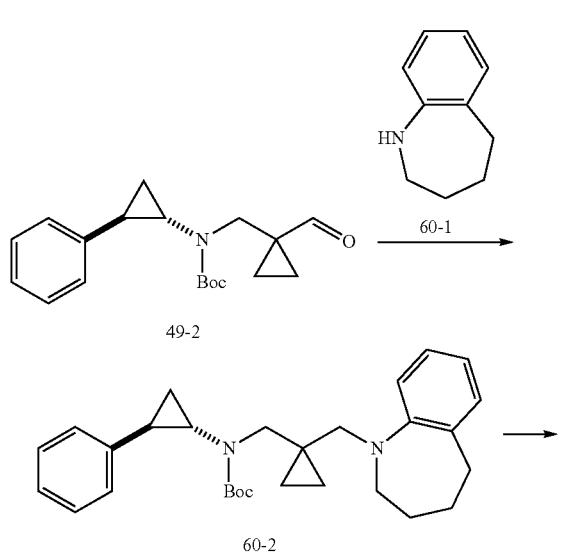

Example 61

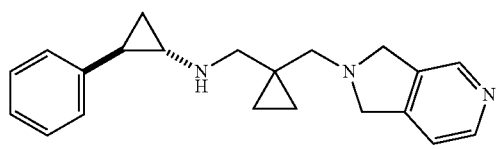

Synthetic Route:

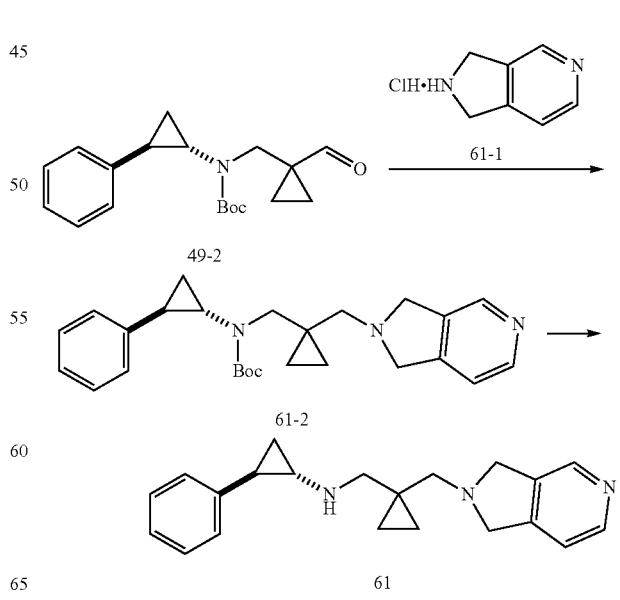

Step 1

The synthesis of compound 61-2 was referred to the first step of example 51. MS-ESI calculated [M+H]⁺ 420, found 420.

Step 2

The synthesis of compound 61 was referred to the third step of example 19. ¹H NMR (400 MHz, Methonal-$d_4$) δ 9.10-8.93 (m, 2H), 8.22-8.21 (m, 1H), 7.32-7.21 (m, 5H), 5.28-5.21 (m, 4H), 3.92-3.80 (m, 2H), 3.67-3.49 (m, 2H), 3.14-3.12 (m, 1H), 2.84-2.81 (m, 1H), 1.81-1.77 (m, 1H), 1.40-1.30 (m, 1H), 1.12-1.09 (m, 4H). MS-ESI calculated [M+H]⁺ 320, found 320.

Example 62

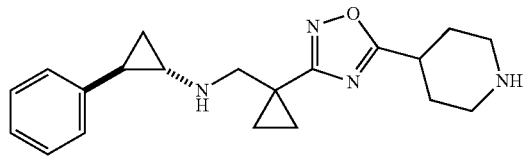

Synthetic Route:

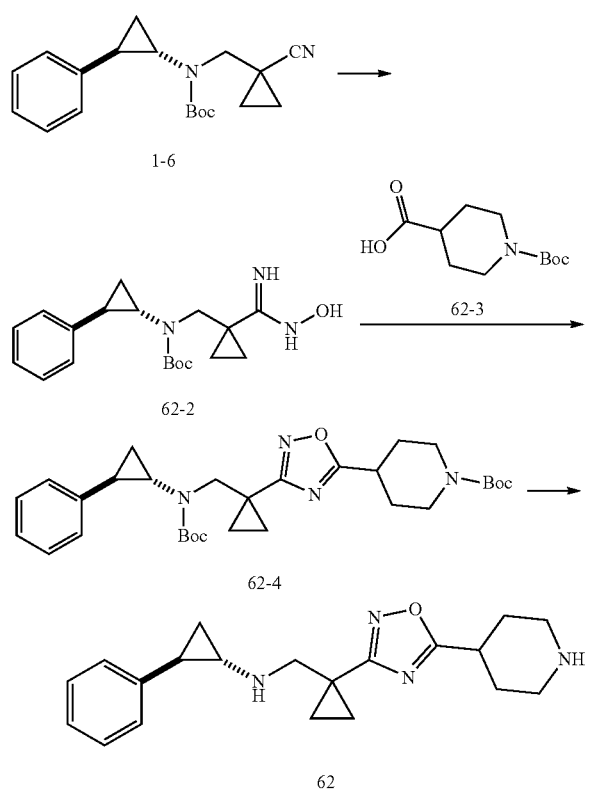

Step 1

Compound 1-6 (500 mg, 1.60 mmol) was dissolved in anhydrous ethanol (10 mL), hydroxylamine hydrochloride (222 mg, 3.20 mmol) and diisopropylethylamine (827 mg, 6.40 mmol) were added under nitrogen, and the mixture was stirred at 80° for 12 h. The reaction mixture was cooled to 0° C. extracted with ethyl acetate (25 mL×2). The organic phases were combined, washed with saturated brine (25 mL×2) and dried over anhydrous sodium sulfate, followed by filtration and concentration under reduced pressure. The crude product was isolated and purified by silica gel column chromatography (2:1 petroleum ether/ethyl acetate, Rf=0.2) to give compound 62-2. MS-ESI calculated [M+H]⁺ 346, found 346.

Step 2

Compound 62-3 (63.7 mg, 0.278 mmol) was dissolved in anhydrous N,N-dimethylformamide (2 mL), carbonyldiimidazole (48.8 mg, 0.301 mmol) was added and the mixture was stirred at 30° C. for 2 h. Compound 62-2 (80.0 mg, 0.232 mmol) was added and the mixture was stirred at 110'C for 12 h. The reaction mixture was cooled to 0° C., water (20 mL) was added to the mixture. The mixture was extracted with ethyl acetate (25 mL×2). The organic phases were combined, washed with saturated brine (25 mL×2) and dried over anhydrous sodium sulfate, followed by filtration and concentration under reduced pressure. The crude product was isolated and purified by preparative thin layer chromatography (2:1 petroleum ether/ethyl acetate, Rf=0.6) to give compound 62-4. MS-ESI calculated [M+Na]⁺ 561, found 561.

Step 3

Compound 62-4 (91.0 mg, 0.169 mmol) was dissolved in anhydrous dichloromethane (5 mL). Trifluoroacetic acid (77.0 mg, 0.676 mmol) was added, and the mixture was stirred at 20° C. for 2 h and concentrated under reduced pressure, and the crude product was isolated and purified by high-performance liquid chromatography to give compound 62. ¹H NMR (400 MHz, Methonal-$d_4$) δ 7.32-7.29 (m, 2H), 7.24-7.21 (m, 1H), 7.18-7.16 (m, 2H), 3.74-3.64 (m, 2H), 3.49-3.40 (m, 3H), 3.24-3.19 (m, 2H), 3.11-3.07 (m, 1H), 2.67-2.62 (m, 1H), 2.35-2.32 (m, 2H), 2.15-2.02 (m, 2H), 1.68-1.63 (m, 1H), 1.45-1.35 (m, 5H). MS-ESI calculated [M+H]⁺ 339, found 339.

Example 63

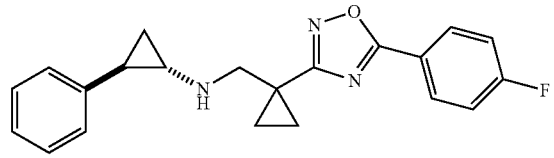

Synthetic Route:

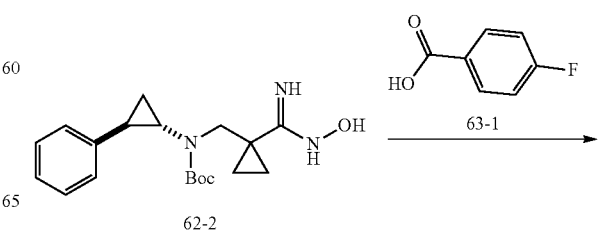

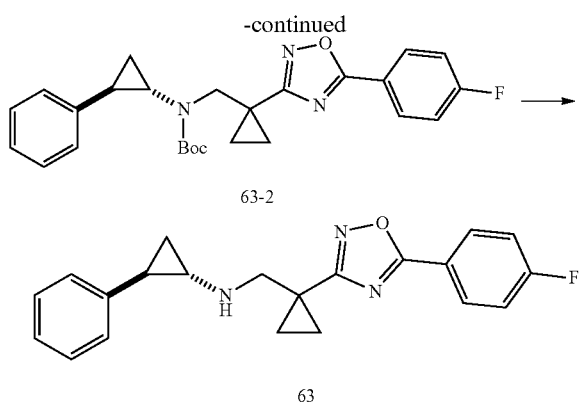

63-2

63

Step 1

The p-fluorobenzoic acid (73.0 mg, 0.521 mmol) was dissolved in anhydrous N,N-dimethylformamide (2 mL), and carbonyldiimidazole (91.5 mg, 0.564 mmol) was added under nitrogen at 30° C. The mixture was stirred for 2 h. The compound 62-2 (150 mg, 0.434 mmol) was added to the reaction mixture, and the mixture was heated to 110° C., and stirred for 10 h. The reaction solution was cooled to room temperature, and water (30 mL) was added to the mixture. The mixture was extracted with ethyl acetate (20 mL×3). The organic phases were combined, washed with saturated brine (20 mL×2), dried over anhydrous sodium sulfate, followed by filtration and concentration under reduced pressure. The crude product was isolated and purified by preparative thin layer chromatography to give compound 63-2. MS-ESI calculated [M+Na]$^+$ 472, found 472.

Step 2

Compound 63-2 (160 mg, 0.356 mmol) was dissolved in anhydrous dichloromethane (3 mL). Trifluoroacetic acid (1 mL) was added dropwise at 0° C. The mixture was stirred at 0° C. for 1 h, concentrated under reduced pressure, and the crude product was purified by high-performance liquid chromatography to give compound 63. $^1$H NMR (400 MHz, Methonal-d$_4$) δ 8.17-8.14 (m, 2H), 7.36-7.26 (m, 4H), 7.25-7.14 (m, 3H), 3.79-3.68 (m, 2H), 3.13-3.11 (m, 1H), 2.57-2.52 (m, 1H), 1.59-1.54 (m, 3H), 1.43-1.38 (m, 3H). MS-ESI calculated [M+H]$^+$ 350, found 350.

Example 64

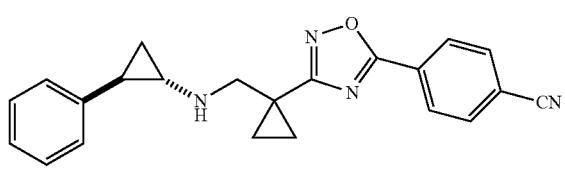

Synthetic Route:

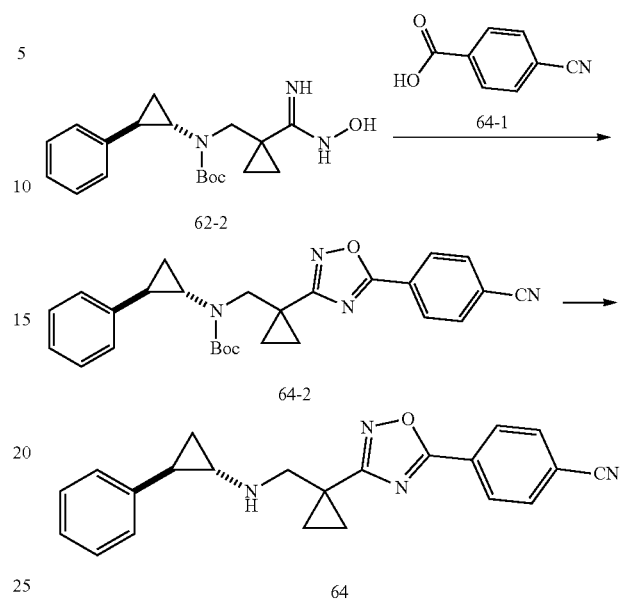

62-2

64-2

64

Step 1

The synthesis of compound 64-2 was referred to the first step of example 63. MS-ESI calculated [M+Na]$^+$ 479, found 479.

Step 2

The synthesis of compound 64 was referred to the second step of example 63. $^1$H NMR (400 MHz. Methonal-d$_4$) δ 8.26 (d, J=8.0 Hz, 2H), 7.97 (d, J=8.0 Hz, 2H), 7.27-7.23 (m, 2H), 7.18-7.12 (m, 3H), 3.80-3.66 (m, 2H), 3.11-3.08 (m, 1H), 2.53-2.49 (m, 1H), 1.58-1.54 (m, 3H), 1.40-1.36 (m, 3H). MS-ESI calculated [M+H]$^+$ 357, found 357.

Example 65

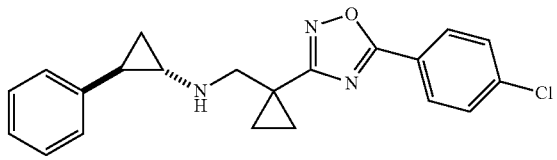

Synthetic Route:

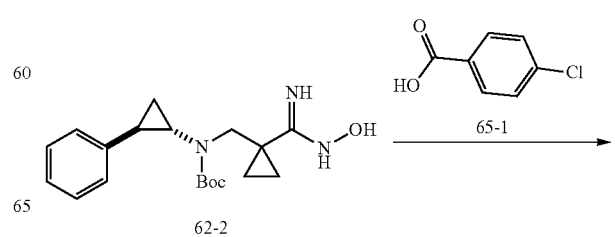

62-2

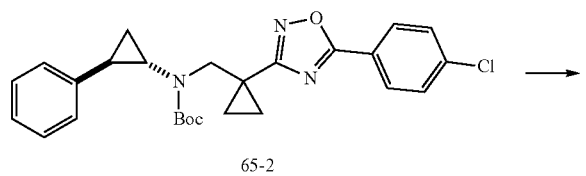

65-2

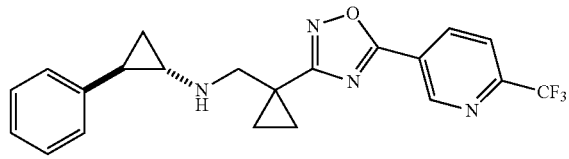

65

Step 1

The synthesis of compound 65-2 was referred to the first step of example 63. MS-ESI calculated [M+Na]$^+$ 488, found 488.

Step 2

The synthesis of compound 65 was referred to the second step of example 63. $^1$H NMR (400 MHz, Methonal-d$_4$) δ 8.09 (d, J=8.4 Hz, 2H), 7.63 (d, J=8.4 Hz, 2H), 7.29-7.25 (m, 2H), 7.20-7.13 (m, 3H), 3.79-3.67 (m, 2H), 3.13-3.10 (m, 1H), 2.56-2.52 (m, 1H), 1.59-1.53 (m, 3H), 1.43-1.39 (m, 3H). MS-ESI calculated [M+H]$^+$ 366, found 366.

Example 66

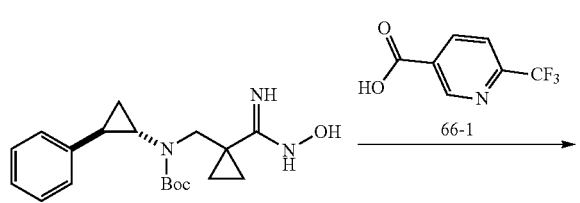

Synthetic Route:

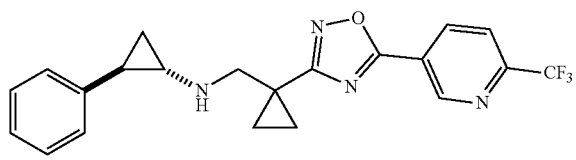

66

Step 1

The synthesis of compound 66-2 was referred to the rust step of example 63. MS-ESI calculated [M+Na]$^+$ 523, found 523.

Step 2

The synthesis of compound 66 was referred to the second step of example 63. $^1$H NMR (400 MHz, Methonal-d$_4$) δ 9.36 (s, 1H), 8.68 (d, J=8.0 Hz, 1H), 8.06 (d, J=8.0 Hz, 1H), 7.26-7.22 (m, 2H), 7.16-7.12 (m, 3H), 3.85-3.70 (m, 2H), 3.23-3.15 (m, 1H), 2.56-2.52 (m, 1H), 1.62-1.57 (m, 3H), 1.45-1.39 (m, 3H). MS-ESI calculated [M+H]$^+$ 401, found 401.

Example 67

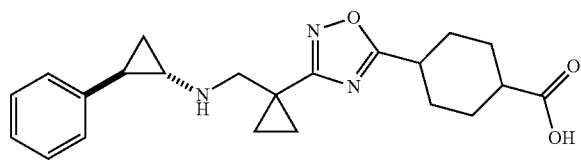

Synthetic Route:

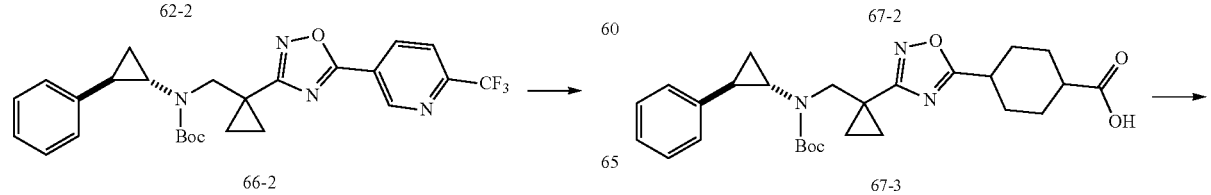

-continued

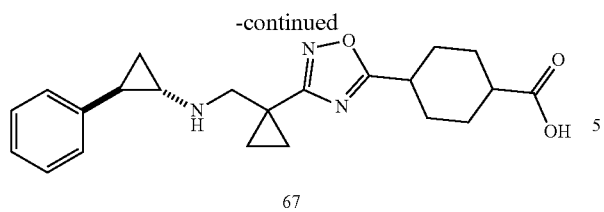

67

Step 1

The synthesis of compound 67-2 was referred to the first step of example 63. MS-ESI calculated [M+H]+ 496, found 496.

Step 2

Compound 67-2 (130 mg, 0.262 mol) was dissolved in water (8 mL) and THF (2 mL), sodium hydroxide (41.9 mg, 1.05 mmol) was added, and the reaction mixture was stirred at 40° C. for 4 h. The reaction solution was cooled to 0° C., water (50 mL) was added to the mixture. The mixture was adjusted to pH=3 with hydrochloric acid (1 mol/L). The mixture was extracted with ethyl acetate (30 mL×3). The combined organic phases were washed with saturated brine (30 mL×3) and dried over anhydrous sodium sulfate, followed by filtration and concentration under reduced pressure to give compound 67-3. MS-ESI calculated [M+Na]+ 504, found 504.

Step 3

The synthesis of compound 67 was referred to the second step of example 63. $^1$H NMR (400 MHz, Methonal-d$_4$) δ 7.34-7.30 (m, 2H), 7.26-7.22 (m, 1H), 7.19-7.17 (m, 2H), 3.73-3.64 (m, 2H), 3.11-3.07 (m, 1H), 2.97-2.90 (m, 1H), 2.64-2.59 (m, 1H), 2.39-2.33 (m, 1H), 2.19-2.11 (m, 4H), 1.67-1.51 (m, 5H), 1.45-1.37 (m, 5H). MS-ESI calculated [M+H]+ 382, found 382.

Example 68

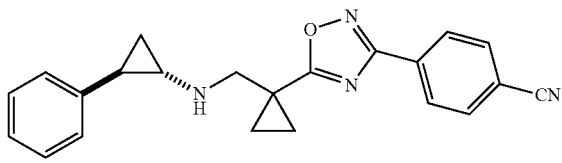

Synthetic Route:

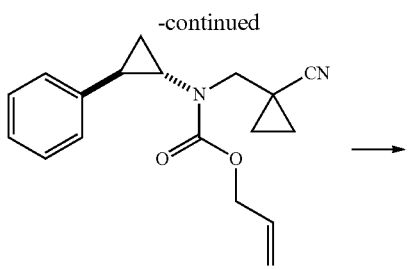

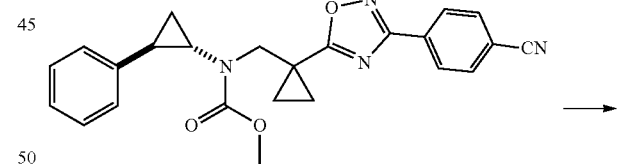

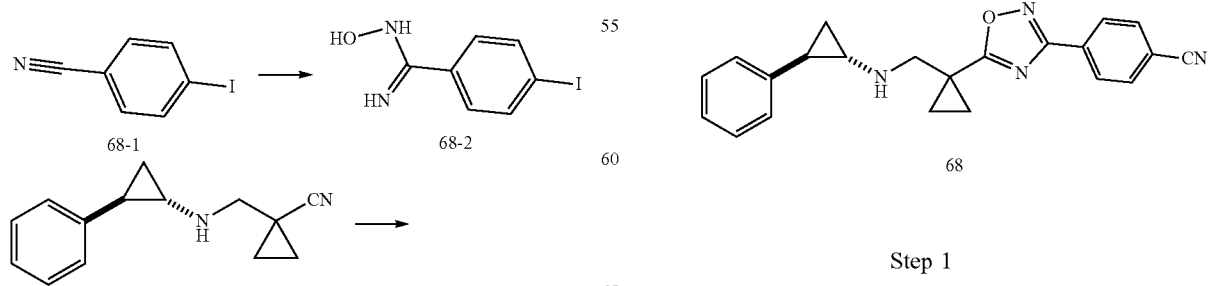

Step 1

The compound 68-1 (4.50 g, 19.6 mmol) was dissolved in anhydrous ethanol (50 mL), hydroxylamine hydrochloride (2.73 g, 39.3 mmol) and diisopropylethylamine (10.2 g, 78.6 mmol) were added. The mixture was stirred at 80° C. for 12 h and concentrated under reduced pressure. The crude product was isolated and purified by silica gel column chromatography (1:1 petroleum ether/ethyl acetate, Rf=0.4) to give compound 68-2. ¹H NMR (400 MHz, DMSO-d₆) δ 9.72 (s, 1H), 7.74-7.65 (m, 2H), 7.47-7.44 (m, 2H), 5.84 (brs, 2H).

Step 2

Compound 1 (640 mg, 3.01 mmol) was dissolved in anhydrous dichloromethane (10 mL), diisopropylethylamine (778 mg, 6.02 mmol) and allyl chloroformate (544 mg, 4.51 mmol) were added. The reaction solution was stirred at 20° C. for 1 h and concentrated under reduced pressure to give compound 68-4. MS-ESI calculated [M+H]⁺ 297, found 297.

Step 3

Compound 68-4 (900 mg, 3.04 mmol) was dissolved in hydrochloric acid/methanol (4 mol/L 10 mL). The mixture was stirred at 30° C. for 1 h. The mixture was heated to 60° C. and stirred for 1 h, and then cooled to 0° C., concentrated sulfuric acid (1 mL) was added dropwise to the reaction mixture, and the mixture was heated to 70° C. and stirred for 36 h. The mixture was concentrated under reduced pressure and the residue was dissolved in water (50 mL) and adjusted to pH=9 with saturated sodium carbonate, extracted with ethyl acetate (30 mL×3). The organic phases were combined, washed with saturated brine (30 mL×3) and dried over anhydrous sodium sulfate, followed by filtration and concentration under reduced pressure, and the obtained crude material was isolated and purified by thin layer chromatography (3:1 petroleum ether/ethyl acetate, Rf=0.4) to give compound 68-5. MS-ESI calculated [M+H]⁺ 330, found 330.

Step 4

The synthesis of compound 68-6 was referred to the second step of example 67. MS-ESI calculated [M+H]⁺ 316, found 316.

Step 5

The synthesis of compound 68-7 was referred to the first step of example 63. MS-ESI calculated [M+H]⁺ 542, found 542.

Step 6

Compound 68-7 (110 mg, 0.203 mmol) was dissolved in anhydrous N,N-dimethylformamide (5 mL), zinc cyanide (47.7 mg, 0.406 mmol), 2-dicyclohexylphosphine-2',4',6'-triisopropylbiphenyl (9.7 mg, 20.3 μmol) and bis(dibenzylideneacetone) palladium (5.8 mg, 10.2 μmol) were added under nitrogen. The reaction solution was stirred at 90° C. for 12 h. And then the mixture was concentrated under reduced pressure. The crude product was isolated and purified by thin layer chromatography (3:1 petroleum ether/ethyl acetate, Rf=0.5) to give compound 68-8. MS-ESI calculated [M+H]⁺ 441, found 441.

Step 7

Compound 68-8 (47.0 mg, 0.107 mmol) was dissolved in anhydrous tetrahydrofuran (5 mL), and then diethylamine (78.0 mg, 1.07 mmol) and tetratriphenylphosphine palladium (12.3 mg, 10.6 μmol) were added. The reaction solution was stirred at 80° C. for 2 hours. The reaction solution was filtered, and the filtrate was concentrated under reduced pressure. The crude product was isolated and purified by high-performance liquid chromatography to give compound 68. ¹H NMR (400 MHz, Methonal-d₄) δ 8.22 (d, J=8.4 Hz, 2H), 7.90 (d, J=8.4 Hz, 2H), 7.28-7.24 (m, 2H), 7.20-7.14 (m, 3H), 3.90-3.77 (m, 2H), 3.21-3.17 (m, 1H), 2.59-2.55 (m, 1H), 1.75-1.73 (m, 2H), 1.62-1.59 (m, 3H), 1.44-1.42 (m, 1H). MS-ESI calculated [M+H]⁺ 357, found 357.

Example 69

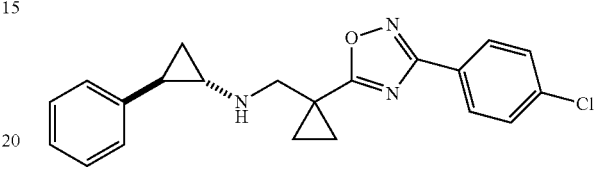

Synthetic Route:

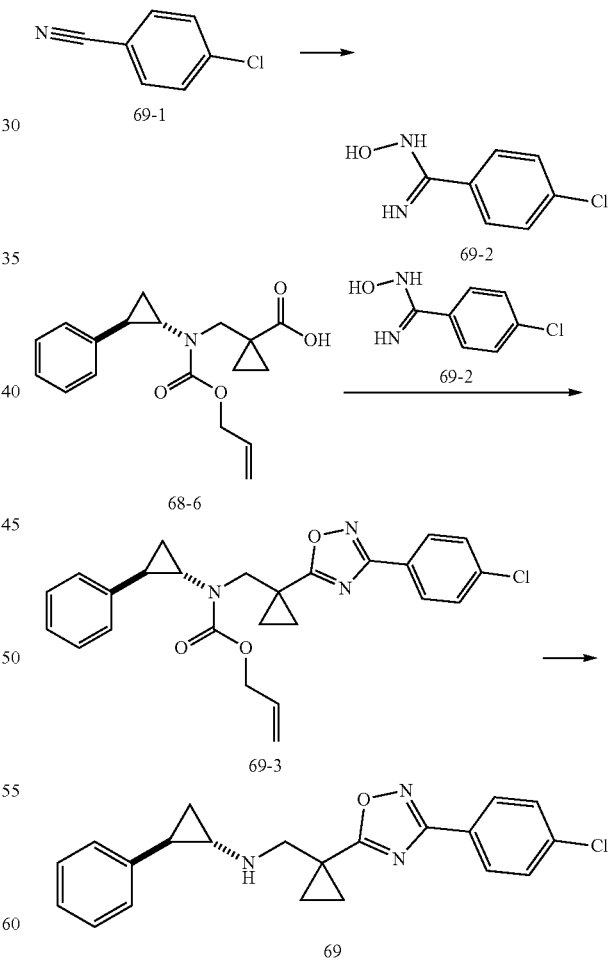

Step 1

The synthesis of compound 69-2 was referred to the first step of example 68. ¹H NMR (400 MHz, DMSO-d₆) δ 9.74

(s, 1H), 7.69-7.67 (m, 2H), 7.45-7.42 (m, 2H), 5.87 (brs, 2H). MS-ESI calculated [M+H]⁺ 171, found 171.

Step 2

The synthesis of compound 69-3 was referred to the first step of example 63. MS-ESI calculated [M+H]⁺ 450, found 450.

Step 3

The synthesis of compound 69 was referred to the seventh step of example 68. ¹H NMR (400 MHz, Methonal-d₄) δ 8.04 (d, J=8.8 Hz, 2H), 7.54 (d, J=8.8 Hz, 2H), 7.29-7.26 (m, 2H), 7.21-7.15 (m, 3H), 3.88-3.76 (m, 2H), 3.20-3.16 (m, 1H), 2.60-2.55 (m, 1H), 1.73-1.71 (m, 2H), 1.64-1.58 (m, 3H), 1.45-1.40 (m, 1H). MS-ESI calculated [M+H]⁺ 366, found 366.

Example 70

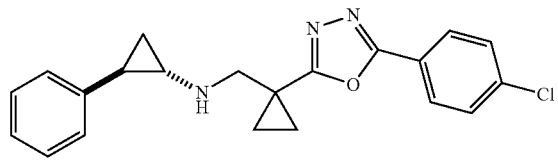

Synthetic Route:

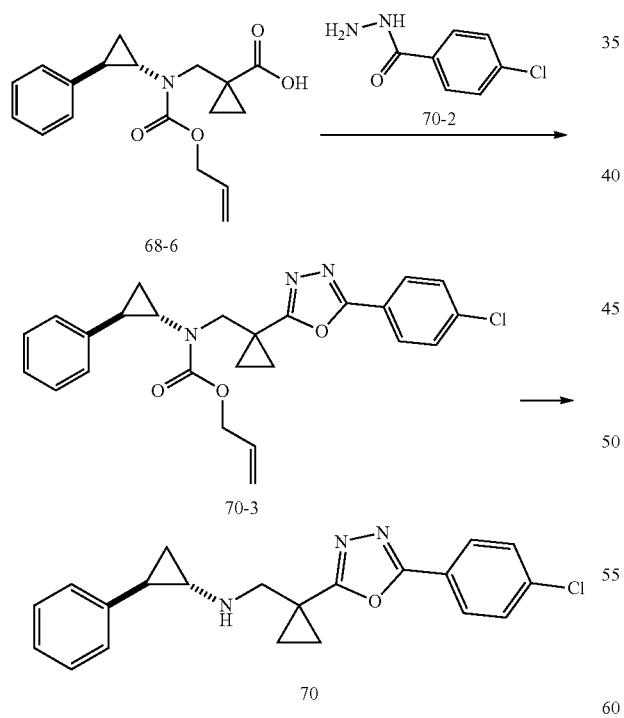

Step 1

Compound 68-6 (88.0 mg, 0.279 mmol) was dissolved in phosphorus oxychloride (1 mL), 4-chlorobenzoic acid hydrazide (47.6 mg, 0.279 mmol) was added under nitrogen and the mixture was stirred at 100° C. for 2 h. The reaction solution was cooled to 0° C., added to water (30 mL) dropwise, and the mixture was adjusted to pH=8 with saturated sodium carbonate. The mixture was extracted with ethyl acetate (20 mL×3). The organic phases were combined, washed with saturated brine (20 mL×2), dried over anhydrous sodium sulfate, followed by filtration and concentration under reduced pressure, and the obtained crude material was isolated and purified by thin layer chromatography (2:1 petroleum ether/ethyl acetate, Rf=0.5) to give compound 70-3. MS-ESI calculated [M+H]⁺ 450, found 450.

Step 2

The synthesis of compound 70 was referred to the seventh step of example 68. ¹H NMR (400 MHz, Methonal-d₄) δ 7.98 (d, J=8.4 Hz, 2H), 7.59 (d, J=8.4 Hz, 2H), 7.28-7.24 (m, 2H), 7.19-7.14 (m, 3H), 3.85-3.72 (m, 2H), 3.17-3.13 (m, 1H), 2.59-2.57 (m, 1H), 1.65-1.59 (m, 3H), 1.55-1.53 (m, 2H), 1.41-1.39 (m, 1H). MS-ESI calculated [M+H]⁺ 366, found 366.

Example 71

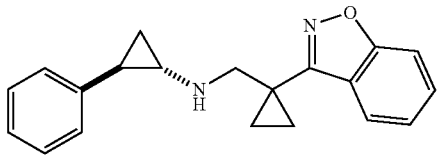

Synthetic Route:

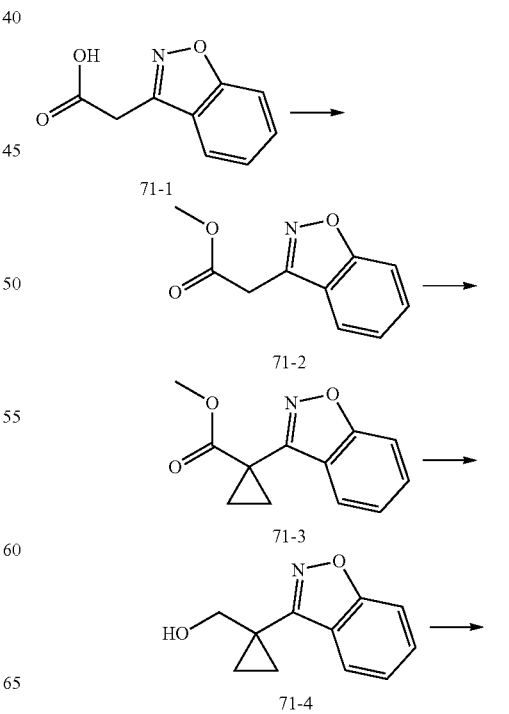

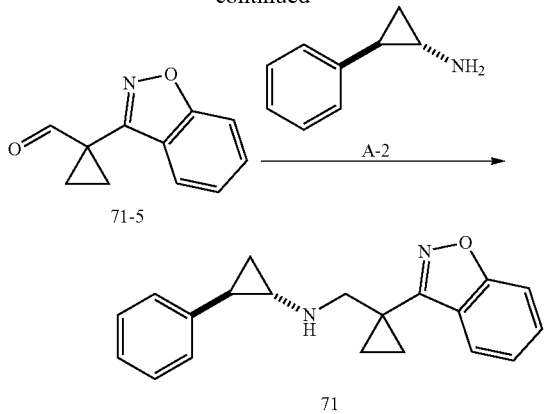

Step 1

Compound 71-1 (1.70 g, 9.60 mmol) was dissolved in anhydrous methanol (20 mL), concentrated sulfuric acid (2 mL) was added dropwise at 0° C. The reaction solution was stirred at 80° C. for 12 hours. The reaction solution was concentrated under reduced pressure. The residue was dissolved in water, adjusted to pH=9 with saturated sodium carbonate and extracted with ethyl acetate (50 mL×3). The organic phases were combined, washed with saturated brine (50 mL×2) and dried over anhydrous sodium sulfate, followed by filtration and concentration under reduced pressure to give compound 71-2. MS-ESI calculated [M+H]$^+$ 192, found 192.

Step 2

Compound 71-2 (1.00 g, 5.23 mmol) was dissolved in anhydrous N,N-dimethylformamide (10 mL), cesium carbonate (6.82 g, 20.9 mmol) and 1,2-dibromoethane (1.97 g, 10.5 mmol) were added, and the reaction mixture was stirred at 50° C. for 12 h. After cooling to room temperature, water (100 mL) was added to the reaction mixture. The mixture was extracted with ethyl acetate (50 mL×3). The organic phases were combined, washed with saturated brine (50 mL×2) and dried over anhydrous sodium sulfate, followed by filtration and concentration under reduced pressure. The obtained crude product was isolated and purified by silica gel column chromatography (3:1 petroleum ether/ethyl acetate, Rf=0.6) to give compound 71-3. MS-ESI calculated [M+H]$^+$ 218, found 218.

Step 3

Compound 71-3 (800 mg, 3.68 mmol) was dissolved in methanol (10 mL), lithium borohydride (321 mg, 14.7 mmol) was added portionwise at 0° C., and the mixture was stirred at 20° C. for 1 hour, and then stirred at 50° C. for 11 h. After cooling to room temperature, water (100 mL) was added to the reaction mixture. The mixture was extracted with ethyl acetate (50 mL×3). The organic phases were combined, washed with saturated brine (50 mL×2) and dried over anhydrous sodium sulfate, followed by filtration and concentration under reduced pressure. The obtained crude product was isolated and purified by silica gel column chromatography (3:1 petroleum ether/ethyl acetate, Rf=0.3) to give compound 714. $^1$H NMR (400 MHz, CDCl$_3$) δ 7.61-7.53 (m, 3H), 7.30-7.28 (m, 1H), 3.95 (d, J=6.8 Hz, 2H), 2.60 (t, J=6.8 Hz, 1H), 1.50 (dd, J$_1$=5.2 Hz, J$_2$=1.2 Hz, 2H), 1.18 (dd, J$_1$=5.2 Hz, J$_2$=1.2 Hz, 2H). MS-ESI calculated [M+H]$^+$ 190, found 190.

Step 4

Compound 71-4 (250 mg, 1.32 mmol) was dissolved in anhydrous dichloromethane (10 mL), Dess-Martin reagent (649 mg, 1.45 mmol, 95%) was added at 0° C., and the reaction mixture was stirred at 25° C. for 12 h. Saturated sodium bicarbonate (30 mL) and saturated sodium thiosulfate (30 mL) were added to the mixture, and the mixture was extracted with ethyl acetate (50 mL×3). The organic phases were combined, washed with saturated brine (30 mL×2) and dried over anhydrous sodium sulfate, followed by filtration and concentration under reduced pressure. The obtained crude product was isolated and purified by thin layer chromatography (3:1 petroleum ether/ethyl acetate, Rf=0.5) to give compound 71-5. MS-ESI calculated [M+H]$^+$ 188, found 188.

Step 5

Compound 71-5 (140 mg, 0.751 mmol) was dissolved in anhydrous dichloromethane (10 mL). Compound A-2 (100 mg, 0.751 mmol) and acetic acid (135 mg, 2.25 mmol) were added, and the mixture was stirred at 30° C. for 1 h. Sodium triacetoxyborohydride (477 mg, 2.25 mmol) was added, and the reaction mixture was stirred at 30° C. for 1 h. The mixture was diluted with dichloromethane (50 mL) and washed successively with saturated sodium bicarbonate (20 mL×3), water (20 mL×3), saturated brine (20 mL×2), then dried over anhydrous sodium sulfate, followed by filtration and concentration under reduced pressure. The obtained crude product was isolated and purified by high performance liquid chromatography to give compound 71. $^1$H NMR (400 MHz, Methonal-d$_4$) δ 7.72-7.71 (m, 1H), 7.68-7.66 (m, 2H), 7.41-7.37 (m, 1H), 7.32-7.22 (m, 3H), 7.16-7.14 (m, 2H), 3.71 (s, 2H), 3.15-3.09 (m, 1H), 2.54-2.48 (m, 1H), 1.74-1.69 (m, 2H), 1.57-1.52 (m, 1H), 1.47-1.37 (m, 3H). MS-ESI calculated [M+H]$^+$ 305, found 305.

Example 72

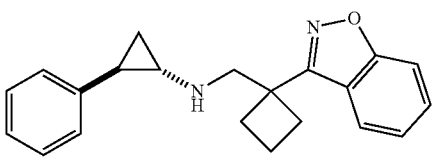

Synthetic Route:

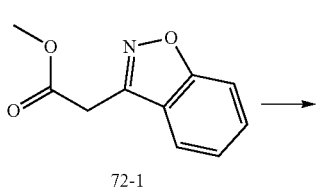

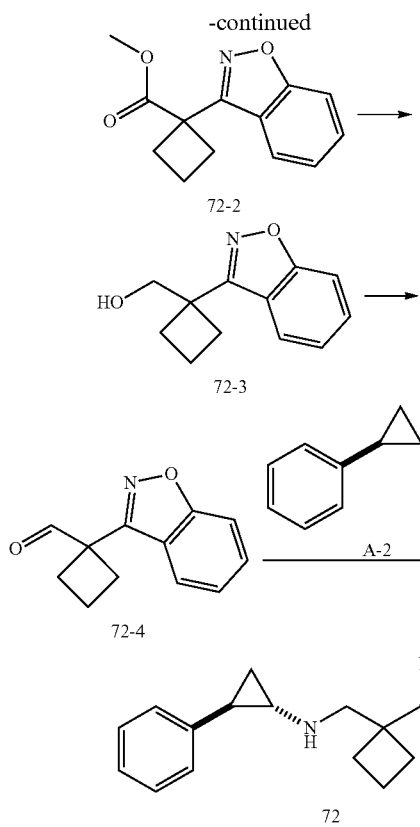

Example 73

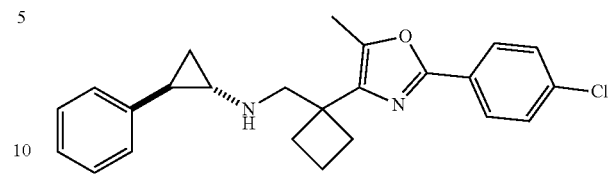

Synthetic Route:

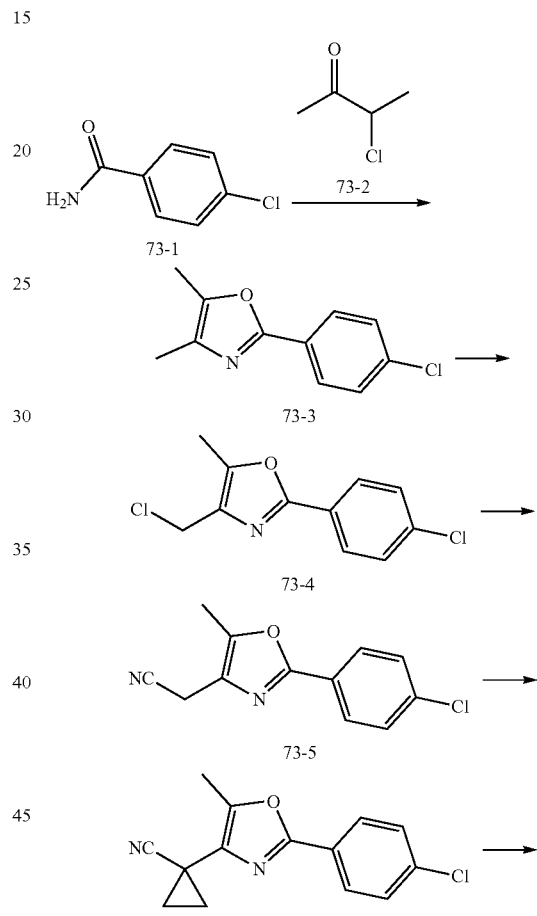

Step 1

The synthesis of compound 72-2 was referred to the second step of example 71. MS-ESI calculated [M+H]$^+$ 232, found 232.

Step 2

The synthesis of compound 72-3 was referred to the second step of example 1. $^1$H NMR (400 MHz, CDCl$_3$) δ 7.80-7.78 (m, 1H), 7.60-7.57 (m, 2H), 7.35-7.33 (m, 1H), 4.12 (s, 2H), 2.77-2.71 (m, 2H), 2.41-2.40 (m, 2H), 2.26-2.20 (m, 2H).

Step 3

The synthesis of compound 72-4 was referred to the fourth step of example 46. MS-ESI calculated [M+H]$^+$ 202, found 202.

Step 4

The synthesis of compound 72 was referred to the fifth step of example 46. $^1$H NMR (400 MHz Methonal-d$_4$) δ 7.75-7.74 (m, 1H), 7.57-7.56 (m, 2H), 7.32-7.30 (m, 1H), 7.15-7.13 (m, 2H), 7.06-7.05 (m, 1H), 6.89-6.87 (m, 2H), 3.36-3.35 (m, 2H), 2.67-2.63 (m, 2H), 2.47-2.36 (m, 2H), 2.25-2.21 (m, 1H), 2.18-1.95 (m, 2H), 1.71-1.69 (m, 1H), 0.92-0.88 (m, 1H), 0.83-0.79 (m, 1H). MS-ESI calculated [M+H]$^+$ 319, found 319.

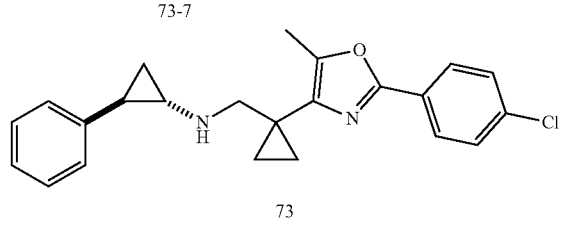

Step 1

Compound 73-1 (2.00 g, 12.9 mmol) and compound 73-2 (685 mg, 6.43 mmol) were dissolved in acetic acid (1 mL), and the mixture was stirred at 120° C. for 48 h. The reaction solution was cooled to room temperature, water (30 mL) was added, and then adjusted to pH=9 with saturated sodium bicarbonate solution, and the mixture was extracted with ethyl acetate (30 mL×3). The organic phases were combined, washed with saturated brine (20 mL×2) and dried over anhydrous sodium sulfate, followed by filtration and concentration under reduced pressure. The obtained crude product was isolated and purified by silica gel column chromatography (3:1 petroleum ether/ethyl acetate, Rf=0.8) to give compound 73-3. $^1$H NMR (400 MHz, CDCl$_3$) δ 7.92 (d, J=8.4 Hz, 2H), 7.41 (d, J=8.4 Hz, 2H), 2.31 (s, 3H), 2.15 (s, 3H).

Step 2

Compound 73-3 (420 mg, 2.02 mmol) was dissolved in acetonitrile (5 mL), and N-chlorosuccinimide (269 mg, 2.02 mmol) was added. The reaction solution was stirred at 60° C. for 12 h. And water (50 mL) was added to the mixture. The mixture was extracted with ethyl acetate (30 mL×2). The organic phases were combined, washed with saturated brine (20 mL×2) and dried over anhydrous sodium sulfate, followed by filtration and concentration under reduced pressure. The obtained crude product was isolated and purified by silica gel column chromatography (10:1 petroleum ether/ethyl acetate, Rf=0.5) to give compound 73-4. $^1$H NMR (400 MHz, CDCl$_3$) δ 7.95 (d, J=8.4 Hz, 2H), 7.43 (d, J=8.4 Hz, 2H), 4.55 (s, 2H), 2.43 (s, 3H).

Step 3

Compound 73-4 (300 mg, 1.24 mmol) was dissolved in anhydrous N,N-dimethylformamide (10 mL), potassium cyanide (121 mg, 1.86 mmol) and potassium iodide (144 mg, 0.869 mmol)) were added. The reaction solution was stirred at 85° C. for 12 h. The reaction solution was cooled to 0° C., water (50 mL) was added to the mixture. The mixture was extracted with ethyl acetate (30 mL×3). The organic phases were combined, washed with saturated brine (30 mL×2) and dried over anhydrous sodium sulfate, followed by filtration and concentration under reduced pressure. The obtained crude product was isolated and purified by thin layer chromatography (3:1 petroleum ether/ethyl acetate, Rf=0.2) to give compound 73-5. $^1$H NMR (400 MHz, CDCl$_3$) δ 7.93 (d, J=8.8 Hz, 2H), 7.44 (d, J=8.8 Hz, 2H), 3.65 (s, 2H), 2.45 (s, 3H).

Step 4

The synthesis of compound 73-6 was referred to the second step of example 71. $^1$H NMR (400 MHz, CDCl$_3$) δ 7.87 (d, J=8.8 Hz, 2H), 7.41 (d, J=8.8 Hz, 2H), 2.58 (s, 3H), 1.66-1.60 (m, 4H).

Step 5

Compound 73-6 (45.0 mg, 0.174 mmol) was dissolved in anhydrous dichloromethane (2 mL), diisobutylaluminum hydride (1 Min toluene, 696 μL, 0.696 mmol) was added dropwise at −78° C., and the mixture was stirred at −78° C. for 2 h. Water (10 mL) was added to the reaction mixture, followed by filtration. The mixture was extracted with dichloromethane (10 mL×2). The organic phases were combined, washed with saturated brine (10 mL×2) and dried over anhydrous sodium sulfate, followed by filtration and concentration under reduced pressure. The obtained crude product was isolated and purified by thin layer chromatography (3:1 petroleum ether/ethyl acetate, Rf=0.6) to give compound 73-7. $^1$H NMR (400 MHz, CDCl$_3$) δ 9.12 (s, 1H), 7.95-7.82 (m, 2H), 7.34-7.32 (m, 2H), 2.30 (s, 3H), 1.58-1.56 (m, 2H), 1.47-1.46 (m, 2H).

Step 6

The synthesis of compound 73 was referred to the fifth step of example 46. $^1$H NMR (400 MHz, Methonal-d$_4$) δ 7.94-7.92 (m, 2H), 7.52-7.49 (m, 2H), 7.26-7.24 (m, 2H), 7.20-7.19 (m, 1H), 7.14-7.12 (m, 2H), 3.46-3.40 (m, 2H), 3.11-3.10 (m, 1H), 2.50-2.47 (m, 1H), 2.43 (s, 3H), 1.53-1.50 (m, 1H), 1.37-1.35 (m, 1H), 1.15-1.08 (m, 4H). MS-ESI calculated [M+H]$^+$ 379, found 379.

Example 74

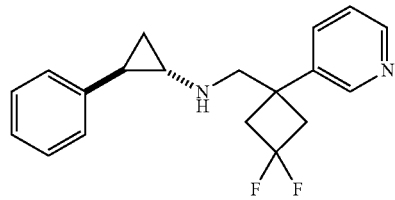

Synthetic Route:

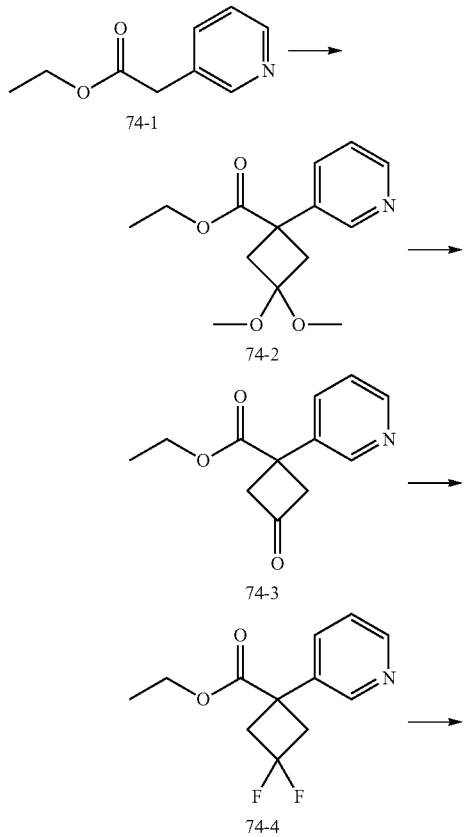

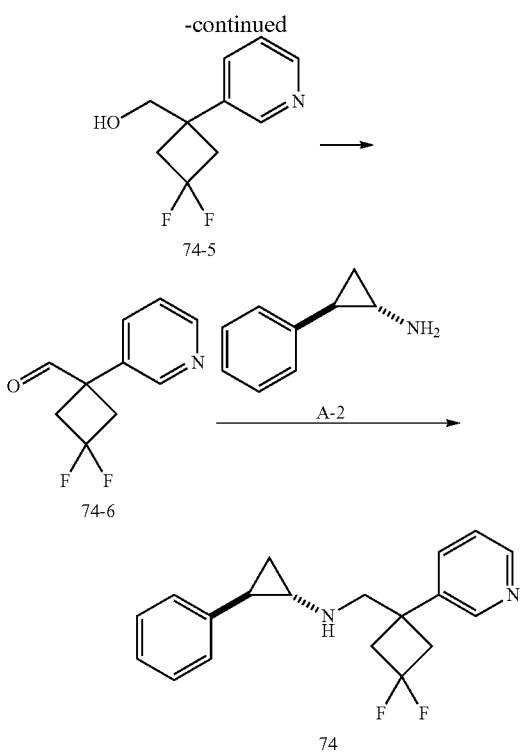

Step 1

Compound 74-1 (5.00 g, 30.3 mmol) was dissolved in anhydrous N,N-dimethylformamide (100 mL), sodium hydride (60%, 2.54 g, 63.6 mmol) was added at 0° C. The mixture was stirred for 0.5 h. 2,2-dimethoxy-1,3-dibromopropane (9.51 g, 36.3 mmol) was added. The reaction solution was heated to 60° C. and stirred for 16 h. The reaction solution was cooled to room temperature, water (300 mL) was added to the mixture. The mixture was extracted with ethyl acetate (100 mL×2). The organic phases were combined, washed with saturated brine (100 mL×2) and dried over anhydrous sodium sulfate, followed by filtration and concentration under reduced pressure. The obtained crude product was isolated and purified by silica gel column chromatography (3:1 petroleum ether/ethyl acetate, Rf=0.4) to give compound 74-2. $^1$H NMR (400 MHz, CDCl$_3$) δ 8.59-8.50 (m, 2H), 7.66-7.62 (m, 1H), 7.27-7.25 (m, 1H), 4.14 (q, J=7.2 Hz, 2H), 3.21 (s, 3H), 3.19-3.17 (m, 2H), 3.14 (s, 3H), 2.59-2.55 (m, 2H), 1.22-1.18 (t, J=7.2 Hz, 3H). MS-ESI calculated [M+H]$^+$ 266, found 266.

Step 2

Compound 74-2 (600 mg, 2.26 mmol) was dissolved in acetone (10 mL), sulfuric acid (2 mol/L, 11.3 mL) was added and the mixture was stirred at 30° C. for 12 h. The mixture was adjusted to pH=8 with saturated sodium bicarbonate aqueous solution, extracted with ethyl acetate (50 mL×2). The organic phases were combined, washed with saturated brine (25 mL×2) and dried over anhydrous sodium sulfate, followed by filtration and concentration under reduced pressure. The obtained crude product was isolated and purified by silica gel column chromatography (1:1 petroleum ether/ethyl acetate, Rf=0.4) to give compound 74-3. MS-ESI calculated [M+Na]$^+$ 242, found 242.

Step 3

Compound 74-3 (130 mg, 0.590 mmol) was dissolved in dichloromethane (5 mL), and diethylamine trifluorosulfide (0.200 mL, 1.48 mmol) was added dropwise at 0° C. The reaction mixture was stirred at 30° C. for 12 h. Saturated sodium bicarbonate aqueous solution (20 mL) was added and the mixture was extracted with dichloromethane (50 mL×2). The organic phases were combined, washed with saturated brine (50 mL×2) and dried over anhydrous sodium sulfate, followed by filtration and concentration under reduced pressure. The obtained crude product was isolated and purified by preparative thin layer chromatography (1:1 petroleum ether/ethyl acetate, Rf=0.5) to give compound 74-4. $^1$H NMR (400 MHz, CDCl$_3$) δ 8.53-8.47 (m, 2H), 7.61-7.55 (m, 1H), 7.28-7.22 (m, 1H), 4.11-4.05 (q, J=7.2 Hz, 2H), 3.50-3.39 (m, 2H), 3.05-2.93 (m, 2H), 1.14-1.11 (t, J=7.2 Hz, 3H).

Step 4

Compound 74-4 (50 mg, 0.210 mmol) was dissolved in anhydrous methanol (3 mL), lithium borohydride (9.03 mg, 0.410 mmol) was added at 0° C. The reaction was stirred at 30° C. for 3 h. The reaction mixture was diluted with ethyl acetate (10 mL), hydrochloric acid (1 mol/L, 5 mL) was added. The mixture was extracted with ethyl acetate (20 mL×3). The organic phases were combined, washed with saturated brine (10 mL×2) and dried over anhydrous sodium sulfate, followed by filtration and concentration under reduced pressure. The obtained crude product was isolated and purified by preparative thin layer chromatography (1:1 petroleum ether/ethyl acetate, Rf=0.2) to give compound 74-5. $^1$H NMR (400 MHz, CDCl$_3$) δ 8.31-8.26 (m, 2H), 7.52-7.50 (m, 1H), 7.26-7.21 (m, 1H), 3.76 (s, 2H), 2.99-2.80 (m, 4H).

Step 5

Oxalyl chloride (105 mg, 0.831 mmol) was dissolved in anhydrous dichloromethane (2 mL), a solution of dimethyl sulfoxide (130 mg, 1.66 mmol) in anhydrous dichloromethane (2 mL) was added dropwise at −78° C. The reaction solution was stirred at −78° C. for 0.5 h, and a solution of compound 74-5 (36.0 mg, 0.181 mmol) in anhydrous dichloromethane (1 mL) was added dropwise, and the mixture was stirred at −78° C. for 1 h. Triethylamine (0.440 mL, 3.18 mmol) was added dropwise, and the mixture was stirred at −78° C. for 2 h. The mixture was warmed to 0° C., saturated ammonium chloride aqueous solution (10 mL) was added, and the mixture was extracted with dichloromethane (25 mL×2). The organic phases were combined, washed with saturated brine (25 mL×2) and dried over anhydrous sodium sulfate, followed by filtration and concentration under reduced pressure. The obtained crude product was isolated and purified by preparative thin layer chromatography (1:1 petroleum ether/ethyl acetate, Rf=0.3) to give compound 74-6. $^1$H NMR (400 MHz, CDCl$_3$) δ 9.8 (s, 1H), 8.62-8.51 (m, 2H), 7.55 (d, J=8.0 Hz, 1H), 7.39-7.36 (m, 1H), 3.47-3.38 (m, 2H), 3.05-2.95 (m, 2H).

Step 6

Compound 74-6 (20.0 mg, 0.101 mmol) and compound A-2 (13.5 mg, 0.101 mmol) were dissolved in anhydrous dichloromethane (2 mL), acetic acid glacial (18.3 mg, 0.304 mmol) was added, and the mixture was stirred at 30° C. for 1 h, sodium borohydride (64.5 mg, 0.304 mmol) was added and stirring was continued for 1 h. The reaction mixture was diluted with dichloromethane (10 mL), saturated sodium bicarbonate aqueous solution (30 mL) was added. The mixture was extracted with dichloromethane (10 mL×2). The organic phases were combined, washed with saturated brine (25 mL×2) and dried over anhydrous sodium sulfate, followed by filtration and concentration under reduced pressure. The obtained crude product was isolated and purified by high-performance liquid chromatography to give compound 74. $^1$H NMR (400 MHz, Methonal-d$_4$) δ 9.12 (s, 1H), 8.88 (d, J=8.0 Hz, 1H), 8.80 (d, J=8.0 Hz, 1H), 8.21-8.17 (m, 1H), 7.32-7.29 (m, 2H), 7.25-7.21 (m, 1H), 7.18 (d, J=7.2 Hz, 2H), 3.90 (s, 2H), 3.39-3.33 (m, 2H), 3.31-3.24 (m, 2H), 3.05-3.01 (m, 1H), 2.73-2.69 (m, 1H), 1.72-1.66 (m, 1H), 1.38-1.34 (m, 1H). MS-ESI calculated [M+H]$^+$ 315, found 315.

Example 75

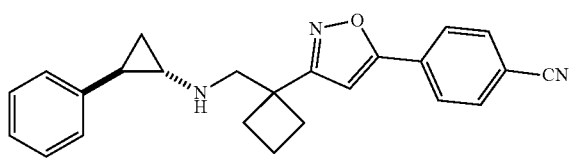

Synthetic Route:

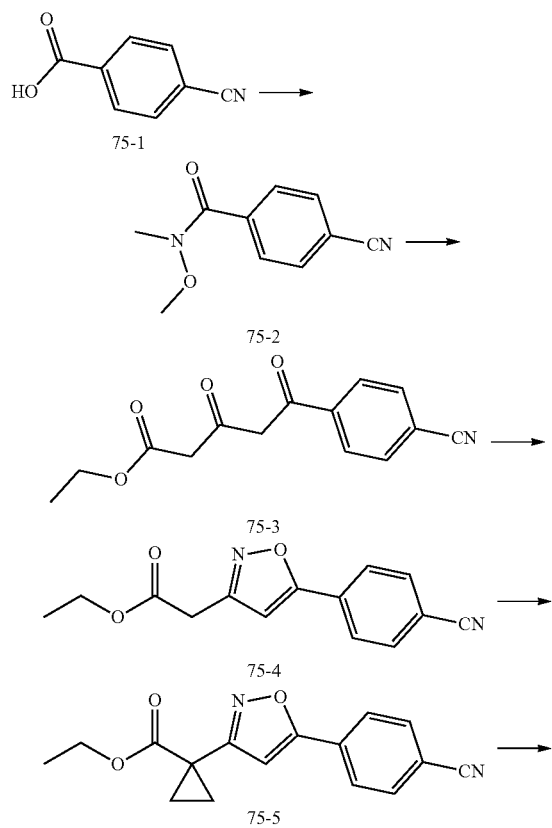

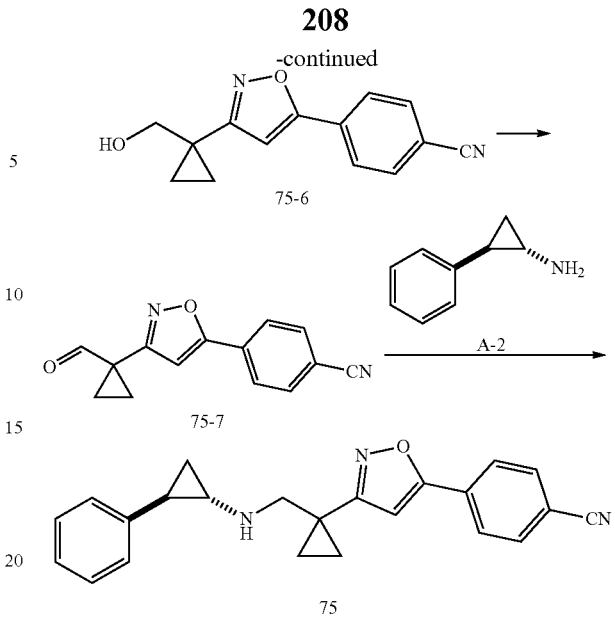

Step 1

75-1 (10.0 g, 68.0 mmol) was dissolved in dichloromethane (50 mL), carbonyldiimidazole (11.0 g, 68.0 mmol) was added portionwise at 0° C., and the mixture was stirred at 0° C. for 0.5 h. hydroxylamine hydrochloride (6.63 g, 68.0 mmol) and triethylamine (6.88 g, 68.0 mmol) were added portionwise, and the reaction mixture was stirred at 0° C. for 1 h. The mixture was warmed to 25° C. and stirred for 12 h. The mixture was cooled to 0° C., hydrochloric acid (1 mol/L, 50 mL) was added to quench. The mixture was extracted with dichloromethane (50 mL×2). The organic phases were combined, washed with saturated brine (50 mL×2) and dried over anhydrous sodium sulfate, followed by filtration and concentration under reduced pressure. The obtained crude product was isolated and purified by silica gel column chromatography (2:1 petroleum ether/ethyl acetate, Rf=0.5) to give compound 75-2. $^1$H NMR (400 MHz, CDCl$_3$) δ 7.80 (d, J=8.0 Hz, 2H), 7.73 (d, J=8.0 Hz, 2H), 3.54 (s, 3H), 3.40 (s, 3H).

Step 2

Sodium hydride (60%, 1.77 g, 44.2 mmol) was added to anhydrous tetrahydrofuran (50 mL), ethyl acetoacetate (4.93 g, 37.9 mmol) was added dropwise at 0° C., and the mixture was stirred at 0° C. for 0.5 h, cooled to −78° C., n-Butyllithium (2 mol/L n-hexane solution, 13.9 mL, 34.7 mmol) was added dropwise, after stirring at −78° C. for 10 minutes. The compound 75-2 (6.00 g, 31.2 mmol) was added dropwise, stirring was continued for 30 minutes. The mixture was warmed to 0° C. and stirred for 1 h, quenched with water (50 mL), extracted with ethyl acetate (50 mL×2). The organic phases were combined, washed with saturated brine (50 mL×2) and dried over anhydrous sodium sulfate, followed by filtration and concentration under reduced pressure. The obtained crude product was isolated and purified by silica gel column chromatography (3:1 petroleum ether/ethyl acetate, Rf=0.2) to give compound 75-3.

Step 3

Compound 75-3 (8.00 g, 30.9 mmol) and hydroxylamine hydrochloride (2.36 g, 34.0 mmol) were dissolved in pyridine (50 mL), and the reaction mixture was stirred under nitrogen for 5 hours at 25° C. and heated to 110° C. for 1 hour. The reaction solution was cooled to 0° C., and hydrochloric acid (1 mol/L, 200 mL) was added dropwise. The mixture was extracted with ethyl acetate (100 mL×2). The organic phases were combined, washed with saturated brine (50 mL×2) and dried over anhydrous sodium sulfate, followed by filtration and concentration under reduced pressure. The obtained crude product was isolated and purified by silica gel column chromatography (3:1 petroleum ether/ethyl acetate, Rf=0.8) to give compound 75-4.

Step 4

Cesium carbonate (2.54 g, 7.80 mmol) was added to anhydrous tetrahydrofuran (5 mL), a solution of the compound 75-4 (400 mg, 1.56 mmol) in anhydrous N,N-dimethylformamide (15 mL) was added dropwise at 0° C., and the mixture was stirred for 0.5 h, 1,2-dibromoethane (351 mg, 1.87 mmol) was added dropwise. The reaction mixture was warmed to 50° C. and stirred for 16 hours, cooled to 0° C. Then added saturated aqueous ammonium chloride (15 mL) to the mixture, the mixture was extracted with ethyl acetate (50 mL×2). The organic phases were combined, washed with saturated brine (50 mL×2) and dried over anhydrous sodium sulfate, followed by filtration and concentration under reduced pressure. The obtained crude product was isolated and purified by preparative thin layer chromatography (3:1 petroleum ether/ethyl acetate, Rf=0.43) to give compound 75-5.

Step 5

The synthesis of compound 75-6 was referred to the third step of example 46. $^1$H NMR (400 MHz, CDCl$_3$) δ 7.86 (d, J=8.0 Hz, 2H), 7.76 (d, J=8.0 Hz, 2H), 6.42 (s, 1H), 3.85 (s, 2H), 1.51-1.08 (m, 4H).

Step 6

Compound 75-6 (50.0 mg, 0.208 mmol) was dissolved in anhydrous dichloromethane (5 mL), Dess Martin reagent (97.1 mg, 0.229 mmol) was added at 25° C., and the mixture was stirred at 25° C. for 2 h. Saturated sodium carbonate (5 mL) was added to the mixture, and the mixture was extracted with dichloromethane (10 mL×3). The organic phases were combined, washed with saturated brine (10 mL×2) and dried over anhydrous sodium sulfate, followed by filtration and concentration under reduced pressure. The obtained crude product was isolated and purified by preparative thin layer chromatography (1:1 petroleum ether/ethyl acetate, Rf=0.7) to give compound 75-7. $^1$H NMR (400 MHz, CDCl$_3$) δ 9.15 (s, 1H), 7.96 (d, J=8.0 Hz, 2H), 7.78 (d, J=8.0 Hz, 2H), 7.03 (s, 1H), 1.86-1.84 (m, 2H), 1.77-1.75 (m, 2H).

Step 7

The synthesis of compound 75 was referred to the sixth step of example 74. $^1$H NMR (400 MHz, Methonal-d$_4$) δ 7.93 (d, J=8.0 Hz, 2H), 7.83 (d, J=8.0 Hz, 2H), 7.20-7.16 (m, 2H), 7.08-7.04 (m, 1H), 7.01-6.99 (m, 2H), 6.80 (s, 1H), 3.08-3.01 (m, 2H), 2.45-2.42 (m, 1H), 1.92-1.88 (m, 1H), 1.14-0.94 (m, 6H). MS-ESI calculated [M+H]$^+$ 356, found 356.

Example 76

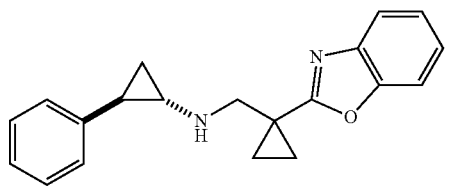

Synthetic Route:

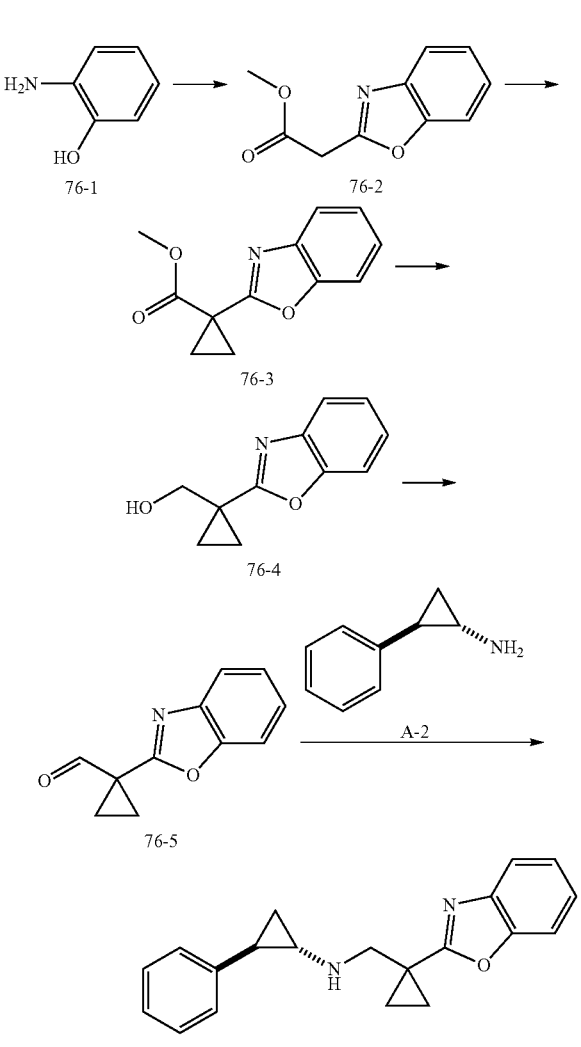

Step 1

The synthesis of compound 76-2 was referred to the first step of example 46. $^1$H NMR (400 MHz, CDCl$_3$) δ 7.76-7.71 (m, 1H), 7.56-7.51 (m, 1H), 7.39-7.32 (m, 2H), 4.04 (s, 2H), 3.79 (s, 3H).

The synthesis of compound 76-3 was referred to the first step of example 1. $^1$H NMR (400 MHz, CDCl$_3$) δ 7.72-7.68 (m, 1H), 7.54-7.52 (m, 1H), 7.38-7.31 (m, 2H), 3.76 (s, 3H), 1.81-1.78 (m, 2H), 1.69-1.66 (m, 2H).

Step 3

The synthesis of compound 76-4 was referred to the second step of example 1. MS-ESI calculated [M+H]⁺ 190, found 190.

Step 4

The synthesis of compound 76-5 was referred to the fourth step of example 46. MS-ESI calculated [M+H]⁺ 188, found 188.

Step 5

The synthesis of compound 76 was referred to the sixth step of example 74. ¹H NMR (400 MHz, Methonal-d₄) δ7.58-7.57 (m, 1H), 7.52-7.45 (m, 1H), 7.33-7.29 (m, 2H), 7.21-7.17 (m, 2H), 7.10-7.07 (m, 1H), 7.02-6.99 (m, 2H), 3.20-3.13 (m, 2H), 2.48-2.44 (m, 1H), 1.96-1.90 (m, 1H), 1.46-1.42 (m, 2H), 1.18-1.08 (m, 3H), 1.01-0.95 (m, 1H). MS-ESI calculated [M+H]⁺ 305, found 305.

Example 77

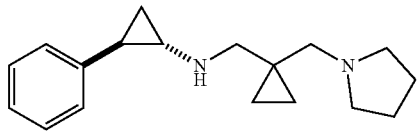

Synthetic Route:

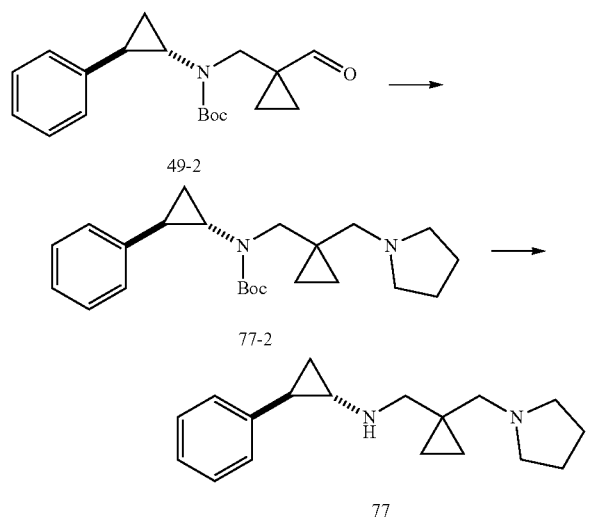

Step 1

The synthesis of compound 77-2 was referred to the first step of example 28. MS-ESI calculated [M+H]⁺ 371, found 371.

Step 2

The synthesis of compound 77 was referred to the third step of example 62. ¹H NMR (400 MHz, Methonal-d₄) δ 7.32-7.29 (m, 2H), 7.24-7.19 (m, 3H), 3.83 (s, 2H), 3.50-3.35 (m, 4H), 3.11-3.07 (m, 3H), 2.78-2.70 (m, 1H), 2.20-2.05 (m, 4H), 1.74-1.71 (m, 1H), 1.39-1.36 (m, 1H), 0.98-0.93 (m, 4H). MS-ESI calculated [M+H]⁺ 271, found 271.

Example 78

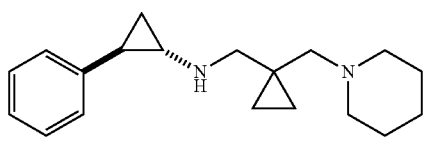

Synthetic Route:

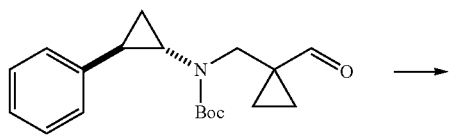

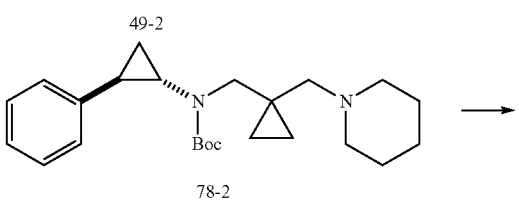

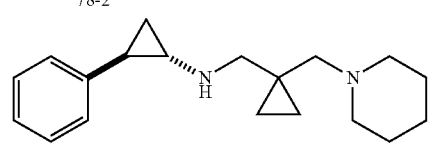

Step 1

The synthesis of compound 78-2 was referred to the first step of example 28. MS-ESI calculated [M+H]⁺ 385, found 385.

Step 2

The synthesis of compound 78 was referred to the third step of example 62. ¹H NMR (400 MHz, Methonal-d₄) δ 7.34-7.30 (m, 2H), 7.26-7.20 (m, 3H), 3.70-3.65 (m, 2H), 3.48-3.44 (m, 1H), 3.38-3.36 (m, 1H), 3.26-3.23 (m, 2H), 3.14-3.12 (m, 1H), 2.97-2.92 (m, 2H), 2.76-2.74 (m, 1H), 2.01-1.92 (m, 5H), 1.75-1.74 (m, 1H), 1.54-1.51 (m, 1H), 1.40-1.35 (m, 1H), 1.02-0.91 (m, 4H). MS-ESI calculated [M+H]⁺ 285, found 285.

Example 79

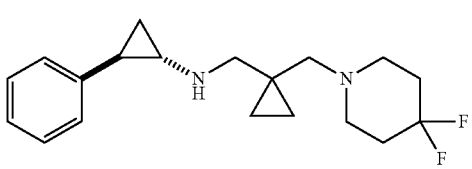

Synthetic Route:

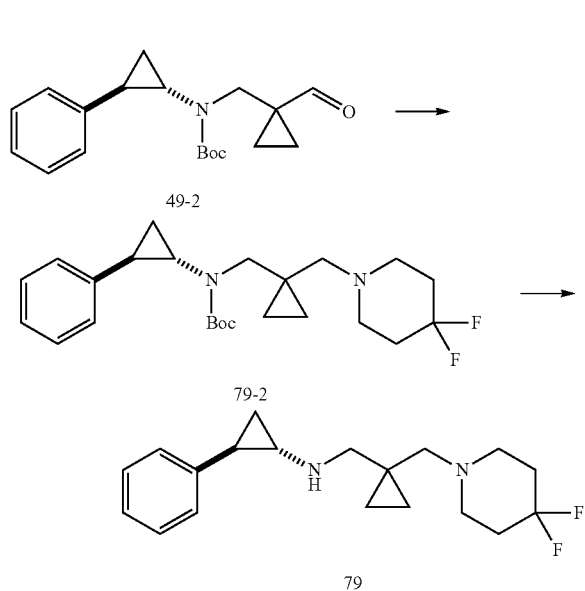

Step 1

The synthesis of compound 79-2 was referred to the first step of example 51. MS-ESI calculated [M+H]+ 421, found 421.

Step 2

The synthesis of compound 79 was referred to the third step of example 62. ¹H NMR (400 MHz, Methonal-$d_4$) δ 7.31-7.28 (m, 2H), 7.23-7.20 (m, 3H), 3.85-3.77 (m, 2H), 3.58-3.55 (m, 1H), 3.47-3.42 (m, 2H), 3.38-3.34 (m, 1H), 3.31-3.24 (m, 2H), 3.21-3.17 (m, 1H), 2.84-2.79 (m, 1H), 2.74-2.59 (m, 2H), 2.44-2.30 (m, 2H), 1.80-1.74 (m, 1H), 1.36-1.29 (m, 1H), 1.07 (s, 2H), 0.95 (s, 2H). MS-ESI calculated [M+H]+ 321, found 321.

Example 80

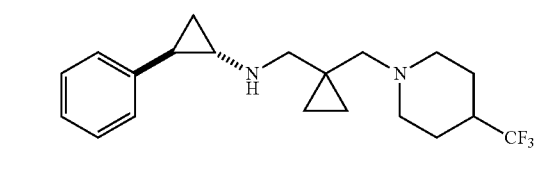

Synthetic Route:

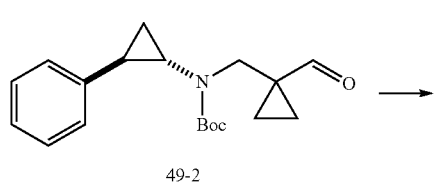

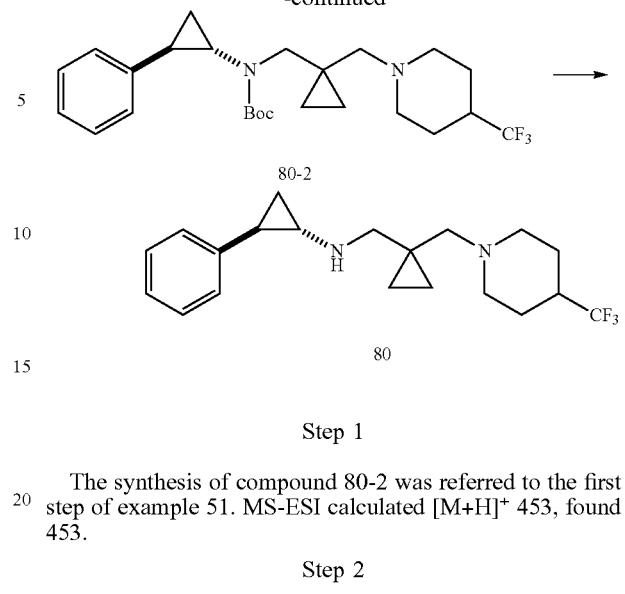

Step 1

The synthesis of compound 80-2 was referred to the first step of example 51. MS-ESI calculated [M+H]+ 453, found 453.

Step 2

The synthesis of compound 80 was referred to the third step of example 62. ¹H NMR (400 MHz, Methonal-$d_4$) δ 7.30-7.28 (m, 2H), 7.23-7.19 (m, 3H), 3.87-3.84 (m, 2H), 3.51-3.47 (m, 1H), 3.40-3.32 (m, 2H), 3.27-3.24 (m, 1H), 3.15-3.12 (m, 1H), 3.07-3.05 (m, 2H), 2.77-2.74 (m, 1H), 2.62-2.56 (m, 1H), 2.17-2.13 (m, 4H), 1.75-1.73 (m, 1H), 1.35-1.34 (m, 1H), 1.02-1.00 (m, 2H), 0.%-0.93 (m, 2H). MS-ESI calculated [M+H]+ 353, found 353.

Example 81

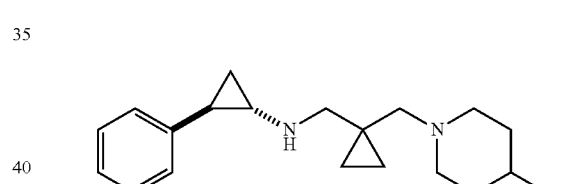

Synthetic Route:

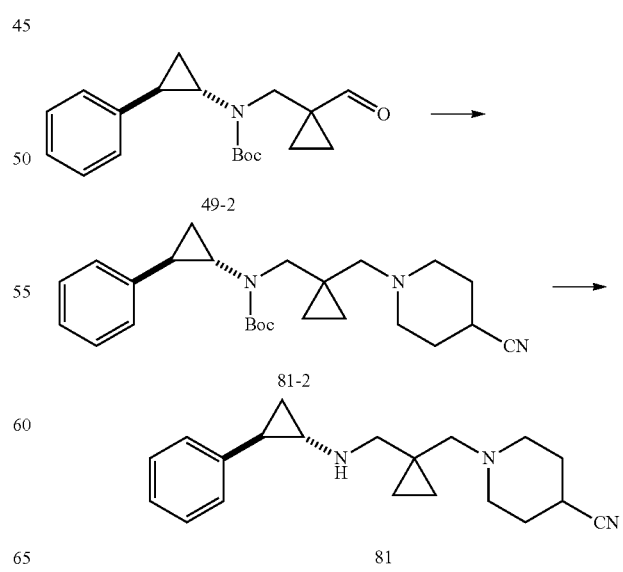

Step 1
The synthesis of compound 81-2 was referred to the first step of example 28. MS-ESI calculated [M+H]$^+$ 410, found 410.
Step 2
The synthesis of compound 81 was referred to the third step of example 62. $^1$H NMR (400 MHz, Methonal-d$_4$) δ 7.32-7.28 (m, 2H), 7.24-7.19 (m, 3H), 3.77-3.74 (m, 2H), 3.50-3.48 (m, 1H), 3.40-3.37 (m, 2H), 3.28-3.13 (m, 3H), 3.04-3.02 (m, 2H), 2.78-2.73 (m, 1H), 2.48-2.34 (m, 3H), 2.23-2.19 (m, 1H), 1.75-1.70 (m, 1H), 1.38-1.33 (m, 1H), 1.02-1.00 (m, 2H), 0.94-0.91 (m, 2H). MS-ESI calculated [M+H]$^+$ 310, found 310.
Example 82
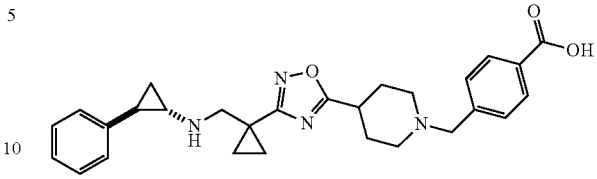
Synthetic Route:
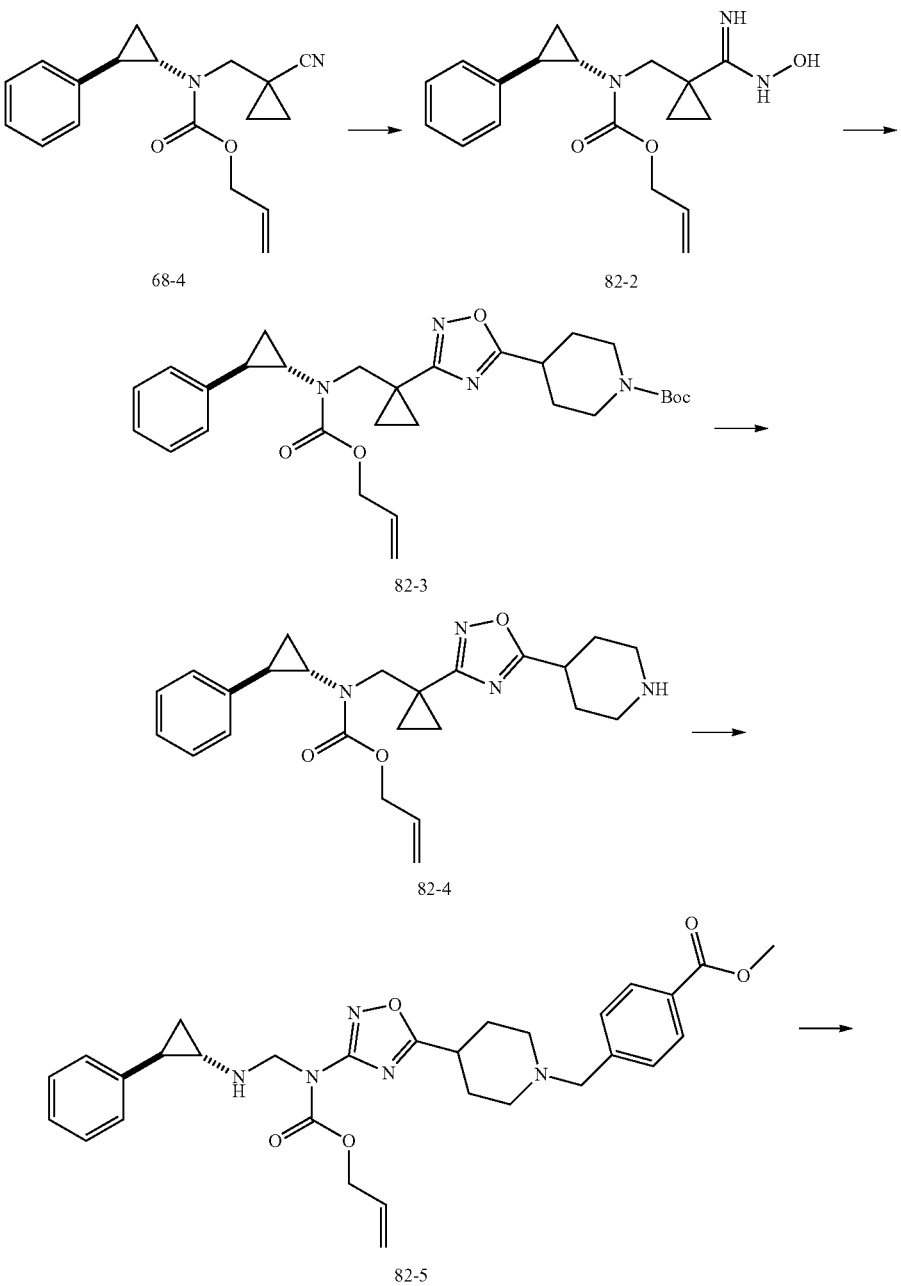

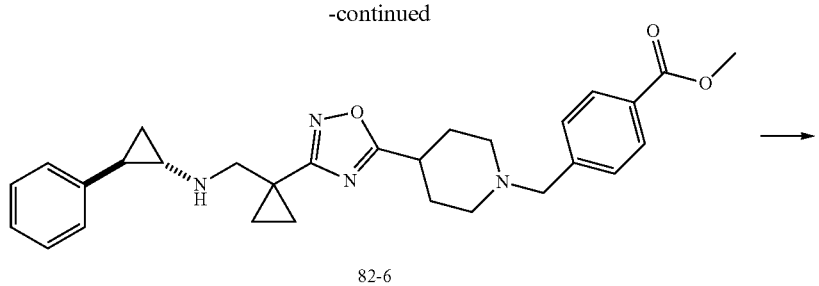

82-6

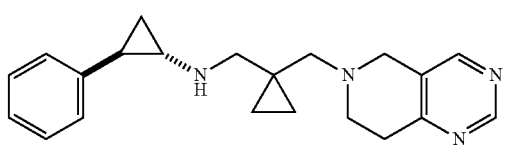

82

Step 1

The synthesis of compound 82-2 was referred to the first step of example 62. MS-ESI calculated [M+H]$^+$ 330, found 330.

Step 2

The synthesis of compound 82-3 was referred to the second step of example 62. MS-ESI calculated [M+Na]$^+$ 545, found 545.

Step 3

The compound 82-3 (460 mg, 0.880 mmol) was dissolved in anhydrous dichloromethane (5 mL). Trifluoroacetic acid (200 mg, 1.76 mmol) was added, and the reaction mixture was stirred at 20° C. for 0.5 hour, and then cooled to 0° C. Saturated sodium carbonate aqueous solution (20 mL) was added dropwise and the mixture was extracted with dichloromethane (25 mL×2). The organic phases were combined, washed with saturated brine (25 mL×2) and dried over anhydrous sodium sulfate, followed by filtration and concentration under reduced pressure to give compound 82-4. MS-ESI calculated[M+H]$^+$ 423, found 423.

Step 4

The synthesis of compound 82-5 was referred to the first step of example 28. MS-ESI calculated [M+H]$^+$ 571, found 571.

Step 5

The synthesis of compound 82-6 was referred to the fourth step of example 48. MS-ESI calculated [M+H]$^+$ 487, found 487.

Step 6

The synthesis of compound 82 was referred to the second step of example 54. $^1$H NMR (400 MHz, Methonal-d$_4$) δ 8.13 (d, J=8.4 Hz, 2H), 7.75 (d, J=8.4 Hz, 2H), 7.32-7.28 (m, 2H), 7.24-7.15 (m, 3H), 4.49-4.47 (m, 2H), 3.74-3.60 (m, 3H), 3.54-3.31 (m, 3H), 3.27-3.24 (m, 1H), 3.09-3.05 (m, 1H), 2.69-2.56 (m, 1H), 2.45-2.12 (m, 4H), 1.71-1.58 (m, 1H), 1.41-1.36 (m, 5H). MS-ESI calculated [M+H]$^+$ 473, found 473.

Example 83

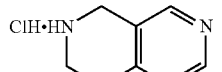

Synthetic Route:

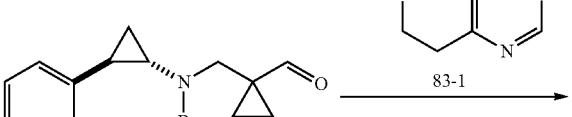

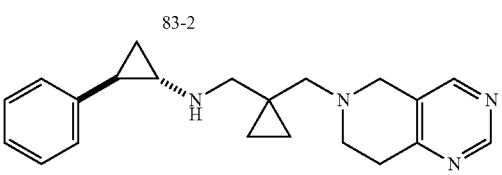

83

Step 1

The synthesis of compound 83-2 was referred to the first step of example 51. MS-ESI calculated [M+H]$^+$ 435, found 435.

Step 2

The synthesis of compound 83 was referred to the second step of example 28. $^1$H NMR (400 MHz, Methonal-d$_4$) δ 9.19 (s, 1H), 8.85 (s, 1H), 7.30-7.29 (m, 2H), 7.23-7.20 (m, 3H), 4.69-4.43 (m, 1H), 4.07-3.47 (m, 7H), 3.19-2.80 (m, 3H), 1.80-1.73 (m, 1H), 1.39-1.10 (m, 6H). MS-ESI calculated [M+H]$^+$ 335, found 335.

Example 84

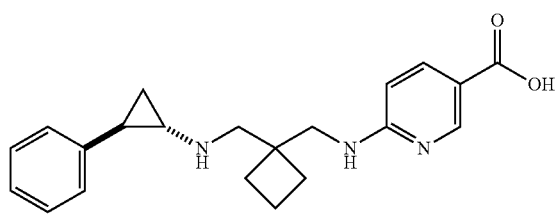

Synthetic Route:

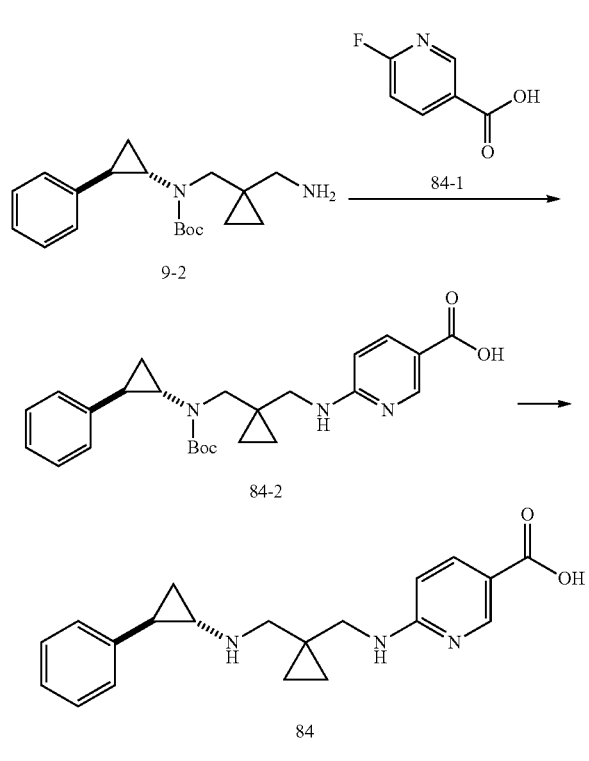

Step 1

Compound 9-2 (50.0 mg, 0.151 mmol) was dissolved in dimethyl sulfoxide (1 mL) under nitrogen, and diisopropylethylamine (58.7 mg, 0.454 mmol) and compound 84-1 (32.0 mg, 0.227 mmol) were added at 25° C. The reaction mixture was stirred at 110° C. for 12 h, water (10 mL) and 1N hydrochloric acid aqueous solution (10 mL) were added to the mixture, and mixture was extracted with dichloromethane (20 mL×5). The organic phase was washed with saturated brine (50 mL×1) and dried over anhydrous sodium sulfate, followed by filtration and concentration under reduced pressure. The residue was purified by thin layer chromatography (10:1 dichloromethane/methanol, Rf=0.1) to give compound 84-2. MS-ESI calculated [M+H]$^+$ 452, found 452.

Step 2

Compound 84-2 (50.0 mg, 0.111 mmol) was dissolved in anhydrous dichloromethane (5 mL) under nitrogen, and trimethylsilyl trifluoromethanesulfonate (49.2 mg, 0.222 mmol) was added dropwise at 0° C. The reaction mixture was stirred at 0° C. for 0.5 h, quenched with 0.5 ml water at 25° C. The mixture was concentrated under reduced pressure, isolated and purified by preparative high-performance liquid chromatography (hydrochloric acid) to give compound 84 (4.40 mg). MS-ESI calculated [M+H]$^+$ 352, found 352.

Example 85

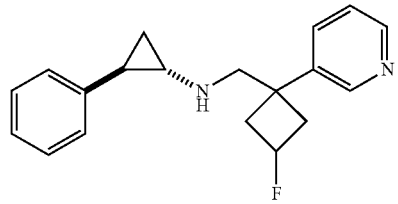

Synthetic Route:

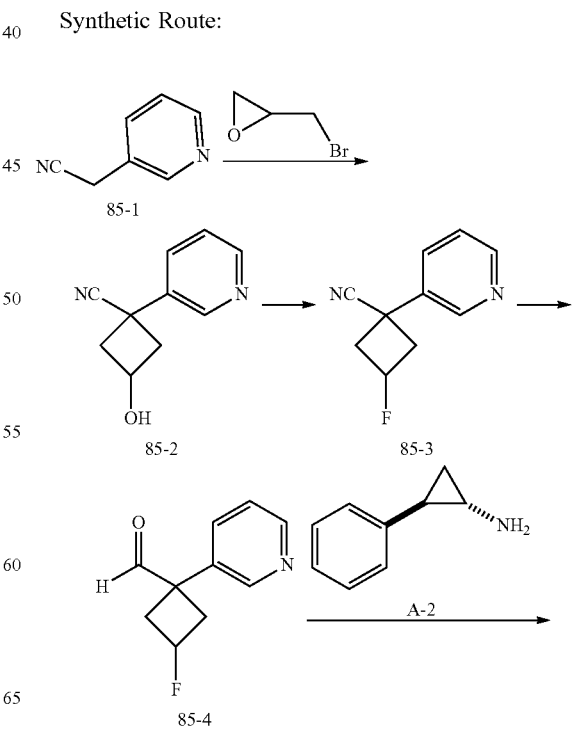

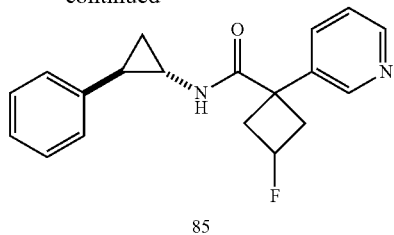

85

Step 1

Compound 85-1 (2.00 g, 16.9 mmol) was dissolved in anhydrous tetrahydrofuran (30 mL) under nitrogen, methyl lithium (1M methyl lithium-tetrahydrofuran solution, 20.3 mL, 20.3 mmol) was added at −78° C. The solution was stirred at −78° C. for 1 h, 1-bromo-2,3-epoxypropane (2.78 g, 20.3 mmol) dissolved in tetrahydrofuran (15 mL) was added dropwise to the reaction solution at −78° C., and the reaction mixture was stirred at −78° C. for 1 h. Methyl magnesium bromide (3M tetrahydrofuran solution, 6.8 mL, 20.3 mmol) was added at −70° C., and the reaction mixture was stirred at 25° C. for 12 hours, and saturated ammonium chloride solution (60 mL) was added to the mixture. The mixture was extracted with ethyl acetate (60 mL×1). The organic phase was washed with saturated brine (60 mL×1) and dried over anhydrous sodium sulfate, followed by filtration and concentration under reduced pressure to give compound 85-2. MS-ESI calculated [M+H]$^+$ 175, found 175.

Step 2

Compound 85-2 (1.44 g, 8.30 mmol) was dissolved in anhydrous dichloromethane (10 mL), and diethylamine trifluorosulfide (2.66 g, 16.5 mmol) was added dropwise at −78° C. The reaction mixture was stirred at 25° C. for 12 h, saturated sodium bicarbonate aqueous solution (50 mL) was added, and the mixture was extracted with dichloromethane (50 mL×1). The organic phase was dried over anhydrous sodium sulfate, followed by filtration and concentration under reduced pressure. The residue was isolated and purified by silica gel column chromatography (1:1 petroleum ether/ethyl acetate, Rf=0.7) to give compound 85-3. $^1$H NMR (400 MHz, CDCl$_3$) δ 8.68 (d, J=2.0 Hz, 1H), 8.57-8.56 (m, 1H), 7.71-7.68 (m, 1H), 7.33-7.30 (m, 1H), 5.47-5.27 (m, 1H), 3.31-3.24 (m, 2H), 2.83-2.73 (m, 2H).

Step 3

Compound 85-3 (300 mg, 1.70 mmol) was dissolved in anhydrous dichloromethane (10 mL) under nitrogen, and diisobutylaluminum hydride (1 M in toluene, 3.4 mL, 3.40 mmol) was added at −78° C. The reaction mixture was stirred at −78° C. for 3 h. Water (20 mL) was added to the reaction mixture. And the mixture was filtered, the filtrate was extracted with dichloromethane (20 mL×1). The organic phase was washed with saturated brine (30 mL×1) and dried over anhydrous sodium sulfate, followed by filtration and concentration under reduced pressure. The residue was purified by thin layer chromatography (1:1 petroleum ether/ethyl acetate, Rf=0.3) to give compound 85-4. $^1$H NMR (400 MHz, CDCl$_3$) δ 9.59 (s, 1H), 8.58-8.57 (m, 1H), 8.45 (d, J=2.0 Hz, 1H), 7.50-7.48 (m, 1H), 7.36-7.33 (m, 1H), 5.19-5.05 (m, 1H), 3.26-3.19 (m, 2H), 2.68-2.59 (m, 2H).

Step 4

Compound 85-4 (70.0 mg, 0.391 mmol) was dissolved in anhydrous dichloromethane (10 mL), acetic acid (70.4 mg, 1.17 mmol) and compound A-2 (52.0 mg, 0.391 mmol) were added, and the reaction mixture was stirred at 25° C. for 1 h, sodium triethoxyborohydride (248 mg, 1.17 mmol) was added, and the reaction mixture was stirred at 25° C. for 11 h. Saturated sodium carbonate aqueous solution (20 mL) was added to the mixture, and the mixture was extracted with dichloromethane (20 mL×1). The organic phase was washed with saturated brine (20 mL×1) and dried over anhydrous sodium sulfate, followed by filtration and concentration under reduced pressure. The residue was purified by thin layer chromatography (10:1 dichloromethane/methanol, Rf=0.5), and then purified by preparative high-performance liquid chromatography (hydrochloric acid) to give compound 85. $^1$H NMR (400 MHz, D$_2$O) δ 8.70-8.69 (m, 1H), 8.53-8.52 (m, 1H), 8.49-8.47 (m, 1H), 7.93-7.89 (m, 1H), 7.27-7.18 (m, 3H), 6.97-6.95 (m, 2H), 5.37-5.17 (m, 1H), 3.70 (s, 2H), 3.05-2.93 (m, 2H), 2.79-2.62 (m, 3H), 2.35-2.29 (m, 1H), 1.41-1.36 (m, 1H), 1.26-1.21 (m, 1H). MS-ESI calculated [M+H]$^+$ 297, found 297.

Example 86

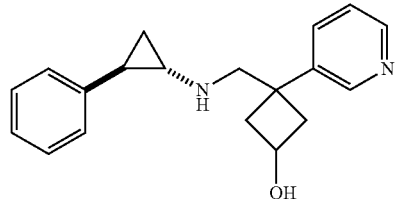

Synthetic Route:

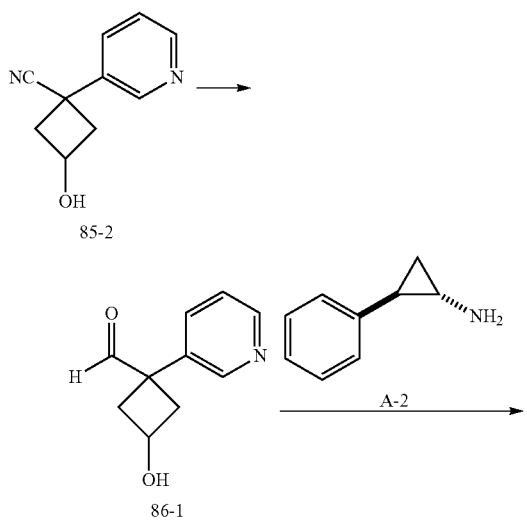

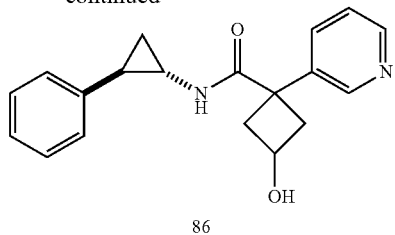

86

Step 1

The synthesis of compound 86-1 was referred to the third step of example 85. $^1$H NMR (400 MHz, CDCl$_3$) δ 9.61 (s, 1H), 8.59-8.56 (m, 2H), 7.60-7.57 (m, 1H), 7.37-7.34 (m, 1H), 4.44-4.38 (m, 1H), 2.89-2.81 (m, 2H), 2.74-2.69 (m, 2H). MS-ESI calculated [M+H]$^+$ 178, found 178.

Step 2

The synthesis of compound 86 was referred to the fourth step of example 85. $^1$H NMR (400 MHz, D$_2$O) δ 8.79 (d, J=1.6 Hz, 0.5H), 8.64 (d, J=1.6 Hz, 0.5H), 8.60-8.58 (m, 0.5H), 8.50-8.47 (m, 1H), 8.45-8.43 (m, 0.5H), 7.91-7.86 (m, 1H), 7.24-7.16 (m, 3H), 6.94-6.92 (m, 2H), 4.51-4.43 (m, 0.5H), 4.12-4.05 (m, 0.5H), 3.73-3.68 (m, 2H), 2.92-2.81 (m, 2H), 2.68-2.64 (m, 1H), 2.39-2.28 (m, 3H), 1.39-1.34 (m, 1H), 1.23-1.17 (m, 1H). MS-ESI calculated [M+H]$^+$ 295, found 295.

Example 87

Step 1

Compound 19-2 (90.2 mg, 0.501 mmol) was dissolved in anhydrous N,N-dimethylformamide (4 mL) under nitrogen, N,N-carbonyldiimidazole (88.0 mg, 0.543 mmol) was added in one portion, and the reaction mixture was stirred at 30° C. for 2 h. Then compound 19-2 (150 mg, 0.417 mmol) was added in one portion. The reaction solution was stirred at 110° C. for 10 h, and cooled to 25° C., water (30 mL) was added to the reaction mixture. The mixture was extracted with ethyl acetate (20 mL×1). The organic phase was washed with saturated brine (20 mL×2), dried over anhydrous sodium sulfate, followed by filtration and concentration under reduced pressure. The residue was purified by thin layer chromatography (4:1 petroleum ether/ethyl acetate. Rf=0.7) to give compound 87-2. MS-ESI calculated [M+H]$^+$ 504, found 504.

Step 2

The synthesis of compound 87 was referred to the second step of example 84. $^1$H NMR (400 MHz, CD$_3$OD) δ 8.09 (d, J=9.2 Hz, 2H), 7.32-7.29 (m, 2H), 7.24-7.22 (m, 1H), 7.19-7.17 (m, 2H), 7.10 (d, J=9.2 Hz, 2H), 4.80-4.73 (m, 1H), 3.87 (s, 2H), 3.11-3.06 (m, 1H), 2.70-2.65 (m, 2H), 2.58-2.52 (m, 1H), 2.45-2.37 (m, 2H), 2.28-2.20 (m, 2H), 1.61-1.53 (m, 1H), 1.43-1.41 (m, 1H), 1.39-1.37 (m, 6H). MS-ESI calculated [M+H]$^+$ 404, found 404.

Example 88

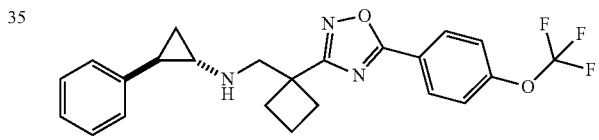

Synthetic Route:

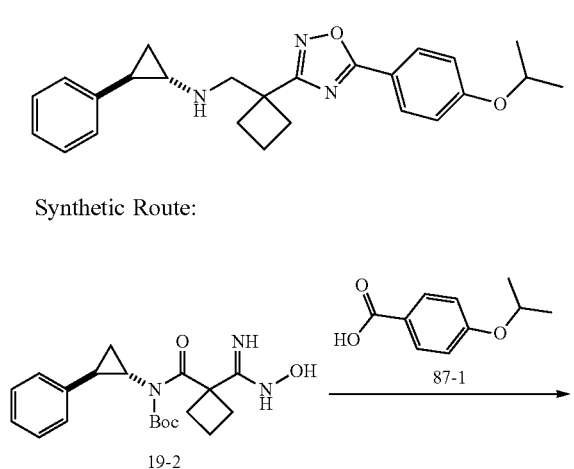

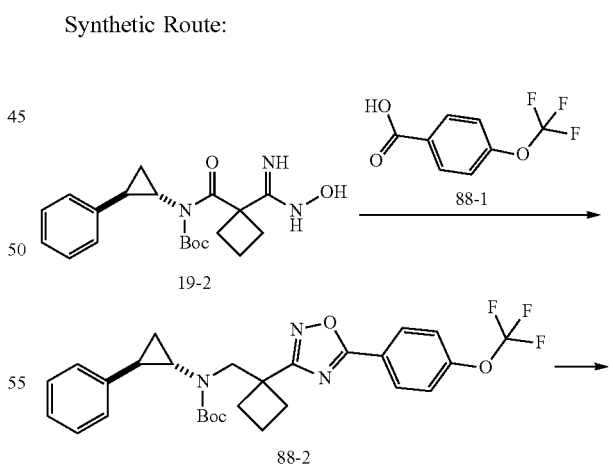

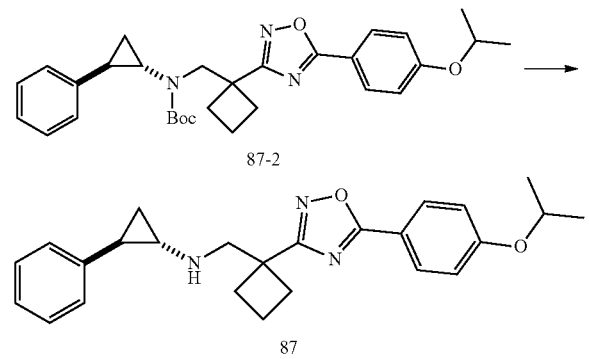

Step 1

The synthesis of compound 88-2 was referred to the first step of example 87. MS-ESI calculated [M+H]+ 530, found 530.

Step 2

The synthesis of compound 88 was referred to the second step of example 84. ¹H NMR (400 MHz, CD₃OD) δ 8.30-8.28 (m, 2H), 7.55-7.53 (m, 2H), 7.31-7.27 (m, 2H), 7.22-7.17 (m, 3H), 3.90 (s, 2H), 3.12-3.08 (m, 1H), 2.74-2.66 (m, 2H), 2.59-2.54 (m, 1H), 2.49-2.38 (m, 2H), 2.29-2.21 (m, 2H), 1.63-1.57 (m, 1H), 1.43-1.37 (m, 1H). MS-ESI calculated [M+H]+ 430, found 430.

Example 89

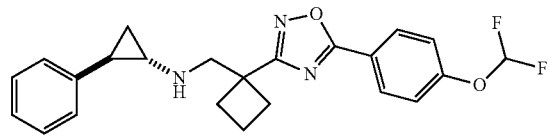

Synthetic Route:

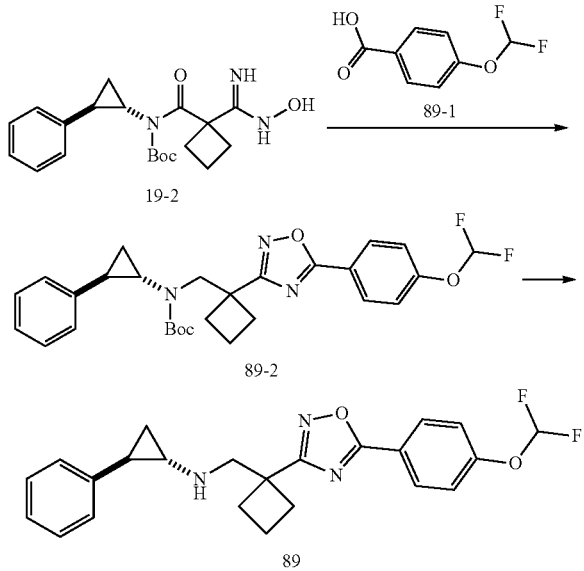

Step 1

The synthesis of compound 89-2 was referred to the first step of example 87. MS-ESI calculated [M+H]+ 512, found 512.

Step 2

The synthesis of compound 89 was referred to the second step of example 84. ¹H NMR (400 MHz, CD₃OD) δ 8.24-8.20 (m, 2H), 7.39-7.37 (m, 2H), 7.32-7.28 (m, 2H), 7.24-7.22 (m, 0.25H), 7.21-7.17 (m, 3H), 7.06 (s, 0.5H), 6.88 (s, 0.25H), 3.90 (s, 2H), 3.12-3.09 (m, 1H), 2.73-2.66 (m, 2H), 2.59-2.54 (m, 1H), 2.48-2.39 (m, 2H), 2.28-2.21 (m, 2H), 1.62-1.57 (m, 1H), 1.43-1.38 (m, 1H). MS-ESI calculated [M+H]+ 412, found 412.

Example 90

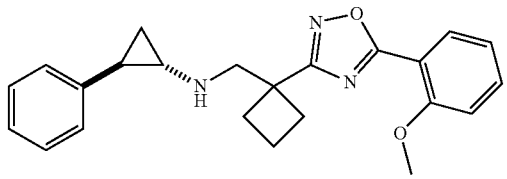

Synthetic Route:

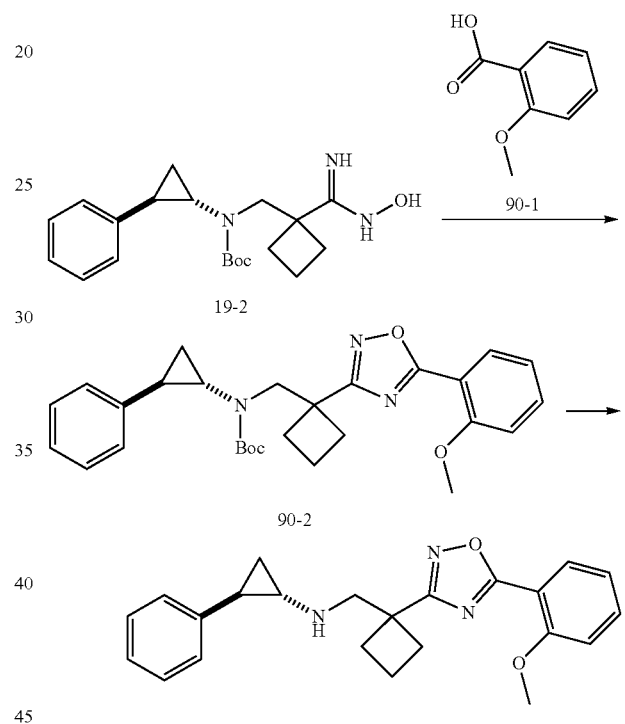

Step 1

Compound 90-1 (76.2 mg, 0.501 mmol) was dissolved in anhydrous N,N-dimethylformamide (4 mL) under nitrogen, N,N-carbonyldiimidazole (88.0 mg, 0.543 mmol) was added in one portion, and the reaction mixture was stirred at 30° C. for 2 h. Then compound 19-2 (150 mg, 0.417 mmol) was added in one portion. The reaction mixture was stirred at 110° C. for 10 h, cooled to 25° C., water (30 mL) was added to the reaction mixture and the mixture was extracted with ethyl acetate (20 mL×1). The organic phase was washed with saturated brine (20 mL×2), dried over anhydrous sodium sulfate, followed by filtration and concentration under reduced pressure to give compound 90-2. MS-ESI calculated [M+H]+ 476, found 476.

Step 2

The synthesis of compound 90 was referred to the second step of example 84. ¹H NMR (400 MHz, CD₃OD) δ

8.09-8.07 (m, 1H), 7.68-7.64 (m, 1H), 7.33-7.13 (m, 7H), 3.98 (s, 3H), 3.89 (s, 2H), 3.14-3.10 (m, 1H), 2.73-2.66 (m, 2H), 2.59-2.55 (m, 1H), 2.44-2.38 (m, 2H), 2.28-2.20 (m, 2H), 1.62-1.56 (m, 1H), 1.44-1.39 (m, 1H). MS-ESI calculated [M+H]+ 376, found 376.

Example 91

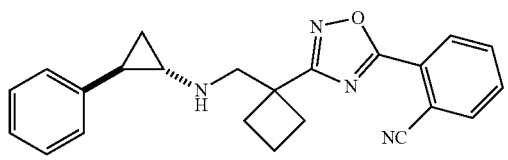

Synthetic Route:

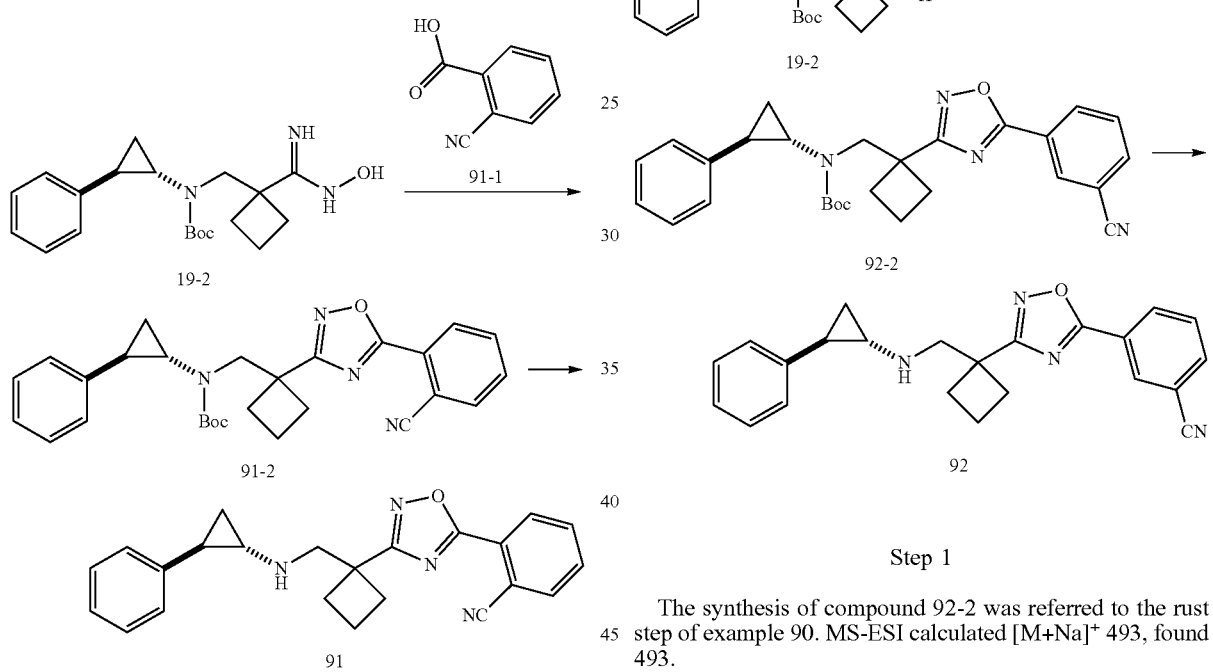

Step 1

The synthesis of compound 91-2 was referred to the first step of example 87. MS-ESI calculated [M+Na]+ 493, found 493.

Step 2

The synthesis of compound 91 was referred to the second step of example 84. $^1$H NMR (400 MHz, CD$_3$OD) δ 8.35 (dd, J=0.8, 8.0 Hz, 1H), 8.05 (dd, J=0.8, 8.0 Hz, 1H), 7.97-7.93 (m, 1H), 7.90-7.86 (m, 1H), 7.30-7.26 (m, 2H), 7.21-7.18 (m, 3H), 3.91 (s, 2H), 3.16-3.12 (m, 1H), 2.74-2.66 (m, 2H), 2.61-2.56 (m, 1H), 2.52-2.44 (m, 2H), 2.32-2.18 (m, 2H), 1.64-1.59 (m, 1H), 1.43-1.37 (m, 1H). MS-ESI calculated [M+H]+ 371, found 371.

Example 92

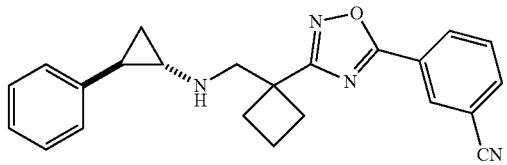

Synthetic Route:

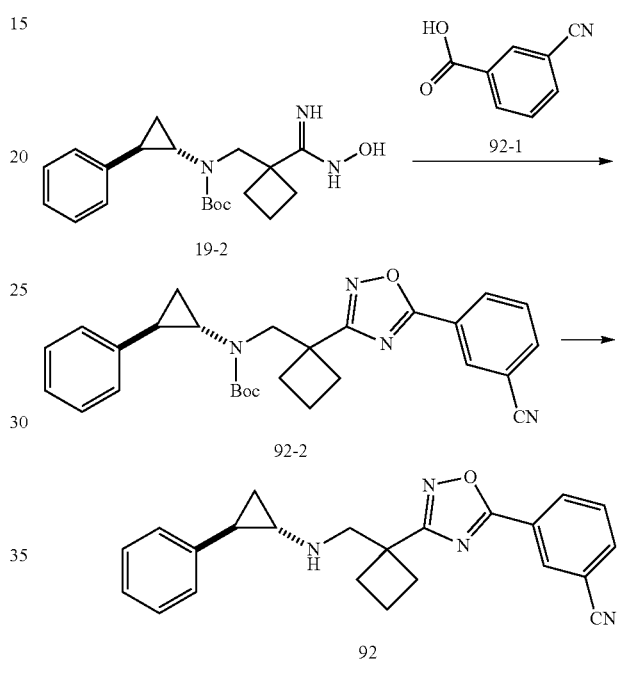

Step 1

The synthesis of compound 92-2 was referred to the rust step of example 90. MS-ESI calculated [M+Na]+ 493, found 493.

The synthesis of compound 92 was referred to the second step of example 84. $^1$H NMR (400 MHz, CD$_3$OD) δ 8.50-8.49 (m, 1H), 8.46-8.43 (m, 1H), 8.06-8.04 (m, 1H), 7.85-7.81 (m, 1H), 7.30-7.27 (m, 2H), 7.22-7.16 (m, 3H), 3.92 (s, 2H), 3.13-3.09 (m, 1H), 2.75-2.67 (m, 2H), 2.58-2.53 (m, 1H), 2.50-2.41 (m, 2H), 2.29-2.21 (m, 2H), 1.62-1.57 (m, 1H), 1.43-1.38 (m, 1H). MS-ESI calculated [M+H]+ 371, found 371.

Example 93

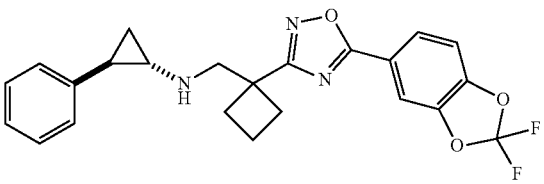

229

Synthetic Route:

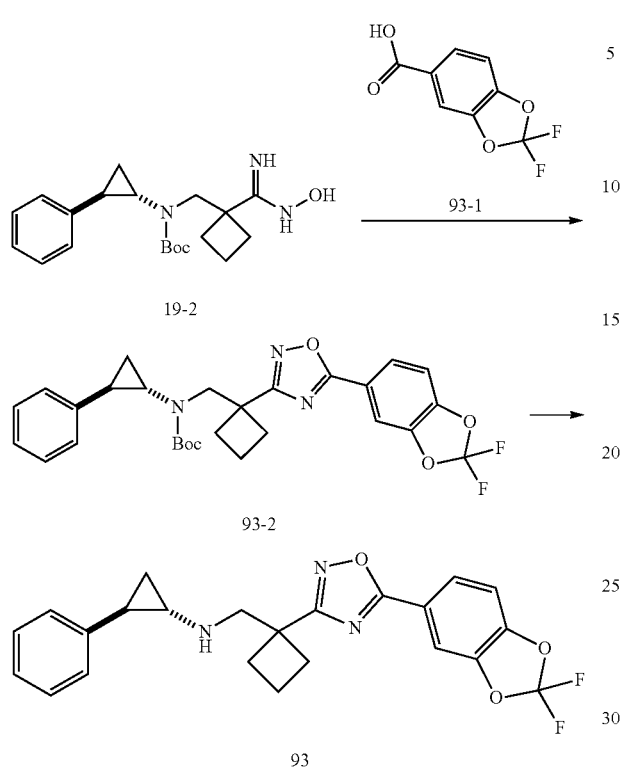

Step 1

The synthesis of compound 93-2 was referred to the first step of example 90. MS-ESI calculated [M+Na]⁺ 548, found 548.

Step 2

The synthesis of compound 93 was referred to the second step of example 84. ¹H NMR (400 MHz, CD$_3$OD) δ 8.07-8.05 (m, 1H), 7.99-7.98 (m, 1H), 7.48-7.46 (m, 1H), 7.31-7.27 (m, 2H), 7.22-7.16 (m, 3H), 3.90 (s, 2H), 3.12-3.08 (m, 1H), 2.73-2.65 (m, 2H), 2.61-2.56 (m, 1H), 2.49-2.41 (m, 2H), 2.29-2.20 (m, 2H), 1.64-1.56 (m, 1H), 1.42-1.37 (m, 1H). MS-ESI calculated [M+H]⁺ 426, found 426.

Example 94

230

Synthetic Route:

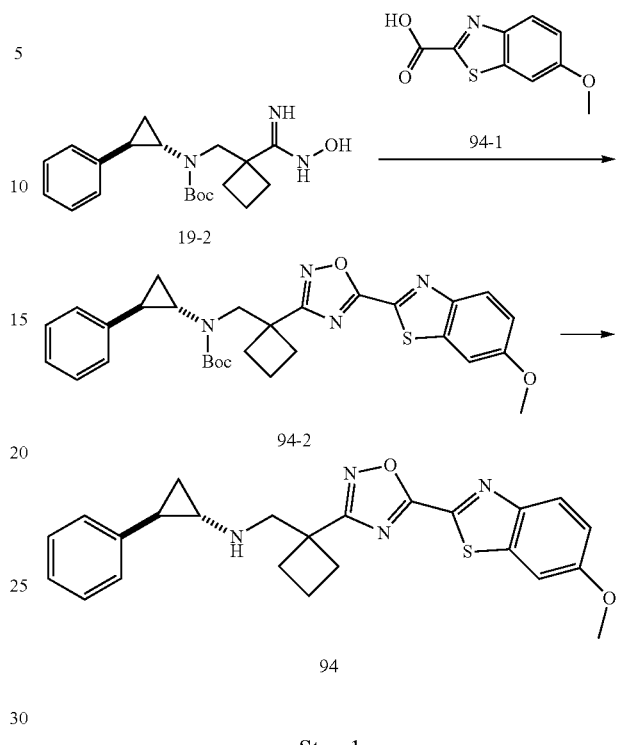

Step 1

The synthesis of compound 94-2 was referred to the first step of example 87. MS-ESI calculated [M+Na]⁺ 555, found 555.

Step 2

The synthesis of compound 94 was referred to the second step of example 84. ¹H NMR (400 MHz, CD$_3$OD) δ 8.08-8.06 (m, 1H), 7.68-7.67 (m, 1H), 7.30-7.26 (m, 3H), 7.21-7.17 (m, 3H), 3.94 (s, 3H), 3.93 (s, 2H), 3.13-3.09 (m, 1H), 2.73-2.68 (m, 2H), 2.60-2.55 (m, 1H), 2.51-2.44 (m, 2H), 2.30-2.22 (m, 2H), 1.64-1.58 (m, 1H), 1.44-1.38 (m, 1H). MS-ESI calculated [M+H]⁺ 433, found 433.

Example 95

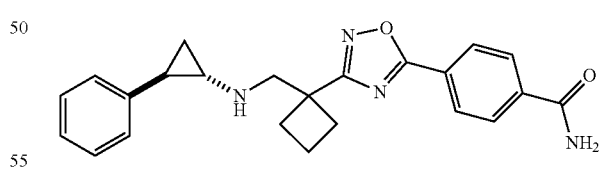

Synthetic Route:

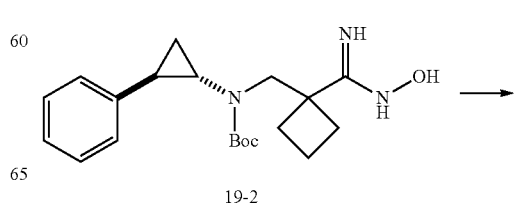

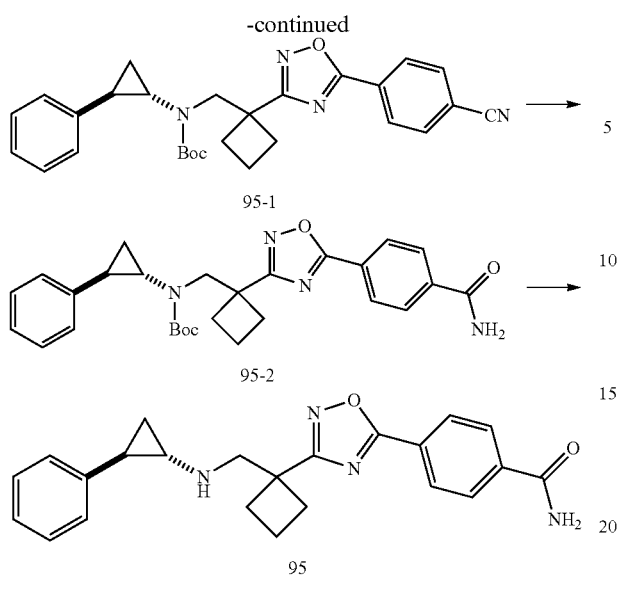

Step 1

The synthesis of compound 95-1 was referred to the first step of example 87. MS-ESI calculated [M+Na]$^+$ 493, found 493.

Step 2

Compound 95-1 (50.0 mg, 0.106 mmol) was dissolved in dimethyl sulfoxide (5 mL) under nitrogen, 30% hydrogen peroxide (120 mg, 1.06 mmol) and potassium carbonate (29.4 mg, 0.213 mmol) were added. The reaction solution was stirred at 25° C. for 2 h. Sodium thiosulfate (20 mL) was added to the reaction mixture, and the mixture was extracted with ethyl acetate (20 mL×1). The organic phase was washed with saturated brine (20 mL×1), dried over anhydrous sodium sulfate, followed by filtration and concentration under reduced pressure to give compound 95-2. MS-ESI calculated [M+Na]$^+$ 511, found 511.

Step 3

The synthesis of compound 95 was referred to the second step of example 84. $^1$H NMR (400 MHz, CD$_3$OD) δ 8.20-8.18 (m, 2H), 8.07-8.05 (m, 2H), 7.17-7.13 (m, 2H), 7.05-7.02 (m, 1H), 6.99-6.97 (m, 2H), 3.32-3.31 (m, 2H), 2.62-2.50 (m, 2H), 2.36-2.32 (m, 1H), 2.31-2.22 (m, 2H), 2.14-2.06 (m, 2H), 1.87-1.83 (m, 1H), 1.06-1.01 (m, 1H), 0.95-0.90 (m, 1H). MS-ESI calculated [M+H]$^+$ 389, found 389.

Example 96

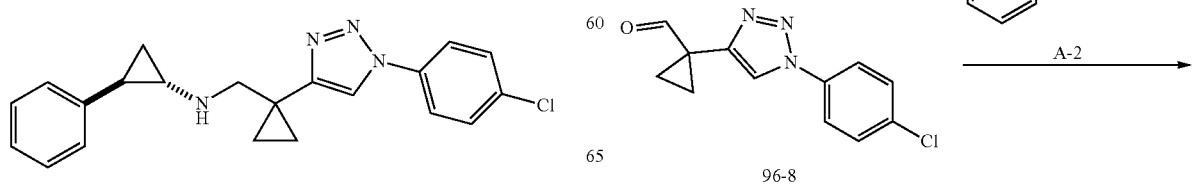

Synthetic Route:

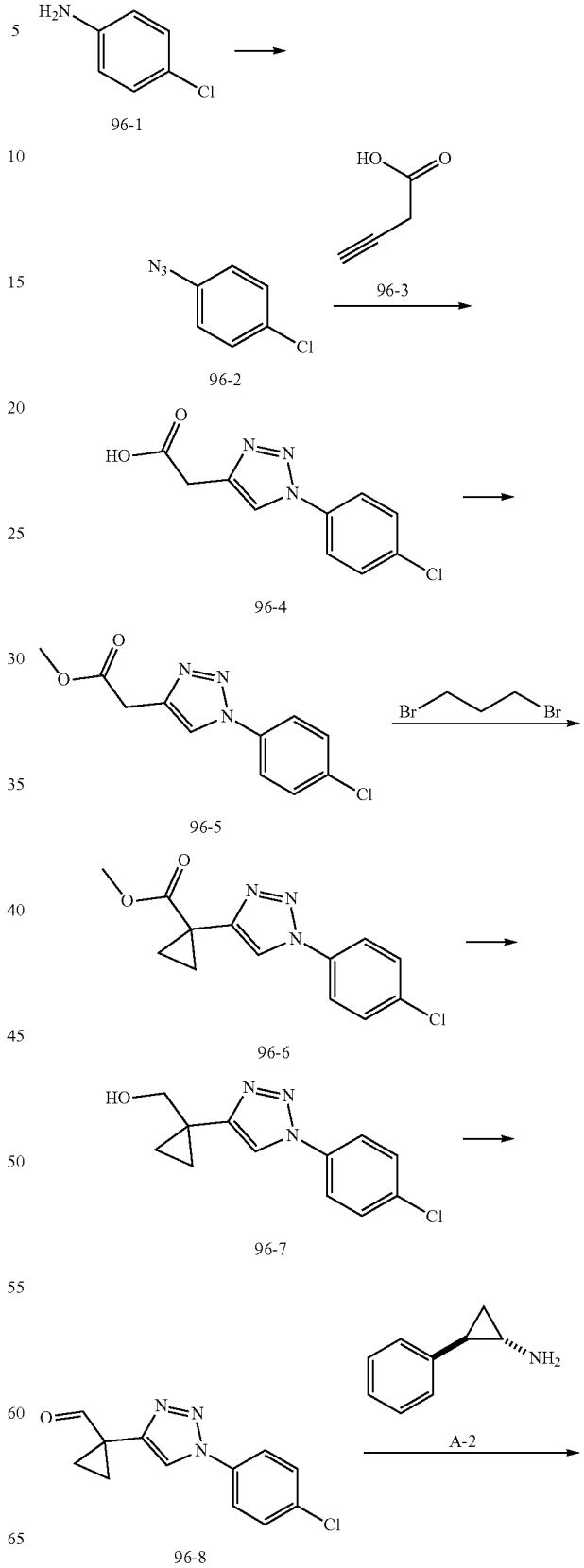

-continued

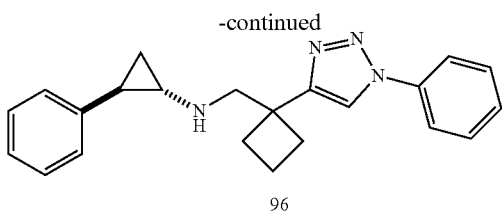

96

Step 1

Compound 96-1 (2.50 g, 19.6 mmol) was dissolved in acetonitrile (10 mL). Tert-butyl nitrite (3.03 g, 29.4 mmol) and azidotrimethylsilane (3.39 g, 29.4 mmol) were added at 0° C. The mixture was stirred at 0° C. for 2 h, N,N-dimethylformamide (30 mL) was added to the mixture and the mixture was concentrated under reduced pressure to give a solution of compound 96-2 in N,N-dimethylformamide (30 mL).

Step 2

Copper sulfate pentahydrate (1 M aqueous solution, 4.3 mL, 4.30 mmol), sodium ascorbate (1.94 g, 9.77 mmol) and compound 96-3 (2.30 g, 27.4 mmol) were added to a solution of compound 96-2 (3.00 g, 19.5 mmol) in N,N-dimethylformamide (30 mL) under nitrogen. The reaction solution was stirred at 25 t for 12 h, water (30 mL) was added to the mixture, and the mixture was extracted with ethyl acetate (40 mL×1), and the aqueous phase was adjusted to pH=3-5 with 1M hydrochloric acid aqueous solution, extracted with ethyl acetate (30 mL×4), dried over anhydrous sodium sulfate, followed by filtration and concentration under reduced pressure to give compound 96-4. MS-ESI calculated [M+H]$^+$ 238, found 238.

Step 3

The compound 96-4 (2.30 g, 4.26 mmol) was dissolved in methanol (20 mL), concentrated sulfuric acid (0.209 g, 2.13 mmol) was added at 0 V, and the reaction mixture was stirred at 80° C. for 4 hours, and then cooled to 25° C. Saturated sodium carbonate aqueous solution (50 mL) was added to the mixture. The mixture was extracted with ethyl acetate (50 mL×1). The organic phase was washed with saturated brine (50 mL), dried over anhydrous sodium sulfate, followed by filtration and concentration under reduced pressure. The residue was purified by silica gel column chromatography (2:1 petroleum ether/ethyl acetate, Rf=0.6) to give compound 96-5. MS-ESI calculated [M+H]$^+$ 252, found 252.

Step 4

Compound 96-5 (245 mg, 0.974 mmol) was dissolved in N,N-dimethylformamide (5 mL), cesium carbonate (1.27 g, 3.89 mmol) and 1,2-dibromoethane (365.8 mg, 1.95 mmol) were added at 25° C., and the reaction solution was stirred at 65° C. for 12 h, cooled to 25° C., and water (20 mL) was added to the reaction mixture. The mixture was extracted with ethyl acetate (20 mL×1). The organic phase was washed with saturated brine (20 mL), dried over anhydrous sodium sulfate, followed by filtration and concentration under reduced pressure. The residue was purified by silica gel column chromatography (2:1 petroleum ether/ethyl acetate, Rf=0.7) to give compound 96-6. MS-ESI calculated [M+H]$^+$ 278, found 278.

Step 5

Compound 96-6 (113 mg, 0.407 mmol) was dissolved in anhydrous methanol (5 mL), and lithium borohydride (35.5 mg, 1.63 mmol) was added at 25° C., and the reaction solution was stirred at 65° C. for 12 h, cooled to 25° C., and water (20 mL) was added to the reaction mixture. The mixture was extracted with ethyl acetate (20 mL×1). The organic phase was washed with saturated brine (20 mL), dried over anhydrous sodium sulfate, followed by filtration and concentration under reduced pressure. The residue was purified by thin layer chromatography (2:1 petroleum ether/ethyl acetate, Rf=0.2) to give compound 96-7. MS-ESI calculated [M+H]$^+$250, found 250.

Step 6

Compound 96-7 (8.00 mg, 0.032 mmol) was dissolved in anhydrous dichloromethane (2 mL), Dess-Martin reagent (27.2 mg, 0.064 mmol) was added at 25° C. The mixture was stirred at 25° C. for 1 h, saturated sodium carbonate aqueous solution (20 mL) was added. The mixture was extracted with dichloromethane (20 mL×1). The organic phase was washed with saturated brine (20 mL), dried over anhydrous sodium sulfate, followed by filtration and concentration under reduced pressure to give compound 96-8. MS-ESI calculated [M+H]$^+$ 248, found 248.

Step 7

The synthesis of compound 96 was referred to the fourth step of example 85. $^1$H NMR (400 MHz, CD$_3$OD) δ 8.44 (s, 1H), 7.86-7.83 (m, 2H), 7.63-7.60 (m, 2H), 7.32-7.28 (m, 2H), 7.24-7.19 (m, 1H), 7.18-7.16 (m, 2H), 3.73-3.65 (m, 2H), 3.14-3.10 (m, 1H), 2.57-2.52 (m, 1H), 1.59-1.55 (m, 1H), 1.43-1.38 (m, 1H), 1.31-1.27 (m, 4H). MS-ESI calculated [M+H]$^+$ 365, found 365.

Example 97

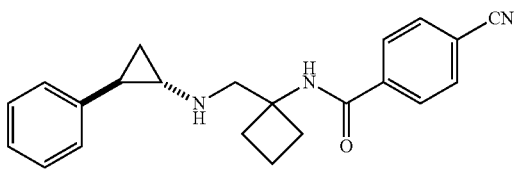

Synthetic Route:

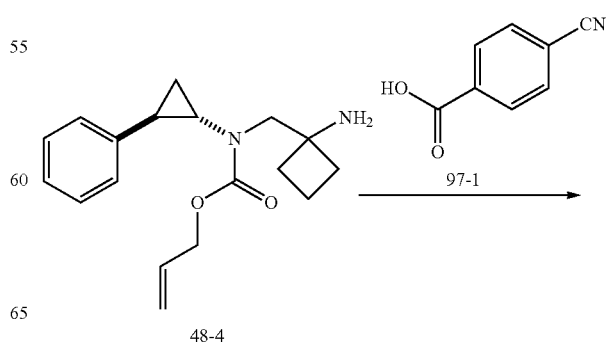

48-4

235

-continued

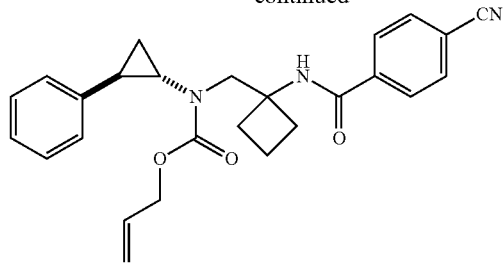

97-2

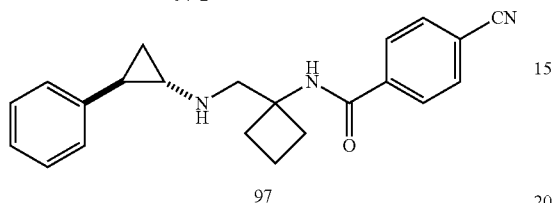

97

Step 1

Compound 97-1 (26.9 mg, 0.183 mmol) was dissolved in N,N-dimethylformamide (5 mL) under nitrogen, 1-hydroxybenzotriazole (27.0 mg, 0.200 mmol), 1-(3-dimethylaminopropyl)-3-acetaldehyde hydrochloride (38.3 mg, 0.200 mmol) and diisopropylethylamine (43.0 mg, 0.333 mmol) were added. The mixture was stirred at 25 t for 0.5 h, compound 48-4 (50.0 mg, 0.166 mmol) was added, and the reaction mixture was stirred at 25° C. for 11.5 h, water (20 mL) was added to the reaction mixture. The mixture was extracted with ethyl acetate (20 mL×1). The organic phase was washed with saturated brine (20 mL), dried over anhydrous sodium sulfate, followed by filtration and concentration under reduced pressure. The residue was purified by silica gel column chromatography (1:1 petroleum ether/ethyl acetate, Rf=0.4) to give compound 97-2. MS-ESI calculated [M+H]$^+$ 430, found 430.

Step 2

Compound 97-2 (14.0 mg, 0.033 mmol) was dissolved in anhydrous tetrahydrofuran (5 mL) under nitrogen, and diethylamine (23.8 mg, 0.222 mmol) and tetratriphenylphosphine palladium (3.80 mg, 0.003 mmol) were added. The reaction mixture was stirred at 70° C. for 12 h, water (20 mL) was added to the reaction mixture. The mixture was extracted with ethyl acetate (20 mL×1). The organic phase was washed with saturated brine (20 mL), dried over anhydrous sodium sulfate, followed by filtration and concentration under reduced pressure. The residue was purified by preparative high-performance liquid chromatography (hydrochloric acid) to give compound 97. $^1$H NMR (400 MHz, CD$_3$OD) δ 8.06-8.04 (m, 2H), 7.89-7.87 (m, 2H), 7.34-7.30 (m, 2H), 7.26-7.22 (m, 1H), 7.20-7.17 (m, 2H), 3.79 (s, 2H), 3.10-3.06 (m, 1H), 2.56-2.52 (m, 1H), 2.47-2.42 (m, 4H), 2.10-2.04 (m, 2H), 1.59-1.53 (m, 1H), 1.41-1.38 (m, 1H). MS-ESI calculated [M+H]$^+$ 346, found 346.

236

Example 98

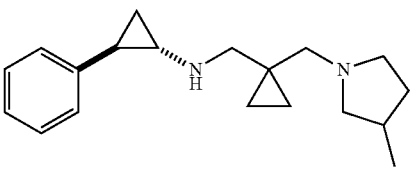

Synthetic Route:

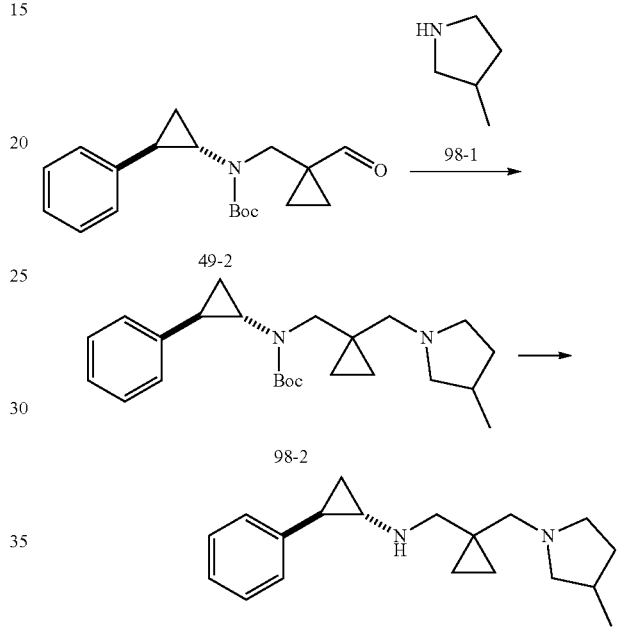

Step 1

The compound 98-1 (100 mg, 0.822 mmol) was dissolved in anhydrous dichloromethane (10 mL). Triethylamine (83.4 mg, 0.824 mmol) was added, and the mixture was stirred for 0.5 hour. Then the compound 49-2 (100 mg, 0.317 mmol) and acetic acid (57.1 mg, 0.951 mmol) were added to the reaction mixture. After stirring at 25° C. for 0.5 h. sodium triacetoxyborohydride (202 mg, 0.951 mmol) was added. The mixture was stirred at 25° C. for 11 h. The mixture was diluted with dichloromethane (20 mL), washed successively with saturated sodium carbonate aqueous solution (20 mL×1), saturated brine (20 mL×1). The organic phase was dried over anhydrous sodium sulfate, followed by filtration and concentration under reduced pressure. The residue was purified by thin layer chromatography (3:1 petroleum ether/ethyl acetate, Rf=0.2) to give compound 98-2. MS-ESI calculated [M+H]$^+$ 385, found 385.

Step 2

The synthesis of compound 98 was referred to the second step of example 84. $^1$H NMR (400 MHz, CD$_3$OD) δ 7.34-7.30 (m, 2H), 7.25-7.21 (m, 3H), 3.95-3.77 (m, 1.5H), 3.58-3.56 (m, 0.5H), 3.45-3.38 (m, 3H), 3.33-3.16 (m, 2.5H), 3.14-3.10 (m, 1H), 2.78-2.75 (m, 1.5H), 2.70-2.50 (m, 1H), 2.35-2.25 (m, 1H), 1.76-1.72 (m, 2H), 1.38-1.36 (m, 1H), 1.19-1.18 (m, 3H), 1.00-0.96 (m, 4H). MS-ESI calculated [M+H]$^+$ 285, found 285.

Example 99

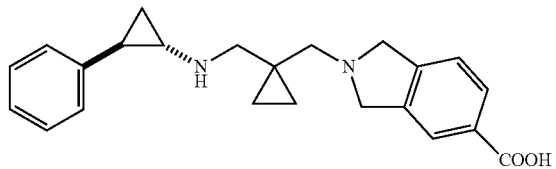

Synthetic Route:

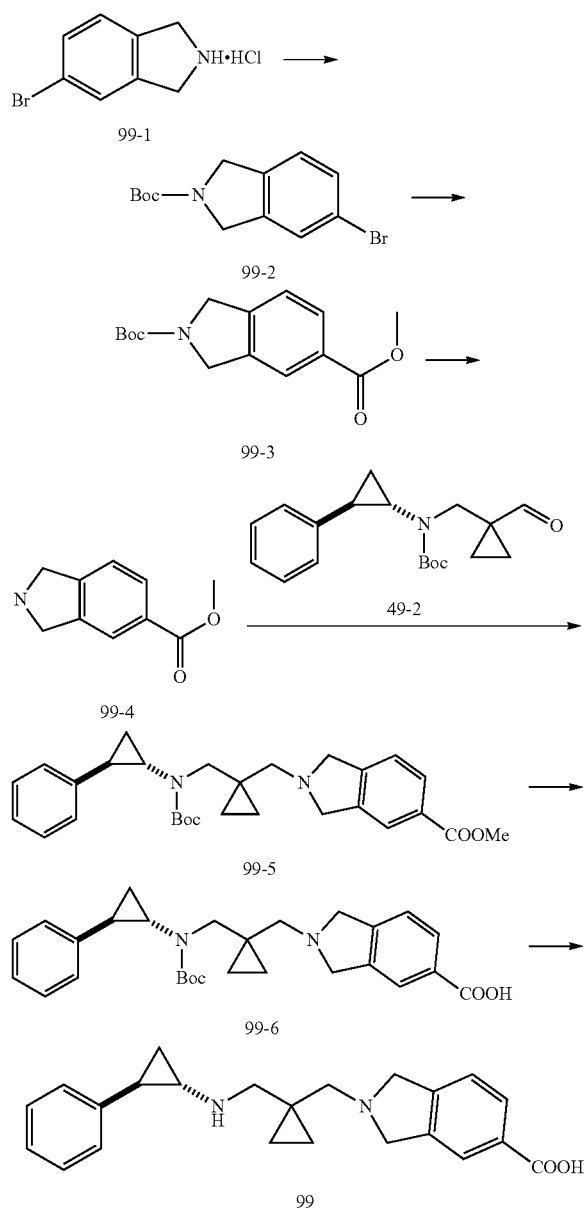

Step 1

Compound 99-1 (0.930 g, 3.97 mmol) was dissolved in N,N-dimethylformamide (30 mL) under nitrogen, di-tert-butyl bicarbonate (1.73 g, 7.93 mmol), p-dimethylamino-pyridine (48.5 mg, 0.397 mmol) and diisopropylethylamine (0.602 g, 5.95 mmol) were added. The mixture was stirred at 25° C. for 12 h. Water (20 mL) was added to the reaction mixture. The mixture was extracted with ethyl acetate (20 mL×1). The organic phase was washed with saturated brine (20 mL×1), dried over anhydrous sodium sulfate, followed by filtration and concentration under reduced pressure. The residue was purified by silica gel column chromatography (4:1 petroleum ether/ethyl acetate, Rf=0.6) to give compound 99-2. $^1$H NMR (400 MHz, CDCl$_3$) δ 7.42-7.36 (m, 2H), 7.16-7.08 (m, 1H), 4.67-4.59 (m, 4H), 1.51 (s, 9H).

Step 2

Compound 99-2 (0.450 g, 1.51 mmol) was dissolved in dimethyl sulfoxide (4.5 mL) and methanol (4.5 mL) under nitrogen, 1, 3-bis (diphenylphosphino) propane (125 mg, 0.302 mmol), palladium acetate (67.8 mg, 0.302 mmol) and triethylamine (1.53 g, 15.09 mmol) were added. The reaction solution was stirred at 80° C. for 12 h in a 15 PSI carbon monoxide atmosphere. The reaction solution was concentrated under reduced pressure, water (20 mL) was added to the reaction mixture. The mixture was extracted with ethyl acetate (20 mL×2). The organic phase was washed with saturated brine (20 mL×3), dried over anhydrous sodium sulfate, followed by filtration and concentration under reduced pressure. The residue was isolated and purified by silica gel column chromatography (4:1 petroleum ether/ethyl acetate, Rf=0.5) to give compound 99-3. MS-ESI calculated [M+H]$^+$ 278, found 278.

Step 3

Compound 99-3 (410 mg, 1.48 mmol) was dissolved in ethyl acetate (5 mL), hydrochloric acid (4M in ethyl acetate, 5 mL, 20 mmol) was added at 25° C., and the mixture was stirred at 25° C. for 1 h. The reaction solution was concentrated under reduced pressure to give compound 994. MS-ESI calculated [M+H]$^+$ 178, found 178.

Step 4

The synthesis of compound 99-5 was referred to the first step of example 98. MS-ESI calculated [M+H]$^+$ 477, found 477.

Step 5

Compound 99-5 (85.0 mg, 0.178 mmol) was dissolved in anhydrous tetrahydrofuran (4 mL) and water (1 mL), sodium hydroxide (100 mg, 2.50 mmol) was added and the reaction mixture was stirred at 40° C. for 46 h and cooled to 25° C. Water (20 mL) was added to the reaction mixture. The mixture was extracted with ethyl acetate (20 mL×1). The organic phase was washed with saturated brine (20 mL), dried over anhydrous sodium sulfate, followed by filtration and concentration under reduced pressure to give compound 99-6. MS-ESI calculated [M+H]$^+$ 463, found 463.

Step 6

The synthesis of compound 99 was referred to the second step of example 84. $^1$H NMR (400 MHz, CD$_3$OD) δ

8.10-8.08 (m, 2H), 7.56-7.54 (m, 1H), 7.33-7.29 (m, 2H), 7.25-7.20 (m, 3H), 5.25-5.05 (m, 2H), 4.86-4.60 (m, 2H), 3.77-3.74 (m, 2H), 3.56-3.53 (m, 1H), 3.45-3.42 (m, 1H), 3.13-3.09 (m, 1H), 2.84-2.79 (m, 1H), 1.81-1.75 (m, 1H), 1.39-1.34 (m, 1H), 1.09-1.05 (m, 4H). MS-ESI calculated [M+H]+ 363, found 363.

Example 100

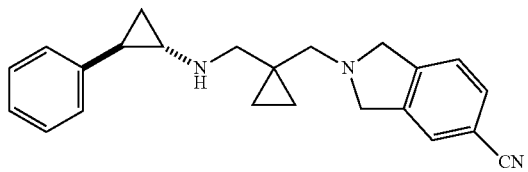

Synthetic Route:

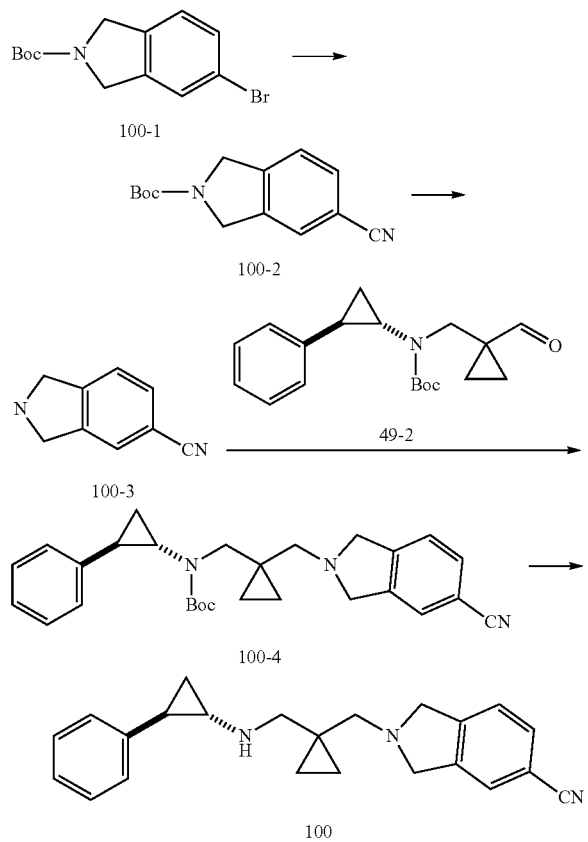

Step 1

Compound 100-1 (100 mg, 0.335 mmol) was dissolved in acetonitrile (10 mL) under nitrogen, and zinc cyanide (78.8 mg, 0.671 mmol) and tetratriphenylphosphine palladium (77.5 mg, 0.067 mmol) were added. The reaction solution was stirred at 80° C. for 12 h. The saturated aqueous solution of sodium carbonate (20 mL) was added to the mixture. The mixture was extracted with ethyl acetate (20 mL×1), the organic phase was washed with saturated brine (20 mL×1), dried over anhydrous sodium sulfate, followed by filtration and concentration under reduced pressure. The residue was isolated and purified by thin layer chromatography (3:1 petroleum ether/ethyl acetate, Rf=0.3) to give compound 100-2. ¹H NMR (400 MHz, CDCl₃) δ 7.51-7.45 (m, 2H), 7.33-7.26 (m, 1H), 4.67-4.62 (m, 4H), 1.45 (s, 9H).

Step 2

The compound 100-2 (52.0 mg, 0.213 mmol) was dissolved in anhydrous dichloromethane (4 mL). Then trifluoroacetic acid (1.54 g, 13.5 mmol) was added and the mixture was stirred at 25° C. for 2 hours. The reaction solution was concentrated under reduced pressure to give compound 100-3. ¹H NMR (400 MHz, CDCl₃) δ 7.83 (s, 1H), 7.79-7.77 (m, 1H), 7.64-7.62 (m, 1H), 4.74-4.72 (m, 4H).

Step 3

The synthesis of compound 100-4 was referred to the first step of example 98. MS-ESI calculated [M+H]+ 444, found 444.

Step 4

The synthesis of compound 100 was referred to the second step of example 84. ¹H NMR (400 MHz, CD₃OD) δ 7.84-7.81 (m, 2H), 7.66-7.64 (m, 1H), 7.35-7.30 (m, 2H), 7.26-7.20 (m, 3H), 5.25-4.96 (m, 2H), 4.86-4.65 (m, 2H), 3.74-3.66 (m, 2H), 3.51-3.41 (m, 2H), 3.14-3.08 (m, 1H), 2.71-2.66 (m, 1H), 1.71-1.66 (m, 1H), 1.43-1.38 (m, 1H), 1.13-1.05 (m, 4H). MS-ESI calculated [M+H]+ 344, found 344.

Example 101

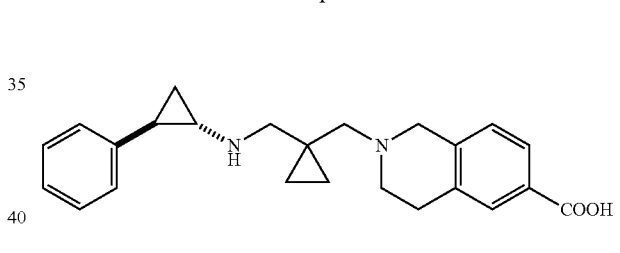

Synthetic Route:

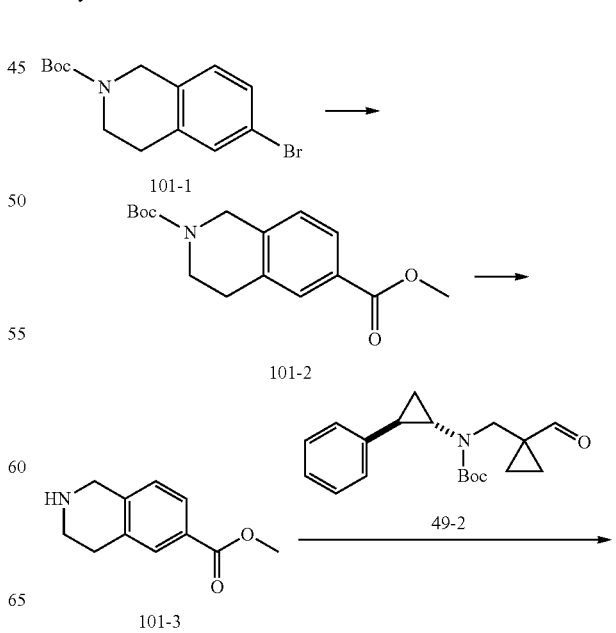

241
-continued

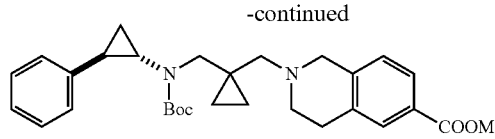
101-4

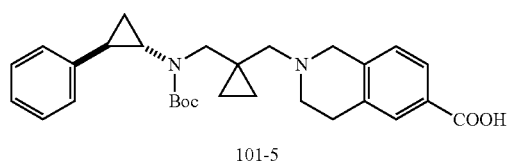
101-5

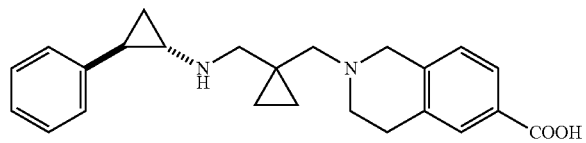
101

Step 1

The synthesis of compound 101-2 was referred to the second step of example 99. MS-ESI calculated [M+H]$^+$ 292, found 292.

Step 2

The synthesis of compound 101-3 was referred to the third step of example 99. MS-ESI calculated [M+H]$^+$ 192, found 192.

Step 3

The synthesis of compound 101-4 was referred to the first step of example 98. MS-ESI calculated [M+H]$^+$ 491, found 491.

Step 4

Compound 1014 (67.0 mg, 0.137 mmol) was dissolved in anhydrous tetrahydrofuran (4 mL) and water (1 mL), sodium hydroxide (100 mg, 2.50 mmol) was added and the reaction mixture was stirred at 25° C. for 168 h. Water (20 mL) was added to the reaction mixture. The mixture was extracted with ethyl acetate (20 mL×1). The organic phase was washed with saturated brine (20 mL), dried over anhydrous sodium sulfate, followed by filtration and concentration to give compound 101-5. MS-ESI calculated [M+H]$^+$ 477, found 477.

Step 5

The synthesis of compound 101 was referred to the second step of example 84. $^1$H NMR (400 MHz, CD$_3$OD) δ 7.95-7.93 (m, 2H), 7.40-7.38 (m, 1H), 7.3-7.29 (m, 2H), 7.25-7.19 (m, 3H), 4.75-4.40 (m, 2H), 4.00-3.50 (m, 6H), 3.12-3.10 (m, 3H), 2.90-2.70 (m, 1H), 1.84-1.70 (m, 1H), 1.38-1.33 (m, 1H), 1.12-0.90 (m, 4H). MS-ESI calculated [M+H]$^+$ 377, found 377.

242

Example 102

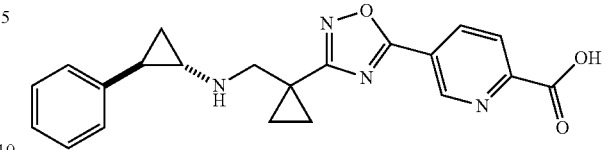
102

Synthetic Route:

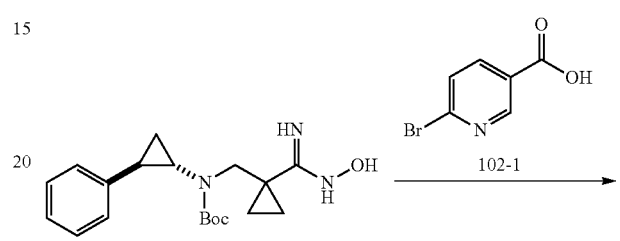

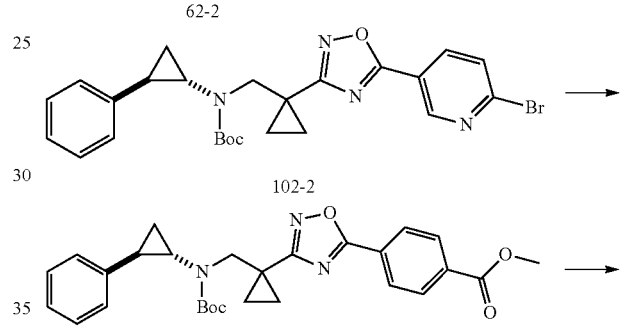

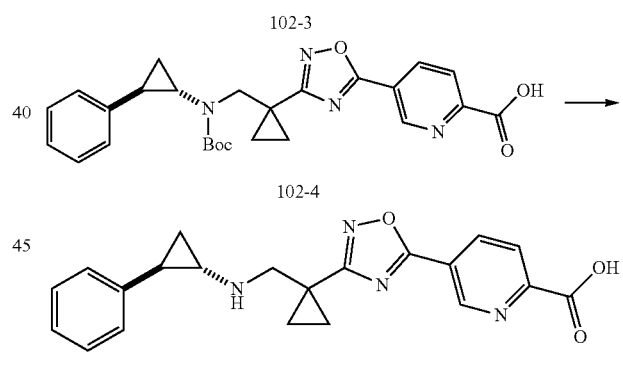
102

Step 1

The synthesis of compound 102-2 was referred to the third step of example 87. MS-ESI calculated [M+H]$^+$ 512, found 512.

Step 2

The synthesis of compound 102-3 was referred to the second step of example 99. MS-ESI calculated [M+H]$^+$ 491, found 491.

Step 3

The compound 102-3 (67.0 mg, 0.137 mmol) was dissolved in anhydrous tetrahydrofuran (4 mL) and water (1 mL), and lithium hydroxide monohydrate (57.3 mg, 1.37 mmol) was added, and the reaction mixture was stirred at 25° C. for 48 h. Water (20 mL) was added to the reaction mixture. The mixture was extracted with ethyl acetate (20 mL×1). The organic phase was washed with saturated brine (20 mL), dried over anhydrous sodium sulfate, followed by filtration and concentration to give compound 102-4. MS-ESI calculated [M+Na]⁺ 499, found 499.

Step 4

The synthesis of compound 102 was referred to the second step of example 84. ¹H NMR (400 MHz, CD₃OD) δ 9.35-9.33 (m, 1H), 8.77-8.68 (m, 1H), 8.44-8.37 (m, 1H), 7.28-7.24 (m, 2H), 7.17-7.14 (m, 3H), 3.89-3.85 (m, 1H), 3.76-3.73 (m, 1H), 3.17-3.16 (m, 1H), 2.61-2.59 (m, 1H), 1.64-1.59 (m, 2H), 1.50-1.38 (m, 4H). MS-ESI calculated [M+H]⁺ 377, found 377.

Example 103

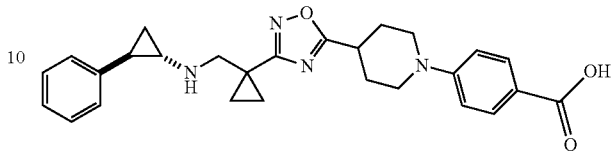

Synthetic Route:

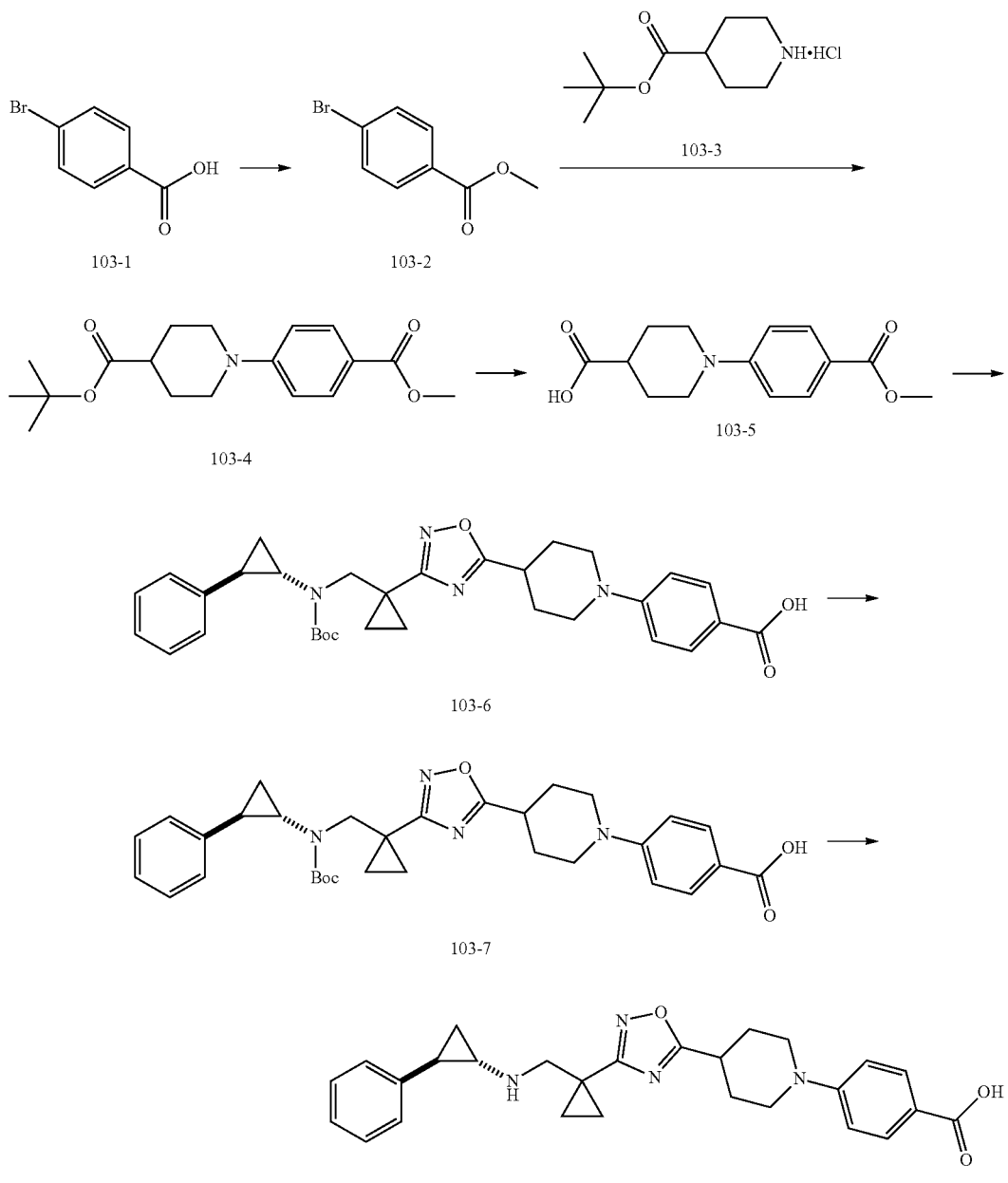

Step 1

Compound 103-1 (400 mg, 1.99 mmol) was dissolved in methanol (10 mL) under nitrogen, concentrated sulfuric acid (97.6 mg, 0.995 mmol) was added at 0° C., and the reaction mixture was stirred at 80° C. for 2 h. The mixture was cooled to 25° C. and concentrated under reduced pressure. Saturated sodium carbonate aqueous solution (20 mL) was added. The mixture was extracted with ethyl acetate (20 mL×1). The organic phase was washed with saturated brine (20 mL×1), dried over anhydrous sodium sulfate, followed by filtration and concentration to give compound 103-2. $^1$H NMR (400 MHz, CDCl$_3$) δ 7.94-7.91 (m, 2H), 7.62-7.59 (m, 2H), 3.94 (s, 3H).

Step 2

Compound 103-3 (200 mg, 0.902 mmol) was dissolved in N,N-dimethylformamide (10 mL) under nitrogen. Triethylamine (95.8 mg, 0.947 mmol) was added, and the reaction mixture was stirred at 25° C. for 0.5 h. Compound 103-2 (213 mg, 0.992 mmol), cesium carbonate (588 mg, 1.80 mmol), tris (dibenzylideneacetone) dipalladium (41.3 mg, 0.045 mmol) and 4,5-bis(diphenyl phosphorus)-9,9-dimethyloxaxan (52.2 mg, 0.090 mmol) were added. The reaction mixture was stirred at 100° C. for 11.5 h. Water (20 mL) was added to the mixture. The mixture was extracted with ethyl acetate (20 mL×1). The organic phase was washed with saturated brine (20 mL×1), dried over anhydrous sodium sulfate, followed by filtration and concentration under reduced pressure. The residue was isolated and purified by silica gel column chromatography (3:1 petroleum ether/ethyl acetate, Rf=0.5) to give compound 103-4. MS-ESI calculated [M+H]$^+$ 320, found 320.

Step 3

The synthesis of compound 103-5 was referred to the third step of example 99. MS-ESI calculated [M+H]$^+$ 264, found 264.

Step 4

The synthesis of compound 103-6 was referred to the third step of example 87. MS-ESI calculated [M+H]$^+$ 573, found 573.

Step 5

The compound 103-6 (56.0 mg, 0.098 mmol) was dissolved in anhydrous tetrahydrofuran (4 mL) and water (1 mL), sodium hydroxide (100 mg, 2.5 mmol) was added, and the mixture was stirred at 50° C. for 72 h. The temperature was cooled to 25° C., water (20 mL) was added to the solution, and the aqueous phase was adjusted to pH=5 with 1 M hydrochloric acid aqueous solution. The mixture was extracted with ethyl acetate (20 mL×1). The organic phase was washed with saturated brine (20 mL), dried over anhydrous sodium sulfate, followed by filtration and concentration under reduced pressure to give compound 103-7. MS-ESI calculated [M+H]$^+$ 559, found 559.

Step 6

The synthesis of compound 103 was referred to the second step of example 84. $^1$H NMR (400 MHz, CD$_3$OD) δ 8.13-8.11 (m, 2H), 7.54-7.52 (m, 2H), 7.35-7.31 (m, 2H), 7.27-7.24 (m, 1H), 7.19-7.17 (m, 2H), 3.95-3.91 (m, 2H), 3.75-3.67 (m, 2H), 3.60-3.55 (m, 2H), 3.49-3.42 (m, 1H), 3.13-3.09 (m, 1H), 2.59-2.54 (m, 1H), 2.42-2.39 (m, 2H), 2.30-2.21 (m, 2H), 1.62-1.57 (m, 1H), 1.50-1.49 (m, 2H), 1.45-1.40 (m, 1H), 1.38-1.35 (m, 2H). MS-ESI calculated [M+H]$^+$ 459, found 459.

Example 104

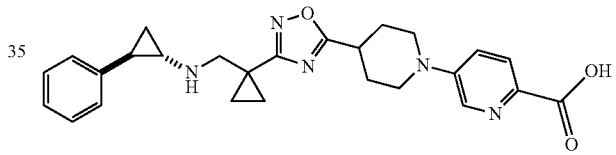

Synthetic Route:

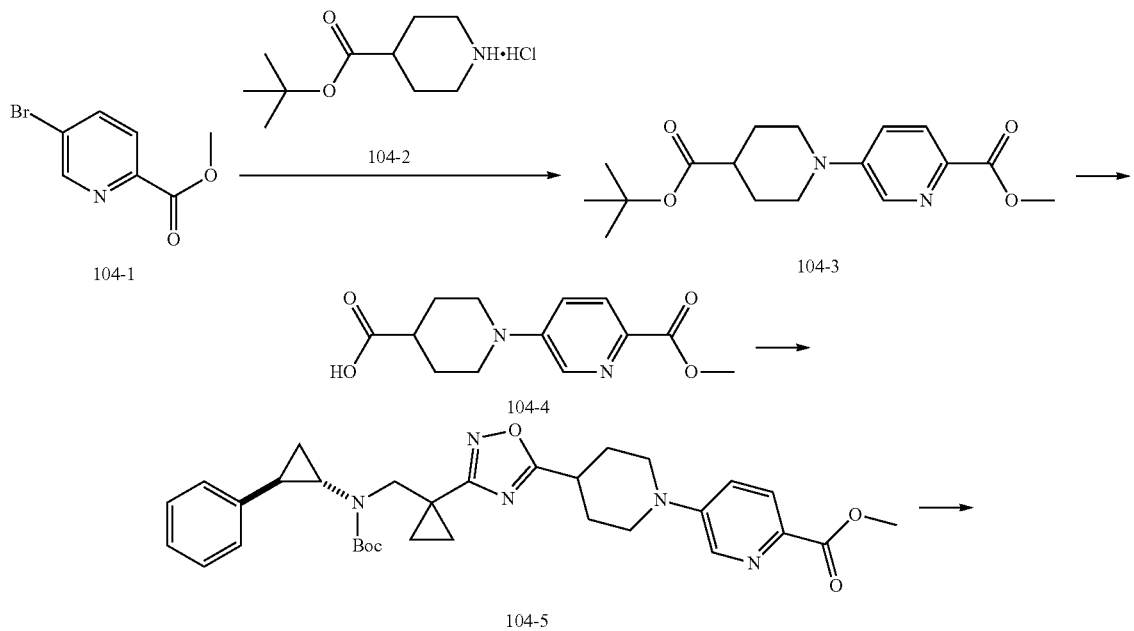

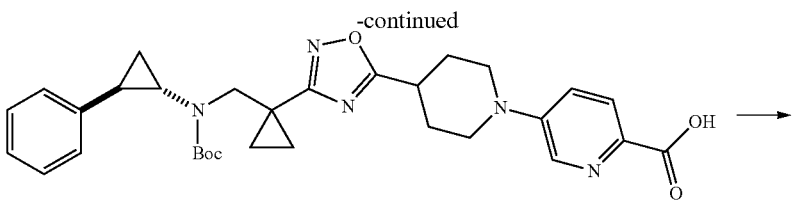

104-6

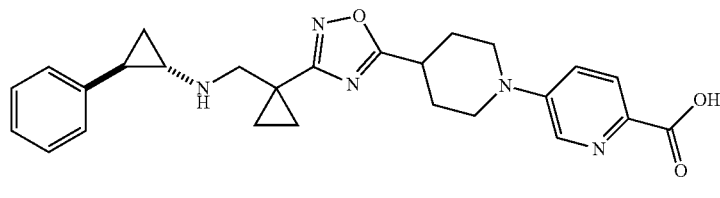

104

Step 1

The synthesis of compound 104-3 was referred to the second step of example 103. MS-ESI calculated [M+H]+ 321, found 321.

Step 2

The synthesis of compound 104-4 was referred to the third step of example 99. MS-ESI calculated [M+H]+ 265, found 265.

Step 3

The synthesis of compound 104-5 was referred to the third step of example 87. MS-ESI calculated [M+H]+ 574, found 574.

Step 4

The compound 104-5 (35.0 mg, 0.061 mmol) was dissolved in anhydrous tetrahydrofuran (4 mL) and water (1 mL), sodium hydroxide (62.4 mg, 1.56 mmol) was added, and the mixture was stirred at 50° C. for 12 h. The mixture was cooled to 25° C., water (20 mL) was added to the solution, and the aqueous phase was adjusted to pH=5 with 1 M hydrochloric acid aqueous solution. The mixture was extracted with ethyl acetate (20 mL×1). The organic phase was washed with saturated brine (20 mL), dried over anhydrous sodium sulfate, followed by filtration and concentration under reduced pressure to give compound 104-6. MS-ESI calculated [M+H]+ 560, found 560.

Step 5

The synthesis of compound 104 was referred to the second step of example 84. $^1$H NMR (400 MHz, CD$_3$OD) δ 8.39-8.38 (m, 1H), 8.30-8.28 (m, 1H), 8.07-8.04 (m, 1H), 7.35-7.31 (m, 2H), 7.27-7.23 (m, 1H), 7.18-7.16 (m, 2H), 4.18-4.15 (m, 2H), 3.74-3.65 (m, 2H), 3.44-3.38 (m, 3H), 3.12-3.08 (m, 1H), 2.58-2.53 (m, 1H), 2.29-2.27 (m, 2H), 2.03-1.94 (m, 2H), 1.60-1.57 (m, 1H), 1.47-1.45 (m, 2H), 1.43-1.39 (m, 1H), 1.36-1.35 (m, 2H). MS-ESI calculated [M+H]+ 460, found 460.

Example 105

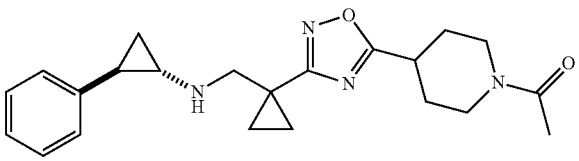

Synthetic Route:

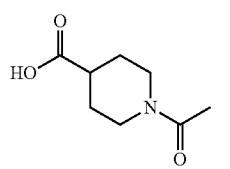

105-1

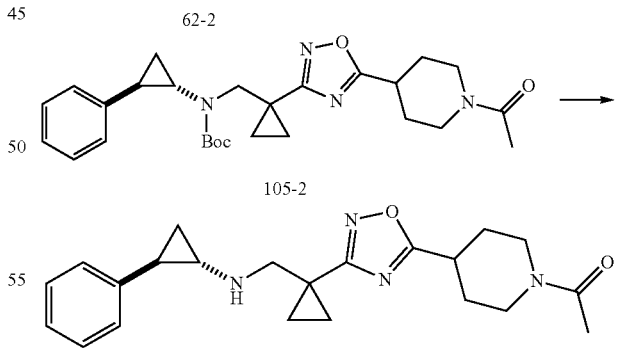

105

Step 1

The synthesis of compound 105-2 was referred to the third step of example 87. MS-ESI calculated [M+Na]+ 503, found 503.

Step 2

The synthesis of compound 105 was referred to the second step of example 84. $^1$H NMR (400 MHz, CD$_3$OD) δ 7.35-7.31 (m, 2H), 7.27-7.23 (m, 1H), 7.19-7.17 (m, 2H), 4.46-4.42 (m, 1H), 4.02-3.99 (m, 1H), 3.74-3.65 (m, 2H), 3.42-3.35 (m, 2H), 3.12-3.02 (m, 2H), 2.60-2.55 (m, 1H), 2.23-2.19 (m, 3H), 2.18-2.12 (m, 2H), 1.90-1.85 (m, 1H), 1.79-1.71 (m, 1H), 1.63-1.57 (m, 1H), 1.47-1.44 (m, 2H), 1.42-1.40 (m, 1H), 1.38-1.35 (m, 2H). MS-ESI calculated [M+H]$^+$ 381, found 381.

Example 106

Synthetic Route:

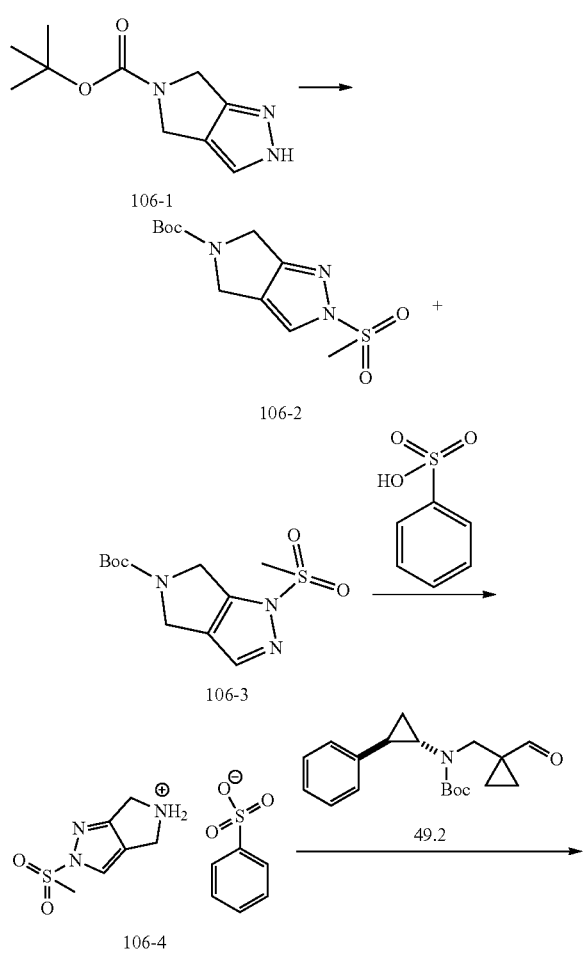

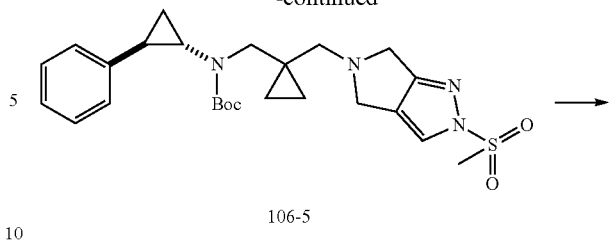

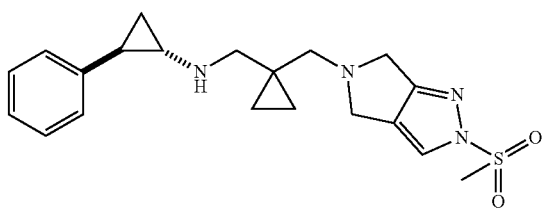

Step 1

Compound 106-1 (320 mg, 1.53 mmol) was dissolved in anhydrous tetrahydrofuran (5 mL). Triethylamine (279 mg, 2.75 mmol) was added and methanesulfonyl chloride (228 mg, 1.99 mmol) was added at 0° C. The reaction solution was stirred at 25° C. for 1 h. Water (20 mL) was added to the mixture. The mixture was extracted with ethyl acetate (20 mL×1). The organic phase was washed with saturated brine (20 mL), dried over anhydrous sodium sulfate, followed by filtration and concentration under reduced pressure to give a mixture of compound 106-2 and compound 106-3. $^1$H NMR (400 MHz, CDCl$_3$) δ 7.82-7.79 (m, 1H), 4.60-4.57 (m, 2H), 4.36-4.33 (m, 2H), 3.55-3.54 (m, 3H), 1.46-1.45 (m, 9H).

Step 2

The mixture of compound 106-2 and compound 106-3 (340 mg, 1.18 mmol) was dissolved in isopropyl acetate (5 mL), benzenesulfonic acid (205.9 mg, 1.30 mmol) dissolved in isopropyl acetate (5 mL) was added dropwise. The mixture was stirred at 30° C. for 1 h and stirred at 15° C. for 12 h. The reaction mixture was filtered. The filter cake was washed once with isopropyl acetate (5 mL) to give compound 106-4. $^1$H NMR (400 MHz, CDCl$_3$) δ 10.03-9.91 (m, 2H), 7.83 (s, 1H), 7.63-7.61 (m, 5H), 4.59-4.53 (m, 2H), 4.33-4.25 (m, 2H), 3.62 (s, 3H).

Step 3

The synthesis of compound 106-5 was referred to the first step of example 98. MS-ESI calculated [M+H]$^+$ 487, found 487.

Step 4

Compound 106-5 (50.0 mg, 0.103 mmol) was dissolved in anhydrous dichloromethane (10 mL) under nitrogen, and trimethylsilyl trifluoromethanesulfonate (45.7 mg, 0.206 mmol) was added dropwise at 0° C. The reaction mixture was stirred at 0° C. for 0.5 h. The reaction was quenched with the saturated sodium bicarbonate (20 mL) at 25° C., extracted with dichloromethane (10 mL×2), dried over anhydrous sodium sulfate, followed by filtration and concentration under reduced pressure. The residue was isolated and purified by preparative high-performance liquid chromatography (neutral) to give compound 106. $^1$H NMR (400 MHz, CD$_3$OD) δ 7.60 (s, 1H), 7.22-7.19 (m, 2H), 7.12-7.08 (m, 1H), 7.04-7.02 (m, 2H), 4.08-4.02 (m, 2H), 3.84-3.78 (m, 2H), 3.37 (s, 3H), 2.81-2.67 (m, 4H), 2.44-2.40 (m, 1H), 1.93-1.86 (m, 1H), 1.10-1.05 (m, 1H), 1.01-0.96 (m, 1H), 0.51-0.37 (m, 4H). MS-ESI calculated [M+H]$^+$ 387, found 387.

Example 107

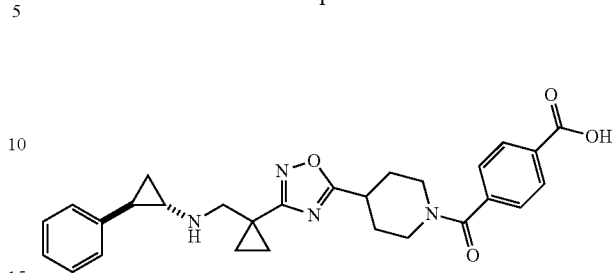

Synthetic Route:

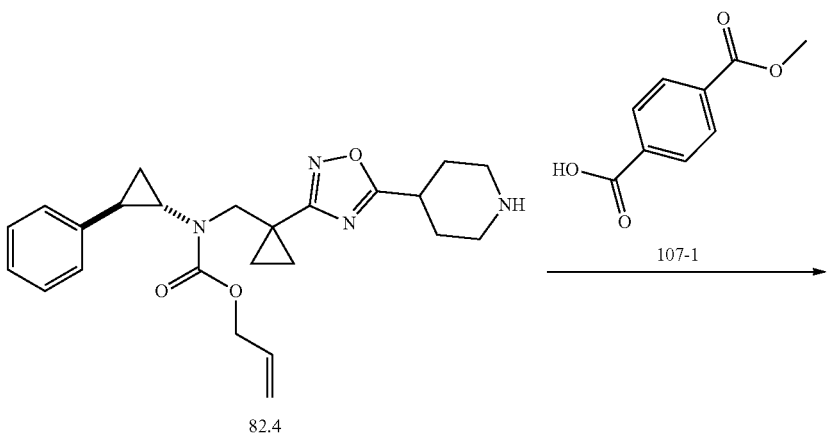

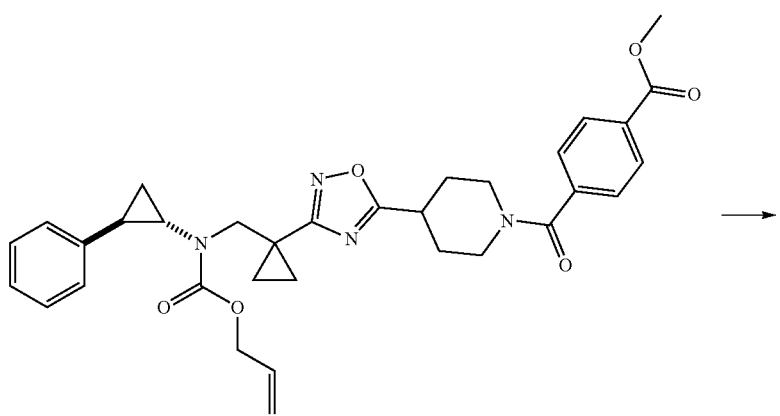

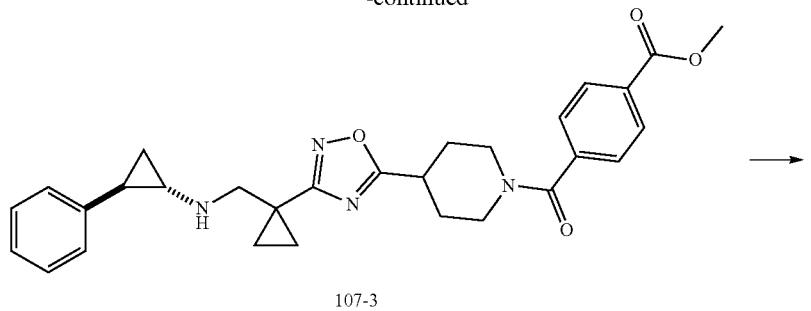

107-3

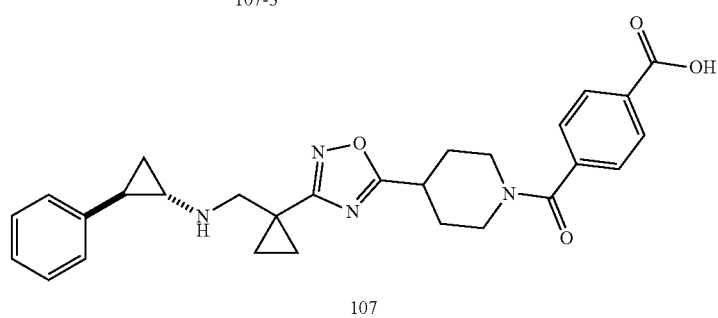

107

Step 1

Compound 82-4 (60.0 mg, 0.142 mmol) was dissolved in anhydrous dichloromethane (10 mL) under nitrogen, 2-(7-Azobenzotriazole)-N,N,N,N-tetramethylurea hexafluorophosphate (70.2 mg, 0.185 mmol), diisopropylethylamine (36.7 mg, 0.284 mmol) and compound 107-1 (38.4 mg, 0.213 mmol) were added, and the reaction mixture was stirred at 25° C. for 1 h. Water (20 mL) was added to the mixture. The mixture was extracted with dichloromethane (20 mL×1). The organic phase was washed with saturated brine (20 mL×1), dried over anhydrous sodium sulfate, followed by filtration and concentration under reduced pressure. The residue was isolated and purified by thin layer chromatography (1:1 petroleum ether/ethyl acetate, Rf=0.4) to give compound 107-2. MS-ESI calculated [M+H]$^+$ 585, found 585.

Step 2

Compound 107-2 (55.0 mg, 0.094 mmol) was dissolved in anhydrous tetrahydrofuran (5 mL) under nitrogen, diethyl amine (68.8 mg, 0.941 mmol) and tetratriphenylphosphine palladium (10.9 mg, mmol) were added. The reaction mixture was stirred at 70° C. for 12 h. Water (20 mL) was added to the solution, and the aqueous phase was adjusted to pH=5 with 1 M hydrochloric acid aqueous solution. The mixture was extracted with ethyl acetate (20 mL×1). The aqueous phase was adjusted to pH=8 with saturated sodium bicarbonate. Then the mixture was extracted with ethyl acetate (20 mL×2). The organic phase was dried over anhydrous sodium sulfate, followed by filtration and concentration under reduced pressure to give compound 107-3. MS-ESI calculated [M+H]$^+$ 501, found 501.

Step 3

The compound 107-3 (40.0 mg, 0.080 mmol) was dissolved in anhydrous tetrahydrofuran (10 mL) and water (4 mL), sodium hydroxide (160 mg, 4.0 mmol) was added, and the reaction mixture was stirred at 50° C. for 12 h. The mixture was concentrated under reduced pressure and purified by preparative high-performance liquid chromatography (hydrochloric acid) to give compound 107. $^1$H NMR (400 MHz, CD$_3$OD) δ 8.15-8.13 (m, 2H), 7.55-7.53 (m, 2H), 7.35-7.31 (m, 2H), 7.27-7.24 (m, 1H), 7.19-7.17 (m, 2H), 4.60-4.52 (m, 1H), 3.74-3.65 (m, 3H), 3.39-3.36 (m, 2H), 3.21-3.19 (m, 1H), 3.12-3.08 (m, 1H), 2.56-2.51 (m, 1H), 2.28-2.16 (m, 1H), 2.10-2.00 (m, 1H), 1.90-1.80 (m, 2H), 1.59-1.54 (m, 1H), 1.49-1.45 (m, 2H), 1.43-1.40 (m, 1H), 1.35-1.34 (m, 2H). MS-ESI calculated [M+H]$^+$ 487, found 487.

Example 108

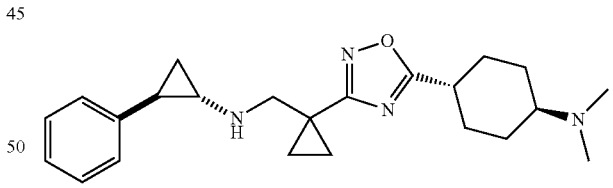

Synthetic Route:

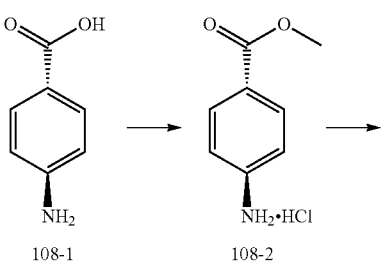

108-1     108-2

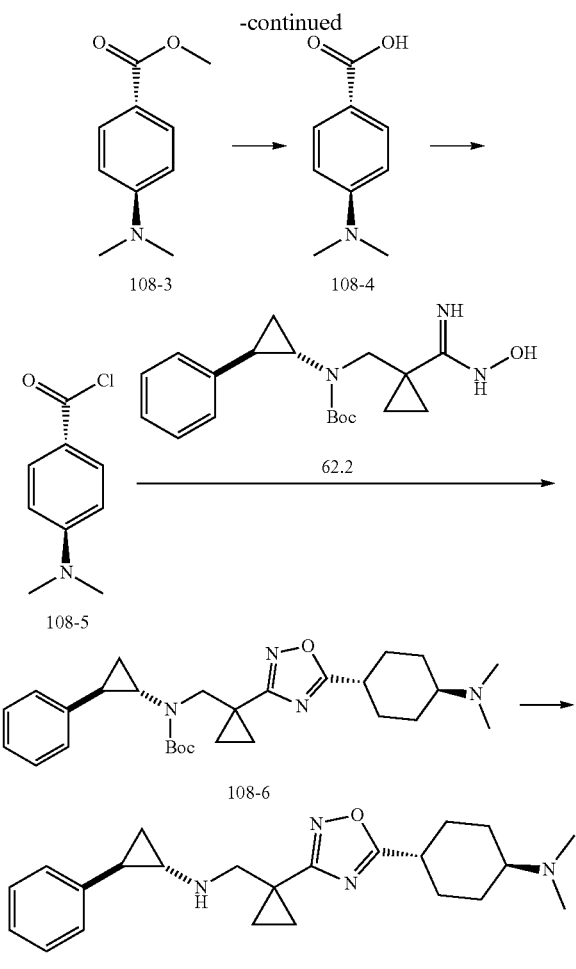

Step 1

Compound 108-1 (500 mg, 3.49 mmol) was dissolved in anhydrous methanol (10 mL) under nitrogen, and then thionyl chloride (1.66 g, 14.0 mmol) was added and the mixture was stirred at 25° C. for 2 hours. The reaction solution was concentrated under reduced pressure to give compound 108-2. $^1$H NMR (400 MHz, CDCl$_3$) δ 8.68-8.22 (m, 3H), 3.69 (s, 3H), 3.25-3.11 (m, 1H), 2.37-2.34 (m, 1H), 2.28-2.25 (m, 2H), 2.15-2.11 (m, 2H), 1.63-1.47 (m, 4H).

Step 2

Compound 108-2 (470 mg, 2.99 mmol) was dissolved in methanol (10 mL) under nitrogen, 37% formaldehyde aqueous solution (594 mg, 7.32 mmol), sodium acetate (245 mg, 2.99 mmol) and 10% wet palladium carbon (70.0 mg) were added. The reaction mixture was stirred at 25° C. for 24 h in a 15 PSI hydrogen atmosphere. The organic phase was concentrated under reduced pressure. The saturated potassium carbonate (20 mL) was added and the mixture was extracted with chloroform (20 mL×1), dried over anhydrous sodium sulfate, followed by filtration and concentration under reduced pressure. The residue was isolated and purified by silica gel column chromatography (10:1 dichloromethane/methanol with a few drops of ammonium hydroxide, Rf=0.1) to give compound 108-3. $^1$H NMR (400 MHz, CDCl$_3$) δ 3.60 (s, 3H), 2.21 (s, 6H), 2.19-2.06 (m, 2H), 2.00-1.89 (m, 4H), 1.44-1.34 (m, 2H), 1.19-1.11 (m, 2H).

Step 3

Compound 108-3 (270 mg, 1.46 mmol) was dissolved in anhydrous tetrahydrofuran (5 mL) and water (1 mL), lithium hydroxide monohydrate (306 mg, 7.29 mmol) was added, and the reaction mixture was stirred at 25° C. for 12 h, then concentrated under reduced pressure. The residue was adjusted to pH=5 with 1M hydrochloric acid aqueous solution, concentrated under reduced pressure, a mixture of dichloromethane:methanol=10:1 (20 mL) was added. The reaction mixture was dried over anhydrous sodium sulfate, followed by filtration and concentration under reduced pressure to give compound 108-4. $^1$H NMR (400 MHz, CD$_3$OD) δ 2.15 (s, 6H), 2.09-2.03 (m, 1H), 1.89-1.84 (m, 3H), 1.78-1.75 (m, 2H), 1.30-1.19 (m, 2H), 1.15-1.05 (m, 2H).

Step 4

Compound 108-4 (200 mg, 0.963 mmol) was dissolved in anhydrous dichloromethane (5 mL). Thionyl chloride (458 mg, 3.85 mmol) was added. The mixture was stirred at 25° C. for 2 h, followed by concentration under reduced pressure to give compound 108-5.

Step 5

Compound 108-5 (131 mg, 0.579 mmol) was dissolved in chloroform (6 mL) under nitrogen, pyridine (980 mg, 12.4 mmol) and compound 62-2 (100 mg, 0.289 mmol) were added. The mixture was stirred at 80 V for 1 h. The reaction solution was concentrated under reduced pressure. The reaction mixture was adjusted to pH=5 with adding 1M hydrochloric acid aqueous solution, and extracted with dichloromethane:methanol=10:1 (20 mL×1). The organic phase was washed with saturated brine (20 mL×1), dried over anhydrous sodium sulfate, followed by filtration and concentration under reduced pressure to give compound 108-6. MS-ESI calculated [M+H]$^+$ 481, found 481.

Step 6

The synthesis of compound 108 was referred to the second step of example 84. $^1$H NMR (400 MHz, CD$_3$OD) δ 7.35-7.31 (m, 2H), 7.28-7.22 (m, 1H), 7.19-7.17 (m, 2H), 3.73-3.64 (m, 2H), 3.11-3.08 (m, 1H), 3.05-2.98 (m, 1H), 2.90 (s, 6H), 2.59-2.54 (m, 1H), 2.35-2.33 (m, 2H), 2.26-2.20 (m, 2H), 1.79-1.68 (m, 4H), 1.61-1.56 (m, 1H), 1.46-1.44 (m, 2H), 1.42-1.38 (m, 2H), 1.36-1.34 (m, 2H). MS-ESI calculated [M+H]$^+$ 381, found 381.

Example 109

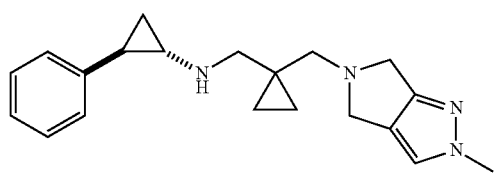

Synthetic Route:

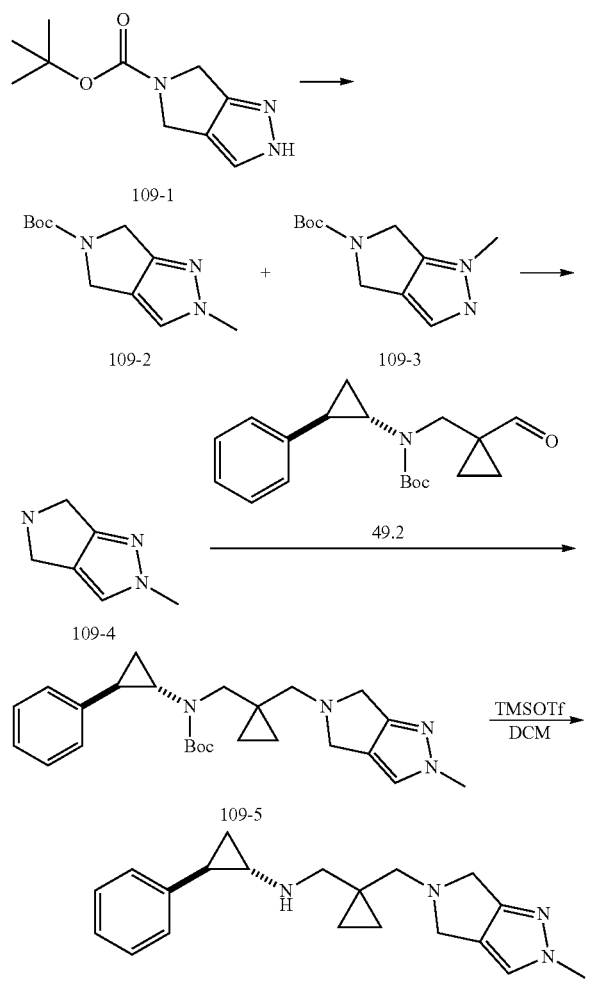

Step 1

Compound 109-1 (500 mg, 2.39 mmol) was dissolved in N,N-dimethylformamide (10 mL), cesium carbonate (1.56 g, 4.78 mmol) and methyl iodide (509 mg, 3.58 mmol) were added and the reaction was stirred at 25° C. for 12 h. Water (20 mL) was added to the mixture. The mixture was extracted with ethyl acetate (20 mL×1). The organic phase was washed with saturated brine (20 mL), dried over anhydrous sodium sulfate, followed by filtration and concentration under reduced pressure. The residue was isolated and purified by silica gel column chromatography (1:1 petroleum ether/ethyl acetate, compound 109-2 Rf=0.4, compound 109-3 Rf=0.3) to give compound 109-2 (180 mg). $^1$H NMR (400 MHz, CDCl$_3$) δ 7.04-7.00 (m, 1H), 4.42-4.33 (m, 4H), 3.83 (s, 3H), 1.44-1.43 (m, 9H). Compound 109-3. $^1$H NMR (400 MHz, CDCl$_3$) δ 7.18-7.14 (m 1H), 4.42-4.31 (m, 4H), 3.75-3.74 (m, 3H), 1.44-1.43 (m, 9H). MS-ESI calculated [M+H]$^+$ 224, found 224.

The compound 109-2 (180 mg, 0.806 mmol) was dissolved in ethyl acetate (5 mL), hydrochloric acid (4M ethyl acetate solution, 5 mL, 20 mmol) was added dropwise, and the mixture was stirred at 25° C. for 2 h. The reaction solution was concentrated under reduced pressure to give compound 1094. MS-ESI calculated [M+H]$^+$ 124, found 124.

Step 3

The synthesis of compound 109-5 was referred to the first step of example 98. MS-ESI calculated [M+H]$^+$ 423, found 423.

Step 4

The synthesis of compound 109 was referred to the second step of example 84. $^1$H NMR (400 MHz, CD$_3$OD) δ 7.56 (s, 1H), 7.38-7.30 (m, 2H), 7.26-7.20 (m, 3H), 4.98-4.95 (m, 2H), 4.50-4.42 (m, 2H), 3.93 (s, 3H), 3.83-3.38 (m, 4H), 3.12-3.08 (m, 1H), 2.82-2.77 (m, 1H), 1.80-1.74 (m, 1H), 1.40-1.35 (m, 1H), 1.06-1.03 (m, 4H). MS-ESI calculated [M+H]$^+$ 323, found 323.

Example 110

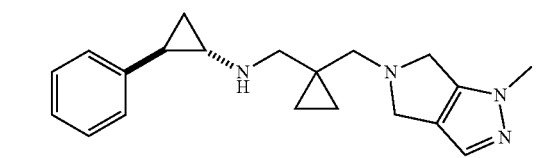

Synthetic Route:

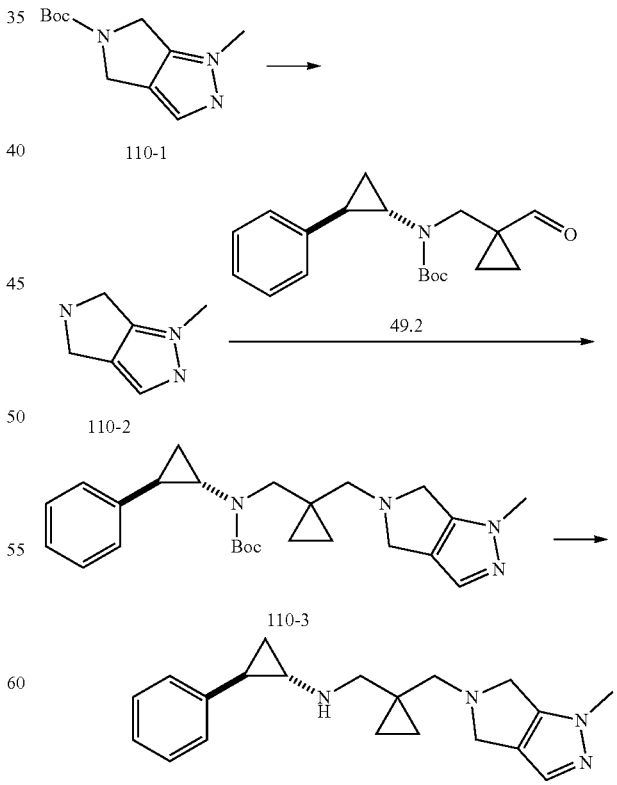

Step 1

The synthesis of compound 110-2 was referred to the second step of example 109. MS-ESI calculated [M+H]⁺ 124, found 124.

Step 2

The synthesis of compound 110-3 was referred to the first step of example 98. MS-ESI calculated [M+H]⁺ 423, found 423.

Step 3

The synthesis of compound 110 was referred to the second step of example 84. ¹H NMR (400 MHz, CD₃OD) δ 7.41 (s, 1H), 7.34-7.30 (m, 2H), 7.26-7.21 (m, 3H), 5.10-5.00 (m, 2H), 4.64-4.47 (m, 2H), 3.90 (s, 3H), 3.75-3.72 (m, 2H), 3.57-3.38 (m, 2H), 3.14-3.10 (m, 1H), 2.83-2.78 (m, 1H), 1.80-1.75 (m, 1H), 1.41-1.36 (m, 1H), 1.07-1.03 (m, 4H). MS-ESI calculated [M+H]⁺ 323, found 323.

Example 111

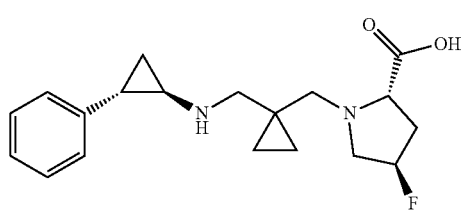 [SMILES: O=C(O)[C@@H]1C[C@@H](F)CN1CC1(CN[C@@H]2C[C@H]2c2ccccc2)CC1]

Synthetic Route:

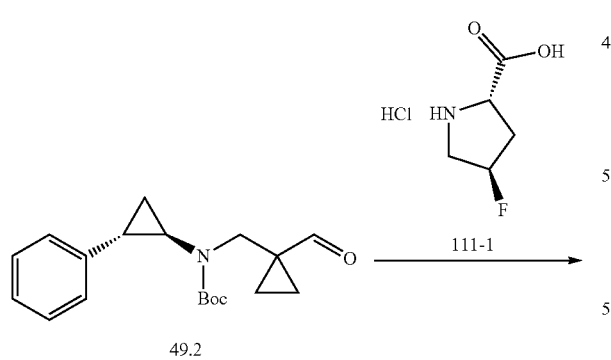

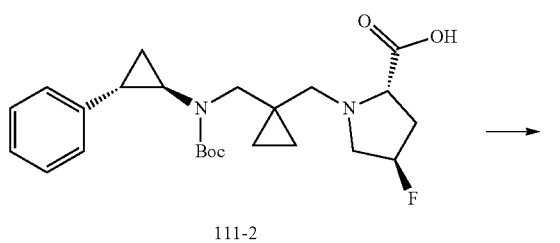

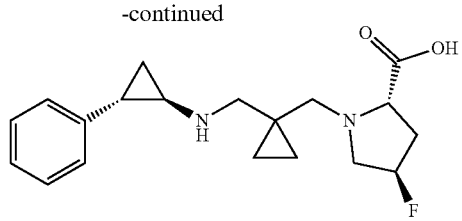

111

Step 1

Compound 111-1 (48.4 mg, 0.285 mmol) was dissolved in anhydrous methanol (10 mL). Triethylamine (28.9 mg, 0.285 mmol) was added, and the mixture was stirred for 0.5 h. Compound 49-2 (100 mg, 0.285 mmol) and acetic acid (57.4 mg, 0.856 mmol) were added to the reaction mixture, and the mixture was stirred at 50° C. for 0.5 h, and sodium cyanoborohydride (53.8 mg, 0.856 mmol) was added. The mixture was stirred at 50° C. for 11 h. The saturated sodium carbonate aqueous solution (20 mL) was added to the mixture, and then methanol was removed by rotary evaporation. The residue was extracted with dichloromethane/methanol (10:1)(20 mL×1). The organic phase was washed with saturated brine (20 mL×1), dried over anhydrous sodium sulfate, followed by filtration and concentration under reduced pressure. The residue was isolated and purified by thin layer chromatography (2:1 petroleum ether/ethyl acetate, Rf=0.5) to give compound 111-2. MS-ESI calculated [M+H]⁺ 433, found 433.

Step 2

The synthesis of compound 111 was referred to the second step of example 84. ¹H NMR (400 MHz, CD₃OD) δ 7.34-7.31 (m, 2H), 7.27-7.21 (m, 3H), 5.50-5.36 (m, 1H), 4.56-4.48 (m, 1H), 4.34-4.24 (m, 1H), 3.58-3.55 (m, 2H), 3.50-3.43 (m, 1H), 3.38 (s, 2H), 3.07-3.03 (m, 1H), 2.82-2.73 (m, 2H), 2.44-2.28 (m, 1H), 1.72-1.66 (m, 1H), 1.42-1.37 (m, 1H), 0.98-0.87 (m, 4H). MS-ESI calculated [M+H]⁺ 333, found 333.

Example 112

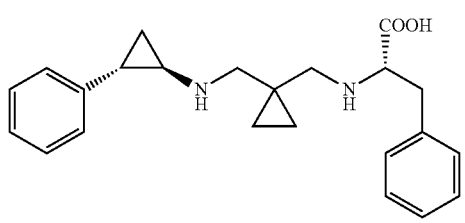 [SMILES: O=C(O)[C@H](Cc1ccccc1)NCC1(CN[C@@H]2C[C@H]2c2ccccc2)CC1]

Synthetic Route:

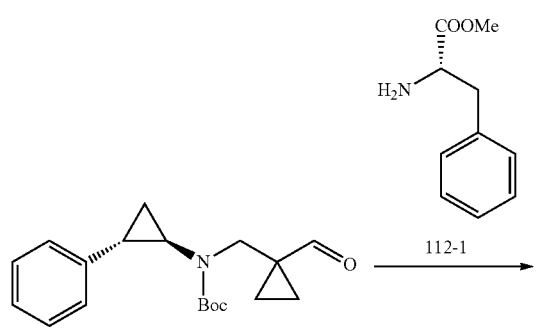

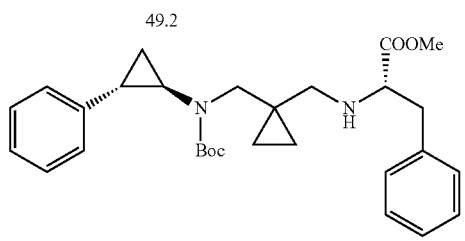

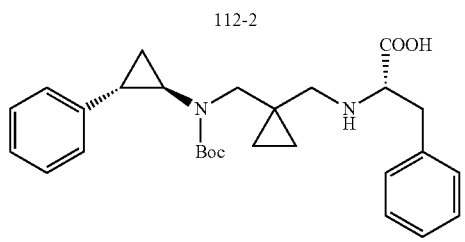

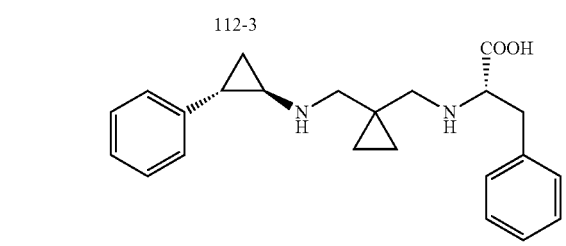

Step 1

The synthesis of compound 112-2 was referred to the first step of example 98. MS-ESI calculated [M+H]+ 479, found 479.

Step 2

Compound 112-2 (97.0 mg, 0.203 mmol) was dissolved in anhydrous tetrahydrofuran (8 mL) and water (2 mL), sodium hydroxide (200 mg, 20.0 mmol) was added and the reaction was stirred at 25° C. for 12 h. Water (20 mL) was added to the solution, and the aqueous phase was adjusted to pH=5 with 1 M hydrochloric acid aqueous solution. The mixture was extracted with ethyl acetate (20 mL×1). The organic phase was washed with saturated brine (20 mL), dried over anhydrous sodium sulfate, followed by filtration and concentration under reduced pressure to give compound 112-3. MS-ESI calculated [M+H]+ 465, found 465.

Step 3

The synthesis of compound 112 was referred to the second step of example 84. $^1$H NMR (400 MHz, CD$_3$OD) δ 7.38-7.31 (m, 7H), 7.27-7.25 (m, 1H), 7.22-7.20 (m, 2H), 4.34-4.30 (m, 1H), 3.60-3.57 (m, 1H), 3.50-3.41 (m, 2H), 3.29-3.23 (m, 2H), 3.07-3.04 (m, 1H), 3.01-2.98 (m, 1H), 2.75-2.73 (m, 1H), 1.69-1.64 (m, 1H), 1.43-1.37 (m, 1H), 0.99-0.91 (m, 4H). MS-ESI calculated [M+H]+ 365, found 365.

Example 113

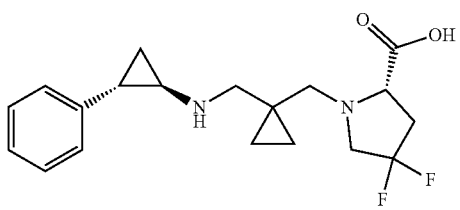 [SMILES: O=C(O)[C@@H]1CC(F)(F)CN1CC1(CN[C@@H]2C[C@H]2c2ccccc2)CC1]

Synthetic Route:

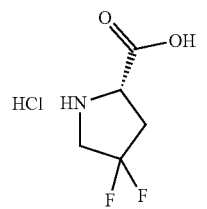

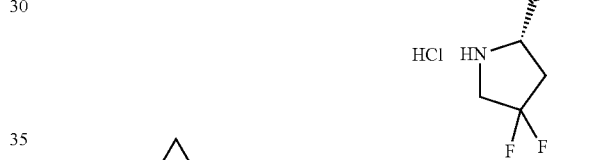

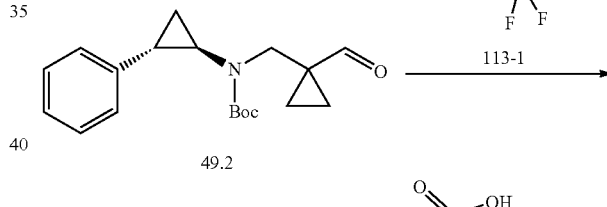

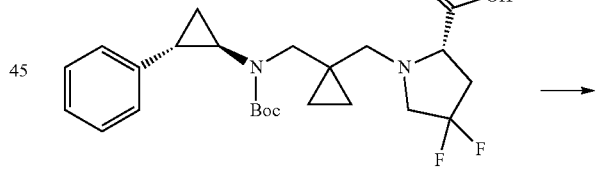

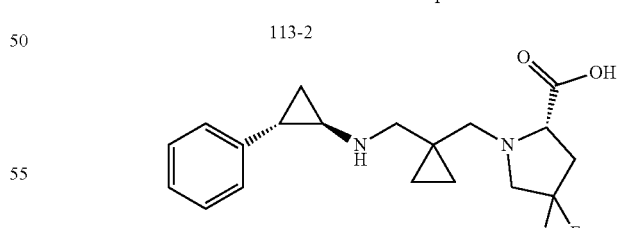

Step 1

The synthesis of compound 113-2 was referred to the first step of example 111. MS-ESI calculated [M+H]+ 451, found 451.

Step 2

The synthesis of compound 113 was referred to the second step of example 84. $^1$H NMR (400 MHz, CD$_3$OD) δ 7.34-7.30 (m, 2H), 7.26-7.19 (m, 3H), 3.84-3.78 (m, 2H), 3.49-3.41 (m, 2H), 3.15-3.11 (m, 1H), 3.03-2.92 (m, 2H), 2.89-2.78 (m, 1H), 2.75-2.70 (m, 1H), 2.49-2.36 (m, 1H), 2.24-2.21 (m, 1H), 1.535-1.50 (m, 1H), 1.42-1.37 (m, 1H), 0.87-0.82 (m, 1H), 0.79-0.74 (m, 1H), 0.68-0.63 (m, 1H), 0.59-0.54 (m, 1H). MS-ESI calculated [M+H]$^+$ 351, found 351.

Example 114

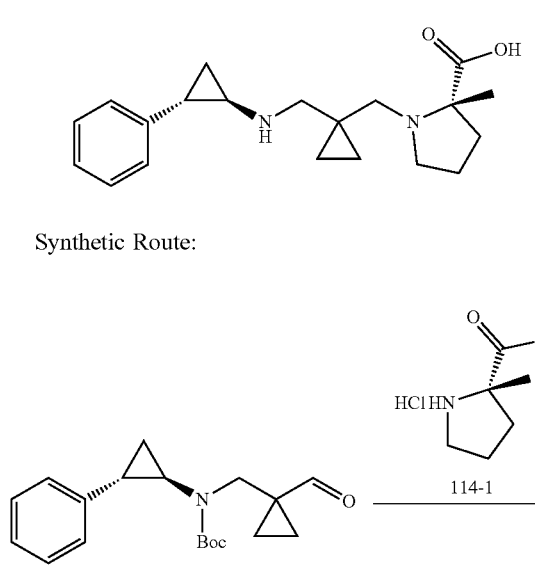

Synthetic Route:

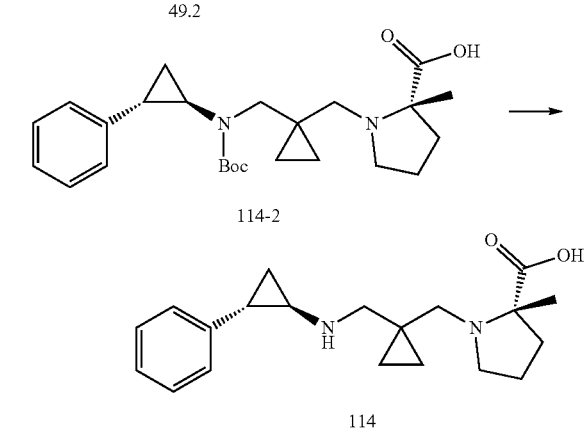

Step 1

The synthesis of compound 114-2 was referred to the first step of example 111. MS-ESI calculated [M+H]$^+$ 429, found 429.

Step 2

The synthesis of compound 114 was referred to the second step of example 84. $^1$H NMR (400 MHz, CD$_3$OD) δ 7.35-7.31 (m, 2H), 7.27-7.11 (m, 3H), 4.12-4.06 (m, 3H), 3.50-3.42 (m, 1H), 3.11-3.05 (m, 2H), 2.97-2.93 (m, 1H), 2.73-2.68 (m, 1H), 2.33-2.31 (m, 3H), 2.26-2.19 (m, 1H), 1.84-1.79 (m, 1H), 1.64 (s, 3H), 1.45-1.39 (m, 1H), 1.07-1.03 (m, 3H), 0.96-0.94 (m, 1H). MS-ESI calculated [M+H]$^+$ 329, found 329.

Example 115

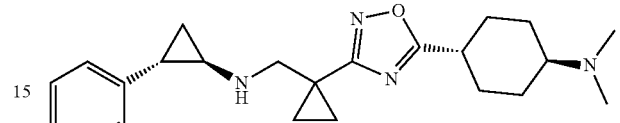

Synthetic Route:

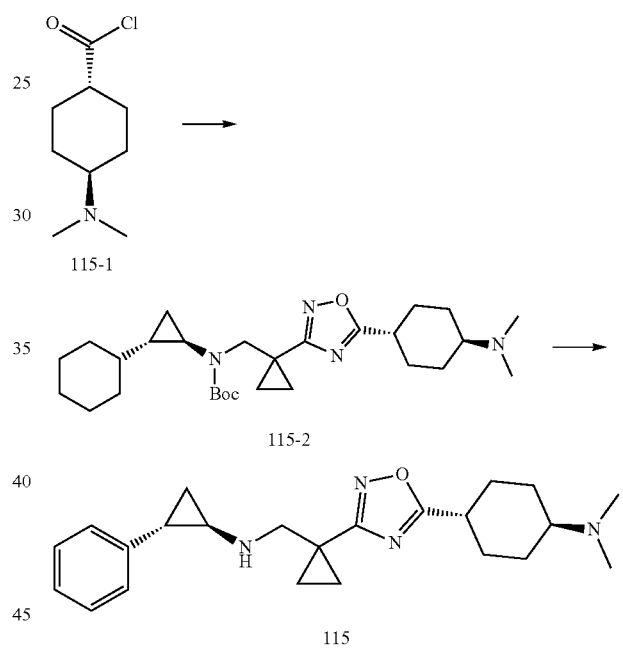

Step 1

The synthesis of compound 115-2 was referred to the fifth step of example 108. MS-ESI calculated [M+H]$^+$ 481, found 481.

Step 2

The synthesis of compound 115 was referred to the sixth step of example 108. $^1$H NMR (400 MHz, CD$_3$OD) δ 7.35-7.31 (m, 2H), 7.27-7.24 (m, 1H), 7.19-7.17 (m, 2H), 3.73-3.64 (m, 2H), 3.37-3.34 (m, 1H), 3.11-3.03 (m, 2H), 2.90 (s, 6H), 2.59-2.54 (m, 1H), 2.35-2.33 (m, 2H), 2.25-2.23 (m, 2H), 1.79-1.68 (m, 4H), 1.62-1.56 (m, 1H), 1.46-1.34 (m, 5H). MS-ESI calculated [M+H]$^+$ 381, found 381.

Example 116

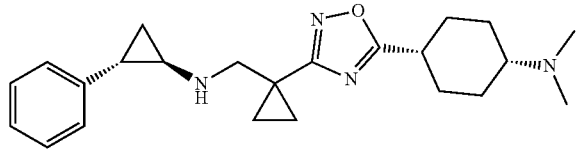 [SMILES: CN(C)[C@H]1CC[C@@H](c2nc(C3(CN[C@@H]4C[C@H]4c4ccccc4)CC3)no2)CC1]

Synthetic Route:

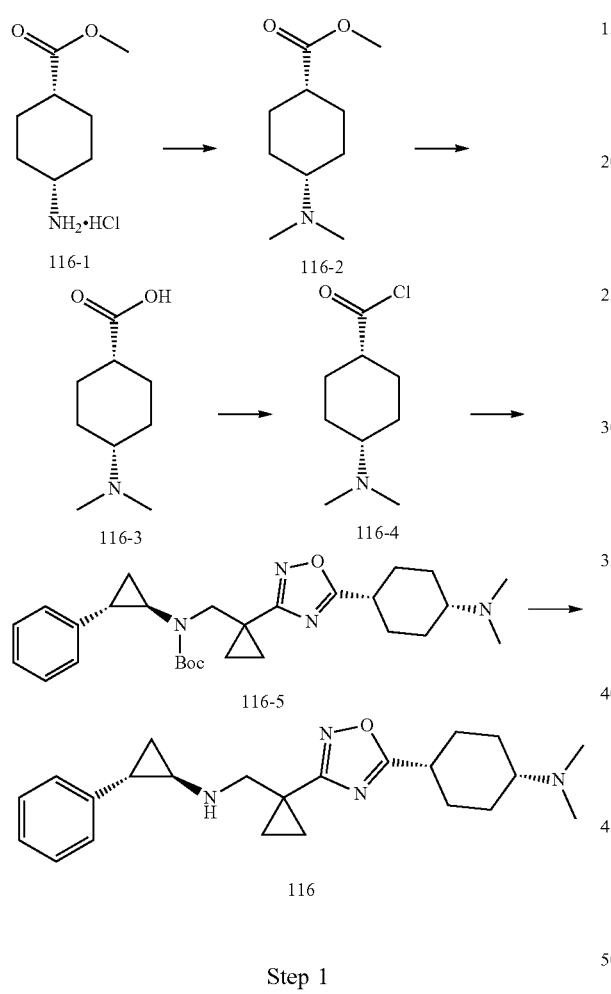

Step 1

The synthesis of compound 116-2 was referred to the second step of example 108. $^1$H NMR (400 MHz, CDCl$_3$) δ 3.69 (s, 3H), 2.26 (s, 6H), 2.15-2.14 (m, 2H), 1.76-1.54 (m, 8H).

Step 2

The synthesis of compound 116-3 was referred to the third step of example 108. $^1$H NMR (400 MHz, CD$_3$OD) δ 3.30-3.23 (m, 1H), 2.85 (s, 6H), 2.74-2.69 (m, 1H), 2.33-2.31 (m, 2H), 2.05-1.99 (m, 2H), 1.75-1.64 (m, 4H).

Step 3

The synthesis of compound 116-4 was referred to the fourth step of example 108.

Step 4

The synthesis of compound 116-5 was referred to the fifth step of example 108. MS-ESI calculated [M+H]$^+$ 481, found 481.

Step 5

The synthesis of compound 116 was referred to the second step of example 84. $^1$H NMR (400 MHz, CD$_3$OD) δ 7.35-7.31 (m, 2H), 7.27-7.24 (m, 1H), 7.20-7.18 (m, 2H), 3.76-3.66 (m, 2H), 3.38-3.36 (m, 1H), 3.31-3.28 (m, 1H), 3.13-3.09 (m, 1H), 2.84 (s, 6H), 2.64-2.58 (m, 1H), 2.41-2.38 (m, 2H), 2.07-2.03 (m, 2H), 2.01-1.93 (m, 2H), 1.80-1.71 (m, 2H), 1.65-1.60 (m, 1H), 1.51-1.49 (m, 2H), 1.41-1.41 (m, 1H), 1.39-1.36 (m, 2H). MS-ESI calculated [M+H]$^+$ 381, found 381.

Example 117

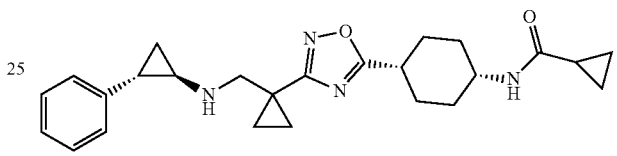

Synthetic Route:

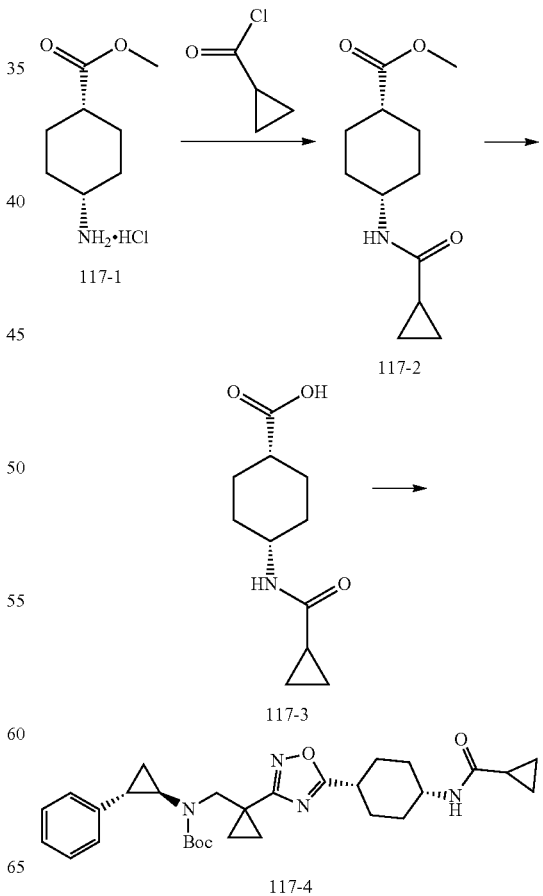

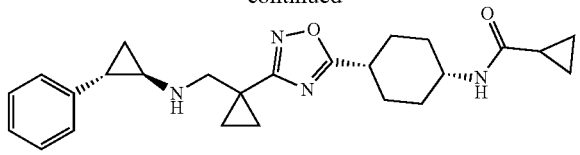

117

Step 1

Compound 117-1 (200 mg, 1.03 mmol) was dissolved in anhydrous dichloromethane (4 mL). Triethylamine (313 mg, 3.10 mmol) and cyclopropyl carboxylic chloride (119 mg, 1.14 mmol) were added and the reaction was stirred at 25° C. for 12 h. Water (20 mL) was added to the mixture. The mixture was extracted with dichloromethane (20 mL×1). The organic phase was dried over anhydrous sodium sulfate, followed by filtration and concentration under reduced pressure. The residue was isolated and purified by silica gel column chromatography (2:1 petroleum ether/ethyl acetate, Rf=0.6) to give compound 117-2. MS-ESI calculated [M+H]$^+$226, found 226.

Step 2

The synthesis of compound 117-3 was referred to the third step of example 108. MS-ESI calculated [M+H]$^+$ 265, found 265.

Step 3

The synthesis of compound 1174 was referred to the first step of example 87. MS-ESI calculated [M+H]$^+$ 521, found 521.

Step 4

The synthesis of compound 117 was referred to the second step of example 84. $^1$H NMR (400 MHz, CD$_3$OD) δ 7.35-7.31 (m, 2H), 7.27-7.24 (m, 1H), 7.19-7.17 (m, 2H), 3.89-3.85 (m, 1H), 3.74-3.66 (m, 2H), 3.18-3.16 (m, 1H), 3.11-3.08 (m, 1H), 2.58-2.53 (m, 1H), 2.14-2.11 (m, 2H), 1.95-1.89 (m, 2H), 1.81-1.76 (m, 2H), 1.69-1.56 (m, 4H), 1.50-1.47 (m, 2H), 1.45-1.40 (m, 1H), 1.37-1.34 (m, 2H), 0.86-0.82 (m, 2H), 0.76-0.71 (m, 2H). MS-ESI calculated [M+H]$^+$ 421, found 421.

Example 118

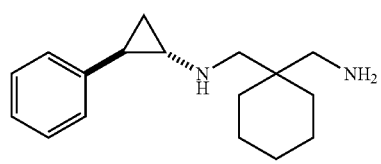

Synthetic Route:

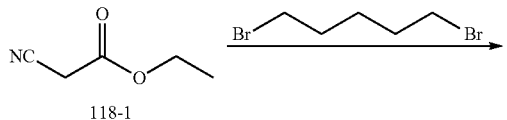

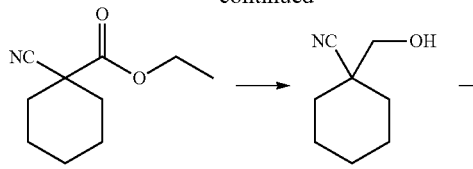

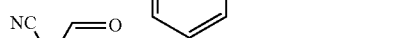

118

Step 1

Compound 118-1 (2.00 g, 17.7 mmol) was dissolved in anhydrous N,N-dimethylformamide (30 mL), and 1,8-diazabicycloundec-7-ene was added dropwise. The mixture was stirred at 0° C. for 0.5 h, 1,5-dibromopentane (4.47 g, 19.5 mmol) was added dropwise. The mixture was heated to 80° C. and stirred for 2 h. The mixture was cooled to 25° C., water (300 mL) was added to the mixture. The mixture was extracted with ethyl acetate (400 mL×2). The organic phase was washed with saturated brine (250 mL×2), dried over anhydrous sodium sulfate, followed by filtration and concentration under reduced pressure. The residue was isolated and purified by silica gel column chromatography (5:1 petroleum ether/ethyl acetate, Rf=0.8) to give compound 118-2. $^1$H NMR (400 MHz, CDCl$_3$) δ 4.29-4.21 (q, J=7.2 Hz, 2H), 2.13-2.09 (m, 2H), 1.83-1.68 (m, 8H), 1.34-1.30 (t, J=7.2 Hz, 3H).

Step 2

Compound 118-2 (3.00 g, 16.6 mmol) was dissolved in anhydrous tetrahydrofuran (50 mL), and lithium borohydride (721 mg, 33.1 mmol) was added at 0° C., and the reaction mixture was stirred at 25° C. for 2 h. Ethyl acetate (200 mL) and hydrochloric acid aqueous solution (50 mL, 1 mol/L) were added to the mixture. Water (300 mL) was added to the mixture. The mixture was extracted with ethyl acetate (200 mL×3). The organic phases were combined, washed with saturated brine (300 mL×2), dried over anhydrous sodium sulfate, followed by filtration and concentration under reduced pressure to give compound 118-3. $^1$H NMR (400 MHz, CDCl$_3$) δ 3.62 (s, 2H), 2.04-2.01 (m, 3H), 1.80-1.76 (m, 3H), 1.64-1.61 (m, 2H), 1.31-1.26 (m, 2H).

Step 3

Oxalyl chloride (2.31 g, 18.2 mmol) was dissolved in anhydrous dichloromethane (30 mL), the solution of dimethyl sulfoxide (2.84 g, 36.3 mmol) in anhydrous dichloromethane (6 mL) was added dropwise at −78° C. The mixture was stirred at −78° C. for 0.5 h, a solution of compound 118-3 (2.84 g, 36.3 mmol) dissolved in anhydrous dichloromethane (6 mL) was added dropwise at −78° C. The mixture was stirred at −78° C. for 1 h, triethylamine (7.03 g, 69.5 mmol) was added dropwise, and the mixture was stirred at −78° C. for 2 h. Hydrochloric acid aqueous solution (30 mL, 1 mol/L) was added. The mixture was extracted with ethyl acetate (50 mL×3). The organic phases were combined, washed with saturated brine (30 mL×2), dried over anhydrous sodium sulfate, followed by filtration and concentration under reduced pressure. The residue was isolated and purified by preparative thin layer chromatography (3:1 petroleum ether/ethyl acetate, Rf=0.2) to give compound 1184. $^1$H NMR (400 MHz, CDCl$_3$) δ 9.48 (s, 1H), 2.04-2.03 (m, 2H), 1.81-1.78 (m, 3H), 1.66-1.62 (m, 3H), 1.28-1.23 (m, 2H).

Step 4

Compound 118-4 (100 mg, 0.729 mmol) and compound A-2 (97.1 mg, 0.729 mmol) were dissolved in anhydrous dichloromethane (1 mL). The reaction solution was stirred at 30° C. for 1 h. And then sodium tricetoxyborohydride (0.46 g, 2.19 mmol) was added, and the reaction mixture was stirred at 30° C. for 1 h. The reaction solution was diluted with dichloromethane (10 mL) and washed successively with saturated sodium carbonate aqueous solution (10 mL×3), water (10 mL×2), saturated brine (10 mL×2). The organic phases were combined, dried over anhydrous sodium sulfate, followed by filtration and concentration under reduced pressure. The residue was isolated and purified by thin layer chromatography (3:1 petroleum ether/ethyl acetate, Rf=0.7) to give compound 118-5. $^1$H NMR (400 MHz, CDCl$_3$) δ 7.18-7.10 (m, 2H), 7.09-7.07 (m, 1H), 6.97-6.95 (m, 2H), 2.79 (s, 2H), 2.37-2.35 (m, 1H), 2.04-1.93 (m, 2H), 1.85-1.80 (m, 1H), 1.78-1.71 (m, 2H), 1.71-1.61 (m, 3H), 1.20-1.13 (m, 3H), 1.03-0.90 (m, 2H).

Step 5

Compound 118-5 (86.0 mg, 0.338 mmol) was dissolved in anhydrous methanol (2 mL), sodium borohydride (102 mg, 2.70 mmol) and cobalt dichloride (0.18 g, 1.35 mmol) were added at 0° C., and stirred at 25° C. for 2 h. The reaction mixture was diluted with ethyl acetate (15 mL), sodium hydroxide aqueous solution (10 mL, 1 mol/L) was added. The mixture was filtered with celite, water (10 mL) was added to the filtrate. The mixture was extracted with ethyl acetate (15 mL×3). The organic phase was washed with saturated brine (20 mL×2), dried over anhydrous sodium sulfate, followed by filtration and concentration under reduced pressure. The residue was isolated and purified by high-performance liquid chromatography (acidic, hydrochloric acid system) to give compound 118. $^1$H NMR (400 MHz, CD$_3$OD) δ 7.24-7.20 (m, 2H), 7.15-7.13 (m, 3H), 3.30-3.24 (m, 1H), 3.12-3.12 (m, 1H), 2.76-2.74 (m, 2H), 2.74-2.72 (m, 1H), 2.72-2.71 (m, 1H), 1.71-1.67 (m, 1H), 1.49-1.45 (m, 10H), 1.29-1.27 (m, 1H). MS-ESI calculated [M+H]$^+$ 259, found 259.

Example 119

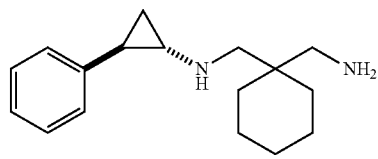

Synthetic Route:

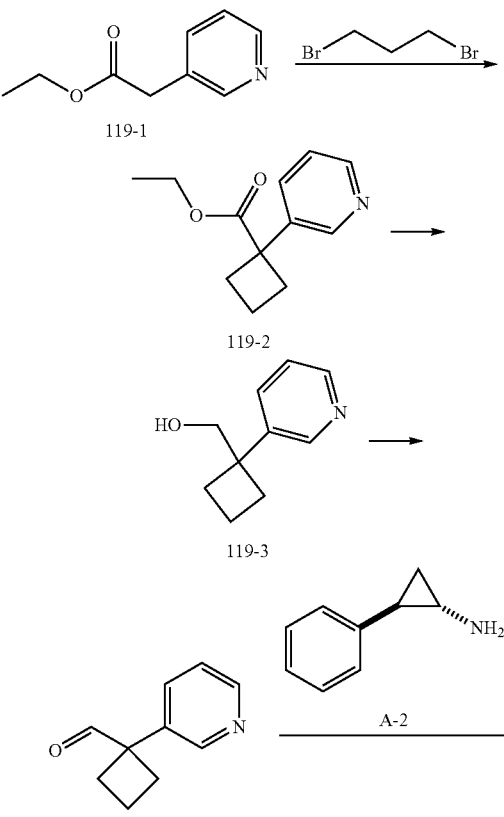

Step 1

The cesium carbonate (9.86 g, 30.3 mmol) was dissolved in anhydrous dimethylformamide (15 mL), compound 119-1 (1.00 g, 6.05 mmol) was added at 0° C., and the reaction was stirred at 0° C. for 0.5 h, 1,3-dibromopropane (1.47 g, 7.26 mmol) was added portionwise at 0° C., and the reaction was stirred at 50° C. for 12 h. The reaction was then quenched with water (100 mL) at 0° C. The mixture was extracted with ethyl acetate (50 mL×2). The organic phases were combined, washed with saturated brine (50 mL×2), dried over anhydrous sodium sulfate, followed by filtration and concentration under reduced pressure. The residue was isolated and purified by silica gel column chromatography (3:1 petroleum ether/ethyl acetate, Rf=0.5) to give compound 119-2. $^1$H NMR (400 MHz, CDCl$_3$) δ 8.48-8.39 (m, 2H), 7.53-7.51 (m, 1H), 7.17-7.14 (m, 1H), 4.01 (q, J=6.8 Hz, 2H), 2.78-2.75 (m, 2H), 2.44-2.41 (m, 2H), 2.02-1.98 (m, 1H), 1.85-1.83 (m, 1H), 1.08 (t, J=6.8 Hz, 3H).

Step 2

Compound 119-2 (780 mg, 3.80 mmol) was dissolved in anhydrous methanol (10 mL), lithium borohydride (165 mg, 7.60 mmol) was added portionwise at 0° C. The reaction was stirred at 30° for 3 h. Hydrochloric acid aqueous solution (20 mL, 1 mol/L) was added to the reaction mixture at 0° C. The mixture was extracted with ethyl acetate (50 mL×2). The organic phases were combined, washed with saturated brine (50 mL×2), dried over anhydrous sodium sulfate, followed by filtration and concentration under reduced pressure. The residue was isolated and purified by silica gel column chromatography (3:1 petroleum ether/ethyl acetate, Rf=0.2) to give compound 119-3. $^1$H NMR (400 MHz, CDCl$_3$) δ 8.44-8.38 (m, 2H), 7.56-7.46 (m, 1H), 7.25-7.21 (m, 1H), 3.81 (s, 2H), 2.39-2.29 (m, 4H), 2.28-2.17 (m, 2H).

Step 3

The synthesis of compound 119-4 was referred to the third step of example 118. $^1$H NMR (400 MHz, CDCl$_3$) δ 9.64 (s, 1H), 8.57-8.47 (m, 2H), 7.51-7.48 (m, 1H), 7.35-7.32 (m, 1H), 2.83-2.78 (m, 2H), 2.52-2.47 (m, 2H), 2.13-2.03 (m, 2H).

Step 4

The synthesis of compound 119 was referred to the fourth step of example 118. $^1$H NMR (400 MHz, CD$_3$OD) δ 8.92 (s, 1H), 8.81 (d, J=5.6 Hz, 1H), 8.65 (d, J=8.0 Hz, 1H), 8.14 (dd, J=5.6, 8.0 Hz, 1H), 7.33-7.29 (m, 2H), 7.24-7.20 (m, 1H), 7.18-7.16 (m, 2H), 3.91 (s, 2H), 3.06-3.02 (m, 1H), 2.68-2.56 (m, 5H), 2.40-2.27 (m, 1H), 2.10-2.00 (m, 1H), 1.70-1.62 (m, 1H), 1.38-1.34 (m, 1H). MS-ESI calculated [M+H]$^+$ 279, found 279.

Example 120

Synthetic Route:

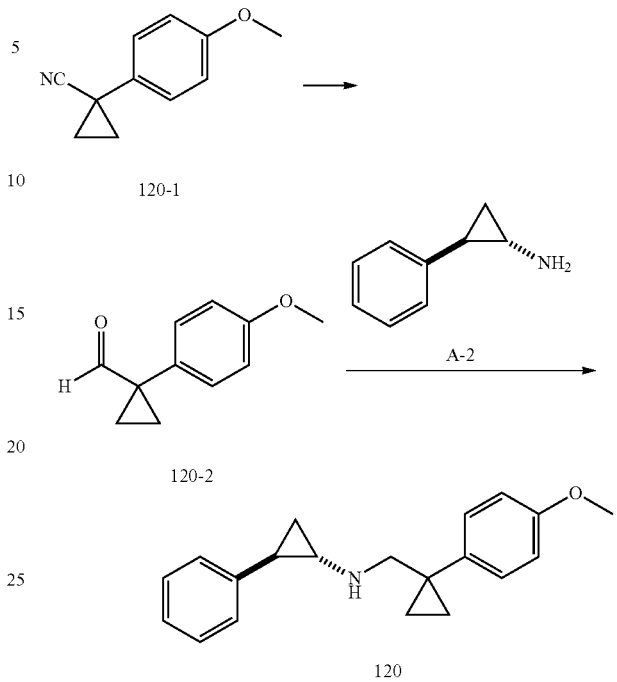

Step 1

Compound 120-1 (200 mg, 1.15 mmol) was dissolved in anhydrous dichloromethane (5 mL), diisobutylaluminum hydride (2.30 mL, 1 mol/L) was added at −78° C. The mixture was stirred at −78° C. for 2 h. Saturated ammonium chloride aqueous solution (10 mL) was added at −78° C. The reaction mixture was warmed to room temperature, the mixture was adjusted to pH=7 with sodium carbonate, and the mixture was extracted with dichloromethane (20 mL×3), dried over anhydrous sodium sulfate, followed by filtration and concentration under reduced pressure. The residue was isolated and purified by thin layer chromatography (3:1 petroleum ether/ethyl acetate, Rf=0.8) to give compound 120-2. $^1$H NMR (400 MHz, CDCl$_3$) δ 9.23 (s, 1H), 7.26-7.24 (m, 2H), 6.92-6.89 (m, 2H), 3.81 (s, 3H), 1.56-1.53 (m, 2H), 1.38-1.36 (m, 2H).

Step 2

The synthesis of compound 120 was referred to the fourth step of example 118. $^1$H NMR (400 MHz, CD$_3$OD) δ 7.40-7.38 (m, 2H), 7.31-7.28 (m, 2H), 7.24-7.21 (m, 1H), 7.12-7.10 (m, 2H), 6.94-6.90 (m, 2H), 3.79 (s, 3H), 3.46-3.39 (m, 2H), 2.89-2.85 (m, 1H), 2.48-2.43 (m, 1H), 1.51-1.45 (m, 1H), 1.31-1.26 (m, 1H), 1.09-1.00 (m, 4H). MS-ESI calculated [M+H]$^+$ 294, found 294.

Example 121

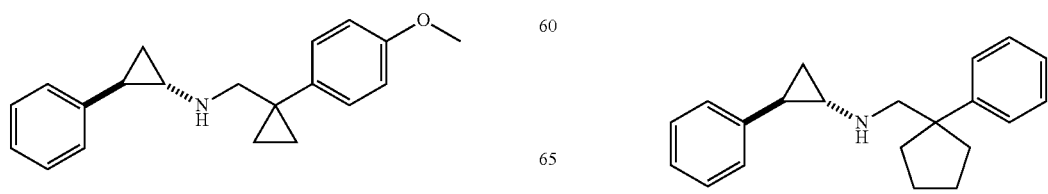

Synthetic Route:

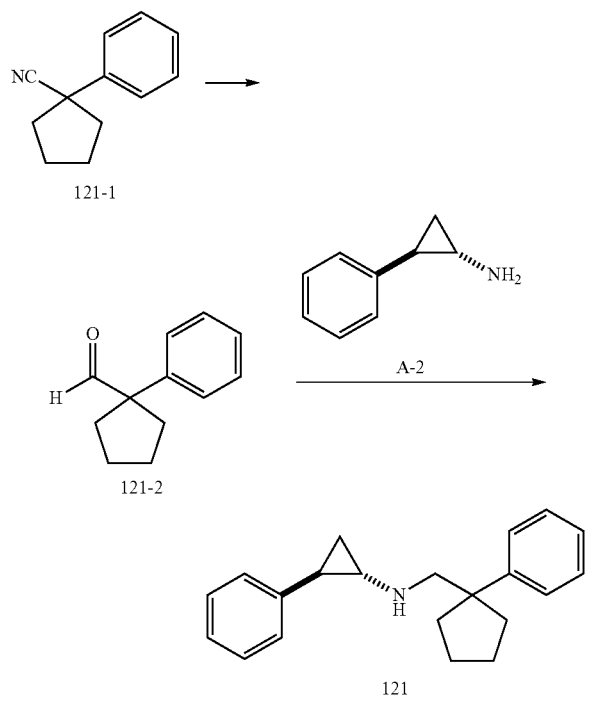

Step 1

The synthesis of compound 121-2 was referred to the first step of example 120. $^1$H NMR (400 MHz, CDCl$_3$) δ 9.41 (s, 1H), 7.38-7.35 (m, 2H), 7.29-7.24 (m, 3H), 2.55-2.51 (m, 2H), 1.91-1.83 (m, 2H), 1.82-1.64 (m, 4H).

Step 2

The synthesis of compound 121 was referred to the fourth step of example 118. $^1$H NMR (400 MHz, CD$_3$OD) δ 7.50-7.48 (m, 2H), 7.42 (t, J=7.6 Hz 2H), 7.33-7.27 (m, 3H), 7.24-7.20 (m, 1H), 7.09 (d, J=7.6 Hz, 2H), 3.58 (s, 2H), 2.75-2.72 (m, 1H), 2.47-2.42 (m, 1H), 2.18-2.15 (m, 2H), 2.05-1.99 (m, 2H), 1.88-1.83 (m, 2H), 1.73-1.72 (m, 2H), 1.49-1.43 (m, 1H), 1.24-1.21 (m, 1H). MS-ESI calculated [M+H]$^+$ 292, found 292.

Example 122

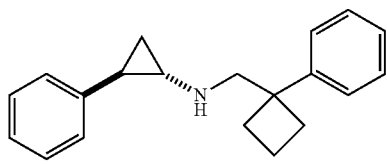

Synthetic Route:

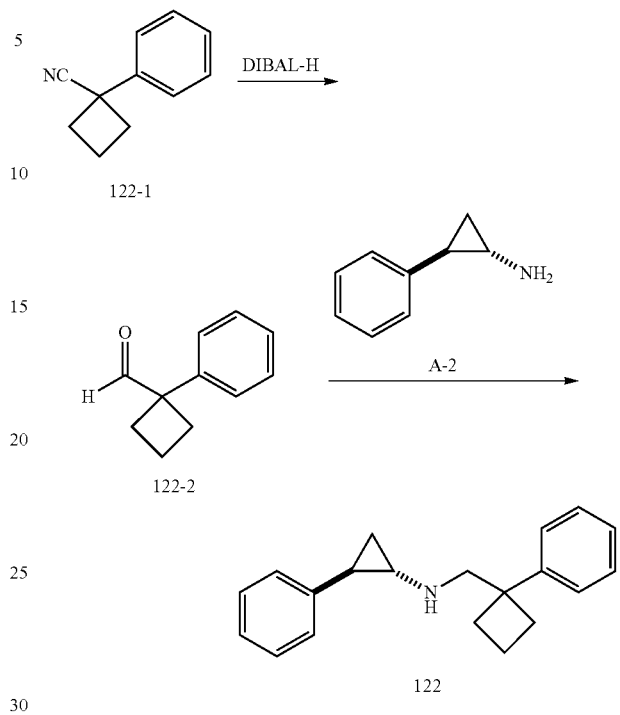

Step 1

The synthesis of compound 122-2 was referred to the first step of example 120. $^1$H NMR (400 MHz, CDCl$_3$) δ 9.54 (s, 1H), 7.40-7.37 (m, 2H), 7.30-7.28 (m, 1H), 7.19-7.15 (m, 2H), 2.75-2.71 (m, 2H), 2.46-2.37 (m, 2H), 2.05-1.94 (m, 2H).

Step 2

The synthesis of compound 122 was referred to the fourth step of example 118. $^1$H NMR (400 MHz, CD$_3$OD) δ 7.42-7.38 (m, 2H), 7.33 (d, J=7.6 Hz, 2H), 7.30-7.26 (m, 3H), 7.22-7.19 (m, 1H), 7.09 (d, J=7.6 Hz, 2H), 3.66 (s, 2H), 2.78-2.78 (m, 1H), 2.54-2.37 (m, 5H), 2.25-2.13 (m, 1H), 1.98-1.88 (m, 1H), 1.50-1.45 (m, 1H), 1.28-1.24 (m, 1H). MS-ESI calculated [M+H]$^+$ 278, found 278.

Example 123

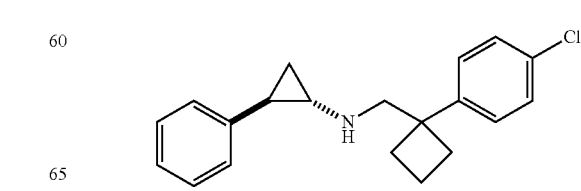

Synthetic Route:

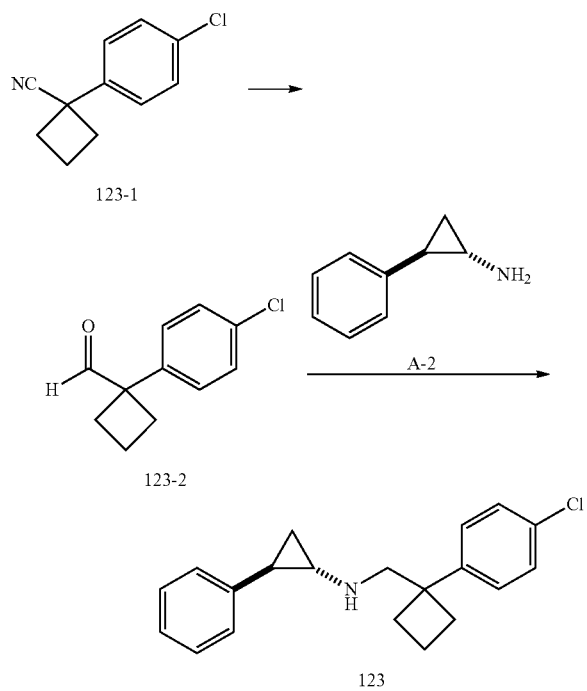

Step 1

The synthesis of compound 123-2 was referred to the first step of example 120. ¹H NMR (400 MHz, CDCl₃) δ 9.46 (s, 1H), 7.29-7.26 (m, 2H), 7.03-7.00 (m, 2H), 2.68-2.63 (m, 2H), 2.32-2.29 (m, 2H), 1.97-1.88 (m, 2H).

Step 2

Compound 123-2 (138 mg, 0.709 mmol) and compound A-2 (94.4 mg, 0.709 mmol) were dissolved in dichloromethane (2 mL), acetic acid (128 mg, 2.13 mmol) was added. The reaction solution was stirred at 30° C. for 1 h. And then sodium triacetoxyborohydride (451 mg, 2.13 mmol) was added, and the reaction mixture was stirred at 30° C. for 1 h. The reaction mixture was quenched with saturated sodium bicarbonate aqueous solution (10 mL), extracted with dichloromethane (25 mL×2). The organic phases were combined, washed with saturated brine (25 mL×2), dried over anhydrous sodium sulfate, followed by filtration and concentration under reduced pressure. The residue was isolated and purified by high-performance liquid chromatography (acidic, hydrochloric acid system) to give compound 123. ¹H NMR (400 MHz, CD₃OD) δ 7.40 (d, J=8.4 Hz, 2H), 7.35-7.28 (m, 4H), 7.24-7.21 (m, 1H), 7.12 (d, J=8.4 Hz, 2H), 3.68 (s, 2H), 2.83-2.81 (m, 1H), 2.53-2.42 (m, 5H), 2.26-2.15 (m, 1H), 2.00-1.90 (m, 1H), 1.54-1.49 (m, 1H), 1.32-1.28 (m, 1H). MS-ESI calculated [M+H]⁺ 312, found 312.

Example 124

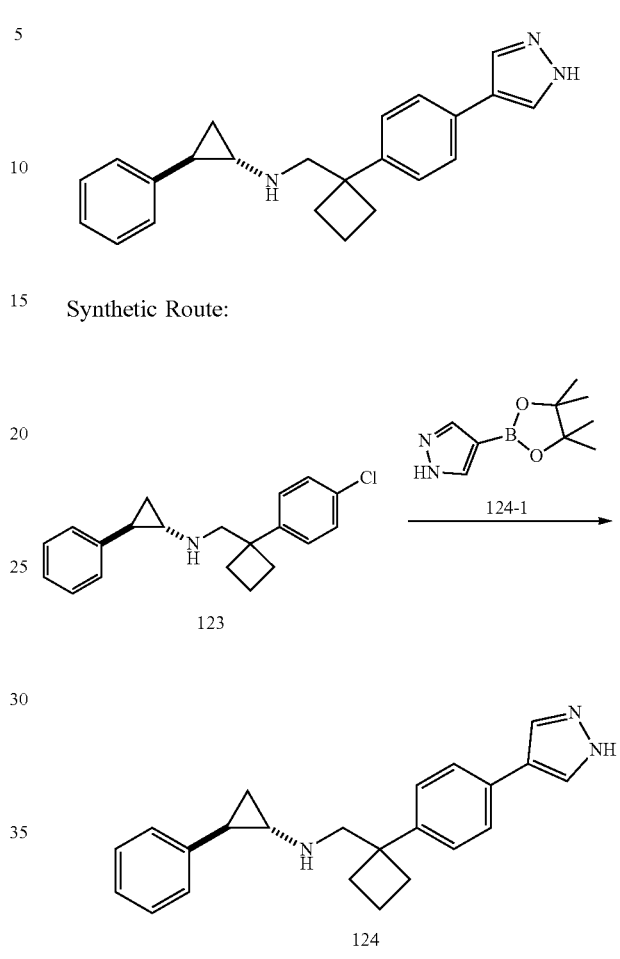

Synthetic Route:

Compound 123 (45.0 mg, 0.144 mmol), compound 124-1 (28.0 mg, 0.144 mmol), potassium carbonate (59.8 mg, 0.433 mmol), tris (dibenzylideneacetone) dipalladium (6.61 mg, 7.22 μmol), 2-dicyclohexylphosphino-2', 4', 6'-triisopropyl-biphenyl (6.88 mg, 14.4 μmol) were dissolved in anhydrous N, N-dimethylformamide (2 mL) and water (0.5 mL). The mixture was stirred at 70° C. for 16 h under nitrogen, cooled to 25° C. Water (10 mL) was added to the mixture. The mixture was extracted with ethyl acetate (25 mL×2). The organic phases were combined, washed with saturated brine (25 mL×2), dried over anhydrous sodium sulfate, followed by filtration and concentration under reduced pressure. The residue was isolated and purified by high-performance liquid chromatography (acidic, hydrochloric acid system) to give compound 124. ¹H NMR (400 MHz, CD₃OD) δ 8.21 (br, 2H), 7.65 (d, J=8.4 Hz, 2H), 7.36 (d, J=8.4 Hz, 2H), 7.28-7.24 (m, 2H), 7.21-7.18 (m, 1H), 7.09-7.07 (m, 2H), 3.68 (s, 2H), 2.82-2.78 (m, 1H), 2.57-2.48 (m, 2H), 2.40-2.38 (m, 2H), 2.25-2.14 (m, 1H), 2.01-1.97 (m, 1H), 1.46-1.40 (m, 1H), 1.32-1.31 (m, 1H), 0.93-0.88 (m, 1H). MS-ESI calculated [M+H]⁺ 344, found 344.

Example 125

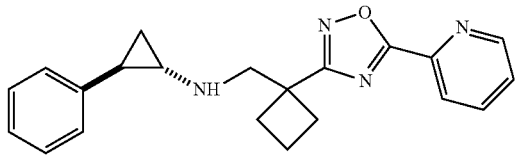

Synthetic Route:

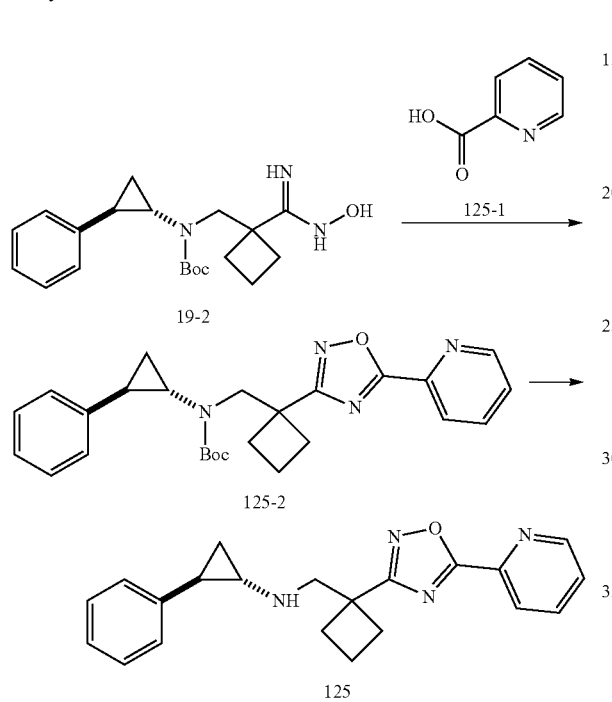

Step 1

Compound 125-1 (61.7 mg, 0.501 mmol) was dissolved in anhydrous dimethylformamide (4 mL), carbonyldiimidazole (88.0 mg, 0.542 mmol) was added, and the reaction mixture was reacted at 30° C. for 2 h. Compound 19-2 (150 mg, 0.417 mmol) was then added and the reaction mixture was stirred at 110° C. for 12 h. The reaction mixture was quenched with water (20 mL) at 0° C., extracted with ethyl acetate (25 mL×2). The organic phases were combined, washed with saturated brine (25 mL×2), dried over anhydrous sodium sulfate, followed by filtration and concentration under reduced pressure to give compound 125-2. MS-ESI calculated [M+Na]$^+$ 469, found 469.

Step 2

Compound 125-2 (120 mg, 0.269 mmol) was dissolved in anhydrous dichloromethane (3 mL). Trimethylsilyl trifluoromethanesulfonate (120 mg, 0.537 mmol) was added at 0° C. After reacting for 0.5 h, water (0.2 mL) was added to the reaction mixture at 0° C. to quench. The mixture was concentrated under reduced pressure, and the compound 125 was obtained by high-performance liquid chromatography (acid, hydrochloric acid). $^1$H NMR (400 MHz, CD$_3$OD) δ 8.90 (d, J=8.0 Hz, 1H), 8.48 (d, J=8.0 Hz, 1H), 8.37-8.33 (m, 1H), 7.93-7.90 (m, 1H), 7.33-7.27 (m, 2H), 7.22-7.17 (m, 3H), 3.93 (s, 2H), 3.14-3.10 (m, 1H), 2.76-2.68 (m, 2H), 2.63-2.57 (m 1H), 2.53-2.45 (m, 2H), 2.30-2.22 (m, 2H), 1.86-1.60 (m, 1H), 1.43-1.39 (m, 1H). MS-ESI calculated [M+H]$^+$ 347, found 347.

Example 126

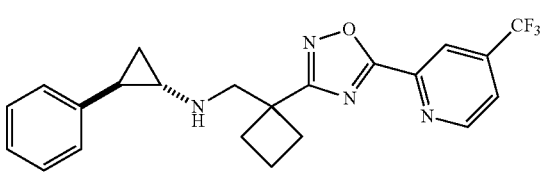

Synthetic Route:

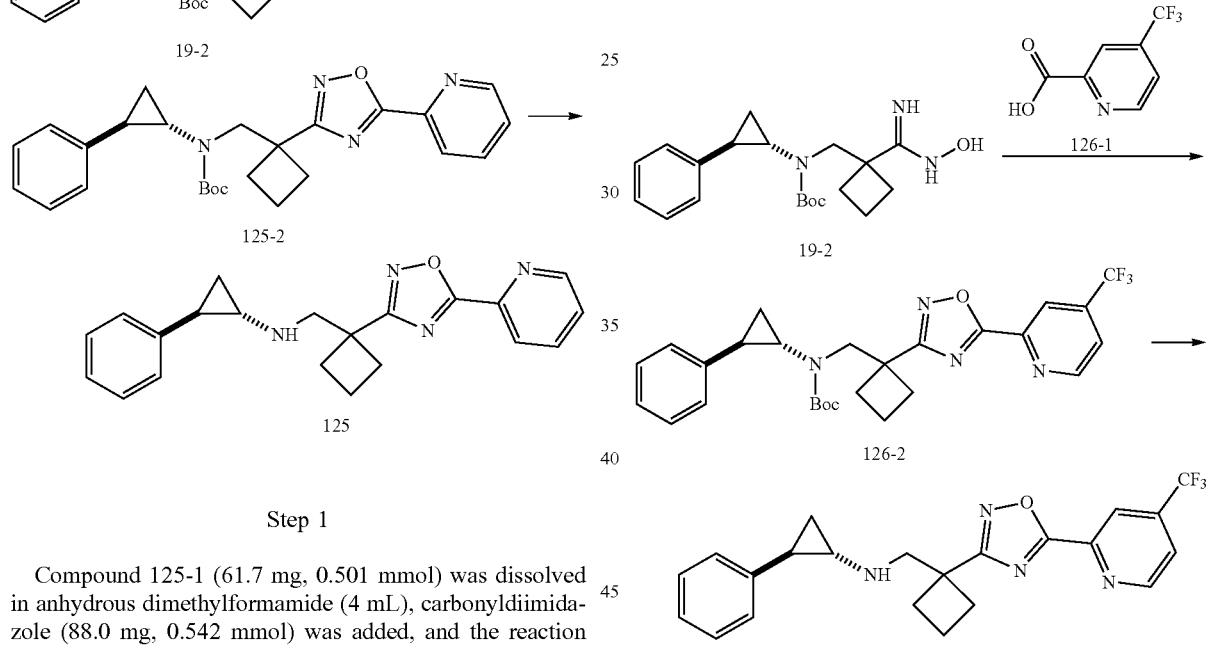

Step 1

The synthesis of compound 126-2 was referred to the first step of example 125. MS-ESI calculated [M+Na]$^+$ 537, found 537.

Step 2

The synthesis of compound 126 was referred to the second step of example 125. $^1$H NMR (400 MHz, CD$_3$OD) δ 9.09 (d, J=5.2 Hz, 1H), 8.54 (s, 1H), 8.04 (d, J=5.2 Hz, 1H) 7.30-7.26 (m, 2H), 7.20-7.15 (m, 3H), 3.93 (s, 2H), 3.13-3.09 (m, 1H), 2.78-2.69 (m, 2H), 2.55-2.42 (m, 3H), 2.31-2.23 (m, 2H), 1.60-1.54 (m, 1H), 1.43-1.40 (m, 1H). MS-ESI calculated [M+H]$^+$ 415, found 415.

Example 127

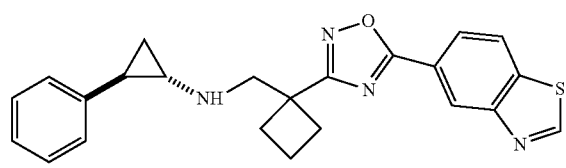

Synthetic Route:

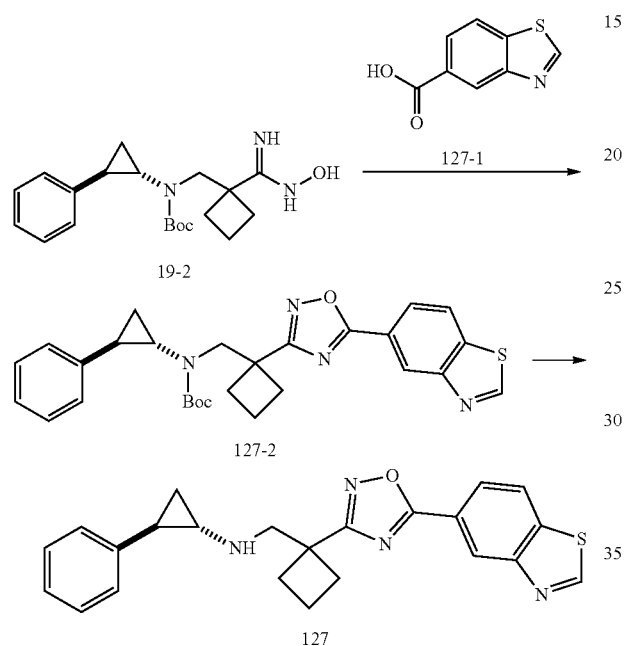

Step 1

The synthesis of compound 127-2 was referred to the first step of example 125. MS-ESI calculated [M+Na]+ 525, found 525.

Step 2

The synthesis of compound 127 was referred to the second step of example 125. ¹H NMR (400 MHz, CD₃OD) δ 9.49 (s, 1H), 8.95 (s, 1H), 8.35-8.26 (m, 2H), 7.31-7.28 (m, 2H), 7.22-7.17 (m, 3H), 3.93 (m, 2H), 3.15-3.11 (m, 1H), 3.28-3.69 (m, 2H), 2.57-2.55 (m, 1H), 2.49-2.41 (m, 2H), 2.31-2.23 (m, 2H), 1.61-1.56 (m, 1H), 1.45-1.39 (m, 1H). MS-ESI calculated [M+H]+ 403, found 403.

Example 128

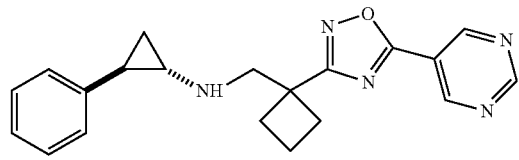

Synthetic Route:

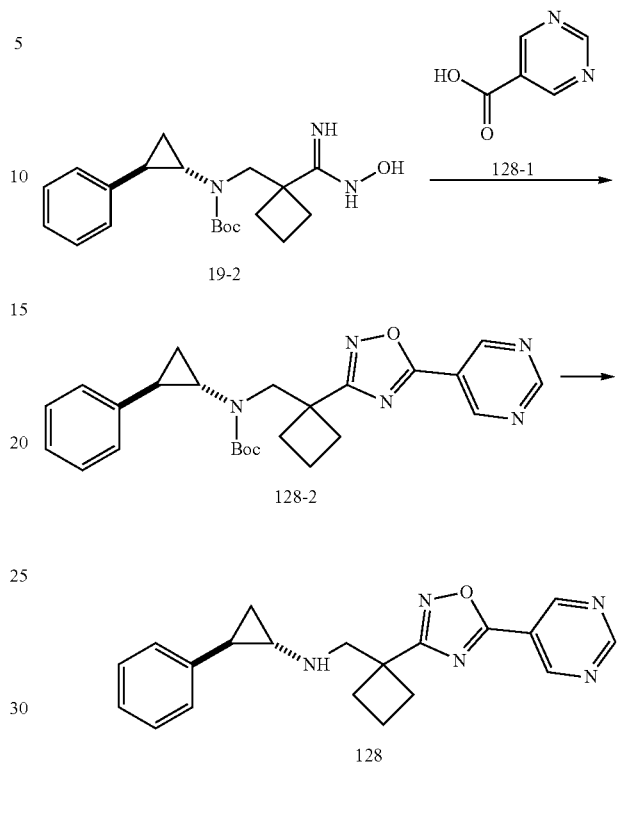

Step 1

The synthesis of compound 128-2 was referred to the first step of example 125. MS-ESI calculated [M+Na]+ 470, found 470.

Step 2

The synthesis of compound 128 was referred to the second step of example 125. ¹H NMR (400 MHz, CD₃OD) δ 9.10-9.09 (m, 2H), 7.79-7.77 (m, 1H), 7.32-7.28 (m, 2H), 7.23-7.18 (m, 3H), 3.93 (s, 2H), 3.15-3.09 (m, 1H), 2.76-2.69 (m, 2H), 2.60-2.54 (m, 1H), 2.51-2.43 (m, 2H), 2.31-2.22 (m, 2H), 1.63-1.54 (m, 1H), 1.44-1.41 (m, 1H). MS-ESI calculated [M+H]+ 348, found 348.

Example 129

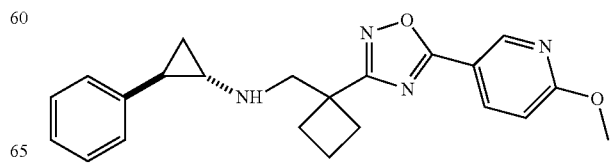

Synthetic Route:

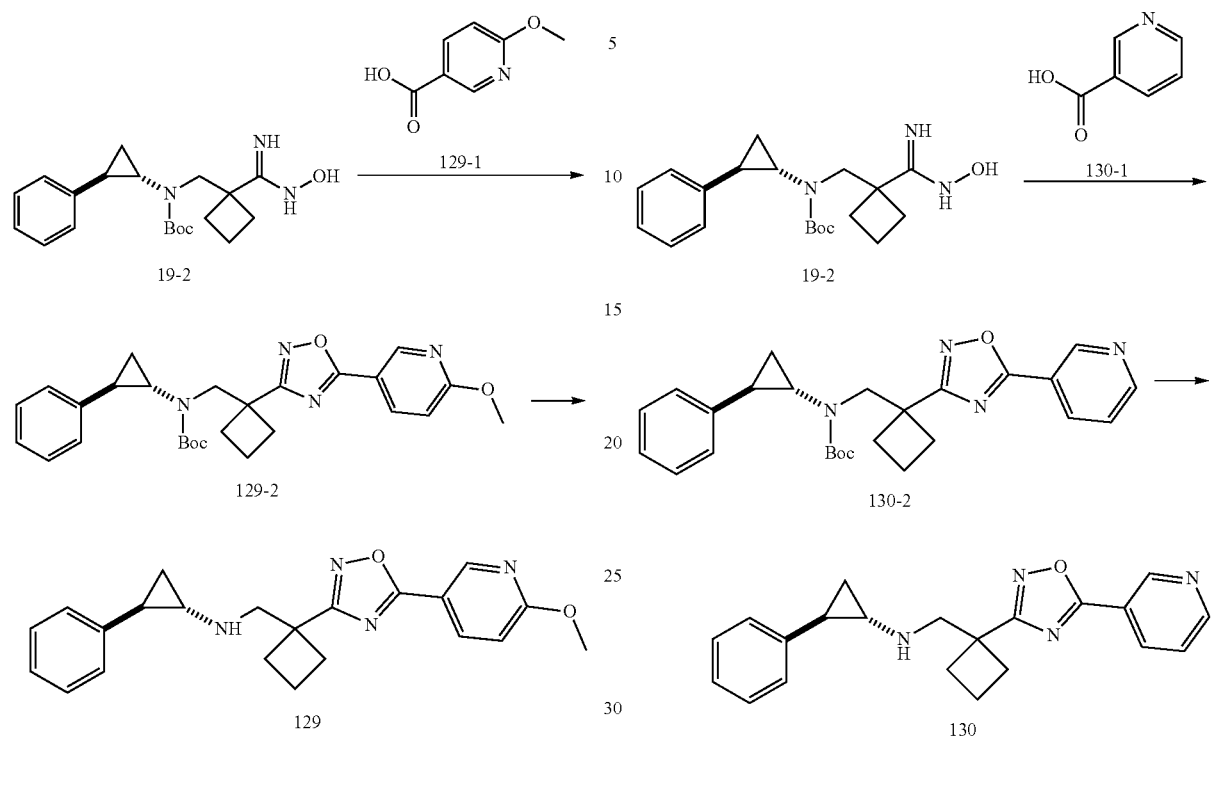

Synthetic Route:

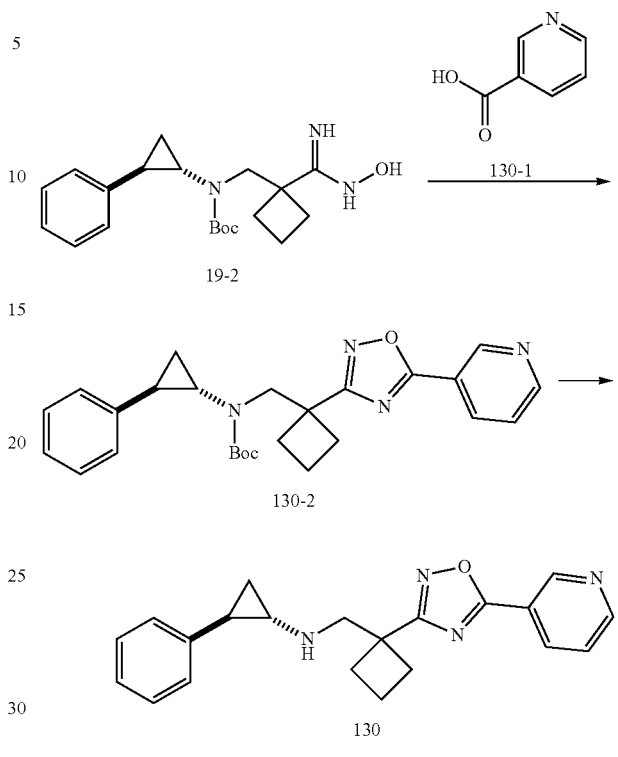

Step 1

The synthesis of compound 129-2 was referred to the first step of example 125. MS-ESI calculated [M+Na]⁺ 499, found 499.

Step 2

The synthesis of compound 129 was referred to the second step of example 125. $^1$H NMR (400 MHz, CD$_3$OD) δ 8.97 (d, J=2.4 Hz, 1H), 8.38 (dd, J=2.4, 8.8 Hz, 1H), 7.32-7.29 (m, 2H), 7.24-7.21 (m, 3H), 7.03-7.01 (d, J=8.8 Hz, 1H), 4.07 (s, 3H), 3.90 (s, 2H), 3.12-3.08 (m, 1H), 2.73-2.66 (m, 2H), 2.56-2.51 (m, 1H), 2.46-2.40 (m, 2H), 2.28-2.23 (m, 2H), 1.60-1.54 (m, 1H), 1.44-1.39 (m, 1H). MS-ESI calculated [M+H]⁺ 377, found 377.

Example 130

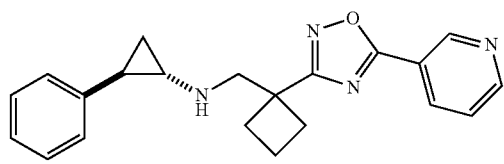

Step 1

The synthesis of compound 130-2 was referred to the first step of example 125. MS-ESI calculated [M+Na]⁺ 469, found 469.

Step 2

The synthesis of compound 130 was referred to the second step of example 125. $^1$H NMR (400 MHz, CD$_3$OD) δ 9.65 (s, 1H), 9.30 (d, J=7.6 Hz, 1H), 9.18 (d, J=7.6 Hz, 1H), 8.39-8.36 (m, 1H), 7.29-7.25 (m, 2H), 7.19-7.16 (m, 3H), 3.94 (s, 2H), 3.10-3.09 (m, 1H), 2.77-2.63 (m, 3H), 2.52-2.49 (m, 2H), 2.29-2.22 (m, 2H), 1.68-1.65 (m, 1H), 1.40-1.37 (m, 1H). MS-ESI calculated [M+H]⁺ 347, found 347.

Example 131

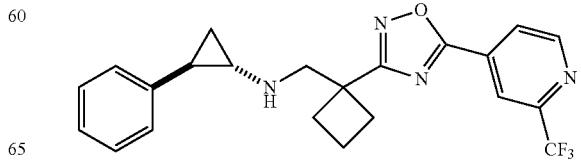

Synthetic Route:

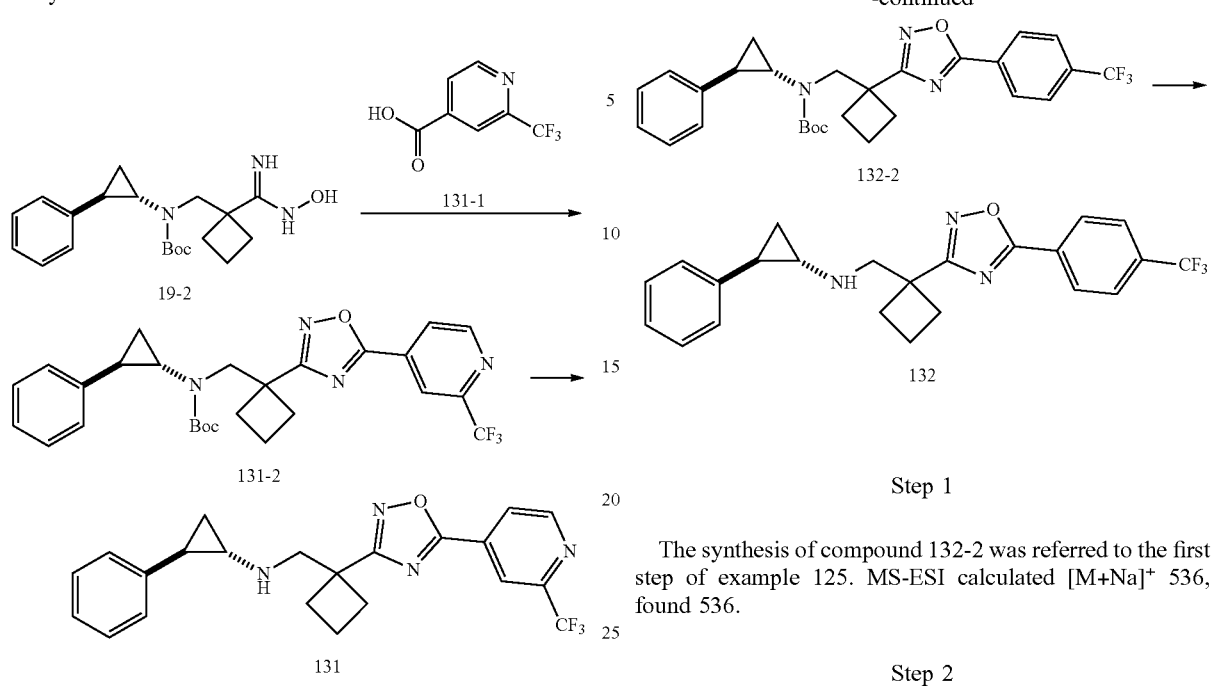

Step 1

The synthesis of compound 131-2 was referred to the first step of example 125. MS-ESI calculated [M+Na]$^+$ 537, found 537.

Step 2

The synthesis of compound 131 was referred to the second step of example 125. $^1$H NMR (400 MHz, CD$_3$OD) δ 9.04 (d, J=4.8 Hz, 1H), 8.43 (s, 1H), 8.34 (d, J=4.8 Hz, 1H), 7.29-7.25 (m, 2H), 7.19-7.08 (m, 3H), 3.97 (s, 2H), 3.11-3.08 (m, 1H), 2.73-2.68 (m, 2H), 2.55-2.43 (m, 3H), 2.30-2.22 (m, 2H), 1.61-1.55 (m, 1H), 1.42-1.39 (m, 1H). MS-ESI calculated [M+H]$^+$ 415, found 415.

Example 132

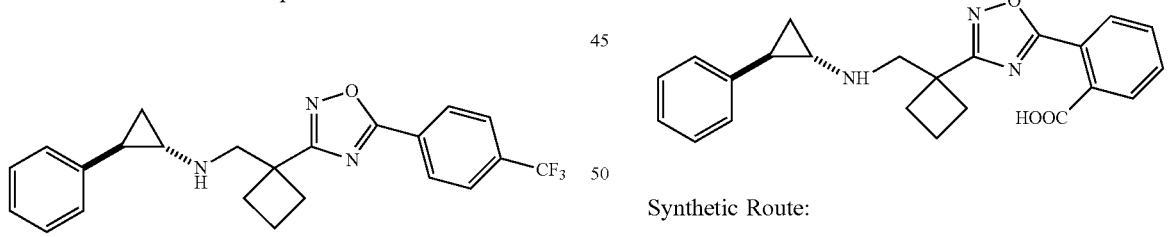

Synthetic Route:

Step 1

The synthesis of compound 132-2 was referred to the first step of example 125. MS-ESI calculated [M+Na]$^+$ 536, found 536.

Step 2

The synthesis of compound 132 was referred to the second step of example 125. $^1$H NMR (400 MHz, CD$_3$OD) δ 8.37 (d, J=8.0 Hz, 2H), 7.95 (d, J=8.0 Hz, 2H), 7.31-7.27 (m, 2H), 7.24-7.16 (m, 3H), 3.91 (s, 2H), 3.12-3.08 (m, 1H), 2.75-2.67 (m, 2H), 2.56-2.51 (m, 1H), 2.49-2.41 (m, 2H), 2.29-2.22 (m, 2H), 1.60-1.55 (m, 1H), 1.43-1.39 (m, 1H). MS-ESI calculated [M+H]$^+$414, found 414.

Example 134

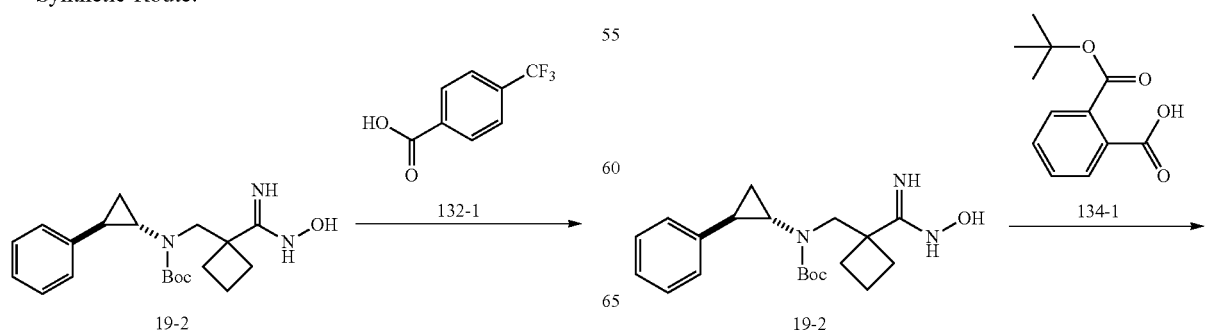

Synthetic Route:

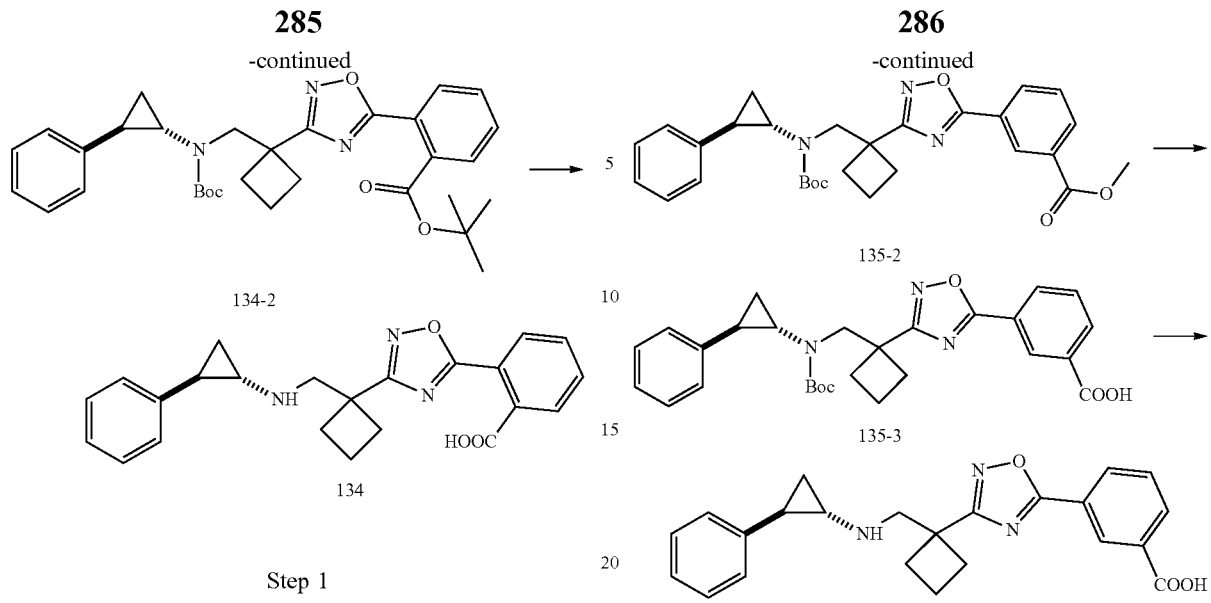

Step 1

The synthesis of compound 134-2 was referred to the first step of example 125. MS-ESI calculated [M+Na]⁺ 568, found 568.

Step 2

Compound 134-2 (46.0 mg, 0.843 mmol) was dissolved in anhydrous dichloromethane (3 mL). Trifluoroacetic acid (127 mg, 1.11 mmol) was added, and the mixture was stirred at 25° C. for 2 h. The mixture was concentrated under reduced pressure, and compound 134 was obtained by high-performance liquid chromatography (acid, hydrochloric acid). ¹H NMR (400 MHz, CD$_3$OD) δ 8.01-8.00 (m, 1H), 7.87-7.85 (m, 1H), 7.80-7.77 (m, 2H), 7.32-7.28 (m, 2H), 7.24-7.22 (m, 1H), 7.21-7.17 (m, 2H), 3.88 (s, 2H), 3.11-3.07 (m, 1H), 2.72-2.65 (m, 2H), 2.59-2.53 (m, 1H), 2.43-2.37 (m, 2H), 2.27-2.22 (m, 2H), 1.59-1.58 (m, 1H), 1.40-1.38 (m, 1H). MS-ESI calculated [M+H]⁺ 390, found 390.

Example 135

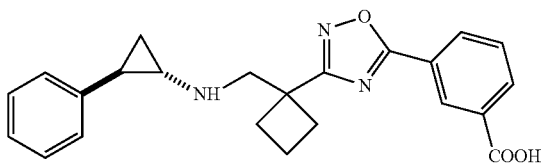

Synthetic Route:

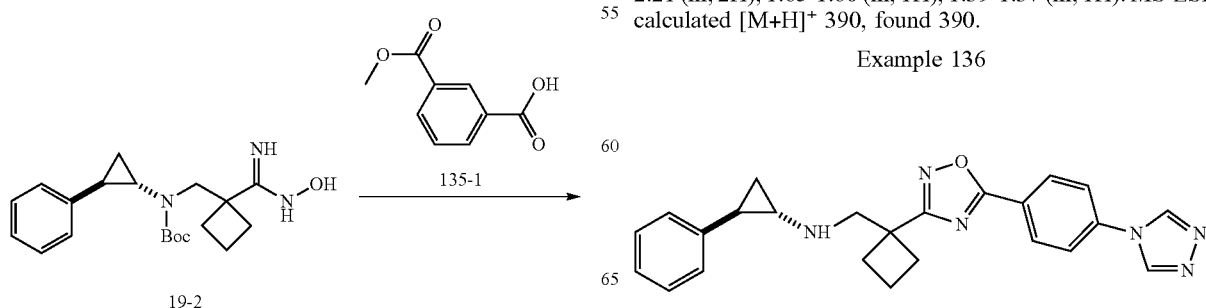

Step 1

The synthesis of compound 135-2 was referred to the first step of example 125. MS-ESI calculated [M+Na]⁺ 526, found 526.

Step 2

Compound 135-2 (56.0 mg, 0.111 mmol) and lithium hydroxide (13.3 mg, 0.556 mmol) were dissolved in tetrahydrofuran (3 mL) and water (1 mL). The mixture was stirred at 25° C. for 2 h, quenched by adding hydrochloric acid aqueous solution (5 mL, 1 mol/L), and extracted with ethyl acetate (5 mL×2). The organic phases were combined, washed with saturated brine (5 mL×2), dried over anhydrous sodium sulfate, followed by filtration and concentration under reduced pressure to give compound 135-3. MS-ESI calculated [M+Na]+512, found 512.

Step 3

Compound 135-2 (45.0 mg, 91.9 μmol) was dissolved in anhydrous dichloromethane (2 mL). Trifluoroacetic acid (52.4 mg, 0.460 mmol) was added, and the mixture was stirred at 25° C. for 2 h. The mixture was concentrated under reduced pressure, and compound 135 was obtained by high-performance liquid chromatography (acid, hydrochloric acid). ¹H NMR (400 MHz, CD$_3$OD) δ 8.75 (s, 1H), 8.38-8.31 (m, 2H), 7.77-7.73 (m, 1H), 7.30-7.26 (m, 2H), 7.21-7.15 (m, 3H), 3.90 (s, 2H), 3.10-3.08 (m, 1H), 2.75-2.68 (m, 2H), 2.62-2.57 (m, 1H), 2.50-2.42 (m, 2H), 2.29-2.21 (m, 2H), 1.65-1.60 (m, 1H), 1.39-1.37 (m, 1H). MS-ESI calculated [M+H]⁺ 390, found 390.

Example 136

Synthetic Route:

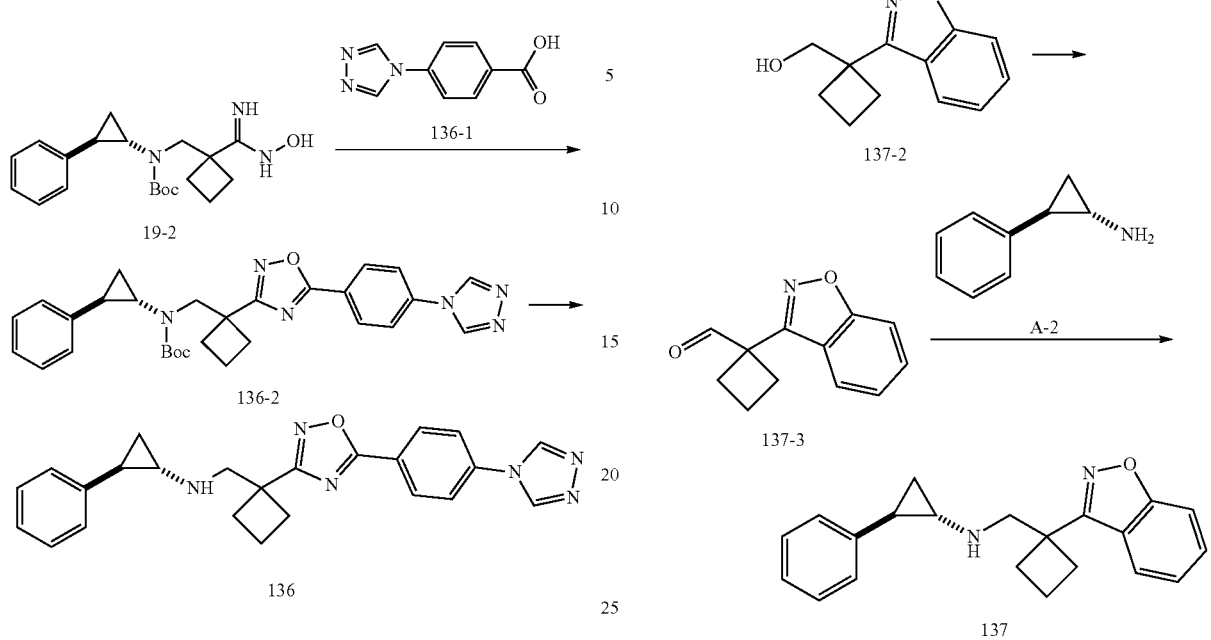

Step 1

The synthesis of compound 136-2 was referred to the first step of example 125. MS-ESI calculated [M+H]$^+$ 513, found 513.

Step 2

The synthesis of compound 136 was referred to the third step of example 135. $^1$H NMR (400 MHz, CD$_3$OD) δ 9.96 (s, 2H), 8.46 (d, J=8.4 Hz, 2H), 8.08 (d, J=8.4 Hz, 2H), 7.31-7.28 (m, 2H), 7.23-7.18 (m, 3H), 3.93 (s, 2H), 3.13-3.10 (m, 1H), 2.76-2.68 (m, 2H), 2.66-2.61 (m, 1H), 2.53-2.47 (m, 2H), 2.30-2.23 (m, 2H), 1.68-1.63 (m 1H), 1.43-1.40 (m, 1H). MS-ESI calculated [M+H]$^+$ 413, found 413.

Example 137

Synthetic Route:

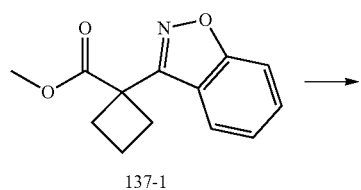

Step 1

Compound 137-1 (700 mg, 3.03 mmol) was dissolved in anhydrous methanol (10 mL), lithium borohydride (132 mg, 6.06 mmol) was added portionwise at 0° C. The reaction was stirred at 30° C. for 16 h. Water (10 mL) was added to the reaction mixture at 0° C. The mixture was extracted with ethyl acetate (25 mL×2). The organic phases were combined, washed with saturated brine (25 mL×2), dried over anhydrous sodium sulfate, followed by filtration and concentration under reduced pressure. The compound 137-2 was isolated and purified by preparative thin layer chromatography (2:1 petroleum ether/ethyl acetate, Rf=0.2). $^1$H NMR (400 MHz, CD$_3$OD) δ 7.80 (d, J=6.8 Hz, 1H), 7.62-7.54 (m, 2H), 7.35-7.33 (m, 1H), 4.12 (d, J=6.8 Hz, 2H), 2.79-2.71 (m, 2H), 2.44-2.37 (m, 2H), 2.31-2.14 (m, 2H).

Step 2

Compound 137-2 (210 mg, 1.03 mmol) was dissolved in anhydrous dichloromethane (5 mL), Dess-Martin oxidant (482 mg, 1.14 mmol) was added. The mixture was stirred at 15° C. for 2 h. Saturated sodium bicarbonate aqueous solution (10 mL) was added to the reaction mixture until no gas released, saturated sodium thiosulfate aqueous solution (10 mL) was added, and the mixture was extracted with dichloromethane (20 mL×3). The organic phases were combined, washed with saturated brine (20 mL×3), dried over anhydrous sodium sulfate, followed by filtration and concentration under reduced pressure to give compound 137-3. MS-ESI calculated [M+H]$^+$202, found 202.

Step 3

Compound 137-3 (215 mg, 1.07 mmol) and compound A-2 (157 mg, 1.18 mmol) were dissolved in anhydrous dichloromethane (5 mL), acetic acid (193 mg, 3.21 mmol)

was added. The reaction solution was stirred at 20° C. for 1 h. And then sodium triacetoxyborohydride (680 mg, 3.21 mmol) was added. The reaction mixture was stirred at 20° C. for 1 h. The reaction solution was diluted with dichloromethane (10 mL) and washed successively with saturated sodium carbonate aqueous solution (10 mL×3), water (10 mL×2), saturated brine (10 mL×2). The organic phases were combined, washed with saturated brine (10 mL×2), dried over anhydrous sodium sulfate, followed by filtration and concentration under reduced pressure. The mixture was separated by high-performance liquid chromatography (neutral system), the product was formed into a salt by hydrochloric acid aqueous solution (0.5 mL, 4 mol/L), and the mixture was concentrated under reduced pressure to give compound 137. $^1$H NMR (400 MHz, CD$_3$OD) δ 7.76-7.74 (m, 1H), 7.60-7.55 (m, 2H), 7.32-7.29 (m, 1H), 7.16-7.13 (m, 2H), 7.08-7.04 (m, 1H), 6.89-6.87 (m, 2H), 3.36-3.35 (m, 2H), 2.70-2.63 (m, 2H), 2.43-2.35 (m, 2H), 2.25-2.20 (m, 1H), 2.17-2.02 (m, 2H), 1.71-1.67 (m, 1H), 0.92-0.88 (m, 1H), 0.83-0.80 (m, 1H). MS-ESI calculated [M+H]$^+$ 1319, found 319.

Example 138

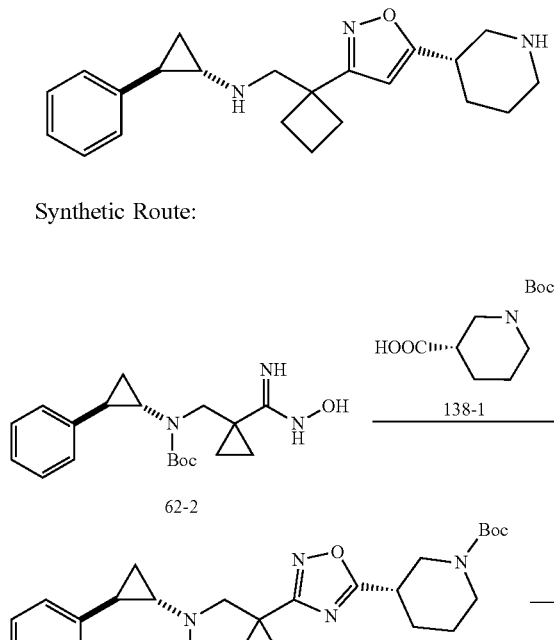

Synthetic Route:

138

Step 1

The synthesis of compound 138-2 was referred to the first step of example 125. MS-ESI calculated [M+Na]$^+$ 561, found 561.

Step 2

Compound 138-2 (100 mg, 0.186 mmol) was dissolved in anhydrous dichloromethane (5 mL). Trifluoroacetic acid (84.7 mg, 0.743 mmol) was added. The mixture was stirred at 20° C. for 2 h, concentrated under reduced pressure, and compound 138 was obtained by high-performance liquid chromatography (acid, hydrochloric acid). $^1$H NMR (400 MHz, CD$_3$OD) δ 7.33-7.29 (m, 2H), 7.25-7.21 (m, 1H), 7.18-7.16 (m, 2H), 3.75-3.57 (m, 4H), 3.42-3.36 (m, 2H), 3.14-3.07 (m, 2H), 2.68-2.62 (m, 1H), 2.29-2.25 (m, 1H), 2.03-1.88 (m, 3H), 1.68-1.63 (m, 1H), 1.47-1.37 (m, 5H). MS-ESI calculated [M+H]$^+$ 339, found 339.

Example 139

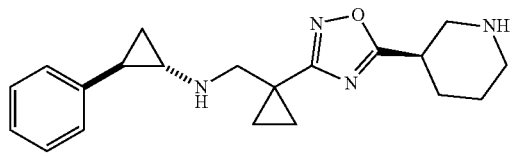

Synthetic Route:

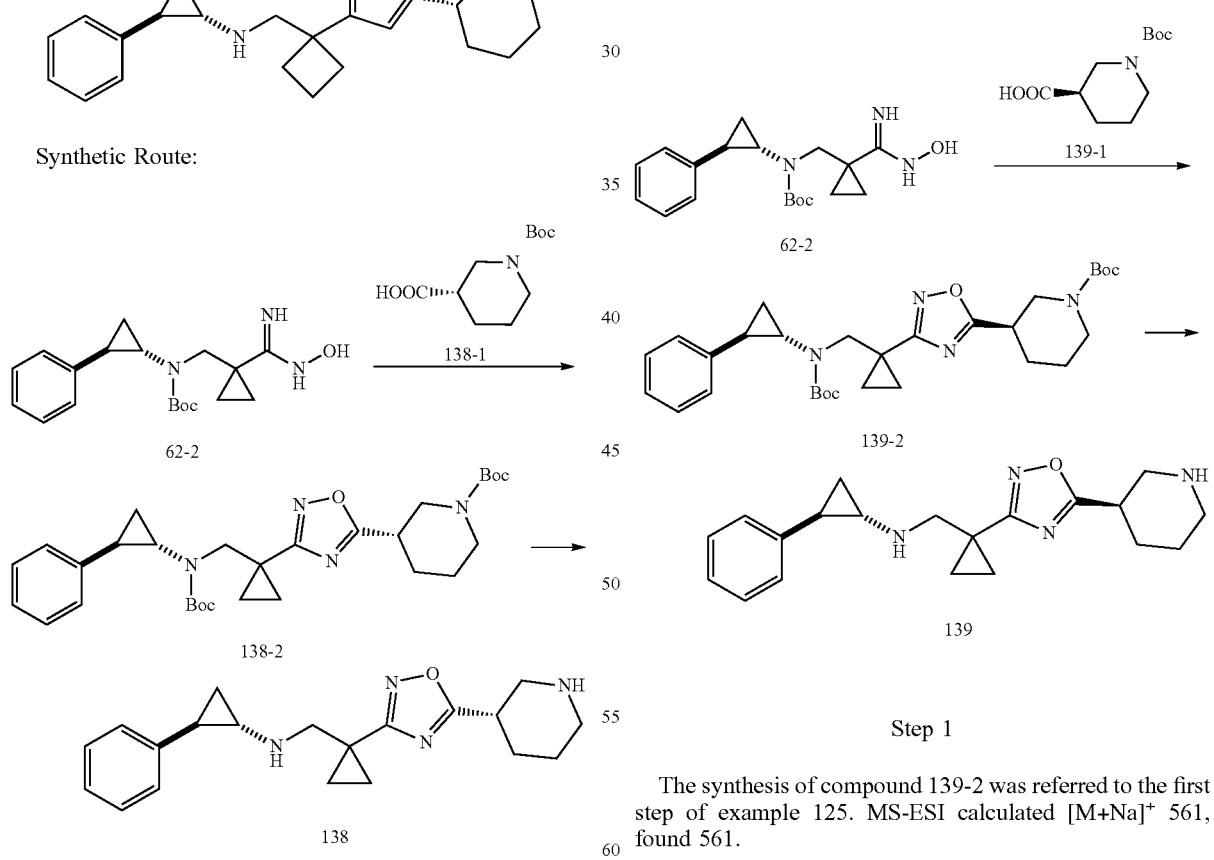

139

Step 1

The synthesis of compound 139-2 was referred to the first step of example 125. MS-ESI calculated [M+Na]$^+$ 561, found 561.

Step 2

The synthesis of compound 139 was referred to the second step of example 138. $^1$H NMR (400 MHz, CD$_3$OD) δ 7.32-7.29 (m, 2H), 7.24-7.21 (m, 1H), 7.18-7.16 (m, 2H), 3.74-3.49 (m, 4H), 3.42-3.36 (m, 2H), 3.14-3.07 (m, 2H), 2.70-2.61 (m, 1H), 2.28-2.26 (m, 1H), 2.03-1.88 (m, 3H), 1.67-1.62 (m, 1H), 1.47-1.37 (m, 5H). MS-ESI calculated [M+H]⁺ 339, found 339.

Example 140, Example 141

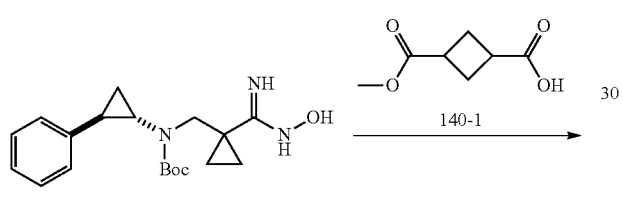

Synthetic Route:

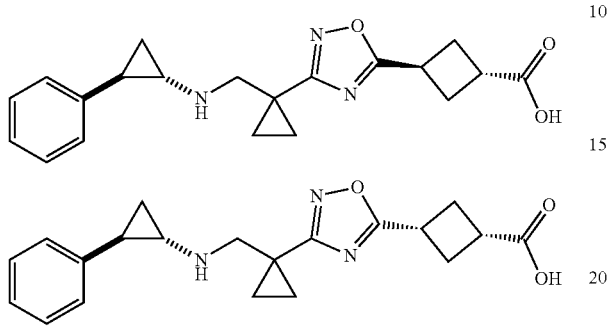

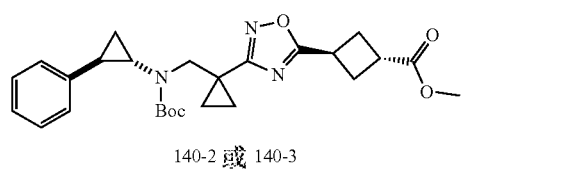

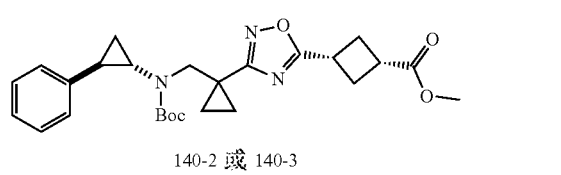

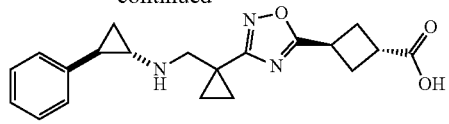

140 或 141

+

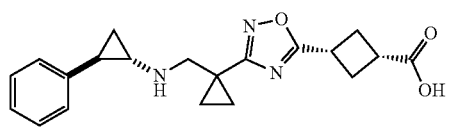

140 或 141

Step 1

The synthesis of crude product was referred to the first step of example 125. The crude product was purified by thin layer chromatography to give compound 140-2 (2:1 petroleum ether/ethyl acetate, Rf=0.7). MS-ESI calculated [M+Na]⁺ 490, found 490. 140-3 (2:1 petroleum ether/ethyl acetate. Rf=0.6). MS-ESI calculated [M+Na]⁺ 490, found 490.

Step 2

Compound 140-2 (115 mg, 0.246 mmol) was dissolved in tetrahydrofuran (2 mL) and water (0.5 mL), lithium hydroxide (103 mg, 2.46 mmol) was added. The mixture was stirred at 50° C. for 12 h. Hydrochloric acid aqueous solution (5 mL, 1 mol/L) was added at 0° C. to the reaction solution to quench. The mixture was extracted with ethyl acetate (10 mL×2). The organic phases were combined, washed with saturated brine (10 mL×2), dried over anhydrous sodium sulfate, followed by filtration and concentration under reduced pressure to give compound 140-4. MS-ESI calculated [M+Na]⁺ 476, found 476. Referring to the same method, compound 140-3 was prepared to obtain compound 141-1. MS-ESI calculated [M+Na]⁺ 476, found 476.

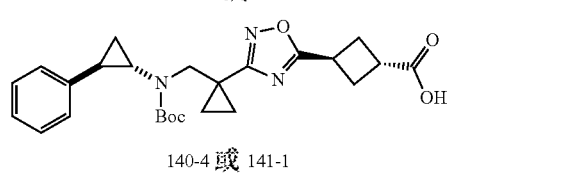

140-4 或 141-1

+

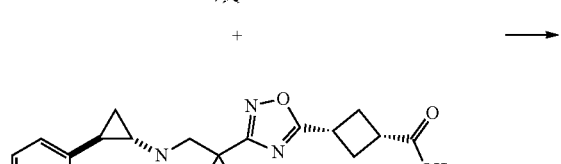

140-4 或 141-1

Step 3

Compound 140-4 (108 mg, 0.238 mmol) was dissolved in anhydrous dichloromethane (2 mL). Trifluoroacetic acid (54.3 mg, 0.476 mmol) was added, and the mixture was stirred at 20° C. for 0.5 h, and concentrated under reduced pressure. Compound 140 was obtained by high-performance liquid chromatography (acidic, hydrochloric acid), that is, example 140. ¹H NMR (400 MHz, CD₃OD) δ 7.33-7.30 (m, 2H), 7.25-7.22 (m, 1H) 7.19-7.17 (m, 2H), 3.76-3.65 (m, 3H), 3.39-3.31 (m, 1H), 3.13-3.10 (m, 1H), 2.77-2.71 (m, 2H), 2.67-2.59 (m, 3H), 1.69-1.64 (m, 1H), 1.48-1.38 (m, 5H). MS-ESI calculated [M+H]⁺ 354, found 354. Referring to the same method, compound 141-1 was prepared to obtain compound 141. That is, example 141. ¹H NMR (400 MHz, CD₃OD) δ 7.32-7.29 (m, 2H), 7.24-7.21 (m, 1H), 7.17-7.15 (m, 2H), 3.72-3.62 (m, 3H), 3.28-3.21 (m, 1H), 3.10-3.06 (m, 1H), 2.77-2.55 (m, 5H), 1.67-1.58 (m, 1H), 1.45-1.36 (m, 5H). MS-ESI calculated [M+H]⁺ 354, found 354.

Example 142

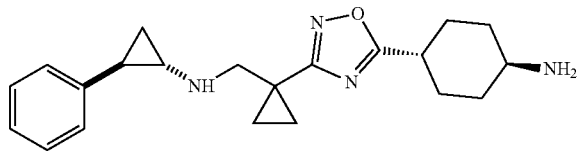

Synthetic Route:

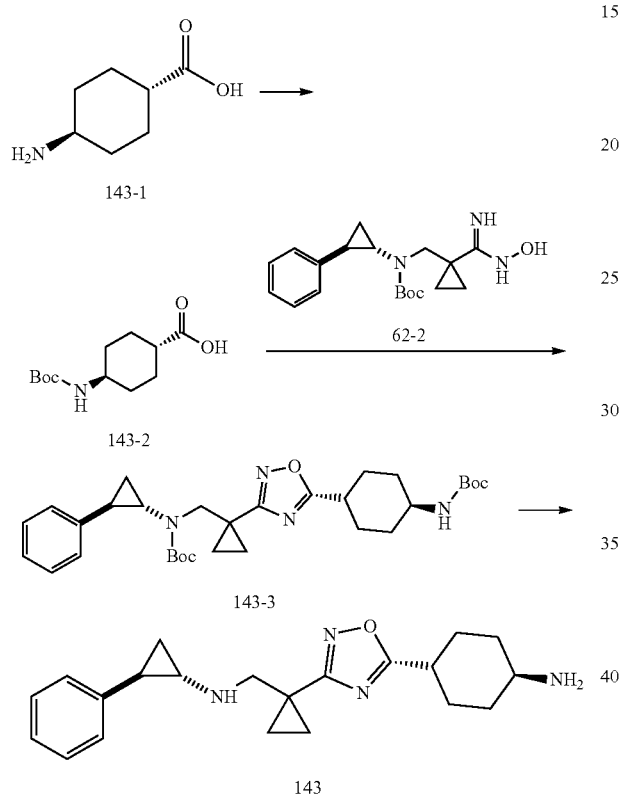

Step 1

Compound 142-1 (200 mg, 1.40 mmol) was dissolved in acetone (5 mL) and water (1 mL), di-tert-butyl dicarbonate (396 mg, 1.82 mmol) and potassium carbonate (232 mg, 1.68 mmol) were added. The mixture was stirred at 20° C. for 12 h. Hydrochloric acid aqueous solution (10 mL, 1 mol/L) was added to the mixture at 0° C. The mixture was extracted with ethyl acetate (10 mL×2). The organic phases were combined, washed with saturated brine (10 mL×2), dried over anhydrous sodium sulfate, followed by filtration and concentration under reduced pressure. The compound 142-2 was isolated and purified by preparative thin layer chromatography (10:1 dichloromethane/methanol, Rf=0.6). $^1$H NMR (400 MHz, CDCl$_3$) δ 3.48-3.47 (m, 1H), 2.51-2.48 (m, 1H), 1.98-1.94 (m, 2H), 1.72-1.54 (m, 6H), 1.45 (s, 9H).

Step 2

The synthesis of compound 142-3 was referred to the first step of example 125. MS-ESI calculated [M+Na]$^+$ 575, found 575.

Step 3

The synthesis of compound 142 was referred to the third step of example 140. $^1$H NMR (400 MHz, CD$_3$OD) δ 7.34-7.30 (m, 2H), 7.26-7.22 (m, 1H), 7.21-7.19 (m, 2H), 3.76-3.66 (m, 2H), 3.32-3.27 (m, 2H), 3.13-3.09 (m, 1H), 2.71-2.66 (m, 1H), 2.30-2.26 (m, 2H), 2.00-1.92 (m, 4H), 1.78-1.64 (m, 3H), 1.52-1.47 (m, 2H), 1.43-1.38 (m, 3H). MS-ESI calculated [M+H]$^+$ 353, found 353.

Example 143

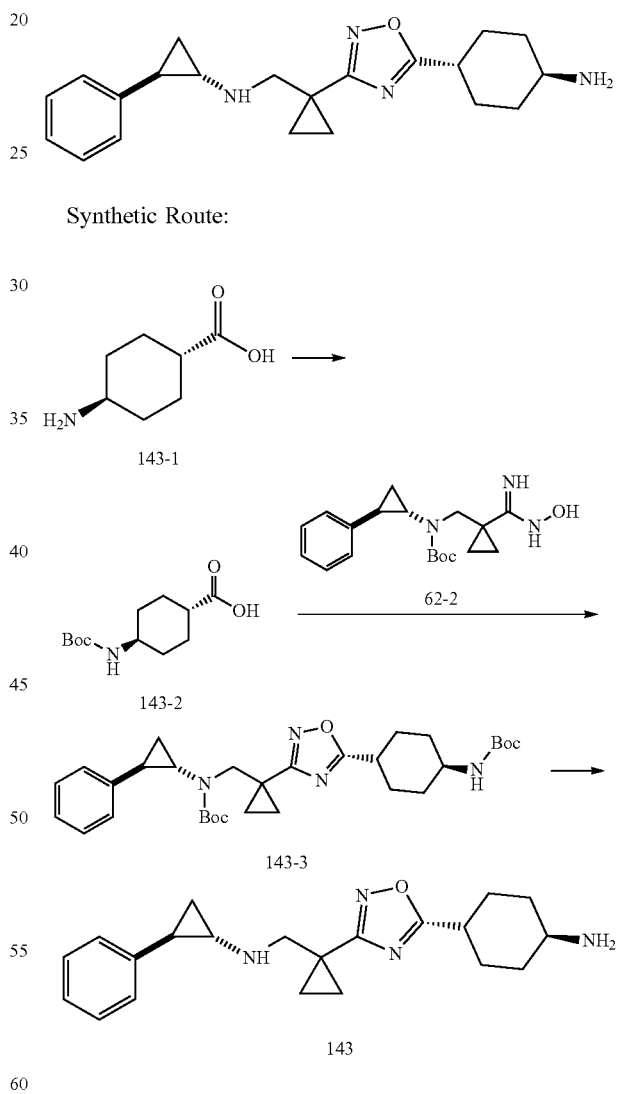

Synthetic Route:

Step 1

The synthesis of compound 143-2 was referred to the first step of example 142. $^1$H NMR (400 MHz, CDCl$_3$) δ4.40 (s, 1H), 3.43 (m, 1H), 2.30-2.24 (m, 2H), 2.07-2.04 (m, 6H), 1.45 (s, 9H).

Step 2

The synthesis of compound 143-3 was referred to the first step of example 125. MS-ESI calculated [M+Na]⁺ 575, found 575.

Step 3

The synthesis of compound 143 was referred to the third step of example 140. ¹H NMR (400 MHz, CD$_3$OD) δ 7.32-7.29 (m, 2H), 7.24-7.22 (m, 1H), 7.15-7.13 (m, 2H), 3.54-3.43 (m, 3H), 3.06-2.94 (m, 3H), 2.10-2.06 (m, 4H), 1.60-1.44 (m, 7H), 1.23-1.23 (m, 3H). MS-ESI calculated [M+H]⁺ 353, found 353.

Example 144

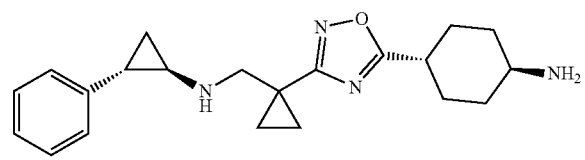 [SMILES: N[C@H]1CC[C@H](c2nc(C3(CN[C@@H]4C[C@H]4c4ccccc4)CC3)no2)CC1]

Synthetic Route:

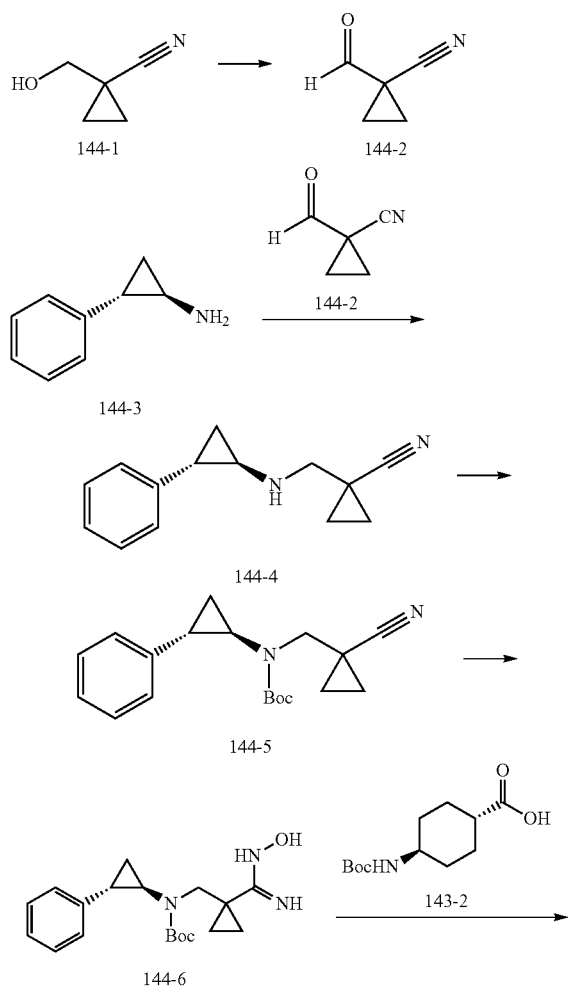

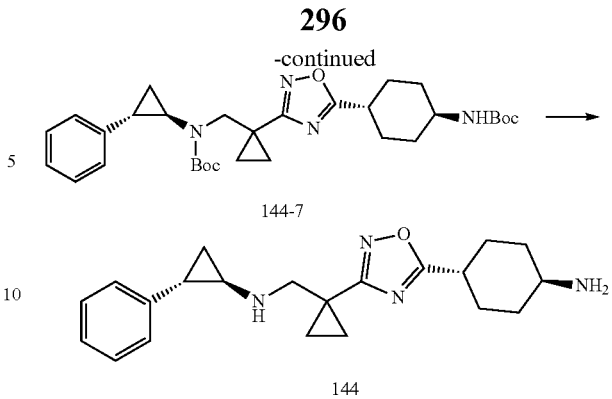

Step 1

Compound 144-1 (5.80 g, 59.7 mmol) was dissolved in anhydrous dichloromethane (100 mL) under nitrogen, Dess Martin reagent (26.6 g, 62.7 mmol) was added. The mixture was stirred at 25° C. for 1 h. Saturated sodium carbonate aqueous solution (200 mL) was added and the mixture was extracted with dichloromethane (100 mL×1). The organic phase was washed with saturated brine (100 mL×1), dried over anhydrous sodium sulfate, followed by filtration and concentration under reduced pressure. The compound 144-2 was isolated and purified by silica gel column chromatography (5:1 petroleum ether/ethyl acetate, Rf=0.6). ¹H NMR (400 MHz, CDCl$_3$) δ 9.31 (s, 1H), 1.71-1.68 (m, 4H).

Step 2

Compound 144-3 (41.2 g, 288 mmol) was dissolved in anhydrous dichloromethane (400 mL), and acetic acid (1.73 g, 28.8 mmol) and compound 144-2 (33.8 g, 316 mmol) were added to the reaction mixture. The reaction solution was stirred at 25° C. for 1 h. Sodium triacetoxyborohydride (91.5 g, 432 mmol) was added. The reaction mixture was stirred at 25° C. for 11 h. And then saturated sodium bicarbonate (500 mL) was added to the mixture, and the mixture was extracted with dichloromethane (500 mL×2). The organic phases were combined, concentrated by rotary evaporation and then added with water (500 mL). The mixture was adjusted to pH=3 with 1N hydrochloric acid aqueous solution, extracted with methyl tert-butyl ether (500 mL×1). The aqueous phase was adjusted to pH=8 with the saturated sodium carbonate aqueous solution. The mixture was extracted with dichloromethane (500 mL×2). The organic phase was washed with saturated brine (500 mL×1), dried over anhydrous sodium sulfate, followed by filtration and concentration under reduced pressure to give compound 144-4. ¹H NMR (400 MHz, CDCl$_3$) δ 7.29-7.26 (m, 2H), 7.19-7.16 (m, 1H), 7.06-7.04 (m, 2H), 2.83 (s, 2H), 2.51-2.48 (m, 1H), 2.01-1.96 (m, 1H), 1.28-1.24 (m, 2H), 1.18-1.13 (m, 1H), 1.05-1.01 (m, 1H), 0.88-0.79 (m, 2H).

Step 3

Compound 144-4 (3.80 g, 17.9 mmol) was dissolved in tetrahydrofuran (30 mL) and water (6 mL), di-tert-butyl dicarbonate (4.30 g, 19.7 mmol) and lithium hydroxide monohydrate (0.901 g, 21.5 mmol), were added to the reaction mixture, and the reaction solution was stirred at 25° C. for 12 h. The reaction solution was concentrated under reduced pressure, and the mixture was was adjusted to pH=5 with 1N hydrochloric acid aqueous solution. The mixture was extracted with ethyl acetate (30 mL×2). The organic phase was washed with saturated brine (40 mL×1), dried over anhydrous sodium sulfate, followed by filtration and concentration under reduced pressure. The compound 144-5 was isolated and purified by silica gel column chromatography (5:1 petroleum ether/ethyl acetate, Rf=0.7). ¹H NMR (400 MHz, CDCl₃) δ 7.23-7.21 (m, 2H), 7.13-7.10 (m, 1H), 7.07-7.05 (m, 2H), 3.42-3.31 (m, 2H), 2.90-2.88 (m, 1H), 2.10-2.05 (m, 1H), 1.37 (s, 9H), 1.28-1.16 (m, 4H), 1.00-0.90 (m, 2H).

Step 4

Compound 144-5 (2.00 g, 5.89 mmol) was dissolved in anhydrous ethanol (40 mL), hydroxylamine hydrochloride (818 mg, 11.8 mmol) and diisopropylethylamine (3.04 g, 23.6 mmol) were added. The mixture was stirred at 80° C. for 12 h. The solvent was removed by concentration under reduced pressure. The crude product obtained was dissolved in ethyl acetate (50 mL) and water (50 mL). The organic phase was washed sequentially with saturated ammonium chloride solution (50 mL×1) and saturated brine (50 mL×1), dried over anhydrous sodium sulfate, followed by filtration and concentration under reduced pressure to give compound 144-6. MS-ESI calculated [M+H]⁺ 346, found 346.

Step 5

Compound 143-2 (174 mg, 0.715 mmol) was dissolved in anhydrous N,N-dimethylformamide (5 mL). The mixture was added with carbonyl diimidazole (127 mg, 0.781 mmol) under nitrogen at 30° C. and stirred for 2 h. Compound 144-6 (250 mg, 0.651 mmol) was added to the reaction mixture, and the reaction mixture was heated to 110° C. and stirred for 10 h. The reaction solution was cooled to room temperature, and water (50 mL) was added to the mixture. The mixture was extracted with ethyl acetate (50 mL×3). The organic phases were combined, washed with saturated brine (50 mL×2), dried over anhydrous sodium sulfate, followed by filtration and concentration under reduced pressure. The compound 144-7 was isolated and purified by preparative thin layer chromatography (2:1 petroleum ether/ethyl acetate, Rf=0.4). MS-ESI calculated [M+Na]⁺ 575, found 575.

Step 6

Compound 144-7 (260 mg, 0.470 mmol) was dissolved in anhydrous dichloromethane (8 mL). Trifluoroacetic acid was added at 0° C. The reaction solution was stirred at 0° C. for 0.5 h, concentrated under reduced pressure, and subjected to high-performance liquid chromatography (acid, hydrochloric acid) to give compound 144. ¹H NMR (400 MHz, CD₃OD) δ 7.32-7.29 (m, 2H), 7.25-7.21 (m, 1H), 7.17-7.14 (m, 2H), 3.70-3.62 (m, 2H), 3.21-3.14 (m, 1H), 3.09-3.05 (m, 1H), 3.01-2.95 (m, 1H), 2.57-2.52 (m, 1H), 2.26-2.22 (m, 2H), 2.18-2.15 (m, 2H), 1.75-1.64 (m, 2H), 1.61-1.54 (m, 3H), 1.44-1.41 (m, 2H), 1.39-1.36 (m, 1H), 1.34-1.32 (m, 2H). MS-ESI calculated [M+H]⁺ 353, found 353.

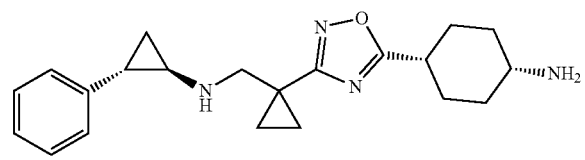 [SMILES: N[C@H]1CC[C@@H](c2nc(C3(CN[C@@H]4C[C@H]4c4ccccc4)CC3)no2)CC1]

Synthetic Route:

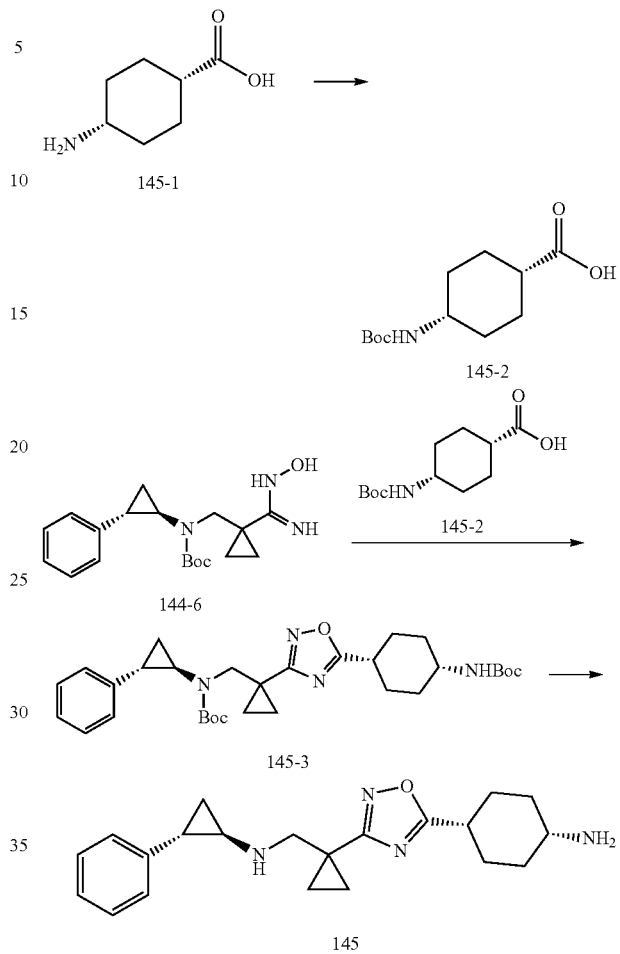

Step 1

The synthesis of compound 145-2 was referred to the third step of example 144. ¹H NMR (400 MHz, CDCl₃) 4.64 (brs, 1H), 3.63-3.58 (m, 1H), 2.53-2.51 (m, 1H), 1.92-1.89 (m, 2H), 1.76-1.59 (m, 6H), 1.45 (s, 9H). MS-ESI calculated [M-Boc+H]⁺ 144, found 144.

Step 2

The synthesis of compound 145-3 was referred to the fifth step of example 144. MS-ESI calculated [M+Na]⁺ 575, found 575.

Step 3

The synthesis of compound 145 was referred to the sixth step of example 144. ¹H NMR (400 MHz, CD₃OD) δ 7.32-7.29 (m, 2H), 7.25-7.21 (m, 1H), 7.17-7.15 (m, 2H), 3.73-3.63 (m, 2H), 3.28-3.25 (m, 2H), 3.08-3.07 (m, 1H), 2.61-2.55 (m, 1H), 2.26-2.22 (m, 21), 1.98-1.92 (m, 4H), 1.72-1.66 (m, 2H), 1.62-1.57 (m, 1H), 1.48-1.45 (m, 2H), 1.42-1.36 (m, 1H), 1.35-1.34 (m, 2H). MS-ESI calculated [M+H]⁺ 353 found 353.

Example 146

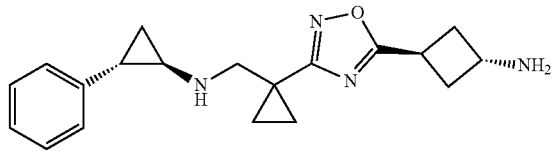 [SMILES: N[C@H]1C[C@H](c2nc(C3(CN[C@@H]4C[C@H]4c4ccccc4)CC3)no2)C1]

Synthetic Route:

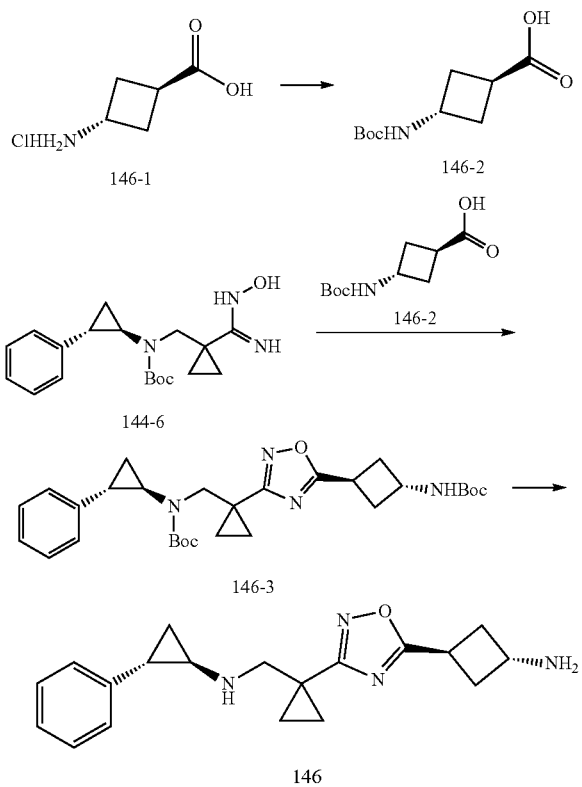

Step 1

The synthesis of compound 146-2 was referred to the third step of example 144. $^1$H NMR (400 MHz, CDCl$_3$) δ 4.76 (brs, 1H), 4.36-4.30 (m, 1H), 3.08-3.04 (m, 1H), 2.72-2.60 (m, 2H), 2.26-2.20 (m, 2H), 1.45 (s, 9H). MS-ESI calculated [M-56+H]$^+$ 160, found 160.

Step 2

The synthesis of compound 146-3 was referred to the fifth step of example 144. MS-ESI calculated [M+Na]$^+$ 547, found 547.

Step 3

The synthesis of compound 146 was referred to the sixth step of example 144. $^1$H NMR (400 MHz, CD$_3$OD) δ 7.32-7.28 (m, 2H), 7.24-7.21 (m, 1H), 7.16-7.14 (m, 2H), 4.08-4.05 (m, 1H), 3.92-3.87 (m, 1H), 3.73-3.63 (m, 2H), 3.09-3.06 (m, 1H), 2.77-2.70 (m, 4H), 2.59-2.54 (m, 1H), 1.61-1.56 (m, 1H), 1.47-1.45 (m, 2H), 1.41-1.34 (m, 3H). MS-ESI calculated [M+H]$^+$ 325 found 325.

Example 147

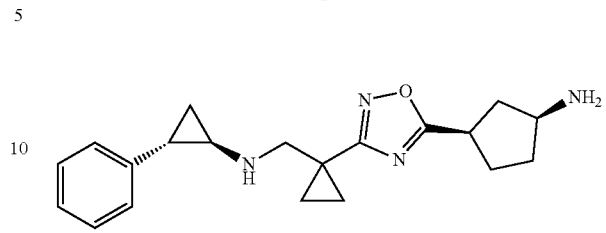

Synthetic Route:

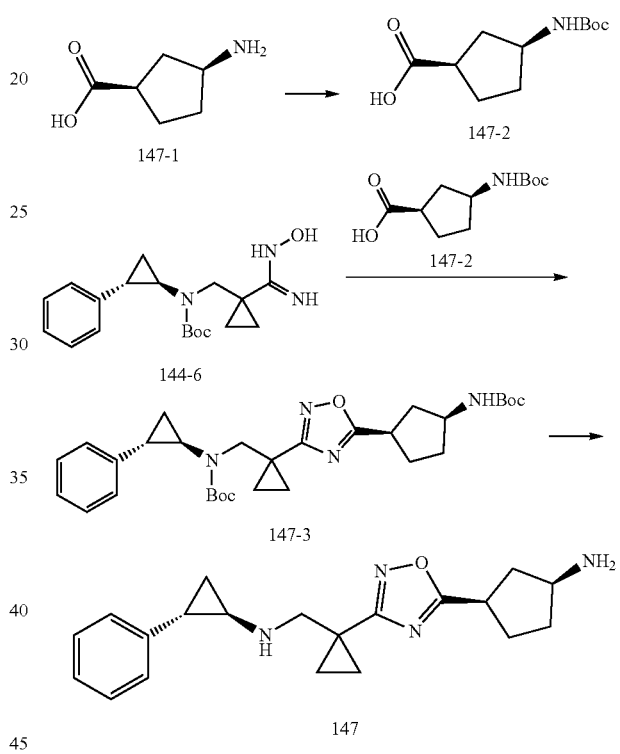

Step 1

The synthesis of compound 147-2 was referred to the third step of example 144. $^1$H NMR (400 MHz, CDCl$_3$) δ 4.89 (brs, 1H), 4.11-3.95 (m, 1H), 2.90-2.83 (m, 1H), 2.30-2.19 (m, 1H), 1.98-1.65 (m, 5H), 1.45 (s, 9H). MS-ESI calculated [M-56+H]$^+$ 174, found 174.

Step 2

The synthesis of compound 147-3 was referred to the fifth step of example 144. MS-ESI calculated [M+Na]$^+$ 561, found 561.

Step 3

The synthesis of compound 147 was referred to the sixth step of example 144. $^1$H NMR (400 MHz, CD$_3$OD) δ 7.32-7.29 (m, 2H), 7.25-7.21 (m, 1H), 7.16-7.15 (m, 2H), 3.77-3.74 (m, 1H), 3.71-3.62 (m, 2H), 3.56-3.50 (m, 1H), 3.08-3.05 (m, 1H), 2.68-2.63 (m, 1H), 2.59-2.54 (m, 1H), 2.28-2.20 (m, 2H), 2.16-2.08 (m, 1H), 2.04-1.96 (m, 1H), 1.90-1.84 (m, 1H), 1.61-1.56 (m, 1H), 1.44-1.41 (m, 2H), 1.40-1.36 (m, 1H), 1.35-1.33 (m, 2H). MS-ESI calculated [M+H]⁺ 339, found 339.

Example 148

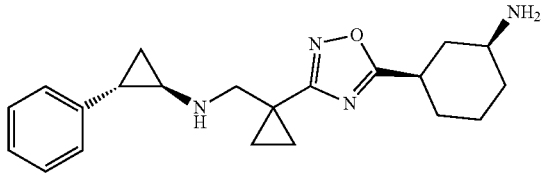 [SMILES: N[C@H]1CCC[C@@H](c2nc(C3(CN[C@@H]4C[C@H]4c4ccccc4)CC3)no2)C1]

Synthetic Route:

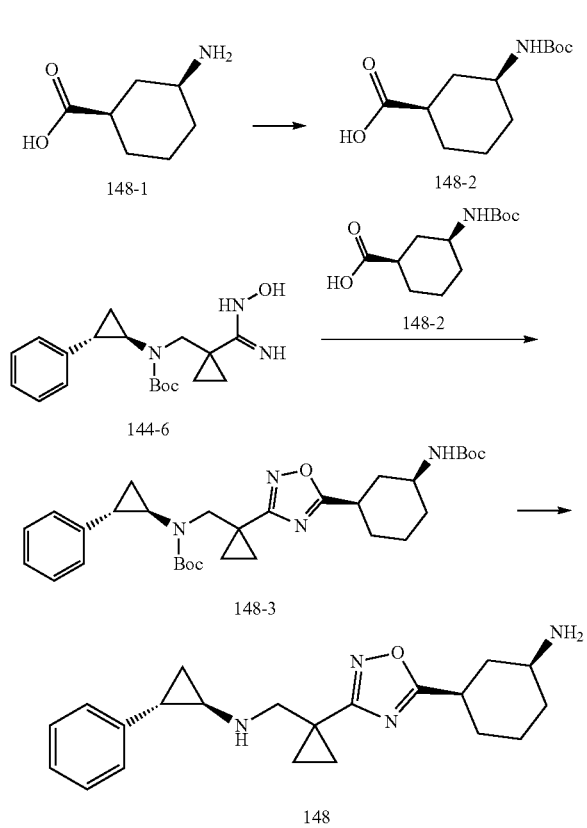

Step 1

The synthesis of compound 148-2 was referred to the third step of example 144. ¹H NMR (400 MHz, CDCl₃) 4.73 (brs, 1H), 3.46-3.32 (m, 1H), 2.90-2.83 (m, 1H), 2.29-2.26 (m, 1H), 1.99-1.96 (m, 2H), 1.87-1.84 (m, 1H), 1.44 (s, 9H), 1.34-1.28 (m, 3H), 1.24-1.06 (m, 1H). MS-ESI calculated [M+Na]⁺ 266, found 266.

Step 2

The synthesis of compound 148-3 was referred to the fifth step of example 144. MS-ESI calculated [M+Na]⁺ 575, found 575.

Step 3

The synthesis of compound 148 (60.0 mg) was referred to the sixth step of example 144. ¹H NMR (400 MHz, CD₃OD) δ 7.32-7.29 (m, 2H), 7.25-7.23 (m, 1H), 7.16-7.14 (m, 2H), 3.71-3.62 (m, 2H), 3.28-3.24 (m, 1H), 3.18-3.11 (m, 1H), 3.08-3.04 (m, 1H), 2.57-2.52 (m, 1H), 2.44-2.41 (m, 1H), 2.16-2.08 (m, 2H), 2.04-1.99 (m, 1H), 1.70-1.64 (m, 1H), 1.61-1.54 (m, 2H), 1.49-1.32 (m, 7H). MS-ESI calculated [M+H]⁺ 353, found 353.

Example 149, Example 150

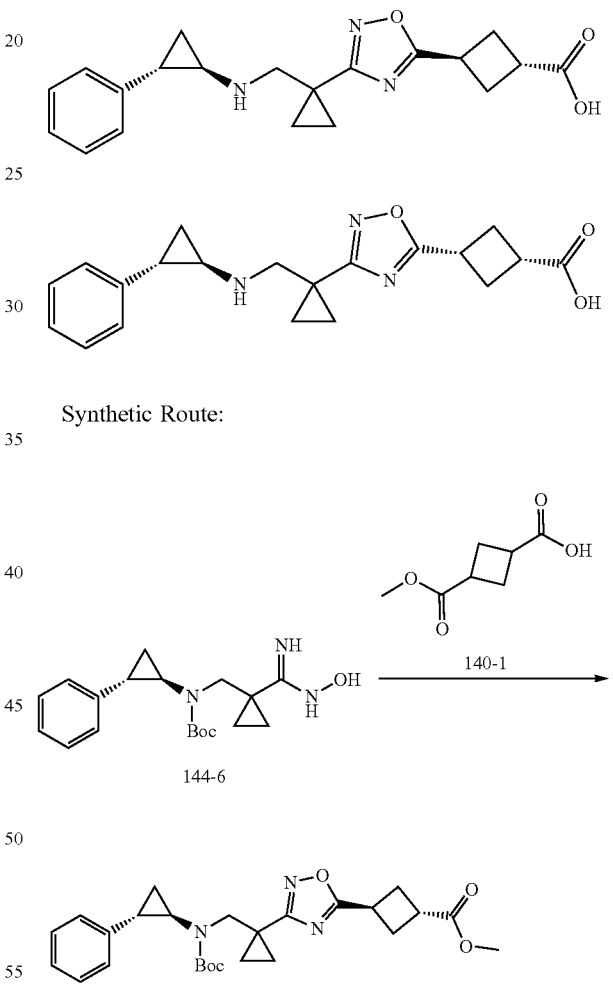

Synthetic Route:

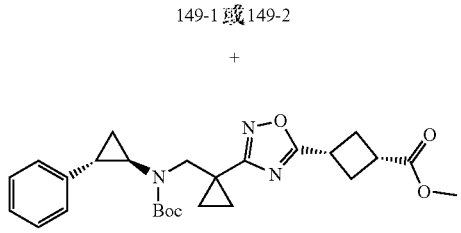

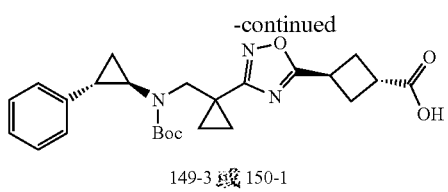

149-3 或 150-1

+

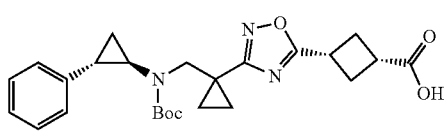

149-3 或 150-1

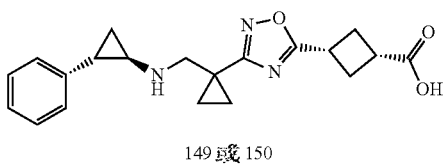

149 或 150

+

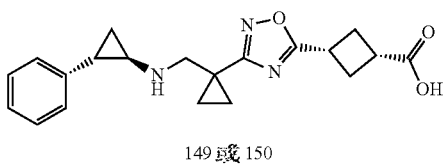

149 或 150

Step 1

The synthesis of crude product was referred to the fifth step of example 144. Compound 149-1 was purified by thin layer chromatography (3:1 petroleum ether/ethyl acetate, Rf=0.4). MS-ESI calculated [M+Na]$^+$ 490, found 490. Compound 149-2, (3:1 petroleum ether/ethyl acetate, Rf=0.32). MS-ESI calculated [M+Na]$^+$ 490, found 490.

Step 2

Compound 149-1 (200 mg, 0.427 mol) was dissolved in water (8 mL) and THF (2 mL), sodium hydroxide (68.4 mg, 1.71 mmol) was added, and the reaction mixture was stirred at 40° C. for 4 h. The reaction solution was cooled to 0° C., water (50 mL) was added to the reaction mixture, and the mixture was adjusted to pH=3 with hydrochloric acid (1 mol/L), and the mixture was extracted with ethyl acetate/tetrahydrofuran=3/1 (50 mL×3). The organic phase was washed with saturated brine (50 mL×2), dried over anhydrous sodium sulfate, followed by filtration and concentration under reduced pressure to give compound 149-3. MS-ESI calculated [M+Na]$^+$ 476, found 476. Referring to the same method, compound 149-2 was prepared to give compound 150-1. MS-ESI calculated [M+Na]$^+$ 476, found 476.

Step 3

The synthesis of 149 was referred to the sixth step of example 144 prepared by 149-3, that is, example 149. $^1$H NMR (400 MHz, CD$_3$OD) δ 7.32-7.29 (m, 2H), 7.25-7.21 (m, 1H), 7.16-7.14 (m, 2H), 3.77-3.70 (m, 1H), 3.67-3.61 (m, 2H), 3.28-2.23 (m, 1H), 3.09-3.05 (m, 1H), 2.71-2.57 (m, 4H), 2.55-2.49 (m, 1H), 1.58-1.52 (m, 1H), 1.46-1.44 (m, 2H), 1.42-1.36 (m, 1H), 1.32-1.30 (m, 2H). MS-ESI calculated [M+H]$^+$ 354, found 354. Referring to the same method, compound 150-1 was prepared to give compound 150, that is, example 150. $^1$H NMR (400 MHz, CD$_3$OD) δ 7.32-7.28 (m, 2H), 7.24-7.21 (m, 1H), 7.16-7.14 (m, 2H), 3.85-3.77 (m, 1H), 3.72-3.62 (m, 2H), 3.29-2.26 (m, 1H), 3.10-3.06 (m, 1H), 2.77-2.69 (m, 2H), 2.66-2.59 (m, 2H), 2.57-2.51 (m, 1H), 1.59-1.54 (m, 1H), 1.48-1.44 (m, 2H), 1.42-1.36 (m, 1H), 1.35-1.32 (m, 2H). MS-ESI calculated [M+H]$^+$ 354, found 354.

Example 151

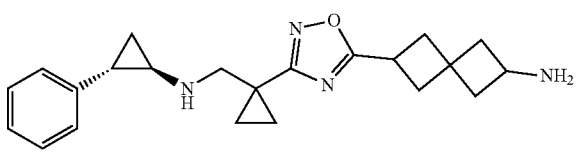 [SMILES: NC1CC2(C1)CC(c1nc(C3(CN[C@@H]4C[C@H]4c4ccccc4)CC3)no1)C2]

Synthetic Route:

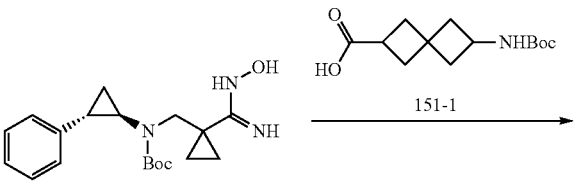

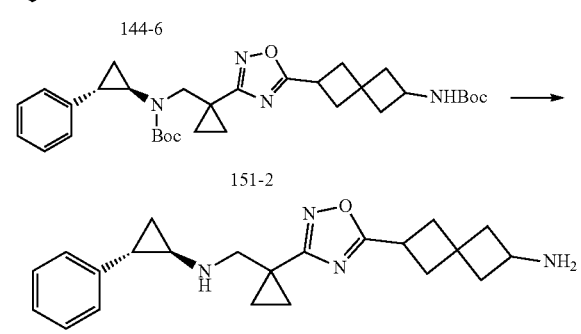

Step 1

The synthesis of compound 151-2 was referred to the fifth step of example 144. MS-ESI calculated [M+Na]$^+$ 587, found 587.

Step 2

The synthesis of compound 151 was referred to the sixth step of example 144. $^1$H NMR (400 MHz, CD$_3$OD) δ 7.32-7.28 (m, 2H), 7.25-7.21 (m, 1H), 7.16-7.14 (m, 2H), 3.73-3.61 (m, 4H), 3.09-3.05 (m, 1H), 2.66-2.59 (m, 2H), 2.56-2.40 (m, 5H), 2.29-2.24 (m, 1H), 2.20-2.15 (m, 1H), 1.59-1.53 (m, 1H), 1.44-1.41 (m, 2H), 1.40-1.36 (m, 1H), 1.33-1.31 (m, 2H). MS-ESI calculated [M+H]$^+$ 365, found 365.

Example 152

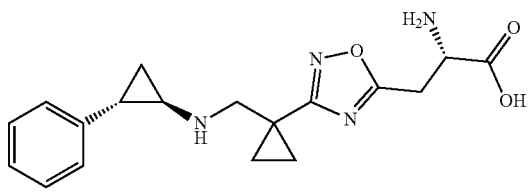 [SMILES: N[C@@H](Cc1nc(C2(CN[C@@H]3C[C@H]3c3ccccc3)CC2)no1)C(=O)O]

Synthetic Route:

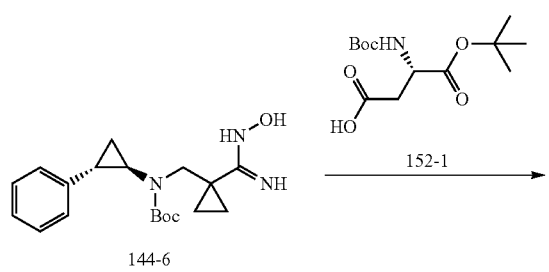

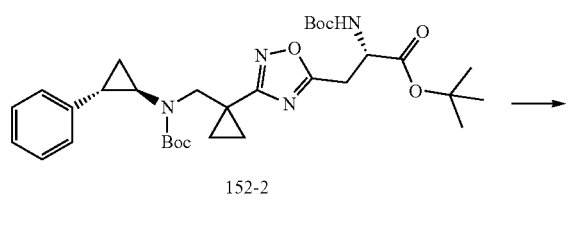

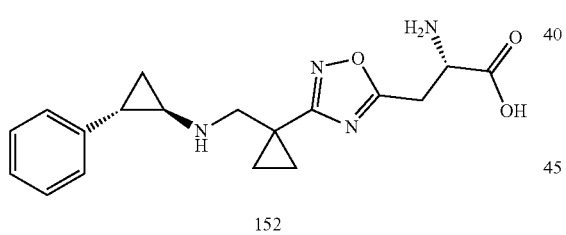

Step 1

The synthesis of compound 152-2 was referred to the fifth step of example 144. MS-ESI calculated [M+Na]⁺ 621, found 621.

Step 2

The synthesis of compound 152 was referred to the sixth step of example 144. ¹H NMR (400 MHz, CD₃OD) δ 7.32-7.29 (m, 2H), 7.25-7.21 (m, 1H), 7.17-7.15 (m, 2H), 4.57 (t, J=6.4 Hz, 1H), 3.72-3.64 (m, 2H), 3.60-3.50 (m, 2H), 3.05-3.04 (m, 1H), 2.61-2.56 (m, 1H), 1.63-1.58 (m, 1H), 1.49-1.46 (m, 2H), 1.41-1.36 (m, 3H). MS-ESI calculated [M+H]⁺ 343, found 343.

Example 153

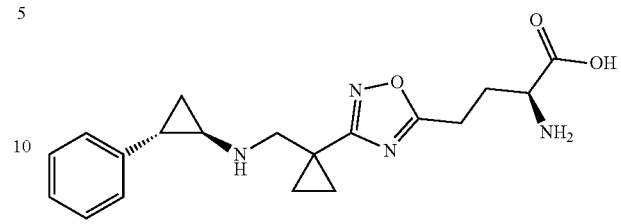

Synthetic Route:

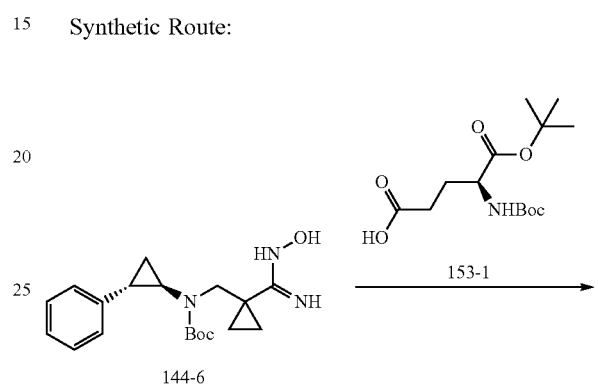

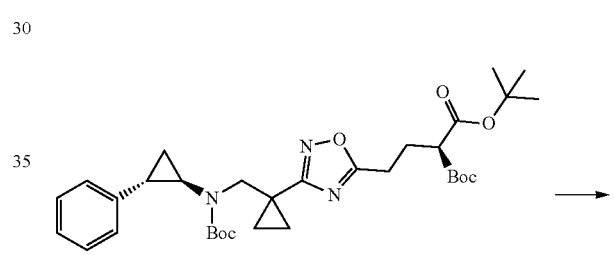

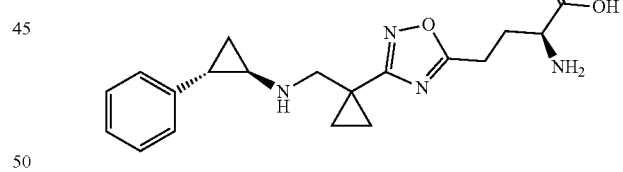

Step 1

The synthesis of compound 153-2 was referred to the fifth step of example 144. MS-ESI calculated [M+Na]⁺ 635, found 635.

The synthesis of compound 153 was referred to the sixth step of example 144. ¹H NMR (400 MHz, CD₃OD) δ 7.32-7.29 (m, 2H), 7.25-7.21 (m, 1H), 7.16-7.14 (m, 2H), 4.13 (t, J=6.8 Hz, 1H), 3.74-3.61 (m, 2H), 3.16-3.05 (m, 3H), 2.56-2.51 (m, 1H), 2.44-2.33 (m, 2H), 1.59-1.54 (m, 1H), 1.46-1.33 (m, 5H). MS-ESI calculated [M+H]⁺ 357, found 357.

307

Example 154

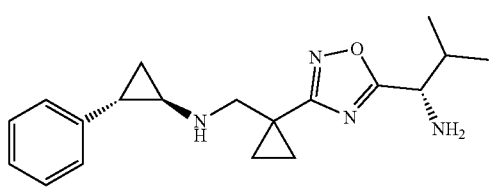 [SMILES: CC(C)[C@H](N)c1nc(C2(CN[C@@H]3C[C@H]3c3ccccc3)CC2)no1]

Synthetic Route:

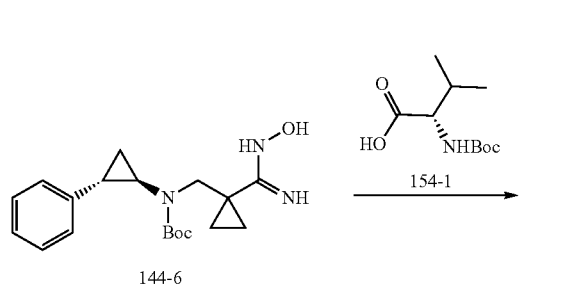

154-2

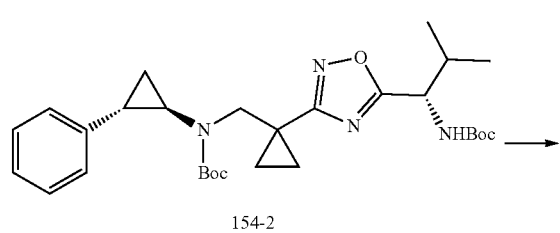

154

Step 1

The synthesis of compound 154-2 was referred to the fifth step of example 144. MS-ESI calculated [M+Na]$^+$ 549, found 549.

Step 2

The synthesis of compound 154 was referred to the sixth step of example 144. $^1$H NMR (400 MHz, CD$_3$OD) δ 7.33-7.28 (m, 2H), 7.25-7.21 (m, 1H), 7.20-7.15 (m, 2H), 4.70 (d, J=6.0 Hz, 1H), 3.77-3.66 (m, 2H), 3.10-3.06 (m, 1H), 2.66-2.61 (m, 1H), 2.44-2.35 (m, 1H), 1.66-1.61 (m, 1H), 1.52-1.49 (m, 2H), 1.45-1.37 (m, 3H), 1.12 (t, J=6.8 Hz, 3H), 1.03 (t, J=6.8 Hz, 3H). MS-ESI calculated [M+H]$^+$ 327, found 327.

308

Example 155

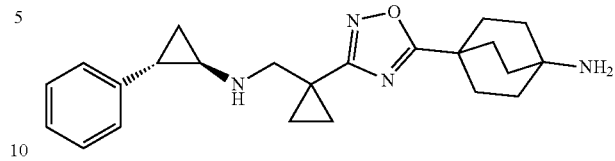

Synthetic Route:

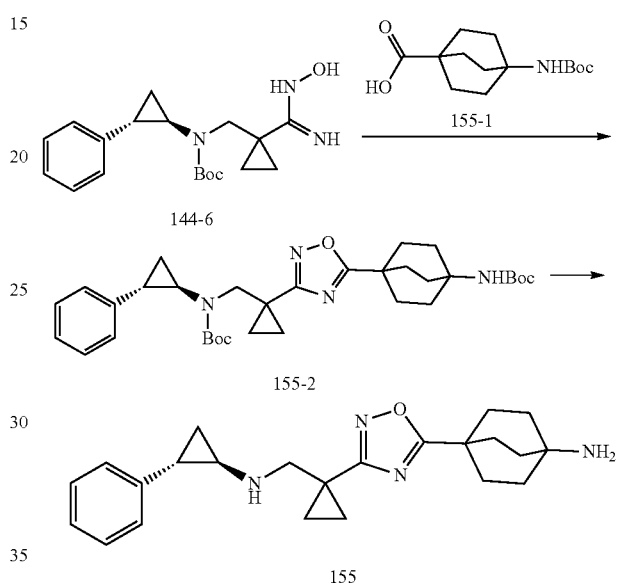

Step 1

The synthesis of compound 155-2 was referred to the fifth step of example 144. MS-ESI calculated [M+H]$^+$ 579, found 579.

Step 2

The synthesis of compound 155 was referred to the sixth step of example 144. $^1$H NMR (400 MHz, CD$_3$OD) δ 7.33-7.29 (m, 2H), 7.25-7.21 (m, 1H), 7.17-7.15 (m, 2H), 3.69-3.61 (m, 2H), 3.08-3.04 (m, 1H), 2.55-2.50 (m, 1H), 2.16-2.12 (m, 6H), 1.94-1.90 (m, 6H), 1.58-1.52 (m, 1H), 1.43-1.37 (m, 3H), 1.32-1.30 (m, 2H). MS-ESI calculated [M+H]$^+$ 379, found 379.

Example 156

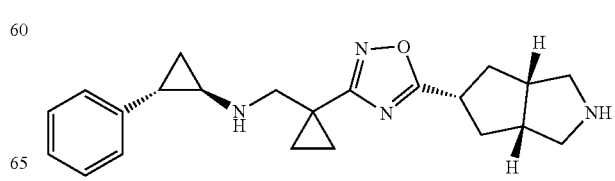

Synthetic Route:

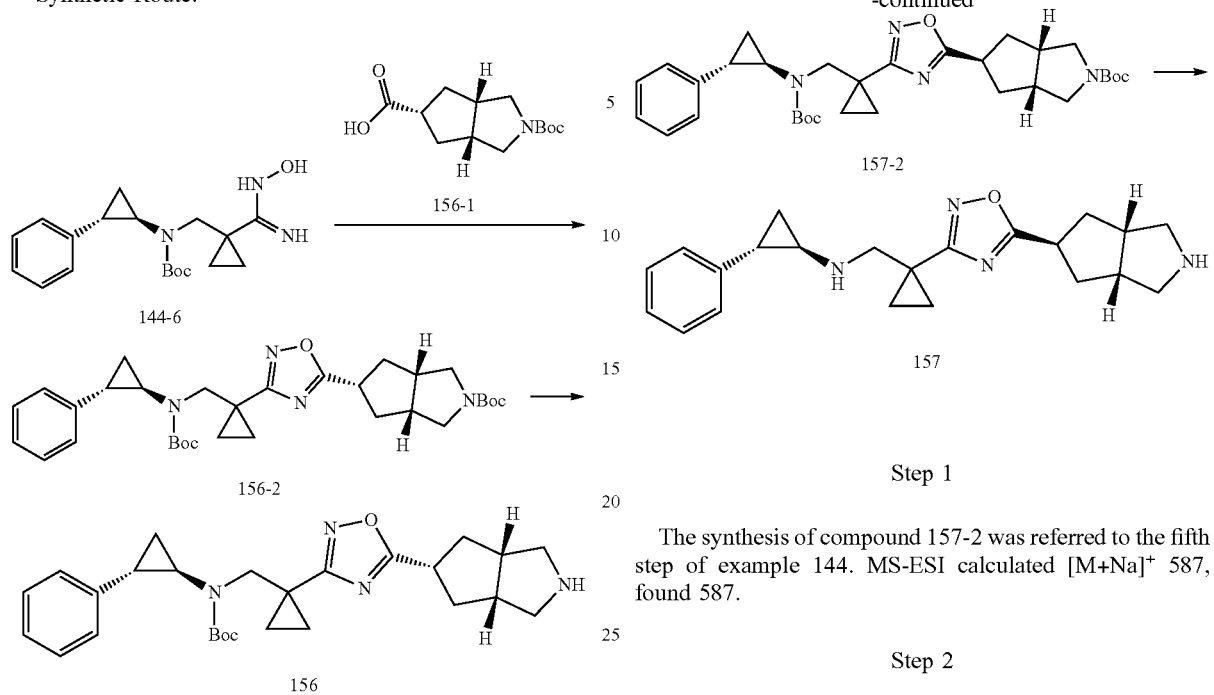

Step 1

The synthesis of compound 156-2 was referred to the fifth step of example 144. MS-ESI calculated [M+Na]⁺ 587, found 587.

The synthesis of compound 156 was referred to the sixth step of example 144. $^1$H NMR (400 MHz, CD$_3$OD) δ 7.32-7.29 (m, 2H), 7.24-7.21 (m, 1H), 7.17-7.15 (m, 2H), 3.70-3.61 (m, 2H), 3.51-3.43 (m, 1H), 3.42-3.35 (m, 2H), 3.27-3.23 (m, 2H), 3.13-3.04 (m, 3H), 2.60-2.48 (m, 3H), 1.87-1.79 (m, 2H), 1.62-1.56 (m, 1H), 1.44-1.41 (m, 2H), 1.39-1.36 (m, 1H), 1.34-1.32 (m, 2H). MS-ESI calculated [M+H]⁺ 365, found 365.

Example 157

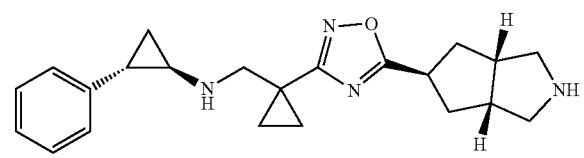 [SMILES: c1ccc([C@@H]2C[C@H]2NCC2(c3noc([C@@H]4C[C@H]5CNC[C@H]5C4)n3)CC2)cc1]

Synthetic Route:

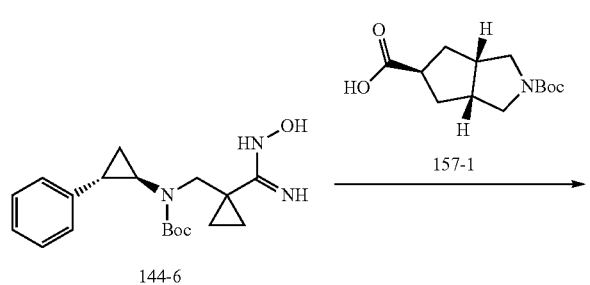

Step 1

The synthesis of compound 157-2 was referred to the fifth step of example 144. MS-ESI calculated [M+Na]⁺ 587, found 587.

Step 2

The synthesis of compound 157 was referred to the sixth step of example 144. $^1$H NMR (400 MHz, CD$_3$OD) δ 7.32-7.29 (m, 2H), 7.25-7.21 (m, 1H), 7.16-7.15 (m, 2H), 3.70-3.61 (m, 3H), 3.57-3.53 (m, 2H), 3.09-3.02 (m, 5H), 2.57-2.52 (m, 1H), 2.24-2.16 (m, 2H), 2.10-2.05 (m, 2H), 1.60-1.54 (m, 1H), 1.44-1.36 (m, 3H), 1.34-1.32 (m, 2H). MS-ESI calculated [M+H]⁺ 365, found 365.

Example 158

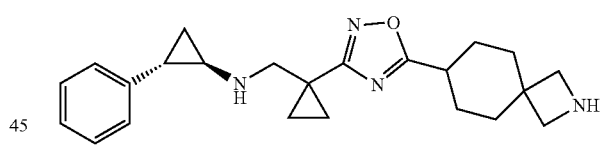

Synthetic Route:

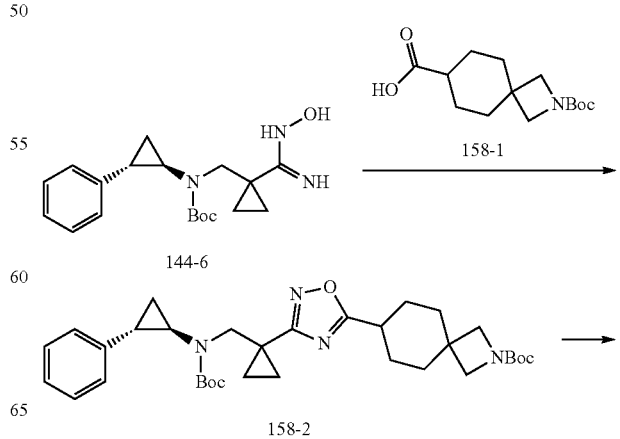

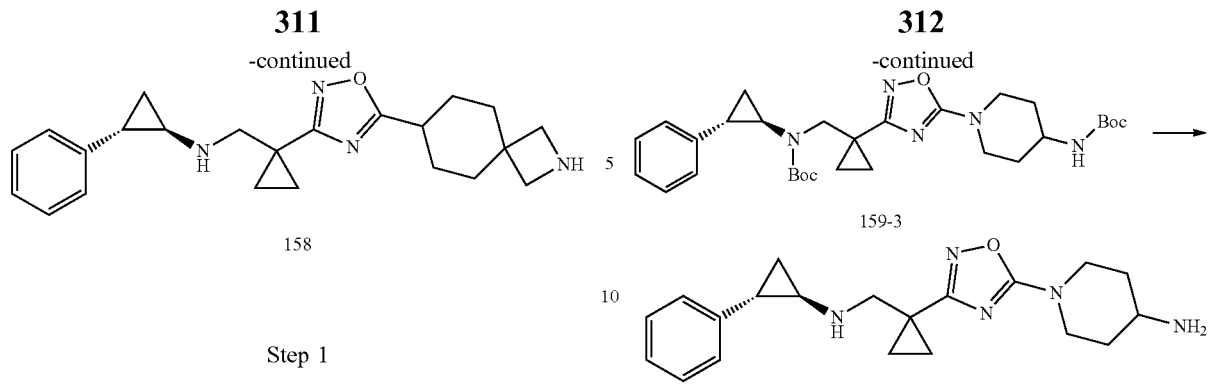

158

Step 1

The synthesis of compound 158-2 was referred to the fifth step of example 144. MS-ESI calculated [M+Na]⁺ 601, found 601.

Step 2

The synthesis of compound 158 was referred to the sixth step of example 144. $^1$H NMR (400 MHz, CD$_3$OD) δ 7.32-7.28 (m, 2H), 7.24-7.20 (m, 1H), 7.16-7.14 (m, 2H), 3.86 (s, 2H), 3.80 (s, 2H), 3.70-3.61 (m, 2H), 3.08-3.04 (m, 1H), 3.00-2.93 (m, 1H), 2.57-2.52 (m, 1H), 2.14-2.11 (m, 2H), 2.07-2.03 (m, 2H), 1.75-1.61 (m, 4H), 1.60-1.54 (m, 1H), 1.42-1.35 (m, 3H), 1.34-1.31 (m, 2H). MS-ESI calculated [M+H]⁺ 379, found 379.

Example 159

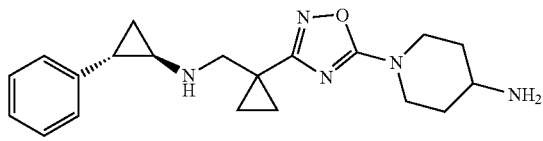 [SMILES: NC1CCN(c2nc(C3(CN[C@@H]4C[C@H]4c4ccccc4)CC3)no2)CC1]

Synthetic Route:

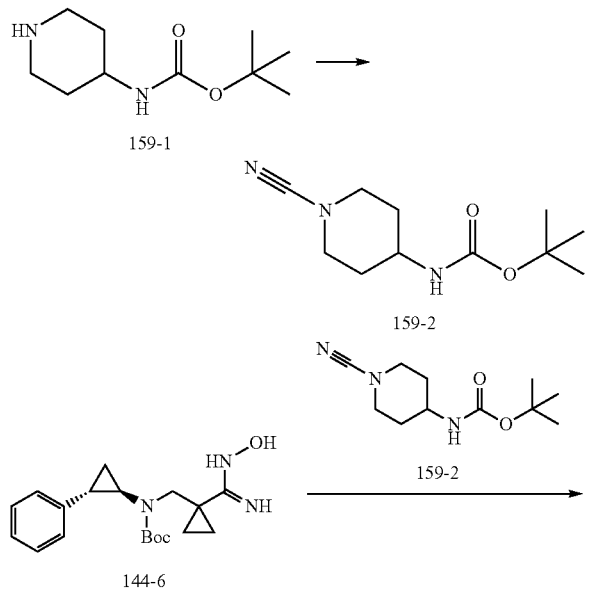

Step 1

Compound 159-1 (2.00 g, 9.99 mmol) was dissolved in anhydrous dichloromethane (30 mL), sodium bicarbonate solution (2.52 g, 29.9 mmol, water 6 mL) was added at 0 t, a solution of cyanogen bromide (1.27 g, 11.9 mmol, dichloromethane 3 mL) was added dropwise. The mixture was stirred at 0° C. for 10 min, then warmed to 25° C. and stirred for 3 h. The reaction mixture was diluted with water (50 mL), and extracted with dichloromethane (20 mL×3). The organic phase was washed successively with saturated sodium bicarbonate solution (30 mL×1) and saturated brine (30 mL×1), dried over anhydrous sodium sulfate, filtered, and concentrated under reduced to give compound 159-2. MS-ESI calculated [M-56+H]⁺ 170, found 170.

Step 2

Compound 144-6 (100 mg, 0.260 mmol) and compound 159-2 (117 mg, 0.520 mmol) were dissolved in anhydrous tetrahydrofuran (15 mL). A solution of zinc dichloride dissolved in diethyl ether (1 M, 312 μL) was added dropwise at room temperature, and the reaction mixture was stirred at 25° C. for 3 h. Toluenesulfonic acid monohydrate (54.5 mg, 0.286 mmol) was added at room temperature, and the reaction mixture was heated to 70° C. and stirred for 10 h. Water (50 mL) was added to the reaction mixture. The mixture was extracted with ethyl acetate (20 mL×3). The organic phase was washed with saturated brine (20 mL×2), dried over anhydrous sodium sulfate, followed by filtration and concentration under reduced pressure. The compound 159-3 was isolated and purified by preparative thin layer chromatography (2:1 petroleum ether/ethyl acetate, Rf=0.4). MS-ESI calculated [M+H]⁺ 554, found 554.

Step 3

The synthesis of compound 159 was referred to the sixth step of example 144. $^1$H NMR (400 MHz, CD$_3$OD) δ 7.32-7.28 (m, 2H), 7.25-7.21 (m, 1H), 7.15-7.14 (m, 2H), 4.18-4.14 (m, 2H), 3.61-3.51 (m, 2H), 3.24-3.17 (m, 2H), 3.07-3.03 (m, 1H), 2.55-2.50 (m, 1H), 2.11-2.08 (m, 2H), 1.69-1.53 (m, 4H), 1.40-1.36 (m, 3H), 1.22-1.16 (m, 2H). MS-ESI calculated [M+H]⁺ 354, found 354.

Example 160

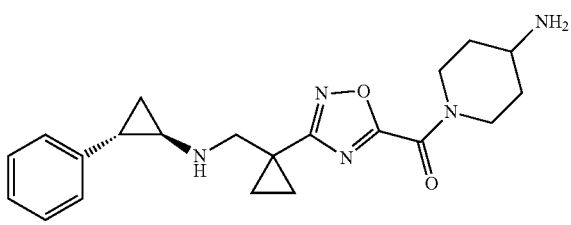 [SMILES: NC1CCN(C(=O)c2nc(C3(CN[C@@H]4C[C@H]4c4ccccc4)CC3)no2)CC1]

Synthetic Route:

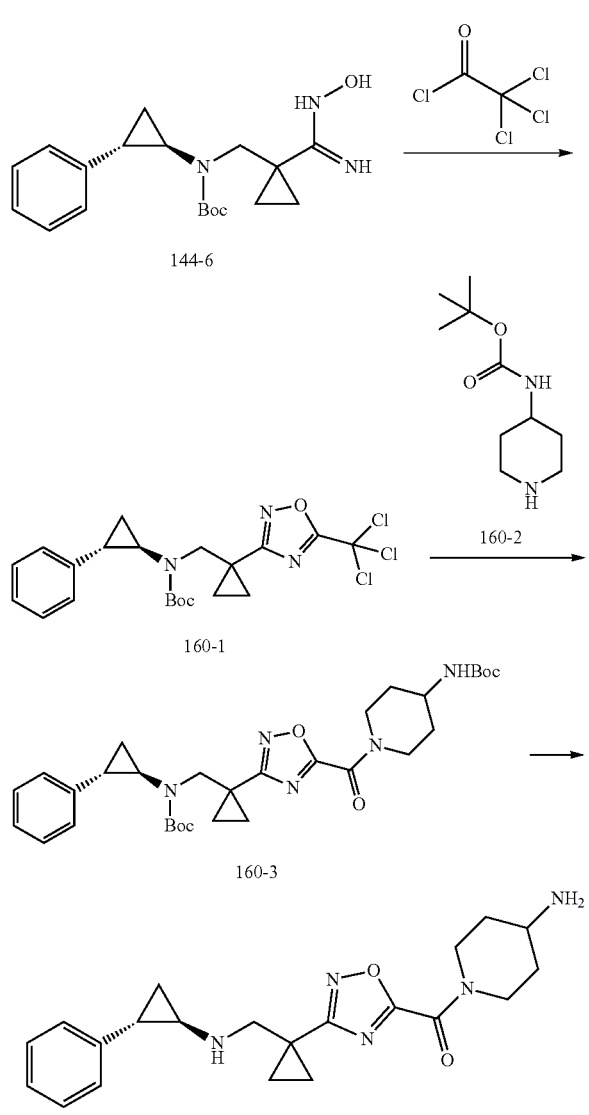

Step 1

Compound 144-6 (500 mg, 1.45 mmol) and pyridine (194 mg, 2.46 mmol) were dissolved in anhydrous dichloromethane (10 mL). The mixture was cooled to −15° C. Trichloroacetyl chloride (316 mg, 1.74 mmol) was added dropwise slowly. The reaction solution was warmed to 25° C. and stirred for 10 h. Water (50 mL) was added to the reaction mixture. The mixture was stirred at room temperature for 30 min, and extracted with dichloromethane (50 mL×2). The mixture was extracted with dichloromethane (50 mL×2). The organic phases were combined, washed with saturated brine (50 mL×2), dried over anhydrous sodium sulfate, followed by filtration and concentration under reduced pressure. The compound 160-1 was isolated and purified by preparative thin layer chromatography (2:1 petroleum ether/ethyl acetate, Rf=0.6). MS-ESI calculated [M+Na]$^+$ 494, found 494.

Step 2

Compound 160-1 (200 mg, 0.423 mmol), diisopropylethylamine (164 mg, 1.27 mmol) and compound 160-2 (169 mg, 0.846 μmol) were dissolved in anhydrous N,N-dimethylformamide (5 mL). The mixture was heated to 60° C. and stirred for 12 hours. The reaction mixture was cooled to 0° C., water (50 mL) was added. The mixture was extracted with ethyl acetate (20 mL×3). The organic phase was washed with saturated brine (20 mL×2), dried over anhydrous sodium sulfate, followed by filtration and concentration under reduced pressure. The compound 160-3 was isolated and purified by preparative thin layer chromatography (2:1 petroleum ether/ethyl acetate. Rf=0.4). MS-ESI calculated [M+Na]$^+$ 604, found 604.

Step 3

The synthesis of compound 160 was referred to the sixth step of example 144. $^1$H NMR (400 MHz, CD$_3$OD) δ 7.33-7.29 (m, 2H), 7.25-7.21 (m, 1H), 7.17-7.15 (m, 2H), 4.70-4.66 (m, 1H), 4.30-4.27 (m, 1H), 3.77-3.69 (m, 2H), 3.51-3.45 (m, 1H), 3.36-3.33 (m, 1H), 3.11-2.99 (m, 2H), 2.58-2.53 (m, 1H), 2.18-2.09 (m, 2H), 1.69-1.55 (m, 3H), 1.49-1.47 (m, 2H), 1.44-1.38 (m, 3H). MS-ESI calculated [M+H]$^+$ 382, found 382.

Example 161

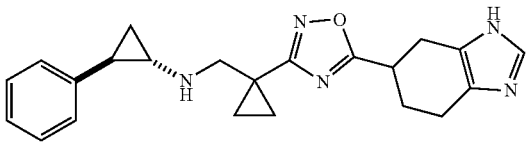

Synthetic Route:

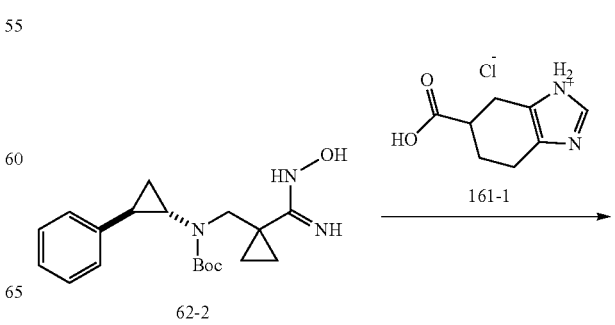

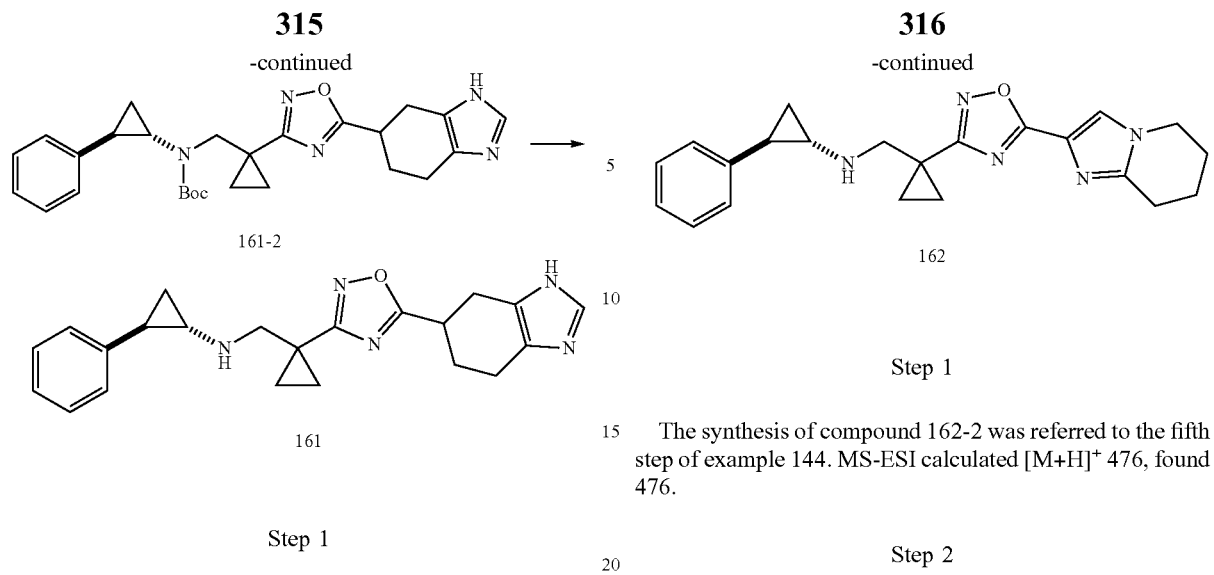

161-2

161

Step 1

The synthesis of compound 161-2 was referred to the fifth step of example 144. MS-ESI calculated [M+H]⁺ 476, found 476.

Step 2

The synthesis of compound 161 was referred to the sixth step of example 144. ¹H NMR (400 MHz, CD₃OD) δ 8.74 (s, 1H), 7.32-7.29 (m, 2H), 7.25-7.21 (m, 1H), 7.16-7.14 (m, 2H), 3.72-3.63 (m, 2H), 3.62-3.57 (m, 1H), 3.23-3.18 (m, 1H), 3.09-3.04 (m, 2H), 2.88-2.78 (m, 2H), 2.57-2.52 (m, 1H), 2.48-2.42 (m, 1H), 2.22-2.13 (m, 1H), 1.60-1.54 (m, 1H), 1.44-1.35 (m, 5H). MS-ESI calculated [M+H]⁺ 376, found 376.

Example 162

162

Step 1

The synthesis of compound 162-2 was referred to the fifth step of example 144. MS-ESI calculated [M+H]⁺ 476, found 476.

Step 2

The synthesis of compound 162 was referred to the sixth step of example 144. ¹H NMR (400 MHz, CD₃OD) δ 8.36 (s, 1H), 7.29-7.26 (m, 2H), 7.21-7.17 (m, 1H), 7.15-7.12 (m, 2H), 4.27 (t, J=6.0 Hz, 2H), 3.81-3.70 (m, 2H), 3.14-3.09 (m, 3H), 2.58-2.53 (m, 1H), 2.18-2.07 (m, 4H), 1.62-1.51 (m, 3H), 1.45-1.38 (m, 3H). MS-ESI calculated [M+H]⁺ 376, found 376.

Example 163

Synthetic Route:

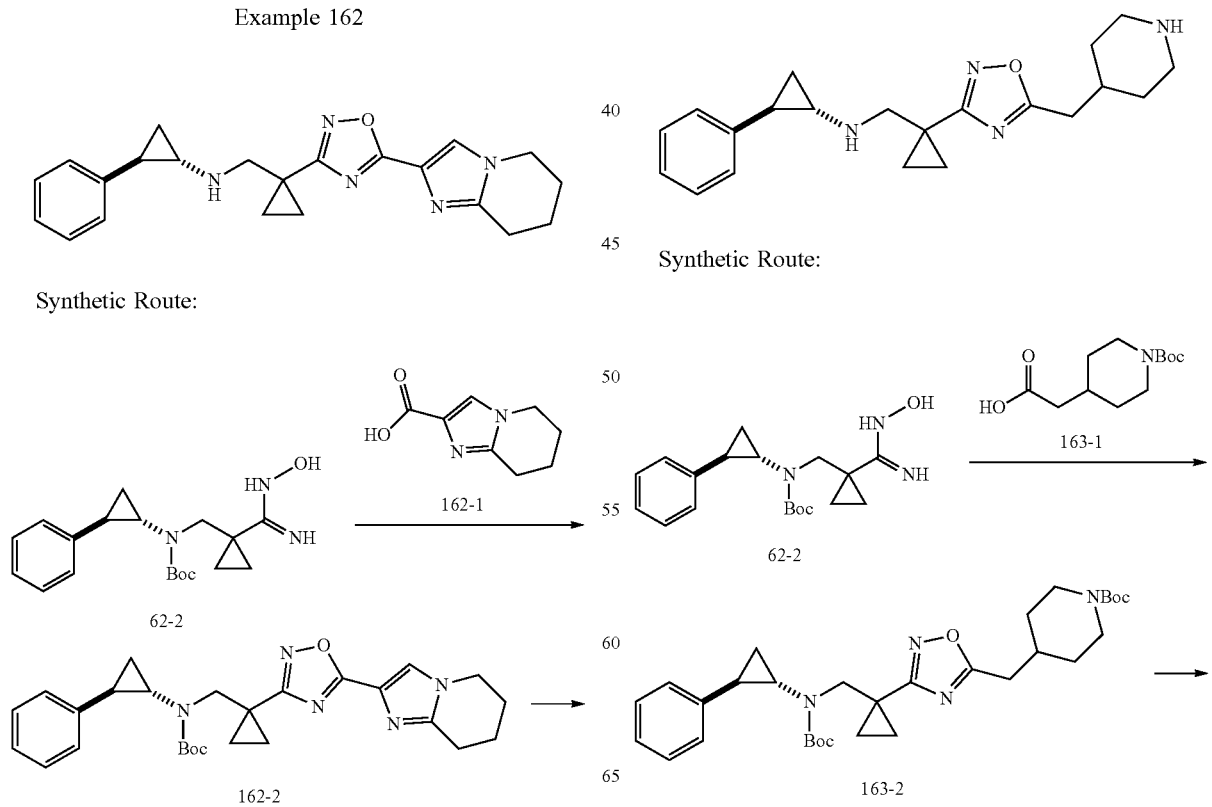

317
-continued
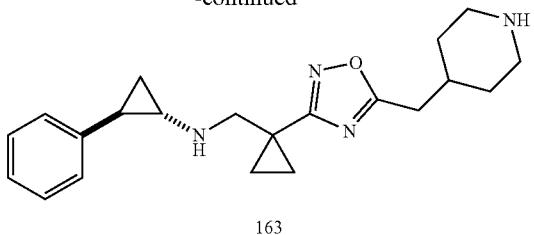
163
Step 1
The synthesis of compound 163-2 was referred to the fifth step of example 144. MS-ESI calculated [M+Na]+ 575, found 575.
The synthesis of compound 163 was referred to the sixth step of example 144. ¹H NMR (400 MHz, CD₃OD) δ 7.32-7.29 (m, 2H), 7.25-7.21 (m, 1H), 7.17-7.15 (m, 2H), 3.72-3.62 (m, 2H), 3.41-3.38 (m, 2H), 3.10-2.97 (m, 3H), 2.92 (d, J=7.2 Hz, 2H), 2.59-2.54 (m, 1H), 2.24-2.15 (m, 1H), 2.04-1.97 (m, 2H), 1.61-1.50 (m, 3H), 1.45-1.33 (m, 5H). MS-ESI calculated [M+H]+ 353, found 353.
Example 164
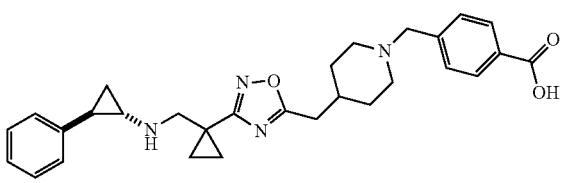
Synthetic Route:
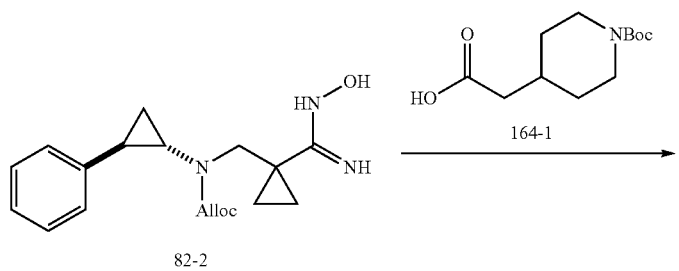
82-2
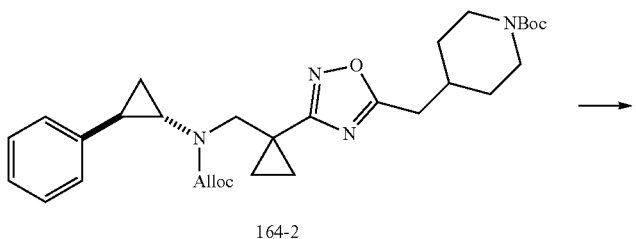
164-2
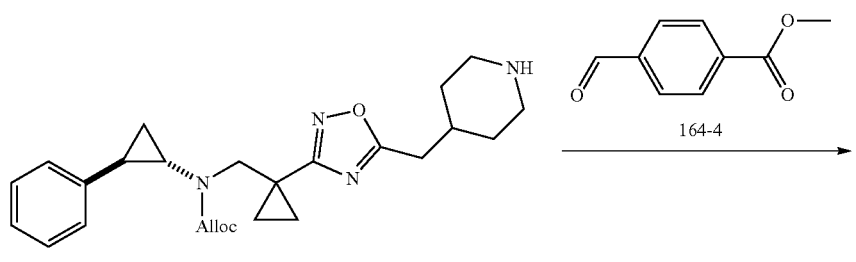
164-3
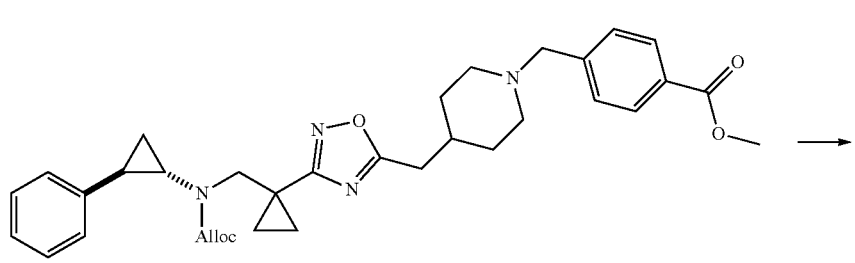
164-5

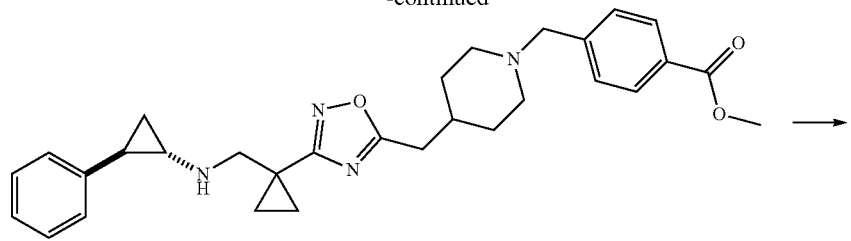

164-6

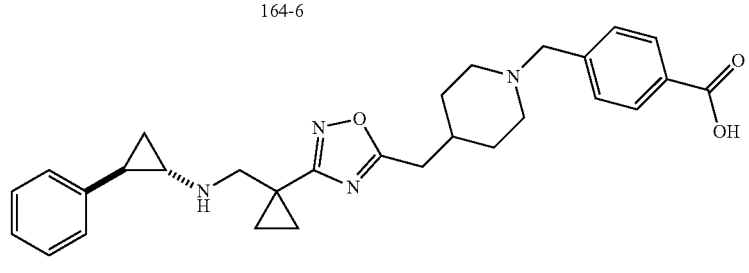

164

Step 1

The synthesis of compound 164-2 was referred to the fifth step of example 144. MS-ESI calculated [M+Na]+ 559, found 559.

Step 2

The synthesis of compound 164-3 was referred to the sixth step of example 144. MS-ESI calculated [M+H]+ 437, found 437.

Step 3

Compound 164-3 (130 mg, 0.298 mmol) and compound 164-4 (58.7 mg, 0.357 mmol) were dissolved in anhydrous dichloromethane (20 mL), acetic acid (53.7 mg, 0.893 mmol) was added. The reaction solution was stirred at 30° C. for 1 h. Sodium triacetoxyborohydride was added. The mixture was stirred for 1 h. Dichloromethane (100 mL) was added. The organic phase was washed successively with saturated sodium carbonate (50 mL×3), saturated brine (50 mL×2), dried over anhydrous sodium sulfate, filtered, and the filtrate was concentrated under reduced pressure. The compound 164-5 was isolated and purified by preparative thin layer chromatography (1:1 petroleum ether/ethyl acetate, Rf=0.5). MS-ESI calculated [M+H]+ 585, found 585.

Step 4

Compound 164-5 (80 mg, 0.137 mmol) was dissolved in tetrahydrofuran (5 mL) under nitrogen, and diethylamine (100 mg, 1.37 mmol) and tetratriphenylphosphine palladium (15.8 mg, 13.7 μmol) were added. The reaction solution was stirred at 80° C. for 2 h, filtered, and concentrated under reduced pressure to give compound 164-6. MS-ESI calculated [M+H]+ 501, found 501.

Step 5

The synthesis of compound 164 was referred to the second step of example 149. 1H NMR (400 MHz, CD3OD) δ 8.12 (d, J=8.0 Hz, 2H), 7.66 (d, J=8.0 Hz, 2H), 7.32-7.28 (m, 2H), 7.24-7.21 (m, 1H), 7.16-7.14 (m, 2H), 4.38 (s, 2H), 3.71-3.61 (m, 2H), 3.51-3.48 (m, 2H), 3.13-3.05 (m, 3H), 2.90 (d, J=6.8 Hz, 2H), 2.57-2.51 (m, 1H), 2.22-2.16 (m, 1H), 2.04-2.01 (m, 2H), 1.70-1.54 (m, 3H), 1.45-1.32 (m, 5H). MS-ESI calculated [M+H]+ 487, found 487.

Example 165

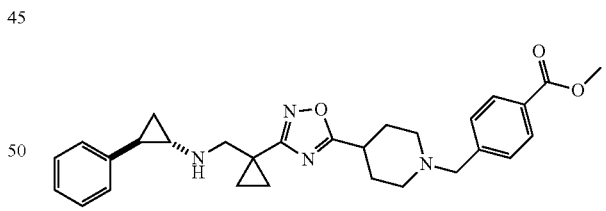

Synthetic Route:

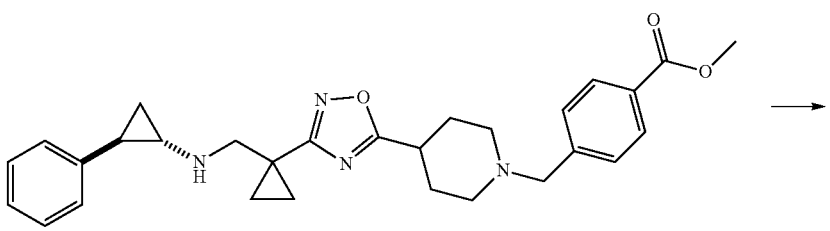

82-6

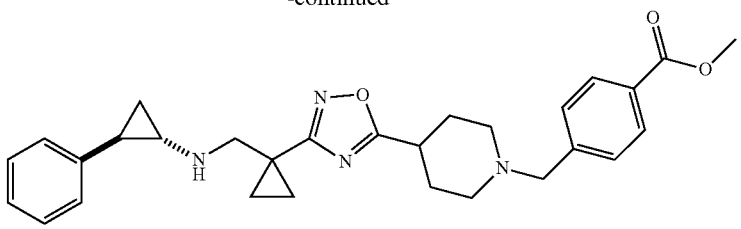

165

Compound 82-6 was separated by chiral column, column OD (particle size 3 um), mobile phase: ethanol (0.05% diethylamine). The step was gradient elution with 5% to 40% ethanol, flow rate: 2.5 ml/min, (retention time: 4.894 min). After separation, the compound 165 was obtained by high-performance liquid chromatography (acidic, hydrochloric acid system). $^1$H NMR (400 MHz, CD$_3$OD) δ 8.14 (d, J=8.0 Hz, 2H), 7.70 (d, J=8.0 Hz, 2H), 7.32-7.28 (m, 2H), 7.25-7.21 (m, 1H), 7.16-7.14 (m, 2H), 4.41 (s, 2H), 3.93 (s, 3H), 3.71-3.48 (m, 5H), 3.20-3.13 (m, 2H), 3.07-3.05 (m, 1H), 2.57-2.48 (m, 1H), 2.40-2.32 (m, 2H), 2.20-2.00 (m, 2H), 1.63-1.59 (m, 1H), 1.42-1.29 (m, 5H). MS-ESI calculated [M+H]$^+$ 487, found 487.

Compound 82-6 was separated by chiral column, column OD (particle size 3 um), mobile phase: ethanol (0.05% diethylamine). The step was gradient elution with 5% to 40% ethanol, flow rate: 2.5 ml/min, (retention time: 5.225 min). After separation, the compound 166 was obtained by high-performance liquid chromatography (acidic, hydrochloric acid system). $^1$H NMR (400 MHz, CD$_3$OD) δ 8.13 (d, J=8.0 Hz, 2H), 7.68 (d, J=8.0 Hz, 2H), 7.32-7.28 (m, 2H), 7.25-7.21 (m, 1H), 7.16-7.14 (m, 2H), 4.39 (s, 2H), 3.93 (s, 3H), 3.70-3.48 (m, 5H), 3.17-3.13 (m, 2H), 3.06-3.05 (m, 1H), 2.55-2.48 (m, 1H), 2.38-2.29 (m, 2H), 2.17-2.01 (m, 2H), 1.59-1.52 (m, 1H), 1.41-1.29 (m, 5H). MS-ESI calculated [M+H]$^+$ 487, found 487.

Example 166

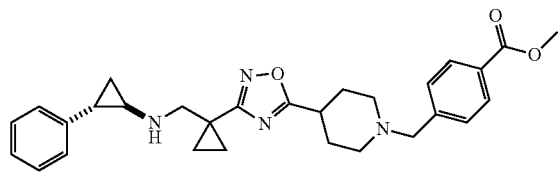

Example 167

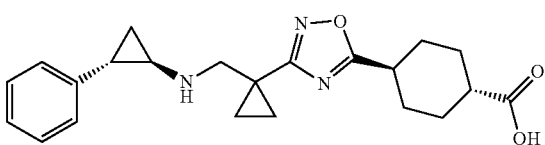 [SMILES: O=C(O)[C@H]1CC[C@H](c2nc(C3(CN[C@@H]4C[C@H]4c4ccccc4)CC3)no2)CC1]

Synthetic Route:

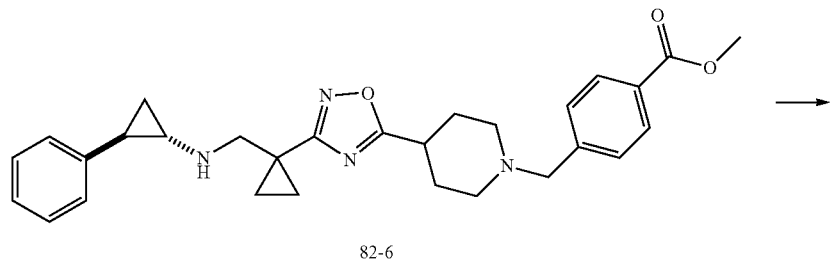

82-6

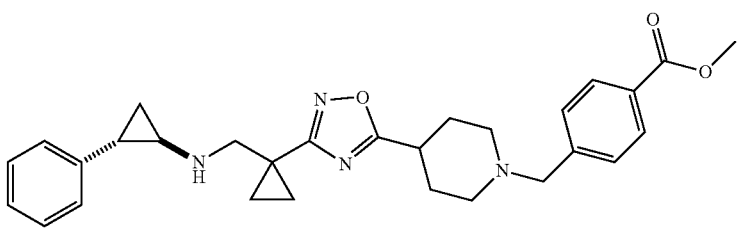

166

Synthetic Route:

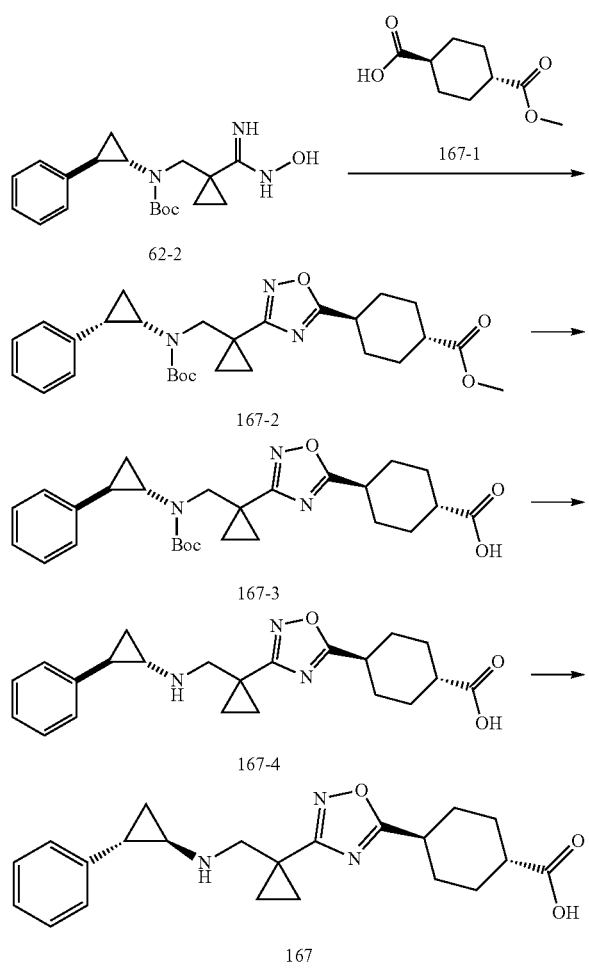

Step 1

The synthesis of compound 167-2 was referred to the first step of example 63. MS-ESI calculated [M+H]+ 496, found 496.

Step 2

Compound 167-2 (1.50 g, 3.03 mol) was dissolved in water (8 mL) and tetrahydrofuran (2 mL), sodium hydroxide (484 mg, 12.1 mmol) was added and the reaction was stirred at 40° C. for 4 h. The reaction solution was cooled to 0° C., water (100 mL) was added and the mixture was adjusted to pH=3 with hydrochloric acid (1 mol/L). The mixture was extracted with ethyl acetate:tetrahydrofuran=3:1 (50 mL×3). The organic phases were combined, washed with saturated brine (50 mL×2), dried over anhydrous sodium sulfate, filtered, and concentrated under reduced pressure to give compound 167-3. MS-ESI calculated [M+Na]+ 504, found 504.

Step 3

The synthesis of compound 167-4 was referred to the second step of example 63. MS-ESI calculated [M+H]+ 382, found 382.

Step 4

Compound 167-4 was separated by chiral column, column Chiralpak AD (particle size 3 um), mobile phase: A: $CO_2$, B: methanol (0.05% diethylamine). The steps were consisted of isocratic elution for 0.2 min with 5% methanol, and gradient elution for 1.05 min with 5% to 40% methanol. Finally, the methanol ratio was changed to 5% and the column was rinsed for 0.35 min; the flow rate was 4 mL/min (retention time: 1.627 min). And after separation, the compound 167 was prepared by high-performance liquid chromatography (acidic, hydrochloric acid system). Optical rotation [a]=−76.753 (0.07 g/100 mL×26° C.). $^1$H NMR (400 MHz, $CD_3OD$) δ 7.32-7.29 (m, 2H), 7.25-7.21 (m, 1H), 7.19-7.15 (m, 2H), 3.70-3.61 (m, 2H), 3.09-3.05 (m, 1H), 2.96-2.90 (m, 1H), 2.56-2.51 (m, 1H), 2.37-2.31 (m, 1H), 2.18-2.10 (m, 4H), 1.66-1.50 (m, 5H), 1.42-1.36 (m, 3H), 1.32-1.27 (m, 2H). MS-ESI calculated [M+H]+ 382, found 382.

Example 168

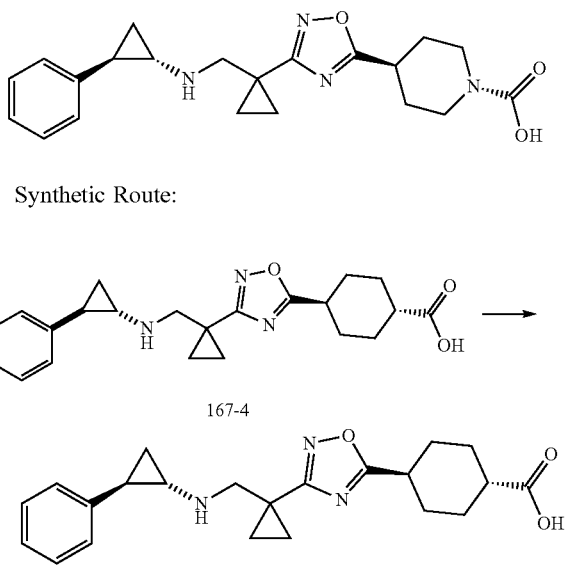

Synthetic Route:

Compound 167-4 was separated by chiral column, column Chiralpak AD (particle size 3 um), mobile phase: A: $CO_2$, B: methanol (0.05% diethylamine). The steps were consisted of isocratic elution for 0.2 min with 5% methanol, and gradient elution for 1.05 min with 5% to 40% methanol. Finally, the methanol ratio was again changed to 5% and the column was rinsed for 0.35 min: the flow rate was 4 mL/min (retention time: 1.867 min). The compound 168 was obtained by high-performance liquid chromatography (acidic, hydrochloric acid system). Optical rotation [a]=+ 22.530 (0.03 g/100 mL×6'C). $^1$H NMR (400 MHz, $CD_3OD$) δ 7.33-7.29 (m, 2H), 7.22-7.22 (m, 1H), 7.17-7.15 (m, 2H), 3.70-3.61 (m, 2H), 3.07-3.06 (m, 1H), 2.97-2.90 (m, 1H), 2.55-2.50 (m, 1H), 2.34-2.32 (m, 1H), 2.18-2.10 (m, 4H), 1.66-1.54 (m, 5H), 1.43-1.37 (m, 3H), 1.31-1.26 (m, 2H). MS-ESI calculated [M+H]+ 382, found 382.

Example 169

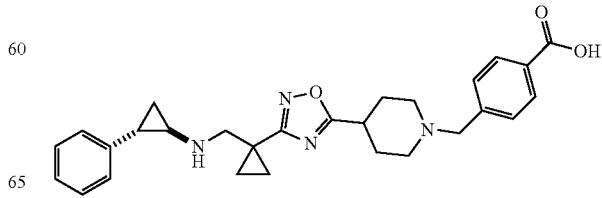

Synthetic Route:
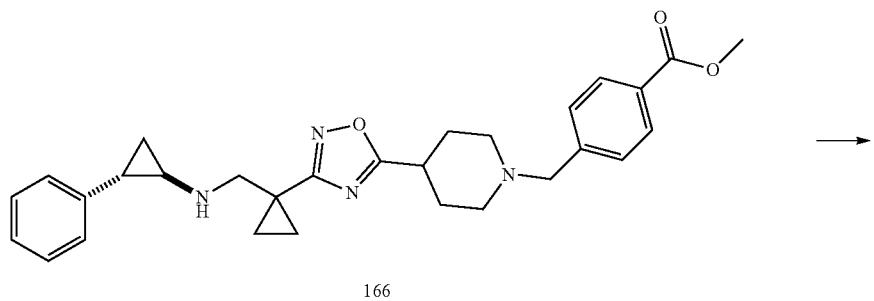
166
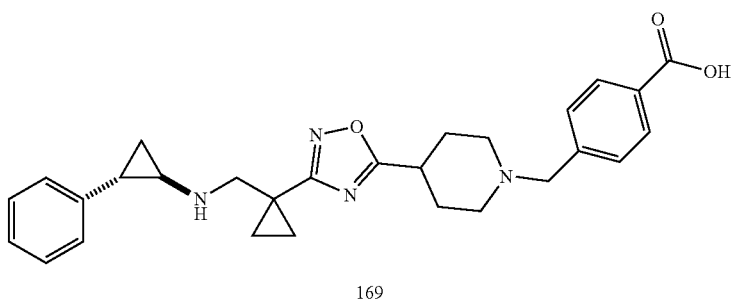
169
The synthesis of compound 169 was referred to the second step of example 149. ¹H NMR (400 MHz, CD$_3$OD) δ 8.14 (d, J=8.0 Hz, 2H), 7.71 (d, J=8.0 Hz, 2H), 7.32-7.28 (m, 2H), 7.24-7.21 (m, 1H), 7.18-7.14 (m, 2H), 4.45 (s, 2H), 3.73-3.60 (m, 3H), 3.54-3.34 (m, 3H), 3.26-3.20 (m, 1H), 3.08-3.04 (m, 1H), 2.64-2.51 (m, 1H), 2.44-2.31 (m, 4H), 1.66-1.54 (m, 1H), 1.42-1.34 (m, 5H). MS-ESI calculated [M+H]$^+$ 473, found 473.
Example 170
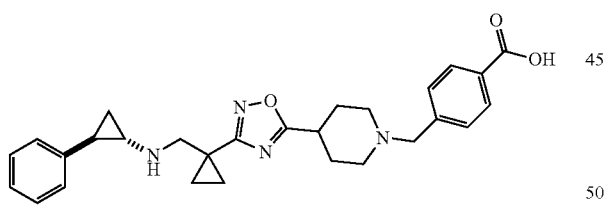
Synthetic Route:
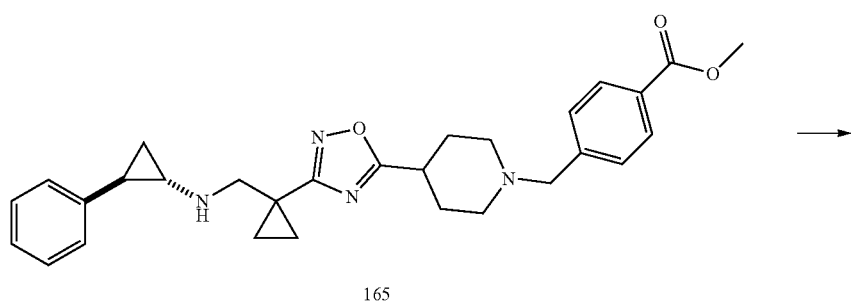
165

-continued

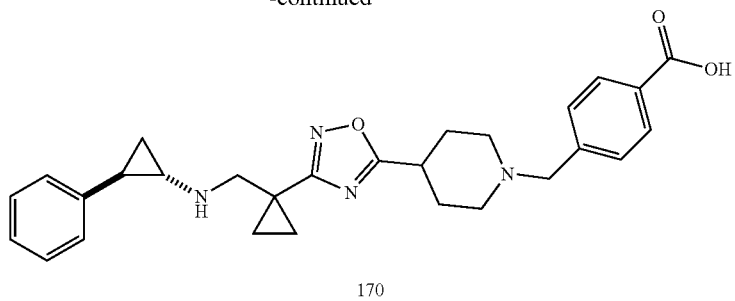

170

The synthesis of compound 170 was referred to the second step of example 149. ¹H NMR (400 MHz, CD₃OD) δ 8.14 (d, J=8.4 Hz, 2H), 7.73 (d, J=8.4 Hz, 2H), 7.31-7.28 (m, 2H), 7.24-7.14 (m, 3H), 4.46 (s, 2H), 3.74-3.59 (m, 3H), 3.54-3.33 (m, 3H), 3.28-3.22 (m, 1H), 3.08-3.05 (m, 1H), 2.59-2.54 (m, 1H), 2.44-2.11 (m, 4H), 1.61-1.56 (m, 1H), 1.41-1.28 (m, 5H). MS-ESI calculated [M+H]⁺ 473, found 473.

Example 171

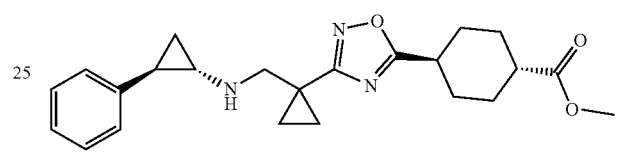

Synthetic Route:

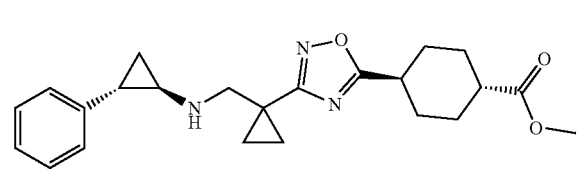 [SMILES: COC(=O)[C@H]1CC[C@H](c2nc(C3(CN[C@@H]4C[C@H]4c4ccccc4)CC3)no2)CC1]

Compound 167 (58.0 mg, 0.152 mmol) was dissolved in methanol (5 mL), and concentrated sulfuric acid (0.1 mL) was added dropwise at 0° C. The mixture was heated to 70° C. and stirred for 1 hour. The mixture was concentrated under reduced pressure, isolated and purified by high-performance liquid chromatography (acid, hydrochloric acid) to give compound 171. ¹H NMR (400 MHz, CD₃OD) δ 7.33-7.29 (m, 2H), 7.25-7.22 (m, 1H), 7.16-7.14 (m, 2H), 3.69-3.61 (m, 5H), 3.08-3.06 (m, 1H), 2.96-2.94 (m, 1H), 2.52-2.49 (m, 1H), 2.40-2.38 (m, 1H), 2.18-2.03 (m, 4H), 1.66-1.51 (m, 5H), 1.43-1.37 (m, 3H), 1.31-1.25 (m, 2H). MS-ESI calculated [M+H]⁺ 396, found 396.

Example 172

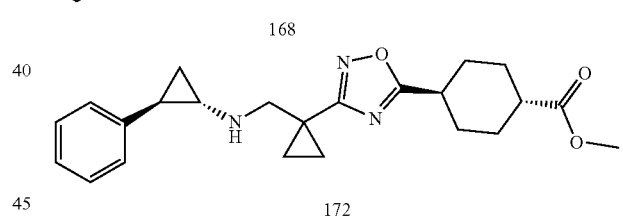

Synthetic Route:

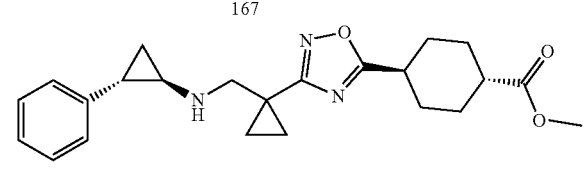

The synthesis of compound 172 was referred to the Example 171. ¹H NMR (400 MHz, CD₃OD) δ 7.33-7.29 (m, 2H), 7.25-7.21 (m, 1H), 7.16-7.14 (m, 2H), 3.69-3.61 (m, 5H), 3.09-3.05 (m, 1H), 2.96-2.94 (m, 1H), 2.53-2.48 (m, 1H), 2.40-2.38 (m, 1H), 2.17-2.08 (m, 4H), 1.66-1.51 (m, 5H), 1.43-1.37 (m, 3H), 1.30-1.29 (m, 2H). MS-ESI calculated [M+H]⁺ 396, found 396.

Example 173

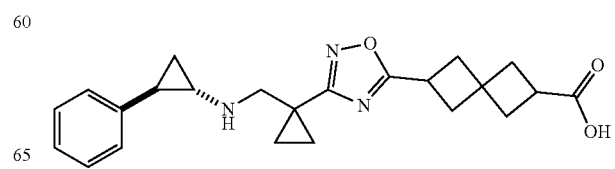

Synthetic Route:

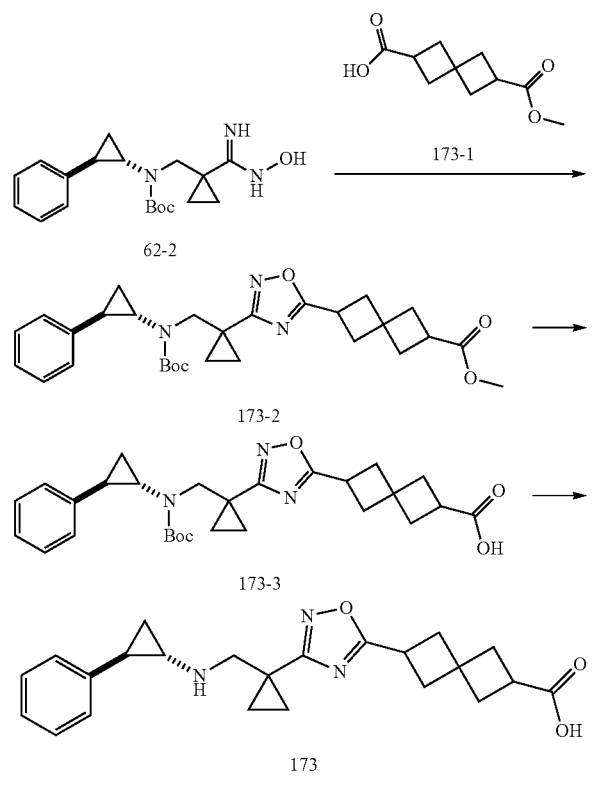

Step 1

The synthesis of compound 173-2 was referred to the fifth step of example 144. MS-ESI calculated [M+Na]⁺ 530, found 530.

Step 2

The synthesis of compound 173-3 was referred to the second step of example 149. MS-ESI calculated [M+Na]⁺ 516, found 516.

Step 3

The synthesis of compound 173 was referred to the sixth step of example 144. $^1$H NMR (400 MHz, CD$_3$OD) δ 7.32-7.29 (m, 2H), 7.25-7.21 (m, 1H), 7.16-7.14 (m, 2H), 3.70-3.58 (m, 3H), 3.09-2.97 (m, 2H), 2.60-2.47 (m, 2H), 2.45-2.31 (m, 5H), 2.25-2.23 (m, 2H), 1.57-1.51 (m, 1H), 1.45-1.42 (m, 2H), 1.40-1.37 (m, 1H), 1.31-1.29 (m, 2H). MS-ESI calculated [M+H]⁺ 394, found 394.

Example 174

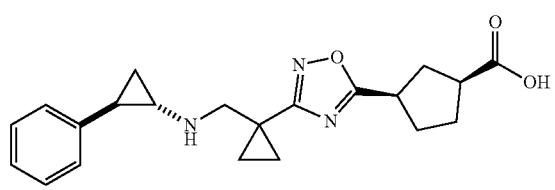

Synthetic Route:

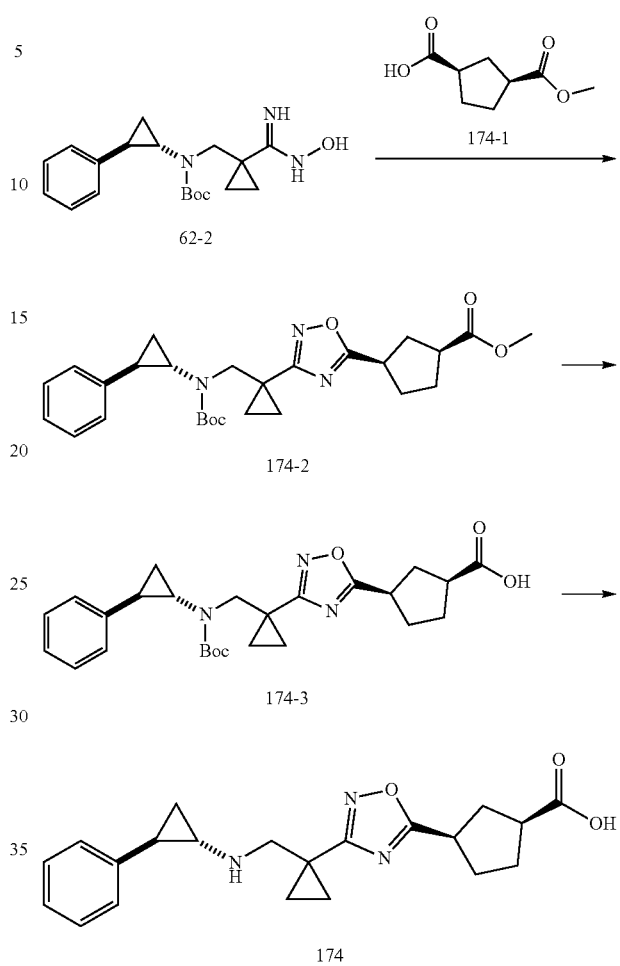

Step 1

The synthesis of compound 174-2 was referred to the fifth step of example 144. MS-ESI calculated [M+H]482, found 482.

Step 2

The synthesis of compound 174-3 was referred to the second step of example 149. MS-ESI calculated [M+Na]⁺ 490, found 490.

Step 3

The synthesis of compound 174 was referred to the sixth step of example 144. $^1$H NMR (400 MHz, CD$_3$OD) δ 7.32-7.29 (m, 2H), 7.24-7.21 (m, 1H), 7.16-7.15 (m, 2H), 3.70-3.61 (m, 2H), 3.55-3.40 (m, 1H), 3.10-3.06 (m, 1H), 3.02-2.93 (m, 1H), 2.58-2.51 (m, 1H), 2.46-2.33 (m, 1H), 2.26-1.90 (m, 5H), 1.59-1.54 (m, 1H), 1.45-1.42 (m, 2H), 1.40-1.35 (m, 1H), 1.32-1.30 (m, 2H). MS-ESI calculated [M+H]⁺ 368, found 368.

Example 175

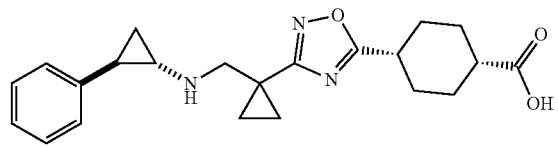

Synthetic Route:

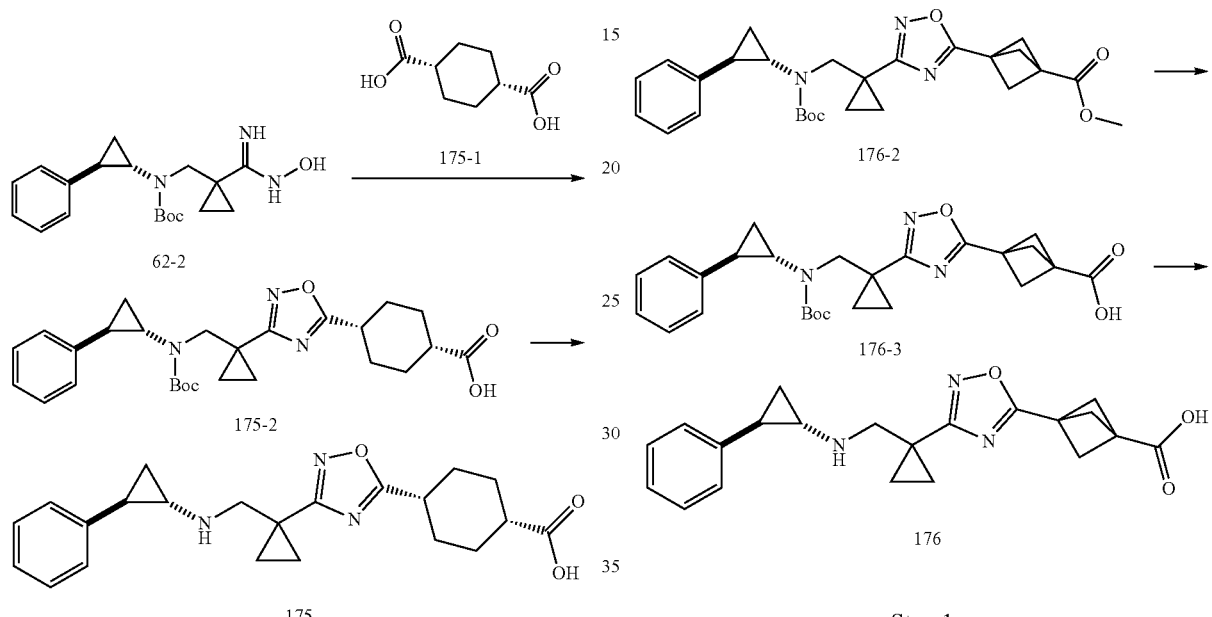

Step 1

The synthesis of compound 175-2 was referred to the fifth step of example 144. MS-ESI calculated [M+Na]+ 504 found 504.

Step 2

The synthesis of compound 175 was referred to the sixth step of example 144. ¹H NMR (400 MHz, CD$_3$OD) δ 7.32-7.29 (m, 2H), 7.25-7.21 (m, 1H), 7.17-7.15 (m, 2H), 3.65 (s, 2H), 3.43-3.39 (m, 1H), 3.12-3.04 (m, 2H), 2.54-2.49 (m, 1H), 2.13-2.00 (m, 3H), 1.90-1.85 (m, 1H), 1.58-1.49 (m, 5H), 1.43-1.35 (m, 3H), 1.31-1.25 (m, 2H). MS-EST calculated [M+H]+ 382, found 382.

Example 176

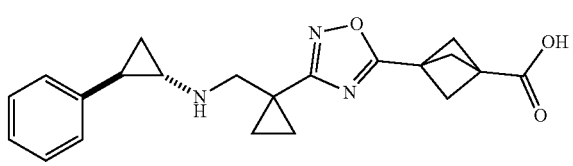

Synthetic Route:

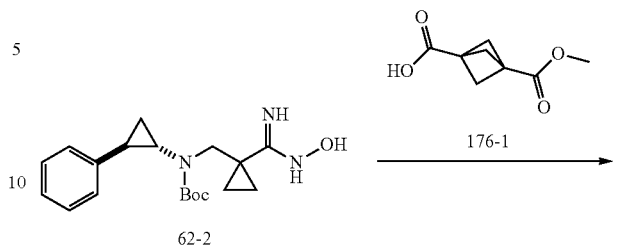

Step 1

The synthesis of compound 176-2 was referred to the fifth step of example 144. MS-ESI calculated [M+Na]+ 502, found 502.

Step 2

The synthesis of compound 176-3 was referred to the second step of example 149. MS-ESI calculated [M+Na]+ 488, found 488.

Step 3

The synthesis of compound 176 was referred to the sixth step of example 144. ¹H NMR (400 MHz, CD$_3$OD) δ 7.33-7.29 (m, 2H), 7.25-7.22 (m, 1H), 7.16-7.14 (m, 2H), 3.71-3.61 (m, 2H), 3.09-3.06 (m, 1H), 2.52-2.46 (m, 7H), 1.56-1.50 (m, 1H), 1.45-1.35 (m, 3H), 1.32-1.29 (m, 2H). MS-ESI calculated [M+H]+ 366, found 366.

Example 177

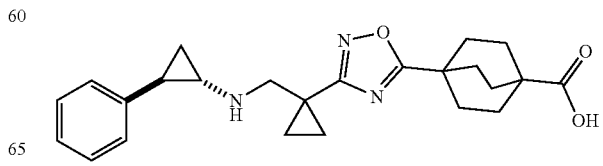

333

Synthetic Route:

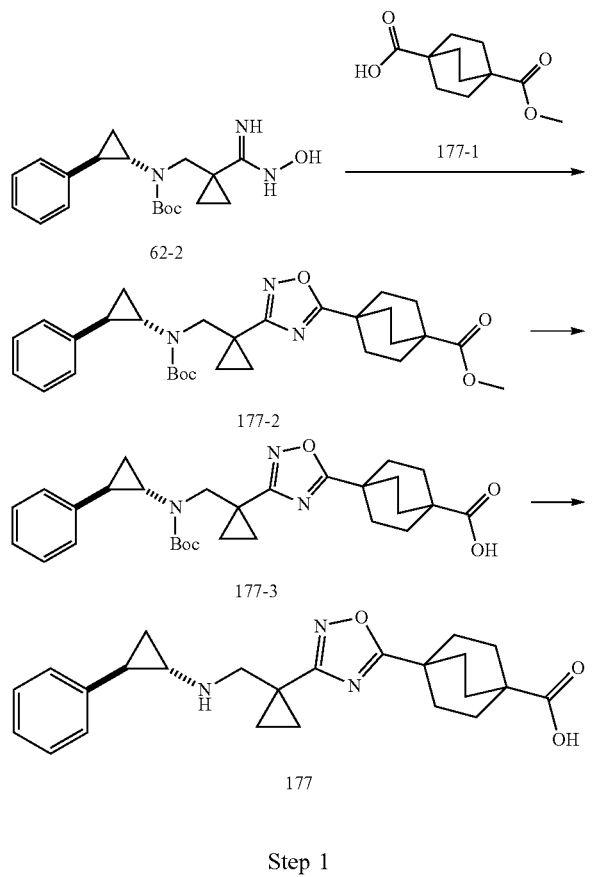

Step 1

The synthesis of compound 177-2 was referred to the fifth step of example 144. MS-ESI calculated [M+H]⁺ 522, found 522.

Step 2

The synthesis of compound 177-3 was referred to the second step of example 149. MS-ESI calculated [M+Na]⁺ 530, found 530.

Step 3

The synthesis of compound 177 was referred to the sixth step of example 144. $^1$H NMR (400 MHz, CD$_3$OD) δ 7.33-7.31 (m, 2H), 7.25-7.22 (m, 1H), 7.17-7.15 (m, 2H), 3.68-3.61 (m, 2H), 3.09-3.05 (m, 1H), 2.54-2.49 (m, 1H), 2.03-1.90 (m, 12H), 1.57-1.52 (m, 1H), 1.44-1.37 (m, 3H), 1.32-1.27 (m, 2H). MS-ES calculated [M+H]⁺ 408, found 408.

Example 178

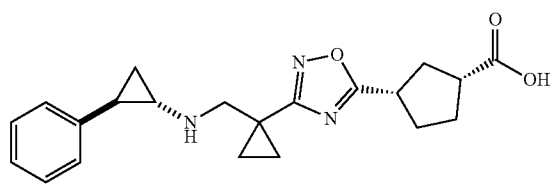

334

Synthetic Route:

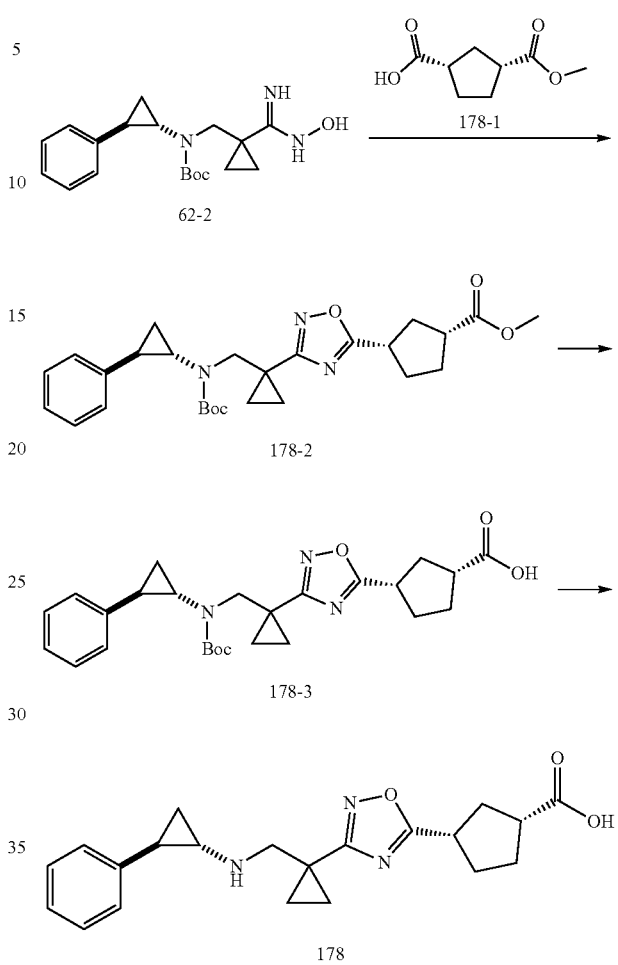

Step 1

The synthesis of compound 178-2 was referred to the fifth step of example 144. MS-ESI calculated [M+Na]⁺ 504, found 504.

Step 2

The synthesis of compound 178-3 was referred to the second step of example 149. MS-ESI calculated [M+Na]⁺ 490, found 490.

Step 3

The synthesis of compound 178 was referred to the sixth step of example 144. $^1$H NMR (400 MHz, CD$_3$OD) δ 7.32-7.29 (m, 2H), 7.24-7.21 (m, 1H), 7.16-7.15 (m, 2H), 3.71-3.62 (m, 2H), 3.55-3.40 (m, 1H), 3.10-3.06 (m, 1H), 3.03-2.95 (m, 1H), 2.57-2.52 (m, 1H), 2.46-2.33 (m, 1H), 2.26-1.88 (m, 5H), 1.60-1.51 (m, 1H), 1.45-1.41 (m, 2H), 1.40-1.36 (m, 1H), 1.34-1.31 (m, 2H). MS-ESI calculated [M+H]⁺ 368, found 368.

Example 179

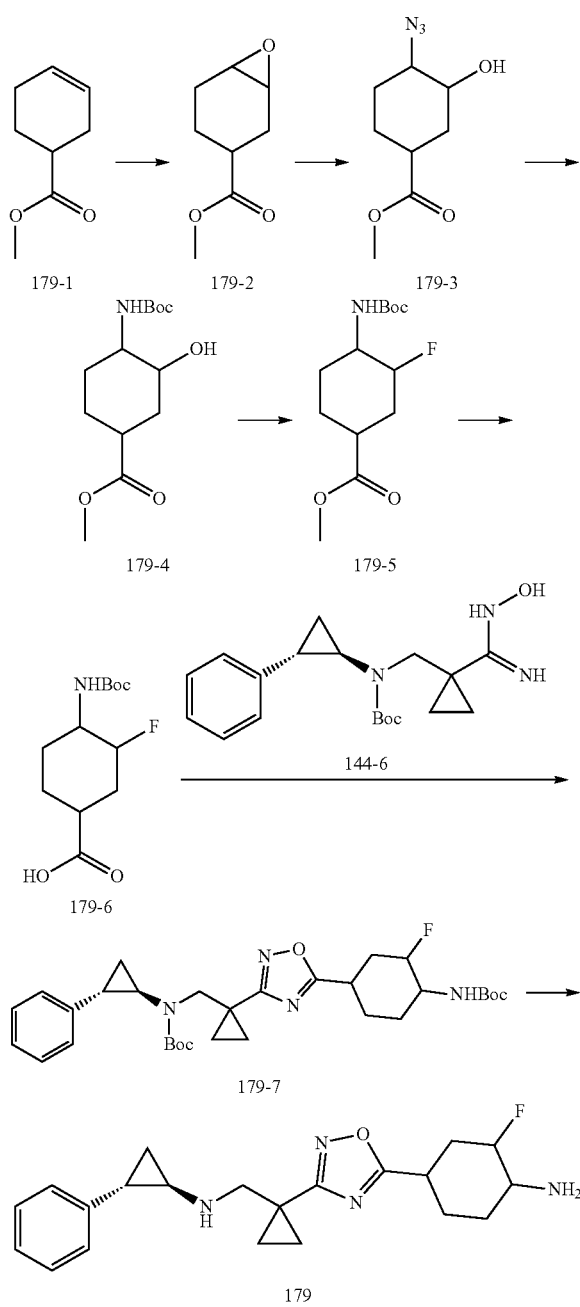

Step 1

Compound 179-1 (5 g, 35.7 mmol) was dissolved in anhydrous dichloromethane (200 mL), m-chloroperoxybenzoic acid (9.23 g, 42.8 mmol, 80% purity) was added at 0° C. The reaction solution was warmed to 25° C. and the reaction was stirred for 24 h. Chloroform (100 mL) and saturated sodium carbonate (100 mL) were added to the reaction mixture. The mixture was stirred for 30 min. Aqueous phase and organic phase were separated, and the organic phase was washed with saturated sodium carbonate (3×100 mL), dried over anhydrous sodium sulfate, filtered, concentrated under reduced pressure, isolated and purified by silica gel column chromatography (10:1 petroleum ether/ethyl acetate, Rf=0.8) to give compound 179-2. $^1$H NMR (400 MHz, CDCl$_3$) δ 3.66 (s, 3H), 3.22-3.12 (m, 2H), 2.53-2.49 (m, 0.5H), 2.25-2.14 (m, 2H), 2.03-1.86 (m, 2H), 1.80-1.72 (m, 1H), 1.65-1.52 (m, 1H), 1.45-1.35 (m, 0.5H).

Step 2

Compound 179-2 (5.00 g, 32.0 mmol) was dissolved in N,N-dimethylformamide (50 mL), and sodium azide (2.71 g, 41.6 mmol) and ammonium chloride (3.08 g) were added to the reaction mixture. The mixture was stirred at 70° C. for 6 h. The reaction was quenched with water (300 mL) and the mixture was extracted with ethyl acetate (200 mL×3). The organic phases were combined, washed with saturated brine (100 mL×2), dried over anhydrous sodium sulfate, filtered and concentrated under reduced pressure to give compound 179-3. $^1$H NMR (400 MHz, CDCl$_3$) δ 3.70-3.61 (m, 4H), 3.57-3.28 (m, 1H), 2.78-2.72 (m, 1H), 2.37-2.23 (m, 1H), 2.12-1.85 (m, 1H), 1.69-1.31 (m, 4H).

Step 3

Compound 179-3 (7.00 g, 35.1 mmol) and di-tert-butyl carbonate (7.67 g, 35.1 mmol) were dissolved in methanol (150 mL), wet palladium on carbon (700 mg, 10% purity) was added under nitrogen. The reaction solution was replaced with hydrogen several times, stirred under hydrogen (15 psi) at 25° C. for 12 h. The mixture was filtered to remove palladium on carbon, concentrated under reduced pressure, isolated and purified by silica gel column chromatography (5:1 petroleum ether/ethyl acetate, Rf=0.2) to give compound 179-4. MS-ESI calculated [M+Na]$^+$ 2%, found 296.

Step 4

Compound 179-4 (1.60 g, 5.85 mmol) was dissolved in anhydrous dichloromethane (30 mL), bis (2-methoxyethyl) aminosulfur trifluoride (1.94 g, 8.78 mmol) was added dropwise at 0° C. The reaction solution was stirred at 25° C. for 12 h. The reaction mixture was quenched with water (50 mL), adjusted to pH=9 with saturated sodium bicarbonate, extracted with dichloromethane (30 mL×3). The organic phases were combined, washed with saturated brine (30 mL×2), dried over anhydrous sodium sulfate, filtered, concentrated under reduced pressure, isolated and purified by silica gel column chromatography (3:1 petroleum ether/ethyl acetate, Rf=0.4) to give compound 179-5. MS-ESI calculated [M-Boc+H]$^+$ 176, found 176.

Step 5

The synthesis of compound 179-6 was referred to the second step of example 149. MS-ESI calculated [M-56+H]$^+$ 206, found 206.

Step 6

The synthesis of compound 179-7 was referred to the fifth step of example 144. MS-ESI calculated [M+Na]$^+$ 593, found 593.

Step 7

The synthesis of compound 179 was referred to the sixth step of example 144. $^1$H NMR (400 MHz, CD$_3$OD) δ

7.32-7.29 (m, 2H), 7.25-7.21 (m, 1H), 7.16-7.14 (m, 2H), 4.68-4.51 (m, 1H), 3.75-3.49 (m, 5H), 3.07-3.05 (m, 1H), 2.58-2.51 (m, 2H), 2.34-2.20 (m, 2H), 2.04-1.94 (m, 1H), 1.86-1.55 (m, 3H), 1.42-1.34 (m, 4H). MS-ESI calculated [M+H]$^+$ 371, found 371.

Example 180

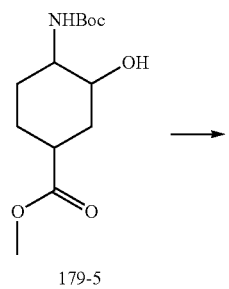

179-5

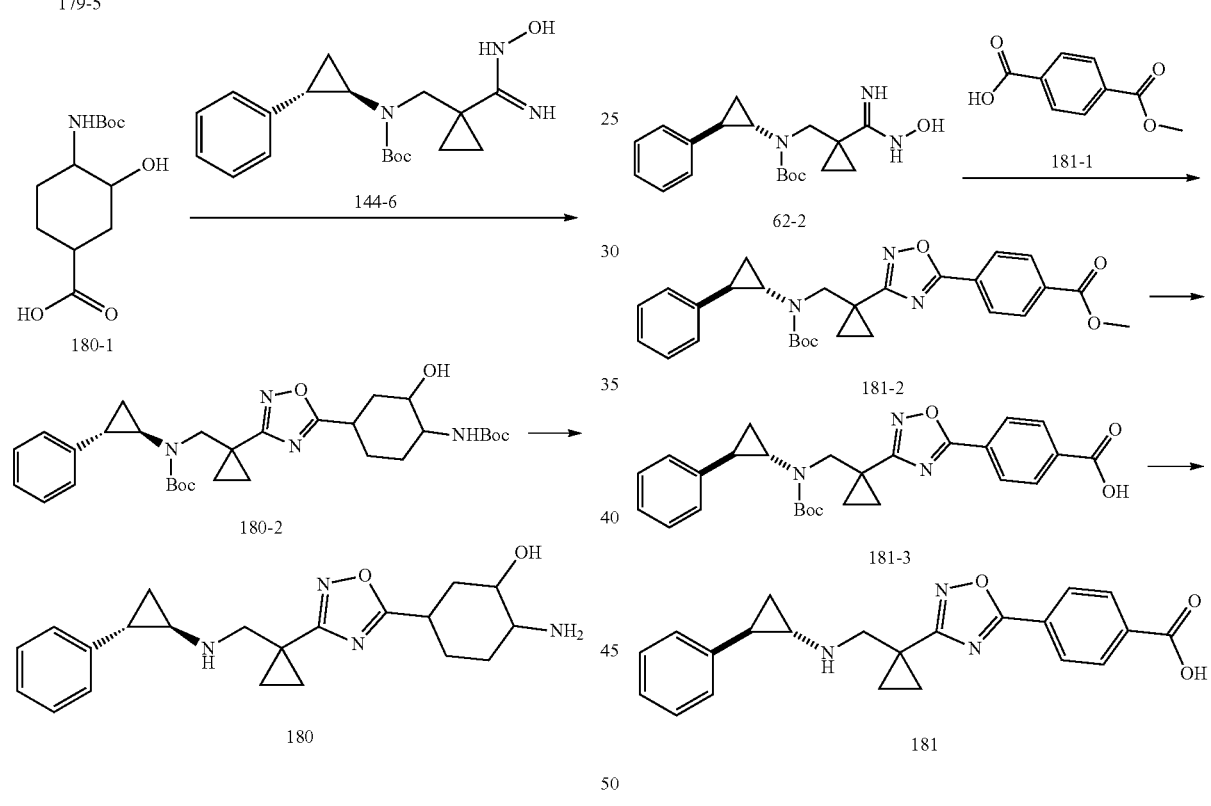

Step 1

The synthesis of compound 180-1 was referred to the second step of example 149. MS-ESI calculated [M+Na]$^+$ 282, found 282.

Step 2

The synthesis of compound 180-2 was referred to the fifth step of example 144. MS-ESI calculated [M+Na]$^+$ 591, found 591.

Step 3

The synthesis of compound 180 was referred to the sixth step of example 144. $^1$H NMR (400 MHz, CD$_3$OD) δ 7.32-7.29 (m, 2H), 7.24-7.21 (m, 1H), 7.17-7.15 (m, 2H), 3.78-3.63 (m, 3H), 3.57-3.49 (m, 1H), 3.25-3.20 (m, 0.5H), 3.08-3.06 (m, 1H), 3.01-2.94 (m, 0.5H), 2.63-2.47 (m, 2H), 2.27-2.18 (m, 1H), 2.02-1.79 (m, 3H), 1.70-1.58 (m, 2H), 1.46-1.35 (m, 5H). MS-ESI calculated [M+H]$^+$ 369, found 369.

Example 181

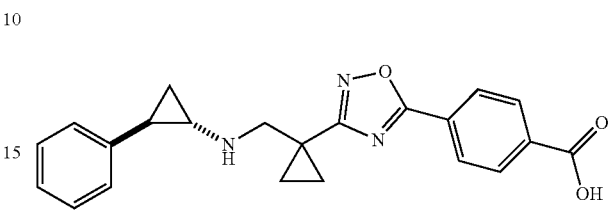

Synthetic Route:

Step 1

The synthesis of compound 181-2 was referred to the fifth step of example 144. MS-ESI calculated [M+Na]$^+$ 512, found 512.

Step 2

The synthesis of compound 181-3 was referred to the second step of example 149. MS-ESI calculated [M+Na]$^+$ 498, found 498.

Step 3

The synthesis of compound 181 was referred to the sixth step of example 144. $^1$H NMR (400 MHz, CD$_3$OD) δ

8.23-8.15 (m, 4H), 7.27-7.23 (m, 2H), 7.18-7.13 (m, 3H), 3.82-3.69 (m, 2H), 3.15-3.11 (m, 1H), 2.61-2.58 (m, 1H), 1.65-1.49 (m, 3H), 1.45-1.37 (m, 3H). MS-ESI calculated [M+H]⁺ 376, found 376.

Example 182

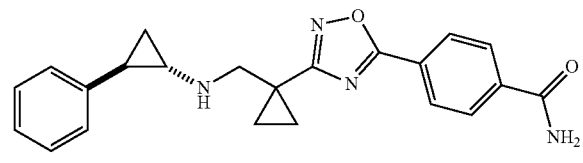

Synthetic Route:

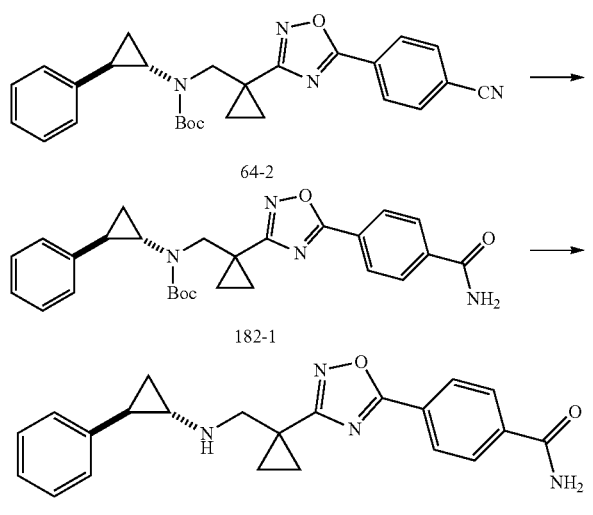

Step 1

Compound 64-2 (260 mg, 0.569 mmol) and anhydrous potassium carbonate (157 mg, 1.14 mmol) were dissolved in dimethyl sulfoxide (2 mL), and hydrogen peroxide (645 mg, 5.70 mmol, 30% purity) was added dropwise at 0° C. The mixture was stirred at room temperature for 25 hours at 25° C. Saturated sodium thiosulfate solution (50 mL) and saturated sodium bicarbonate solution (50 mL) were added to the reaction mixture at 0° C., and stirred for 30 minutes. The mixture was extracted with ethyl acetate (50 mL×3). The organic phases were combined, washed with saturated brine (50 mL×2), dried over anhydrous sodium sulfate, filtered, concentrated under reduced pressure, isolated and purified by preparative thin layer chromatography (ethyl acetate, Rf=0.5) to give compound 182-1. ¹H NMR (400 MHz, CDCl₃) δ 8.13 (d, J=8.4 Hz, 2H), 7.94 (d, J=8.4 Hz, 2H), 7.18-7.15 (m, 2H), 7.09-7.01 (m, 3H), 6.16 (brs, 1H), 5.73 (brs, 1H), 3.96-3.76 (m, 2H), 2.83-2.79 (m, 1H), 2.11-2.05 (m, 1H), 1.40 (s, 9H), 1.34-1.29 (m, 2H), 1.22-1.06 (m, 4H). MS-ESI calculated [M+Na]⁺ 497, found 497.

Step 2

The synthesis of compound 182 was referred to the sixth step of example 144. ¹H NMR (400 MHz, CD₃OD) δ 8.18 (d, J=8.4 Hz, 2H), 8.06 (d, J=8.4 Hz, 2H), 7.28-7.25 (m, 2H), 7.19-7.14 (m, 3H), 3.82-3.69 (m, 2H), 3.15-3.11 (m, 1H), 2.59-2.54 (m, 1H), 1.62-1.50 (m, 3H), 1.42-1.38 (m, 3H). MS-ESI calculated [M+H]⁺ 375, found 375.

Example 183

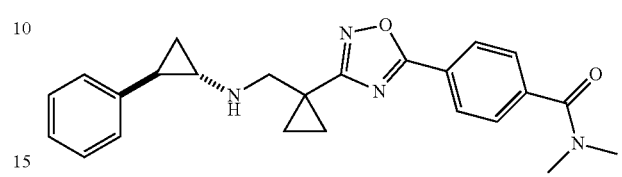

Synthetic Route:

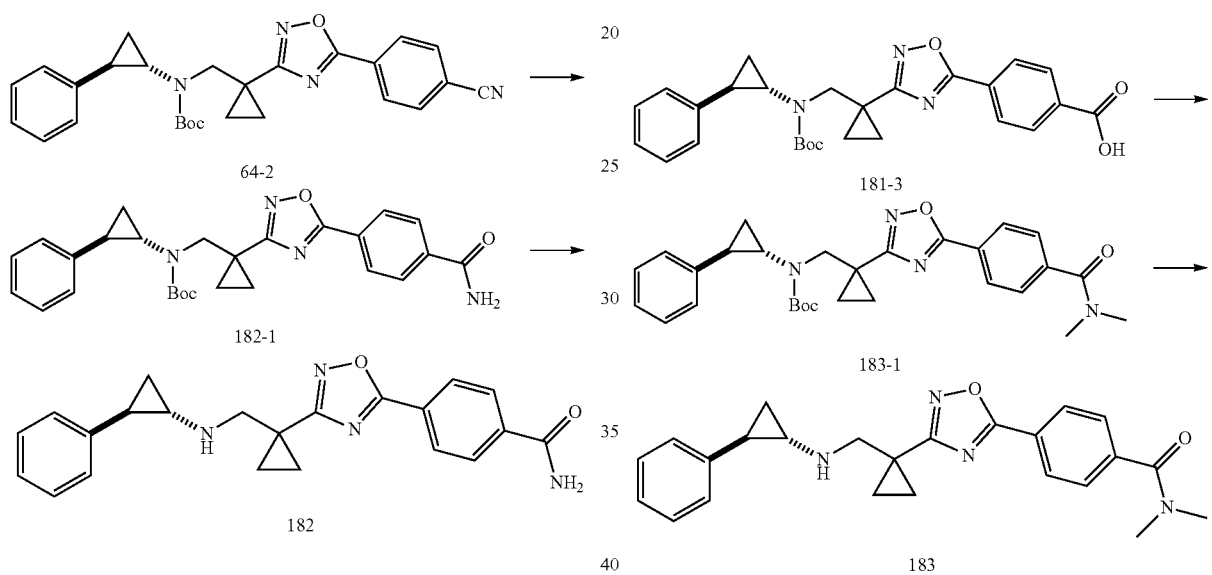

Step 1

The compound 181-3 (100 mg, 0.210 mmol) was dissolved in anhydrous N,N-dimethylformamide (2 mL), dimethylamine hydrochloride (18.9 mg, 0.231 mmol), 2-(7-azobenzotriazole)-N,N,N,N-tetramethyluronium hexafluorophosphate (79.9 mg, 0.210 mmol) and diisopropylethylamine (81.5 mg, 0.630 mmol), were added. The mixture was stirred at 25° C. for 25 h. Water (30 mL) was added to the reaction mixture. The mixture was extracted with ethyl acetate (20 mL×3). The organic phases were combined, washed with saturated brine (20 mL×2), dried over anhydrous sodium sulfate, filtered, concentrated under reduced pressure, isolated and purified by preparative thin layer chromatography (1:1 petroleum ether/ethyl acetate, Rf=0.3) to give compound 183-1. MS-ESI calculated [M+Na]⁺ 525, found 525.

Step 2

The synthesis of compound 183 was referred to the sixth step of example 144. ¹H NMR (400 MHz, CD₃OD) δ 8.18 (d, J=8.4 Hz, 2H), 7.65 (d, J=8.4 Hz, 2H), 7.28-7.24 (m, 2H), 7.16-7.13 (m, 3H), 3.82-3.69 (m, 2H), 3.14-3.11 (m, 4H), 3.01 (s, 3H), 2.62-2.57 (m, 1H), 1.65-1.60 (m, 1H), 1.58-1.51 (m, 2H), 1.47-1.36 (m, 3H). MS-ESI calculated [M+H]$^+$ 403, found 403.

Example 184

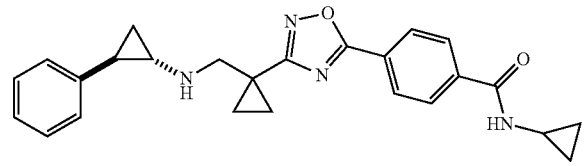

Synthetic Route:

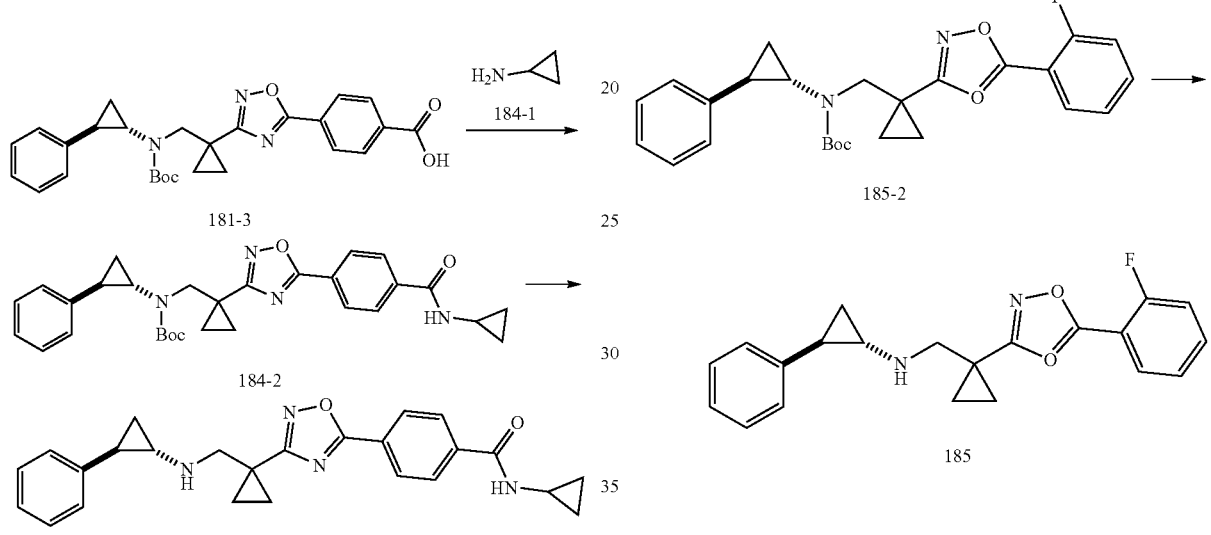

Step 1

The synthesis of compound 184-2 was referred to the first step of example 183. MS-ESI calculated [M+Na]$^+$ 537, found 537.

Step 2

The synthesis of compound 184 was referred to the sixth step of example 144. $^1$H NMR (400 MHz, CD$_3$OD) δ 8.15 (d, J=8.4 Hz, 2H), 7.98 (d, J=8.4 Hz, 2H), 7.33-7.24 (m, 2H), 7.19-7.07 (m, 3H), 3.90-3.57 (m, 2H), 3.15-3.11 (m, 1H), 2.90-2.86 (m, 1H), 2.60-2.55 (m, 1H), 1.67-1.54 (m, 3H), 1.45-1.32 (m, 3H), 0.87-0.78 (m, 2H), 0.69-0.62 (m, 2H). MS-ESI calculated [M+H]$^+$ 415, found 415.

Example 185

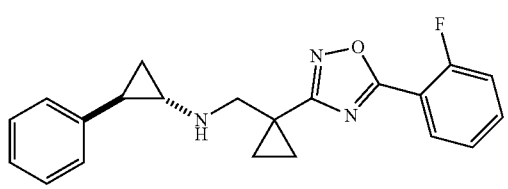

Synthetic Route:

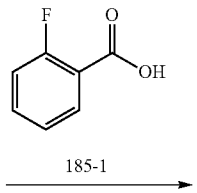

Step 1

The synthesis of compound 185-2 was referred to the fifth step of example 144. MS-ESI calculated [M+Na]$^+$ 472, found 472.

Step 2

The synthesis of compound 185 was referred to the sixth step of example 144. $^1$H NMR (400 Hz, CD$_3$OD) δ 8.12-8.09 (m, 1H), 7.74-7.69 (m, 1H), 7.42-7.35 (m, 2H), 7.29-7.25 (m, 2H), 7.20-7.13 (m, 3H), 3.79-3.67 (m, 2H), 3.12-3.10 (m, 1H), 2.53-2.49 (m, 1H), 1.58-1.50 (m, 3H), 1.43-1.38 (m, 3H). MS-ESI calculated [M+H]$^+$ 350, found 350.

Example 186

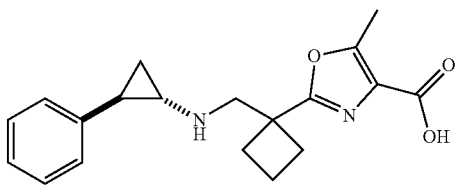

Synthetic Route:

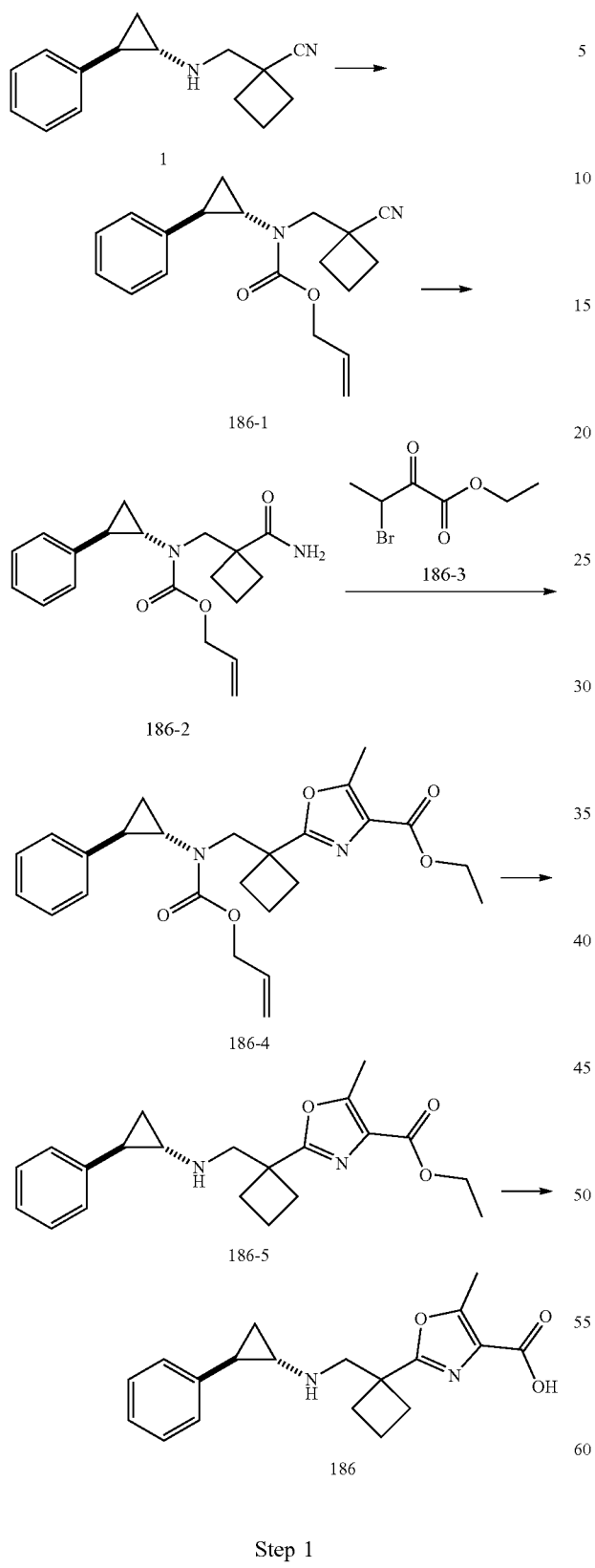

Step 1

Compound 1 (600 mg, 2.65 mmol) was dissolved in anhydrous dichloromethane (5 mL), diisopropylethylamine (685 mg, 5.30 mmol) was added at 25° C., and allyl chloroformate (479 mg, 3.98 mmol) was added. The reaction mixture was stirred at 20° C. for 1 h. The reaction mixture was concentrated under reduced pressure, isolated and purified by silica gel column chromatography (3:1 petroleum ether/ethyl acetate, Rf=0.6) to give 186-1. $^1$H NMR (400 MHz, CDCl$_3$) δ 7.28-7.26 (m, 2H), 7.19-7.15 (m, 3H), 5.96-5.90 (m, 1H), 5.30-5.19 (m, 2H), 4.70-4.61 (m, 2H), 3.97-3.94 (m, 1H), 3.51-3.47 (m, 1H), 2.89-2.85 (m, 1H), 2.52-2.41 (m, 2H), 2.28-2.16 (m, 4H), 2.05-2.03 (m, 1H), 1.38-1.26 (m, 2H). MS-EST calculated [M+H]$^+$ 311, found 311.

Step 2

The synthesis of compound 186-2 was referred to the first step of example 182. $^1$H NMR (400 MHz, CDCl$_3$) δ 7.28-7.24 (m, 2H), 7.20-7.16 (m, 1H), 7.12-7.11 (m, 2H), 5.96-5.86 (m, 1H), 5.30-5.18 (m, 2H), 4.66-4.56 (m, 2H), 3.92 (d, J=14.8 Hz, 1H), 3.62 (d, J=14.8 Hz, 1H), 2.76-2.72 (m, 1H), 2.44-2.28 (m, 2H), 2.21-2.01 (m, 3H), 1.95-1.86 (m, 2H), 1.31-1.26 (m, 2H). MS-ESI calculated [M+Na]$^+$ 351, found 351.

Step 3

Compound 186-2 (110 mg, 0.335 mmol) and compound 186-3 (140 mg, 0.670 mmol) were dissolved in dichloroethane, silver hexafluoroantimonate (115 mg, 0.335 mmol) was added. The mixture was heated to 100° C. and stirred for 48 h. The mixture was concentrated under reduced pressure, isolated and purified by thin layer chromatography (3:1 petroleum ether/ethyl acetate, Rf=0.4) to give compound 1864. MS-ESI calculated [M+H]$^+$ 439, found 439.

Step 4

Compound 186-4 (50.0 mg, 0.114 mmol) was dissolved in anhydrous tetrahydrofuran (5 mL), diethylamine (83.4 mg, 1.14 mmol) and tetratriphenylphosphine palladium (13.2 mg, 11.4 μmol) were added. The solution was stirred at 80° C. for 3 hours. The mixture was filtered and concentrated under reduced pressure to give compound 186-5. MS-ESI calculated [M+H]$^+$ 355, found 355.

Step 5

The synthesis of compound 186 was referred to the second step of example 149. $^1$H NMR (400 MHz, CD$_3$OD) δ 7.33-7.29 (m, 2H), 7.25-7.18 (m, 3H), 3.82 (s, 2H), 3.17-3.13 (m, 1H), 2.67-2.59 (m, 6H), 2.36-2.14 (m, 4H), 1.64-1.59 (m, 1H), 1.42-1.37 (m, 1H). MS-ESI calculated [M+H]$^+$ 327, found 327.

Example 187

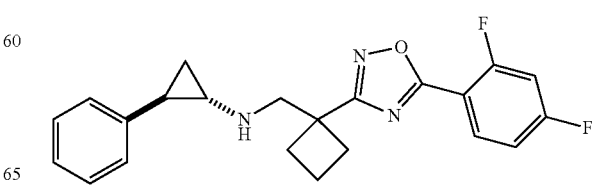

Synthetic Route:

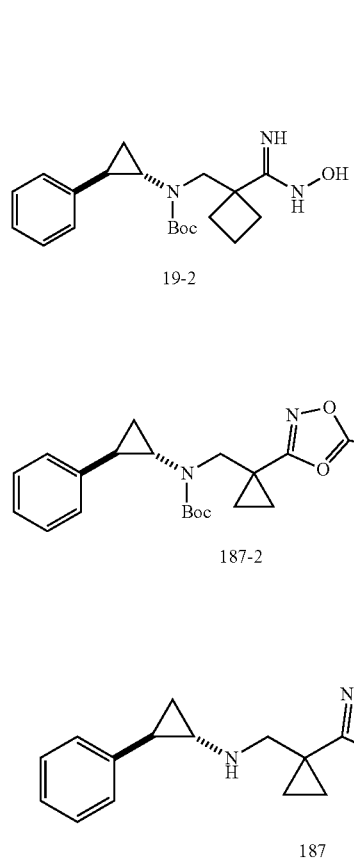

Step 1

The synthesis of compound 187-2 was referred to the fifth step of example 144. MS-ESI calculated [M+Na]⁺ 504, found 504.

Step 2

The synthesis of compound 187 was referred to the sixth step of example 144. ¹H NMR (400 MHz, CD₃OD) δ 8.27-8.21 (m, 1H), 7.31-7.14 (m, 7H), 3.88 (s, 2H), 3.08-3.06 (m, 1H), 2.72-2.64 (m, 2H), 2.56-2.52 (m, 1H), 2.45-2.40 (m, 2H), 2.26-2.18 (m, 2H), 1.61-1.55 (m, 1H), 1.40-1.35 (m, 1H). MS-ESI calculated [M+H]⁺ 382, found 382.

Example 188

Synthetic Route:

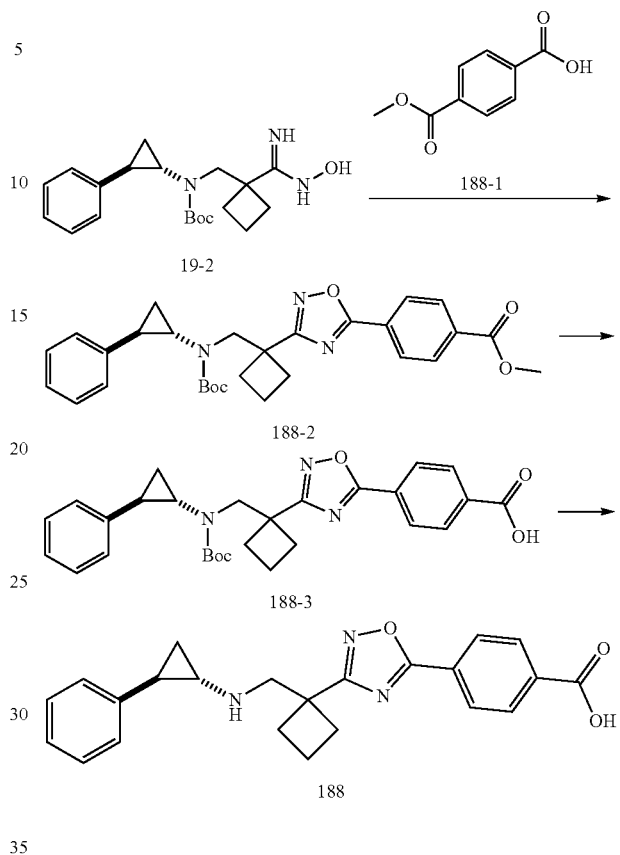

Step 1

The synthesis of compound 188-2 was referred to the fifth step of example 144. MS-ESI calculated [M+Na]⁺ 526, found 526.

The synthesis of compound 188-3 was referred to the second step of example 149. MS-ESI calculated [M+Na]⁺ 512, found 512.

Step 3

The synthesis of compound 188 was referred to the sixth step of example 144. ¹H NMR (400 MHz, CD₃OD) δ 8.28-8.21 (m, 4H), 7.30-7.26 (m, 2H), 7.22-7.15 (m, 3H), 3.89 (s, 2H), 3.11-3.07 (m, 1H), 2.74-2.66 (m, 2H), 2.56-2.51 (m, 1H), 2.47-2.38 (m, 2H), 2.28-2.20 (m, 2H), 1.59-1.54 (m, 1H), 1.42-1.33 (m, 1H). MS-ESI calculated [M+H]⁺ 390, found 390.

Example 189

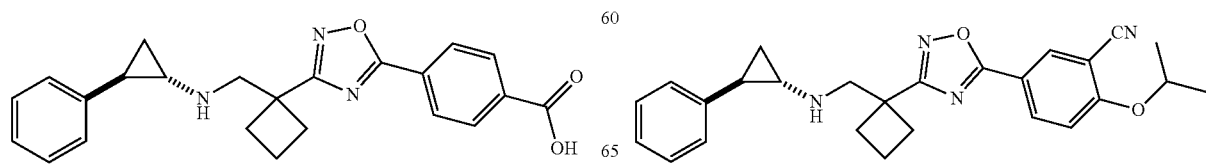

Synthetic Route:

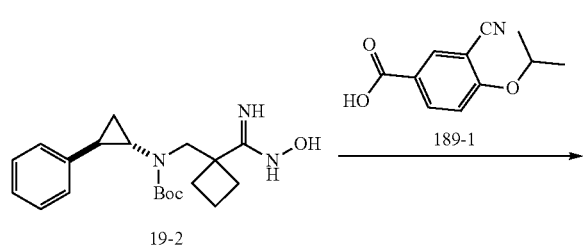

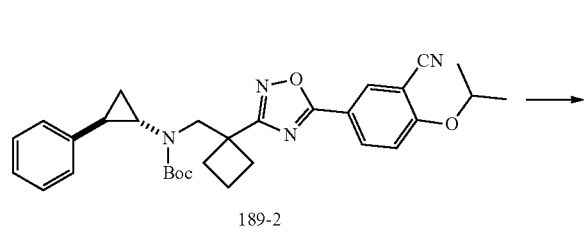

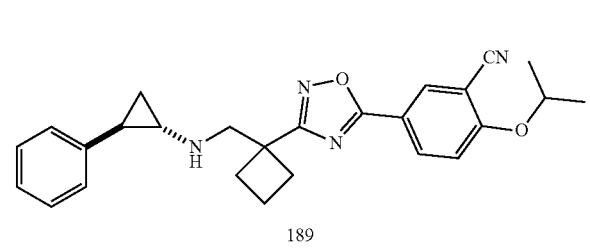

Step 1

The synthesis of compound 189-2 was referred to the fifth step of example 144. MS-ESI calculated [M+Na]⁺ 551, found 551.

Step 2

The synthesis of compound 189 was referred to the sixth step of example 144. $^1$H NMR (400 MHz, CD$_3$OD) δ 8.37 (s, 1H), 8.34 (d, J=9.2 Hz, 1H), 7.34 (d, J=9.2 Hz, 1H), 7.29-7.25 (m, 2H), 7.20-7.14 (m, 3H), 4.98-4.91 (m, 1H), 3.67 (s, 2H), 3.08-3.06 (m, 1H), 2.71-2.62 (m, 2H), 2.57-2.52 (m, 1H), 2.46-2.37 (m, 2H), 2.26-2.18 (m, 2H), 1.61-1.56 (m, 1H), 1.45 (d, J=6.0 Hz, 6H), 1.40-1.35 (m, 1H). MS-ESI calculated [M+H]⁺ 429, found 429.

Example 190

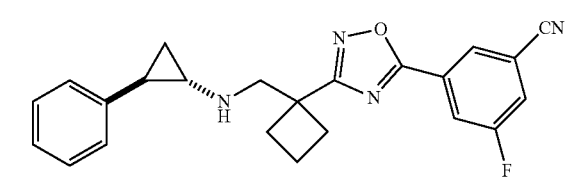

Synthetic Route:

(same initial scheme with 190-1, 190-2, 190)

Step 1

The synthesis of compound 190-2 was referred to the fifth step of example 144. MS-ESI calculated [M+Na]⁺ 511, found 511.

Step 2

The synthesis of compound 190 was referred to the sixth step of example 144. $^1$H NMR (400 MHz, CD$_3$OD) δ 8.34 (s, 1H), 8.20 (d, J=8.4 Hz, 1H), 7.93 (d, J=6.8 Hz, 1H), 7.33-7.24 (m, 2H), 7.19-7.14 (m, 3H), 3.89 (s, 2H), 3.08-3.06 (m, 1H), 2.72-2.64 (m, 2H), 2.58-2.53 (m, 1H), 2.47-2.42 (m, 2H), 2.26-2.21 (m, 2H), 1.62-1.57 (m, 1H), 1.40-1.34 (m, 1H). MS-ESI calculated [M+H]⁺ 389, found 389.

Example 191

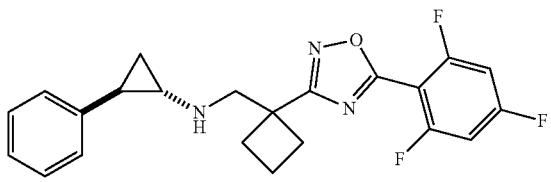

Synthetic Route:

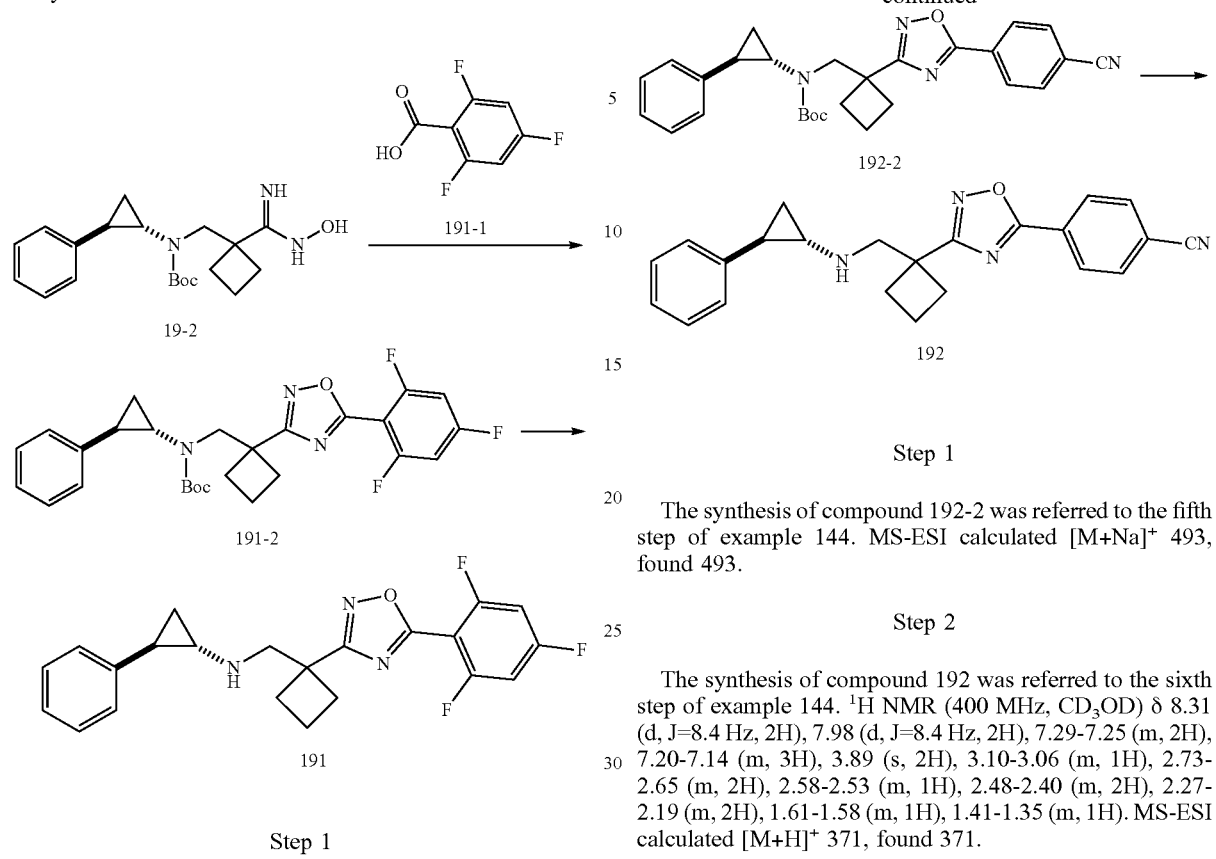

Step 1

The synthesis of compound 191-2 was referred to the fifth step of example 144. MS-ESI calculated [M+Na]+ 522, found 522.

Step 2

The synthesis of compound 191 was referred to the sixth step of example 144. ¹H NMR (400 MHz, CD₃OD) δ 7.31-7.15 (m, 7H), 3.89 (s, 2H), 3.09-3.05 (m, 1H), 2.72-2.65 (m, 2H), 2.53-2.48 (m, 1H), 2.44-2.38 (m, 2H), 2.25-2.21 (m, 2H), 1.57-1.52 (m, 1H), 1.42-1.37 (m, 1H). MS-ESI calculated [M+H]+ 400, found 400.

Example 192

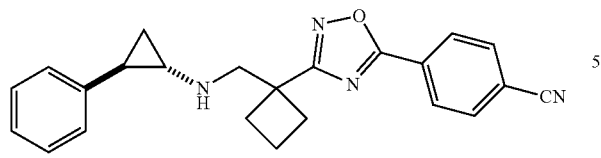

Synthetic Route:

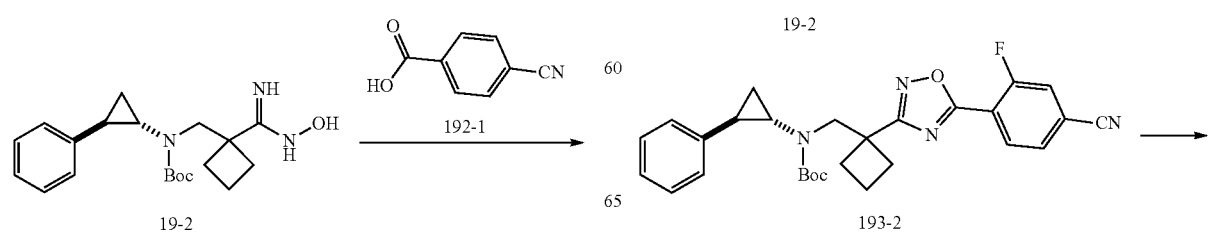

Step 1

The synthesis of compound 192-2 was referred to the fifth step of example 144. MS-ESI calculated [M+Na]+ 493, found 493.

Step 2

The synthesis of compound 192 was referred to the sixth step of example 144. ¹H NMR (400 MHz, CD₃OD) δ 8.31 (d, J=8.4 Hz, 2H), 7.98 (d, J=8.4 Hz, 2H), 7.29-7.25 (m, 2H), 7.20-7.14 (m, 3H), 3.89 (s, 2H), 3.10-3.06 (m, 1H), 2.73-2.65 (m, 2H), 2.58-2.53 (m, 1H), 2.48-2.40 (m, 2H), 2.27-2.19 (m, 2H), 1.61-1.58 (m, 1H), 1.41-1.35 (m, 1H). MS-ESI calculated [M+H]+ 371, found 371.

Example 193

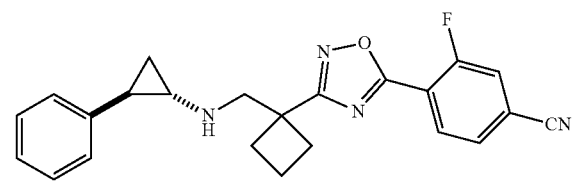

Synthetic Route:

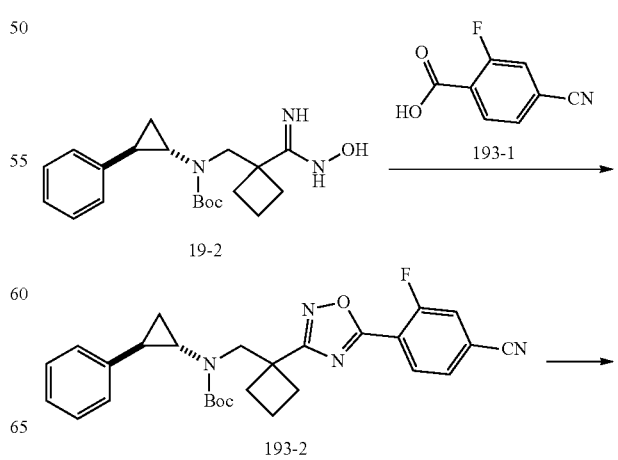

-continued

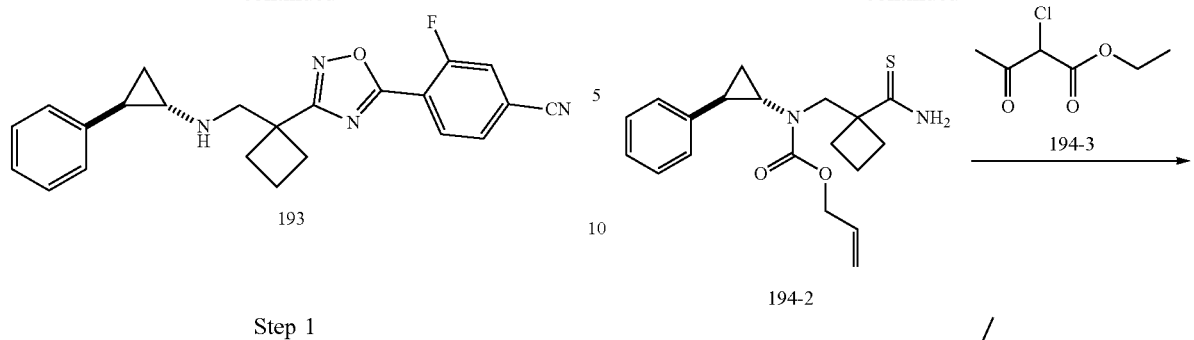

Step 1

The synthesis of compound 193-2 was referred to the fifth step of example 144. MS-ESI calculated [M+Na]$^+$ 511, found 511.

Step 2

The synthesis of compound 193 was referred to the sixth step of example 144. $^1$H NMR (400 MHz, CD$_3$OD) δ 8.35 (t, J=6.8 Hz, 1H), 7.90 (dd, J=10.0 Hz, J=1.2 Hz, 1H), 7.81 (dd, J=10.0 Hz, J=1.2 Hz, 1H), 7.29-7.25 (m, 2H), 7.20-7.13 (m, 3H), 3.90 (s, 2H), 3.09-3.05 (m, 1H), 2.73-2.65 (m, 2H), 2.54-2.49 (m, 1H), 2.47-2.39 (m, 2H), 2.27-2.19 (m, 2H), 1.58-1.53 (m, 1H), 1.41-1.36 (m, 1H). MS-EST calculated [M+H]$^+$ 389, found 389.

Example 194

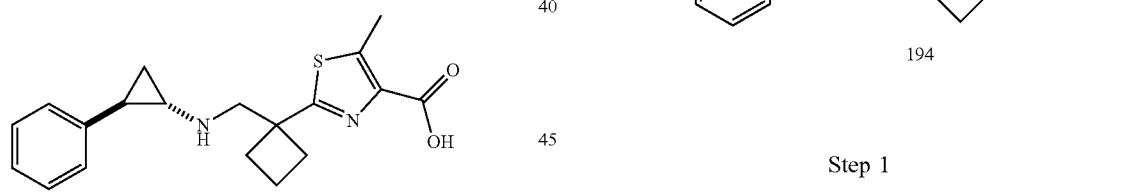

Synthetic Route:

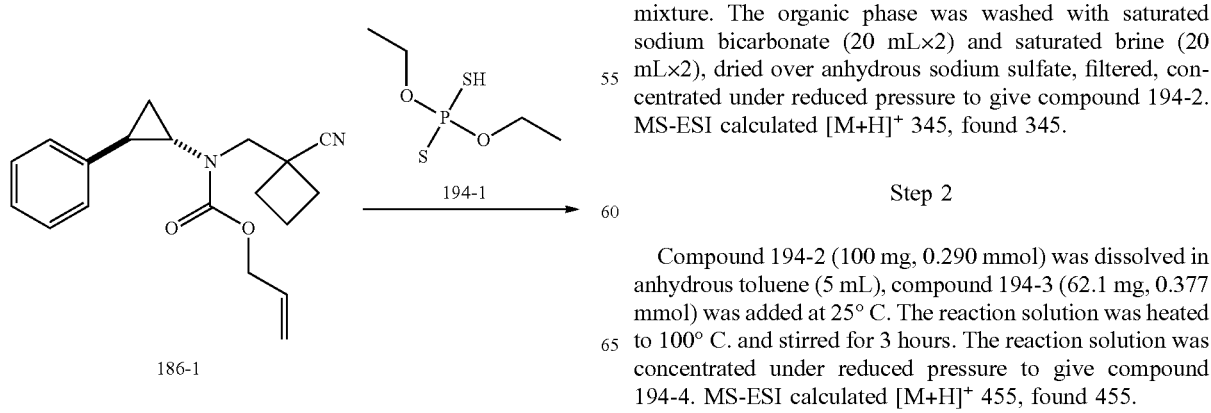

Step 1

The compound 186-1 (100 mg, 0.322 mmol) was dissolved in ethyl acetate (10 mL), compound 194-1 (120 mg, 0.644 mmol) was added and the reaction mixture was stirred at 30° C. for 12 h. Ethyl acetate (50 mL) was added to the mixture. The organic phase was washed with saturated sodium bicarbonate (20 mL×2) and saturated brine (20 mL×2), dried over anhydrous sodium sulfate, filtered, concentrated under reduced pressure to give compound 194-2. MS-ESI calculated [M+H]$^+$ 345, found 345.

Step 2

Compound 194-2 (100 mg, 0.290 mmol) was dissolved in anhydrous toluene (5 mL), compound 194-3 (62.1 mg, 0.377 mmol) was added at 25° C. The reaction solution was heated to 100° C. and stirred for 3 hours. The reaction solution was concentrated under reduced pressure to give compound 194-4. MS-ESI calculated [M+H]$^+$ 455, found 455.

Step 3

The synthesis of compound 194-5 was referred to the fourth step of example 186. MS-ESI calculated [M+H]⁺ 371, found 371.

Step 4

The synthesis of compound 194 was referred to the second step of example 149. ¹H NMR (400 MHz, CD₃OD) δ 7.32-7.28 (m, 2H), 7.24-7.16 (m, 3H), 3.87 (s, 2H), 3.17-3.13 (m, 1H), 2.67 (m, 3H), 2.58-2.51 (m, 5H), 2.23-2.17 (m, 2H), 1.64-1.59 (m, 1H), 1.42-1.38 (m, 1H). MS-ESI calculated [M+H]⁺ 343, found 343.

Example 195

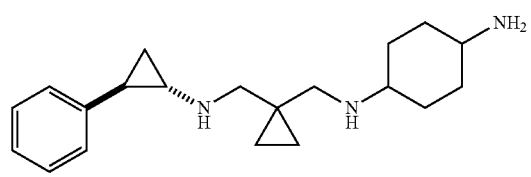

Synthetic Route:

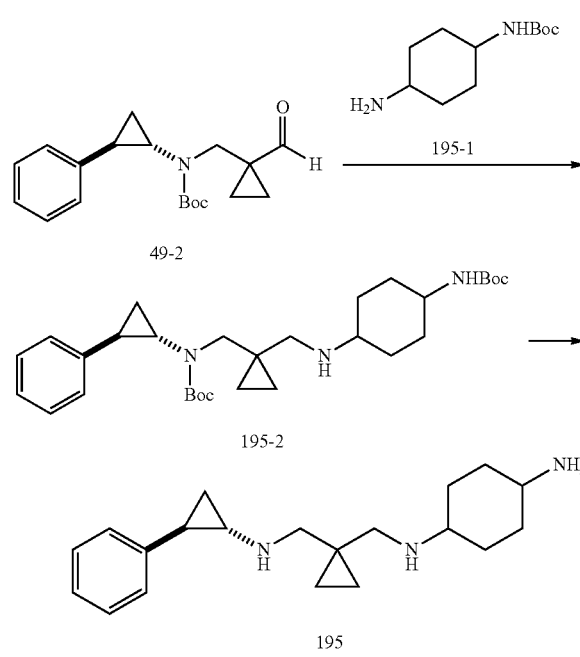

Step 1

Compound 49-2 (100 mg, 0.317 mmol) was dissolved in anhydrous dichloromethane (10 mL), compound 195-1 (81.5 mg, 0.380 mmol) and acetic acid (57.1 mg, 0.951 mmol) were added. The mixture was stirred at 30 V for 1 h, sodium triacetoxyborohydride (201 mg, 0.951 mmol) was added, and the mixture was stirred at 30° C. for 1 h. The mixture was diluted with dichloromethane (30 mL) and washed with saturated sodium carbonate aqueous solution (30 mL×3), water (30 mL×2), saturated brine (30 mL×2). The organic phase was dried over anhydrous sodium sulfate, filtered, concentrated under reduced pressure. The residue was isolated and purified by thin layer chromatography (3:1 petroleum ether/ethyl acetate, Rf=0.3) to give compound 195-2. MS-ESI calculated [M+H]⁺ 514, found 514.

Step 2

The synthesis of compound 195 was referred to the sixth step of example 144. ¹H NMR (400 MHz, CD₃OD) δ 7.32-7.29 (m, 2H), 7.24-7.18 (m, 3H), 3.52-3.45 (m, 2H), 3.38-3.33 (m, 2H), 3.29-3.25 (m, 1H), 3.19-3.10 (m, 2H), 2.74-2.69 (m, 1H), 2.06-1.91 (m, 8H), 1.72-1.67 (m, 1H), 1.39-1.34 (m, 1H), 0.98-0.94 (m, 4H). MS-ESI calculated [M+H]⁺ 314, found 314.

Example 196

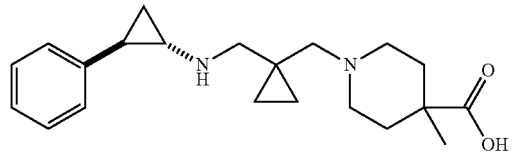

Synthetic Route:

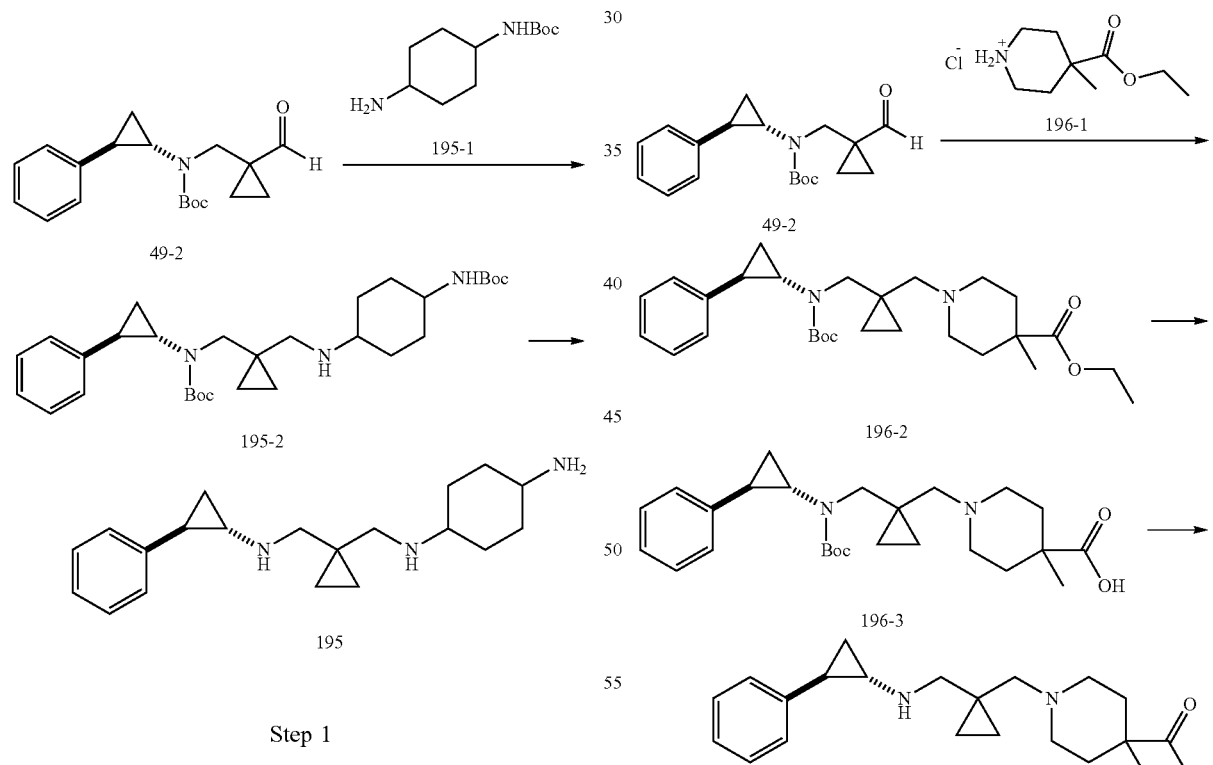

Step 1

The synthesis of compound 196-2 was referred to the first step of example 195. MS-ESI calculated [M+H]⁺ 471, found 471.

Step 2

The synthesis of compound 1%-3 was referred to the second step of example 149. MS-ESI calculated [M+H]+ 443, found 443.

Step 3

The synthesis of compound 1% was referred to the sixth step of example 144. ¹H NMR (400 MHz, CD₃OD) δ 7.32-7.28 (m, 2H), 7.24-7.18 (m, 3H), 3.69-3.64 (m, 2H), 3.52-3.38 (m, 2H), 3.26-3.10 (m, 3H), 3.00-2.94 (m, 2H), 2.76-2.71 (m, 1H), 2.38-2.34 (m, 2H), 2.03-1.91 (m, 2H), 1.73-1.68 (m, 1H), 1.39-1.31 (m, 4H), 1.01-0.86 (m, 4H). MS-ESI calculated [M+H]+ 343, found 343.

Example 197

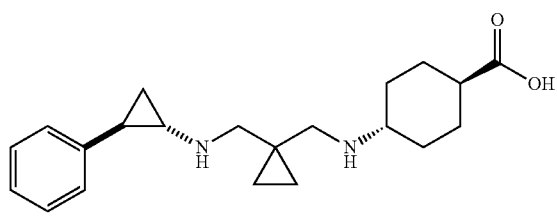

Synthetic Route:

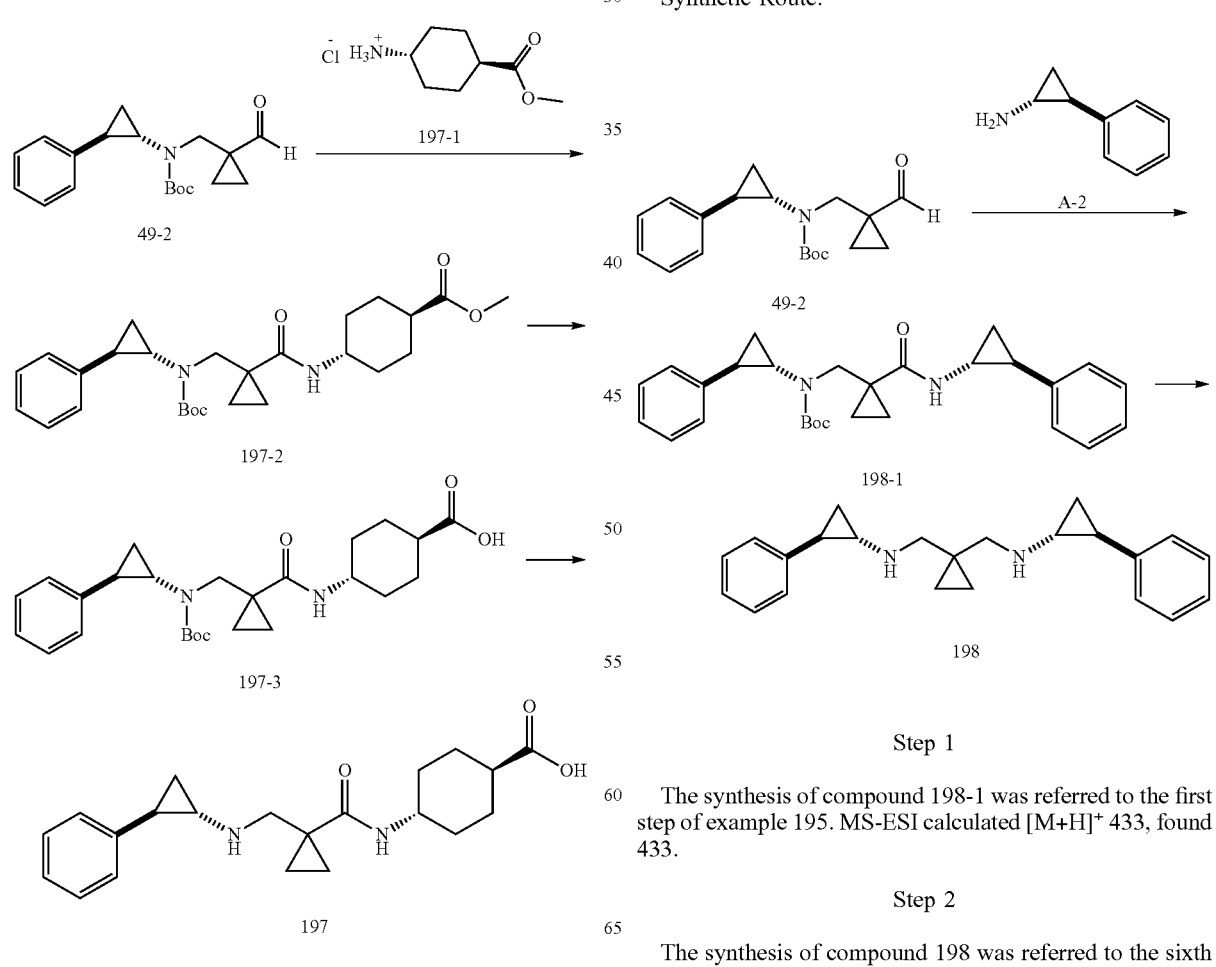

The synthesis of compound 197-2 was referred to the first step of example 195. MS-ESI calculated [M+H]+ 457, found 457.

Step 2

The synthesis of compound 197-3 was referred to the second step of example 149. MS-ESI calculated [M+H]+ 443, found 443.

Step 3

The synthesis of compound 197 was referred to the sixth step of example 144. ¹H NMR (400 MHz, CD₃OD) δ 7.32-7.28 (m, 2H), 7.24-7.18 (m, 3H), 3.44-3.34 (m, 2H), 3.25-3.14 (m, 3H), 3.09-3.05 (m, 1H), 2.75-2.70 (m, 1H), 2.34-2.22 (m, 3H), 2.15-2.12 (m, 2H), 1.74-1.68 (m, 1H), 1.60-1.44 (m, 4H), 1.39-1.34 (m, 1H), 0.97-0.90 (m, 4H). MS-ESI calculated [M+H]+ 343, found 343.

Example 198

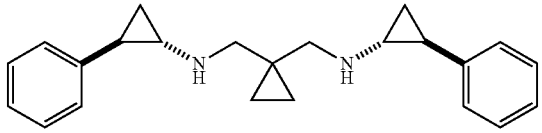

Synthetic Route:

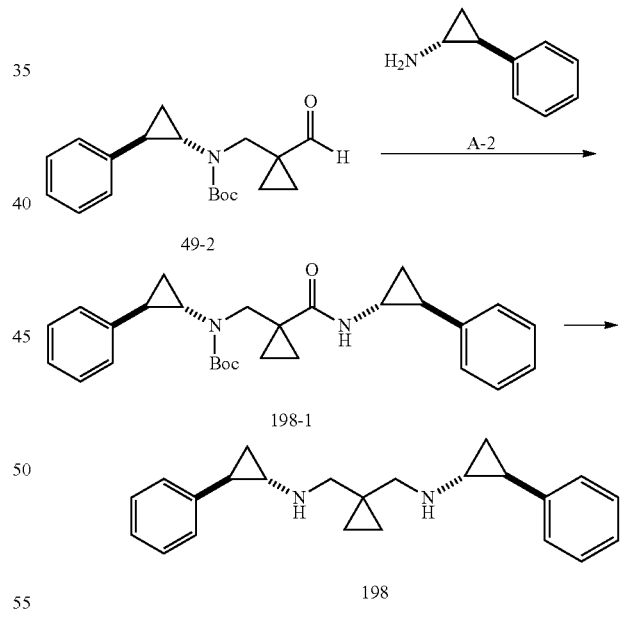

Step 1

The synthesis of compound 198-1 was referred to the first step of example 195. MS-ESI calculated [M+H]+ 433, found 433.

Step 2

The synthesis of compound 198 was referred to the sixth step of example 144. ¹H NMR (400 MHz, CD₃OD) δ

7.34-7.30 (m, 4H), 7.26-7.19 (m, 6H), 3.48-3.34 (m, 4H), 3.06-3.02 (m, 2H), 2.72-2.68 (m, 2H), 1.77-1.66 (m, 2H), 1.38-1.33 (m, 2H), 0.93 (s, 4H). MS-ESI calculated [M+H]+ 333, found 333.

Example 199

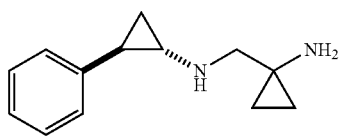

Synthetic Route:

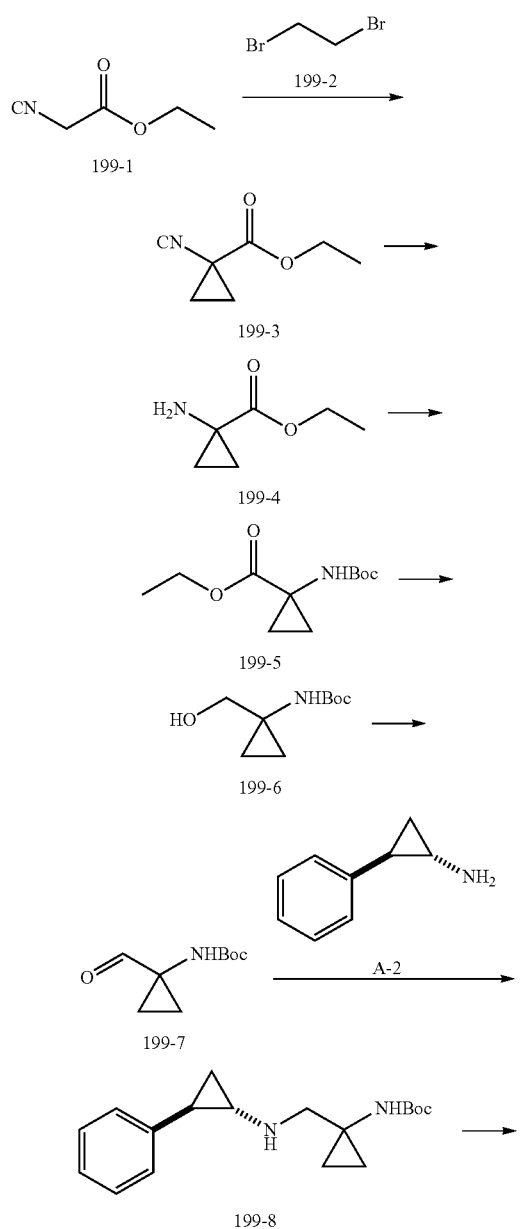

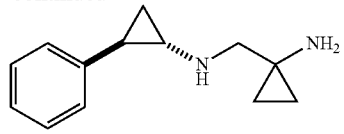
199

Step 1

Compound 199-1 (20.0 g, 177 mmol) was dissolved in anhydrous acetonitrile (300 mL), anhydrous potassium carbonate (61.1 g, 442 mmol) and compound 199-2 (66.4 g, 354 mmol) were added at 0° C., and the reaction mixture was stirred at 70° C. for 24 hours. The reaction mixture was filtered to remove solids, and the filtrate was concentrated under reduced pressure, isolated and purified by silica gel column chromatography (3:1 petroleum ether/ethyl acetate, Rf=0.7) to give compound 199-3. $^1$H NMR (400 MHz, CDCl$_3$) δ 4.27 (q, J=6.8 Hz, 2H), 1.67-1.64 (m, 2H), 1.58-1.54 (m, 2H), 1.34 (t, J=6.8 Hz, 3H).

Step 2

The compound 199-3 (6.00 g, 43.1 mmol) was dissolved in ethanol (60 mL), and concentrated hydrochloric acid (8.73 g, 86.2 mmol, 8.6 mL, 36% purity) was added dropwise to the reaction mixture. The reaction mixture was stirred at 25° C. for 24 hours. The reaction solution was concentrated under reduced pressure to give compound 199-4. $^1$H NMR (400 MHz, CDCl$_3$) 4.13 (q, J=6.8 Hz, 2H), 1.98 (brs, 2H), 1.29-1.23 (m, 5H), 0.99-0.96 (m, 2H).

Step 3

Compound 199-4 (2.00 g, 15.5 mmol) was dissolved in anhydrous dichloromethane (40 mL). Triethylamine (1.57 g, 15.5 mmol) and di-tert-butyl carbonate (3.38 g, 15.5 mmol) were added. The reaction solution was stirred at 20° C. for 24 h. The mixture was concentrated under reduced pressure, isolated and purified by silica gel column chromatography (3:1 petroleum ether/ethyl acetate, Rf=0.6) to give compound 199-5. $^1$H NMR (400 MHz, CDCl$_3$) δ 5.11 (brs, 1H), 4.15 (q, J=7.2 Hz, 2H), 1.56-1.48 (m, 2H), 1.45 (s, 9H), 1.24 (t, J=7.2 Hz, 3H), 1.17-1.08 (m, 2H).

Step 4

Compound 199-5 (1.80 g, 7.85 mmol) was dissolved in anhydrous methanol (20 mL), lithium borohydride (513 mg, 23.6 mmol) was added at 0° C., and the reaction mixture was stirred at 70° C. for 12 h. The saturated ammonium chloride solution (200 mL) was added to the reaction mixture. The mixture was extract with ethyl acetate (100 mL×3). The organic phase was washed with saturated brine (100.2 mL), dried over anhydrous sodium sulfate, filtered, concentrated under reduced pressure, isolated and purified by silica gel column chromatography (1:1 petroleum ether/ethyl acetate, Rf=0.3) to give compound 199-6. $^1$H NMR (400 MHz, CDCl$_3$) δ 5.07 (brs, 1H), 3.59 (s, 2H), 3.42 (brs, 1H), 1.45 (s, 9H), 0.84-0.83 (m, 4H).

Step 5

Compound 199-6 (250 mg, 1.34 mmol) was dissolved in anhydrous dichloromethane (10 mL), Dess Martin reagent (597 mg, 1.41 mmol) was added at 0° C., and the reaction was stirred at 25° C. for 12 h. Saturated sodium bicarbonate solution (30 mL), saturated sodium thiosulfate solution (30 mL) were added to the mixture. The mixture was extracted with dichloromethane (30 mL×3). The organic phase was washed with saturated brine (30 mL×2), dried over anhydrous sodium sulfate, filtered, concentrated under reduced pressure, isolated and purified by chromatography (3:1 petroleum ether/ethyl acetate, Rf=0.7) to give compound 199-7. $^1$H NMR (400 MHz, CDCl$_3$) δ 9.18 (brs, 1H), 5.15 (brs, 1H), 1.52-1.48 (m, 2H), 1.46 (s, 9H), 1.34-1.28 (m, 2H).

Step 6

The synthesis of compound 199-8 was referred to the first step of example 195. MS-ESI calculated [M+H]$^+$ 303, found 303.

Step 7

The synthesis of compound 199 was referred to the sixth step of example 144. $^1$H NMR (400 MHz, CD$_3$OD) δ 7.33-7.29 (m, 2H), 7.25-7.18 (m, 3H), 3.60 (s, 2H), 3.06-3.02 (m, 1H), 2.78-2.73 (m, 1H), 1.78-1.72 (m, 1H), 1.43-1.38 (m, 1H), 1.22 (s, 4H). MS-ESI calculated [M+H]$^+$203, found 203.

Example 200

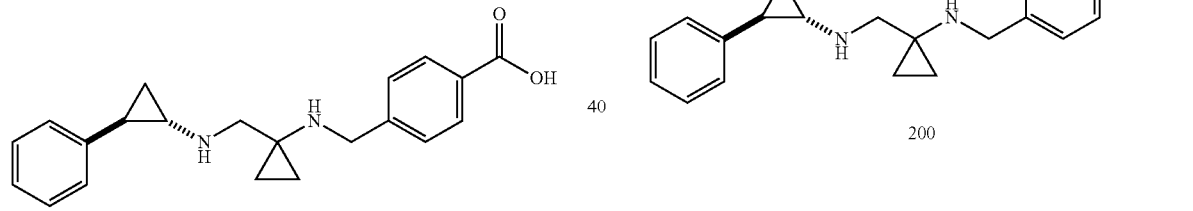

Synthetic Route:

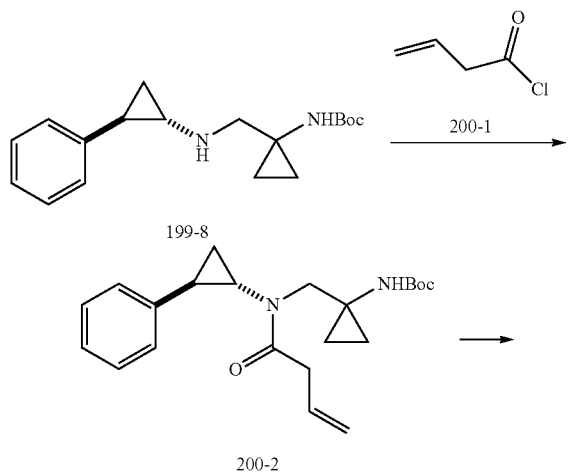

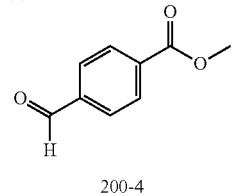

Step 1

The synthesis of compound 200-2 was referred to the first step of example 186. MS-ESI calculated [M-56+H]$^+$ 331, found 331.

Step 2

The synthesis of compound 200-3 was referred to the sixth step of example 144. $^1$H NMR (400 MHz, CDCl$_3$) δ 7.30-7.29 (m, 2H), 7.22-7.18 (m, 1H), 7.15-7.14 (m, 2H), 6.00-5.90 (m, 1H), 5.33-5.20 (m, 2H), 4.70-4.60 (m, 2H), 3.61-3.50 (m, 1H), 3.21-3.17 (m, 1H), 2.84-2.81 (m, 1H), 2.23-2.16 (m, 1H), 1.32-1.24 (m, 2H), 0.66-0.53 (m, 3H), 0.45-0.40 (m, 1H). MS-ESI calculated [M+H]$^+$ 287, found 287.

Step 3

The synthesis of compound 200-5 was referred to the first step of example 195. MS-ESI calculated [M+H]$^+$ 435, found 435.

Step 4

The synthesis of compound 200-6 was referred to the fourth step of example 186. MS-ESI calculated [M+H]+ 351, found 351.

Step 5

The synthesis of compound 200 was referred to the second step of example 149. ¹H NMR (400 MHz, CD$_3$OD) δ 8.09 (d, J=8.4 Hz, 2H), 7.79 (d, J=8.4 Hz, 2H), 7.33-7.29 (m, 2H), 7.25-7.19 (m, 3H), 4.62-4.54 (m, 2H), 3.81-3.68 (m, 2H), 3.09-3.05 (m, 1H), 2.79-2.74 (m, 1H), 1.81-1.76 (m, 1H), 1.43-1.31 (m, 5H). MS-ESI calculated [M+H]+ 337, found 337.

Example 201

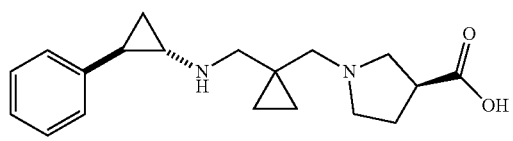

Synthetic Route:

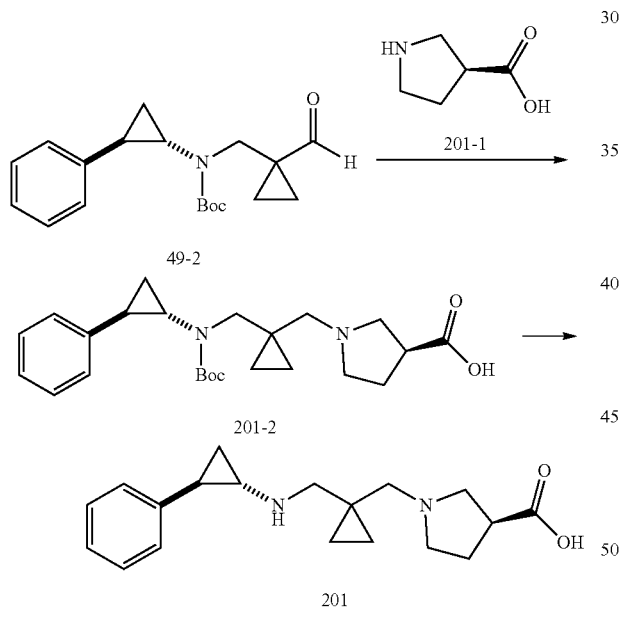

Step 1

The synthesis of compound 201-2 was referred to the first step of example 195. MS-ESI calculated [M+H]+ 415, found 415.

Step 2

The synthesis of compound 201 was referred to the sixth step of example 144. ¹H NMR (400 MHz, CD$_3$OD) δ 7.32-7.26 (m, 2H), 7.24-7.19 (m, 3H), 4.15-3.89 (m, 2H), 3.53-3.34 (m, 6H), 3.22-3.09 (m, 2H), 2.77-2.72 (m, 1H), 2.51-2.30 (m, 2H), 1.73-1.72 (m, 1H), 1.39-1.34 (m, 1H), 0.98-0.95 (m, 4H). MS-ESI calculated [M+H]+ 315, found 315.

Example 202

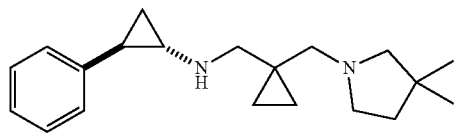

Synthetic Route:

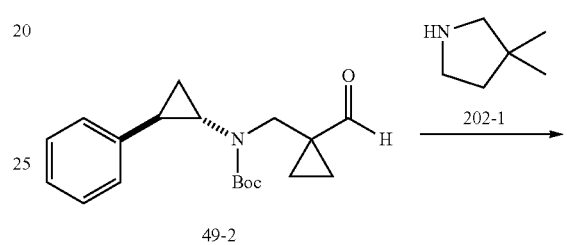

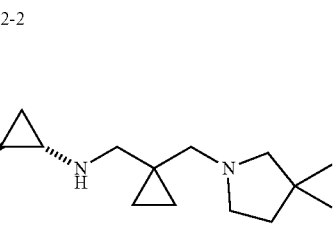

Step 1

The synthesis of compound 202-2 was referred to the first step of example 195. MS-ESI calculated [M+H]+ 399, found 399.

Step 2

The synthesis of compound 202 was referred to the sixth step of example 144. ¹H NMR (400 MHz, CD$_3$OD) δ 7.32-7.28 (m, 2H), 7.23-7.19 (m, 3H), 3.89-3.84 (m, 1H), 3.62 (d, J=11.2 Hz, 1H), 3.52-3.33 (m, 5H), 3.12-3.11 (m, 1H), 2.97-2.94 (m, 1H), 2.79-2.72 (m, 1H), 1.99-1.95 (m, 2H), 1.76-1.69 (m, 1H), 1.37-1.31 (m, 1H), 1.28 (s, 3H), 1.24 (s, 3H), 0.97-0.94 (m, 4H). MS-ESI calculated [M+H]+ 299, found 299.

Example 203

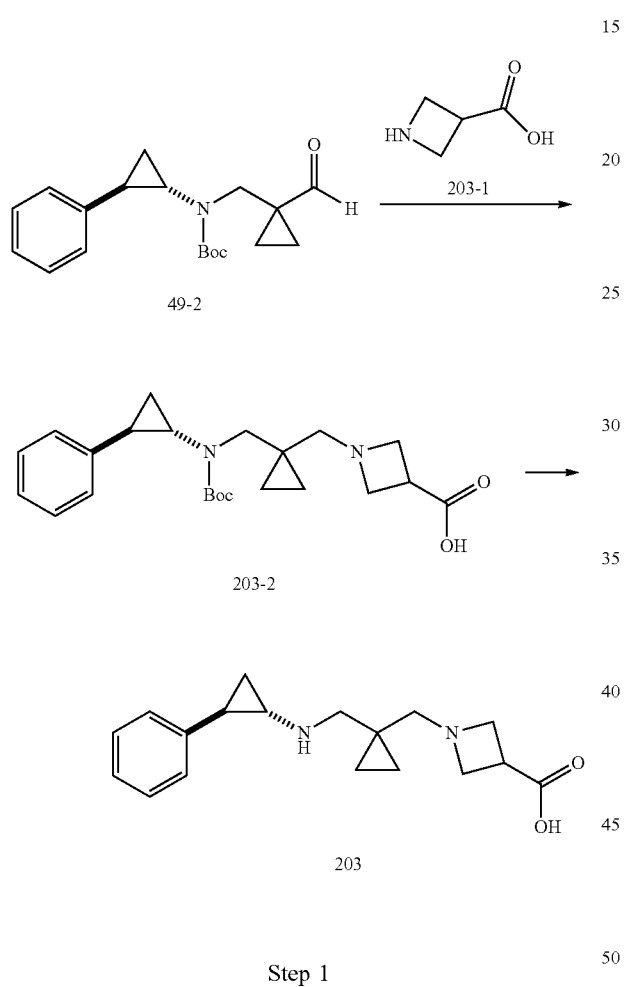

Step 1

The synthesis of compound 203-2 was referred to the first step of example 195. MS-ESI calculated [M+H]$^+$ 401, found 401.

Step 2

The synthesis of compound 203 was referred to the sixth step of example 144. $^1$H NMR (400 MHz, CD$_3$OD) δ 7.32-7.28 (m, 2H), 7.23-7.19 (m, 3H), 4.61-4.51 (m, 2H), 4.44-4.26 (m, 2H), 3.88-3.64 (m, 1H), 3.58-3.34 (m, 4H), 3.07-3.01 (m, 1H), 2.77-2.72 (m, 1H), 1.76-1.69 (m, 1H), 1.38-1.32 (m, 1H), 0.95-0.92 (m, 4H). MS-ESI calculated [M+H]$^+$ 301, found 301.

Example 204

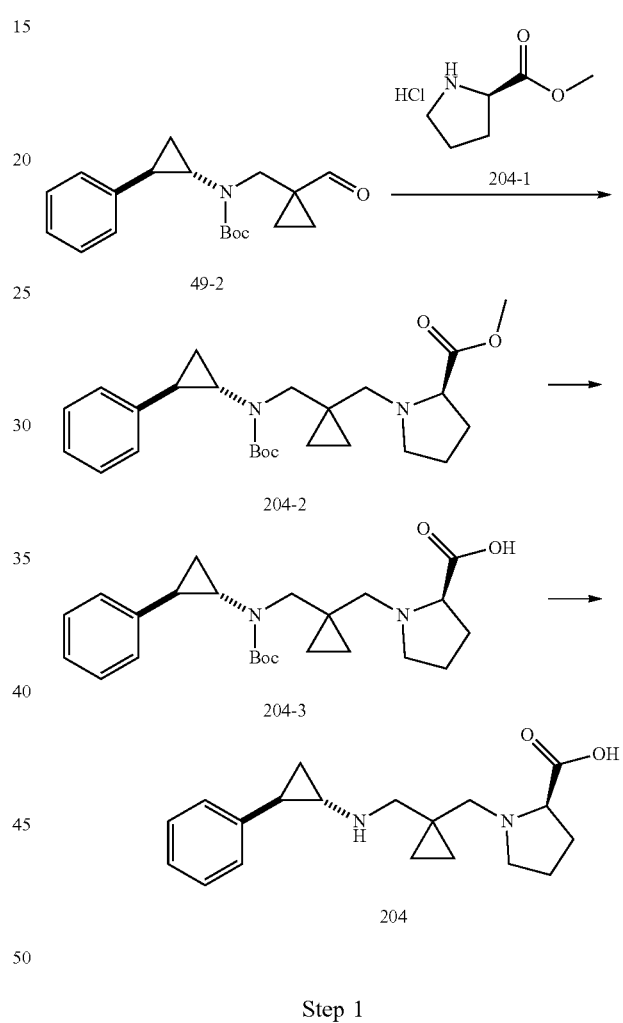

Step 1

Compound 49-2 (80.0 mg, 0.254 mmol) and 204-1 (46.2 mg, 0.279 mmol) were dissolved in dichloromethane (6 mL) under nitrogen, acetic acid (45.7 mg, 0.761 mmol) was added, the mixture was stirred at 26° C. for 1 h. Sodium triacetoxyborohydride (161 mg, 0.761 mmol) was added and the reaction was stirred at 26° C. for 1 h. The saturated sodium carbonate solution (15 mL) was added to the mixture and the mixture was extracted with dichloromethane (25 mL×2). The organic phases were combined, washed with saturated brine (50 mL×1), dried over anhydrous sodium sulfate, filtered, concentrated under reduced pressure, isolated and purified by thin layer chromatography (5:1 petroleum ether/ethyl acetate. Rf=0.6) to give compound 204-2. MS-ESI calculated [M+H]$^+$ 429, found 429.

Step 2

Compound 204-2 (60.0 mg, 0.140 mmol) was dissolved in the mixture of tetrahydrofuran (6 mL) and water (2 mL) under nitrogen, lithium hydroxide dihydrate (29.4 mg, 0.700 mmol) were added in one portion. The reaction solution was stirred at 26° C. for 12 h. The mixture was adjusted to pH=3-4 by adding hydrochloric acid aqueous solution (1 mol/L), extracted with dichloromethane (25 mL×3). The organic phases were combined, washed with saturated brine (40 mL×2), dried over anhydrous sodium sulfate, filtered, concentrated under reduced pressure, isolated and purified by thin layer chromatography (8:1 petroleum ether/ethyl acetate, Rf=0.1) to give compound 204-3. MS-ESI calculated [M+H]$^+$ 415, found 415.

Step 3

Compound 204-3 (56.0 mg, 0.135 mmol) was dissolved in dichloromethane (5 mL). Trifluoroacetic acid (46.2 mg, 0.405 mmol) was added, and the mixture was stirred at 18° C. for 1 h. The mixture was concentrated under reduced pressure and purified by preparative high-performance liquid chromatography (hydrochloride) to give compound 204. $^1$H NMR (400 MHz, CH$_3$OD) δ 7.34-7.27 (m, 2H), 7.26-7.17 (m, 3H), 4.53-4.40 (m, 1H), 4.11-4.00 (m, 1H), 3.80-3.35 (m, 4H), 3.29-3.21 (m, 1H), 3.12-2.97 (m, 1H), 2.85-2.69 (m, 1H), 2.56-2.68 (m, 1H), 2.31-2.10 (m, 3H), 1.81-1.68 (m, 1H), 1.43-1.34 (m, 1H), 1.08-0.88 (m, 4H). MS-EST calculated [M+H]$^+$ 315, found 315.

Example 205

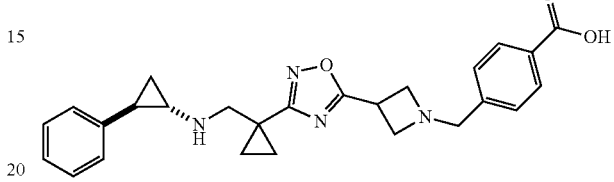

Synthetic Route:

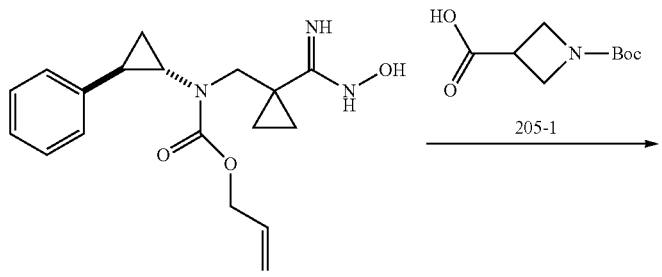

82-2

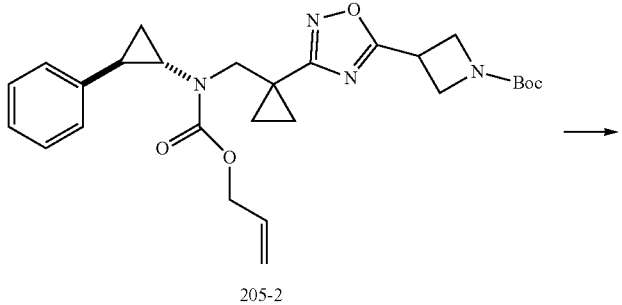

205-2

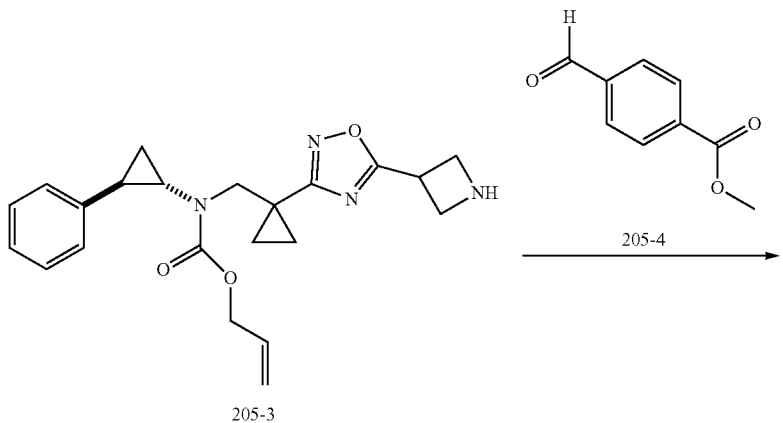

205-3

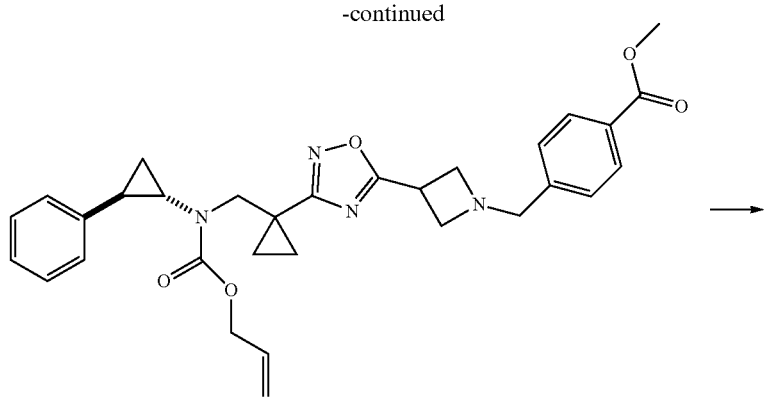

205-5

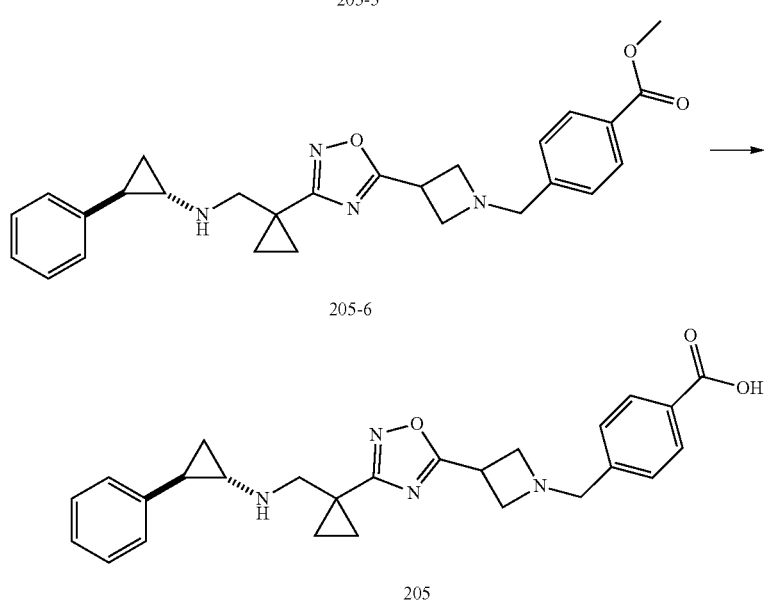

205-6

205

Step 1

Compound 205-1 (66.0 mg, 0.328 mmol) was dissolved in anhydrous N,N-dimethylformamide (8 mL), N,N-carbonyldiimidazole (57.6 mg, 0.355 mmol) was added. The reaction solution was stirred at 30° C. for 2 h. Then compound 82-2 (90.0 mg, 0.273 mmol) was added, and the mixture was stirred at 110° C. for 10 h. Water (10 mL) was added to the mixture and the mixture was extracted with ethyl acetate (20 mL×2). The organic phases were combined, washed with saturated brine (40 mL×2), dried over anhydrous sodium sulfate, filtered, concentrated under reduced pressure to give compound 205-2. MS-ESI calculated [M+Na]$^+$ 517, found 517.

Step 2

Compound 205-2 (110 mg, 0.222 mmol) was dissolved in dichloromethane (4 mL). Trifluoroacetic acid (101 mg, 0.890 mmol) was added, and the reaction mixture was stirred at 20° C. for 0.5 h. The mixture was concentrated under reduced pressure to give compound 205-3. MS-ESI calculated [M+H]$^+$ 395, found 395.

Step 3

The synthesis of compound 205-5 was referred to the first step of example 204. MS-ESI calculated [M+Na]$^+$ 565, found 565.

Step 4

Compound 205-5 (104 mg, 0.192 mmol) was dissolved in anhydrous tetrahydrofuran (6 mL) under nitrogen. Tetrakis(triphenylphosphine) palladium (0) (22.1 mg, 19.1 µmol) and diethylamine (140 mg, 1.92 mmol) were added, and the reaction mixture was stirred at 80° C. for 3 h. The mixture was concentrated under reduced pressure, isolated and purified by thin layer chromatography (1:10 petroleum ether/ethyl acetate, Rf=0.2) to give compound 205-6. MS-ESI calculated [M+H]$^+$ 459, found 459.

Step 5

Compound 205-6 (63.0 mg, 0.137 mmol) was dissolved in the mixture of tetrahydrofuran (2 mL) and water (2 mL) under nitrogen, and sodium hydroxide (11.0 mg, 0.275 mmol) was added in one portion. The reaction solution was stirred at 50° C. for 36 h. The solution was adjusted to pH=1-2 by adding the hydrochloric acid solution (1 mol/L), concentrated under reduced pressure, isolated and purified by preparative high performance liquid chromatography (hydrochloric acid) to give compound 205. $^1$H NMR (400 MHz D$_2$O) δ 8.06 (d, J=8.2 Hz, 2H), 7.61-7.51 (m, 2H), 7.32-7.20 (m, 3H), 7.08-7.00 (m, 2H), 4.61-4.46 (m, 4H), 4.42-4.19 (m, 3H), 3.84-3.76 (m, 1H), 3.66-3.54 (m, 1H), 3.08-3.00 (m, 1H), 2.48-2.39 (m, 1H), 1.53-1.39 (m, 2H), 1.36-1.24 (m, 4H). MS-ESI calculated [M+H]$^+$ 445, found 445.
Example 206
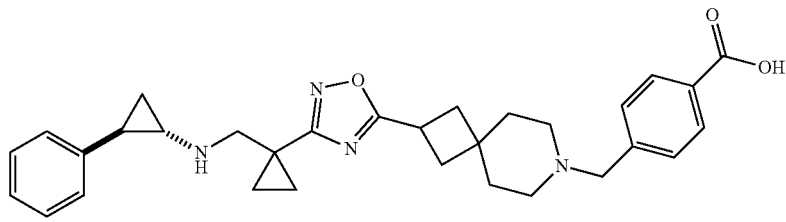
Synthetic Route:
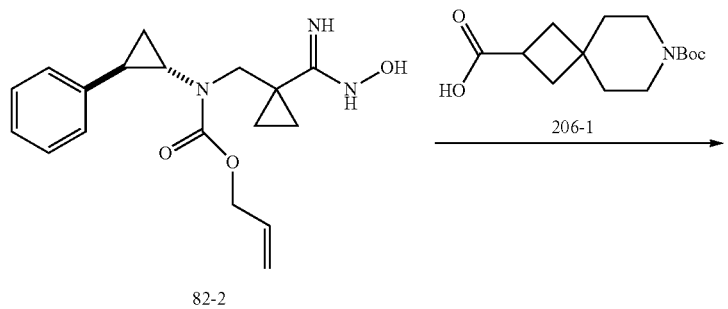
82-2
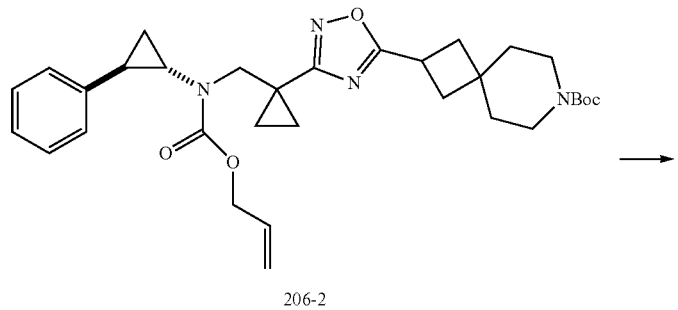
206-2
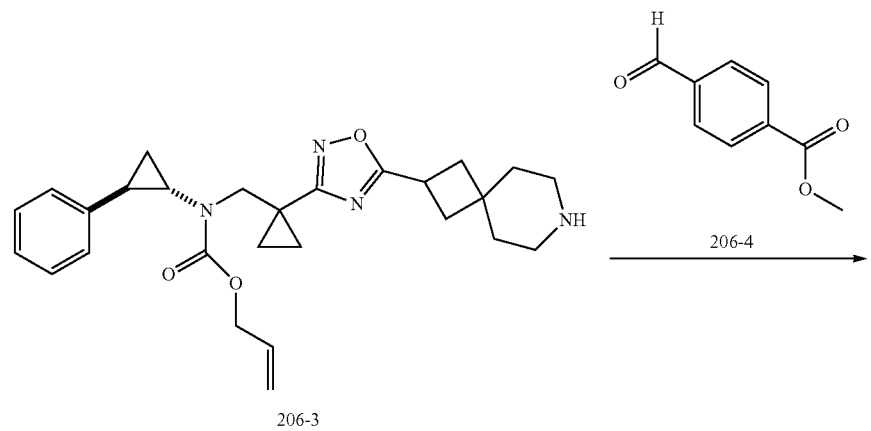
206-3

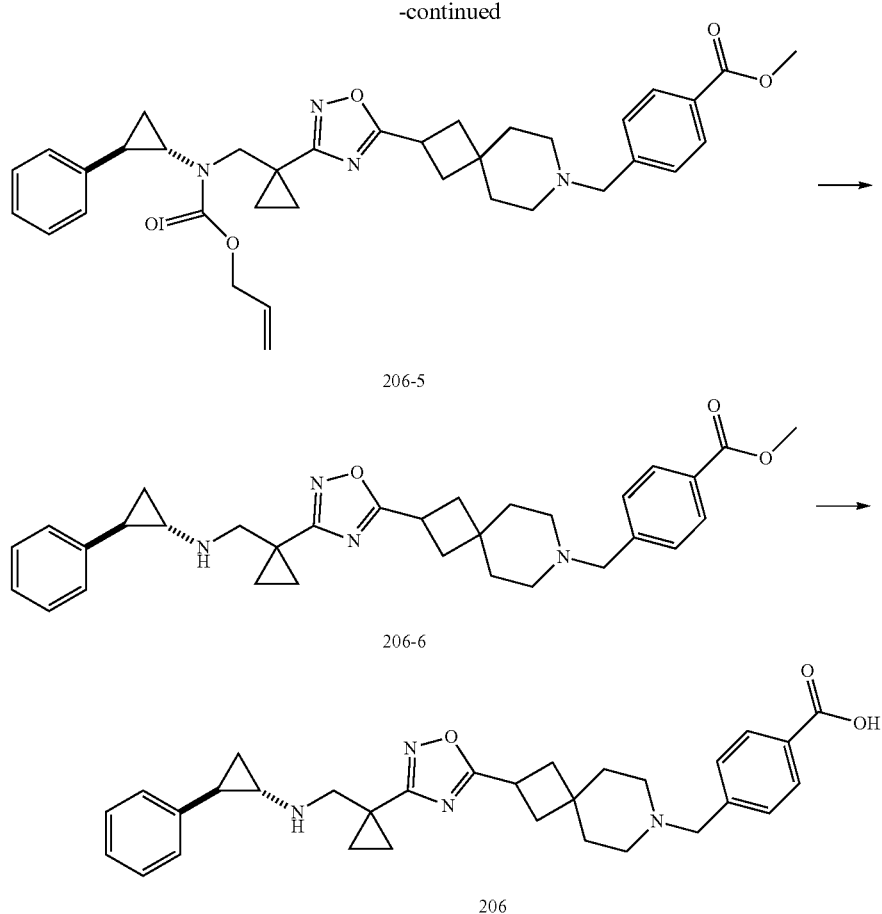

206-5

206-6

206

Step 1

The synthesis of compound 206-2 was referred to the first step of example 205. MS-ESI calculated [M+Na]⁺ 585, found 585.

Step 2

Compound 206-2 (170 mg, 302 μmol) was dissolved in dichloromethane (20 mL) under nitrogen. Trifluoroacetic acid (138 mg, 121 mmol) was added and the reaction was stirred at 20-C for 1 h. The mixture was concentrated under reduced pressure to give compound 206-3. MS-ESI calculated [M+H]⁺ 463, found 463.

Step 3

The synthesis of compound 206-5 was referred to the first step of example 204. MS-ESI calculated[M+H]⁺ 611, found 2611.

Step 4

The synthesis of compound 206-6 was referred to the fourth step of example 205. MS-ESI calculated [M+H]⁺ 527, found 527.

Step 5

Compound 206-6 (50.0 mg, 95.0 μmol) was dissolved in the mixture of tetrahydrofuran (4 mL) and water (4 mL) under nitrogen, and sodium hydroxide (19.0 mg, 0.475 mmol) was added in one portion. The reaction solution was stirred at 50° C. for 9 h. The solution was adjusted to pH=1-2 by adding the 1 N hydrochloric acid solution, concentrated under reduced pressure, isolated and purified by preparative high-performance liquid chromatography (hydrochloric acid) to give compound 206. ¹H NMR (400 MHz, CH₃OD) δ 8.13 (d, J=8.2 Hz, 2H), 7.68 (d, J=8.2 Hz, 2H), 7.36-7.27 (m, 2H), 7.27-7.19 (m, 1H), 7.19-7.12 (m, 2H), 4.44-4.35 (m, 2H), 3.87-3.74 (m, 1H), 3.74-3.61 (m, 2H), 3.48-3.33 (m, 2H), 3.20-2.95 (m, 3H), 2.61-2.48 (m, 2H), 2.40-2.14 (m, 4H), 2.04-1.80 (m, 3H), 1.64-1.53 (m, 1H), 1.50-1.27 (m, 5H). MS-ESI calculated [M+H]⁺ 513, found 513.

Example 207

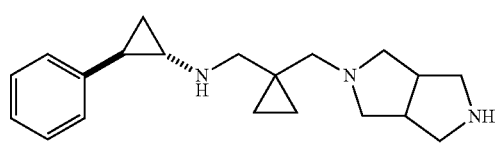

373

Synthetic Route:

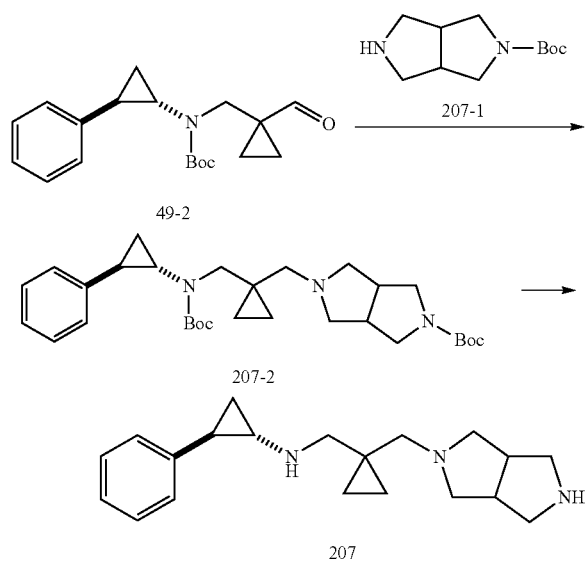

Step 1

The synthesis of compound 207-2 was referred to the first step of example 204. MS-ESI calculated [M+H]+ 512, found 512.

Step 2

Compound 207-2 (55.0 mg, 0.107 mmol) was dissolved in dichloromethane (6 mL), and then trifluoroacetic acid (49.0 mg, 0.440 mol) was added and the mixture was stirred at 20° C. for 1 h. The mixture was concentrated under reduced pressure, isolated and purified by preparative high-performance liquid chromatography (hydrochloride) to give compound 207. ¹H NMR (400 MHz, CH₃OD) δ 7.34-7.26 (m, 2H), 7.26-7.17 (m, 3H), 4.17-4.05 (m, 1H), 4.01-3.86 (m, 1H), 3.74-3.61 (m, 2H), 3.61-3.33 (m, 10H), 3.22-3.07 (m, 1H), 2.82-2.70 (m, 1H), 1.79-1.66 (m, 1H), 1.42-1.31 (m, 1H), 1.07-0.87 (m, 4H). MS-ESI calculated [M+H]+ 312, found 312.

Example 208

374

Synthetic Route:

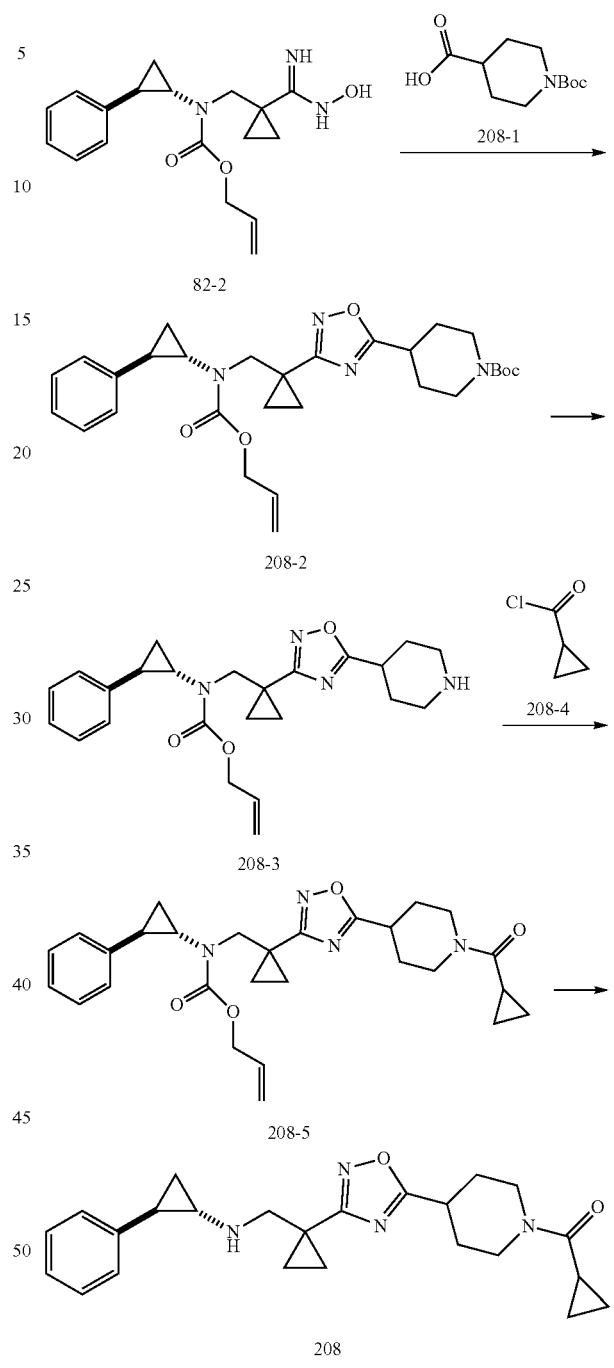

Step 1

Compound 208-1 (292 mg, 1.28 mmol) was dissolved in anhydrous N,N-dimethylformamide (10 mL) under nitrogen, N,N-carbonyldiimidazole (241 mg, 1.49 mmol) was added, and the mixture was stirred at 30° C. for 2 h. Then compound 82-2 (350 mg, 1.06 mmol) was added, and the mixture was stirred at 110° C. for 12 h. Water (10 mL) was added to the mixture and the mixture was extracted with ethyl acetate (20 mL×2). The organic phases were combined, washed with saturated brine (40 mL×2), dried over anhydrous sodium sulfate, filtered, concentrated under reduced pressure to give compound 208-2. MS-ESI calculated [M+Na]+ 545, found 545.

Step 2

The synthesis of compound 208-3 was referred to the second step of example 207. MS-ESI calculated [M+H]+ 424, found 424.

Step 3

Compound 208-3 (67.0 mg, 0.159 mmol) was dissolved in anhydrous dichloromethane (12 mL) under nitrogen, compound 208-4 (33.2 mg, 0.317 mmol) and 4-dimethylaminopyridine (3.87 mg, 31.7 μmol) and N,N-diisopropylethylamine (82.0 mg, 0.634 mmol) were added in one portion at 0° C. The reaction solution was stirred at 20° C. for 1.5 h. The mixture was concentrated under reduced pressure, isolated and purified by thin layer chromatography (3:1 petroleum ether/ethyl acetate, Rf=0.7) to give compound 208-5. MS-ESI calculated [M+H]+ 491, found 491.

Step 4

The synthesis of compound 208 was referred to the fourth step of example 205. $^1$H NMR (400 MHz CH$_3$OD) δ 7.35-7.28 (m, 2H), 7.27-7.20 (m, 1H), 7.19-7.13 (m, 2H), 4.46-4.30 (m, 2H), 3.72-3.61 (m, 2H), 3.48-3.32 (m, 2H), 3.12-3.04 (m, 1H), 3.03-2.89 (m, 1H), 2.56-2.46 (m, 1H), 2.23-2.03 (m, 2H), 2.02-1.95 (m, 1H), 1.88-1.62 (m, 2H), 1.59-1.51 (m, 1H), 1.47-1.37 (m, 3H), 1.35-1.29 (m, 2H), 0.94-0.77 (m, 4H). MS-ESI calculated [M+H]+ 407, found 407.

Example 209

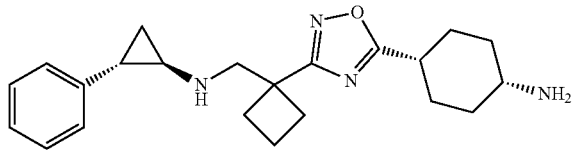 [SMILES: N[C@H]1CC[C@@H](c2nc(C3(CN[C@@H]4C[C@H]4c4ccccc4)CCC3)no2)CC1]

Synthetic Route:

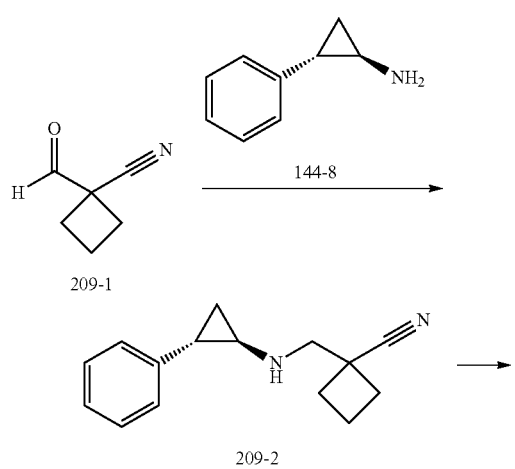

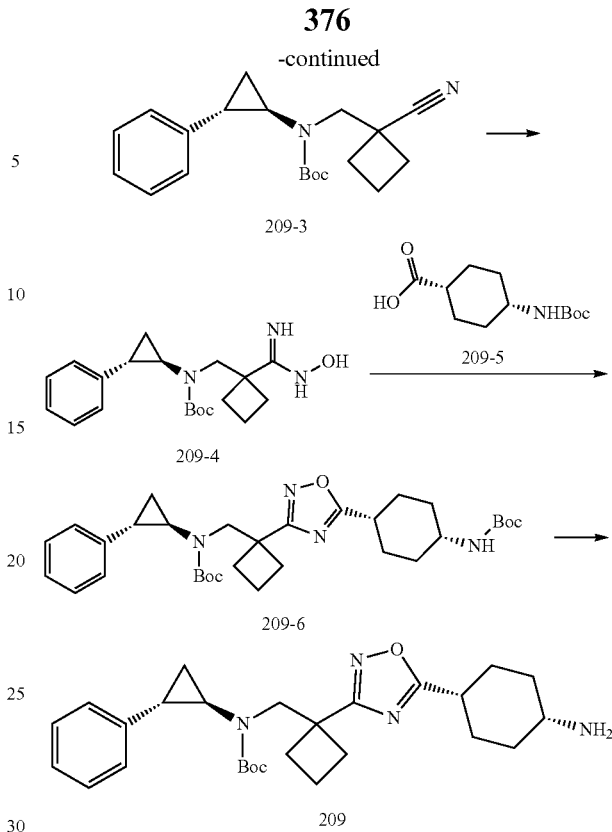

Step 1

Compound 209-1 (1.89 g, 17.3 mmol) and 144-8 (2.31 g, 17.3 mmol) were dissolved in dichloromethane (8 mL) under nitrogen, and acetic acid (104 mg, 1.73 mmol) was added. The reaction solution was stirred at 30° C. for 1 h. Sodium triacetoxyborohydride (5.51 mg, 26.0 mmol) was added, and the reaction mixture was stirred at 30° C. for 4 h. The solution was adjusted to pH=9-10 by adding the saturated sodium carbonate solution, extracted with dichloromethane (40 mL 2). The organic phases were combined, washed with saturated brine (70 mL×1), dried over anhydrous sodium sulfate, filtered, concentrated under reduced pressure, isolated and purified by silica gel column chromatography (2:1 petroleum ether/ethyl acetate, Rf=0.3) to give compound 209-2. $^1$H NMR (400 MHz, CDCl$_3$) δ 7.20-7.15 (m, 2H), 7.12-7.04 (m, 1H), 7.00-6.93 (m, 2H), 2.98-2.90 (m, 2H), 2.45-2.34 (m, 3H), 2.16-1.95 (m, 4H), 1.89-1.84 (m, 1H), 1.09-0.98 (m, 1H), 0.97-0.87 (m, 1H).

Step 2

Di-tert-butyl dicarbonate (964 mg, 4.42 mmol) was added to compound 209-2 (0.50 g, 2.21 mmol) under nitrogen. The mixture was stirred at 90° C. for 12 h. The mixture was isolated and purified by column chromatography (5:1 petroleum ether/ethyl acetate, Rf=0.6) to give compound 209-3. $^1$H NMR (400 MHz, CDCl$_3$) δ 7.23-7.18 (m, 2H), 7.13-6.97 (m, 3H), 3.95-3.70 (m, 1H), 3.44-3.27 (m, 1H), 2.85-2.72 (m, 1H), 2.52-2.30 (m, 2H), 2.20-2.08 (m, 3H), 2.07-1.90 (m, 2H), 1.37-1.29 (m, 9H), 1.27-1.14 (m, 2H).

Step 3

Compound 209-3 (0.70 g, 2.14 mmol) was dissolved in anhydrous ethanol (20 mL) under nitrogen, hydroxylamine hydrochloride (298 mg, 4.29 mmol) and N,N-dimethylisopropylethylamine (1.11 g, 8.58 mmol) were added, and the mixture was stirred at 80° C. for 12 h. The reaction was quenched with water (30 mL), the mixture was extracted with ethyl acetate (30 mL×2). The organic phases were combined, washed with saturated brine (30 mL×2), dried over anhydrous sodium sulfate, filtered, concentrated under reduced pressure, isolated and purified by silica gel column chromatography (2:1 petroleum ether/ethyl acetate, Rf=0.4) to give compound 209-4. MS-ESI calculated [M+H]+ 360, found 360.

Step 4

The synthesis of compound 209-6 was referred to the first step of example 205. MS-ESI calculated [M+Na]+ 589 found 589.

Step 5

The synthesis of compound 209 was referred to the second step of example 207. ¹H NMR (400 MHz CH₃OD) δ 7.36-7.27 (m, 2H), 7.27-7.21 (m, 1H), 7.23-7.16 (m, 2H), 3.83 (s, 2H), 3.37-3.32 (m, 2H), 3.11-3.01 (m, 1H), 2.69-2.53 (m, 3H), 2.44-2.29 (m, 4H), 2.23-2.12 (m, 2H), 2.06-1.92 (m, 4H), 1.84-1.71 (m, 2H), 1.68-1.55 (m, 1H), 1.42-1.32 (m, 1H). MS-ESI calculated [M+H]+ 367, found 367.

Example 210

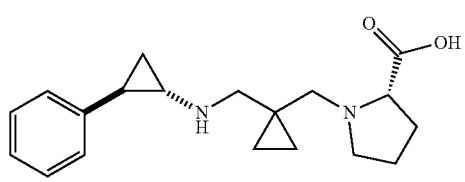

Synthetic Route:

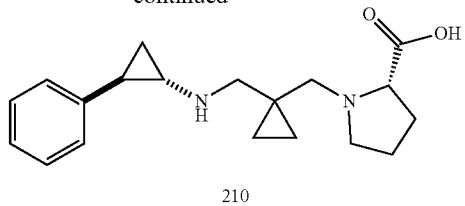

210

Step 1

The synthesis of compound 210-2 was referred to the first step of example 204. MS-ESI calculated [M+H]+ 429, found 429.

Step 2

The synthesis of compound 210-3 was referred to the second step of example 204. MS-ESI calculated [M+H]+ 415, found 415.

Step 3

The synthesis of compound 210 was referred to the third step of example 204. ¹H NMR (400 MHz, CH₃OD) δ 7.34-7.26 (m, 2H), 7.25-7.18 (m, 3H), 4.55-4.49 (m, 1H), 4.12-3.99 (m, 1H), 3.80-3.35 (m, 4H), 3.30-3.19 (m, 1H), 3.12-2.93 (m, 1H), 2.84-2.71 (m, 1H), 2.63 (m, 1H), 2.29-2.05 (m, 3H), 1.82-1.68 (m, 1H), 1.44-1.33 (m, 1H), 1.08-0.89 (m, 4H). MS-ESI calculated [M+H]+ 315, found 315.

Example 211

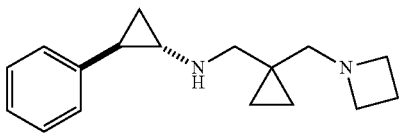

Synthetic Route:

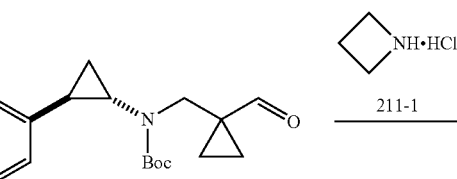

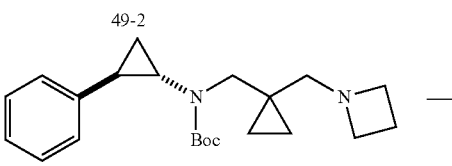

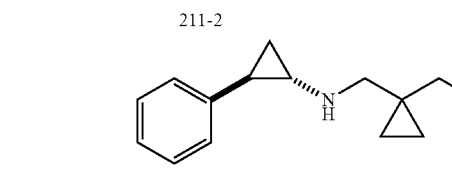

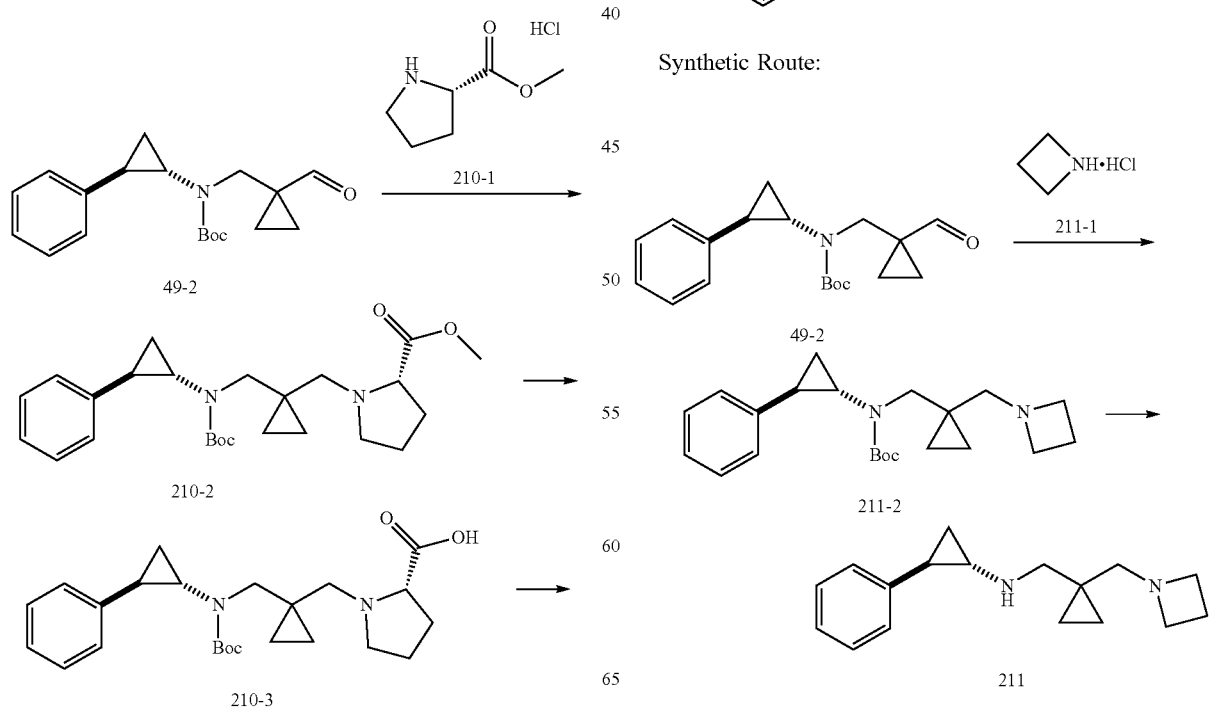

Step 1

The synthesis of compound 211-2 was referred to the first step of example 204. MS-ESI calculated [M+H]$^+$ 357, found 357.

Step 2

The synthesis of compound 211 was referred to the third step of example 204. $^1$H NMR (400 MHz, CH$_3$OD) δ 7.33-7.26 (m, 2H), 7.26-7.17 (m, 3H), 4.39-4.14 (m, 4H), 3.48-3.33 (m, 3H), 3.30-3.24 (m, 1H), 3.11-3.01 (m, 1H), 2.81-2.74 (m, 1H), 2.73-2.61 (m, 1H), 2.44-2.29 (m, 1H), 1.79-1.68 (m, 1H), 1.42-1.30 (m, 1H), 0.91 (s, 4H). MS-ESI calculated [M+H]$^+$ 257, found 257.

Example 212

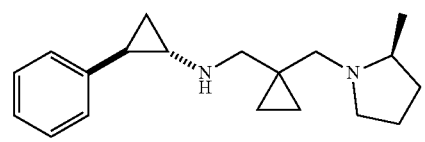

Synthetic Route:

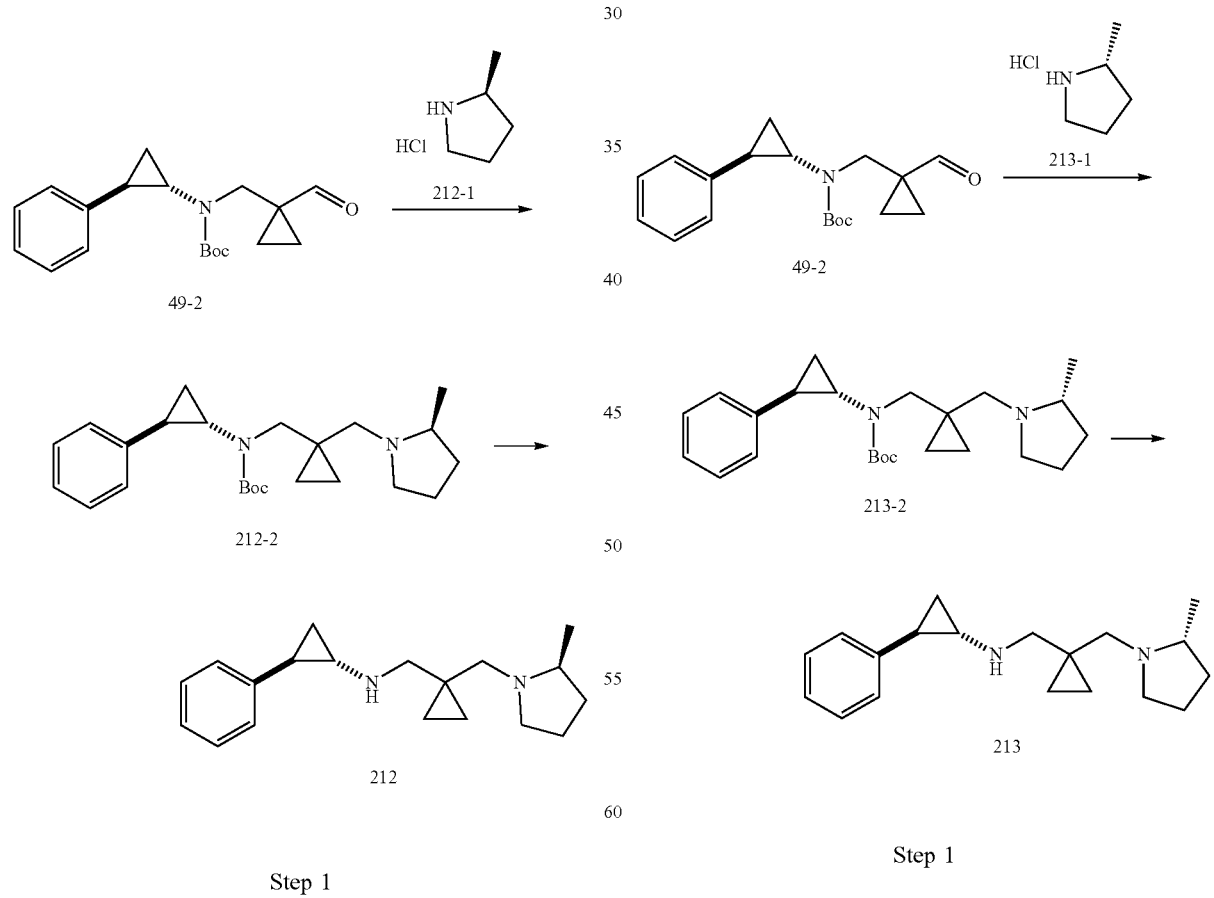

Step 1

The synthesis of compound 212-2 was referred to the first step of example 204. MS-ESI calculated [M+H]$^+$ 385, found 385.

Step 2

The synthesis of compound 212 was referred to the third step of example 204. $^1$H NMR (400 MHz. CH$_3$OD) δ 7.37-7.29 (m, 2H), 7.28-7.19 (m, 3H), 3.92-3.71 (m, 3H), 3.61-3.42 (m, 1H), 3.24-3.07 (m, 2H), 3.00-2.85 (m, 1H), 2.84-2.68 (m, 1H), 2.43-2.28 (m, 1H), 2.23-2.08 (m, 2H), 1.93-1.66 (m, 2H), 1.65-1.51 (m, 3H), 1.50-1.09 (m, 2H), 1.09-0.84 (m, 4H). MS-ESI calculated [M+H]$^+$ 285, found 285.

Example 213

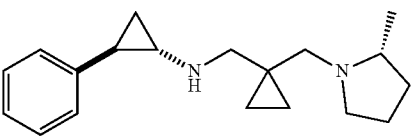

Synthetic Route:

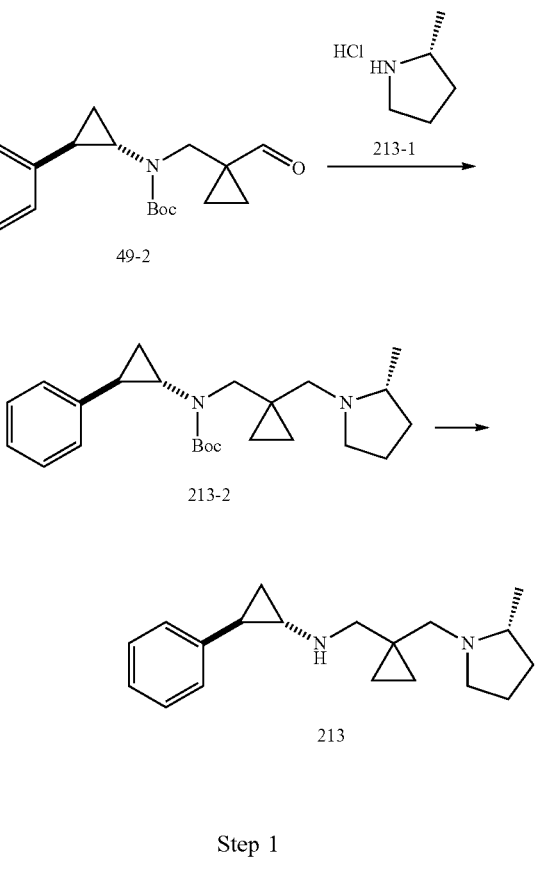

Step 1

The synthesis of compound 213-2 was referred to the first step of example 204. MS-ESI calculated [M+H]$^+$ 385, found 385.

Step 2

The synthesis of compound 213 was referred to the third step of example 204. ¹H NMR (400 MHz CH₃OD) δ 7.33-7.26 (m, 2H), 7.25-7.18 (m, 3H), 3.90-3.73 (m, 3H), 3.58-3.42 (m, 1H), 3.23-3.04 (m, 2H), 2.97-2.85 (m, 1H), 2.83-2.68 (m, 1H), 2.40-2.25 (m, 1H), 2.22-2.07 (m, 2H), 1.92-1.65 (m, 2H), 1.64-1.52 (m, 3H), 1.43-1.08 (m, 2H), 1.07-0.97 (m, 3H), 0.94-0.85 (m, 1H). MS-ESI calculated [M+H]⁺ 285, found 285.

Example 214

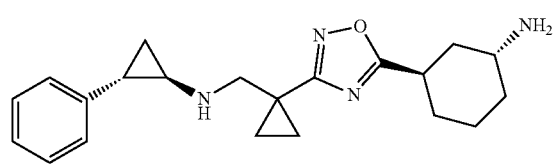 [SMILES: N[C@@H]1CCC[C@@H](c2nc(C3(CN[C@@H]4C[C@H]4c4ccccc4)CC3)no2)C1]

Synthetic Route:

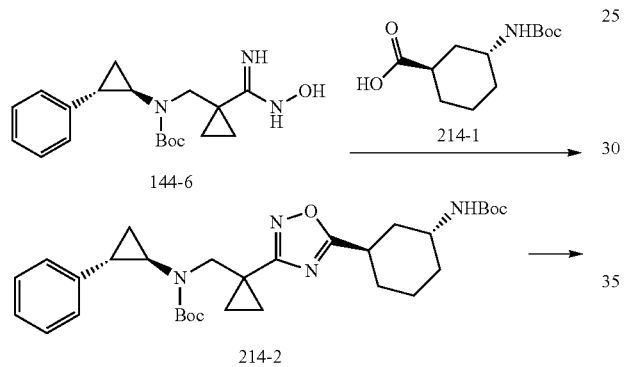

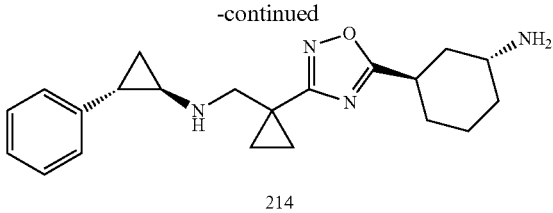

Step 1

The synthesis of compound 214-2 was referred to the first step of example 205. MS-ESI calculated [M+Na]⁺ 575, found 575.

Step 2

The synthesis of compound 214 (13.4 mg) was referred to the second step of example 207. ¹H NMR (400 MHz, CH₃OD) δ 7.34-7.27 (m, 2H), 7.27-7.20 (m, 1H), 7.19-7.13 (m, 2H), 3.76-3.61 (m, 2H), 3.58-3.40 (m, 2H), 3.12-3.03 (m, 1H), 2.63-2.53 (m, 1H), 2.49-2.39 (m, 1H), 2.15-1.96 (m, 2H), 1.%-1.75 (m, 3H), 1.64-1.48 (m, 3H), 1.47-1.33 (m, 5H). MS-ESI calculated [M+H]⁺ 353, found 353.

Example 215

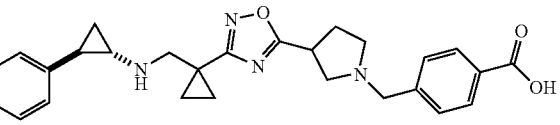

Synthetic Route:

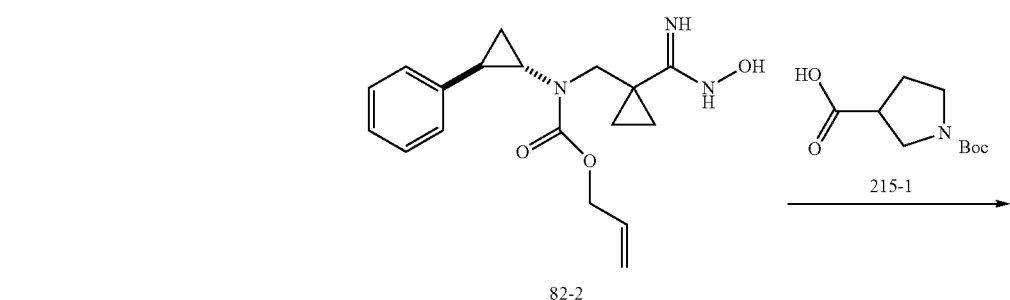

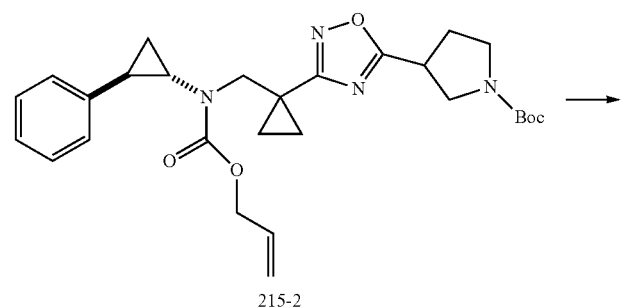

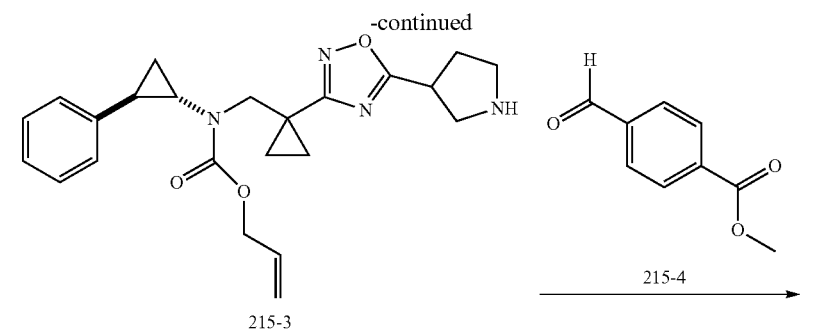

Step 1

The synthesis of compound 215-2 was referred to the first step of example 205. MS-ESI calculated [M+Na]$^+$ 531, found 531.

Step 2

The synthesis of compound 215-3 was referred to the second step of example 205. MS-ESI calculated [M+H]$^+$ 409, found 409.

Step 3

The synthesis of compound 215-5 was referred to the first step of example 204. MS-ESI calculated [M+Na]$^+$ 579, found 579.

Step 4

The synthesis of compound 215-6 was referred to the fourth step of example 205. MS-ESI calculated [M+H]$^+$ 473, found 473.

Step 5

The synthesis of compound 215 was referred to the fifth step of example 205. $^1$H NMR (400 MHz, D$_2$O) δ 8.07 (d, J=8.0 Hz, 2H), 7.60 (d, J=8.0 Hz, 21), 7.30-7.18 (m, 3H), 7.07-6.09 (m, 21), 4.73-3.39 (m, 3H), 4.00-3.73 (m, 3H), 3.64-3.46 (m, 3H), 3.10-2.98 (m, 1H), 2.64-2.19 (m, 3H), 1.52-1.37 (m, 2H), 1.36-1.27 (m, 4H). MS-ESI calculated [M+H]$^+$ 459, found 459.

Example 216

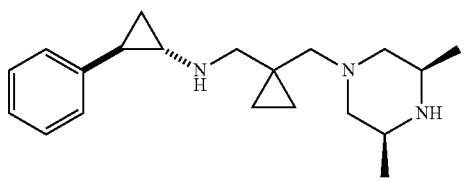

Synthetic Route:

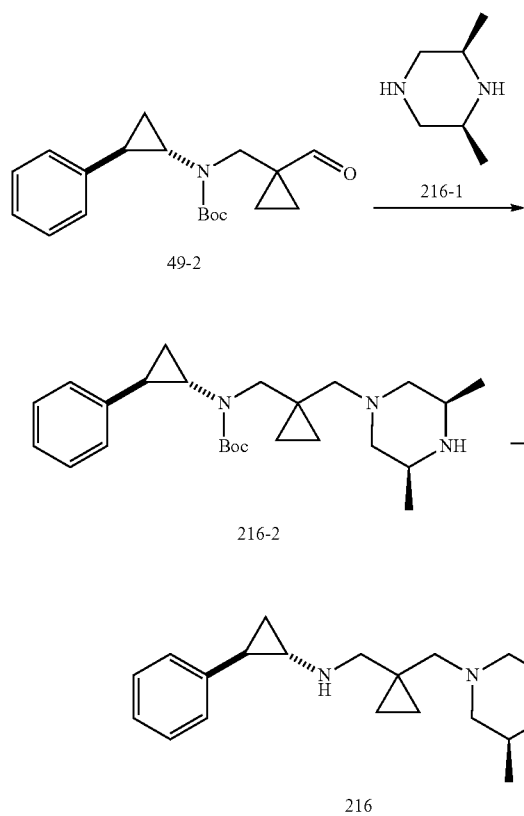

Step 1

The synthesis of compound 216-2 was referred to the first step of example 204. MS-ESI calculated [M+H]$^+$ 414, found 414.

Step 2

The synthesis of compound 216 was referred to the third step of example 204. $^1$H NMR (400 MHz, D$_2$O) δ 7.41-7.24 (m, 3H), 7.23-7.16 (m, 2H), 3.85-3.55 (m, 4H), 3.38-3.30 (m, 2H), 3.29-3.07 (m, 2H), 3.04-2.97 (m, 1H), 2.95-2.70 (m, 2H), 2.61-2.51 (m, 1H), 1.61-1.51 (m, 1H), 1.46-1.28 (m, 7H), 1.03-0.80 (m, 4H). MS-ESI calculated [M+H]$^+$ 314, found 314.

Example 217

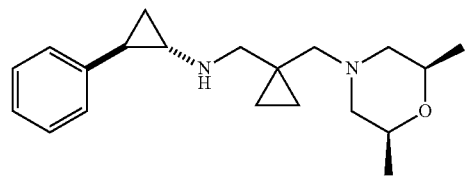

Synthetic Route:

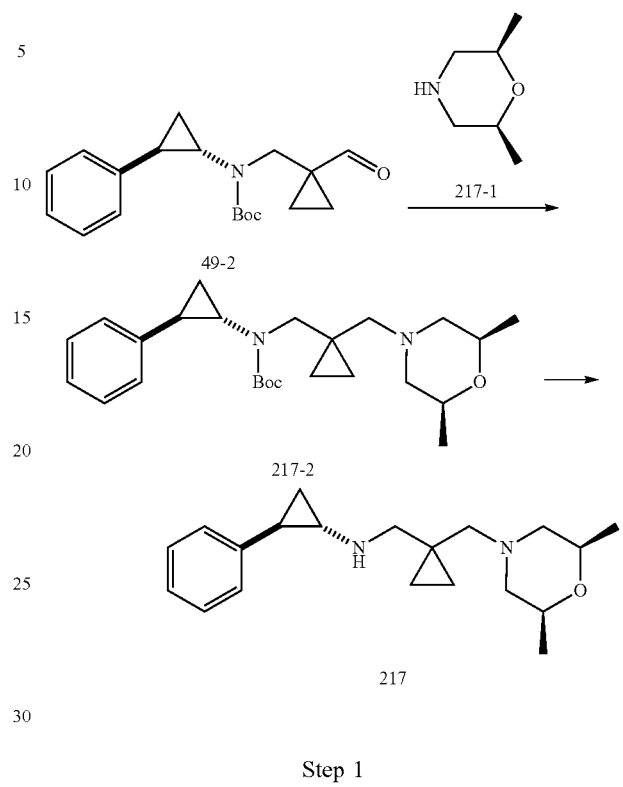

Step 1

The synthesis of compound 217-2 was referred to the first step of example 204. MS-ESI calculated [M+H]$^+$ 415, found 415.

Step 2

The synthesis of compound 217 was referred to the third step of example 204. $^1$H NMR (400 MHz, CH$_3$OD) δ 7.34-7.27 (m, 2H), 7.26-7.15 (m, 3H), 4.18-4.05 (m, 2H), 3.68-3.45 (m, 4H), 3.43-3.33 (m, 2H), 3.16-3.10 (m, 1H), 2.80-2.64 (m, 3H), 1.77-1.66 (m, 1H), 1.44-1.32 (m, 1H), 1.28-1.20 (m, 6H), 1.09-0.84 (m, 4H). MS-ESI calculated [M+H]$^+$ 315, found 315.

Example 218

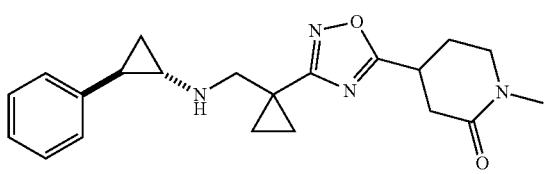

Synthetic Route:

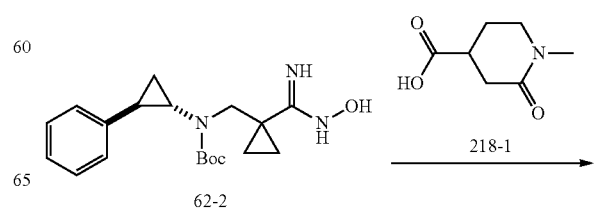

-continued

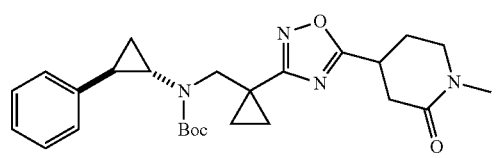

218-2

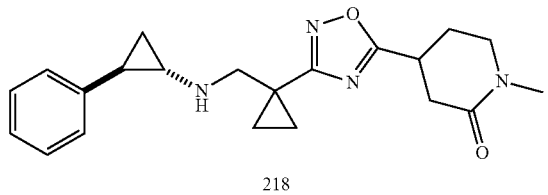

218

Step 1

The synthesis of compound 218-2 was referred to the first step of example 205. MS-ESI calculated [M+Na]⁺ 490, found 490.

Step 2

The synthesis of compound 218 was referred to the third step of example 204. ¹H NMR (400 MHz, CH₃OD) δ 7.35-7.28 (m, 2H), 7.27-7.20 (m, 1H), 7.19-7.11 (m, 2H), 3.73-3.47 (m, 4H), 3.45-3.35 (m, 1H), 3.12-3.02 (m, 1H), 2.86-2.63 (s, 3H), 2.87-2.62 (m, 2H), 2.59-2.50 (m, 1H), 2.40-2.28 (m, 1H), 2.18-2.03 (m, 1H), 1.62-1.52 (m, 1H), 1.47-1.31 (m, 5H). MS-ESI calculated [M+H]⁺ 367, found 367.

Example 219

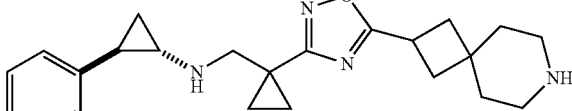

219

Synthetic Route:

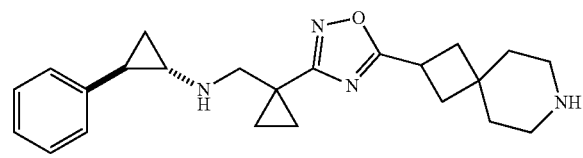

-continued

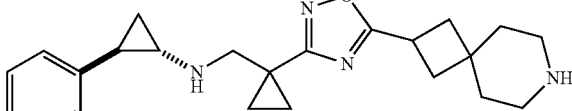

219

Step 1

The synthesis of compound 219-2 was referred to the first step of example 205. MS-ESI calculated [M+Na]⁺ 601, found 601.

Step 2

The synthesis of compound 219 was referred to the third step of example 204. ¹H NMR (400 MHz, CH₃OD) δ 7.35-7.27 (m, 2H), 7.27-7.20 (m, 1H), 7.19-7.12 (m, 2H), 3.86-3.74 (m, 1H), 3.74-3.60 (m, 2H), 3.22-3.15 (m, 2H), 3.14-3.04 (m, 3H), 2.62-2.51 (m, 1H), 2.48-2.36 (m, 2H), 2.33-2.20 (m, 2H), 2.04-1.94 (m, 2H), 1.91-1.83 (m, 2H), 1.63-1.52 (m, 1H), 1.50-1.29 (m, 5H). MS-ESI calculated [M+H]⁺ 379, found 379.

Example 220

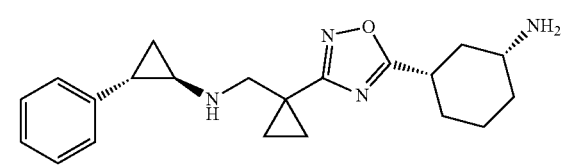 [SMILES: N[C@@H]1CCC[C@H](c2nc(C3(CN[C@@H]4C[C@H]4c4ccccc4)CC3)no2)C1]

Synthetic Route:

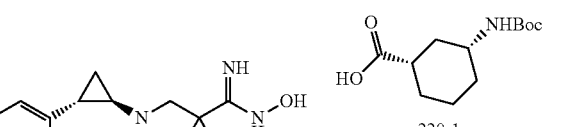

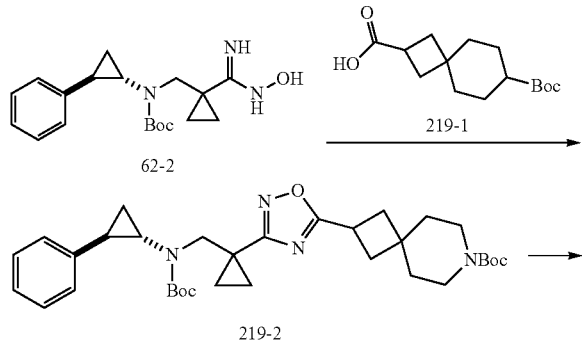

Step 1

The synthesis of compound 220-2 was referred to the first step of example 205. MS-ESI calculated [M+Na]$^+$ 575, found 575.

Step 2

The synthesis of compound 220 was referred to the second step of example 207. $^1$H NMR (400 MHz, CH$_3$OD) δ 7.36-7.27 (m, 2H), 7.27-7.19 (m, 1H), 7.18-7.12 (m, 2H), 3.73-3.62 (m, 2H), 3.29-3.25 (m, 1H), 3.19-3.05 (m, 2H), 2.58-2.49 (m, 1H), 2.47-2.36 (m, 1H), 2.17-1.99 (m, 3H), 1.70-1.54 (m, 3H), 1.52-1.32 (m, 7H). MS-ESI calculated [M+H]$^+$ 353, found 353.

Example 221

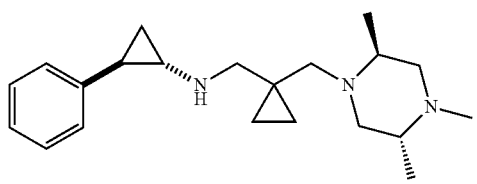

Synthetic Route:

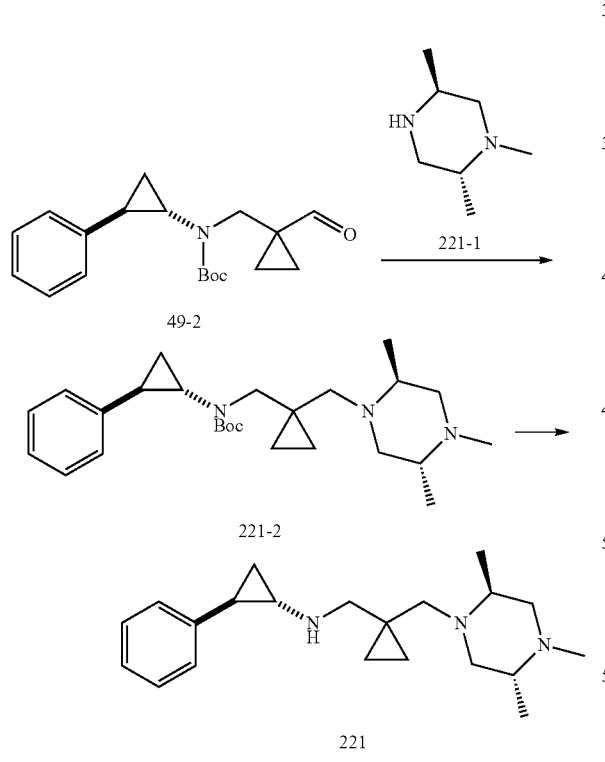

Step 1

Compound 49-2 (150 mg, 0.476 mmol) and 221-1 (61.0 mg, 0.476 mmol) were dissolved in dichloromethane (8 mL), acetic acid (85.7 mg, 1.43 mmol) was added, and the mixture was stirred at 26° C. for 20 h. Sodium triacetoxyborohydride (302 mg, 1.43 mmol) was added and the reaction was stirred at 26° C. for 36 h. The saturated sodium carbonate solution (15 mL) was added to the mixture and the mixture was extracted with dichloromethane (25 mL×2). The combined organic layer was washed with saturated brine (50 mL×1), dried over anhydrous sodium sulfate, filtered, isolated and purified by thin layer chromatography (1:3 petroleum ether/ethyl acetate, Rf=0.2) to give compound 221-2. MS-ESI calculated [M+H]$^+$ 428, found 428.

Step 2

The compound 221-2 (60.0 mg, 0.140 mmol) was dissolved in dichloromethane (6 mL), and then trifluoroacetic acid (64.0 mg, 0.561 mmol) was added, and the mixture was stirred at 20° C. for 3 h. The mixture was concentrated under reduced pressure, isolated and purified by preparative high-performance liquid chromatography (hydrochloride) to give compound 221. $^1$H NMR (400 MHz, CH$_3$OD) δ 7.34-7.26 (m, 2H), 7.26-7.16 (m, 3H), 4.40-4.07 (m, 3H), 4.07-3.85 (m, 2H), 3.84-3.67 (m, 2H), 3.55-3.37 (m, 1H), 3.29-3.18 (m, 1H), 3.03 (s, 3H), 2.96-2.56 (m, 3H), 1.88-1.60 (m, 1H), 1.60-1.46 (m, 6H), 1.41-1.29 (m, 1H), 1.23-1.01 (m, 3H), 0.93-0.80 (m, 1H). MS-ESI calculated [M+H]$^+$ 328, found 328.

Example 222

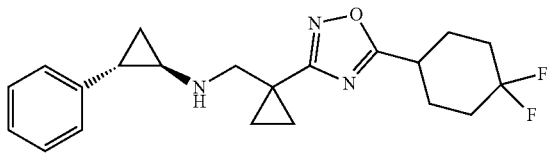 [SMILES: FC1(F)CCC(c2nc(C3(CN[C@@H]4C[C@H]4c4ccccc4)CC3)no2)CC1]

Synthetic Route:

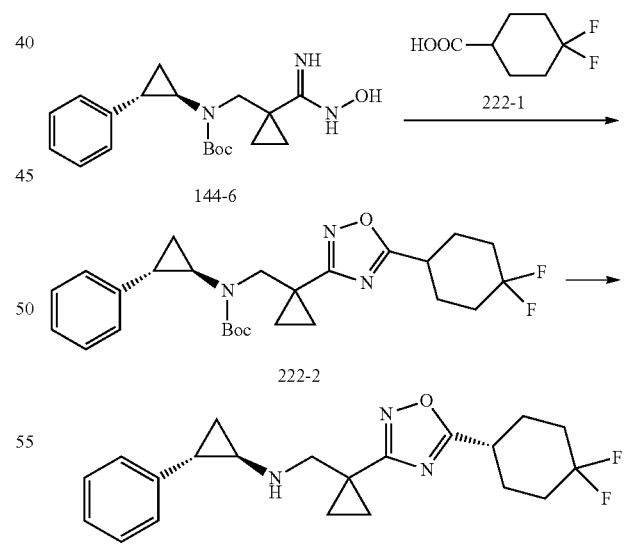

Step 1

The synthesis of compound 222-2 was referred to the first step of example 205. MS-ESI calculated [M+Na]$^+$ 496, found 496.

Step 2

The synthesis of compound 222 was referred to the second step of example 207. ¹H NMR (400 MHz. CH₃OD) δ 7.34-7.27 (m, 2H), 7.27-7.20 (m, 1H), 7.19-7.12 (m, 2H), 3.72-3.62 (m, 2H), 3.20-3.11 (m, 1H), 3.10-3.04 (m, 1H), 2.57-2.48 (m, 1H), 2.19-2.07 (m, 4H), 2.04-1.88 (m, 4H), 1.56 (m, 1H), 1.46-1.37 (m, 3H), 1.35-1.32 (m, 2H). MS-ESI calculated [M+H]⁺ 374, found 374.

Example 223

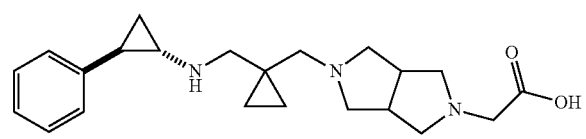

Synthetic Route:

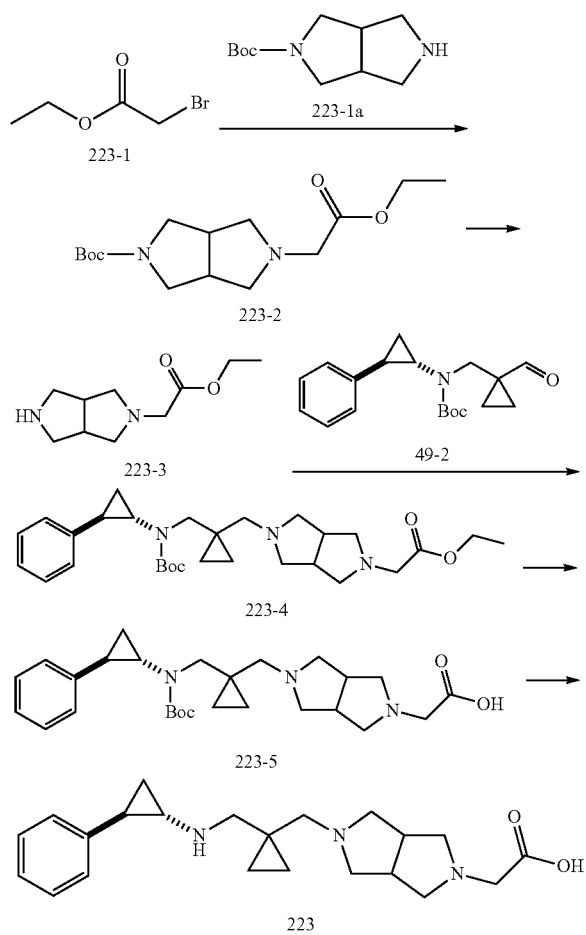

Step 1

Compound 223-1 (153 mg, 0.919 mmol) and 223-1a (150 mg, 0.707 mmol) were dissolved in anhydrous N,N-dimethylformamide (8 mL) under nitrogen, potassium carbonate (195 mg, 1.41 mmol) was added in one portion, and the reaction mixture was stirred at 20° C. for 2 hours. The solid was removed by filtration, water (40 mL) was added to the filtrate. The reaction solution was extracted with ethyl acetate (40 mL×3). The combined organic layers were washed with saturated brine (90 mL×1), dried over anhydrous sodium sulfate, filtered, concentrated under reduced pressure to give compound 223-2. ¹H NMR (400 MHz, CDCl₃) δ 4.11 (q, J=7.0 Hz, 2H), 3.48-3.40 (m, 2H), 3.28-3.23 (m, 2H), 3.23-3.12 (m, 2H), 2.89-2.84 (m, 2H), 2.81-2.72 (m, 2H), 2.42-2.32 (m, 2H), 1.38 (s, 9H), 1.20 (t, J=7.0 Hz, 3H).

Step 2

Compound 223-2 (203 mg, 0.680 mmol) was dissolved in dichloromethane (4 mL). Trifluoroacetic acid (155 mg, 1.36 mmol) was added and the reaction was stirred at 20° C. for 1.5 h. The mixture was concentrated under reduced pressure to give compound 223-3. ¹H NMR (400 MHz. CH₃OD) δ 4.89-4.58 (m, 2H), 4.38-4.26 (m, 2H), 4.24 (s, 1H), 3.92-3.61 (m, 2H), 3.61-3.51 (m, 2H), 3.50-3.32 (m, 5H), 1.37-1.30 (m, 3H).

Step 3

The synthesis of compound 223-4 was referred to the first step of example 204. MS-ESI calculated [M+H]⁺ 498, found 498.

Step 4

The synthesis of compound 223-5 was referred to the fifth step of example 206. MS-ESI calculated [M+H]⁺ 470, found 470.

Step 5

The synthesis of compound 223 was referred to the second step of example 207. ¹H NMR (400 MHz, CH₃OD) δ 7.34-7.27 (m, 2H), 7.26-7.17 (m, 3H), 4.43-4.16 (m, 2H), 4.16-3.98 (m, 2H), 3.97-3.88 (m, 2H), 3.87-3.56 (m, 3H), 3.55-3.35 (m, 7H), 3.25-3.06 (m, 1H), 2.80-2.69 (m, 1H), 1.78-1.63 (m, 1H), 1.42-1.30 (m, 1H), 1.08-0.87 (m, 4H). MS-ESI calculated [M+H]⁺ 370, found 370.

Example 224

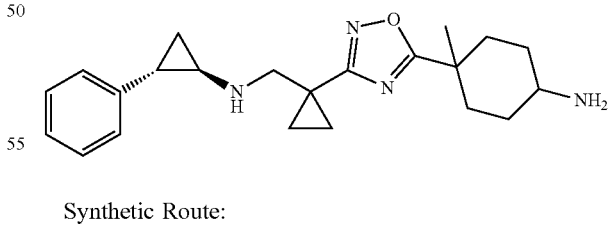

Synthetic Route:

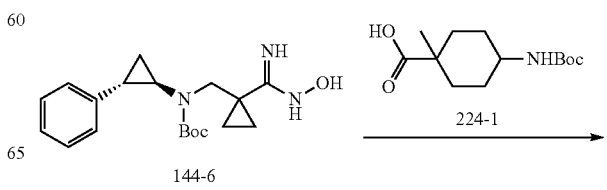

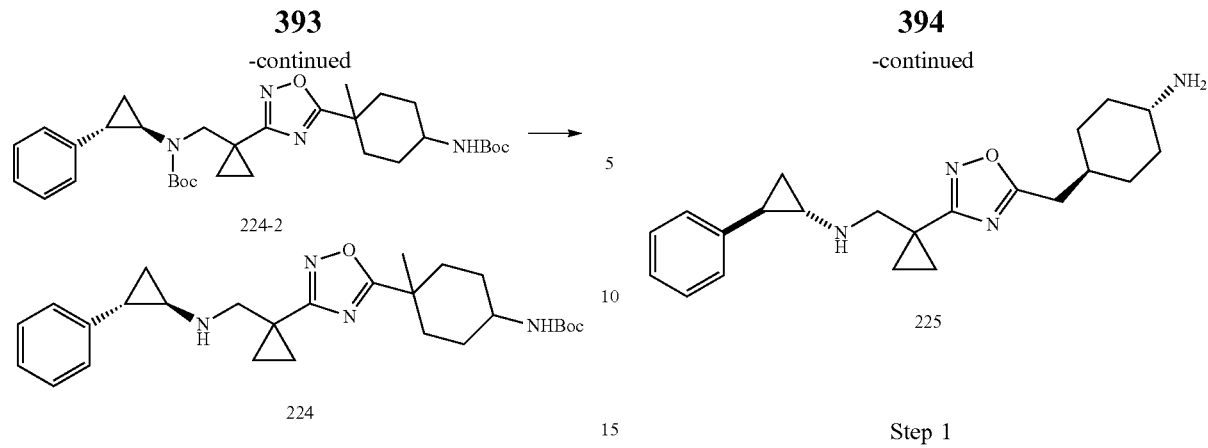

Step 1

The synthesis of compound 224-2 was referred to the first step of example 205. MS-ESI calculated [M+Na]$^+$ 589, found 589.

Step 2

The synthesis of compound 224 was referred to the second step of example 207. $^1$H NMR (400 MHz, CH$_3$OD) δ 7.36-7.28 (m, 2H), 7.28-7.21 (m, 1H), 7.24-7.16 (m, 2H), 3.76-3.64 (m, 2H), 3.21-3.11 (m, 1H), 3.10-3.02 (m, 1H), 2.68-2.56 (m, 1H), 2.48-2.39 (m, 2H), 1.99-1.92 (m, 2H), 1.75-1.60 (m, 3H), 1.57-1.39 (m, 5H), 1.37-1.31 (m, 5H). MS-ESI calculated [M+H]$^+$ 367, found 367.

Example 225

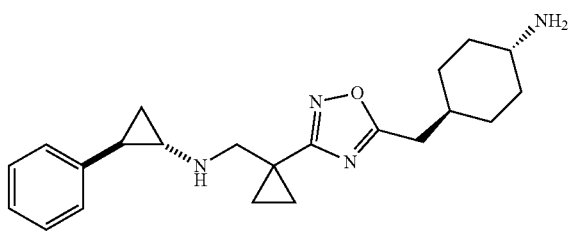

Synthetic Route:

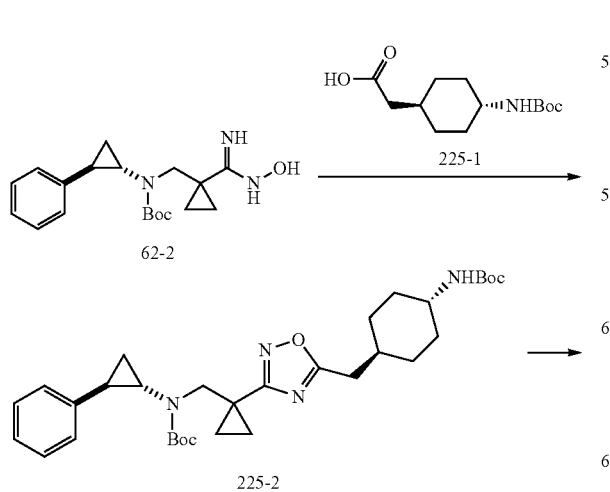

Step 1

The synthesis of compound 225-2 was referred to the first step of example 208. MS-ESI calculated [M+Na]$^+$ 589, found 589.

Step 2

Compound 225-2 (130 mg, 0.229 mmol) was dissolved in dichloromethane (6 mL), and then trifluoroacetic acid (26.2 mg, 0.229 mmol) was added, and the mixture was stirred at 20° C. for 1.5 h. The mixture was concentrated under reduced pressure, isolate and purified by preparative high-performance liquid chromatography to give compound 225. $^1$H NMR (400 MHz, CH$_3$OD) δ 7.34-7.28 (m, 2H), 7.26-7.20 (m, 1H), 7.20-7.12 (m, 2H), 3.73-3.61 (m, 2H), 3.13-3.01 (m, 2H), 2.81 (d, J=6.8 Hz, 2H), 2.60-2.51 (m, 1H), 2.10-2.00 (m, 2H), 1.95-1.79 (m, 3H), 1.64-1.54 (m, 1H), 1.49-1.33 (m, 7H), 1.30-1.20 (m, 2H). MS-ESI calculated [M+H]$^+$ 367, found 367.

Example 226

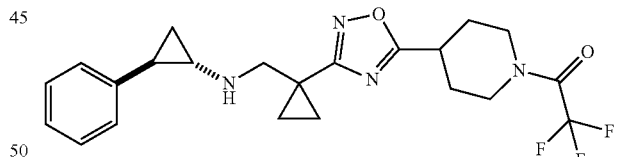

Synthetic Route:

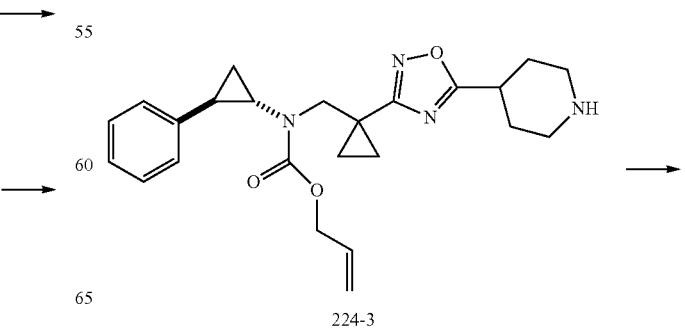

Synthetic Route:

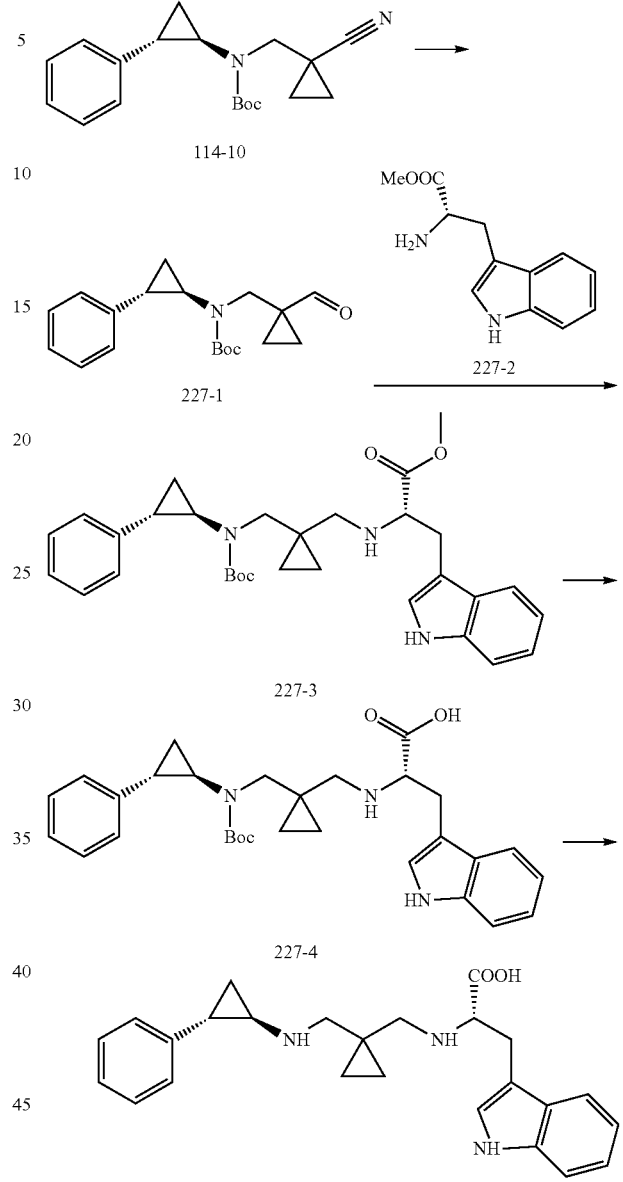

Step 1

Compound 114-10 (5.00 g, 16.0 mmol) was dissolved in dichloromethane (16 mL) under nitrogen, and diisobutyl-aluminum hydride (2.49 g, 17.6 mmol) was added at −78° C. The reaction solution was stirred at −78° C. for 1.5 h. Saturated sodium potassium tartrate solution (150 mL) and dichloromethane (70 mL) were added to the reaction mixture, and the mixture was stirred at room temperature for 30 minutes. The mixture was extracted with dichloromethane (200 mL×2). The organic phases were combined, washed with saturated brine (300 mL×3), dried over anhydrous sodium sulfate, filtered, isolated and purified by column chromatography (5:1 petroleum ether/ethyl acetate, Rf=0.5) to give compound 227-1. MS-ESI calculated [M−100+H]$^+$ 216, found 216.

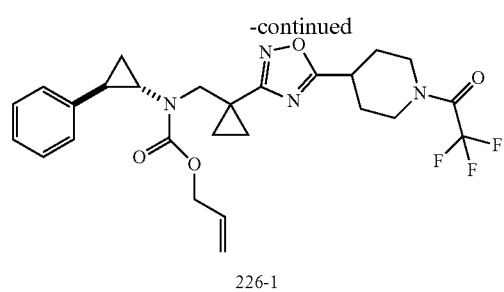

226-1

226

Step 1

Compound 224-3 (97.0 mg, 0.230 mmol) was dissolved in anhydrous dichloromethane (16 mL). Triethylamine (46.5 mg, 0.459 mmol) and trifluoroacetic anhydride (96.4 mg, 0.459 mmol) were added in one portion at 0° C., and the mixture was stirred at 20° C. for 18 h. The mixture was concentrated under reduced pressure, isolated and purified by thin layer chromatography (5:1 petroleum ether/ethyl acetate, Rf=0.6) to give compound 226-1. MS-ESI calculated [M+Na]$^+$ 541, found 541.

Step 2

Compound 226-1 (50.0 mg, 96.4 μmol) was dissolved in anhydrous tetrahydrofuran (8 mL) under nitrogen, and tetrakis (triphenylphosphine) palladium(0) (11.1 mg, 9.64 μmol) and diethylamine (70.5 mg, 0.964 mmol) were added, and the reaction mixture was stirred at 80° C. for 2.5 h. The mixture was concentrated under reduced pressure, isolated and purified by thin layer chromatography (1:2 petroleum ether/ethyl acetate. Rf=0.4) to give compound 226. $^1$H NMR (400 MHz, CH$_3$OD) δ 7.34-7.27 (m, 2H), 7.27-7.20 (m, 1H), 7.22-7.12 (m, 2H), 4.38 (m, 1H), 4.44-4.30 (m, 1H), 3.74-3.59 (m, 2H), 3.51-3.34 (m, 2H), 3.23-3.04 (m, 2H), 2.57-2.45 (m, 1H), 2.27-2.12 (m, 2H), 1.90-1.72 (m, 2H), 1.60-1.50 (m, 1H), 1.48-1.37 (m, 3H), 1.35-1.28 (m, 2H). MS-ESI calculated [M+H]$^+$ 435, found 435.

Example 227

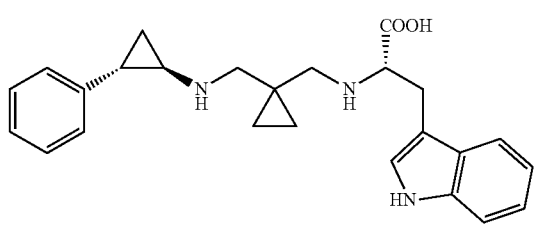 [SMILES: O=C(O)[C@H](Cc1c[nH]c2ccccc12)NCC1(CN[C@@H]2C[C@H]2c2ccccc2)CC1]

Step 2

Compounds 227-1 (80.0 mg, 0.254 mmol) and 227-2 (90.5 mg, 0.355 mmol) were dissolved in dichloromethane (8 mL) under nitrogen, and acetic acid (30.5 mg, 0.507 mmol) was added. The reaction solution was stirred at 30'C for 1 h. Sodium tricetoxyborohydride (161 mg, 0.761 mmol) was added, and the reaction mixture was stirred at 30° C. for 3 h. The saturated sodium carbonate solution (30 mL) was added to the mixture. The mixture was extracted with dichloromethane (40 mL×2). The organic phases were combined, washed with saturated brine (70 mL×1), dried over anhydrous sodium sulfate, filtered, concentrated under reduced pressure, isolated and purified by thin layer chromatography (2:1 petroleum ether/ethyl acetate, Rf=0.5) to give compound 227-3. MS-ESI calculated [M+H]$^+$ 518, found 518.

Step 3

Compound 227-3 (70.0 mg, 0.135 mmol) was dissolved in the mixture of tetrahydrofuran (4 mL) and water (4 mL) under nitrogen, sodium hydroxide (27.0 mg, 0.676 mmol) was added in one portion. The reaction solution was stirred at 50° C. for 20 h. The mixture was adjusted to pH=1-2 by adding 1 N hydrochloric acid solution, and concentrated under reduced pressure to give compound 227-4. MS-ESI calculated [M+H]$^+$ 504, found 504.

Step 4

The synthesis of compound 227 was referred to the second step of example 205. $^1$H NMR (400 MHz, CH$_3$OD) δ 7.69 (d, J=7.8 Hz, 1H), 7.37 (d, J=7.8 Hz, 1H), 7.34-7.27 (m, 3H), 7.26-7.20 (m, 1H), 7.17 (d, J=7.2 Hz, 2H), 7.13 (t, J=7.2 Hz, 1H), 7.08-7.02 (m, 1H), 4.36-4.28 (m, 1H), 3.57 (d, J=6.0 Hz, 2H), 3.43-3.32 (m, 2H), 3.18-3.12 (m, 1H), 3.08-3.02 (m, 1H), 2.99-2.92 (m, 1H), 2.73-2.64 (m, 1H), 1.67-1.54 (m, 1H), 1.36-1.30 (m, 1H), 0.93-0.79 (m, 4H). MS-ESI calculated [M+H]$^+$ 404, found 404.

Example 228

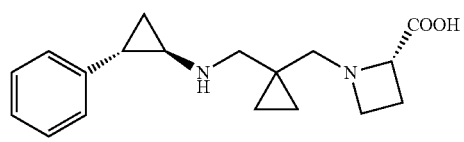 [SMILES: O=C(O)[C@@H]1CCN1CC1(CN[C@@H]2C[C@H]2c2ccccc2)CC1]

Synthetic Route:

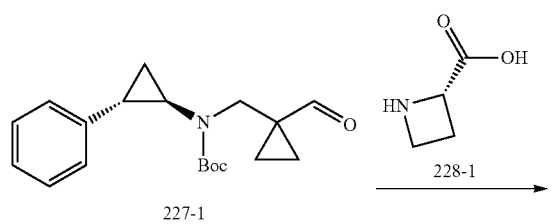

227-1

-continued

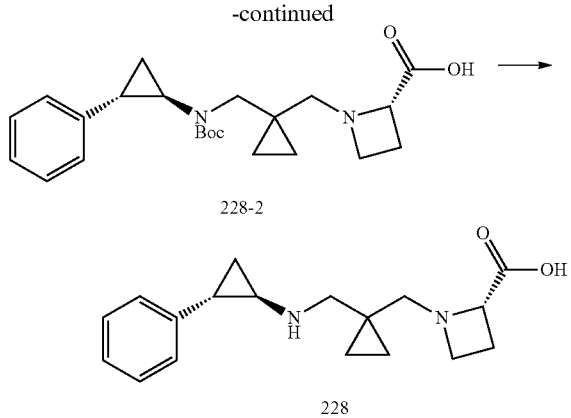

228-2

228

Step 1

Compounds 227-1 (120 mg, 0.380 mmol) and 228-1 (53.9 mg, 0.533 mmol) were dissolved in anhydrous ethanol (8 mL) under nitrogen, acetic acid (45.7 mg, 0.761 mmol) was added. The reaction solution was stirred at 50° C. for 1 h. Sodium cyanoborohydride (71.7 mg, 1.14 mmol) was added and the mixture was stirred at 50° C. for 15 h. The mixture was concentrated under reduced pressure, isolated and purified by thin layer chromatography (4:1 petroleum ether/ethyl acetate, Rf=0.5) to give compound 228-2. MS-ESI calculated [M+H]$^+$ 401, found 401.

Step 2

Compound 228-2 (76.0 mg, 0.190 mmol) was dissolved in dichloromethane (8 mL) under nitrogen. Trifluoroacetic acid (86.5 mg, 0.759 mmol) was added, and the reaction mixture was stirred at 20° C. for 2 h. The mixture was concentrated under reduced pressure, isolated and purified by preparative high-performance liquid chromatography to give compound 228. $^1$H NMR (400 MHz, CH$_3$OD) δ 7.35-7.27 (m, 2H), 7.27-7.17 (m, 3H), 5.44-5.34 (m, 1H), 4.27-4.06 (m, 2H), 3.92-3.77 (m, 2H), 3.18-3.12 (m, 1H), 3.07-2.95 (m, 2H), 2.82-2.69 (m, 3H), 1.73-1.62 (m, 1H), 1.40-1.30 (m, 1H), 1.04-0.92 (m, 2H), 0.90-0.77 (m, 2H). MS-ESI calculated [M+H]$^+$ 301, found 301.

Example 229

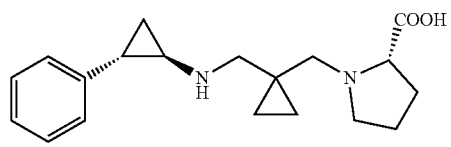 [SMILES: O=C(O)[C@@H]1CCCN1CC1(CN[C@@H]2C[C@H]2c2ccccc2)CC1]

Synthetic Route:

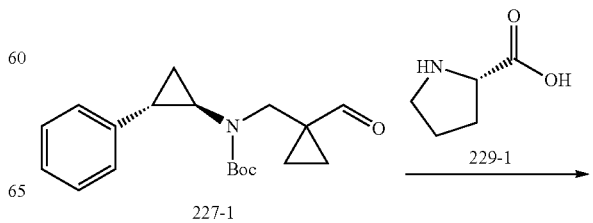

227-1        229-1

-continued

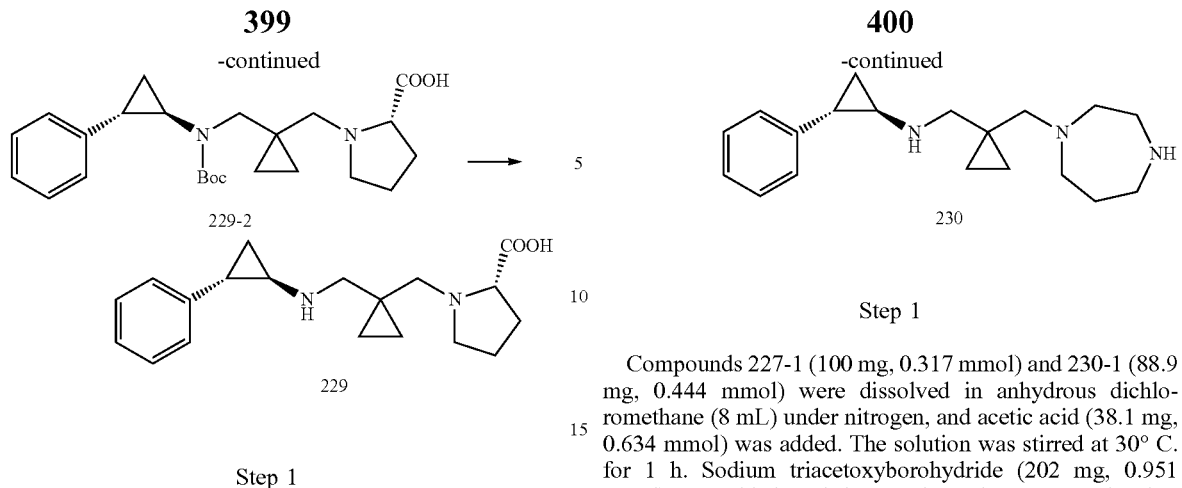

229-2

229

Step 1

Compounds 227-1 (180 mg, 0.571 mmol) and 229-1 (121 mg, 0.799 mmol) were dissolved in anhydrous ethanol (8 mL) under nitrogen, acetic acid (68.5 mg, 1.14 μmol) was added. The reaction solution was stirred at 30° C. for 1 h. Sodium triacetoxyborohydride (363 mg, 1.71 mmol) was added, and the reaction mixture was stirred at 30° C. for 2 h. The mixture was concentrated under reduced pressure, isolated and purified by thin layer chromatography (5:1 petroleum ether/ethyl acetate, Rf=0.6) to give compound 229-2. MS-ESI calculated [M+H]$^+$ 415, found 415.

Step 2

The synthesis of compound 229 was referred to the second step of example 207. $^1$H NMR (400 MHz, CH$_3$OD) δ 7.34-7.28 (m, 2H), 7.27-7.17 (m, 3H), 4.52-4.40 (m, 1H), 4.10-3.98 (m, 1H), 3.74-3.57 (m, 2H), 3.48-3.32 (m, 2H), 3.30-3.24 (m, 1H), 3.09-2.99 (m, 1H), 2.80-2.70 (m, 1H), 2.68-2.55 (m, 1H), 2.27-2.08 (m, 3H), 1.78-1.67 (m, 1H), 1.44-1.36 (m, 1H), 1.06-0.92 (m, 4H). MS-ESI calculated [M+H]$^+$ 315, found 315.

Example 230

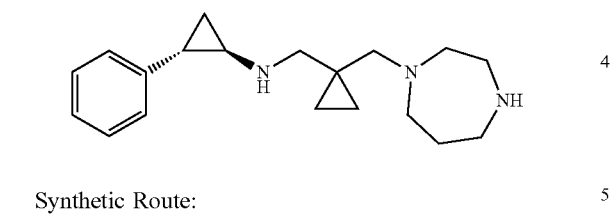

Synthetic Route:

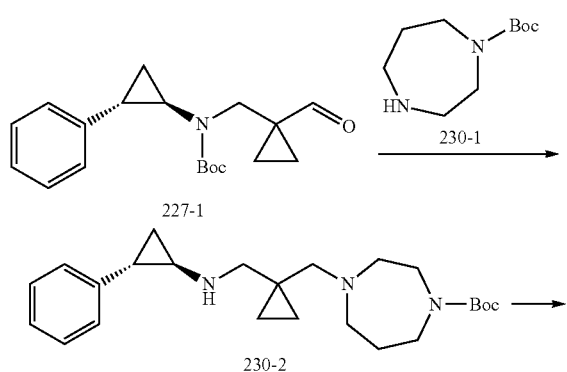

-continued

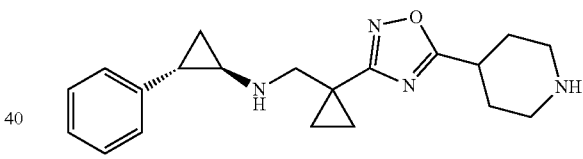

230

Step 1

Compounds 227-1 (100 mg, 0.317 mmol) and 230-1 (88.9 mg, 0.444 mmol) were dissolved in anhydrous dichloromethane (8 mL) under nitrogen, and acetic acid (38.1 mg, 0.634 mmol) was added. The solution was stirred at 30° C. for 1 h. Sodium triacetoxyborohydride (202 mg, 0.951 mmol) was added, and the reaction mixture was stirred at 30° for 11 h. The mixture was concentrated under reduced pressure to give compound 230-2. MS-ESI calculated [M+H]$^+$500, found 500.

Step 2

The synthesis of compound 230 was referred to the second step of example 206. $^1$H NMR (400 MHz, CH$_3$OD) δ 7.34-7.27 (m, 2H), 7.27-7.17 (m, 3H), 3.99-3.63 (m, 4H), 3.62-3.32 (m, 8H), 3.17-3.12 (m, 1H), 2.77-2.65 (m, 1H), 2.49-2.23 (m, 2H), 1.74-1.62 (m, 1H), 1.40-1.32 (m, 1H), 1.10-0.86 (m, 4H). MS-ESI calculated [M+H]$^+$ 300, found 300.

Example 231

Synthetic Route:

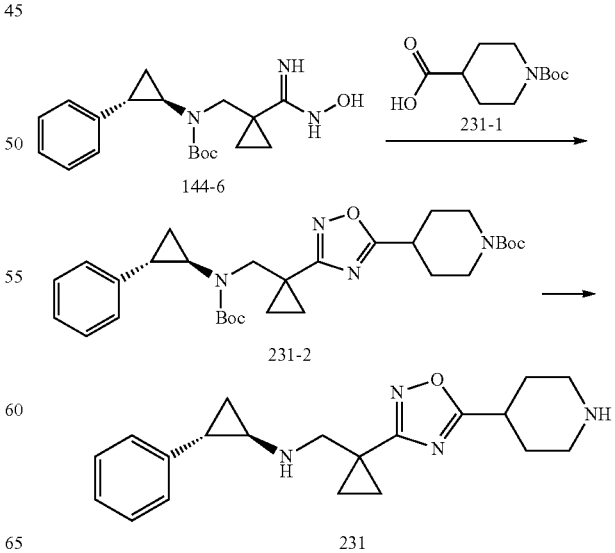

Step 1

The synthesis of compound 231-2 was referred to the first step of example 205. MS-ESI calculated [M+Na]⁺ 561, found 561.

Step 2

The synthesis of compound 231 was referred to the second step of example 207. ¹H NMR (400 MHz, CH₃OD) δ 7.36-7.27 (m, 2H), 7.27-7.20 (m, 1H), 7.20-7.14 (m, 2H), 3.75-3.62 (m, 2H), 3.52-3.37 (m, 3H), 3.25-3.14 (m, 2H), 3.11-3.04 (m, 1H), 2.62-2.53 (m, 1H), 2.38-2.27 (m, 2H), 2.13-1.97 (m, 2H), 1.64-1.55 (m, 1H), 1.48-1.32 (m, 5H). MS-ESI calculated [M+H]⁺ 339, found 339.

Example 232

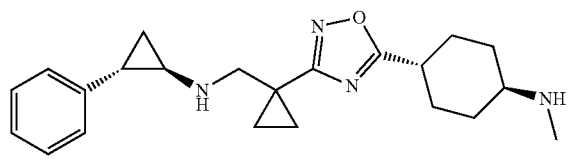 [SMILES: CN[C@H]1CC[C@H](c2nc(C3(CN[C@@H]4C[C@H]4c4ccccc4)CC3)no2)CC1]

Synthetic Route:

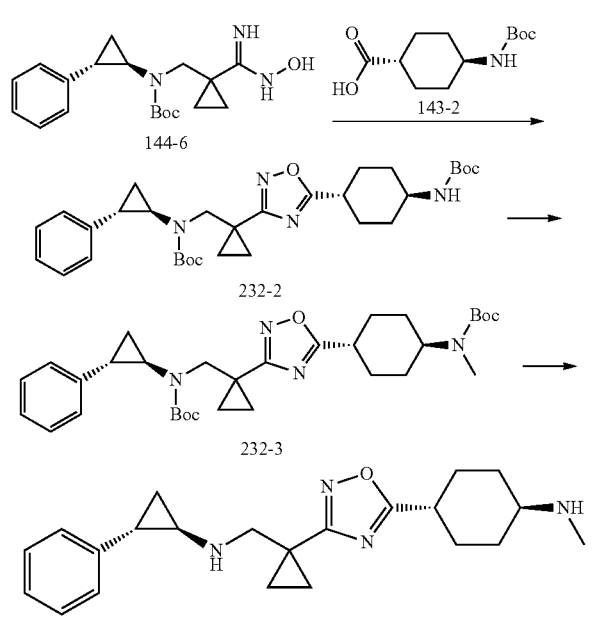

Step 1

The synthesis of compound 232-2 was referred to the first step of example 208. MS-ESI calculated [M+Na]⁺ 575, found 575.

Step 2

Compound 232-2 (112 mg, 0.145 mmol) was dissolved in anhydrous N,N-dimethylformamide (12 mL) under nitrogen, sodium hydride (8.71 mg, 0.218 mmol) was added, and the reaction mixture was stirred at 0° C. for 0.5 h. Iodomethane (246 mg, 1.73 mmol) was added at 0° C., and the reaction was stirred at 20 V for 2.5 h. The saturated ammonium chloride solution (30 mL) was added to the mixture, and the mixture was extracted with ethyl acetate (40 mL×2). The combined organic layer was washed with saturated brine (80 mL×1), dried over anhydrous sodium sulfate, filtered, concentrated under reduced pressure, isolated and purified by thin layer chromatography (3:1 petroleum ether/ethyl acetate, Rf=0.37) to give compound 232-3. MS-EST calculated [M+Na]⁺ 589, found 589.

Step 3

The synthesis of compound 232 was referred to the second step of example 207. ¹H NMR (400 MHz, CH₃OD) δ 7.35-7.27 (m, 2H), 7.27-7.20 (m, 1H), 7.19-7.13 (m, 2H), 3.72-3.60 (m, 2H), 3.19-2.88 (m, 3H), 2.72 (s, 3H), 2.55 (m, 1H), 2.36-2.17 (m, 4H), 1.74-1.62 (m, 2H), 1.62-1.47 (m, 3H), 1.46-1.30 (m, 5H). MS-ESI calculated [M+H]⁺ 367, found 367.

Example 233

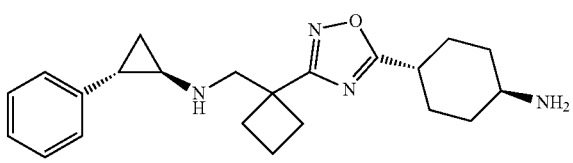 [SMILES: N[C@H]1CC[C@H](c2nc(C3(CN[C@@H]4C[C@H]4c4ccccc4)CCC3)no2)CC1]

Synthetic Route:

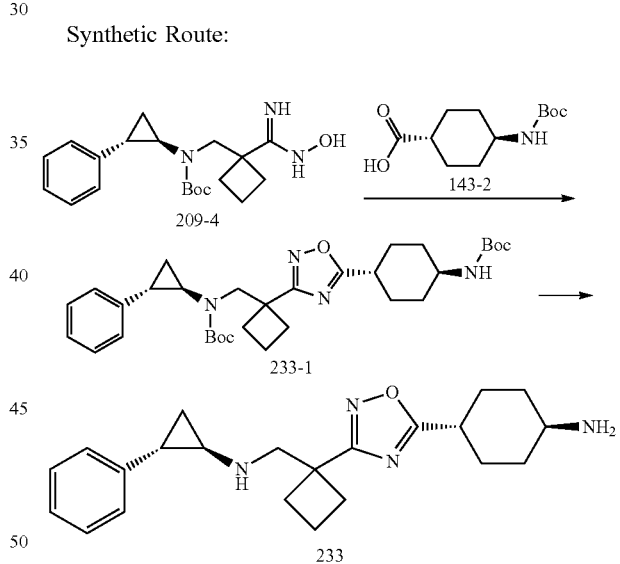

Step 1

The synthesis of compound 233-1 was referred to the first step of example 205. MS-ESI calculated [M+Na]⁺ 589, found 589.

Step 2

The synthesis of compound 233 was referred to the second step of example 207. ¹H NMR (400 MHz, CH₃OD) δ 7.35-7.27 (m, 2H), 7.27-7.21 (m, 1H), 7.22-7.16 (m, 2H), 3.81 (s, 2H), 3.25-3.16 (m, 1H), 3.09-2.99 (m, 2H), 2.66-2.51 (m, 3H), 2.40-2.27 (m, 4H), 2.24-2.13 (m, 4H), 1.84-1.68 (m, 2H), 1.66-1.53 (m, 3H), 1.44-1.34 (m, 1H). MS-ESI calculated [M+H]⁺ 367, found 367.

Example 235
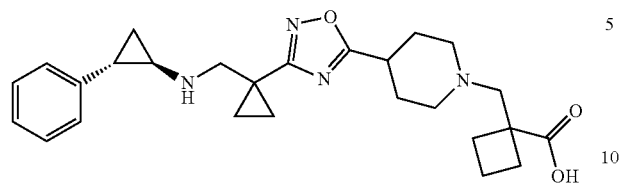
Synthetic Route:
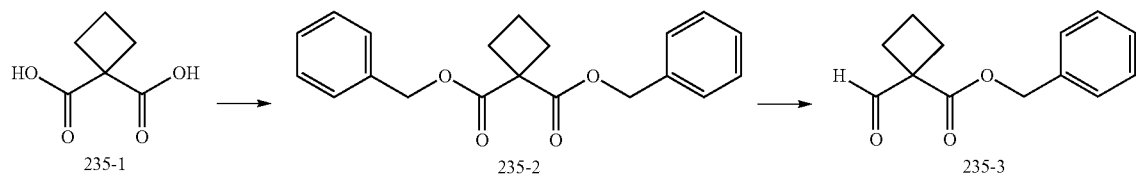
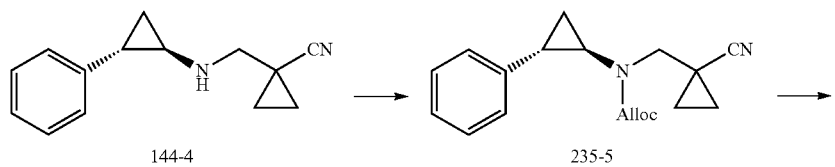
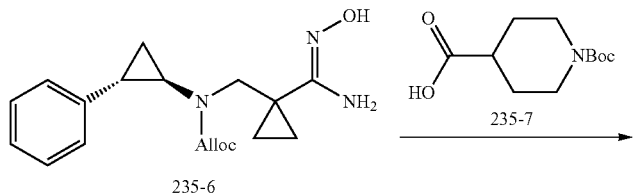
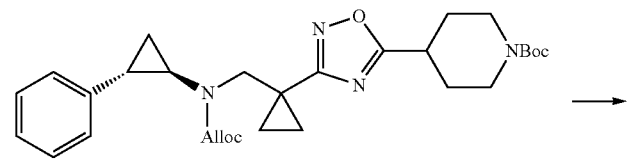
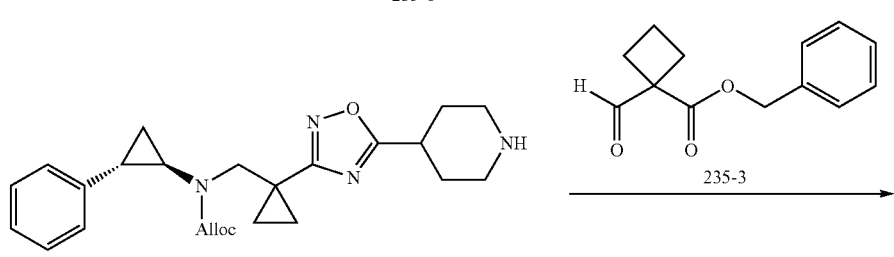

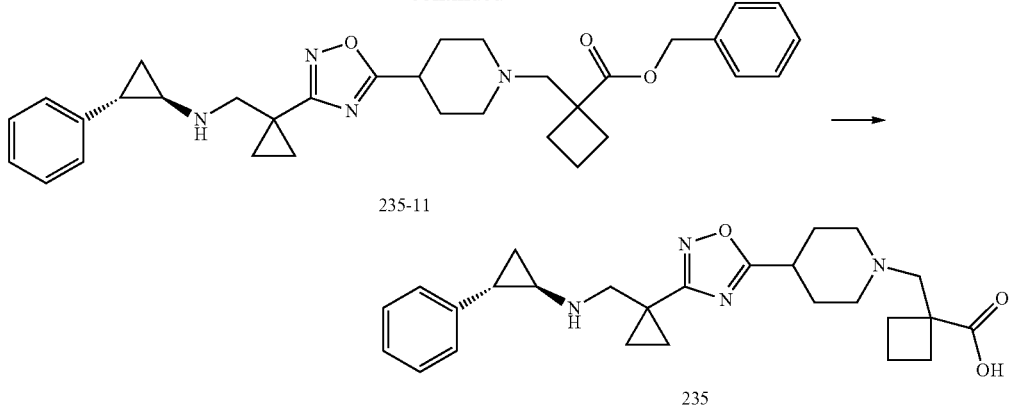

Step 1

Compound 235-1 (1 g, 6.94 mmol) was dissolved in anhydrous N,N-dimethylformamide (10 mL). Triethylamine (2.81 g, 27.8 mmol) was added at 0° C. The mixture was stirred for 15 min. Benzyl bromide (4.15 g, 24.3 mmol) was added, and the mixture was stirred at 0° C. for 15 min. Then warmed to 25° C. and stirred for 11.5 h. The reaction was quenched with water (50 mL). The mixture was extracted with ethyl acetate (50 mL×3). The organic phase was washed with saturated sodium bicarbonate (50 mL×1), sodium brine (50 mL×1). The organic phase was dried over anhydrous sodium sulfate, filtered, concentrated under reduced pressure, isolated and purified by preparative thin layer chromatography (10:1 petroleum ether/ethyl acetate, Rf=0.78) to give compound 235-2. $^1$H NMR (400 MHz, CDCl$_3$) δ 7.36-7.28 (m, 10H), 5.18 (s, 4H), 2.63-2.59 (m, 4H), 2.07-1.98 (m, 2H).

Step 2

Compound 235-2 (6.00 g, 18.5 mmol) was dissolved in anhydrous dichloromethane (120 mL), diisobutylaluminum hydride (1.5 M in toluene, 24.7 mL, 36.9 mmol) was added dropwise at −78° C. The reaction solution was stirred at −78° C. for 2 h. The reaction was quenched by the addition of hydrochloric acid (1 M, 36.9 mL) and water (100 mL) at −78° C., and the mixture was stirred at 25° C. for 30 min and extracted with ethyl acetate (100 mL×3). The organic phase was washed with saturated sodium bicarbonate (100 mL), sodium brine (100 mL). The organic phase was dried over anhydrous sodium sulfate, filtered, concentrated under reduced pressure, isolated and purified by silica gel column chromatography (10:1 petroleum ether/ethyl acetate, Rf=0.5) to give compound 235-3. $^1$H NMR (400 MHz, CDCl$_3$) δ 9.81 (s, 1H), 7.40-7.34 (m, 5H), 5.23 (s, 2H), 2.52-2.48 (m, 4H), 2.05-1.88 (m, 2H).

Step 3

Compound 144-4 (6.00 g, 22.7 mmol) was dissolved in anhydrous dichloromethane (50 mL), diisopropylethylamine (5.88 g, 45.5 mmol) and allyl chloroformate (4.11 g, 34.12 mmol) were added at 0° C. The reaction solution was stirred at 25° C. for 1 h. The solvent was removed by concentrating under reduced pressure, water (60 mL) was added and the mixture extracted with ethyl acetate (80 mL×3). The organic phases were combined, washed with citric acid (10%, 150 mL), saturated brine (150 mL). The organic phase was dried over anhydrous sodium sulfate, filtered, concentrated under reduced pressure to give compound 235-5. MS-ESI calculated [M+H]$^+$ 297, found 297.

Step 4

Compound 235-5 (8.71 g, 21.51 mmol) was dissolved in anhydrous ethanol (50 mL), hydromethanol hydrochloride (3.74 g, 53.77 mmol) and diisopropylethylamine (13.90 g, 107.54 mmol) were added. The reaction solution was stirred at 80° C. for 11 h. The solvent was removed by concentrating under reduced pressure. The obtained crude product was dissolved in ethyl acetate (50 mL) and water (50 mL), extracted with ethyl acetate (50 mL×3). The organic phases were combined, washed with saturated ammonium chloride solution (100 mL×1), saturated brine (100 mL×1). The organic phase was dried over anhydrous sodium sulfate, filtered, concentrated under reduced pressure to give compound 235-6. $^1$H NMR (400 MHz, CDCl$_3$) δ 7.28-7.25 (m, 2H), 7.20-7.18 (m, 1H), 7.16-7.141 (m, 2H), 5.95-5.91 (m, 1H), 5.30-5.17 (m, 2H), 4.85 (s, 2H), 4.62-4.60 (m, 2H), 3.70-3.67 (m, 1H), 3.35-3.31 (m, 1H), 2.87-2.83 (m, 1H), 2.16-2.13 (m, 1H), 1.27-1.24 (m, 2H), 1.10-0.99 (m, 1H), 0.89-0.88 (m, 1H), 0.71-0.70 (m, 1H), 0.61-0.60 (m, 1H). MS-ESI calculated [M+H]$^+$ 330 found 330.

Step 5

Compound 235-7 (681.12 mg, 2.97 mmol) was dissolved in anhydrous N,N-dimethylformamide (15 mL), N,N-carbonyldiimidazole (578.06 mg, 3.56 mmol) was added, and the mixture was stirred at 30° C. for 2 h. And then compound 235-6 (1.1 g, 2.97 mmol) was added, and the reaction mixture was stirred at 110° C. for 10 h. The reaction solution was cooled to room temperature, water (50 mL) was added. The mixture was extracted with ethyl acetate (50 mL×3). The organic phases were combined, washed with saturated brine (50 mL×2), dried over anhydrous sodium sulfate, filtered, concentrated under reduced pressure. The residue was purified by silica gel column chromatography (1:1 petroleum ether/ethyl acetate, Rf=0.41) to give compound 235-8. MS-ESI calculated [M+Na]$^+$ 523, found 523.

Step 6

Compound 235-8 (1.50 g, 2.87 mmol) was dissolved in ethyl acetate (5 mL) and hydrochloric acid-ethyl acetate (4

M 10 mL). The reaction was stirred at 20 V for 1 h. The mixture was concentrated under reduced pressure to give compound 235-9. MS-ESI calculated [M+H]$^+$ 423, found 423.

Step 7

Compound 235-9 (1.3 g, 2.83 mmol), triethylamine (859 mg, 8.50 mmol) and compound 235-3 (618 mg, 2.83 mmol) were dissolved in anhydrous dichloromethane (30 mL), anhydrous sodium sulfate (1.21 g, 8.50 mmol) was added, and the mixture was stirred at 25° C. for 5 h. Sodium triacetoxyborohydride (1.50 g, 7.08 mmol) was added and the mixture was stirred for 7 h. The reaction mixture was diluted with dichloromethane (100 mL). The organic phase was washed successively with saturated sodium carbonate aqueous solution (50 mL×2), saturated brine (50 mL×2). The organic phase was dried over anhydrous sodium sulfate, filtered, concentrated under reduced pressure to give compound 235-10. MS-EST calculated [M+H]$^+$ 625, found 625.

Step 8

Compound 235-10 (1.80 g, 2.73 mmol) was dissolved in tetrahydrofuran (10 mL) under nitrogen. Then diethylamine (2.00 g, 27.3 mmol) and tetratriphenylphosphine palladium (315 mg, 0.273 mmol) were added. The reaction solution was stirred at 80° C. for 3 h. The mixture was filtered, water (50 mL) was added to the filtrate and extracted with ethyl acetate (30 mL×3). The organic phases were combined, washed with saturated brine (30 mL×1), dried over anhydrous sodium sulfate, filtered, concentrated under reduced pressure. The residue was isolated and purified by silica gel column chromatography (2:1 petroleum ether/ethyl acetate, Rf=0.49) to give compound 235-11. MS-ESI calculated [M+H]$^+$ 541, found 541.

Step 9

Compound 235-11 (900 mg, 1.01 mmol) and sodium hydroxide (202 mg, 5.06 mmol) were dissolved in water (4 mL) and methanol (8 mL), and the mixture was stirred at 60° C. for 12 h. The reaction solution was cooled to 0° C., and the mixture was adjusted to pH=5 with hydrochloric acid (1 mol/L). The mixture was extracted with dichloromethane/methanol=9/1 (20 mL×3). The organic phase was dried over anhydrous sodium sulfate, filtered, concentrated under reduced pressure. The crude product was isolated and purified by high performance liquid chromatography (acidic, hydrochloric acid) to give compound 235. $^1$H NMR (400 MHz, 20) δ 7.39-7.30 (m, 3H), 7.13-7.12 (m, 2H), 3.84-3.76 (m, 1H), 3.66-3.63 (m, 5H), 3.27-3.21 (m, 3H), 3.11-3.09 (m, 1H), 2.55-2.51 (m, 3H), 2.28-2.05 (m, 8H), 1.44-1.33 (m, 6H). MS-ESI calculated [M+H]$^+$ 451, found 451.

Example 236

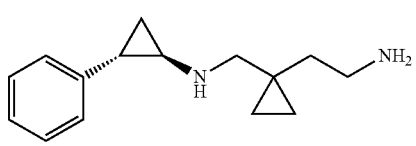 [SMILES: NCCC1(CN[C@@H]2C[C@H]2c2ccccc2)CC1]

Synthetic Route:

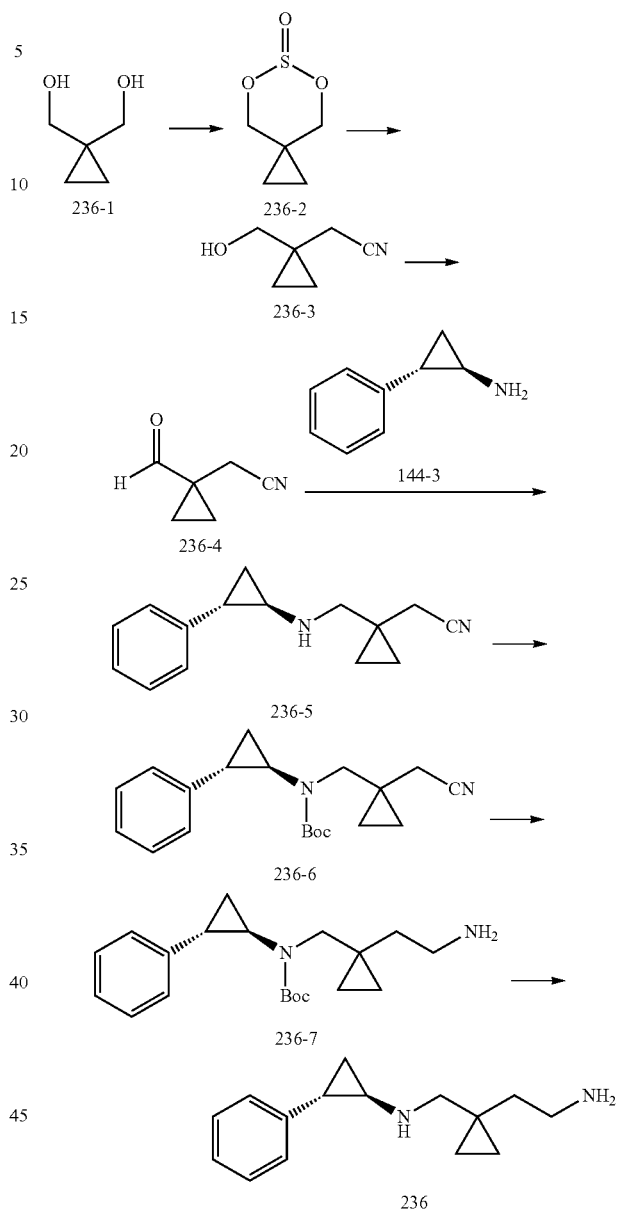

Step 1

Compound 236-1 (10.0 g, 97.9 mmol) and diisopropylethylamine (41.8 g, 323 mmol) were dissolved in anhydrous dichloromethane (200 mL), and thionyl chloride (12.8 g, 108 mmol) was added dropwise at −5° C. The reaction mixture was stirred at −5° C. for 3 h under nitrogen. The reaction was quenched with water (300 mL) at 0° C. The mixture was extracted with dichloromethane (200 mL×2). The combined organic layer was washed with saturated brine (200 mL×2), dried over anhydrous sodium sulfate, filtered, concentrated under reduced pressure. The crude product was isolated and purified by silica gel column chromatography (10:1 petroleum ether/ethyl acetate, Rf=0.78) to give compound 236-2. $^1$H NMR (400 MHz, CDCl$_3$) 5.28 (d, J=12.0 Hz, 2H), 3.08 (d, J=12.0 Hz, 2H), 0.87-0.83 (m, 2H), 0.51-0.47 (m, 2H).

Step 2

Compound 236-2 (3.00 g, 20.3 mmol) was dissolved in N,N-dimethylformamide (5 mL), sodium cyanide (1.19 g, 24.3 mmol) and potassium iodide (0.672 g, 4.05 mmol) were added. The reaction was stirred at 110° C. for 12 h. The reaction was quenched by adding water (50 mL) at 0° C. The mixture was extracted with ethyl acetate (30 mL×3). The organic phase was washed with saturated brine (30 mL×2), dried over anhydrous sodium sulfate, filtered, concentrated under reduced pressure to give compound 236-3. $^1$H NMR (400 MHz, CDCl$_3$) 3.50 (s, 2H), 2.56 (s, 2H), 0.63-0.57 (m, 4H).

Step 3

Compound 236-3 (1.75 g, 15.8 mmol) was dissolved in anhydrous dichloromethane (40 mL), Dess-Martin periodinane (8.01 g, 18.9 mmol) was added under nitrogen at 0° C., and the reaction mixture was warmed to 20° C. and stirred for 16 hours. Saturated sodium bicarbonate solution (50 mL) was added to the reaction solution until no bubbles were formed in the solution. Then the saturated sodium thiosulfate solution (50 mL) was added until the starch potassium iodide test paper was not change blue. The solution was stirred for 30 minutes, extracted with dichloromethane (100 mL×3). The organic phase was dried over anhydrous sodium sulfate, filtered, concentrated under reduced pressure to give crude compound 236-4. $^1$H NMR (400 MHz, CDCl$_3$) 8.60 (s, 1H), 2.78 (s, 2H), 1.38-1.27 (m, 4H).

Step 4

Compound 236-4 (2.5 g, 22.9 mmol) was dissolved in anhydrous dichloromethane (30 mL), acetic acid (125 mg, 2.08 mmol) and 144-3 (2.77 g, 20.8 mmol) were added. The reaction solution was stirred at 25° C. for 1 h. Then sodium triacetoxyborohydride (6.62 g, 31.2 mmol) was added and the mixture was stirred for 11 h. After the reaction was completed. The saturated sodium carbonate solution (20 mL) was added to the reaction mixture until no bubbles were formed. The mixture was extracted with dichloromethane (20 mL×3), and the organic phases were combined, concentrated under reduced pressure, and water (20 mL) was added to the residue. The mixture was adjusted to pH=3 with 1 M hydrochloric acid, extracted with methyl tert-butyl ether (20 mL×2), and the aqueous phase was adjusted to pH=8 with saturated sodium carbonate solution, extracted with ethyl acetate (20 mL×3). The organic phases were combined and washed with saturated brine (20 mL×1). The organic phase was dried over anhydrous sodium sulfate, filtered, concentrated under reduced pressure to give compound 236-5. MS-ESI calculated [M+H]$^+$ 227, found 227.

Step 5

Compound 236-5 (1.6 g, 7.07 mmol) was dissolved in anhydrous dichloromethane (20 mL), di-tert-butyl dicarbonate (1.85 g, 8.48 mmol) and diisopropylethylamine (1.43 g, 14.1 mmol) were added, and the reaction solution was stirred at 25° C. for 4 h. 10% citric acid (10 mL) and water (100 mL) were added to the mixture, and the mixture was extracted with ethyl acetate (100 mL×2). The organic phase was dried over anhydrous sodium sulfate, filtered, concentrated under reduced pressure to give crude compound 236-6. MS-ESI calculated [M-56+H]$^+$ 271, found 271.

Step 6

Compound 236-6 (100 mg, 0.306 mmol) was dissolved in anhydrous methanol (3 mL), cobalt chloride (159 mg, 1.23 mmol) was added at 0° C., sodium borohydride (92.7 mg, 2.45 mmol) was added slowly, and the reaction mixture was stirred at 20° C. for 1 h. The reaction solution was filtered through celite, water (10 mL) was added to the filtrate. The mixture was extracted with ethyl acetate (10 mL×3). The organic phases were combined, dried with anhydrous sodium sulfate, filtered, concentrated under reduced pressure to give crude compound 236-7. MS-ESI calculated [M+H]$^+$ 331, found 331.

Step 7

Compound 236-7 (80 mg, 0.242 mmol) was dissolved in ethyl acetate (2 mL), hydrochloric acid-ethyl acetate (0.5 mL) was added dropwise at 0° C. The reaction solution was stirred at 0° C. for 1 h. The solvent was concentrated under reduced pressure, and the crude product was purified by high-purity chromatography (acid, hydrochloric acid) to give compound 236. $^1$H NMR (400 MHz, MeOD) δ 7.33-7.29 (m, 2H), 7.25-7.22 (m, 1H), 7.21-7.18 (m, 2H), 3.15-3.11 (m, 4H), 3.02-2.98 (m, 1H), 2.68-2.63 (m, 1H), 1.83-1.79 (m, 2H), 1.67-1.62 (m, 1H), 1.39-1.34 (m, 1H), 0.75-0.72 (m, 2H), 0.65-0.63 (m, 2H). MS-ESI calculated [M+H]$^+$ 231, found 231.

Example 237

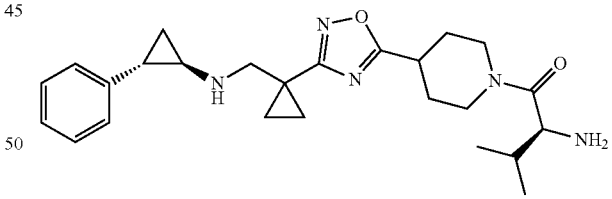

Synthetic Route:

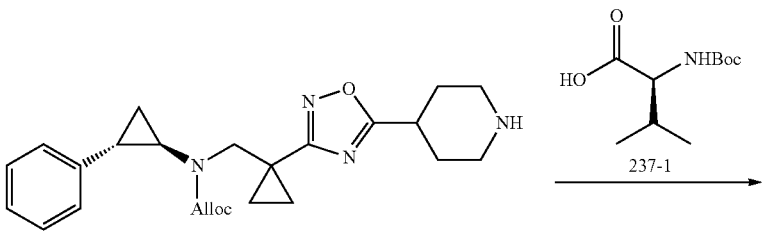

235-9

-continued

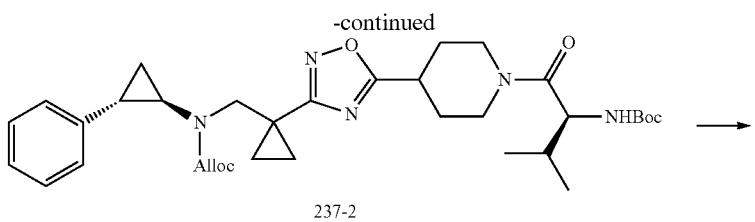
237-2

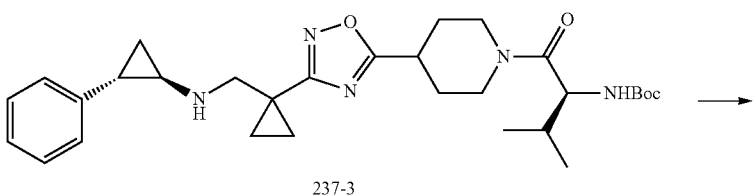
237-3

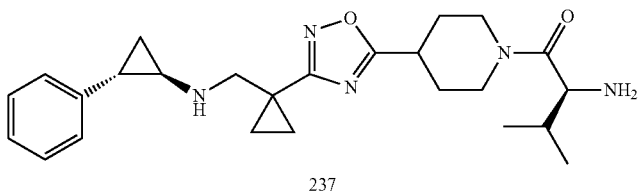
237

Step 1

Compound 235-9 (300 mg, 0.653 mmol) was dissolved in anhydrous dioxane (10 mL), compound 237-1 (213 mg, 0.980 mmol) was added under nitrogen at 0° C. Then tri-n-propylphosphoric anhydride (50% ethyl acetate solution, 1.17 mL, 1.96 mmol) and diisopropylethylamine (338 mg, 0.980 mmol) were added. The reaction solution was stirred under an oil bath at 60° C. for 1 h. Water (20 mL) was added to the reaction mixture at 0° C., and extracted with ethyl acetate (30 mL×3). The organic phases were combined, dried over anhydrous sodium sulfate, filtered, concentrated under reduced pressure. The crude product was isolated and purified by preparative thin layer chromatography (2:1 petroleum ether/ethyl acetate, Rf=0.53) to give compound 237-2. MS-ESI calculated [M+H]$^+$ 622, found 622.

Step 2

The synthesis of compound 237-3 was referred to the eighth step of example 235. MS-ESI calculated [M-Boc+H]$^+$ 438, found 438.

Step 3

The synthesis of compound 237 was referred to the seventh step of example 236. $^1$H NMR (400 MHz, MeOD) δ 7.34-7.31 (m, 2H), 7.27-7.24 (m, 1H), 7.23-7.17 (m, 2H), 4.52-4.35 (m, 2H), 4.06-3.96 (m, 1H), 3.69-3.41 (m, 2H), 3.39-3.36 (m, 2H), 3.11-3.09 (m, 2H), 2.58-2.53 (m, 1H), 2.22-2.17 (m, 3H), 1.91-1.72 (m, 2H), 1.61-1.56 (m, 1H), 1.45-1.34 (m, 5H), 1.14-1.11 (m, 3H), 1.04-1.02 (m, 3H). MS-ESI calculated [M+H]$^+$ 438, found 438.

Example 238

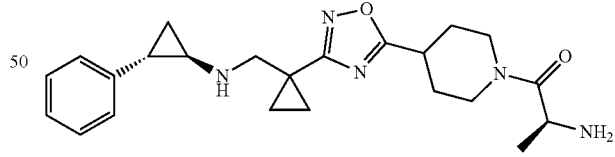

Synthetic Route:

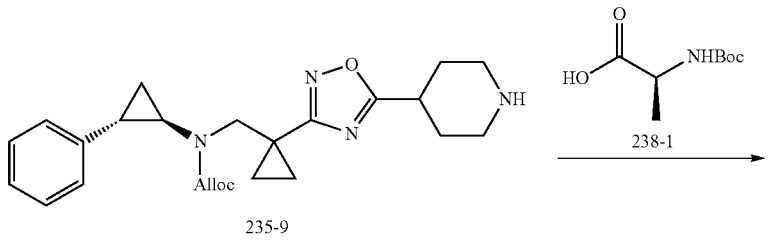
235-9

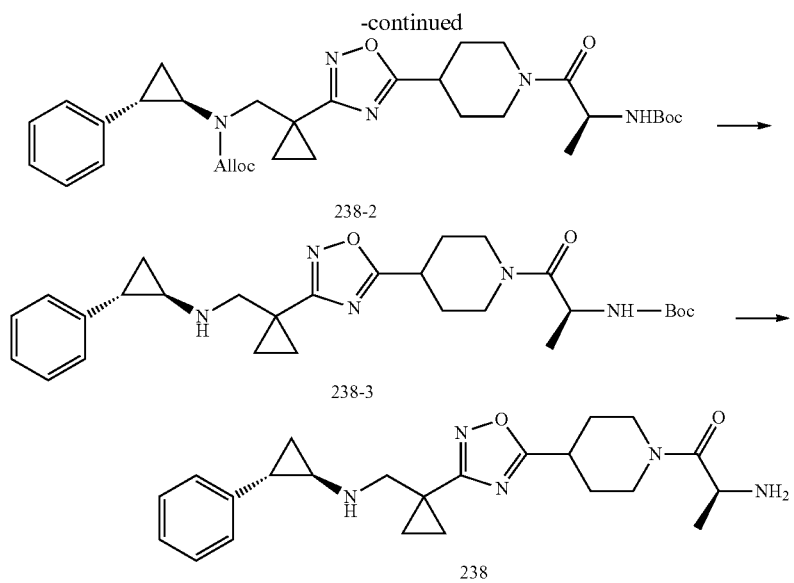

Step 1

The synthesis of compound 238-2 was referred to the first step of example 237. MS-ESI calculated [M+H]$^+$ 594, found 594.

Step 2

The synthesis of compound 238-3 was referred to the eighth step of example 235. MS-ESI calculated [M+H]$^+$ 510, found 510.

Step 3

The synthesis of compound 238 was referred to the seventh step of example 236. $^1$H NMR (400 MHz, MeOD) δ 7.35-7.31 (m, 2H), 7.27-7.24 (m, 1H), 7.19-7.16 (m, 2H), 4.49-4.39 (m, 2H), 3.97-3.90 (m, 1H), 3.73-3.64 (m, 2H), 3.51-3.35 (m, 2H), 3.15-3.08 (m, 2H), 2.59-2.53 (m, 1H), 2.23-2.14 (m, 2H), 1.90-1.77 (m, 2H), 1.61-1.56 (m, 1H), 1.49-1.34 (m, 8H). MS-ESI calculated [M+H]$^+$ 410, found 410.

Example 239

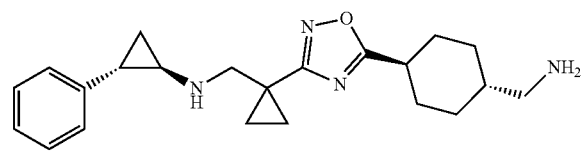 [SMILES: NC[C@H]1CC[C@H](c2nc(C3(CN[C@@H]4C[C@H]4c4ccccc4)CC3)no2)CC1]

Synthetic Route:

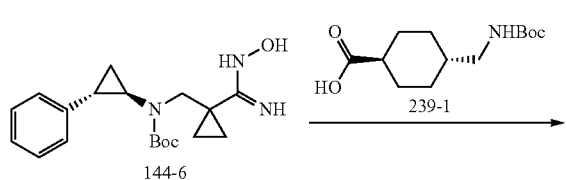

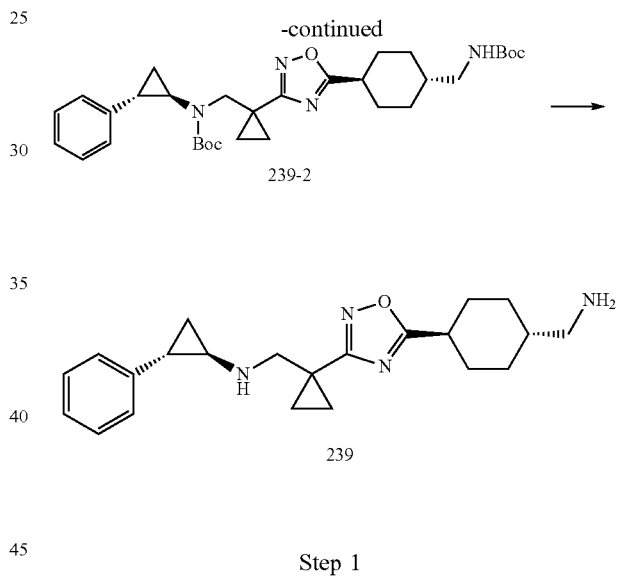

Step 1

The synthesis of compound 239-2 was referred to the first step of example 237. MS-ESI calculated [M+H]$^+$ 567, found 567.

Compound 239-2 (40 mg, 70.6 μmol) was dissolved in anhydrous dichloromethane (1 mL), and trifluoroacetic acid (924 mg, 8.1 mmol) was added to the reaction mixture, and the mixture was stirred at 0° C. for 1 h. The mixture was concentrated under reduced pressure to remove the solvent, and the crude product was prepared by high-performance liquid chromatography (acidic, hydrochloric acid) to give compound 239. $^1$H NMR (400 MHz, CD$_3$OD) δ 7.32-7.29 (m, 2H), 7.25-7.21 (m, 1H), 7.16-7.14 (m, 2H), 3.71-3.63 (m, 2H), 3.13-2.99 (m, 2H), 2.86-2.80 (m, 2H), 2.56-2.51 (m, 1H), 2.06-2.03 (m, 2H), 1.91-1.82 (m, 3H), 1.59-1.54 (m, 1H), 1.46-1.12 (m, 9H). MS-ESI calculated [M+H]$^+$ 367, found 367.

Example 240
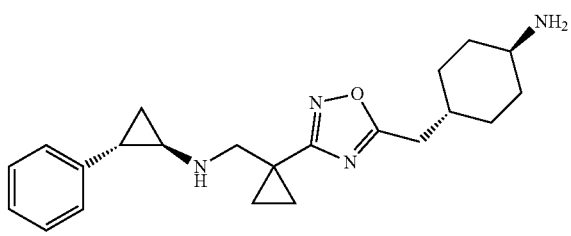 [SMILES: N[C@H]1CC[C@H](Cc2nc(C3(CN[C@@H]4C[C@H]4c4ccccc4)CC3)no2)CC1]
Example 241
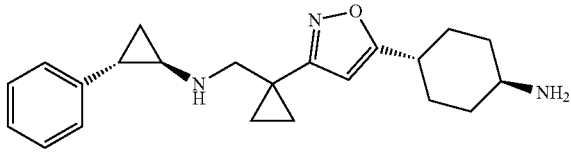 [SMILES: N[C@H]1CC[C@H](c2cc(C3(CN[C@@H]4C[C@H]4c4ccccc4)CC3)no2)CC1]
Synthetic Route:
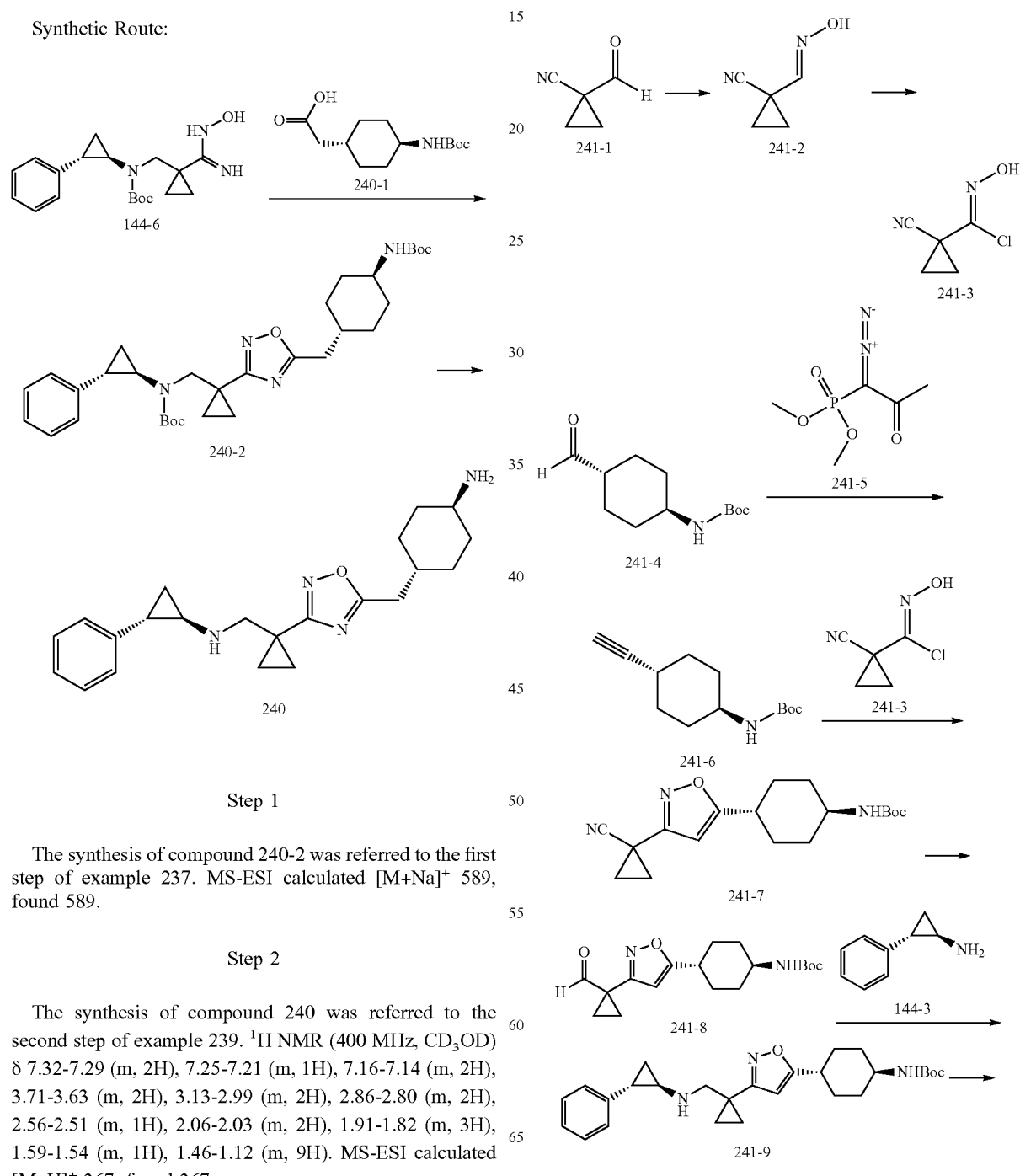
Step 1
The synthesis of compound 240-2 was referred to the first step of example 237. MS-ESI calculated [M+Na]$^+$ 589, found 589.
Step 2
The synthesis of compound 240 was referred to the second step of example 239. $^1$H NMR (400 MHz, CD$_3$OD) δ 7.32-7.29 (m, 2H), 7.25-7.21 (m, 1H), 7.16-7.14 (m, 2H), 3.71-3.63 (m, 2H), 3.13-2.99 (m, 2H), 2.86-2.80 (m, 2H), 2.56-2.51 (m, 1H), 2.06-2.03 (m, 2H), 1.91-1.82 (m, 3H), 1.59-1.54 (m, 1H), 1.46-1.12 (m, 9H). MS-ESI calculated [M+H]$^+$ 367, found 367.

-continued

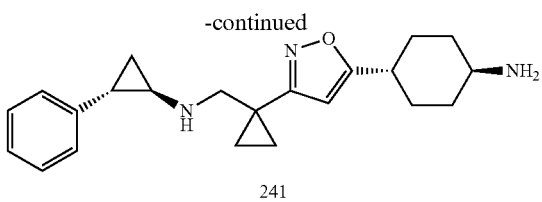

241

Step 1

Hydroxylamine hydrochloride (1.61 g, 23.1 mmol) was added to anhydrous ethanol (30 mL), sodium bicarbonate (2.65 g, 31.5 mmol) was added, and the reaction was stirred at 0° C. for 15 min. Compound 241-1 (2.00 g, 21.0 mmol) was then added and the reaction was stirred at 0° C. for 20 min. Water (60 mL) was added to the reaction mixture, and the mixture was extracted with ethyl acetate (30 mL×4). The organic phase was dried over anhydrous sodium sulfate, filtered, concentrated under reduced pressure. The crude product was isolated and purified by silica gel column chromatography (2:1 petroleum ether/ethyl acetate, Rf=0.5) to give compound 241-2. $^1$H NMR (400 MHz, CDCl$_3$) δ 8.26 (s, 1H), 7.04 (s, 1H), 1.65-1.62 (m, 2H), 1.38-1.35 (m, 2H).

Step 2

Compound 241-2 (890 mg, 8.08 mmol) was dissolved in dichloromethane (40 mL), N-chlorosuccinimide (1.08 g, 8.08 mmol) was added to the reaction mixture at 25° C. and the mixture was stirred for 2 h. Nuclear magnetic monitoring showed the presence of the material and the mixture was stirred at 25° C. for 12 h, nuclear magnetic monitoring showed complete reaction. Water was added to the reaction mixture (50 mL). The mixture was extracted with dichloromethane (30 mL×3). The organic phase was dried over anhydrous sodium sulfate, filtered, concentrated under reduced pressure to give crude product 241-3. $^1$H NMR (400 MHz, CDCl$_3$) δ 8.71 (s, 1H), 1.71-1.66 (m, 2H), 1.65-1.60 (m, 2H).

Step 3

Compound 2414 (1 g, 4.40 mmol) and potassium carbonate (1.82 g, 13.2 mmol) were dissolved in methanol (30 mL), 241-5 (929 mg, 4.84 mmol) was added. The reaction solution was stirred at 25° C. for 12 h. The reaction was quenched by the addition of saturated ammonium chloride solution (60 mL). The mixture was extracted with ethyl acetate (30 mL×3). The organic phase was dried over anhydrous sodium sulfate, filtered, concentrated under reduced pressure to give crude product 241-6. $^1$H NMR (400 MHz, CDCl$_3$) δ 4.41 (brs, 1H), 3.45-3.35 (m, 1H), 2.20-2.19 (m, 1H), 2.03-1.95 (m, 5H), 1.73-1.47 (m, 2H), 1.43 (s, 9H), 1.11-1.08 (m, 2H).

Step 4

Compound 241-6 (630 mg, 2.82 mmol) and compound 241-3 (816 mg, 5.64 mmol) were dissolved in tetrahydrofuran (20 mL), potassium carbonate (780 mg, 5.64 mmol) and cuprous iodide (107 mg) were added. The reaction solution was stirred at 25° C. for 2 hours under nitrogen. Water (50 mL) was added to the reaction mixture. The mixture was extracted with ethyl acetate (30 mL×3). The organic phase was dried over anhydrous sodium sulfate, filtered, concentrated under reduced pressure. The crude product was isolated and purified by silica gel column chromatography (5:1 petroleum ether/ethyl acetate, Rf=0.25) to give compound 241-7. $^1$H NMR (400 MHz, DMSO-d δ 6.79 (d, J=7.6 Hz, 1H), 6.24 (s, 1H), 3.7-3.21 (m, 1H), 2.70-2.64 (m, 1H), 1.95-1.84 (m, 2H), 1.85-1.82 (m, 4H), 1.60-1.54 (m, 2H), 1.40-1.38 (m, 2H), 1.37 (s, 9H), 1.31-1.18 (m, 2H). MS-ESI calculated [M-56+H]$^+$ 276 found 276.

Step 5

Compound 241-7 (496 mg, 1.50 mmol) was dissolved in toluene (20 mL). The mixture was cooled to −78° C. Then diisobutylaluminum hydride (1.5 M in toluene, 2.00 mL, 3.00 mmol) was added. The reaction solution was stirred at −78° C. for 1 h. The reaction was quenched by the addition of methanol (1 mL) at −78° C. After the temperature is restored to 0° C., 30% sodium potassium tartrate aqueous solution (30 mL) was added to the mixture. The mixture was stirred at 25° C. for 12 h, extracted with ethyl acetate (30 mL×3). The organic phase was dried over anhydrous sodium sulfate, filtered, concentrated under reduced pressure. The crude product was isolated and purified by silica gel column chromatography (3:1 petroleum ether/ethyl acetate, Rf=0.4) to give compound 241-8. $^1$H NMR (400 MHz, DMSO-d$_6$) 9.17 (s, 1H), 6.81 (d, J=7.6 Hz, 1H), 6.41 (s, 1H), 3.25-3.22 (m, 1H), 2.71-2.68 (m, 1H), 2.07-1.94 (m, 2H), 1.89-1.82 (m, 2H), 1.71-1.64 (m, 2H), 1.59-1.53 (m, 2H), 1.49-1.41 (m, 2H), 1.40 (s, 9H), 1.38-1.25 (m, 2H). MS-ESI calculated [M-56+H]$^+$ 279, found 279.

Step 6

Compound 241-8 (500 mg, 1.50 mmol) and compound 144-3 (199 mg, 1.50 mmol) were dissolved in dichloromethane (20 mL), and acetic acid (89.8 mg, 1.50 mmol) was added. After stirring at 25° C. for 2 hours, sodium triacetoxyborohydride (634 mg, 2.99 mmol) was added and the mixture was stirred at 25° C. for 1 h. Water (50 mL) was added to the reaction mixture and the mixture was extracted with dichloromethane (30 mL×3). The organic phase was dried over anhydrous sodium sulfate, filtered, concentrated under reduced pressure. The crude product was isolated and purified by silica gel column chromatography (3:1 petroleum ether/ethyl acetate, Rf=0.3) to give compound 241-9. $^1$H NMR (400 MHz. DMSO-d$_6$) δ 7.23-7.19 (m, 2H), 7.11-7.09 (m, 1H), 7.02-7.00 (m, 2H), 6.78 (d, J=7.6 Hz, 1H), 6.08 (s, 1H), 3.27-3.14 (m, 1H), 2.92-2.80 (m, 2H), 2.69-2.54 (m, 1H), 2.31-2.24 (m, 1H), 1.98-1.77 (m, 5H), 1.38 (s, 9H), 1.33 (br s, 2H), 1.31-1.21 (m, 2H), 0.96-0.82 (m, 6H). MS-ESI calculated [M+H]$^+$ 452, found 452.

Step 7

Compound 241-9 (415 mg, 0.919 mmol) was dissolved in hydrochloric acid (4M ethyl acetate solution, 5 mL). The mixture was stirred at 25° C. for 0.5 h. The mixture was concentrated under reduced pressure. The obtained crude product was diluted with water (40 mL). The mixture was adjusted to pH=8 with the saturated sodium carbonate aqueous solution, extracted with ethyl acetate (30 mL×3). The organic phase was dried over anhydrous sodium sulfate, filtered, concentrated under reduced pressure. The crude product was prepared by high-performance liquid chromatography (acidic, hydrochloric acid) to give compound 241.

¹H NMR (400 MHz, CD₃OD) δ 7.32-7.29 (m, 2H), 7.24-7.21 (m, 1H), 7.16-7.14 (m, 2H), 5.97 (s, 1H), 3.59 (s, 2H), 3.16-3.13 (m, 1H), 3.04-3.02 (m, 1H), 2.89-2.72 (m, 1H), 2.58-2.45 (m, 1H), 2.18-2.14 (m, 4H), 1.59-1.53 (m, 5H), 1.37-1.36 (m, 1H), 1.33-1.25 (m, 2H), 1.21-1.20 (m, 2H). MS-ESI calculated [M+H]⁺ 352, found 352.

Example 242

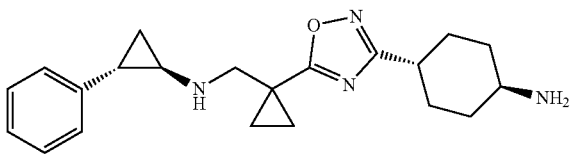

Synthetic Route:

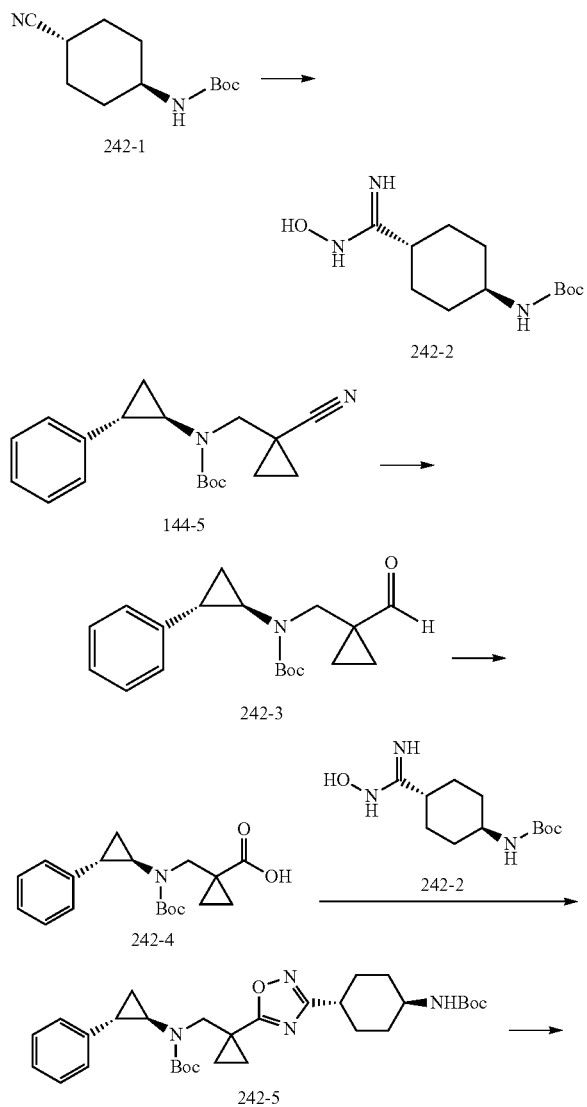

-continued

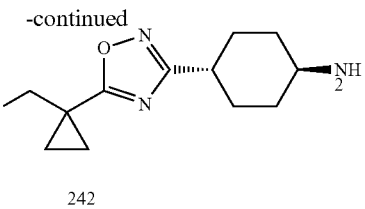

242

Step 1

Compound 242-1 (250 mg, 1.11 mmol) was dissolved in anhydrous ethanol (6 mL), and hydroxylamine hydrochloride (194 mg, 2.79 mmol) and diisopropylethylamine (1 M tetrahydrofuran solution) were added to the reaction mixture. The reaction solution was stirred at 80° C. for 15 h. The reaction solution was cooled to 30° C. and concentrated under reduced pressure to remove solvent. The obtained crude product was dissolved in ethyl acetate (30 mL) and water (20 mL), and the mixture was extracted with ethyl acetate (25 mL×3). The organic phase was washed successively with saturated ammonium chloride solution (30 mL×1), saturated brine (30 mL×1). The organic phase was dried over anhydrous sodium sulfate, filtered and concentrated under reduced pressure to give compound 242-2. MS-ESI calculated [M+H]⁺ 258, found 258.

Step 2

Compound 144-5 (8.00 g 25.6 mmol) was dissolved in anhydrous toluene (60 mL), and diisobutylaluminum hydride (1 M toluene, 51.2 mL, 51.2 mmol) was added dropwise under nitrogen at −78° C. The reaction solution was stirred at −78° C. for 3 h. The reaction mixture was quenched with methanol (15 mL) at −60° C., stirred for 30 minutes until no gas was produced. The mixture was adjusted to pH=3 with hydrochloric acid (1 N, 150 mL) at mom temperature and stirred at 30° C. for 16 h. After clarification, the mixture was extracted with ethyl acetate (100 mL×3). The organic phase was washed successively with saturated ammonium chloride solution (80 mL×1), dried over anhydrous sodium sulfate, filtered and concentrated under reduced pressure. The crude product was isolated and purified by preparative thin layer chromatography (5:1 petroleum ether/ethyl acetate, Rf=0.52) to give compound 242-3. MS-ESI calculated [M+Na]⁺ 338, found 338.

Step 3

Compound 242-3 (3.08 g, 9.76 mmol) was dissolved in t-butanol (45 mL), sodium chlorite (2.65 g, 29.3 mmol), 2-methyl-2-butene (2.74 g, 39.0 mmol) and sodium dihydrogen phosphate (3.51 g, 29.3 mmol) in water (40 mL) were added at 0° C. The reaction solution was stirred at 30'C for 16 h. The reaction solution was concentrated under reduced pressure to remove t-butanol, water (15 mL) was added to the reaction mixture, and the mixture was extracted with ethyl acetate (50 mL×3). The organic phases were combined, washed with saturated brine (50 mL×1), dried over anhydrous sodium sulfate, filtered and concentrated under reduced pressure. The crude product was crystallized (10:1 petroleum ether/ethyl acetate, 11 mL) to give compound 242-4. MS-ESI calculated [M+Na]⁺ 354, found 354.

Step 4

The compound 242-4 (231 mg, 0.698 mmol) was dissolved in anhydrous N,N-dimethylformamide (5 mL), and carbonyldiimidazole (136 mg, 0.837 mmol) was added under nitrogen at 30° C. The mixture was stirred for 2 h. Compound 242-2 (214 mg, 0.767 mmol) was added to the reaction mixture, and the reaction mixture was heated to 110° C. and stirred for 10 h. The reaction solution was cooled to room temperature, and water (60 mL) was added to the mixture, and the mixture was extracted with ethyl acetate (50 mL×3). The organic phases were combined, washed with saturated brine (50 mL×1), dried over anhydrous sodium sulfate, filtered and concentrated under reduced pressure. The crude product was isolated and purified by preparative thin layer chromatography (2:1 petroleum ether/ethyl acetate, Rf=0.8) to give compound 242-5. MS-ESI calculated [M+Na]$^+$ 575, found 575.

Step 5

Compound 242-5 (161 mg, 0.277 mmol) was dissolved in anhydrous dichloromethane (16 mL). Trifluoroacetic acid (8 mL) was added dropwise at 0° C. The reaction solution was stirred at 0° C. for 1 h. concentrated under reduced pressure to remove the solvent. The crude product was prepared by high-performance liquid chromatography (acidic, hydrochloric acid) to give compound 242. $^1$H NMR (400 MHz, CD$_3$OD) δ 7.33-7.29 (m, 2H), 7.25-7.22 (m, 1H), 7.18-7.16 (m, 2H), 3.79-3.72 (m, 2H), 3.15-3.10 (m, 2H), 2.80-2.75 (m, 1H), 2.62-2.58 (m, 1H), 2.20-2.17 (m, 4H), 1.67-1.54 (m, 9H), 1.43-1.37 (m, 1H). MS-ESI calculated [M+H]$^+$ 353, found 353.

Example 243

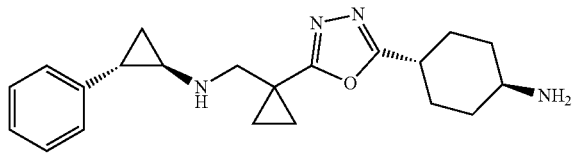 [SMILES: N[C@H]1CC[C@H](c2nnc(C3(CN[C@@H]4C[C@H]4c4ccccc4)CC3)o2)CC1]

Synthetic Route:

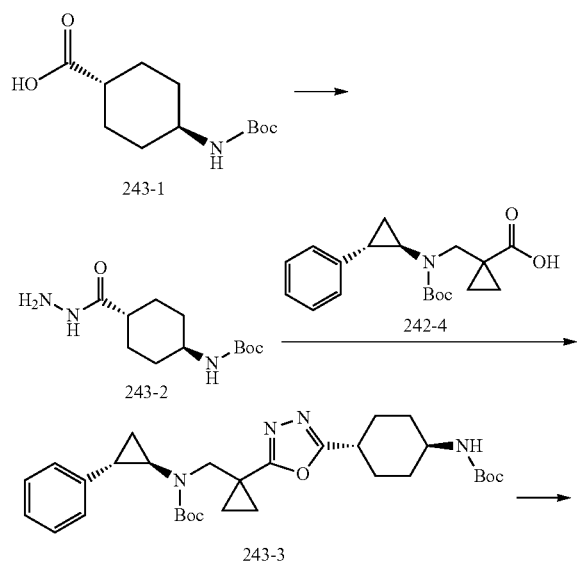

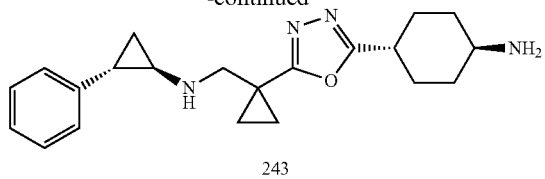

Step 1

Compound 243-1 (5.00 g, 20.6 mmol) was dissolved in N,N-dimethylformamide (100 mL), respectively, hydrazine hydrate (1.57 g, 85%, 26.7 mmol), 1-hydroxybenzotriazole (4.17 g, 30.8 mmol), 1-(3-dimethylaminopropyl)-3-ethylcarbodiimide hydrochloride (5.91 g, 30.8 mmol) were added. The mixture was stirred at 25 V for 60 h. The reaction mixture was quenched with water (150 mL), extracted with ethyl acetate (200 mL×3). The organic phases were combined, washed with saturated brine (300 mL×2), dried over anhydrous sodium sulfate, filtered and concentrated under reduced pressure. The crude product was was isolated and purified by silica gel column chromatography (1:1 petroleum ether/ethyl acetate, Rf=0.3) to give compound 243-2. MS-ESI calculated [M-56+H]$^+$ 202, found 202.

Step 2

Compound 242-4 (250 mg, 0.754 mmol), compound 243-2 (366 mg, 0.830 mmol) was dissolved in anhydrous dioxane (50 mL). Tri-n-propylcyclophosphoric anhydride (50% ethyl acetate solution, 1.35 mL, 2.26 mmol) and diisopropylethylamine (292 mg, 2.26 mmol) were added under nitrogen at 30° C. The reaction was heated to 70° C. and stirred for 1 h. Tri-n-propylcyclophosphoric anhydride (50% ethyl acetate solution, 1.35 mL, 2.26 mmol) and N,N-diisopropylethylamine (292 mg, 2.26 mmol) were added. The mixture was heated to 135° C. and stirred for 24 h. The reaction solution was cooled to room temperature, concentrated under reduced pressure to remove solvent. The residue was dissolved in water (20 mL), extracted with ethyl acetate (25 mL×3). The organic phases were combined, washed with saturated brine (40 mL×1), dried over anhydrous sodium sulfate, filtered and concentrated under reduced pressure. The crude product was isolated and purified by preparative thin layer chromatography (1:1 petroleum ether/ethyl acetate, Rf=0.83) to give compound 243-3. $^1$H NMR (400 MHz, CDCl$_3$) δ 7.16-7.24 (m, 2H), 7.11-7.07 (m, 1H), 6.98-6.96 (m, 2H), 4.34-43.1 (m, 1H), 3.75-3.52 (m, 2H), 3.41-3.39 (m, 1H), 2.72-2.70 (m, 1H), 2.60-2.55 (m, 1H), 2.06-2.03 (m, 4H), 1.45 (s, 9H), 1.36 (s, 9H), 1.27-0.87 (m, 10H). MS-EST calculated [M+H]$^+$ 553, found 553.

Step 3

The synthesis of compound 243 was referred to the fifth step of example 242. $^1$H NMR (400 MHz, CD$_3$OD) δ 7.37-7.26 (m, 3H), 7.04-7.02 (m, 2H), 3.87-3.84 (m, 1H), 3.61-3.57 (m, 1H), 3.17-3.05 (m, 1H), 3.04-3.02 (m, 1H), 2.65-2.58 (m, 1H), 2.46-2.43 (m, 1H), 2.11-2.09 (m, 4H), 1.59-1.39 (m, 10H). MS-ESI calculated [M+H]$^+$ 353, found 353.

Example 244

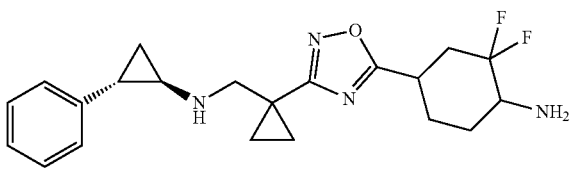 [SMILES: NC1CCC(c2nc(C3(CN[C@@H]4C[C@H]4c4ccccc4)CC3)no2)CC1(F)F]

Synthetic Route:

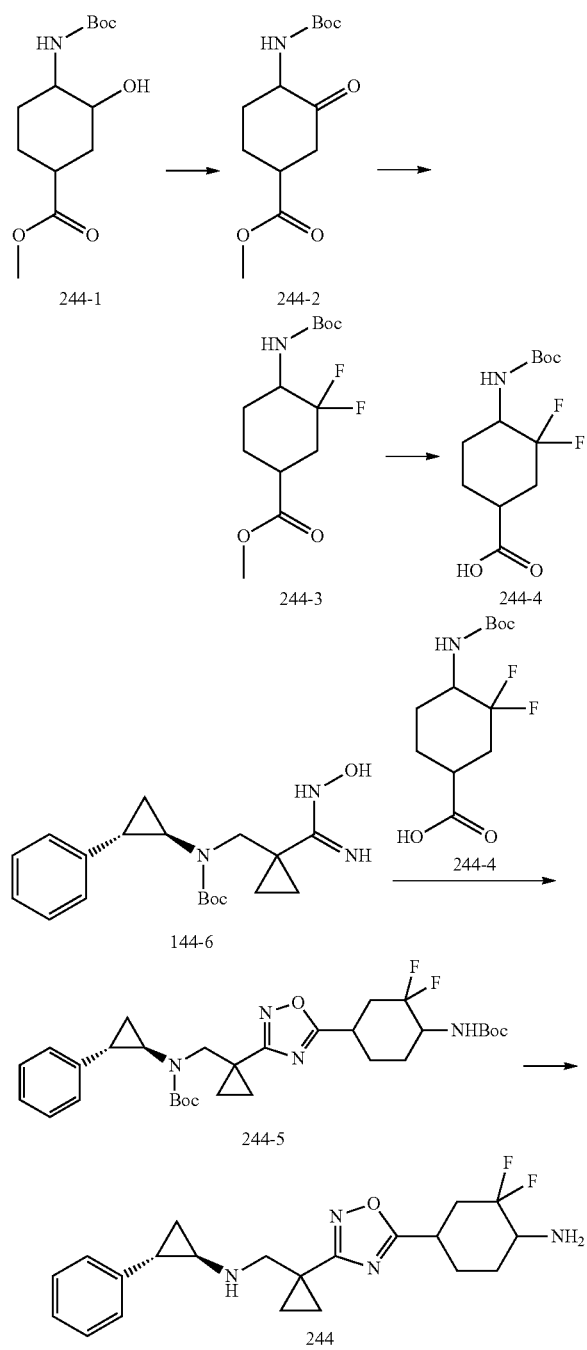

Step 1

Compound 244-1 (8.00 g, 29.3 mmol) was dissolved in dichloromethane (100 mL). The mixture was cooled to 0° C. and Dess-Martin periodine (16.7 g, 32.2 mmol) was added. The mixture was stirred at 20° C. for 12 h under nitrogen. Saturated sodium bicarbonate solution (200 mL) was added to the mixture until no bubbles were formed. The mixture was quenched with saturated sodium thiosulfate solution (300 mL), extract with ethyl acetate (500 mL×2). The organic phase was washed with saturated brine (500 mL×1), dried over anhydrous sodium sulfate, filtered and concentrated under reduced pressure. The crude product was isolated and purified by silica gel column chromatography (2:1 petroleum ether/ethyl acetate, Rf=0.5) to give compound 244-2. MS-ESI calculated $[M+Na]^+$ 294, found 294.

Step 2

Compound 244-2 (1.00 g, 3.00 mmol) was dissolved in dichloromethane (10 mL) and the mixture was cooled to 0° C., diethylaminosulfur trifluoride (2.42 g, 15.0 mmol) was added to the solution. The mixture was stirred at 20° C. for 12 h. The mixture was quenched with saturated aqueous sodium bicarbonate (30 mL). The aqueous phase was extracted with dichloromethane (20 mL 3). The organic phase was washed with the saturated sodium bicarbonate solution until pH=7. The organic phase was dried over anhydrous sodium sulfate, filtered and concentrated under reduced pressure to give crude compound 244-3. MS-ESI calculated $[M-56+H]^+$ 238, found 238.

Step 3

Compound 244-3 (1.06 g, 3.60 mmol) was dissolved in the mixture of tetrahydrofuran (10 mL) and water (5 mL), and sodium hydroxide (432 mg, 10.8 mmol) was added under nitrogen at 20° C. and the mixture was stirred for 12 h. The reaction solution was concentrated under reduced pressure to remove solvent. The mixture was adjusted to pH 5 with hydrochloric acid (1 M), extracted with ethyl acetate (15 mL×3). The organic phases were combined, dried over anhydrous sodium sulfate, filtered and concentrated under reduced pressure to give compound 244-4. MS-ESI calculated $[M-56+H]^+$ 224, found 224.

Step 4

Compound 244-4 (444 mg, 1.59 mmol) was dissolved in anhydrous N,N-dimethylformamide (5 mL), and carbodiimidazole (352 mg, 2.17 mmol) was added at 20° C. under nitrogen. The mixture was stirred for 2 h. Compound 144-6 (500 mg, 1.45 mmol) was added to the reaction mixture, and the reaction mixture was heated to 110° C. and stirred for 10 h. The reaction solution was cooled to room temperature, water (50 mL) was added to the mixture, and the mixture was extracted with ethyl acetate (30 mL×3). The organic phases were combined, dried over anhydrous sodium sulfate, filtered and concentrated under reduced pressure. The crude product was isolated and purified by silica gel column chromatography (3:1 petroleum ether/ethyl acetate, Rf=0.56) to give compound 244-5. MS-ESI calculated $[M+Na]^+$ 611, found 611.

Step 5

The compound 244-5 (388 mg, 0.411 mmol) was dissolved in ethyl acetate (3 mL), hydrochloric acid (4M ethyl acetate solution, 3 mL, 12.0 mmol) was added under nitrogen at 20° C. and the mixture was stirred for 0.5 h. The reaction solution was concentrated under reduced pressure. The crude product was isolated and purified by high performance liquid chromatography (hydrochloric acid) to give compound 244. $^1$H NMR (400 MHz, D$_2$O) δ 7.31-7.21 (m, 3H), 7.06-7.04 (m, 2H), 3.84-3.71 (m, 2H), 3.58-3.54 (m, 1H), 3.45-3.40 (m, 1H), 3.03-3.00 (m, 1H), 2.51-2.42 (m, 2H), 2.20-1.98 (m, 4H), 1.92-1.82 (m, 1H), 1.50-1.40 (m, 2H), 1.37-1.23 (m, 4H). MS-ESI calculated [M+H]$^+$ 389, found 389.

Example 245

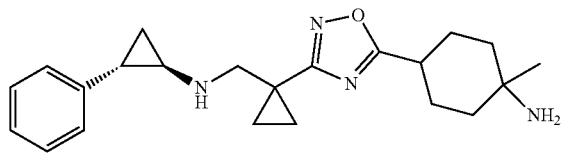 [SMILES: CC1(N)CCC(c2nc(C3(CN[C@@H]4C[C@H]4c4ccccc4)CC3)no2)CC1]

Synthetic Route:

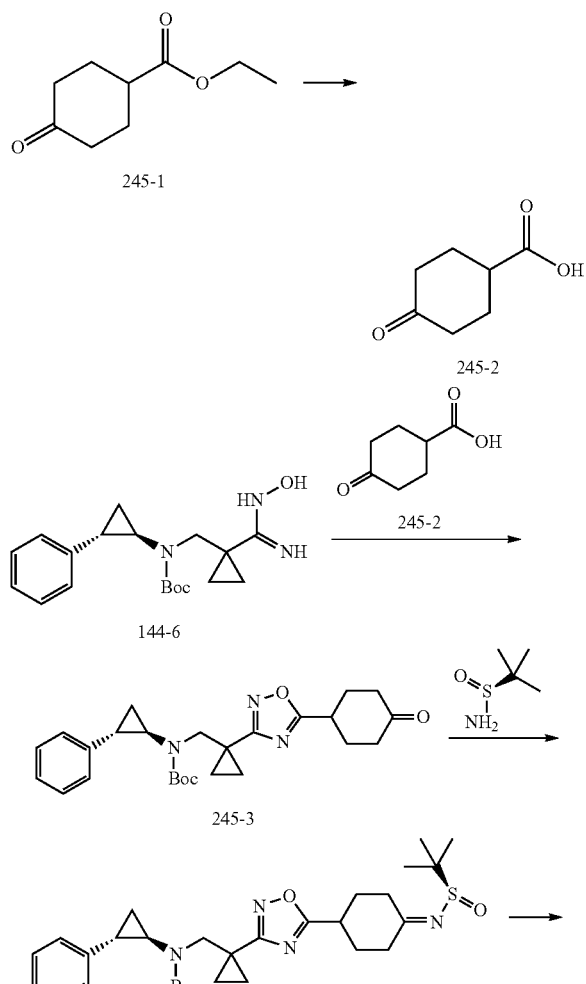

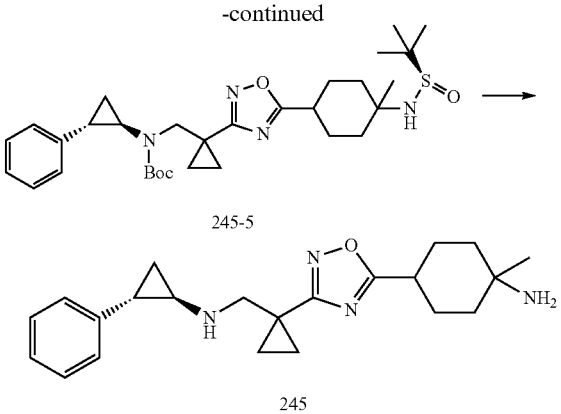

Step 1

The compound 245-1 (10.0 g, 58.8 mmol) was dissolved in tetrahydrofuran (10 mL), and the saturated sodium hydroxide solution (20 mL) was added to the reaction mixture, and the mixture was stirred at 60 V for 10 h. The mixture was added with hydrochloric acid (1 M) to adjust the pH=5 at room temperature, water (300 mL) was added. The mixture was extracted with ethyl acetate (300 mL×3). The combined the organic phases washed with saturated brine (300 mL×1), dried over anhydrous sodium sulfate, filtered and concentrated under reduced pressure to give compound 245-2.

Step 2

The synthesis of compound 245-3 was referred to the fourth step of example 244. MS-ESI calculated [M+Na]$^+$ 474, found 474.

Step 3

Compound 245-3 (200 mg, 387 μmol) and tetraethyl titanate (265 mg, 1.16 mmol) were dissolved in tetrahydrofuran (8 mL), (R)-(+)-tert-butylsulfinamide (56.3 mg, 0.464 mmol) was dissolved in tetrahydrofuran (2 mL) and added dropwise to the system. The mixture was stirred at 75° C. for 2 h. The reaction system was quenched by adding the saturated sodium bicarbonate solution (20 mL) dropwise. The mixture was filtered and the filtrate was extracted with ethyl acetate (30 mL×1). The organic phase was washed with saturated brine (30 mL), dried over anhydrous sodium sulfate, filtered and concentrated under reduced pressure. The crude product was isolated and purified by silica gel column chromatography (2:1 petroleum ether/ethyl acetate, Rf=0.4) to give compound 245-4.

Step 4

Compound 245-4 (154 mg, 0.278 mmol) was dissolved in tetrahydrofuran (3 mL). The mixture was cooled to −78° C., and methyl magnesium bromide (3M diethyl ether solution, 99.3 mg, 0.833 mmol) was added dropwise to the system. The reaction was maintained at −78° C. for 1 hour and then the system was gradually warmed to 25° C. and stirred for 3 h. The mixture was quenched by saturated aqueous ammonium chloride (3 mL), diluted with water (5 mL), extracted with ethyl acetate (10 mL×3). The organic phases were combined, washed with saturated brine (30 mL), dried over anhydrous sodium sulfate, filtered and concentrated under reduced pressure to give compound 245-5. MS-ESI calculated [M+Na]$^+$ 593, found 593.

Step 5

The synthesis of compound 245 was referred to the fifth step of example 244. $^1$H NMR (400 MHz, D$_2$O) δ 7.29-7.19 (m, 3H), 7.03-7.01 (m, 2H), 3.70-3.53 (m, 2H), 3.00-2.98 (m, 1H), 2.91-2.86 (m, 1H), 2.40-2.39 (m, 1H), 1.96-1.90 (m, 2H), 1.83-1.77 (m, 2H), 1.69-1.66 (m, 4H), 1.48-1.43 (m, 1H), 1.34-1.22 (m, 8H). MS-ESI calculated [M+H]$^+$ 367, found 367.

Example 246

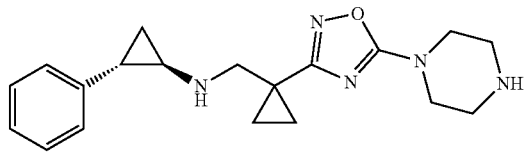

Synthetic Route:

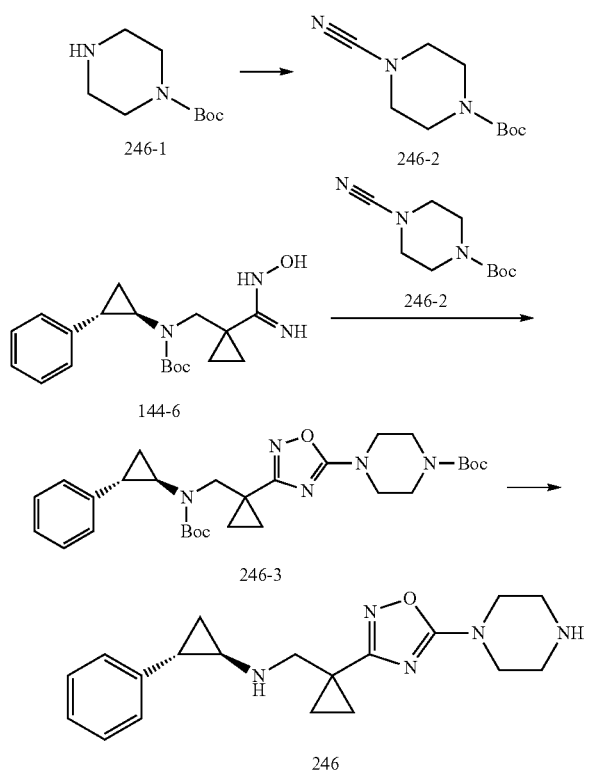

Step 1

Compound 246-1 (2.00 g, 8.98 mmol) was dissolved in dichloromethane (30 mL), sodium bicarbonate (2.26 g, 26.9 mmol) was dissolved in water (6 mL) and added to the reaction mixture. After cooling the system to 0° C., cyanogen bromide (1.14 g, 10.8 mmol) was dissolved in dichloromethane (3 mL) and added dropwise to the reaction system, and the mixture was stirred at 25° C. for 3 h. The mixture was diluted with water (50 mL) and filtered the precipitate. The aqueous phase was extracted with dichloromethane (20 mL×3). The organic phases were combined, washed with saturated sodium bicarbonate (30 mL×1) and saturated brine (30 mL×1). The organic phase was dried over anhydrous sodium sulfate, filtered and concentrated under reduced pressure to give crude compound 246-2. MS-ESI calculated [M-56+H]$^+$ 156, found 156.

Step 2

Compound 144-6 (200 mg, 0.579 mmol) and compound 246-2 (245 mg, 1.16 mmol) were dissolved in tetrahydrofuran (30 mL), and zinc chloride (1M diethyl ether solution, 1.16 mL, 1.16 mmol) was added dropwise. The reaction was stirred at 30° C. for 1 h, and then heated to 70° C. and stirred for 3 h. P-toluenesulfonic acid monohydrate (121 mg, 0.637 mmol) was added and the reaction was stirred at 70° C. for 4 h. The reaction mixture was concentrated under reduced pressure. The obtained product was diluted with water (50 mL) and extracted with ethyl acetate (40 mL×3). The organic phases were combined, washed with saturated brine (40 mL×2). The organic phase was dried over anhydrous sodium sulfate, filtered and concentrated under reduced pressure. The crude product was isolated and purified by silica gel column chromatography (5:1 petroleum ether/ethyl acetate, Rf=0.42) to give compound 246-3. MS-ESI calculated [M+H]$^+$ 540, found 540.

Step 3

The synthesis of compound 246 was referred to the fifth step of example 244. $^1$H NMR (400 MHz, CD$_3$OD) δ 7.35-7.31 (m, 2H), 7.28-7.24 (m, 1H), 7.18-7.16 (m, 2H), 3.87 (t, J=5.6 Hz, 4H), 3.65-3.54 (m, 2H), 3.38 (t, J=5.6 Hz, 4H), 3.10-3.06 (m, 1H), 2.57-2.52 (m, 1H), 1.60-1.55 (m, 1H) 1.43-1.38 (m, 3H), 1.27-1.25 (m, 2H). MS-ESI calculated [M+H]$^+$ 340, found 340.

Example 247

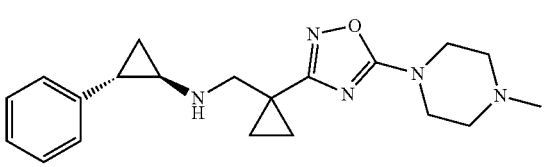 [SMILES: CN1CCN(c2nc(C3(CN[C@@H]4C[C@H]4c4ccccc4)CC3)no2)CC1]

Synthetic Route:

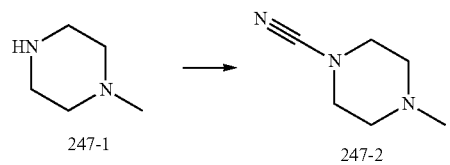

429

-continued

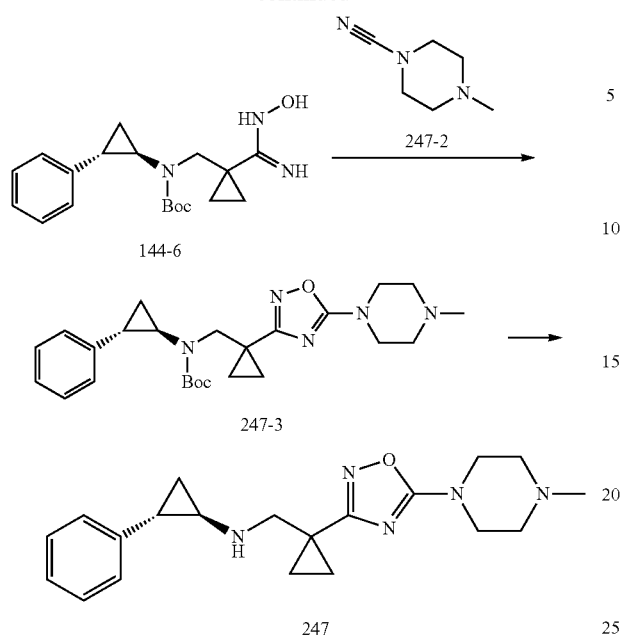

Step 1

The synthesis of compound 247-2 was referred to the first step of example 246. $^1$H NMR (400 MHz, DMSO-d$_6$) δ 3.20 (t, J=5.2 Hz, 4H), 2.35 (t, J=5.2 Hz, 4H), 2.18 (s, 3H). MS-ESI calculated [M+H]$^+$ 126, found 126.

Step 2

The synthesis of compound 247-3 was referred to the second step of example 246. MS-ESI calculated [M+H]$^+$ 454, found 454.

Step 3

The synthesis of compound 247 was referred to the fifth step of example 244. $^1$H NMR (400 MHz, CD$_3$OD) δ 7.35-7.31 (m, 2H), 7.28-7.24 (m, 1H), 7.18-7.16 (m, 2H), 3.65-3.50 (m, 6H), 3.35-3.30 (m, 4H), 3.10-3.06 (m, 1H), 2.99 (s, 3H), 2.57-2.52 (m, 1H) 1.60-1.55 (m, 1H), 1.43-1.38 (m, 3H), 1.27-1.25 (m, 2H). MS-ESI calculated [M+H]$^+$ 354, found 354.

Example 248

430

Synthetic Route:

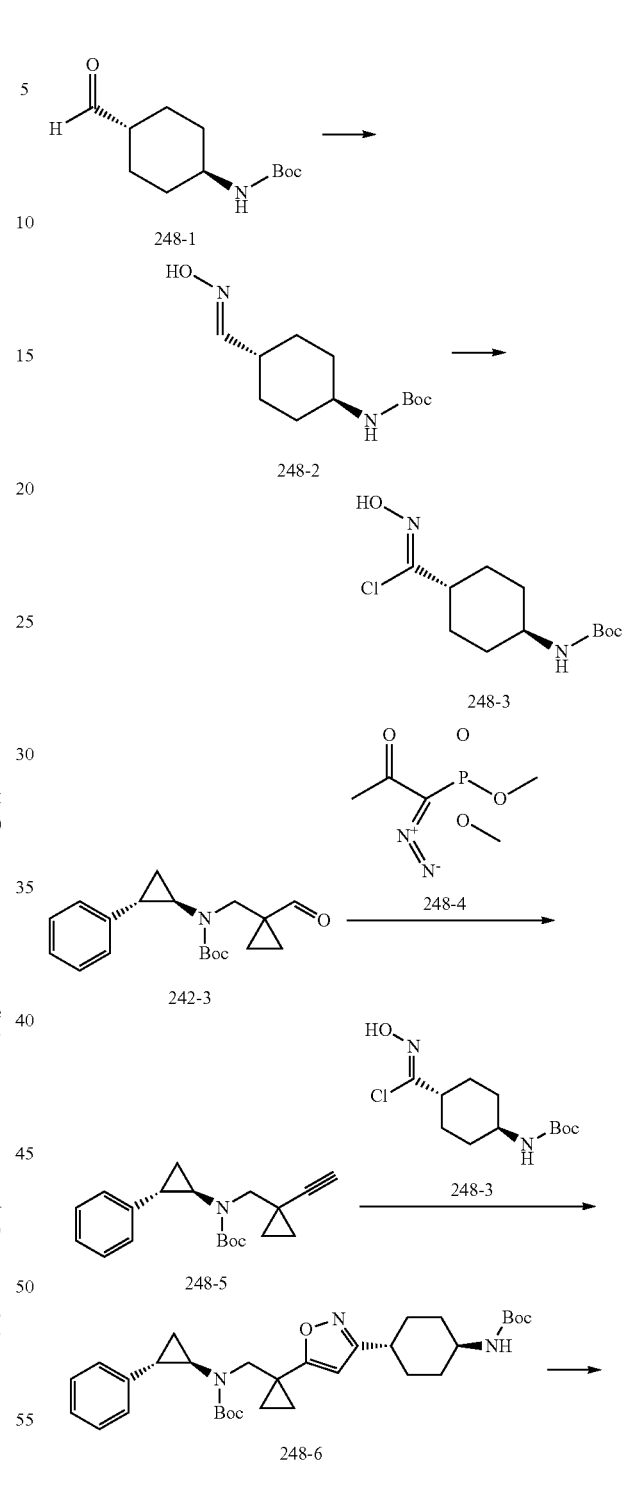

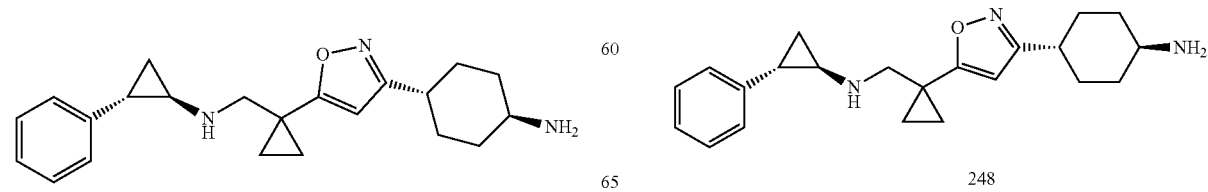

Step 1

Hydroxylamine hydrochloride (336 mg, 4.84 mmol) was added to a mixed solution of ethanol (6 mL) and water (2 mL), sodium carbonate (933 mg, 8.80 mmol) was added, and the reaction was stirred at 25° C. for 15 min. Compound 248-1 (1 g, 4.40 mmol) was added, and the reaction was stirred at 25° C. for 12 h. The mixture was concentrated under reduced pressure to remove organic solvent, water (50 mL) was added to the mixture and the mixture was extracted with ethyl acetate (40 mL×3). The organic phase was washed with saturated brine (40 mL×2), dried over anhydrous sodium sulfate, filtered and concentrated under reduced pressure to give compound 248-2. $^1$H NMR (400 MHz, CDCl$_3$) δ 7.48 (br s, 1H), 7.33 (d, J=6.0 Hz, 1H), 4.53-4.30 (m, 1H), 3.49-3.31 (m, 1H), 2.24-2.05 (m, 2H), 1.95-1.83 (m, 2H), 1.45 (s, 9H), 1.40-1.25 (m, 2H), 1.22-1.08 (m, 2H). MS-ESI calculated [M+H]$^+$ 243, found 243.

Step 2

Compound 248-2 (600 mg, 2.48 mmol) was dissolved in dichloromethane (20 mL), N-chlorosuccinimide (331 mg, 2.48 mmol) was added to the reaction mixture, and the mixture was stirred at 35° C. for 2 h. Nuclear magnetic monitoring detected the remaining material and the mixture was stirred at 35° C. for 12 h, nuclear magnetic monitoring showed complete reaction. Water (30 mL) was added to the reaction mixture, and the mixture was extracted with dichloromethane (30 mL×3). The organic phase was washed with saturated brine (20 mL×1), dried over anhydrous sodium sulfate, filtered and concentrated under reduced pressure to give compound 248-3. $^1$H NMR (400 MHz, CDCl$_3$) δ 9.07 (br s, 1H), 4.70-4.22 (m, 1H), 3.62-3.26 (m, 1H), 2.44-2.28 (m, 1H), 2.20-200 (m, 4H), 1.60-1.50 (m, 2H), 1.45 (s, 9H), 1.22-1.06 (m, 2H).

Step 3

Compound 242-3 (750 mg, 2.38 mmol) and potassium carbonate (986 mg, 7.13 mmol) were dissolved in methanol (10 mL), 248-4 (503 mg, 2.62 mmol) was added. The reaction solution was stirred at 25° C. for 12 h. The mixture was concentrated under reduced pressure to remove solvent, diluted with water (50 mL) and extracted with ethyl acetate (30 mL×3). The organic phase was washed with saturated brine (20 mL×1), dried over anhydrous sodium sulfate, filtered and concentrated under reduced pressure. The crude product was isolated and purified by silica gel column chromatography (5:1 petroleum ether/ethyl acetate, Rf=0.5) to give compound 248-5. $^1$H NMR (400 MHz, CDCl$_3$) δ 7.29-7.25 (m, 2H), 7.22-7.09 (m, 3H), 3.60-3.14 (m, 2H), 3.05-2.95 (m, 1H), 2.18-2.05 (m, 1H), 1.78 (s, 1H), 1.45 (s, 9H), 1.34-1.18 (m, 2H), 0.99-0.67 (m, 4H). MS-ESI calculated [M+Na]$^+$ 334, found 334.

Step 4

Compound 248-5 (200 mg, 0.642 mmol) and compound 248-3 (355 mg, 1.28 mmol) were dissolved in tetrahydrofuran (5 mL), potassium carbonate (266 mg, 1.93 mmol) and cuprous iodide (24.5 mg), 0.128 mmol) were added. The reaction solution was stirred at 25° C. for 12 h under nitrogen. Water (50 mL) was added to the reaction mixture. The mixture was extracted with ethyl acetate (20 mL×2). The organic phase was washed with saturated brine (20 mL×2), dried over anhydrous sodium sulfate, filtered and concentrated under reduced pressure. The crude product was separated by silica gel chromatography (3:1 petroleum ether/ethyl acetate, Rf=0.4) to give compound 248-6. $^1$H NMR (400 MHz, CDCl$_3$) δ 7.28-7.24 (m, 2H), 7.21-7.14 (m, 1H), 7.05-7.04 (m, 2H), 6.00 (s, 1H), 4.49-4.33 (m, 1H), 3.85-3.70 (m, 1H), 3.57-3.28 (m, 2H), 2.77-2.66 (m, 1H), 2.63-2.49 (m, 1H), 2.17-2.05 (m, 3H), 2.01-1.90 (m, 2H), 1.57-1.47 (m, 2H), 1.45 (s, 9H), 1.39 (s, 9H), 1.22-1.09 (m, 5H), 1.08-0.84 (m, 3H). MS-ESI calculated [M+Na]$^+$ 574, found 574.

Step 5

Compound 248-6 (204 mg, 370 μmol) was dissolved in methanol (4 mL). Then hydrochloric acid/methanol (4 M, 4 mL) was added and the mixture was stirred at 20° C. for 0.5 h. The remaining material was detected by LCMS. The mixture was stirred at 20° C. for 12 h. The mixture was concentrated under reduced pressure to remove solvent. The obtained crude product was diluted with water (40 mL). The mixture was adjusted to pH=8 with the saturated aqueous solution of sodium carbonate and extracted with ethyl acetate (30 mL×3). The organic phase was washed with saturated brine (20 mL×2), dried over anhydrous sodium sulfate, filtered and concentrated under reduced pressure. The crude product was prepared by high performance liquid chromatography (acidic, hydrochloric acid) to give compound 248. $^1$H NMR (400 MHz, CD$_3$OD) δ 7.35-7.27 (m, 2H), 7.27-7.19 (m, 1H), 7.19-7.12 (m, 2H), 6.31 (s, 1H), 3.62 (s, 2H), 3.25-3.09 (m, 1H), 3.06-2.97 (m, 1H), 2.76-2.63 (m, 1H), 2.59-2.48 (m, 1H), 2.22-2.00 (m, 4H), 1.66-1.46 (m, 5H), 1.41-1.28 (m, 5H). MS-ESI calculated [M+H]$^+$ 352, found 352.

Example 249

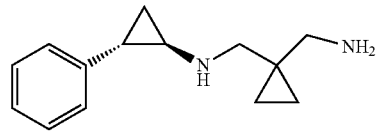 [SMILES: NCC1(CN[C@@H]2C[C@H]2c2ccccc2)CC1]

Synthetic Route:

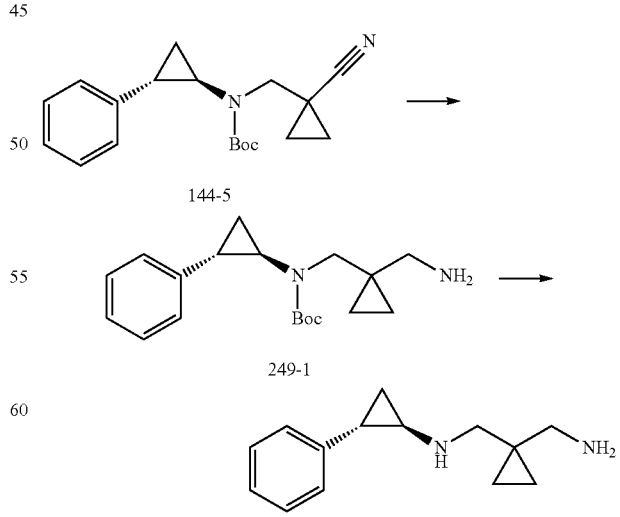

Step 1

Compound 144-5 (400 mg, 1.12 mmol) was dissolved in anhydrous methanol (12 mL), sodium borohydride (339 mg, 8.96 mmol) and cobalt dichloride (582 mg, 4.48 mmol) were added to the reaction mixture at 0° C. The reaction solution was stirred at 20° C. for 1 h. The mixture is filtered by celite. The filtrate was diluted with water (50 mL) and extracted with ethyl acetate (50 mL×3). The organic phases were combined, dried over anhydrous sodium sulfate, filtered and concentrated under reduced pressure to give compound 249-1. MS-ESI calculated [M+H]$^+$317, found 317.

Step 2

Compound 249-1 (413 mg, 1.02 mmol) was dissolved in ethyl acetate (2 mL), hydrochloric acid/ethyl acetate (4 M, 10.2 mL) was added dropwise at 0° C. The reaction solution was stirred under nitrogen at 0° C. for 0.5 h. The solvent was concentrated under reduced pressure, and the crude product was purified by high-purity chromatography (acid, hydrochloric acid) to give compound 249. $^1$H NMR (400 MHz, D$_2$O) δ 7.35-7.32 (m, 2H), 7.28-7.24 (m, 1H), 7.18-7.16 (m, 2H), 3.34-3.24 (m, 2H), 3.11-3.02 (m, 2H), 2.99-2.95 (m, 1H), 2.59-2.54 (m, 1H), 1.58-1.52 (m, 1H), 1.40-1.34 (m, 1H), 0.87-0.82 (m, 4H). MS-ESI calculated [M+H]$^+$ 217, found 217.

Example 250

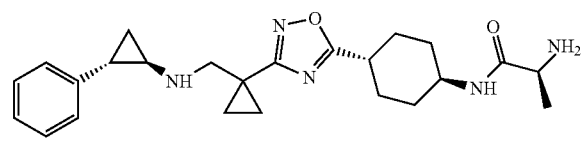 [SMILES: C[C@H](N)C(=O)N[C@H]1CC[C@H](c2nc(C3(CN[C@@H]4C[C@H]4c4ccccc4)CC3)no2)CC1]

Synthetic Route:

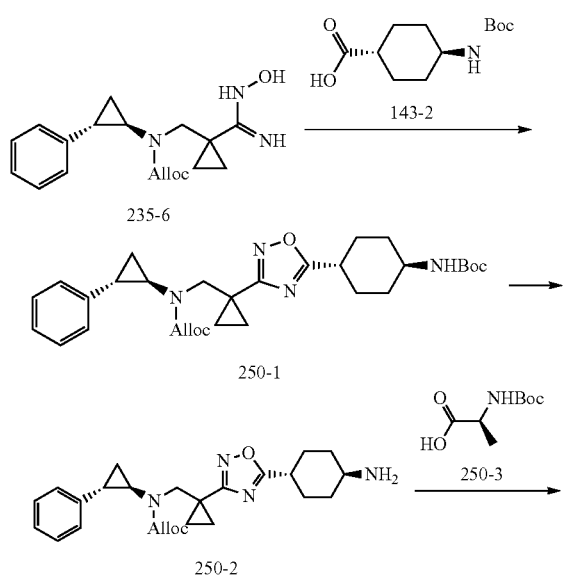

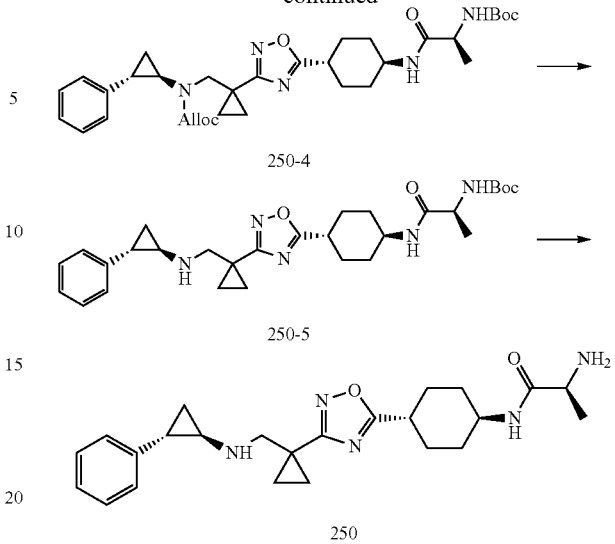

Step 1

Compound 143-2 (3.75 g, 15.2 mmol) was dissolved in anhydrous N,N-dimethylformamide (50 mL), and carbonyldiimidazole (2.68 g, 16.5 mmol) was added and the mixture was stirred for 2 h at 30° C. under nitrogen. Compound 235-6 (5.00 g, 13.8 mmol) was added to the reaction mixture, and the reaction mixture was heated to 110° C. and stirred for 10 h. The reaction solution was cooled to room temperature, concentrated under reduced pressure to remove solvent DMF (10 mL). Water (200 mL) was added to the reaction mixture, and the mixture was extracted with ethyl acetate (150 mL×3). The organic phases were combined, washed with saturated brine (200 mL×2), dried over anhydrous sodium sulfate, filtered and concentrated under reduced pressure. The crude product was isolated and purified by column chromatography (2:1 petroleum ether/ethyl acetate, Rf=0.8) to give compound 250-1. $^1$H NMR (400 MHz, CD$_3$Cl) δ 7.28-7.24 (m, 2H), 7.20-7.16 (m, 1H), 7.11-7.09 (m, 2H), 5.98-5.88 (m, 1H), 5.30-5.18 (m, 2H), 4.66-4.57 (m, 2H), 4.51-4.42 (m, 1H), 3.93 (d, J=14.8 Hz, 1H), 3.73 (d, J=14.8 Hz, 1H), 3.51-3.38 (m, 1H), 2.76-2.66 (m, 2H), 2.18-2.09 (m, 5H), 1.82-1.70 (m, 1H), 1.67-1.57 (m, 2H), 1.46 (s, 9H), 1.22-1.18 (m, 3H), 1.16-1.07 (m, 2H), 1.00-0.85 (m, 1H). MS-ESI calculated [M+Na]$^+$ 537, found 537.

Step 2

Compound 250-1 (1.07 g, 1.92 mmol) was dissolved in ethyl acetate (3 mL), hydrochloric acid/ethyl acetate (4 M, 12 mL) was added dropwise at 0 V. The reaction solution was stirred under nitrogen at 0 t for 1 h, and concentrated under reduced pressure to give Compound 250-2. MS-ESI calculated [M+H]$^+$ 437, found 437.

Step 3

Compound 250-2 (120 mg, 0.252 mmol), compound 250-3 (47.6 mg, 0.252 mmol) was dissolved in anhydrous dioxane (3 mL). Tri-n-propylcyclophosphoric anhydride (50% ethyl acetate solution, 449 μL, 0.755 mmol) and N,N-diisopropylethylamine (130 mg, 1.01 mmol) were added to the reaction mixture at 0° C. The mixture was heated to 60° C. and stirred for 1 h under nitrogen. LCMS detected compound 250-2. The reaction solution was cooled to 0° C., and tri-n-propylcyclophosphoric anhydride (50% ethyl acetate solution, 449 μL, 0.755 mmol) and N,N-diisopropylethylamine (130 mg, 1.01 mmol) were added to the reaction mixture. The mixture was stirred at 60° C. for 1 h. The reaction mixture was quenched with water (10 mL), extracted with ethyl acetate (20 mL×3). The organic phases were combined, washed with saturated brine (30 mL×1), dried over anhydrous sodium sulfate, filtered and concentrated under reduced pressure to give Compound 250-4. MS-ESI calculated [M+Na]$^+$ 630 found 630.

Step 4

The synthesis of compound 250-5 was referred to the eighth step of example 235. MS-ESI calculated [M+H]$^+$ 524, found 524.

Step 5

The synthesis of compound 250 was referred to the seven step of example 236. $^1$H NMR (400 MHz, D$_2$O) δ 7.31-7.29 (m, 2H), 7.28-7.22 (m, 1H), 7.05-7.03 (m, 2H), 3.93 (q, J=7.2 Hz, 1H), 3.70-3.55 (m, 3H), 3.02-2.98 (m, 1H), 2.81-2.73 (m, 1H), 2.44-2.39 (m, 1H), 2.04-1.92 (m, 4H), 1.58-1.47 (m, 3H), 1.44 (d, J=7.2 Hz, 3H), 1.38-1.24 (m, 7H). MS-ESI calculated [M+H]$^+$ 424, found 424.

Example 251

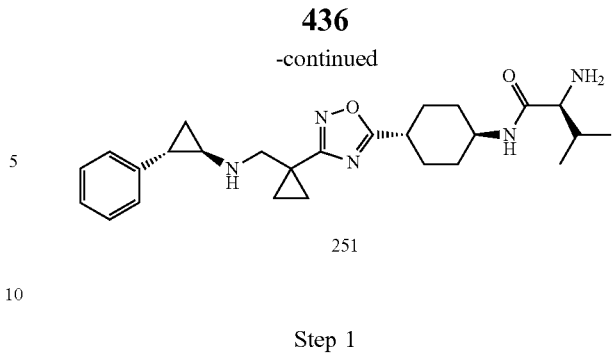

251

Step 1

The synthesis of compound 251-2 was referred to the third step of example 250. MS-ESI calculated [M+H]$^+$ 636, found 636.

Step 2

The synthesis of compound 251-3 was referred to the eighth step of example 235. MS-ESI calculated [M+H]$^+$ 552, found 552.

Step 3

The synthesis of compound 251 was referred to the seventh step of example 236. $^1$H NMR (400 MHz, D$_2$O) δ 7.33-7.29 (m, 2H), 7.27-7.24 (m, 1H), 7.06-7.04 (m, 2H), 3.72-3.57 (m, 4H), 3.04-3.00 (m, 1H), 2.85-2.75 (m, 1H), 2.46-2.41 (m, 1H), 2.18-2.10 (m, 1H), 2.07-1.94 (m, 4H), 1.58-1.46 (m, 3H), 1.42-1.26 (m, 7H), 1.00-0.97 (m, 6H). MS-ESI calculated [M+H]$^+$ 452, found 452.

Example 252

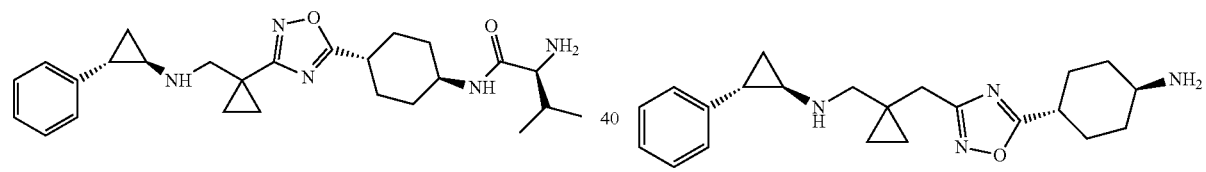

Synthetic Route:

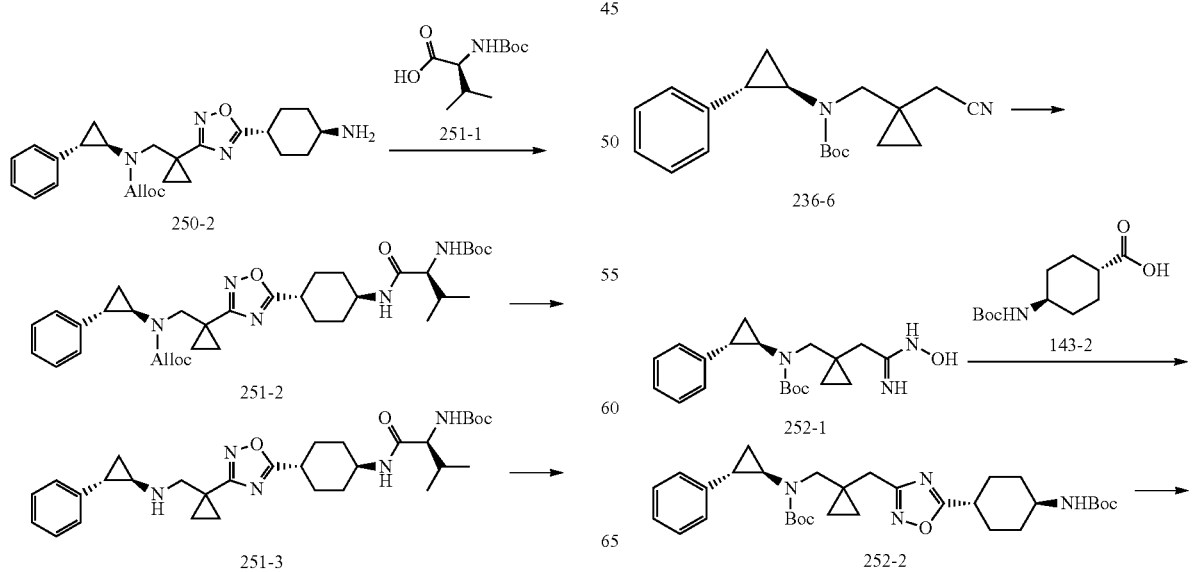

-continued

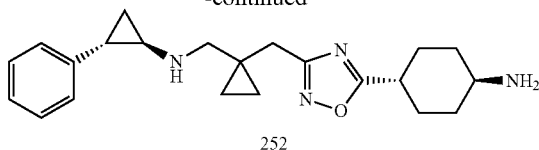

252

Step 1

The synthesis of compound 252-1 was referred to the fourth step of example 235. MS-ESI calculated [M+H]⁺ 360, found 360.

Step 2

The synthesis of compound 252-2 was referred to the fifth step of example 235. MS-ESI calculated [M+H]⁺ 567, found 567.

Step 3

The synthesis of compound 252 was referred to the seventh step of example 236. $^1$H NMR (400 MHz, D$_2$O) δ 7.36-7.32 (m, 2H), 7.28-7.25 (m, 1H), 7.16-7.15 (m, 2H), 3.21-3.12 (m, 3H), 3.03-2.97 (m, 2H), 2.86-2.82 (m, 2H), 2.53-2.48 (m, 1H), 2.21-2.17 (m, 2H), 2.12-2.09 (m, 2H), 1.65-1.47 (m, 5H), 1.40-1.34 (m, 1H), 0.75-0.68 (m, 4H). MS-ESI calculated [M+H]⁺ 367, found 367.

Example 253

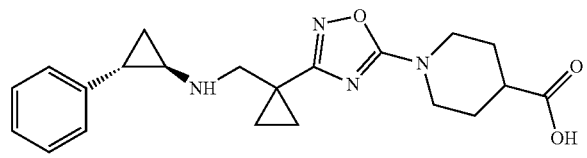 [SMILES: O=C(O)C1CCN(c2nc(C3(CN[C@@H]4C[C@H]4c4ccccc4)CC3)no2)CC1]

Synthetic Route:

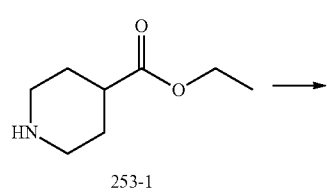

253-1

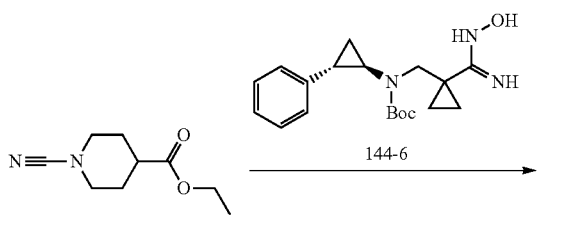

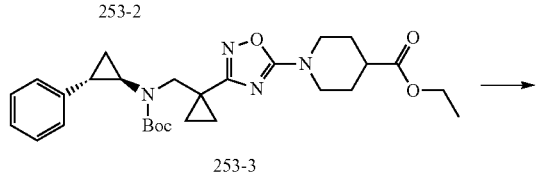

253-3

-continued

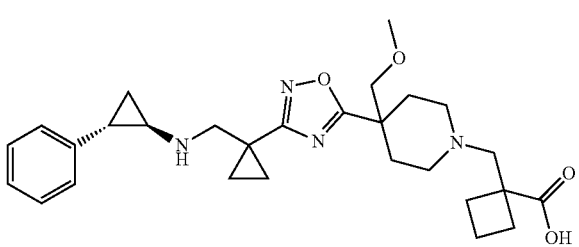 [SMILES: COCC1(c2nc(C3(CN[C@@H]4C[C@H]4c4ccccc4)CC3)no2)CCN(CC2(C(=O)O)CCC2)CC1]

253-4

253

Step 1

The synthesis of compound 253-2 was referred to the first step of example 246. $^1$H NMR (400 MHz, CDCl$_3$) δ 4.15 (q, J=6.8 Hz, 2H), 3.43-3.39 (m, 2H), 3.09-3.03 (m, 2H), 2.42-2.35 (m, 1H), 1.97-1.93 (m, 2H), 1.84-1.80 (m, 2H), 1.24 (t, J=6.8 Hz, 3H). MS-ESI calculated [M+H]⁺ 183, found 183.

Step 2

The synthesis of compound 253-3 was referred to the second step of example 246 MS-ESI calculated [M+H]⁺ 511, found 511.

Step 3

The synthesis of compound 253-4 was referred to the ninth step of example 235. MS-ESI calculated [M+H]⁺ 483, found 483.

Step 4

The synthesis of compound 253 was referred to the fifth step of example 244. $^1$H NMR (400 MHz, D$_2$O) s 7.30-7.22 (m, 3H), 7.01-6.99 (m, 2H), 3.74-3.71 (m, 2H), 3.65-3.44 (m, 2H), 3.06-3.03 (m, 3H), 2.62-2.59 (m, 1H), 2.45-2.39 (m, 1H), 1.93-1.89 (m, 2H) 1.59-1.47 (m, 3H), 1.29-1.16 (m, 5H). MS-ESI calculated [M+H]⁺ 383, found 383.

Example 254

Synthetic Route:
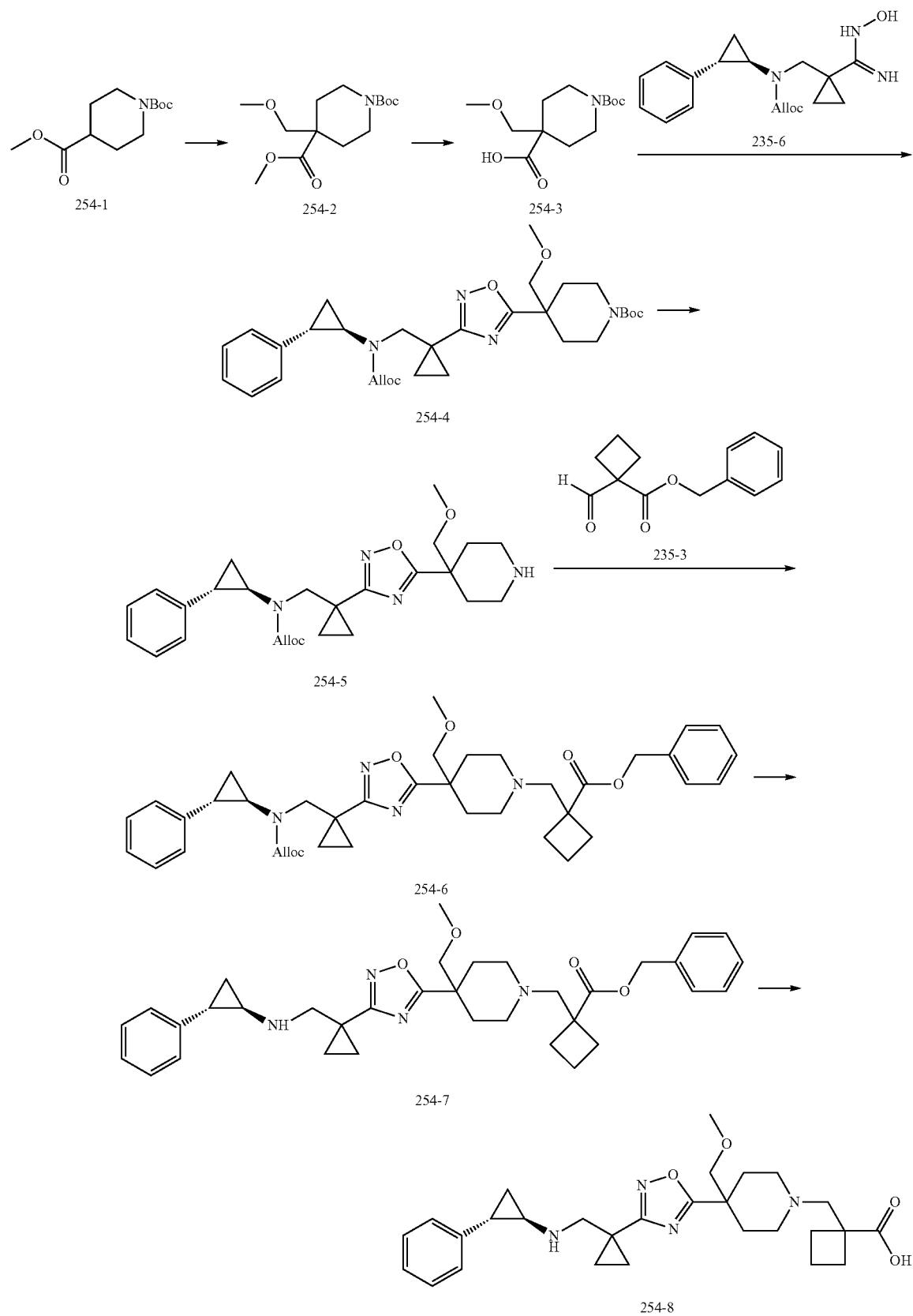

441

Step 1

Lithium diisopropylamide (2.0 M in THF, 32.9 mL, 65.8 mmol was added to the compound 254-1 (10.0 g, 41.1 mmol) in tetrahydrofuran (150 mL). The reaction solution was reacted at −78° C. for 10 min and warmed to 40° C. in 1 h. After the reaction mixture was cooled to −78° C., chloromethyl ether (4.96 g, 61.7 mmol) was added dropwise. After the addition was completed. The reaction was stirred at −78° C. for 2.5 h and warmed to 25° C. in 1 h. The reaction mixture was quenched with saturated aqueous ammonium chloride (300 mL) and extracted with ethyl acetate (200 mL×3). The organic phases were combined, washed with saturated brine (300 mL), dried over anhydrous sodium sulfate (15 g), filtered and concentrated under reduced pressure. The crude product was isolated and purified by silica gel column chromatography (10:1, petroleum ether/ethyl acetate, Rf=0.45) to give compound 254-2. $^1$H NMR (400 MHz, CDCl$_3$) δ 3.91-3.78 (in, 2H), 3.74 (s, 3H), 3.39 (s, 2H), 3.31 (s, 3H), 3.05-2.87 (m, 2H), 2.10-2.07 (m, 2H), 1.48-1.40 (s, 11H).

Step 2

The synthesis of compound 254-3 was referred to the ninth step of example 235. $^1$H NMR (400 MHz, CDCl$_3$) δ 4.01-3.83 (m, 2H), 3.44 (s, 2H), 3.34 (s, 3H), 3.16-2.98 (m, 2H), 2.06-2.05 (m, 2H), 1.49-1.38 (m, 11H).

Step 3

The synthesis of compound 254-4 was referred to the fifth step of example 235. MS-ESI calculated [M+Na]$^+$ 589, found 589.

442

Step 4

The synthesis of compound 254-5 was referred to the sixth step of example 235. MS-ESI calculated [M+H]$^+$ 467, found 467.

Step 5

The synthesis of compound 254-6 was referred to the seventh step of example 235. MS-ESI calculated [M+H]$^+$ 669, found 669.

Step 6

The synthesis of compound 254-7 was referred to the eighth step of example 235. MS-ESI calculated [M+H]$^+$ 585, found 585.

Step 7

The synthesis of compound 254 was referred to the ninth step of example 235. $^1$H NMR (400 MHz, D$_2$O) δ 7.36-7.31 (m, 2H), 7.26-7.25 (m, 1H), 7.15-7.13 (m, 2H), 3.71-3.58 (m, 4H), 3.50-3.39 (m, 4H), 3.22 (s, 3H), 3.05-2.97 (m, 2H), 2.52-2.40 (m, 5H), 2.27-2.20 (m, 1H), 2.11-1.94 (m, 6H), 1.54-1.49 (m, 1H), 1.42-1.25 (m, 5H). MS-ESI calculated [M+H]$^+$ 495, found 495.

Example 255

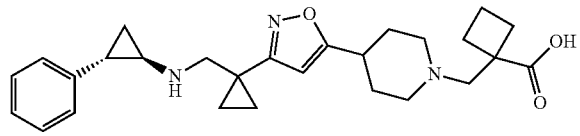 [SMILES: O=C(O)C1(CN2CCC(c3cc(C4(CN[C@@H]5C[C@H]5c5ccccc5)CC4)no3)CC2)CCC1]

Synthetic Route:

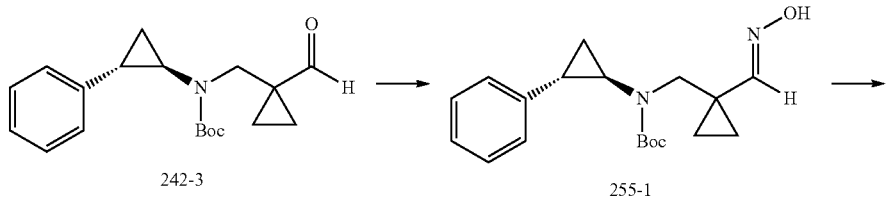

242-3 → 255-1

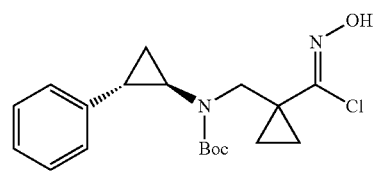

255-2

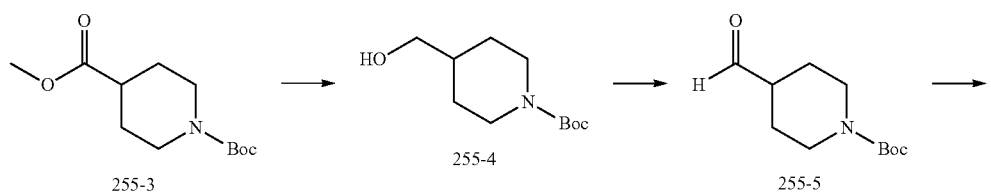

255-3 → 255-4 → 255-5

-continued

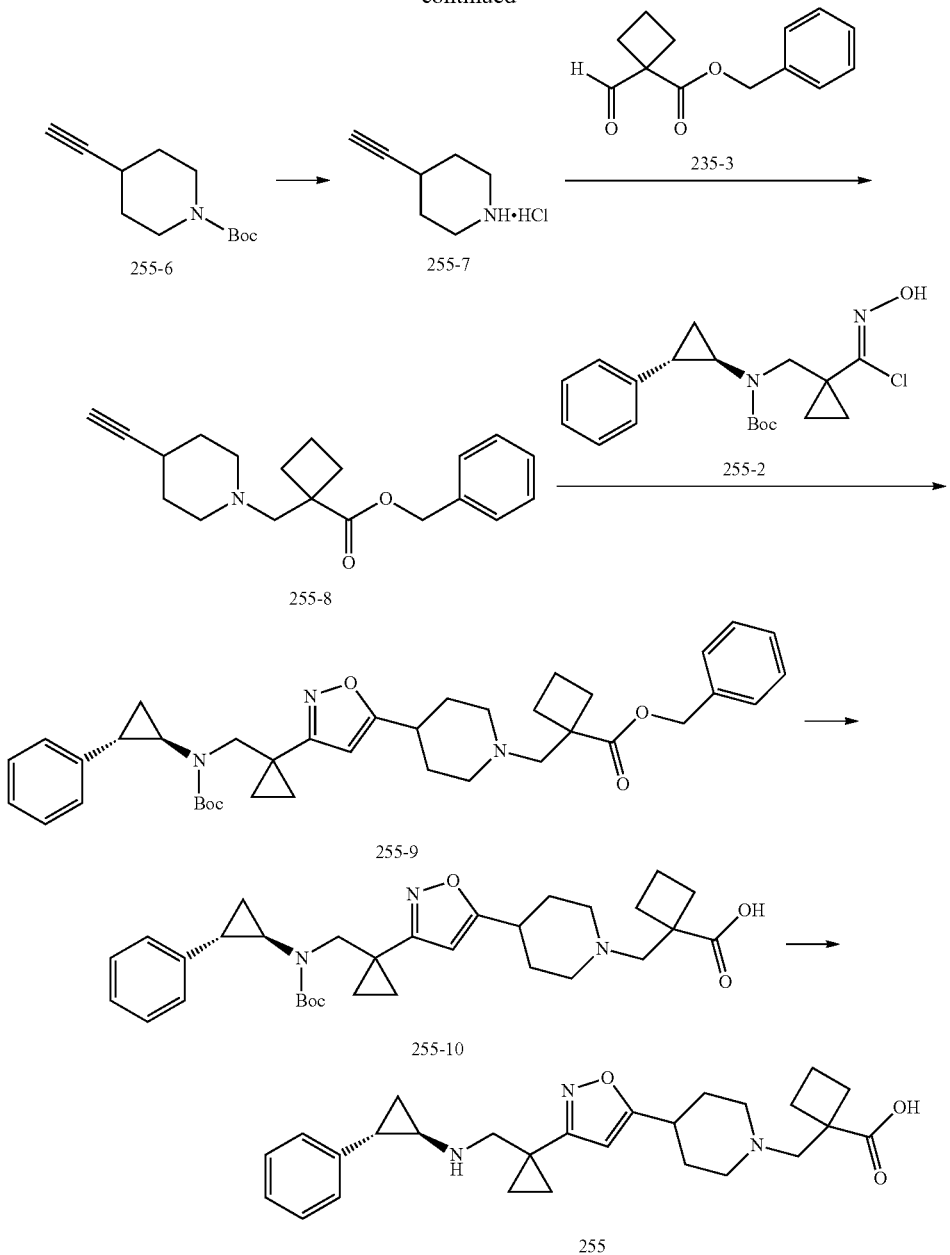

Step 1

Sodium bicarbonate (442 mg, 5.26 mmol) was added to the solution of hydroxylamine hydrochloride (366 mg, 5.26 mmol) in water (5 mL). After the absence of bubbles, a mixture of compound 242-3 (1.58 g, 5.01 mmol) dissolved in anhydrous ethanol (10 mL) was added dropwise, and the mixture was stirred at 20° C. for 1 h. The mixture was concentrated under reduced pressure to remove solvent, and the obtained crude product was dissolved in water (30 mL). The mixture was extracted with ethyl acetate (40 mL×3). The organic phase was washed with saturated brine (100 mL×1), dried over anhydrous sodium sulfate, filtered and concentrated under reduced pressure to give compound 255-1. MS-ESI calculated [M+Na]$^+$ 353, found 353.

Step 2

Compound 255-1 (1.65 g, 4.99 mmol) was dissolved in N,N-dimethylformamide (10 mL), N-chlorosuccinimide (667 mg, 4.99 mmol) was added, and the reaction mixture was stirred at 20° C. under nitrogen for 1 h. The reaction mixture was quenched with water (150 mL), extracted with ethyl acetate (150 mL×3). The organic phase was washed with water (300 mL×3), dried over anhydrous sodium sulfate, filtered and concentrated under reduced pressure to give compound 255-2. $^1$H NMR (400 MHz, DMSO-d$_6$) δ 11.63 (s, 1H), 7.28-7.24 (m, 2H), 7.18-7.10 (m, 3H), 3.62 (d, J=14.4 Hz, 1H), 3.28 (d, J=14.4 Hz, 1H), 2.67-2.63 (m, 1H), 2.08-2.04 (m, 1H), 1.33 (s, 9H), 1.24-1.15 (m, 2H), 0.96-0.91 (m, 2H), 0.85-0.80 (m, 1H), 0.75-0.74 (m, 1H). MS-ESI calculated [M+Na]$^+$ 387, found 387.

Step 3

Compound 255-3 (5.00 g, 20.6 mmol) was dissolved in tetrahydrofuran (50 mL). The mixture was cooled to 0° C. and sodium borohydride (1.55 g, 41.1 mmol) was added to the solution. The mixture was heated to 70° C. and stirred for 3 h. The reaction mixture was quenched with water (50 mL), extracted with ethyl acetate (30 mL×3). The organic phase was washed with saturated brine (50 mL×2), dried over anhydrous sodium sulfate, filtered and concentrated under reduced pressure. The crude product was isolated and purified by silica gel column chromatography (3:1 petroleum ether/ethyl acetate, Rf=0.1) to give compound 255-4. $^1$H NMR (400 MHz, CDCl$_3$) δ 3.51 (d, J=6.4 Hz, 2H), 1.74-1.60 (m, 4H), 1.52-1.41 (m, 12H), 1.20-1.10 (m, 2H). MS-ESI calculated [M-56+H]$^+$ 160, found 160.

Step 4

Compound 255-4 (1.43 g, 6.65 mmol) was dissolved in dichloromethane (15 mL). The mixture was cooled to 0° C. and Dess-Martin reagent (3.38 g, 7.98 mmol) was added to the solution. The reaction was stirred for 4 hours under nitrogen at 10° C. The reaction solution was quenched by adding saturated sodium thiosulfate solution (50 mL) and saturated sodium hydrogen carbonate solution (50 mL), extracted with ethyl acetate (80 mL×3). The organic phase was washed with saturated brine (100 mL×2), dried over anhydrous sodium sulfate, filtered and concentrated under reduced pressure to give compound 255-5. $^1$H NMR (400 MHz, CDCl$_3$) δ 9.66 (d, J=4.8 Hz, 1H), 4.13-3.99 (m, 2H), 2.95-2.83 (m, 2H), 2.74-2.38 (m, 1H), 1.90-1.87 (m, 2H), 1.70-1.50 (m, 2H), 1.46 (m, 9H).

Step 5

Compound 255-5 (1.12 g, 5.27 mmol) and potassium carbonate (2.18 g, 15.8 mmol) were dissolved in methanol (10 mL), dimethyl (1-diazo-2-oxopropyl) phosphonate (1.21 g, 6.32 mmol) was added and the mixture was stirred at 20° C. for 12 h. The reaction solution was quenched by saturated ammonium chloride solution (30 mL), extracted with ethyl acetate (30 mL×3). The organic phases were combined, dried over anhydrous sodium sulfate, filtered and concentrated under reduced pressure. The crude product was isolated and purified by silica gel column chromatography (5:1 petroleum ether/ethyl acetate, Rf=0.7) to give compound 255-6. $^1$H NMR (400 MHz, CDCl$_3$) δ 3.72-3.68 (m, 2H), 3.22-3.16 (m, 2H), 2.62-2.56 (m, 1H), 2.11 (d, J=2.4 Hz, 1H), 1.82-1.77 (m, 2H), 1.64-1.55 (m, 2H), 1.46 (s, 9H).

Step 6

The compound 255-6 (558 mg, 2.67 mmol) was dissolved in methanol (5 mL), hydrochloric acid (4M in methanol, 5 mL, 20.0 mmol) was added at 15° C. and the mixture was stirred for 0.5 h. The reaction solution was concentrated under reduced pressure to give crude compound 255-7. $^1$H NMR (400 MHz, CD$_3$OD) δ 3.36-3.31 (m, 2H), 3.14-3.08 (m, 2H), 2.85-2.79 (m, 1H), 2.59 (d, J=2.4 Hz, 1H), 2.09-2.03 (m, 2H), 1.87-1.78 (m, 2H).

Step 7

Compound 255-7 (399 mg, 2.74 mmol), compound 235-3 (598 mg, 2.74 mmol) and triethylamine (832 mg, 8.22 mmol) were dissolved in dichloromethane (10 mL), anhydrous sodium sulfate (1.17 g, 8.22 mmol) was added. The mixture was stirred at 25° C. for 3 h, sodium triacetoxyborohydride (1.45 g, 6.85 mmol) was added and the mixture was stirred at 25° C. for 9 h. The mixture was quenched with water (20 mL), extracted with dichloromethane (10 mL×3). The organic phases were combined, washed with saturated brine (30 mL×1), dried over anhydrous sodium sulfate, filtered and concentrated under reduced pressure. The crude product was isolated and purified by silica gel column chromatography (10:1 petroleum ether/ethyl acetate, Rf=0.4) to give compound 255-8. $^1$H NMR (400 MHz, CDCl$_3$) δ 7.41-7.29 (m, 5H), 5.18 (s, 2H), 2.70 (s, 2H), 2.64-2.59 (m, 2H), 2.51-2.44 (m, 2H), 2.35-2.25 (m, 1H), 2.13-2.08 (m, 2H), 2.06-2.05 (m, 1H), 2.03-1.98 (m, 2H), 1.95-1.81 (m, 2H), 1.75-1.68 (m, 2H), 1.59-1.50 (m, 2H). MS-ESI calculated [M+H]$^+$ 312, found 312.

Step 8

Compound 255-8 (350 mg, 1.12 mmol) was dissolved in tetrahydrofuran (5 mL), potassium carbonate (466 mg, 3.37 mmol) and cuprous iodide (42.8 mg, 0.225 mmol) were added and the mixture was stirred at 15° C. for 0.5 h. Compound 255-2 (820 mg, 2.25 mmol) was added to the reaction system, and the mixture was stirred at 15° C. for 5.5 h. The reaction was quenched with saturated aqueous ammonium chloride (10 mL), and then extracted with ethyl acetate (10 mL×3). The organic phases were combined, washed with saturated brine (10 mL×1), dried over anhydrous sodium sulfate, filtered and concentrated under reduced pressure. The crude product was isolated and purified by silica gel column chromatography (5:1 petroleum ether/ethyl acetate, Rf=0.2) to give compound 255-9. MS-ESI calculated [M+H]$^+$ 640, found 640.

Step 9

Compound 255-9 (320 mg, 0.500 mmol) was dissolved in methanol (10 mL), a solution of sodium hydroxide (100 mg, 2.5 mmol) dissolved in water (5 mL) was added. The reaction solution was stirred at 60° C. for 12 h. The reaction solution was concentrated under reduced pressure to remove methanol, water (20 mL) was added to the mixture. The mixture was extracted with ethyl acetate (20 mL×2). The aqueous phase was adjusted to pH=3 with 1M HCl and extracted with ethyl acetate (20 mL×4). The organic phases were combined, washed with saturated brine (50 mL×1), dried over anhydrous sodium sulfate, filtered and concentrated under reduced pressure to give compound 255-10. MS-ESI calculated [M+H]$^+$ 550, found 550.

Step 10

Compound 255-10 (340 mg, 0.585 mmol) was dissolved in anhydrous dichloromethane (8 mL). Trifluoroacetic acid (4 mL) was added dropwise at 0° C. The reaction solution was stirred under nitrogen at 0° C. for 2 h, and then concentrated under reduced pressure to remove solvent. The crude product was subjected to high performance liquid chromatography (neutral system) to give compound 255. $^1$H NMR (400 MHz, CD$_3$OD) δ 7.33-7.29 (m, 2H), 7.25-7.21 (m, 1H), 7.17-7.15 (m, 2H), 6.08 (s, 1H), 3.65-3.59 (m, 6H), 3.27-3.15 (m, 2H), 3.06-3.02 (m, 1H), 2.60-2.54 (m, 3H), 2.25-2.19 (m, 6H), 2.15-1.94 (m, 3H), 1.59-1.54 (m, 1H), 1.40-1.35 (m, 1H), 1.32-1.28 (m, 2H), 1.26-1.22 (m, 2H). MS-ESI calculated [M+H]$^+$ 450, found 450.

Biochemical Testing

Example 1: Evaluation of Enzyme Activity

The purpose of this test is to test the in vitro inhibitory activities of the compounds against LSD1. The enzyme used in this experiment was human LSD1, and the standard substrate was histone H3(1-21)K4me2 peptide (10 μM). HCI-2509 (SP2509) was used as reference compound, and the fluorescence coupling enzyme assay was employed. The production of FAD-dependent $H_2O_2$ as a result of demethylase activity of LSD1 was measured by coupling with HRP and Amplex Red. Compounds as well as control compound HCl-2509 were tested in 10-dose IC50 mode with a 3-fold serial dilution in duplicate starting at 10 μm. All compounds were pre-incubated 30 mins with enzyme before added substrate to start reaction. Fluorescence measurement: Ex/Em=535/590 by EnVision.

The test compound's inhibitory activities against LSD11 was classified as: + for $IC_{50} \leq 50$ nM; ++ for $IC_{50} > 50$ nM and $\leq 100$ nM; +++ for $IC_{50} > 100$ nM and $\leq 500$ nM, and the results are shown in Table 1.

TABLE 1

Results of screening test results of in vitro enzyme activities of the compounds of the present invention

| Compound number | $IC_{50}$ (nM) |
|---|---|
| Example 1 | +++ |
| Example 3 | ++ |
| Example 4 | + |
| Example 5 | ++ |
| Example 6 | +++ |
| Example 7 | +++ |
| Example 8 | ++ |
| Example 9 | + |
| Example 10 | + |
| Example 11 | + |
| Example 12 | ++ |
| Example 13 | + |
| Example 14 | +++ |
| Example 15 | ++ |
| Example 16 | +++ |
| Example 17 | ++ |
| Example 46 | + |
| Example 47 | ++ |
| Example 48 | + |
| Example 63 | + |
| Example 64 | + |
| Example 65 | + |
| Example 66 | + |
| Example 69 | + |
| Example 70 | + |
| Example 71 | + |
| Example 72 | + |
| Example 75 | + |
| Example 76 | ++ |
| Example 84 | +++ |
| Example 85 | + |
| Example 86 | + |
| Example 87 | + |
| Example 88 | + |
| Example 89 | + |
| Example 90 | + |
| Example 91 | + |
| Example 92 | + |
| Example 93 | + |
| Example 94 | + |
| Example 95 | + |
| Example 97 | + |
| Example 98 | ++ |
| Example 99 | +++ |
| Example 100 | + |
| Example 102 | +++ |
| Example 103 | +++ |
| Example 104 | + |
| Example 105 | ++ |
| Example 106 | +++ |
| Example 107 | +++ |
| Example 108 | +++ |
| Example 109 | + |
| Example 110 | + |
| Example 112 | +++ |
| Example 115 | +++ |
| Example 116 | + |
| Example 117 | + |
| Example 119 | + |
| Example 121 | + |
| Example 122 | + |
| Example 123 | + |
| Example 125 | + |
| Example 126 | + |
| Example 127 | + |
| Example 128 | ++ |
| Example 129 | + |
| Example 130 | + |
| Example 131 | + |
| Example 132 | + |
| Example 134 | +++ |
| Example 135 | +++ |
| Example 136 | + |
| Example 137 | + |
| Example 138 | ++ |
| Example 139 | ++ |
| Example 142 | + |
| Example 143 | ++ |
| Example 144 | + |
| Example 145 | + |
| Example 146 | + |
| Example 147 | + |
| Example 148 | + |
| Example 149 | ++ |
| Example 150 | + |
| Example 151 | + |
| Example 152 | +++ |
| Example 153 | +++ |
| Example 154 | +++ |
| Example 155 | + |
| Example 156 | ++ |
| Example 157 | ++ |
| Example 158 | + |
| Example 159 | ++ |
| Example 160 | + |
| Example 161 | + |
| Example 162 | + |
| Example 163 | +++ |
| Example 164 | + |
| Example 165 | +++ |
| Example 167 | +++ |
| Example 169 | ++ |
| Example 170 | +++ |
| Example 171 | + |
| Example 172 | + |
| Example 173 | +++ |
| Example 174 | +++ |
| Example 175 | +++ |
| Example 177 | +++ |
| Example 178 | +++ |
| Example 181 | + |
| Example 182 | + |
| Example 183 | + |
| Example 184 | + |
| Example 185 | + |
| Example 186 | +++ |
| Example 187 | + |
| Example 188 | + |
| Example 189 | + |
| Example 190 | + |
| Example 191 | + |

TABLE 1-continued

Results of screening test results of in vitro enzyme activities of the compounds of the present invention

| Compound number | IC$_{50}$ (nM) |
|---|---|
| Example 192 | + |
| Example 193 | + |
| Example 194 | +++ |
| Example 195 | + |
| Example 198 | + |
| Example 199 | ++ |
| Example 200 | +++ |
| Example 202 | ++ |
| Example 205 | +++ |
| Example 206 | +++ |
| Example 207 | + |
| Example 208 | + |
| Example 209 | + |
| Example 210 | + |
| Example 211 | ++ |
| Example 212 | +++ |
| Example 213 | + |
| Example 214 | ++ |
| Example 215 | +++ |
| Example 216 | +++ |
| Example 217 | +++ |
| Example 218 | +++ |
| Example 219 | + |
| Example 220 | ++ |
| Example 221 | +++ |
| Example 225 | + |
| Example 226 | + |
| Example 227 | +++ |
| Example 228 | +++ |
| Example 230 | +++ |
| Example 231 | ++ |
| Example 232 | ++ |
| Example 233 | +++ |
| Example 235 | +++ |
| Example 239 | + |
| Example 240 | ++ |
| Example 241 | + |
| Example 242 | + |
| Example 243 | +++ |
| Example 244 | + |
| Example 245 | + |
| Example 246 | + |
| Example 247 | + |
| Example 253 | +++ |
| HCI-2509 | + |

Conclusion: The compounds of the present invention have significant inhibitory activities against LSD1.

Example 2: Evaluation of Cell Proliferation Inhibitory Activity

Experimental purposes: To test the proliferation inhibitory activities of the test compounds on H1417 cells.

Experimental materials: RPMI 1640 medium, fetal bovine serum, Promega CellTiter-Glo reagent. The H1417 cell line purchased from ATCC. Envision Multi-Label Analyzer (PerkinElmer).

Experimental method: H1417 cells were seeded in a black 384-well plate, 1000 cells per well in 30 mL of cell suspension. The test compounds were diluted 3-fold with Epmotion to the 10th concentration i.e, the compounds were diluted from 10 mmol to 0.5 mmol, and a double duplicate well experiment was set. 198 μL medium was added to the middle plate, according to the corresponding position, 2 μL gradient diluted compounds were added to the middle plate. The mixture was mixed evenly and transferred 20 μL per well to the cell plates. The cell plates were incubated in a carbon dioxide incubator for 10 days. 25 μL of Promega CellTiter-Glo reagent per well was added to the cell plate and the mixture was incubated for 10 minutes at room temperature to stabilize the luminescence signal. Readings were performed by PerkinElmer Envision multi-label analyzer.

Data analysis: The original data was converted to the inhibition rate by the equation (Max-Ratio)/(Max-Min)*100%, and the value of IC$_{50}$ can be obtained by curve fitting with four parameters. (Model 205 in XLFIT5, iDBS)

The growth inhibitory activities of the test compounds on H1417 cells were classified as + for IC$_{50}$≤100 nM; ++ for IC$_{50}$>100 nM and ≤500 nM; +++ for IC$_{50}$>500 nM and ≤1000 nM; the highest percentage inhibition of cell viability was classified as: 100%≤A≤90%; 90%>B≥70%; 70%>C≥50%. The results are shown in Table 2.

TABLE 2

Screening test results of the compounds of the present invention on in vitro inhibitory activities of cell proliferation

| Compound No. | IC$_{50}$ (nM) | Maximum inhibition percentage (%) |
|---|---|---|
| Example 1 | + | A |
| Example 4 | + | C |
| Example 6 | +++ | C |
| Example 8 | ++ | C |
| Example 9 | + | B |
| Example 47 | ++ | C |
| Example 49 | +++ | A |
| Example 51 | ++ | B |
| Example 53 | +++ | A |
| Example 54 | +++ | C |
| Example 55 | ++ | B |
| Example 56 | +++ | C |
| Example 58 | ++ | B |
| Example 60 | +++ | C |
| Example 61 | +++ | C |
| Example 64 | ++ | A |
| Example 65 | ++ | A |
| Example 66 | +++ | A |
| Example 67 | ++ | C |
| Example 69 | +++ | C |
| Example 70 | ++ | A |
| Example 73 | + | B |
| Example 75 | + | C |
| Example 76 | ++ | C |
| Example 77 | + | B |
| Example 80 | ++ | C |
| Example 81 | + | C |
| Example 82 | ++ | C |
| Example 87 | ++ | C |
| Example 88 | ++ | C |
| Example 89 | ++ | C |
| Example 95 | + | C |
| Example 96 | +++ | C |
| Example 98 | ++ | C |
| Example 100 | ++ | C |
| Example 101 | +++ | C |
| Example 103 | +++ | C |
| Example 105 | ++ | B |
| Example 106 | +++ | C |
| Example 108 | +++ | B |
| Example 116 | ++ | B |
| Example 117 | ++ | B |
| Example 127 | ++ | C |
| Example 129 | ++ | C |
| Example 132 | ++ | C |
| Example 140 | ++ | A |
| Example 142 | +++ | B |
| Example 143 | +++ | C |
| Example 144 | ++ | A |
| Example 145 | ++ | B |
| Example 146 | +++ | A |
| Example 147 | +++ | A |
| Example 149 | +++ | C |
| Example 151 | ++ | A |
| Example 153 | +++ | A |
| Example 155 | ++ | A |

TABLE 2-continued

Screening test results of the compounds of the present invention on in vitro inhibitory activities of cell proliferation

| Compound No. | IC$_{50}$ (nM) | Maximum inhibition percentage (%) |
|---|---|---|
| Example 156 | ++ | B |
| Example 157 | +++ | B |
| Example 158 | +++ | A |
| Example 159 | ++ | A |
| Example 161 | ++ | B |
| Example 162 | +++ | A |
| Example 163 | ++ | B |
| Example 169 | +++ | C |
| Example 171 | ++ | C |
| Example 174 | +++ | C |
| Example 177 | +++ | C |
| Example 178 | +++ | B |
| Example 182 | +++ | A |
| Example 183 | +++ | A |
| Example 184 | ++ | A |
| Example 192 | ++ | C |
| Example 193 | ++ | C |
| Example 195 | ++ | C |
| Example 198 | ++ | C |
| Example 199 | +++ | B |
| Example 202 | ++ | B |
| Example 206 | +++ | C |
| Example 207 | +++ | C |
| Example 208 | ++ | B |
| Example 210 | +++ | C |
| Example 211 | ++ | C |
| Example 212 | ++ | C |
| Example 213 | ++ | C |
| Example 214 | ++ | B |
| Example 216 | + | A |
| Example 217 | +++ | C |
| Example 218 | ++ | B |
| Example 219 | +++ | A |
| Example 220 | ++ | B |
| Example 225 | ++ | A |
| Example 226 | + | A |
| Example 227 | + | C |
| Example 230 | ++ | C |
| Example 232 | +++ | B |
| Example 233 | ++ | B |
| Example 235 | + | B |
| Example 241 | + | B |
| Example 242 | + | A |
| Example 244 | + | B |
| Example 246 | +++ | A |
| Example 247 | +++ | A |

Conclusion: The compounds of the present invention have significant inhibitor activities on proliferation of H1417 cells.

Example 3: Compound Pharmacokinetic Evaluation

Experimental purposes: To test the pharmacokinetics of compounds in C57BL/6 mice Experimental Materials:

C57BL/6 mice (male, 7-9 weeks old, Shanghai Slack)

Experimental Operation:

Test the pharmacokinetics characteristics of rodents after intravenous and oral administration in accordance with standard protocols, and the candidate compound was formulated into a clear solution in the experiment. The mice were administered by intravenous injection and orally once. The intravenous and oral vehicle is a 10% aqueous solution of hydroxypropyl β-cyclodextrin or a physiological saline solution. Six male C57BL/6 mice were employed in this assay, three of them were administered intravenously at a dose of 1 mg/kg, plasma samples were collected at 0 h (before administration) and 0.0833, 0.25, 0.5, 1, 2, 4, 7, 24 h after administration. Another three mice were administered by oral gavage at a dose of 2 mg/kg, plasma samples were collected at 0 h (before administration) and 0.5, 1, 2, 3, 4, 6, 24 h after administration. Collect whole blood samples within 24 hours, centrifuge at 3000 g for 15 minutes, separate the supernatant to obtain a plasma sample, 4 times volume of the internal standard acetonitrile solution was added to precipitate the protein. Centrifuge the supernatant and add an equal volume of water and centrifuge to take the supernatant. LC-MS/MS was used to quantitatively analyze plasma concentrations and calculate pharmacokinetic parameters such as max concentration (Cmax), clearance (CL), half-life (T$_{1/2}$), volumes of distribution (Vdss), the area under the plasma concentration-time curve (AUC0-last), bioavailability (F), etc.

The experimental results were shown in Table 3:

TABLE 3

Pharmacokinetic test results

| Example | max concentration Cmax (ng/mL) | clearance CL (mL/min/kg) | volumes of distribution Vdss (L/kg) | half-life T$_{1/2}$ (IV, h) | the area under the plasma concentration-time curve AUC0-last PO (nM · hr) | bioavailability F (%) |
|---|---|---|---|---|---|---|
| 64 | 1287 | 21.9 | 1.9 | 1.3 | 1877 | 44 |
| 65 | 2070 | 10.6 | 3.0 | 4.2 | 3383 | 49 |
| 66 | 2137 | 13.1 | 1.4 | 1.5 | 3509 | 57 |
| 144 | 25.3 | 92.0 | 28.5 | 4.5 | 170 | 21.5 |
| 145 | 11.9 | 108 | 81.8 | 11.7 | 65.4 | 9.1 |
| 167 | 5093 | 11.6 | 0.4 | 1.4 | 3509 | 48.1 |
| 169 | 763 | 43.4 | 0.5 | 1.0 | 329 | 20.6 |
| 177 | 3207 | 9.9 | 0.5 | 1.6 | 3862 | 51.5 |
| 210 | 815 | 37.7 | 2.6 | 2.7 | 1130 | 40.5 |
| 224 | 58.5 | 112 | 21.7 | 2.97 | 273 | 35.1 |
| 235 | 497 | 62.4 | 0.99 | 0.34 | 370 | 28 |
| 241 | 49.5 | 104 | 20.9 | 2.4 | 271 | 36.7 |
| 242 | 179 | 72.1 | 10.3 | 2.0 | 712 | 57.5 |

Conclusion: The compounds of the invention have good pharmacokinetic properties, including good oral bioavailability, oral exposure, half-life and clearance.

Example 4 Assay on Inhibiting hERG Potassium Channel

Experimental purpose: Using automatic patch clamp method to detect the effect of the sample to be tested on hERG potassium channel.

Experimental Method 4.1. Cell Culture 4.1.1 CHO-hERG cells were cultured in 175 cm² flasks. When the cell density was increased to 60-80%, the culture solution was removed and the resultant was washed with 7 mL PBS (Phosphate Buffered Saline phosphate buffer), then 3 mL of digestive juice was added to digest.

4.1.2 After the digestion finished, 7 mL culture solution was added to neutralize. Then centrifuge, aspirate the supernatant, and then resuspend by adding 5 mL culture solution to ensure a cell density of 2-5×106/mL.

4.2 Solution Preparation

TABLE 4.1

Components of intracellular fluid and external fluid

| Reagent | Extracellular fluid (mM) | Intracellular fluid (mM) |
|---|---|---|
| CaCl$_2$ | 2 | 5.374 |
| MgCl$_2$ | 1 | 1.75 |
| KCl | 4 | 120 |
| NaCl | 145 | — |
| Glucose | 10 | — |
| HEPES | 10 | 10 |
| EGTA | — | 5 |
| Na$_2$ATP | — | 4 |
| pH | Adjust pH to 7.4 with NaOH | Adjust pH to 7.4 with KOH |

4.3 Electrophysiological Recording Process

Single cell high impedance sealing and whole cell pattern formation were all done automatically by the Qpatch instrument. After the whole-cell recording mode was obtained, the cells were clamped at −80 mV. 50-Millisecond−50 mV preamplifier was applied prior to a 5 second+40 mV depolarization stimulus. Then the voltage was repolarized to −50 mV for 5 seconds and back to −80 mV. This voltage stimulation was applied every 15 seconds, and the extracellular fluid was recorded over 5 minutes after 2 minutes' record, and then the administration process was started. The compound concentration was started from the lowest test concentration, and each test concentration was given for 2.5 minutes. Test at least 3 cells (n≥3) for each concentration.

4.4 Compound Processing 4.4.1 Dilute 20 mM mother liquor of the compound with extracellular fluid 5 μL of 20 mM mother liquor of the compound was added to 2495 μL extracellular fluid, and the mixture was 500-fold diluted to 40 μM. Then 0.2% DMSO in extracellular fluid was 3-fold diluted sequentially to obtain the final concentration to be tested.

4.4.2 The max test concentration was 40 μM, 6 concentrations were 40, 13.33, 4.44, 1.48, 0.49, and 0.16 μM respectively.

4.5 Data Analysis

Experimental data was analyzed by XLFit software.

4.6 Results

The IC50 values of the example compounds on hERG were shown in Table 4.2.

TABLE 4.2

Results of IC50 Values of the Example Compounds on hERG

| Test sample | hERG IC50 (μM) | Number of tests |
|---|---|---|
| Example 144 | >40 | N = 2 |
| Example 145 | >40 | N = 2 |
| Example 146 | >40 | N = 2 |
| Example 155 | >40 | N = 2 |
| Example 232 | >40 | N = 2 |
| Example 241 | >40 | N = 2 |

Conclusion: The compounds of the present invention have no inhibitory effects on the hERG potassium channel.

Example 5 In Vivo Pharmacodynamic Study of Compound on Human Small Cell Lung Cancer NCI-H1417 Cells Subcutaneous Xenograft Tumor CB-17 SCID Mouse Model 5.1 Experimental Purposes:

The purpose of this experiment was to investigate the efficacy of some of the compounds of the present invention in the in vivo xenograft tumor of human small cell lung cancer NCI-H1417 cells in a CB-17 SCID mouse model.

5.2 Experimental Animals:

Species: mice

Line: CB-17 SCID mice

Week age and weight: 6-8 weeks old, weight 18-23 g

Gender: Female

Supplier: Beijing Huakangkang Biotechnology Co., Ltd.

5.3 Experimental Methods and Procedures 5.3.1 Cell Culture

Human small cell lung cancer NCI-H1417 cells were cultured in vitro in a single layer cultured in RPMI-1640 medium (Sigma-aldrich, R0883), supplemented with 10% fetal bovine serum and cultured at 37° C. 5% CO$_2$. When the cell saturation is 80%-90%. The cells are harvested, counted, and inoculated.

5.3.2 Tumor Cell Inoculation 0.2 mL of 10×10$^6$ (NCI-H1417 cells were subcutaneously inoculated into the right back of each mouse (PBS:Matrigel=1:1). After 21 days of tumor inoculation, group administration was started when the average volume reached 107 mm$^3$.

5.3.3 Preparation of Test Materials

The experimental solvent was the 10% hydroxypropyl-β-cyclodextrin solution. The preparation method was as follows: 100 g of hydroxypropyl-β-cyclodextrin was weighed into a 1000 mL jar, 800 mL of ultrapure water was added, stirred overnight until completely dissolved, and then made up to 1000 mL. The test substance was dissolved in a solvent, and was prepared into a uniform solution of a certain concentration and stored at 4° C.

5.3.4 Tumor Measurement and Experimental Indicators

The experimental indicator is to investigate whether tumor growth is inhibited, delayed or cured. Tumor diameters were measured twice a week using vernier calipers. The tumor volume is calculated as: V=0.5a×b$^2$, and a and b represent the long and short diameters of the tumor, respectively.

The antitumor effect of the compound was evaluated by TG (%). TGI (%), reflecting the tumor growth inhibition rate. TGI (%) calculation: TGI (%)=[1−(the average tumor volume at the end of a treatment group−the average tumor volume at the beginning of the treatment group)/(the average tumor volume at the end of the treatment of the solvent control group−The average tumor volume at the start of treatment in the solvent control group) was ×100%. Solvent control: Vehicle (10% hydroxypropyl-β-cyclodextrin solution).

5.4 Experimental Results

TABLE 5.1

Anti-tumor efficacy evaluation of test compound in human small cell lung cancer NCI-H1417 xenograft model (Based on the tumor volume calculated on the 34th day after administration)

| Group | Tumor volume (mm³) (Day 34) | TGI (%) |
|---|---|---|
| Vehicle (10% hydroxypropyl-β-cyclodextrin solution) | 677 ± 39 | — |
| Example 167 (5 mg/kg, PO, QD) | 231 ± 28 | 78.2 |
| Example 167 (2.5 mg/kg, PO, BID) | 213 ± 37 | 81.4 |
| Cisplatin (1 mg/kg, ip, BIW) | 328 ± 37 | 61.2 |
| Cisplatin + Example 167 (1 mg/kg, ip, BIW + 1.5 mg/kg, PO, QD) | 143 ± 16 | 93.7 |
| Example 143 (5 mg/kg, PO, QD) | 145 ± 29 | 93.3 |
| Example 142 (5 mg/kg, PO, QD) | 136 ± 21 | 94.9 |

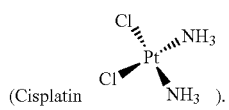

(Cisplatin).

TABLE 5.2

Evaluation of anti-tumor effect of test compound on human small cell lung cancer NCI-H1417 xenograft model (Based on tumor volume calculated on day 27 after administration)

| Group | Tumor volume (mm³) (Day 27) | TGI (%) |
|---|---|---|
| Vehicle | 524 ± 84 | — |
| Example 144 (1.5 mg/kg, PO, QD) | 180 ± 21 | 83.5 |
| Example 145 (1.5 mg/kg, PO, QD) | 250 ± 40 | 66.6 |
| Example 151 (1.5 mg/kg, PO, QD) | 250 ± 50 | 66.3 |
| Example 155 (1.5 mg/kg, PO, QD) | 200 ± 15 | 78.7 |
| Example 232 (1.5 mg/kg, PO, QD) | 313 ± 28 | 51.1 |

TABLE 5.3

Evaluation of anti-tumor effect of test compound on human small cell lung cancer NCI-H1417 xenograft model (Based on the calculation of tumor volume on the 28th day after administration)

| Group | Tumor volume (mm³) (Day 28) | TGI (%) |
|---|---|---|
| Vehicle | 543 ± 43 | — |
| Cisplatin (1 mg/kg, ip, BIW) | 150 ± 9 | 90 |
| Example 241 (1.5 mg/kg, PO, QD) | 251 ± 35 | 66 |
| Example 241 (5 mg/kg, PO, QD) | 61 ± 10 | 110 |
| Cisplatin + Example 241 (1 mg/kg, ip, BIW + 0.5 mg/kg, PO, QD) | 118 ± 8 | 97 |

Conclusion: The compounds of the present invention had an excellent antitumor effect on the human small cell lung cancer NCI-H1417 xenograft model.

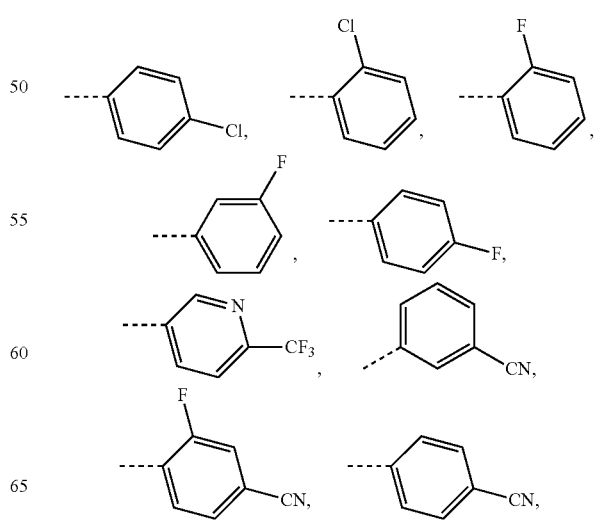

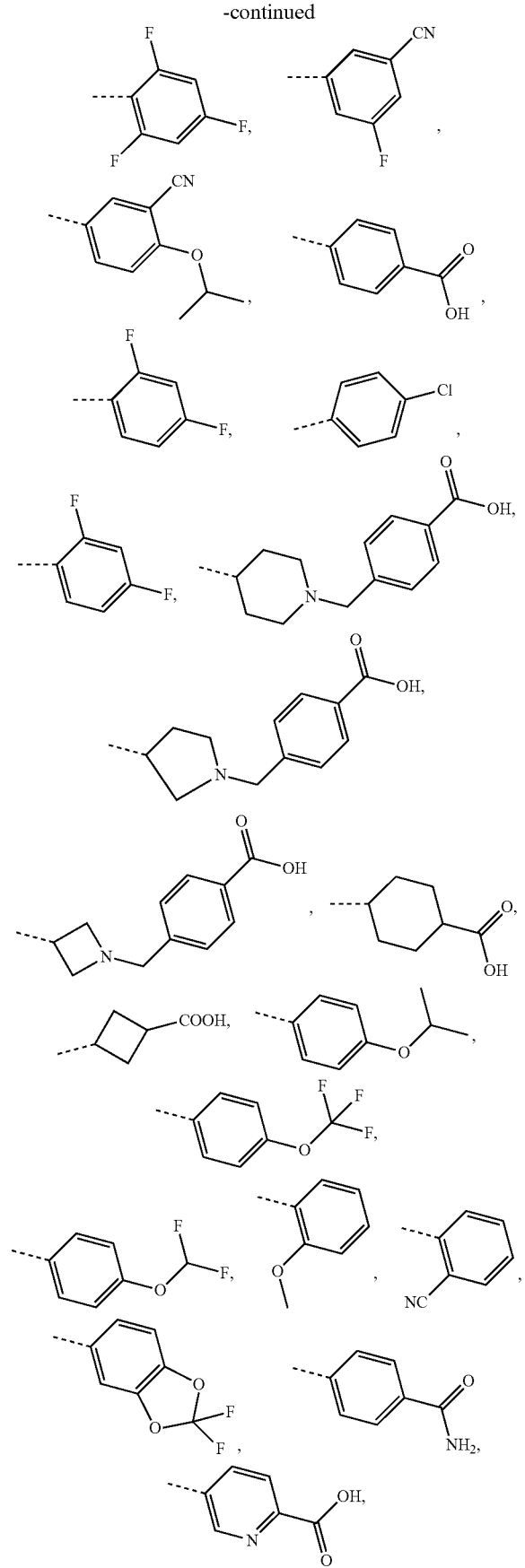
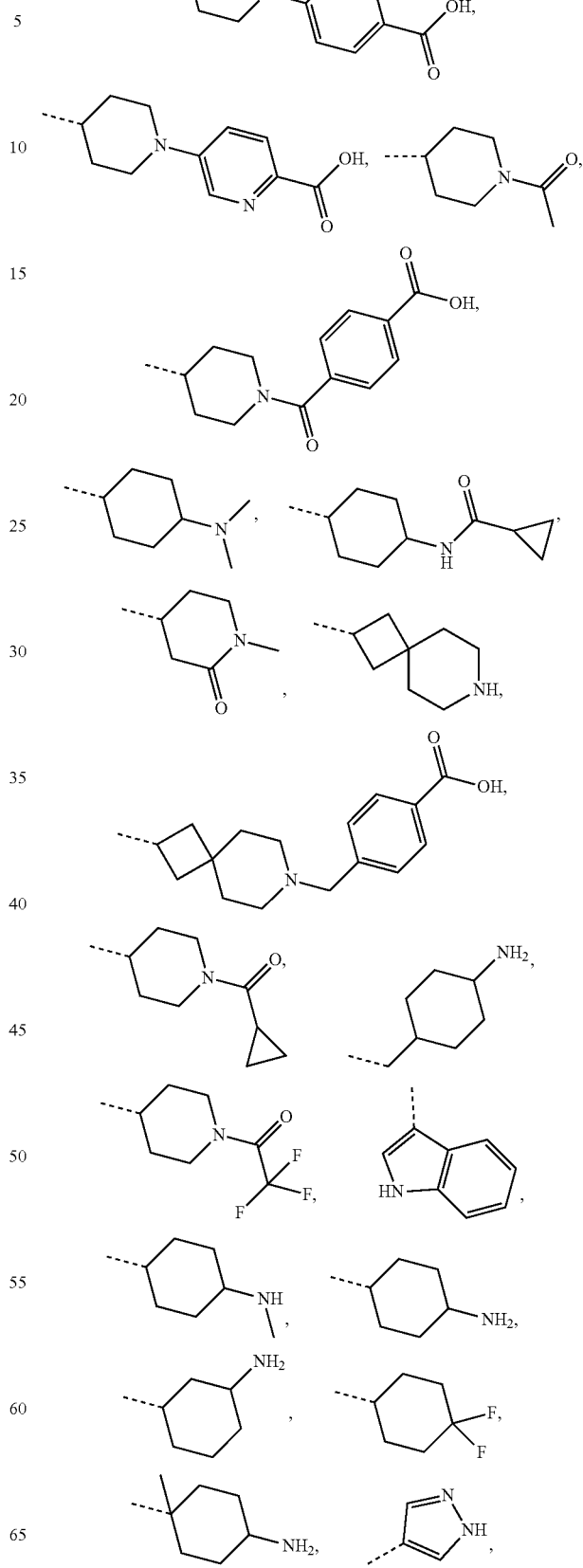

495
-continued
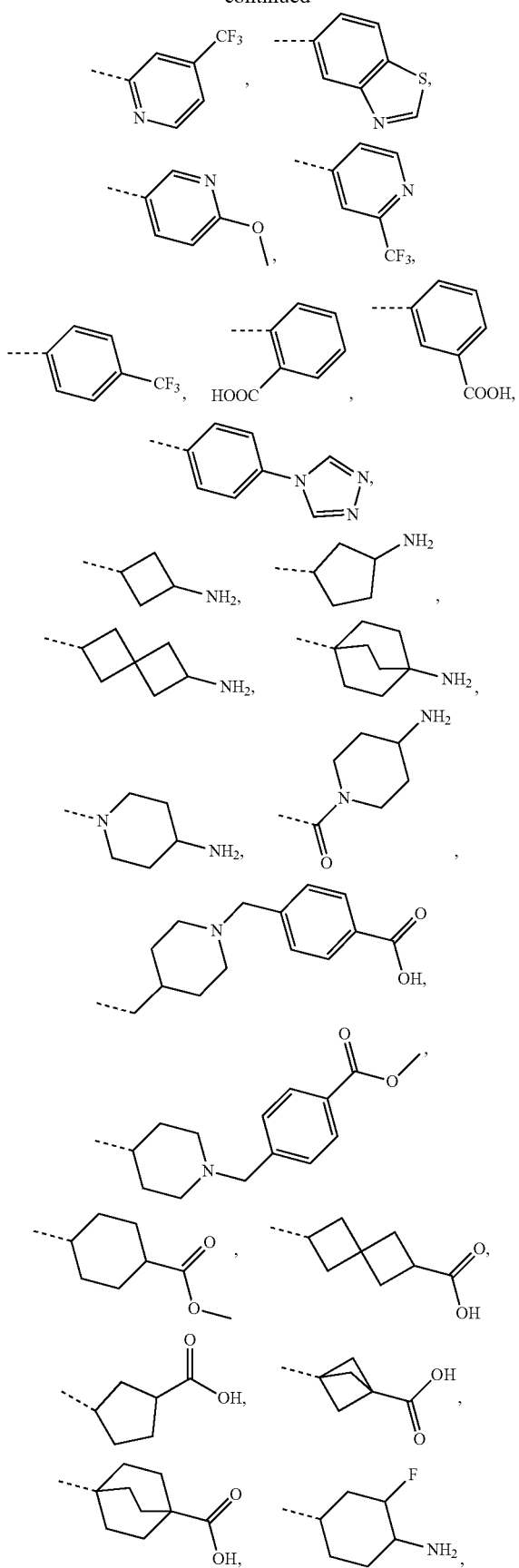
496
-continued
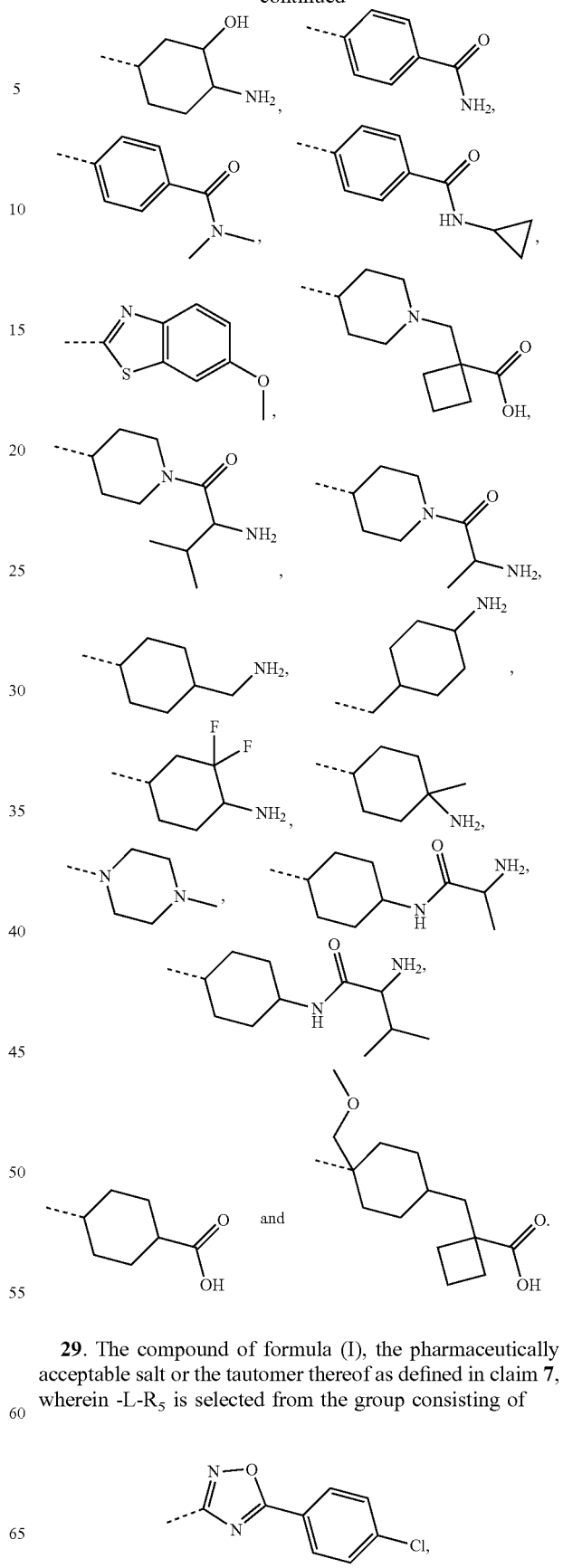
29. The compound of formula (I), the pharmaceutically acceptable salt or the tautomer thereof as defined in claim 7, wherein -L-R$_5$ is selected from the group consisting of 497
-continued
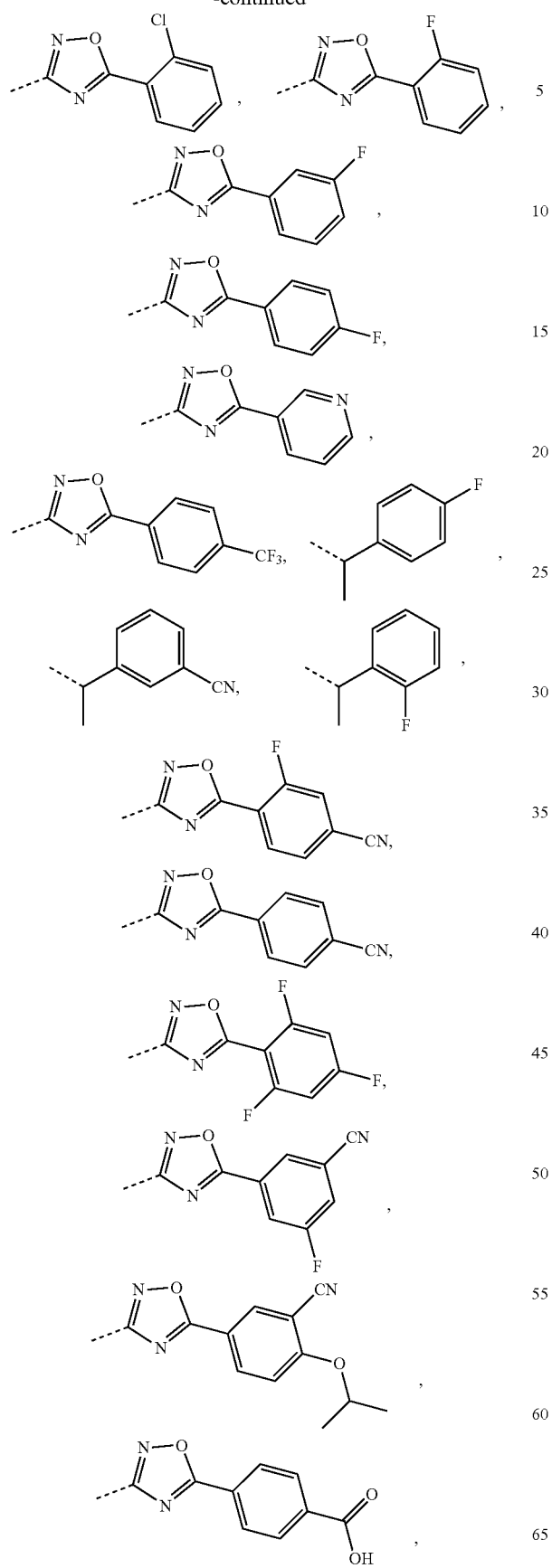
498
-continued
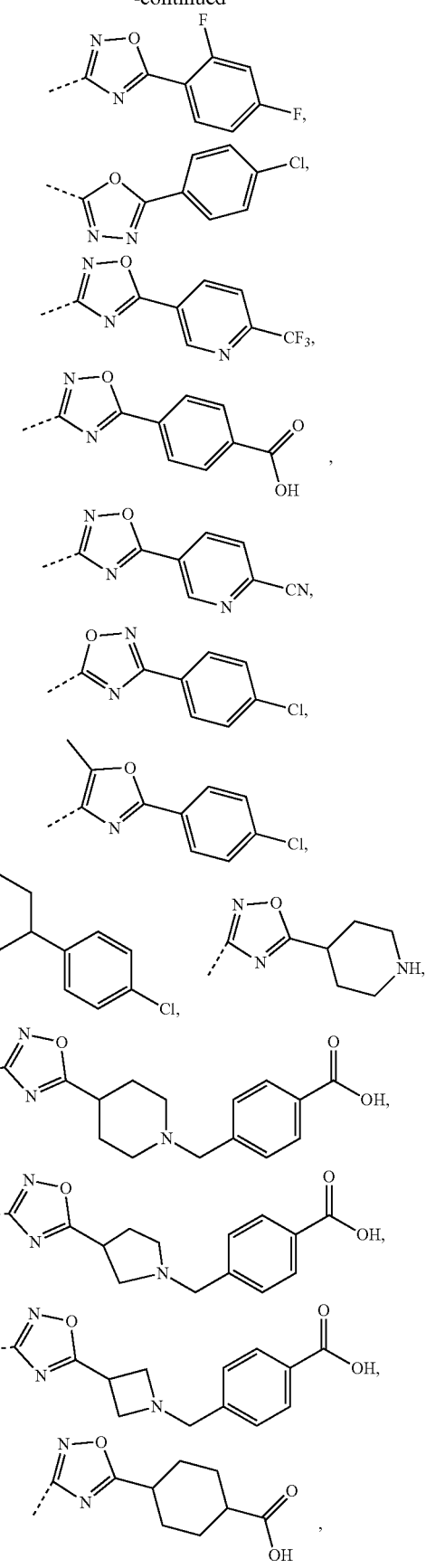

499
-continued
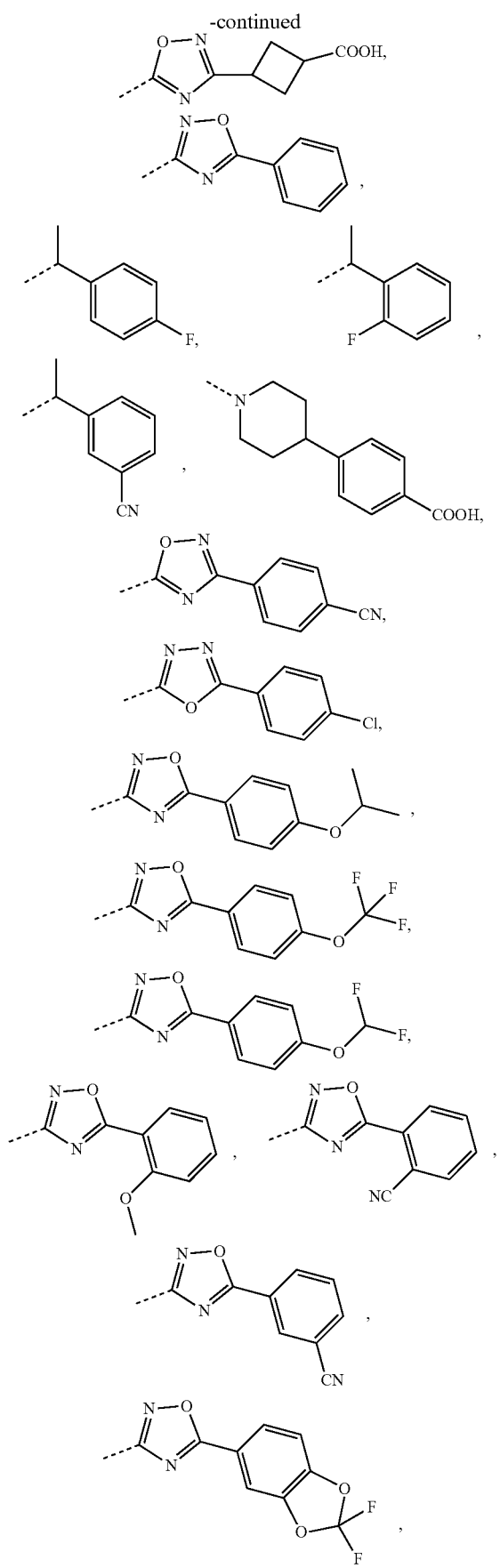
500
-continued
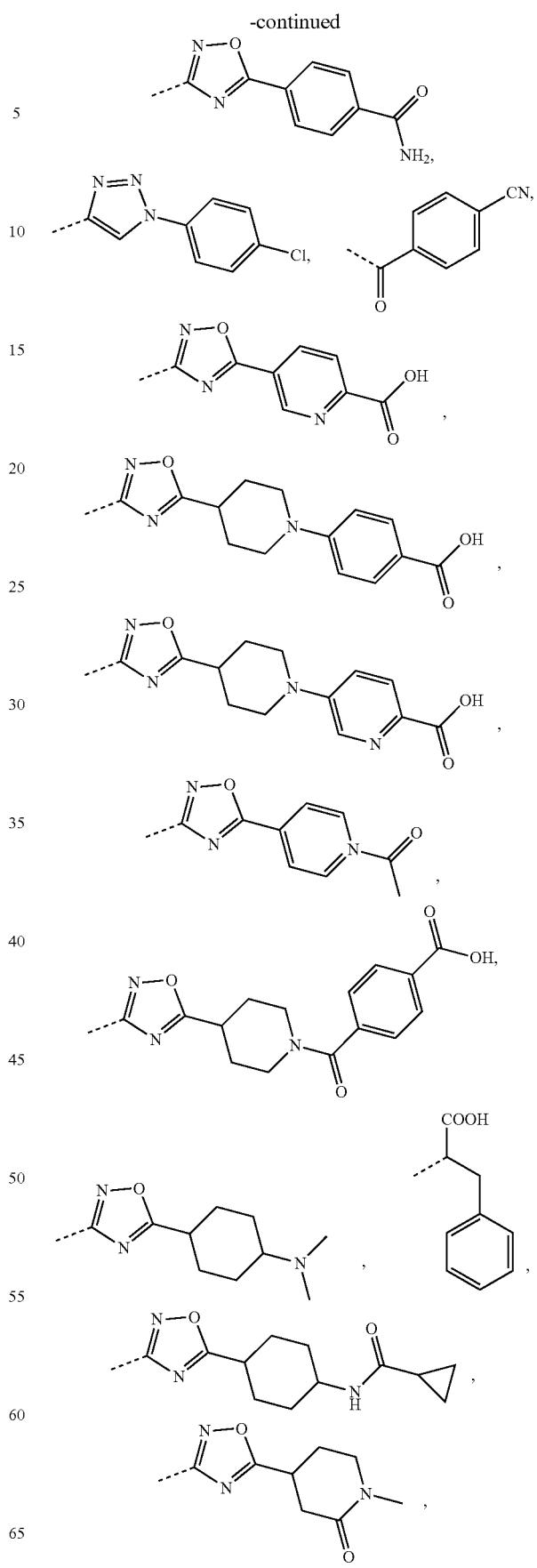

501
-continued
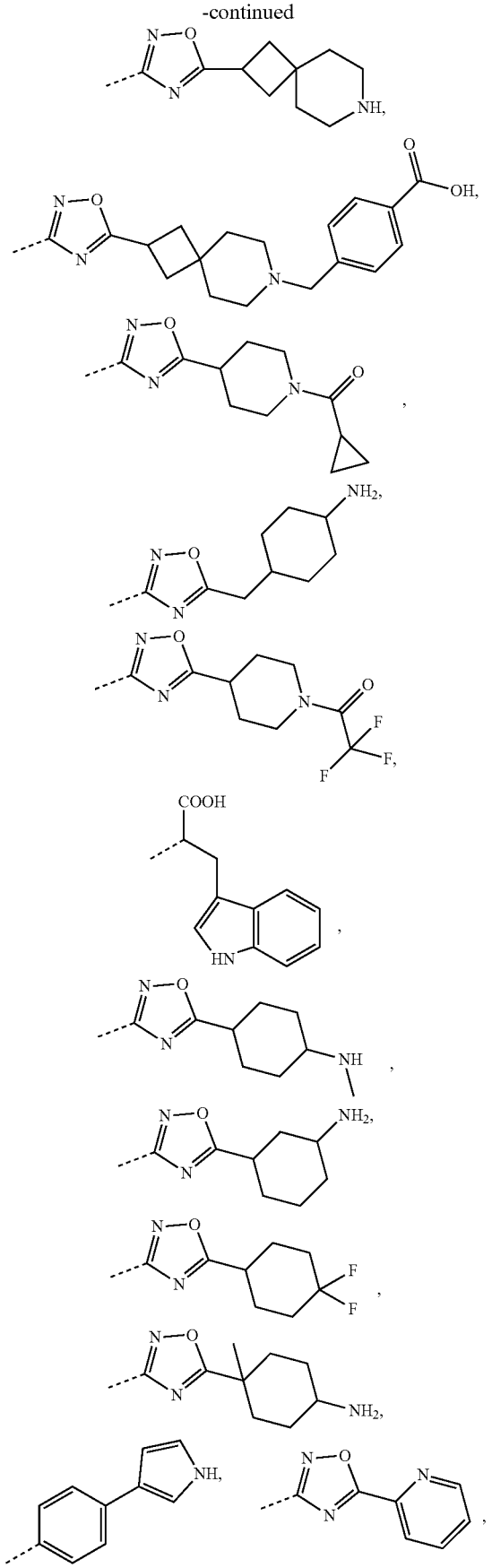
502
-continued
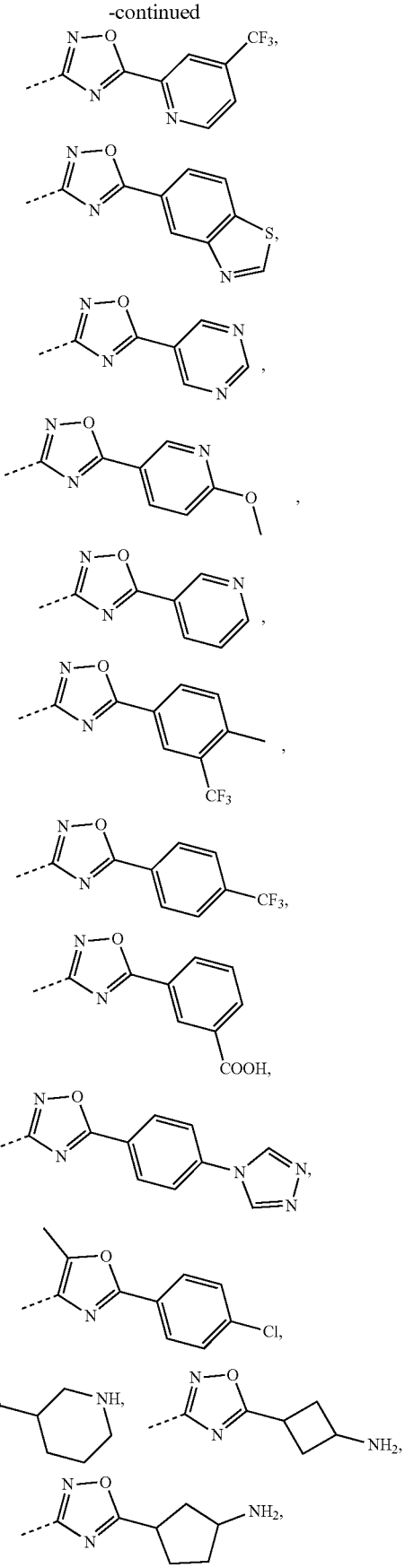

503
-continued
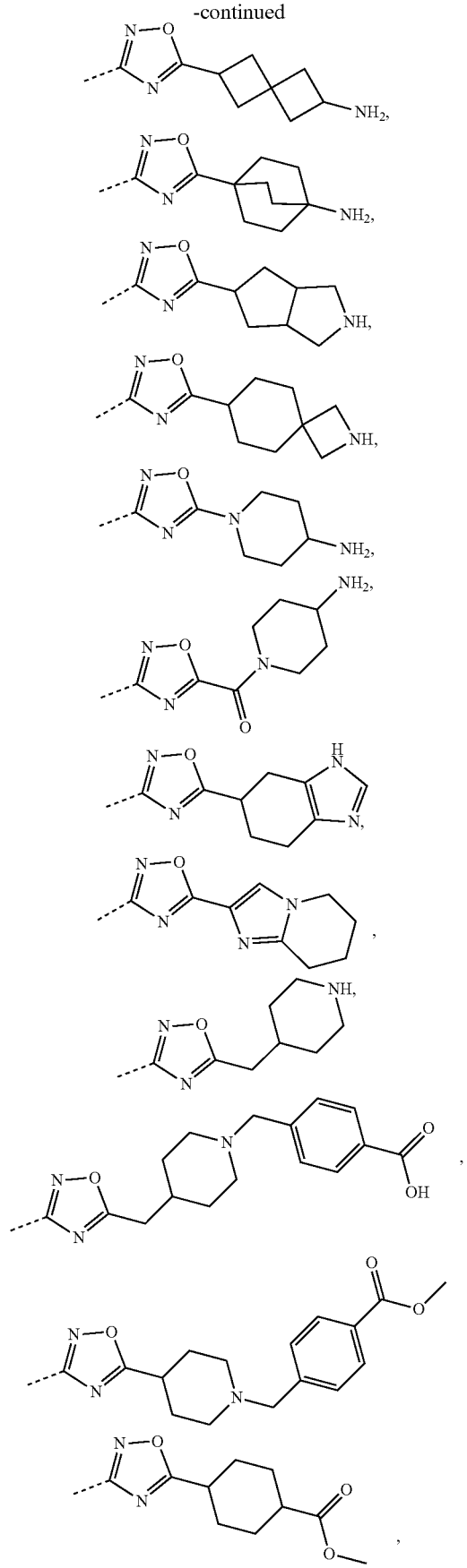
504
-continued
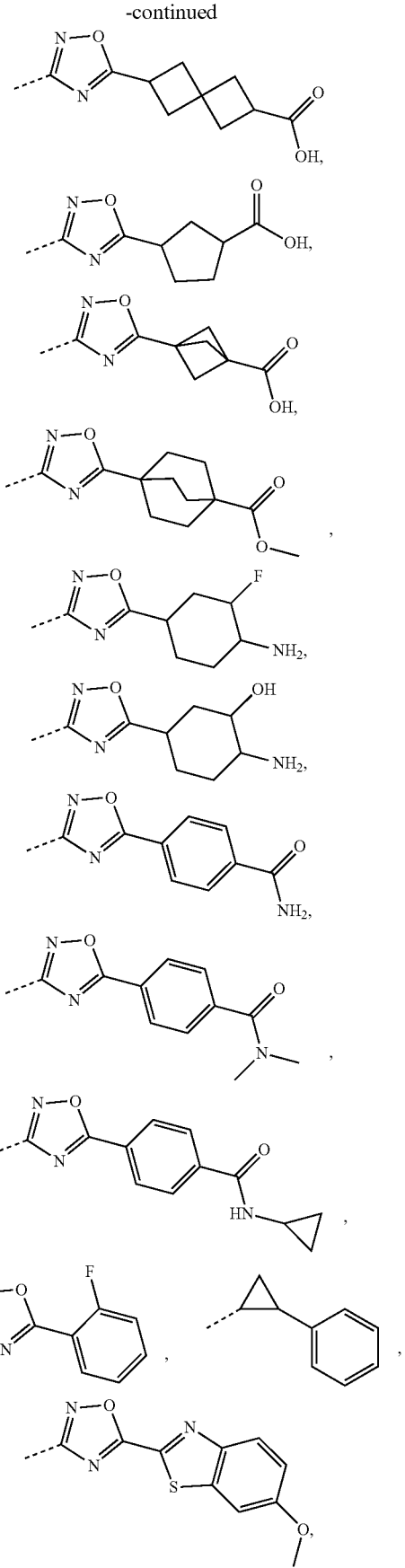

505
-continued
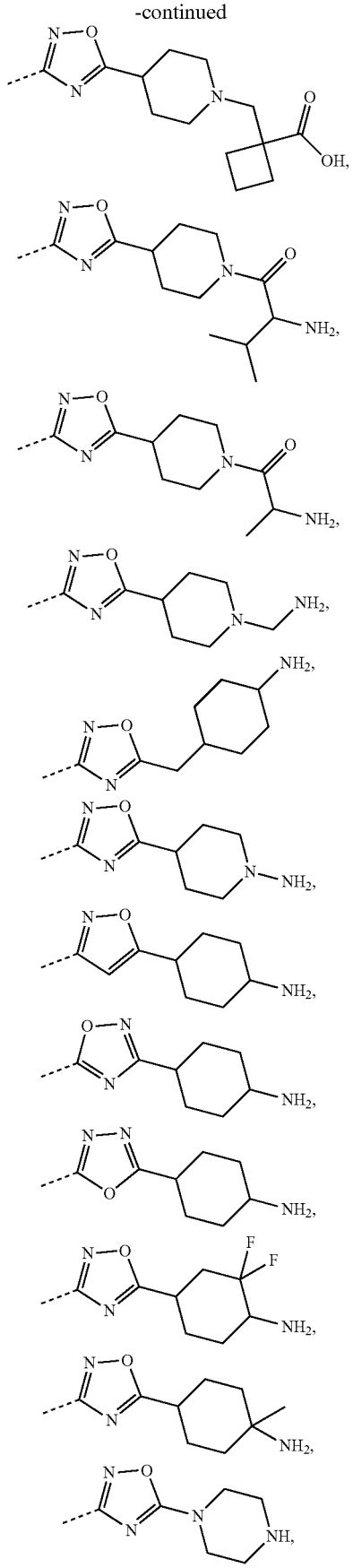
506
-continued
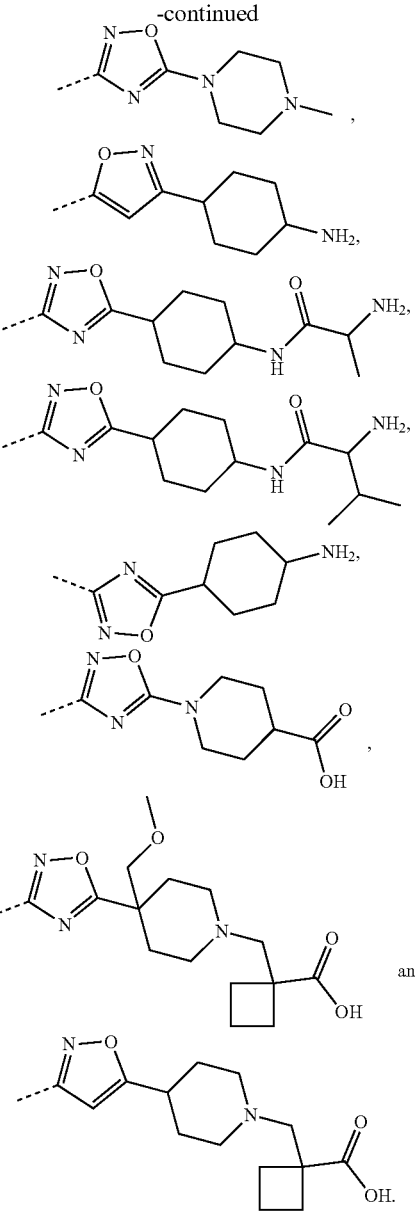
30. The compound of formula (I), the pharmaceutically acceptable salt or the tautomer thereof as defined in claim 8, wherein $R_3$ is selected from the group consisting of
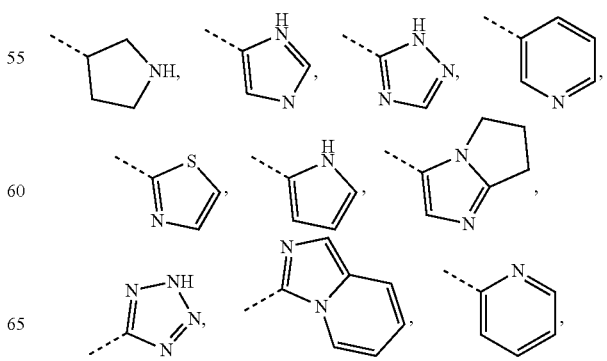

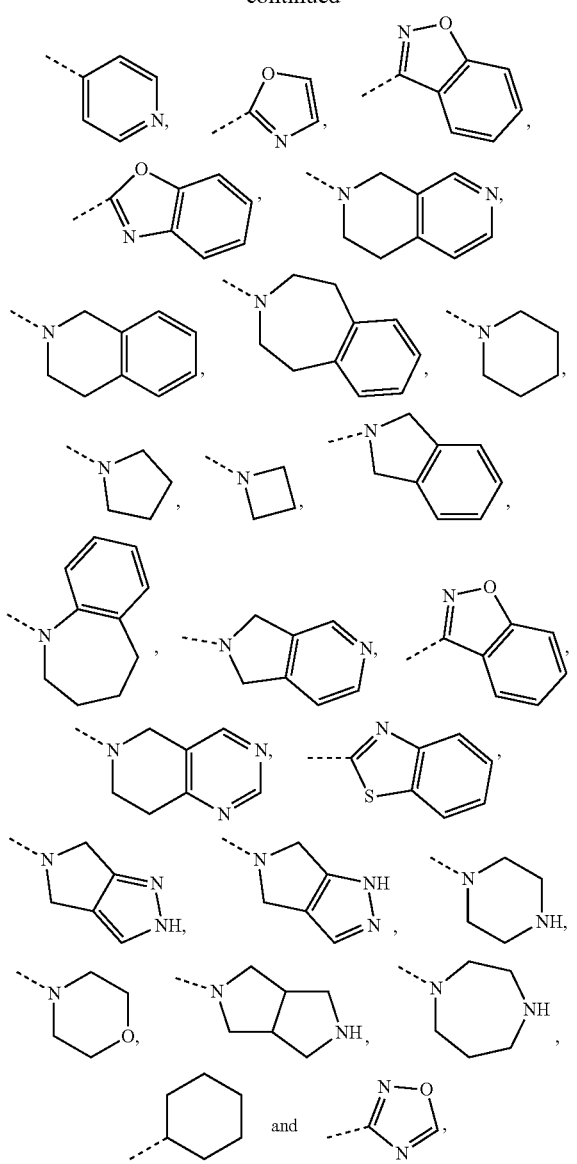
or, R₃ is selected from the group consisting of
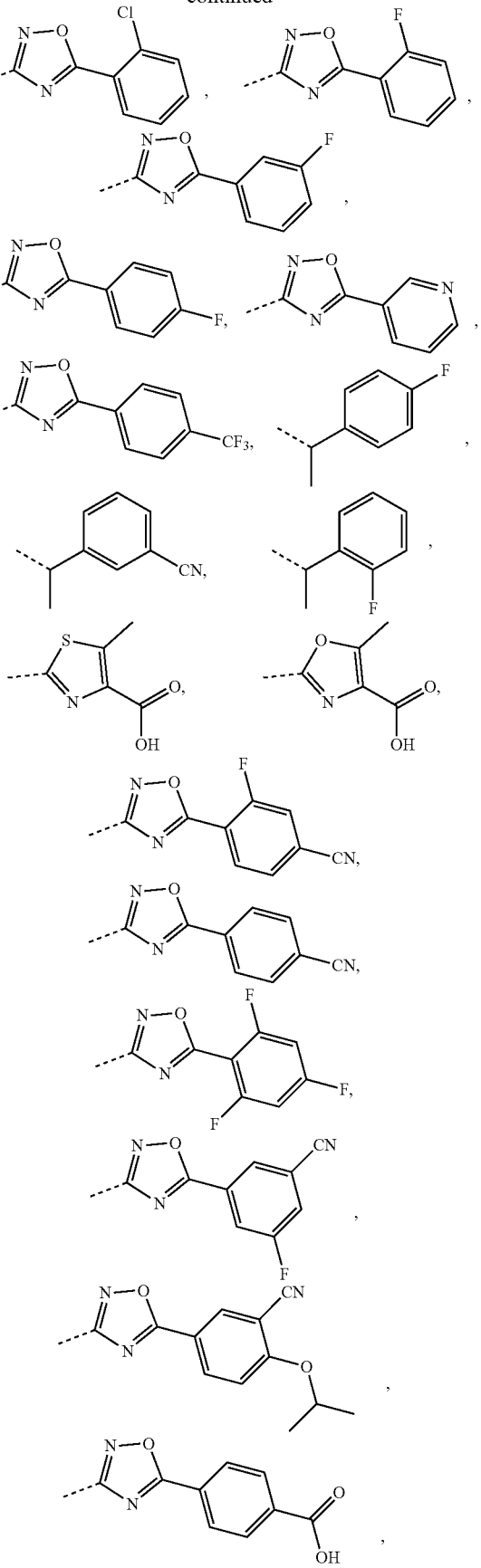

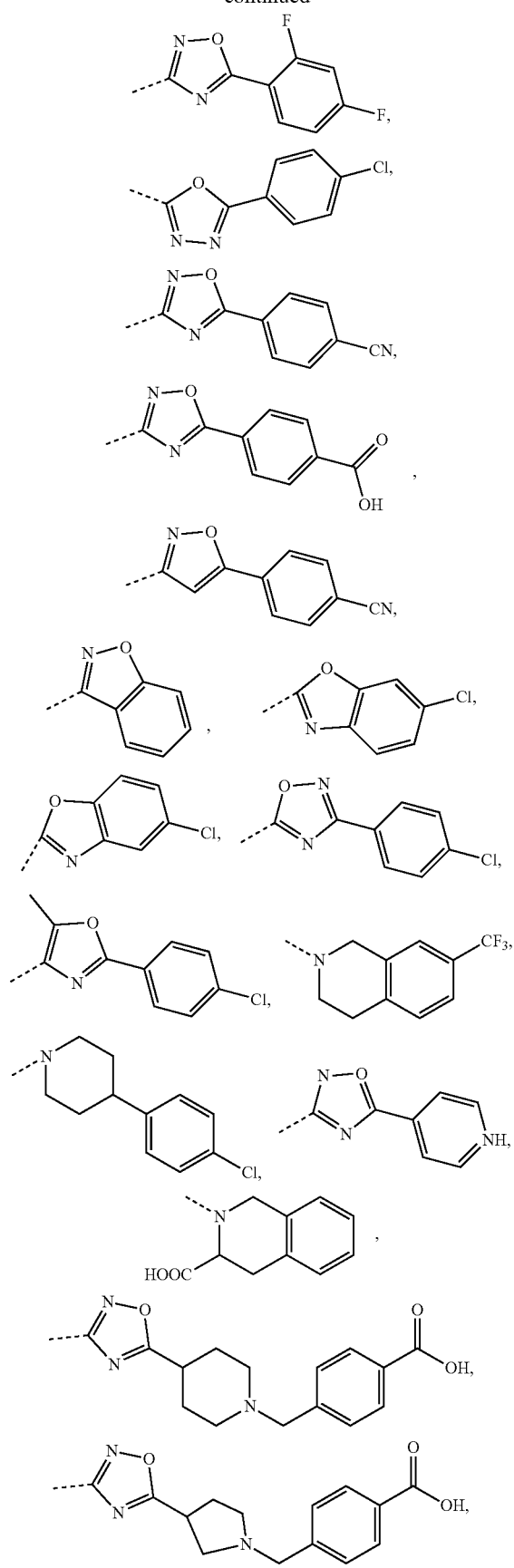
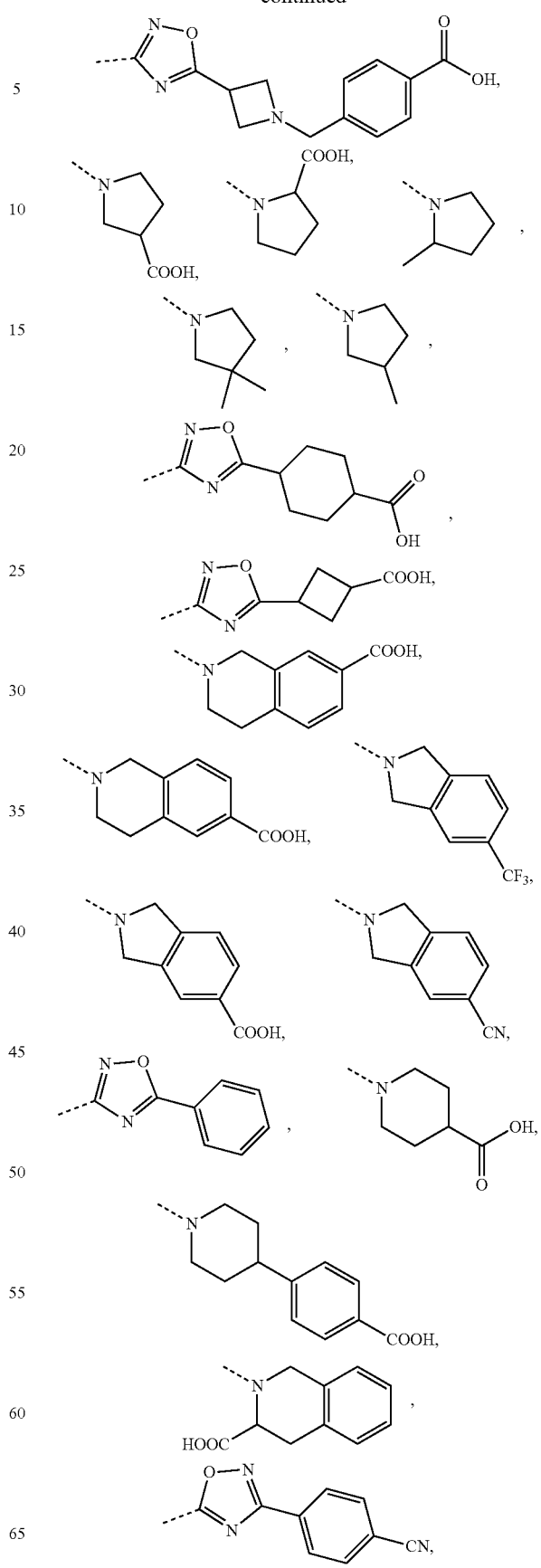

511
-continued
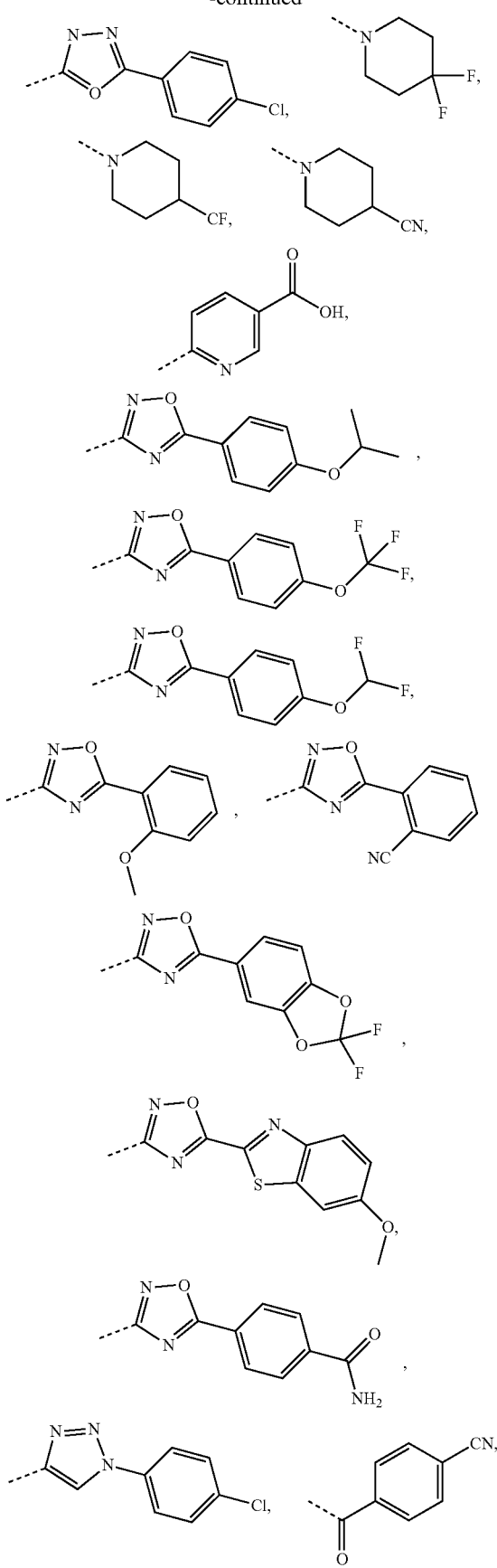
512
-continued
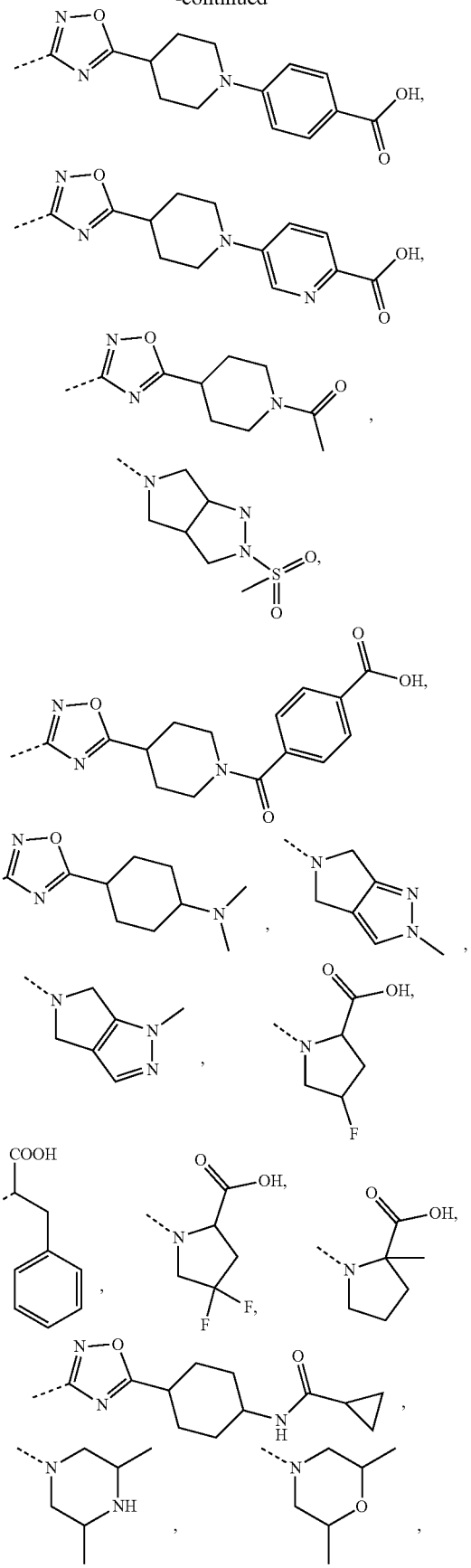

513
-continued
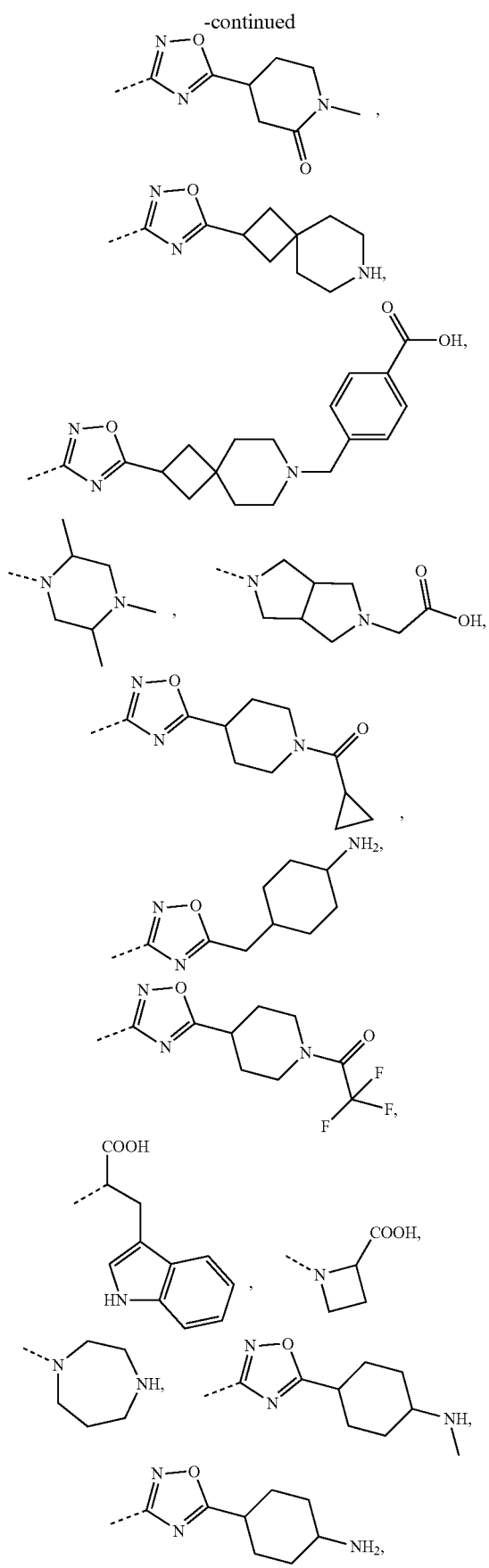
514
-continued
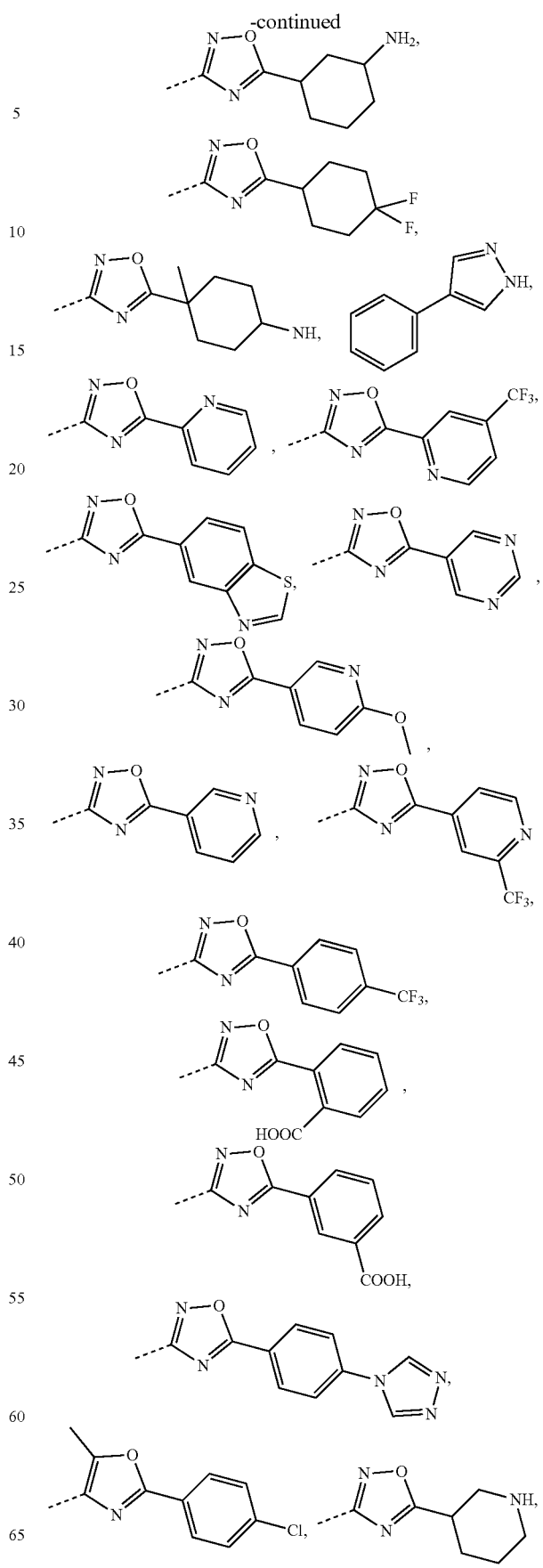

-continued
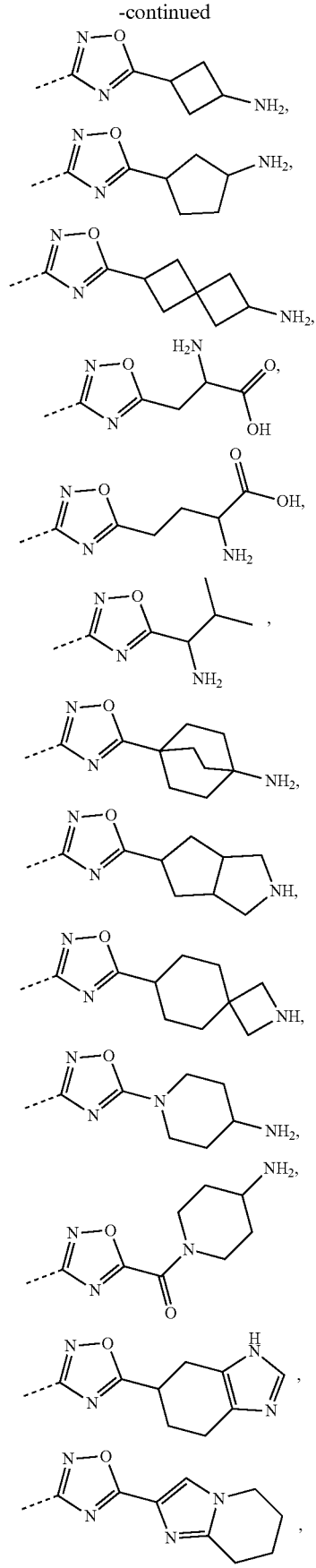
-continued
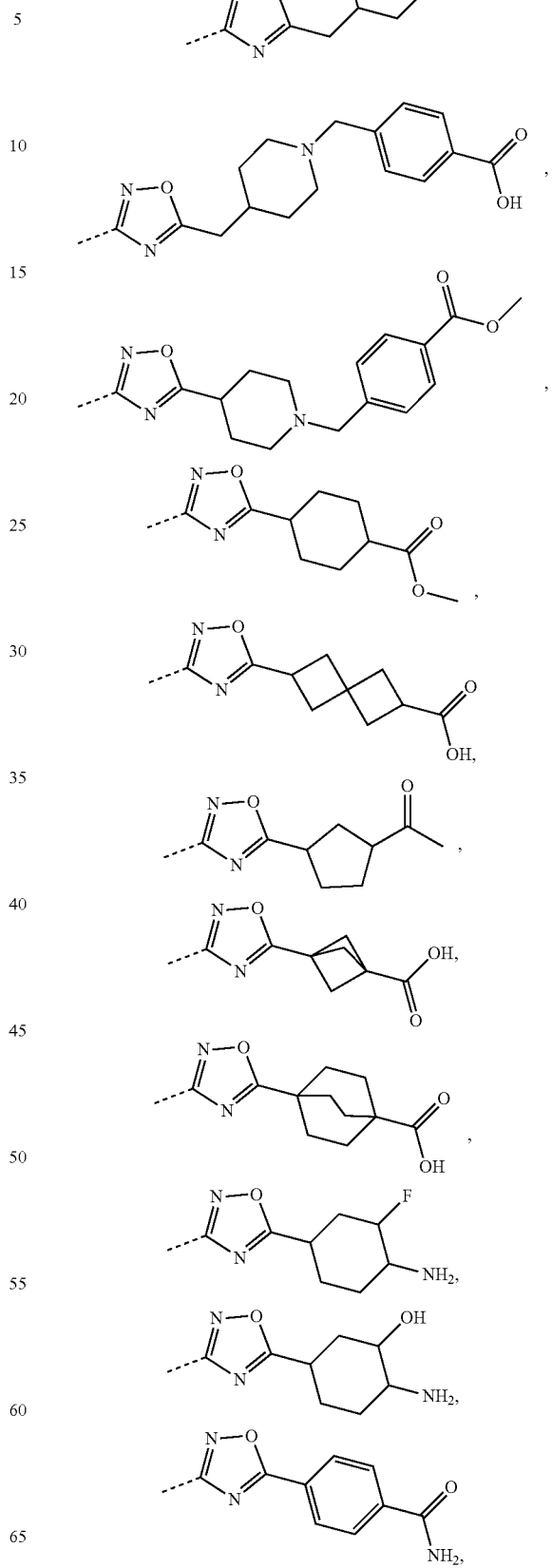

517
-continued
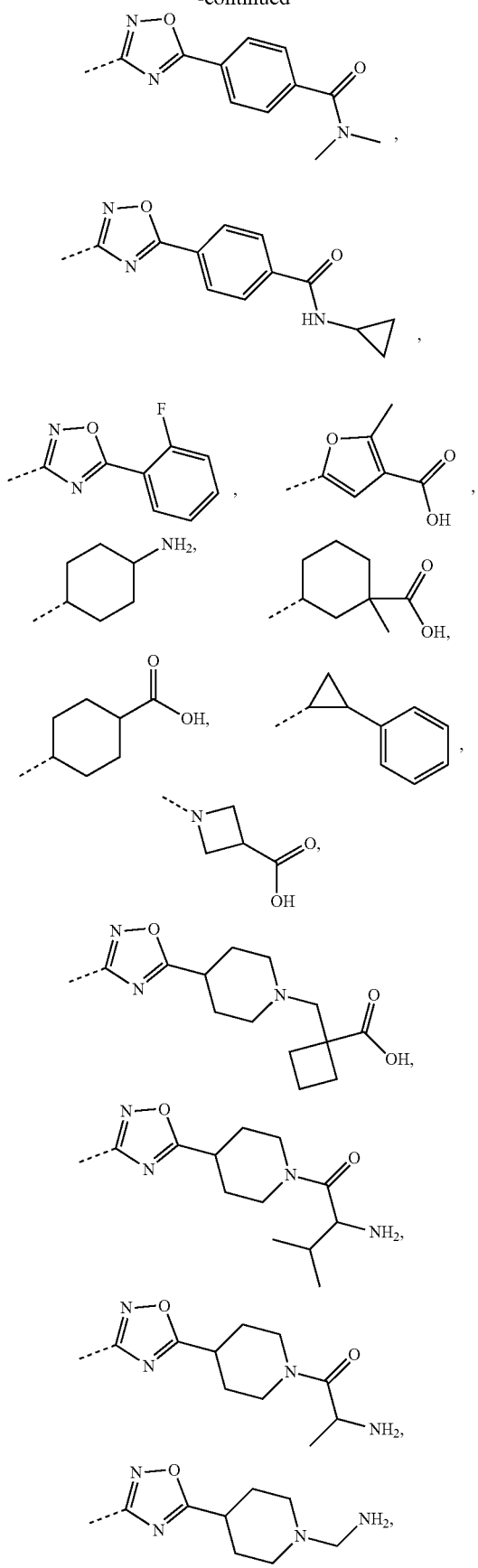
518
-continued
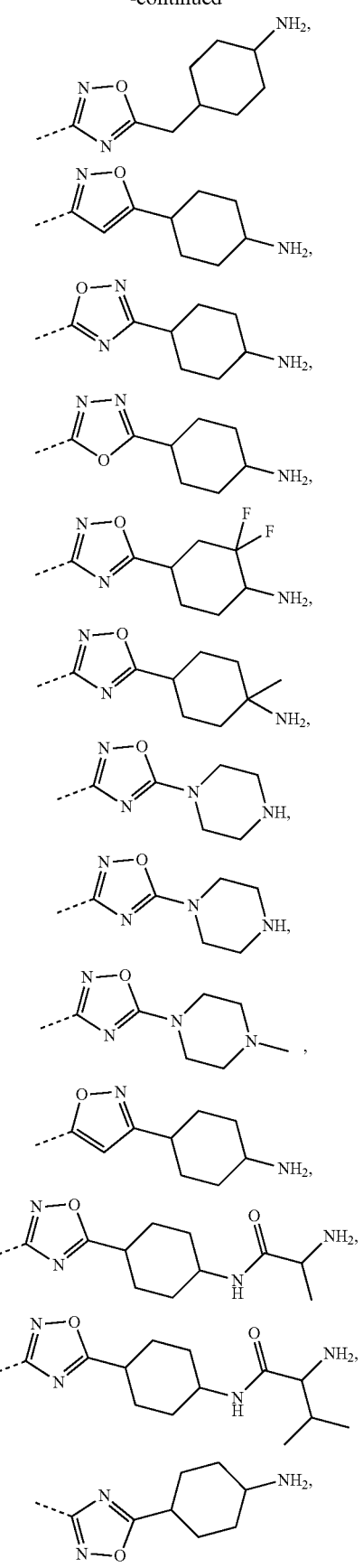

-continued
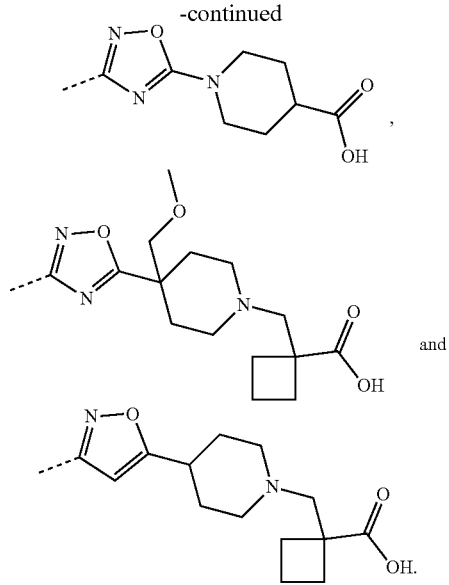

What is claimed is:

1. A compound of formula (I), a pharmaceutically acceptable salt thereof or a tautomer thereof,

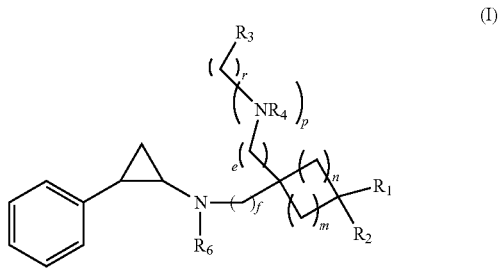

wherein,
f is 1 or 2;
r is 0, 1 or 2;
e is 0, 1, or 2;
p is 0 or 1;
m is 0, 1 or 2; n is 1 or 2; or the structural unit

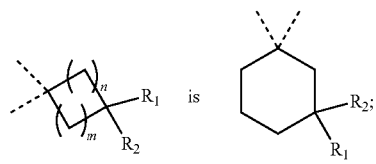

each of $R_1$ and $R_2$ is independently selected from the group consisting of H, F, Cl, Br, I, OH, CN, $NH_2$ and —COOH, or is a $C_{1-3}$ alkyl optionally substituted by 1, 2 or 3 of R; or, $R_1$ and $R_2$ are connected together to form a 3-6-membered ring;
$R_3$ is -L-$R_5$, or selected from the group consisting of a 5-12 membered heteroaryl, a $C_{3-7}$ cycloalkyl and a 4-8 membered heterocycloalkyl, each of which is optionally substituted by 1, 2 or 3 of R;
$R_4$ is H, or selected from the group consisting of a $C_{1-6}$ alkyl and a $C_{1-6}$ heteroalkyl, each of which is optionally substituted by 1, 2 or 3 of R;
$R_5$ is selected from the group consisting of cyclohexyl-$CH_2$—, phenyl, a 5-10 membered heteroaryl, a $C_{3-10}$ cycloalkyl, a 4-10 membered heterocycloalkyl, a 5-6 membered heterocycloalkyl-C(=O)— and a 5-6 membered heterocycloalkyl-$C_{1-3}$ alkyl-, each of which is optionally substituted by 1, 2 or 3 of R;
$R_6$ is H, or selected from the group consisting of a $C_{1-6}$ alkyl and a $C_{1-6}$ heteroalkyl, each of which is optionally substituted by 1, 2 or 3 of R;
L is —C(=O)—, or selected from the group consisting of —$C_{1-6}$ alkyl- and -5-9 membered heteroaryl-, -4-8 membered heterocycloalkyl-, -phenyl- and —$C_{3-6}$ cycloalkyl-, each of which is optionally substituted by 1, 2 or 3 of R;
R is selected from the group consisting of H, F, Cl, Br, I, OH, $NH_2$, CN, —COOH and $NH_2$—C(=O)—, or selected from the group consisting of $C_{1-6}$ alkyl, $C_{1-6}$ heteroalkyl, phenyl-$C_{1-6}$ alkyl-, phenyl, 5-6 membered heteroaryl, phenyl-C(=O)—, $C_{3-6}$ cycloalkyl-C(=O)—, $C_{3-6}$ cycloalkyl-C(=O)—NH, $C_{3-6}$ cycloalkyl-NH—C(=O)— and $C_{3-6}$ cycloalkyl-$C_{1-3}$ alkyl-, each of which is optionally substituted by 1, 2 or 3 of R';
R' is selected from the group consisting of F, Cl, Br, I, OH, $NH_2$, COOH, $C_{1-3}$ alkyl, $C_{1-3}$ alkyl substituted by 1-3 halogen(s), $C_{1-3}$ alkyl-NH—, N,N-di($C_{1-3}$ alkyl)-amino, $C_{1-3}$ alkyl-O—C(=O)—, $C_{3-6}$ cycloalkyl and $C_{1-3}$ alkoxyl;

each of the "hetero" in the 5-12 membered heteroaryl, 4-8 membered heterocycloalkyl, $C_{1-6}$ heteroalkyl, 5-10 membered heteroaryl, 5-6 membered heteroaryl, 5-6 membered heterocycloalkyl, 4-10 membered heterocycloalkyl is independently selected from the group consisting of —NH—, —S—, N, —O—, =O, —C(=O)—, —NH—C(=O)—, —O—C(=O)—, —S(=O)$_2$—, —S(=O)—, —C(=O)—NH—;

in any above cases, the number of the heteroatom or the heteroatomic group in the 5-12 membered heteroaryl, 4-8 membered heterocycloalkyl, $C_{1-6}$ heteroalkyl, 5-10 membered heteroaryl, 5-6 membered heteroaryl, 5-6 membered heterocycloalkyl, 4-10 membered heterocycloalkyl is independently 1, 2, 3 or 4.

2. The compound of formula (I), the pharmaceutically acceptable salt or the tautomer thereof as defined in claim 1, wherein R' is selected from the group consisting of F, Cl, Br, I, OH, $NH_2$, Me, Et, $CF_3$, $CHF_2$, $CH_2F$, $NHCH_3$, $N(CH_3)_2$, COOH, —C(=O)—O—$CH_3$, —O—$CH_3$ and

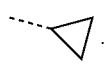

3. The compound of formula (I), the pharmaceutically acceptable salt or the tautomer thereof as defined in claim 1, wherein R is selected from the group consisting of H, F, Cl, Br, I, OH, $NH_2$, CN, COOH, $NH_2$—C(=O)—, or selected from the group consisting of methyl, ethyl, propyl, isobutyl, tert-butyl, $C_{1-6}$ alkoxyl, phenyl-$C_{1-3}$ alkyl-, phenyl, pyridyl, 1,2,4-triazolyl, phenyl-C(=O)—, $C_{1-3}$ alkyl-C(=O)—, $C_{1-3}$ alkyl-NH—, cyclopropyl-C(=O)—, $C_{1-3}$ alkyl-O—C(=O)—$C_{1-3}$ alkyl-, $C_{1-3}$ alkyl-O—C(=O)—, $C_{1-3}$ alkyl-S(=O)$_2$—, cyclopropyl-C(=O)—NH—, cyclopropyl-NH—C(=O)—, $C_{1-3}$ alkyl-NH—C(=O)—, cyclobutane-$CH_2$— and $C_{1-3}$ alkyl-C(=O)—NH—, each of which is optionally substituted by 1, 2 or 3 of R'.

4. The compound of formula (I), the pharmaceutically acceptable salt or the tautomer thereof as defined in claim 1, wherein each of $R_1$ and $R_2$ is independently selected from the group consisting of H, F, Cl, Br, I, OH, CN, $NH_2$, —COOH, Me and Et.

5. The compound of formula (I), the pharmaceutically acceptable salt or the tautomer thereof as defined in claim 1, wherein L is —C(=O)—, or selected from the group consisting of -1,2,4-oxadiazolyl-, -methylene-, -ethyl-, -1,3,4-oxadiazolyl-, -isoxazolyl-, -oxazolyl-, -piperidyl-, -1,2,3-triazolyl-, -cyclopropanyl- and -phenyl-, each of which is optionally substituted by 1, 2 or 3 of R.

6. The compound of formula (I), the pharmaceutically acceptable salt or the tautomer thereof as defined in claim 1, wherein $R_5$ is selected from the group consisting of phenyl, pyridyl, piperidinyl, pyrrolidinyl, azetidinyl, cyclohexyl, cyclobutyl, benzo[d][1,3] m-dioxacyclopentenyl, piperidyl-2-keto, 7-azaspiro[3.5]nonyl, cyclohexyl-$CH_2$—, 3a,7a-dihydro-1H-indolyl, pyrazolyl, 3a,7a-dihydrobenzo[d]thiazolyl, pyrimidinyl, cyclopentyl, spiro[3.3]heptanyl, bicyclo[2.2.2]octyl, octahydrocyclopenta[c]pyrrolyl, 2-azaspiro[3.5]nonyl, piperidinyl-C(=O)—, 4,5,6,7-tetrahydro-1H-benzo [d]imidazolyl, 5,6,7,8-tetrahydroimidazo[1,2-a]pyridyl, piperidinyl-$CH_2$—, bicyclo[1.1.1]pentyl and piperazinyl, each of which is optionally substituted by 1, 2 or 3 of R.

7. The compound of formula (I), the pharmaceutically acceptable salt or the tautomer thereof as defined in claim 5, wherein -L-$R_5$ is selected from the group consisting of

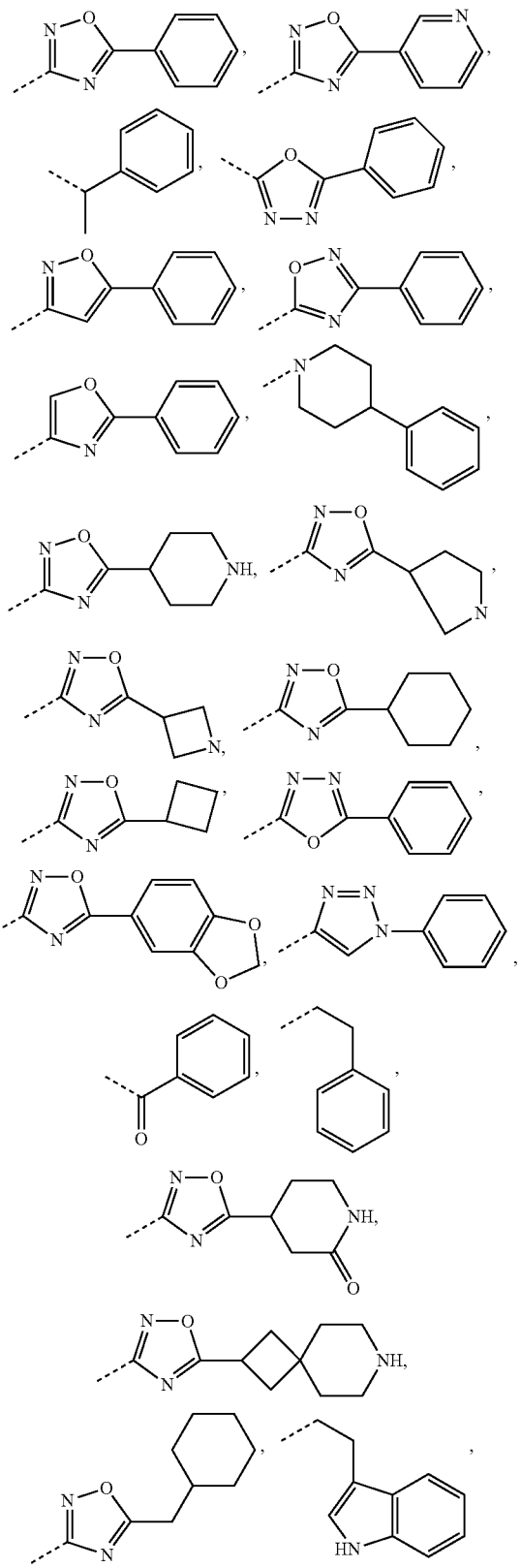

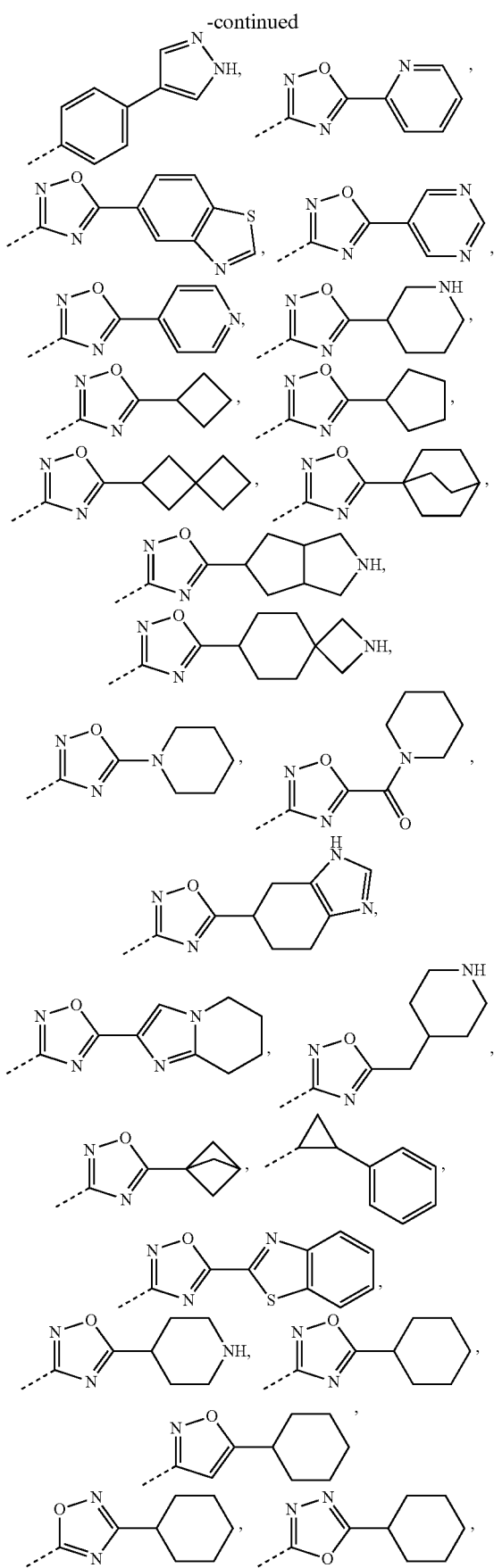

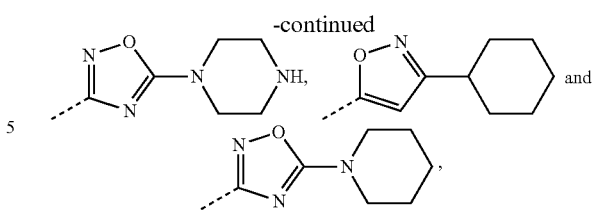

each of which is optionally substituted by 1, 2 or 3 of R.

8. The compound of formula (I), the pharmaceutically acceptable salt or the tautomer thereof as defined in claim 1, wherein $R_3$ is -L-$R_5$, or selected from the group consisting of pyrrolidinyl, 1H-imidazolyl, 1H-1,2,4-triazolyl, pyridyl, thiazolyl, thienyl, pyrrolyl, 2H-tetrazolyl, 6,7-dihydro-5H-pyrrolo[1,2-a]imidazolyl, imidazo[1,5-a]pyridyl, oxazolyl, benzo[d]isoxazolyl, benzo[d]oxazolyl, 1,2,3,4-4H-2,7-naphthyridinyl, 1,2,3,4-tetrahydroisoquinolinyl, 2,3,4,5-tetrahydro-1H-benzo[d]azepinyl, azetidinyl, isoindolyl, piperidinyl, 2,3,4,5-tetrahydro-1H-benzo [b]azepinyl, 2,3-dihydro-1H-pyrrolo [3,4-c]pyridyl, benzoisoxazolyl, 5,6,7,8-tetrahydropyridopyrimidinyl, 3a,7a-dihydrobenzo[d] thiazolyl, 2,4,5,6-tetrahydropyrrolo[3,4-c]pyrazolyl, 1,4,5,6-tetrahydropyrrolo[3,4-c]pyrazolyl, piperazinyl, morpholinyl, octahydropyrrolo[3,4-c]pyrrolyl, 1,4-diazepine, cyclohexyl and 1,2,4-oxadiazolyl, each of which is optionally substituted by 1, 2 or 3 of R.

9. The compound of formula (I), the pharmaceutically acceptable salt or the tautomer thereof as defined in claim 1, wherein $R_4$ is selected from the group consisting of H, Me, Et and

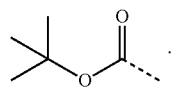

10. The compound of formula (I), the pharmaceutically acceptable salt or the tautomer thereof as defined in claim 1, wherein $R_6$ is selected from the group consisting of H, Me, Et and

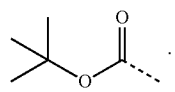

11. The compound of formula (I), the pharmaceutically acceptable salt or the tautomer thereof as defined in claim 1, wherein the structural unit

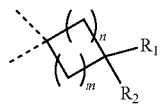

is selected from the group consisting of

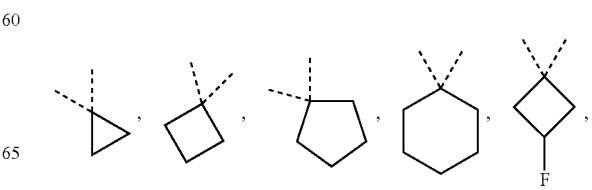

-continued

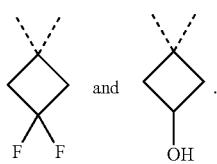

and

12. The compound of formula (I), the pharmaceutically acceptable salt or the tautomer thereof as defined in claim 1, which is selected from the group consisting of (I-1)
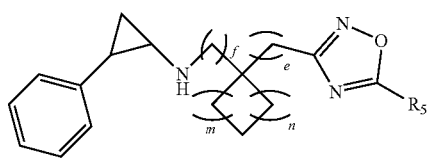

(I-2)
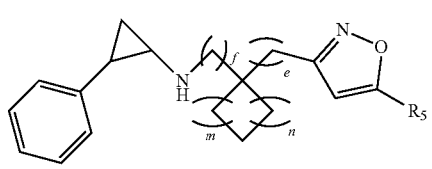

(I-3)
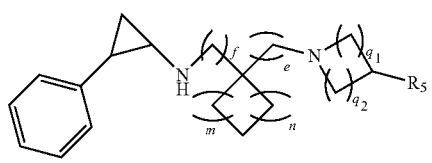

(I-4)
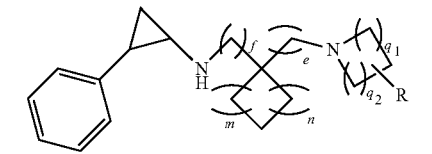

(I-5)
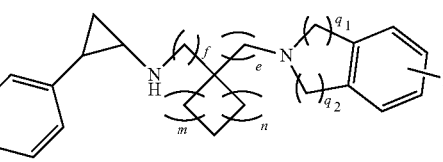

(I-6)
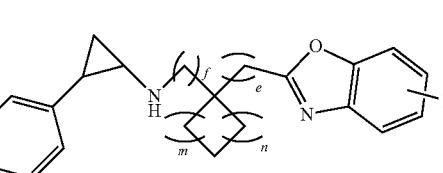

(I-7)
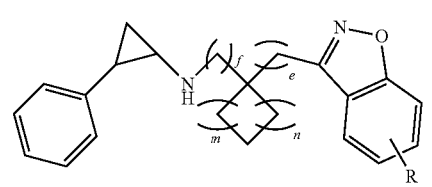

-continued (I-8)
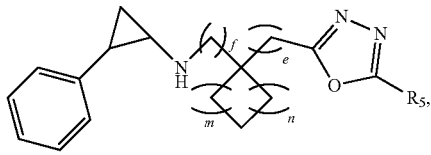

wherein, e, f, m and n are as defined in claim 1;

R is as defined in claim 1;

$R_5$ is as defined in claim 1;

each of $q_1$ and $q_2$ is independently 1 or 2.

13. A compound, pharmaceutically acceptable salt or tautomer thereof selected from the group consisting of

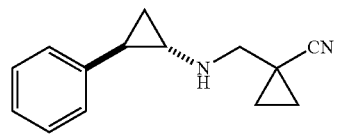

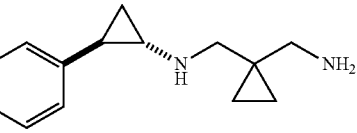

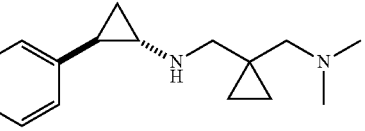

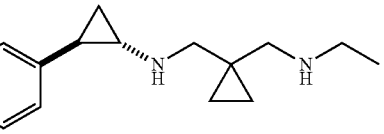

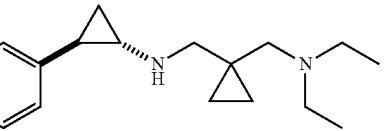

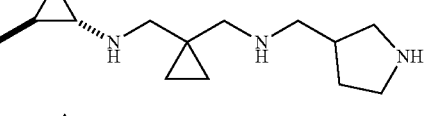

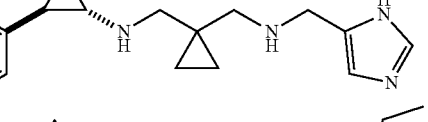

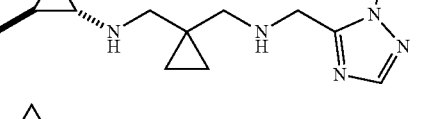

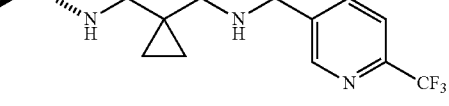

463
-continued
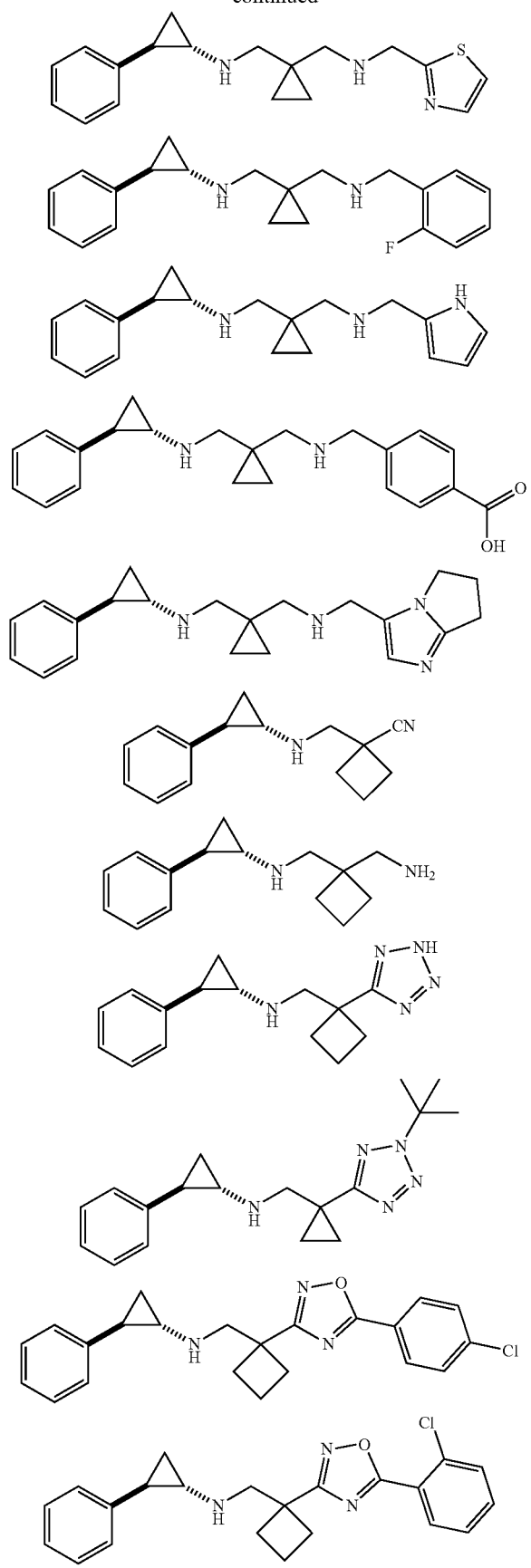
464
-continued
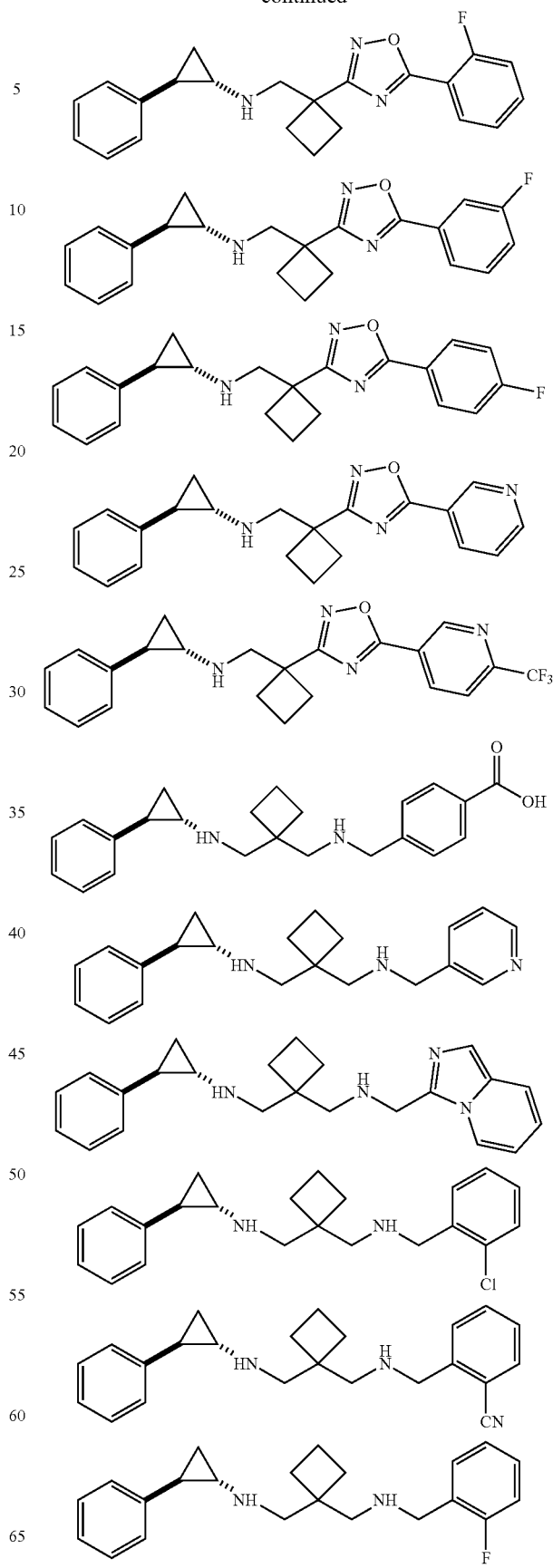

465
-continued
466
-continued
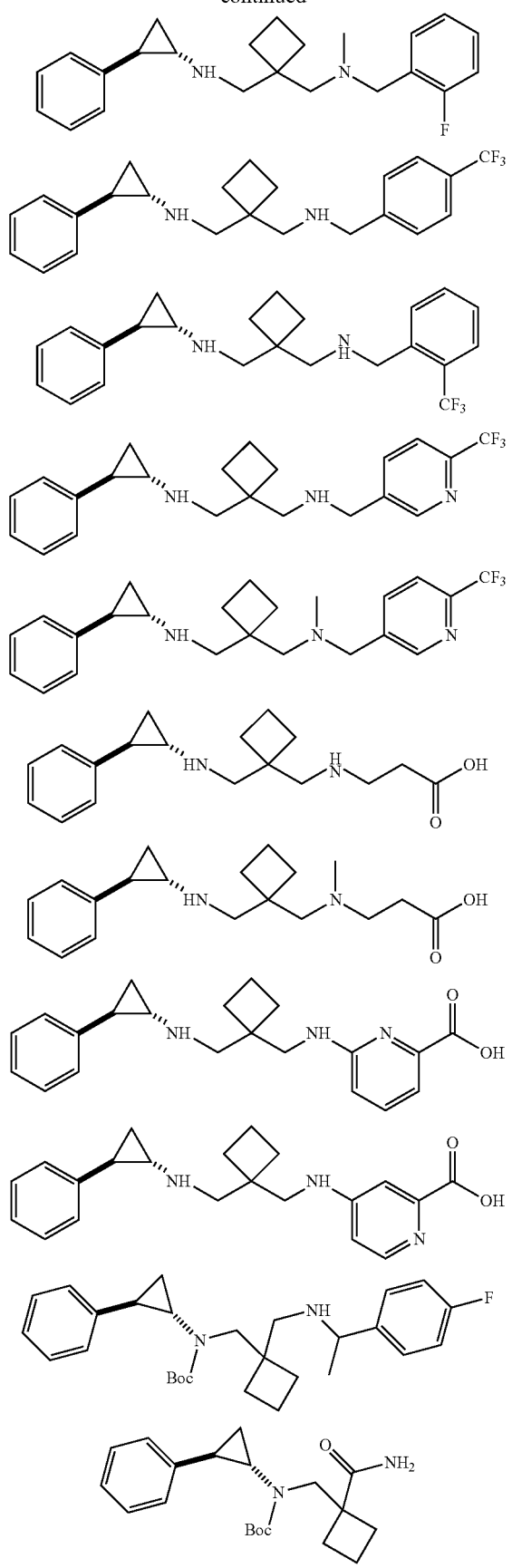
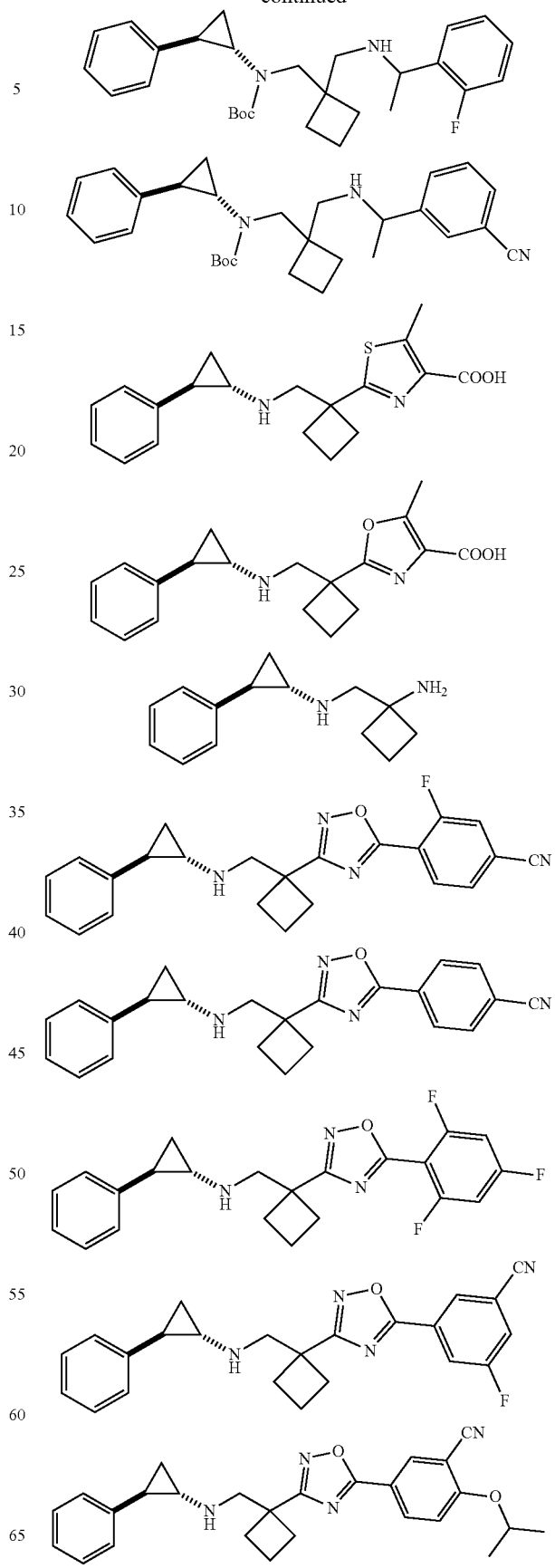

-continued
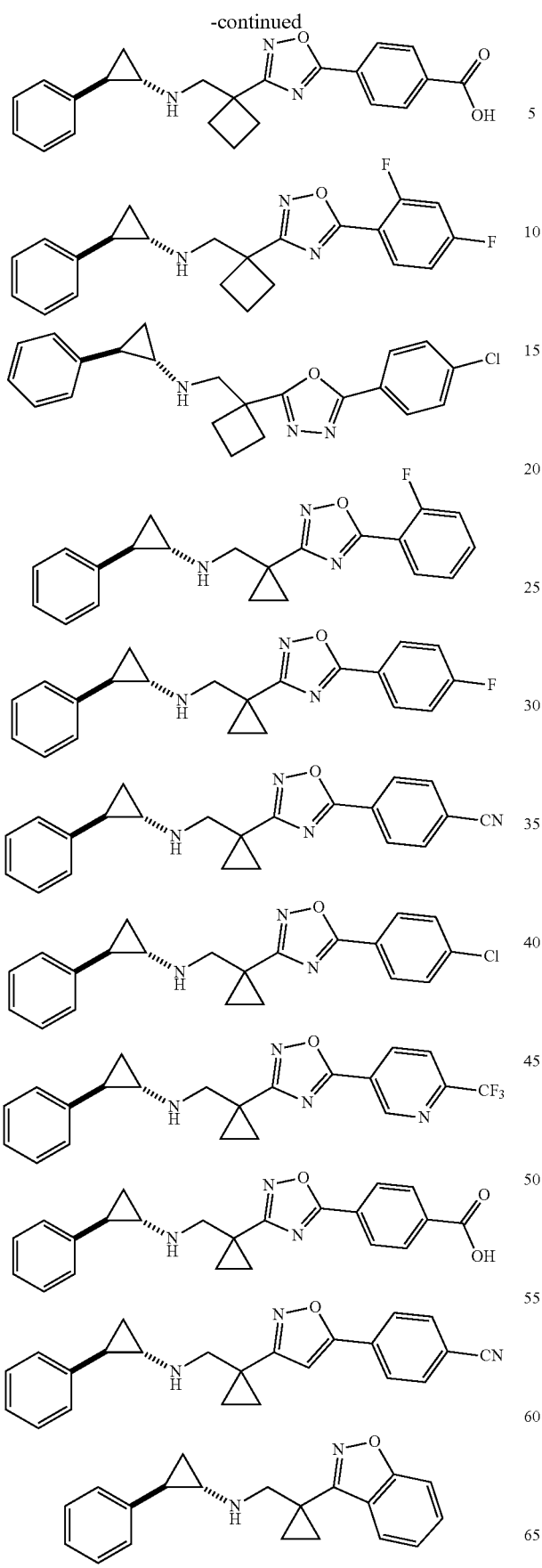
-continued
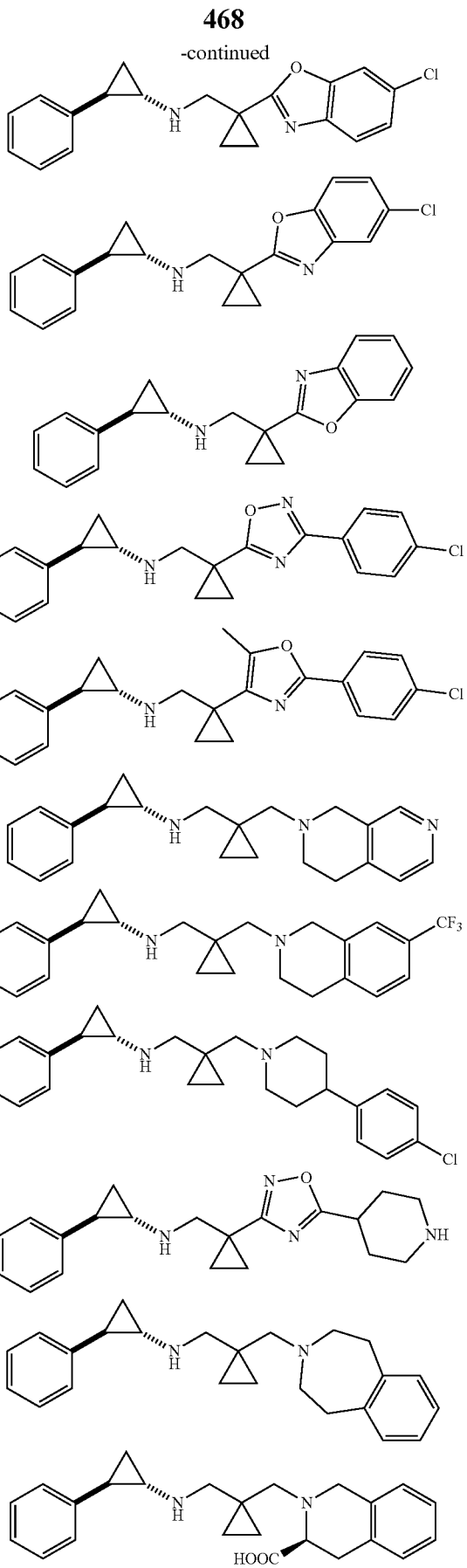

469
-continued
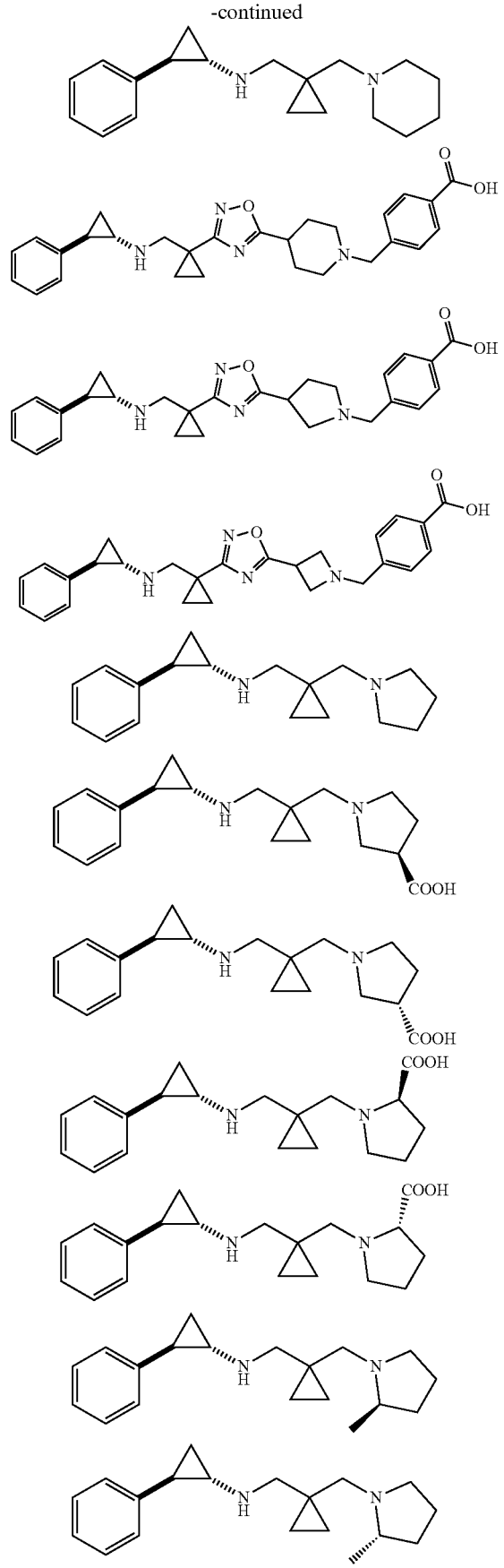
470
-continued
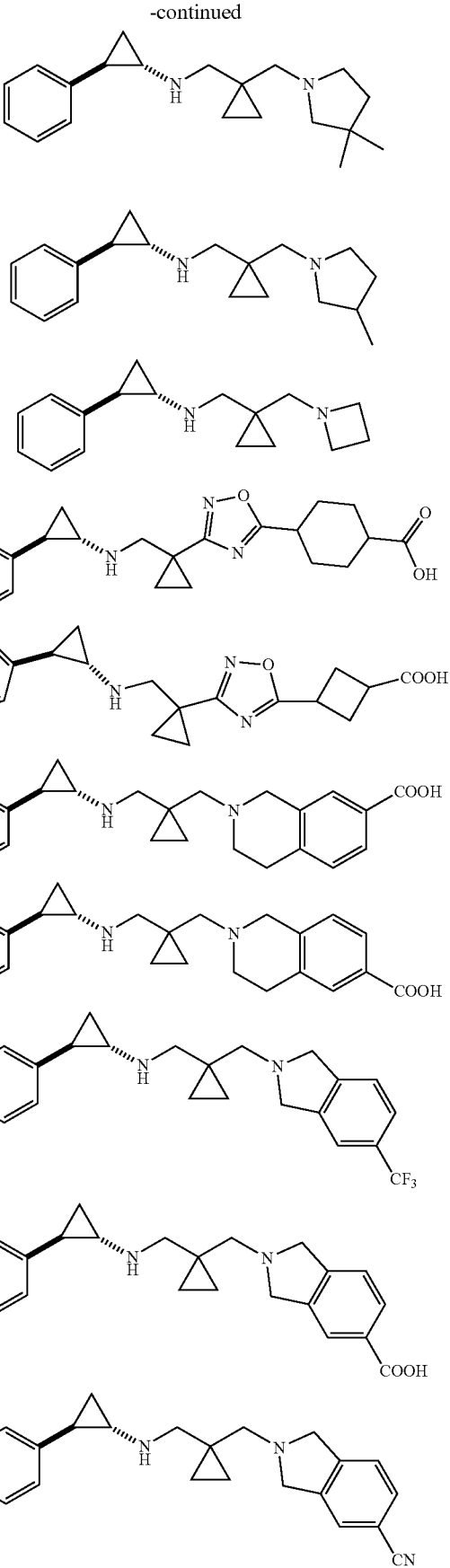

471 -continued

472 -continued

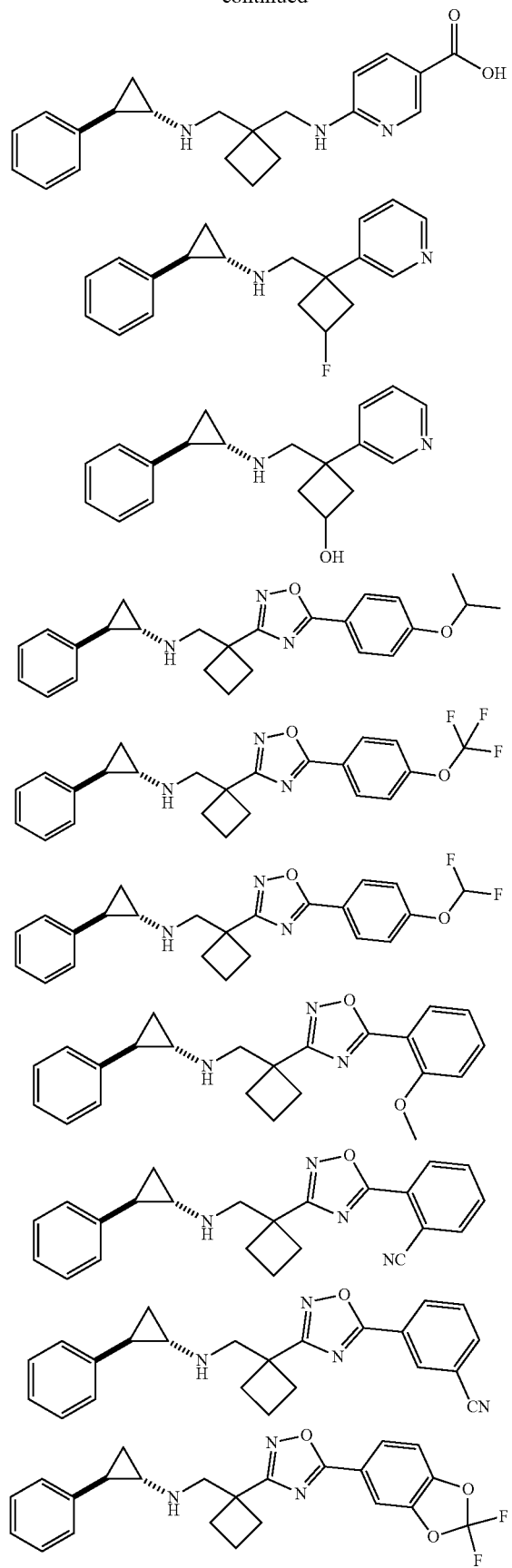
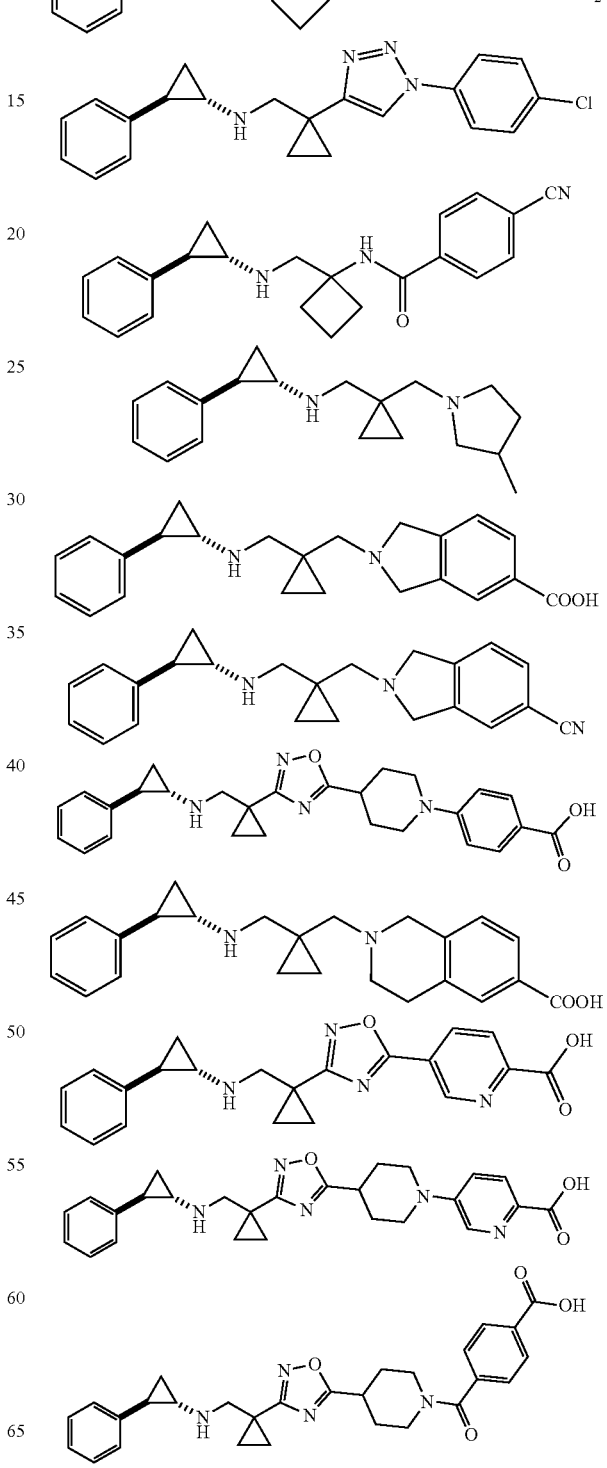

475
-continued

476
-continued

477
-continued
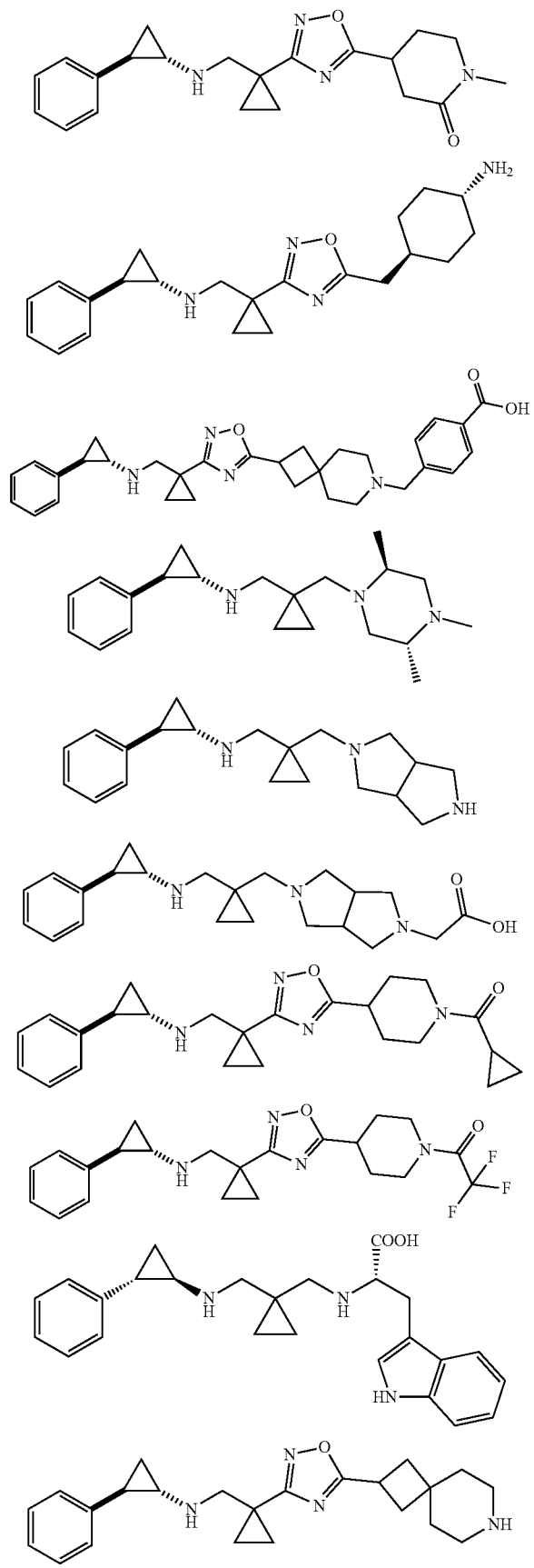
478
-continued
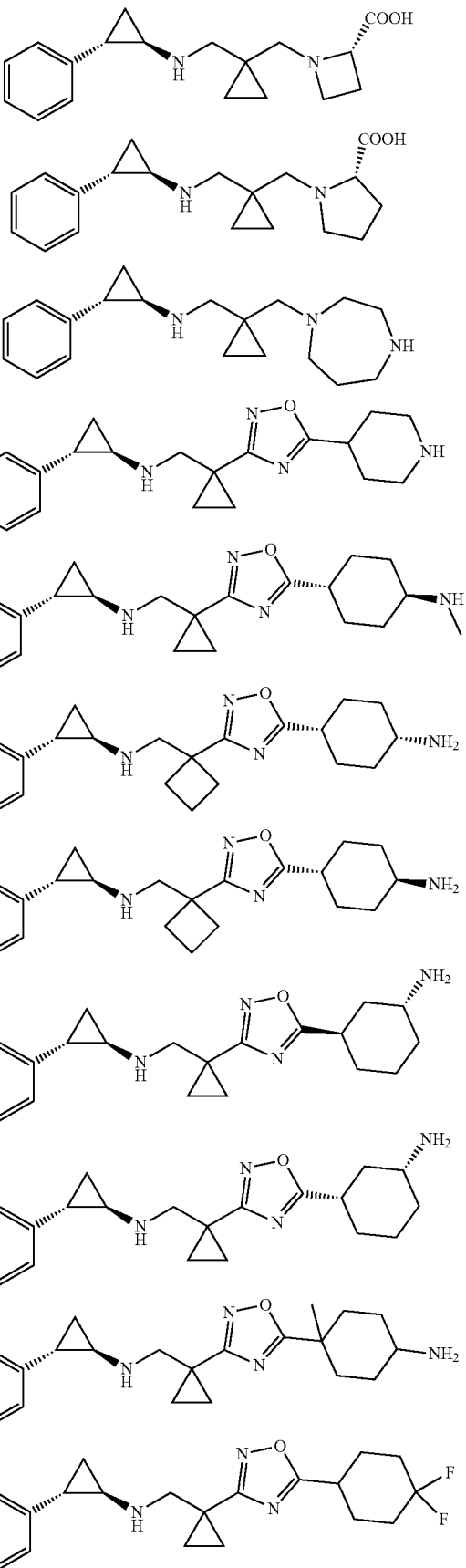

479
-continued
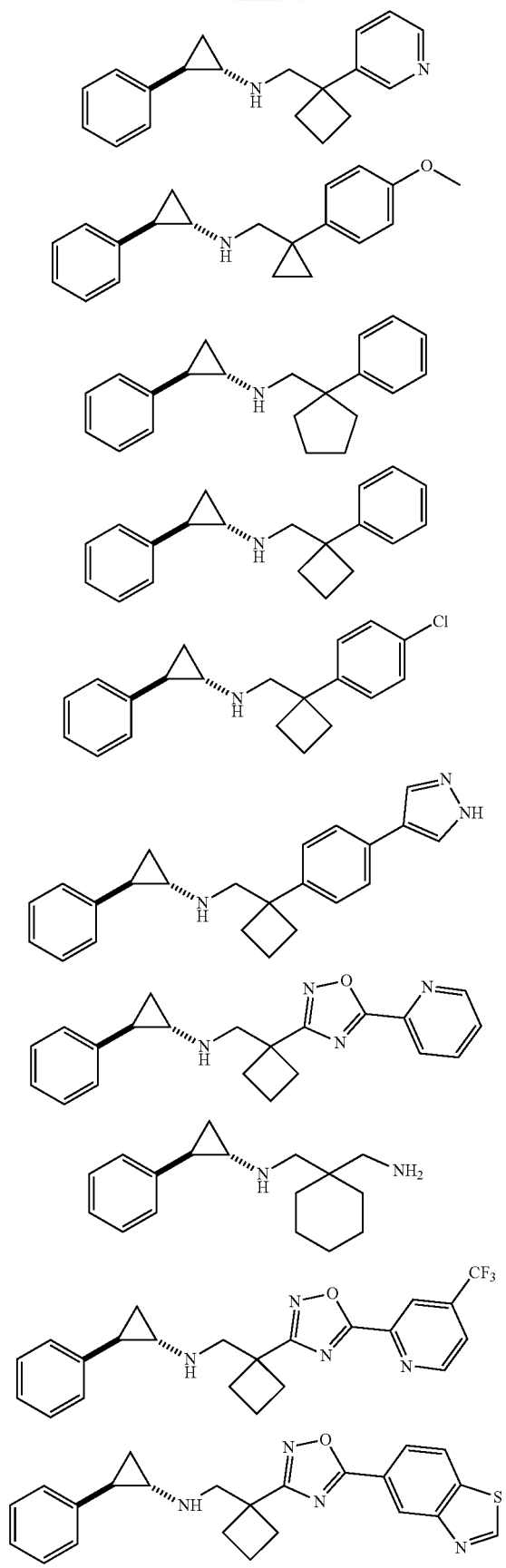
480
-continued
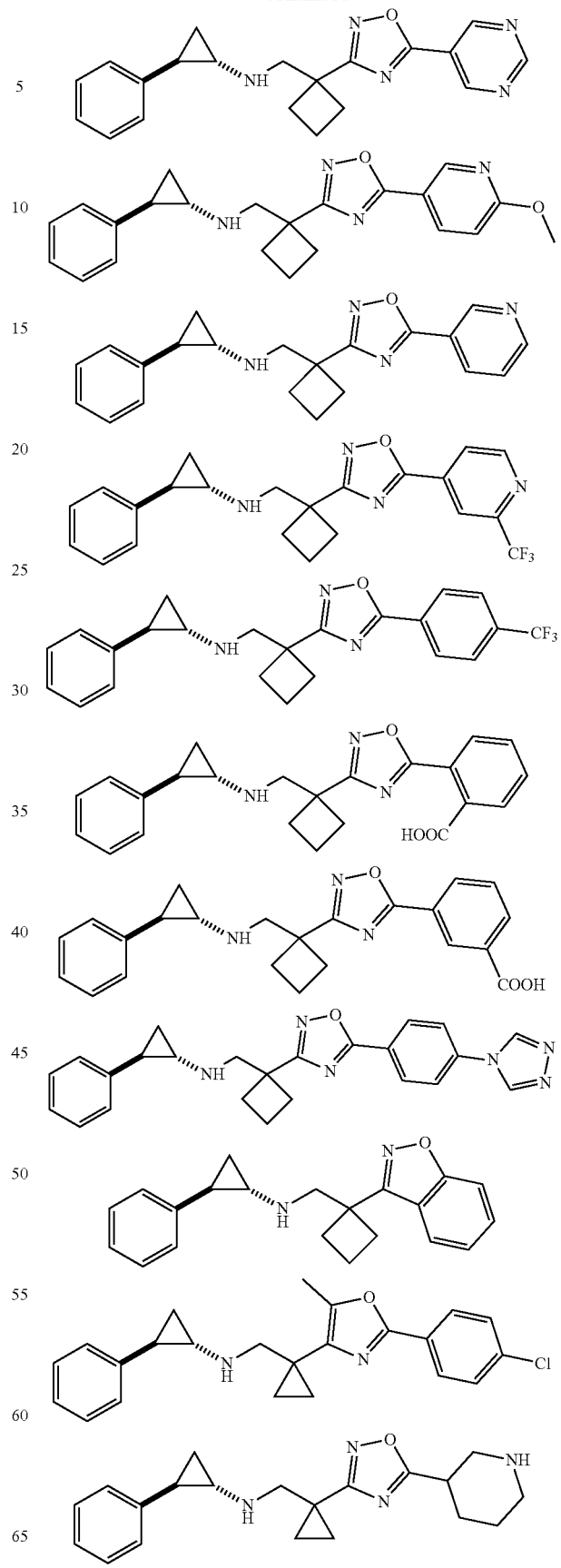

481
-continued
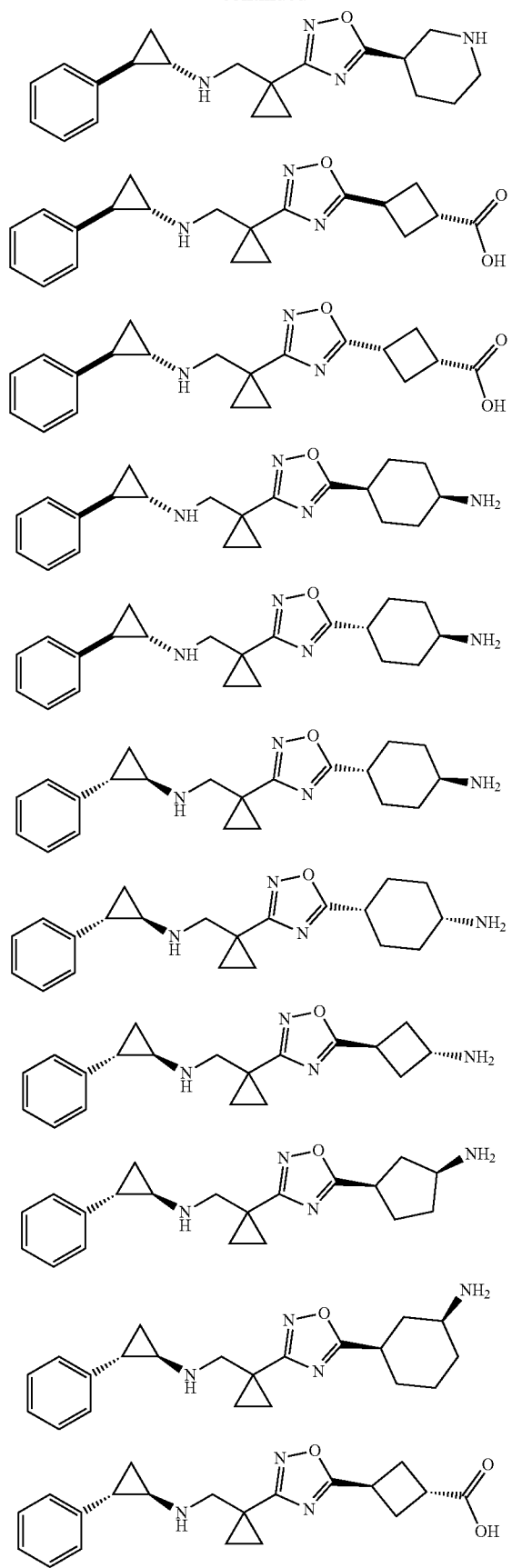
482
-continued
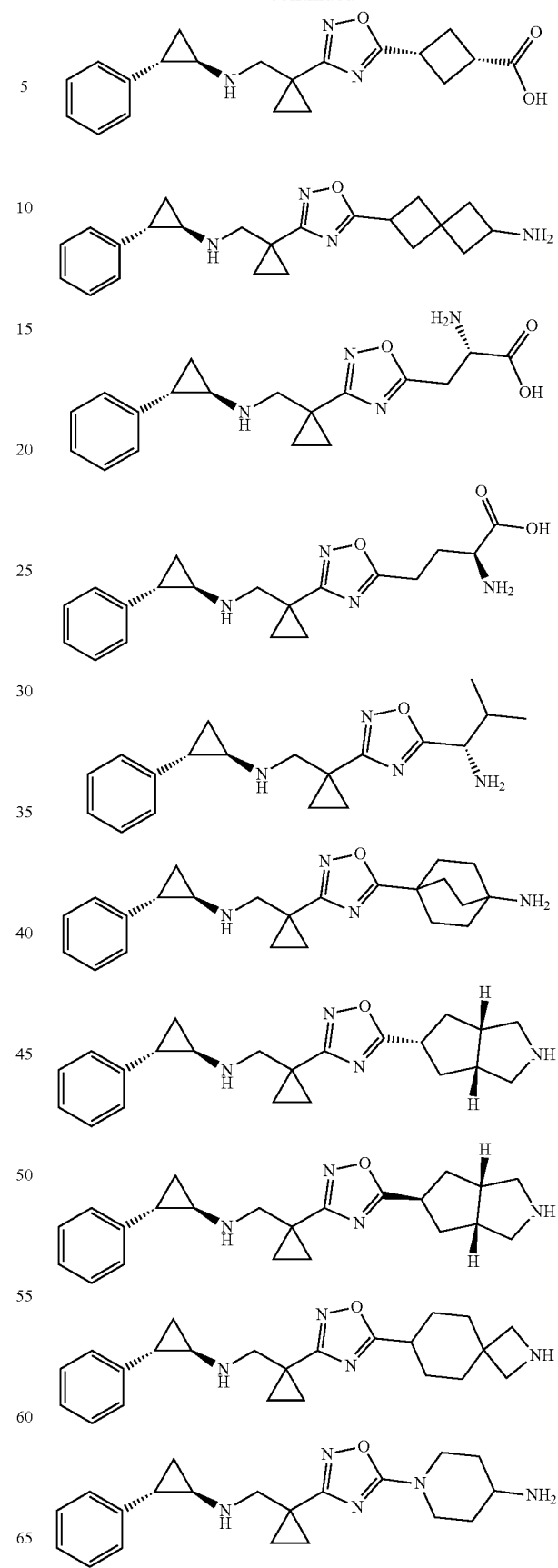

483
-continued
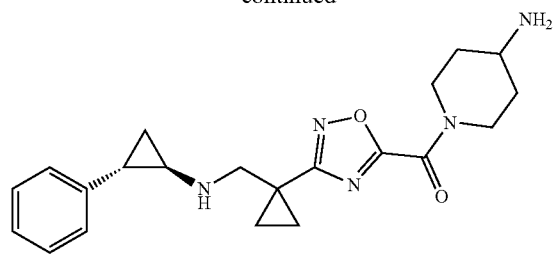
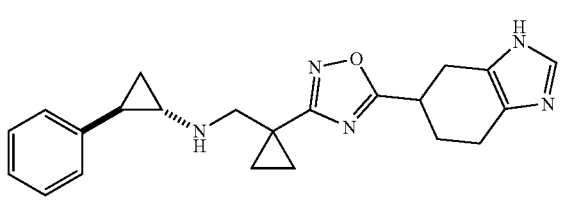
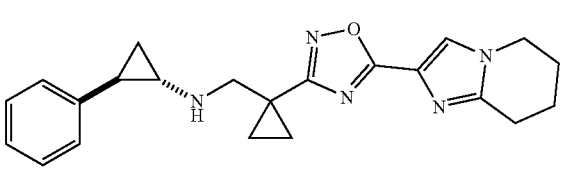
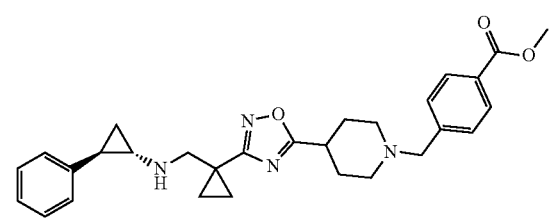
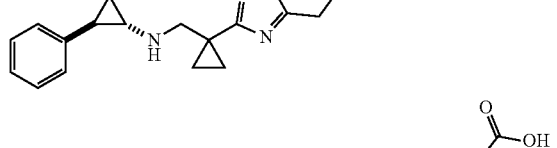
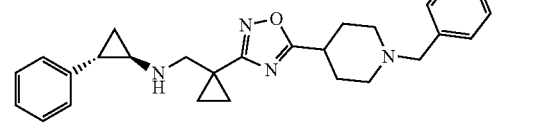
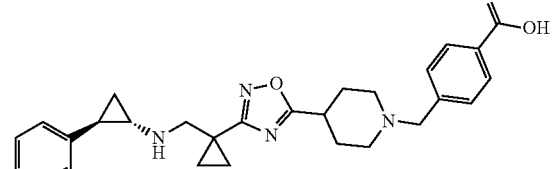
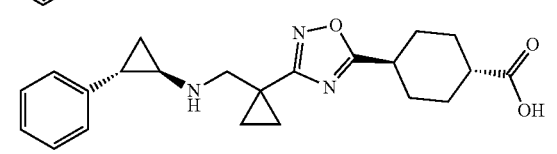
484
-continued
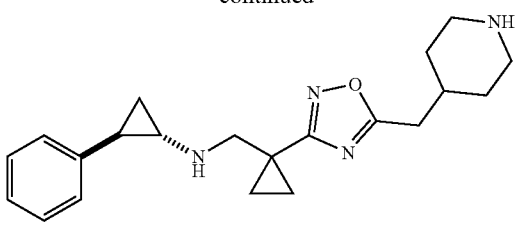
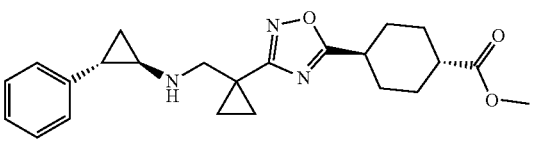
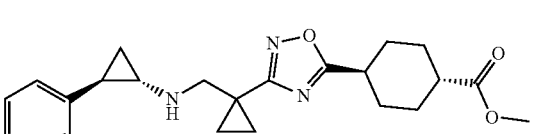
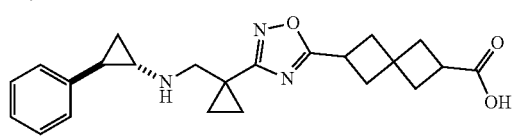
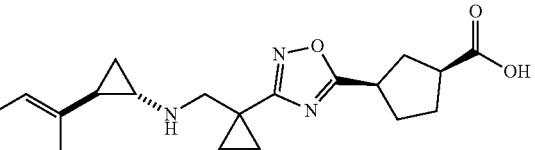
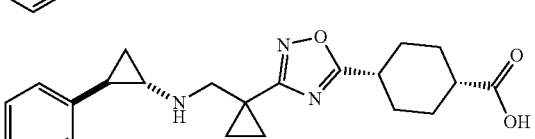
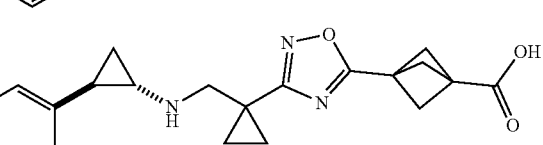
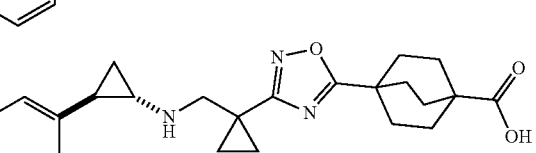
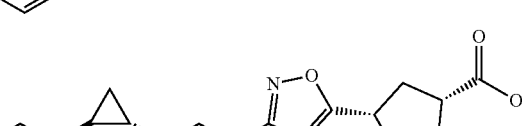
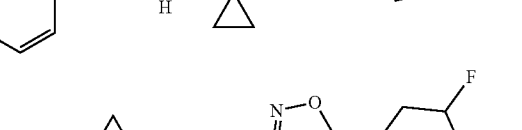

485
-continued
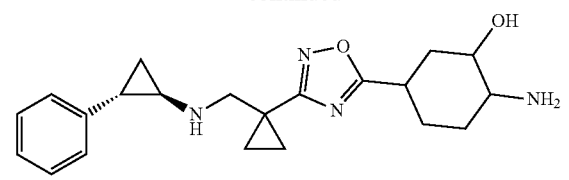
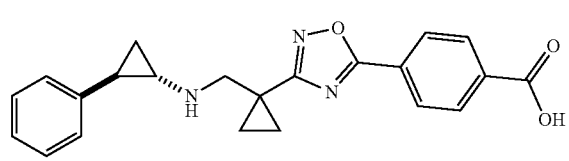
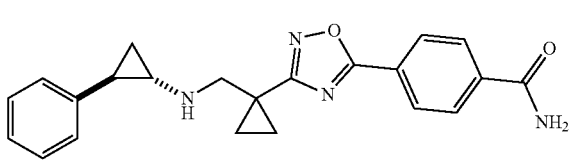
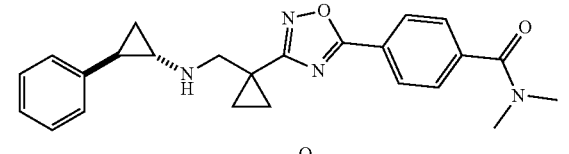
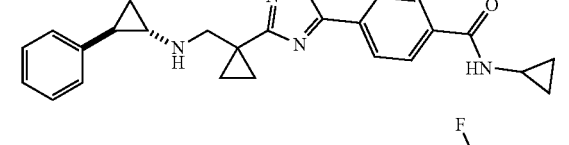
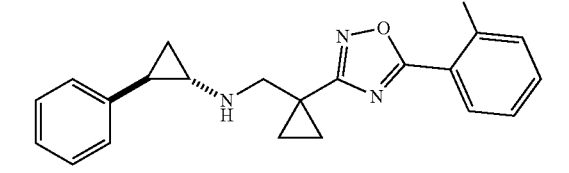
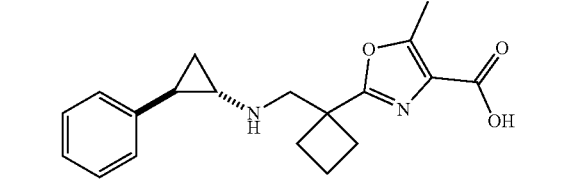
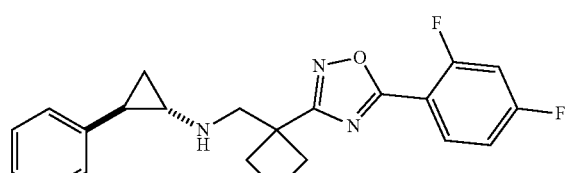
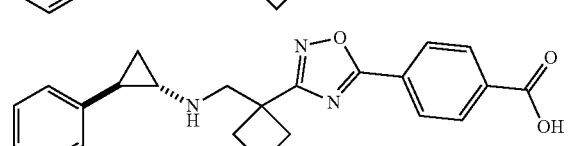
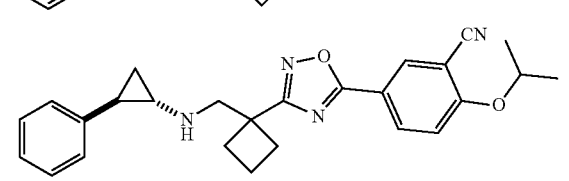
486
-continued
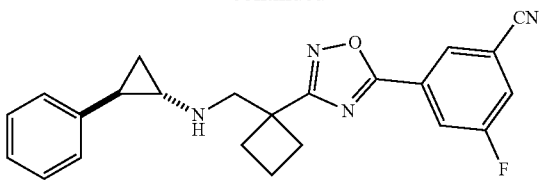
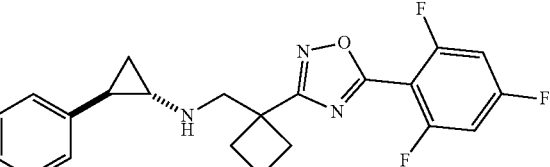
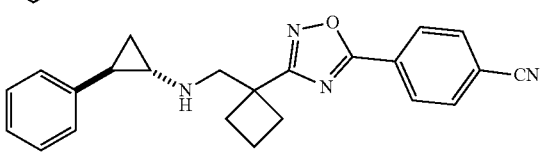
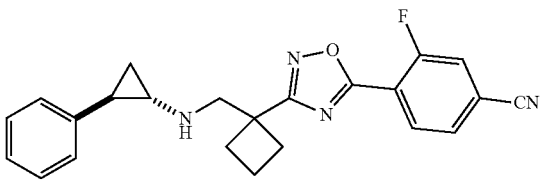
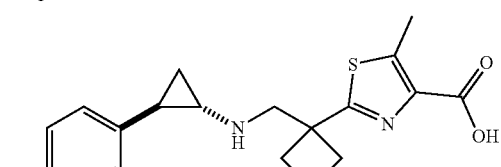
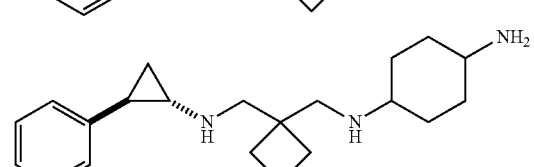
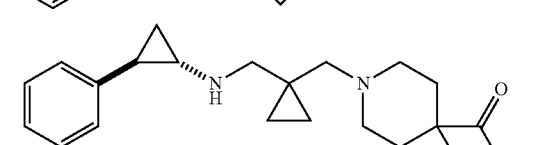
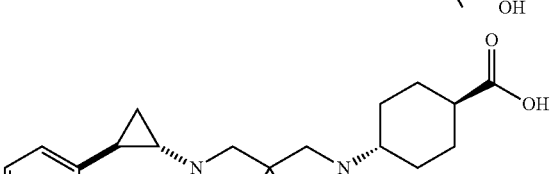
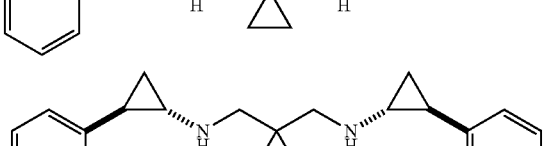
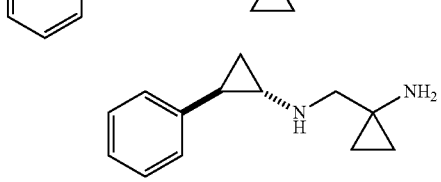

487
-continued
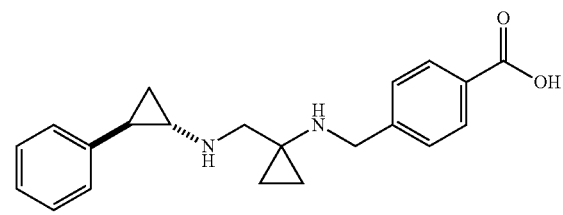
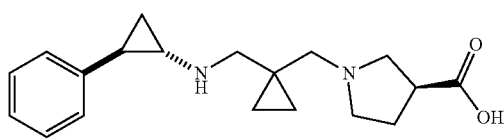
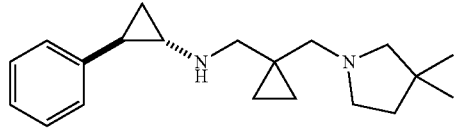
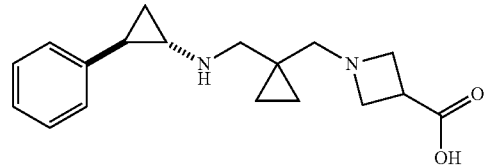
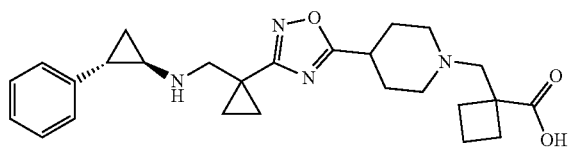
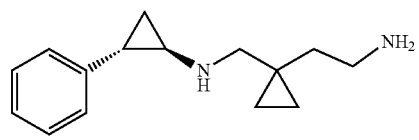
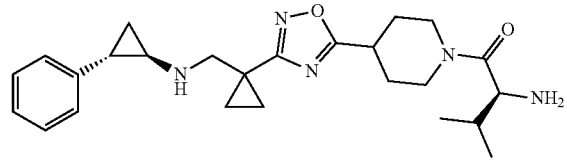
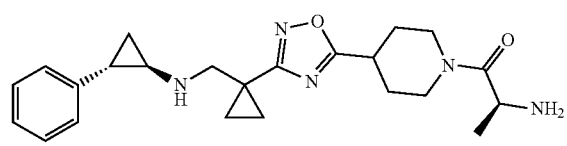
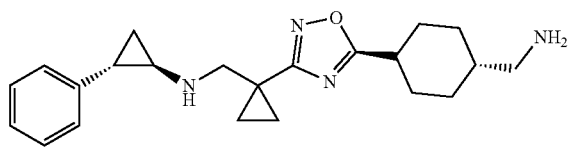
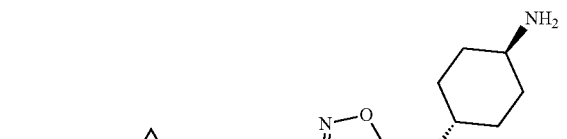
488
-continued
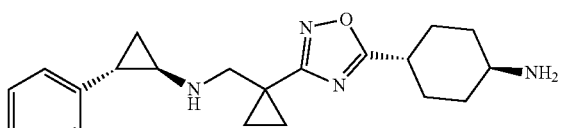
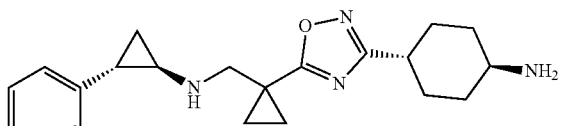
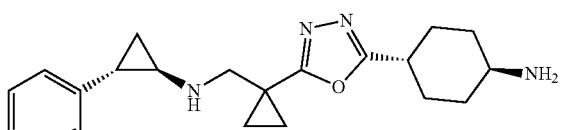
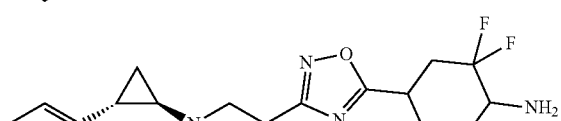
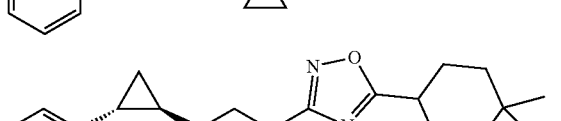
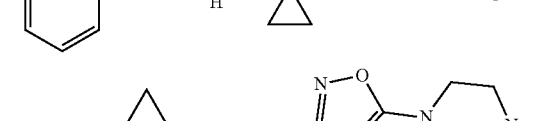
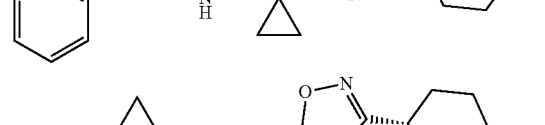
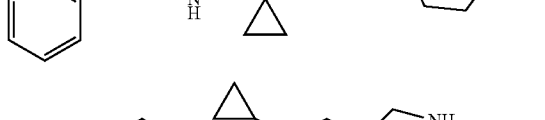
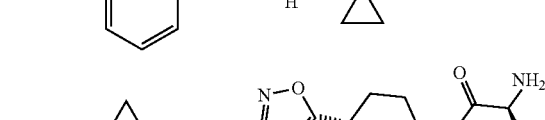
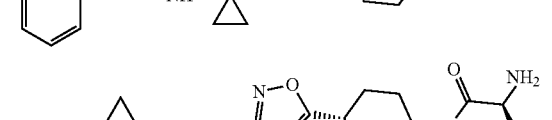

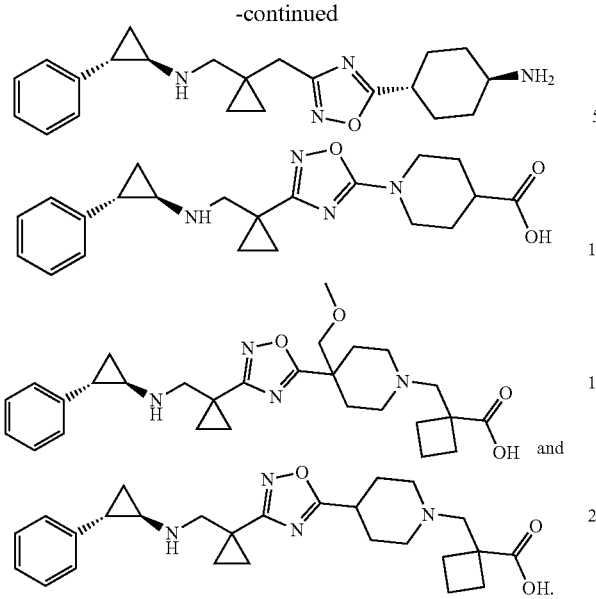

14. A pharmaceutical composition, comprising a therapeutically effective amount of the compound of formula (I), the pharmaceutically acceptable salt or the tautomer thereof as defined in claim 1 as an active ingredient, and a pharmaceutically acceptable carrier.

15. A method for treating LSD1-related disease in a subject in need thereof, comprising administering the compound of formula (I), the pharmaceutically acceptable salt or the tautomer thereof as defined in claim 1 to the subject.

16. A method for treating LSD1-related disease in a subject in need thereof, comprising administering the pharmaceutical composition as defined in claim 14 to the subject.

17. A method for treating LSD1-related disease in a subject in need thereof, comprising administering the compound, the pharmaceutically acceptable salt or the tautomer thereof as defined in claim 13 to the subject.

18. A pharmaceutical composition, comprising a therapeutically effective amount of the compound, the pharmaceutically acceptable salt or the tautomer thereof as defined in claim 13 as an active ingredient, and a pharmaceutically acceptable carrier.

19. A method for treating LSD1-related disease in a subject in need thereof, comprising administering the pharmaceutical composition as defined in claim 18 to the subject.

20. The method as defined in claim 15, wherein the LSD1-related disease is small cell lung cancer.

21. The method as defined in claim 16, wherein the LSD1-related disease is small cell lung cancer.

22. The method as defined in claim 17, wherein the LSD1-related disease is small cell lung cancer.

23. The method as defined in claim 19, wherein the LSD1-related disease is small cell lung cancer.

24. A pharmaceutical composition, comprising the compound of formula (I), the pharmaceutically acceptable salt or the tautomer thereof as defined in claim 1 and Cisplatin.

25. A pharmaceutical composition, comprising the compound, the pharmaceutically acceptable salt or the tautomer thereof as defined in claim 13 and Cisplatin.

26. The compound of formula (I), the pharmaceutically acceptable salt or the tautomer thereof as defined in claim 3, wherein R is selected from the group consisting of

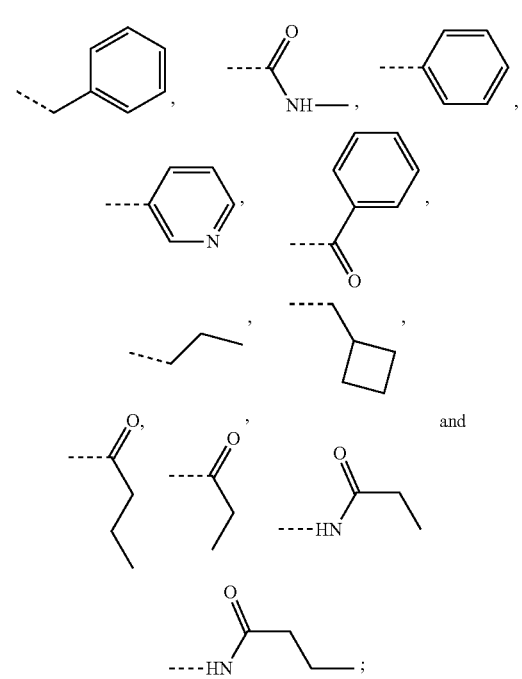

or R is selected from the group consisting of H, F, Cl, Br, I, OH, NH$_2$, Me, Et, —CF$_3$, CN, COOH,

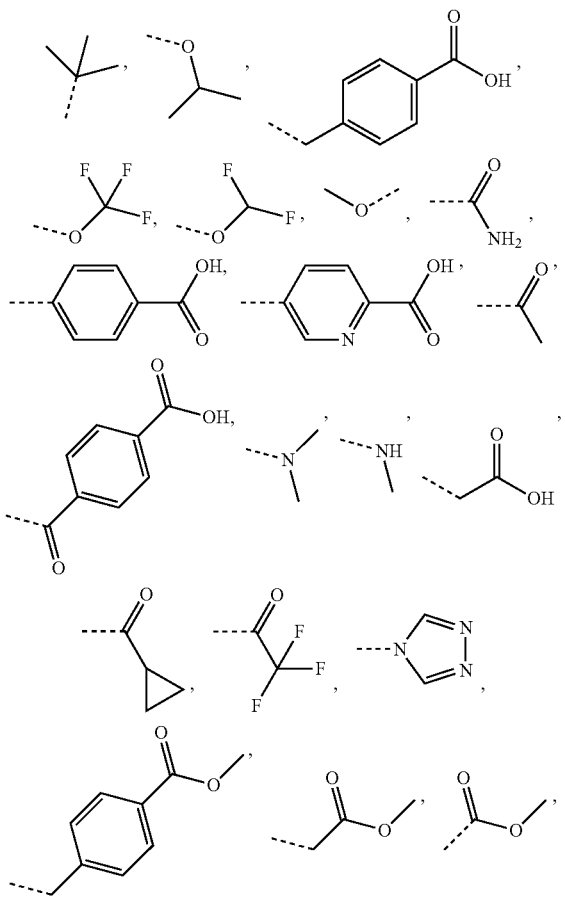

491

-continued

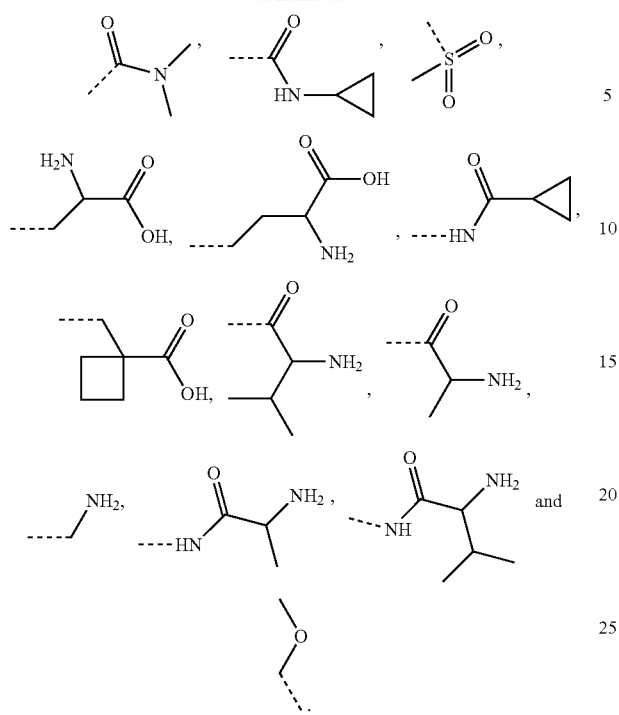

27. The compound of formula (I), the pharmaceutically acceptable salt or the tautomer thereof as defined in claim 5, wherein L is —C(=O)—, or selected from the group consisting of

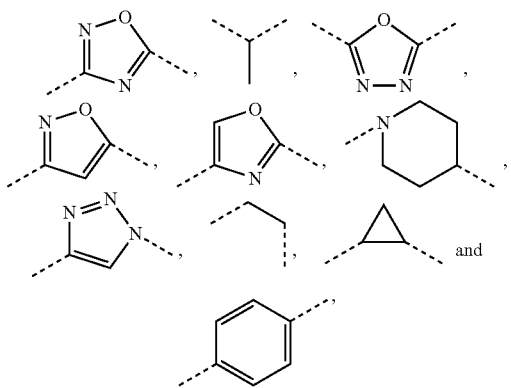

each of which is optionally substituted by 1, 2 or 3 of R.

28. The compound of formula (I), the pharmaceutically acceptable salt or the tautomer thereof as defined in claim 6, wherein $R_5$ is selected from the group consisting of

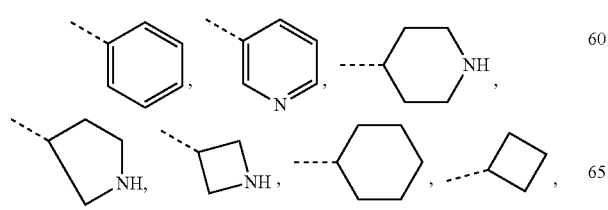

492

-continued

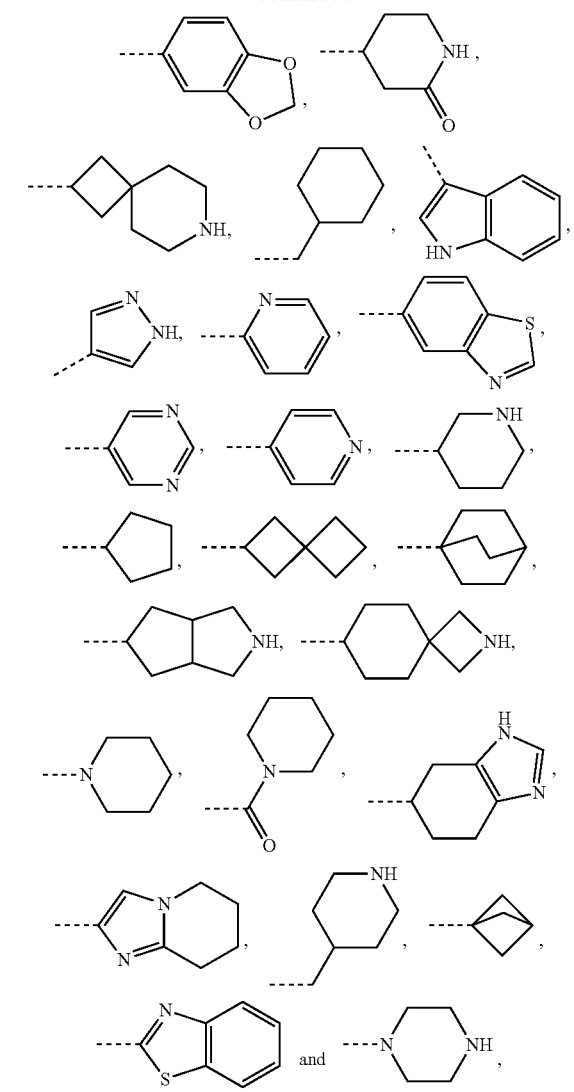

or, $R_5$ is selected from the group consisting of